US010927105B1

(12) United States Patent
Grice et al.

(10) Patent No.: US 10,927,105 B1
(45) Date of Patent: *Feb. 23, 2021

(54) PYRAZOLE MAGL INHIBITORS

(71) Applicant: Lundbeck La Jolla Research Center, Inc., San Diego, CA (US)

(72) Inventors: Cheryl A. Grice, Encinitas, CA (US); John J. M. Wiener, La Jolla, CA (US); Olivia D. Weber, San Diego, CA (US); Katharine K. Duncan, San Diego, CA (US)

(73) Assignee: LUNDBECK LA JOLLA RESEARCH CENTER, INC., San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/900,661

(22) Filed: Jun. 12, 2020

Related U.S. Application Data

(63) Continuation of application No. 16/615,747, filed as application No. PCT/US2018/033959 on May 22, 2018.

(60) Provisional application No. 62/510,213, filed on May 23, 2017.

(51) Int. Cl.
| | |
|---|---|
| C07D 413/14 | (2006.01) |
| C07D 401/14 | (2006.01) |
| C07D 403/06 | (2006.01) |
| C07D 403/14 | (2006.01) |
| C07D 405/10 | (2006.01) |
| C07D 417/14 | (2006.01) |
| C07D 471/10 | (2006.01) |
| C07D 487/04 | (2006.01) |
| C07D 491/08 | (2006.01) |
| C07D 519/00 | (2006.01) |
| A61P 29/00 | (2006.01) |
| C07D 471/04 | (2006.01) |

(52) U.S. Cl.
CPC .......... *C07D 413/14* (2013.01); *A61P 29/00* (2018.01); *C07D 401/14* (2013.01); *C07D 403/06* (2013.01); *C07D 403/14* (2013.01); *C07D 405/10* (2013.01); *C07D 417/14* (2013.01); *C07D 471/04* (2013.01); *C07D 471/10* (2013.01); *C07D 487/04* (2013.01); *C07D 491/08* (2013.01); *C07D 519/00* (2013.01)

(58) Field of Classification Search
CPC .. C07D 413/14; C07D 401/14; C07D 403/06; C07D 403/14; C07D 405/10; C07D 417/14; C07D 471/10; C07D 487/04; C07D 491/08; C07D 519/00
See application file for complete search history.

(56) References Cited

U.S. PATENT DOCUMENTS

| | | |
|---|---|---|
| 3,308,130 A | 3/1967 | Bousquet |
| 7,772,236 B2 | 8/2010 | Beavers et al. |
| 10,266,497 B2 | 4/2019 | Grice |
| 10,323,038 B2 | 6/2019 | Grice et al. |
| 10,385,057 B2 | 8/2019 | Grice et al. |
| 10,519,134 B2 | 12/2019 | Grice et al. |
| 10,583,137 B2 | 3/2020 | Cravatt et al. |
| 2003/0013712 A1 | 1/2003 | Tullis et al. |
| 2011/0172230 A1 | 7/2011 | Ishii et al. |
| 2012/0065191 A1 | 3/2012 | Kiss et al. |
| 2014/0018318 A1 | 1/2014 | Cravatt et al. |
| 2015/0051211 A1 | 2/2015 | Ji et al. |
| 2017/0029390 A1 | 2/2017 | Butler et al. |
| 2017/0190669 A1* | 7/2017 | Boger .................. C07D 231/14 |
| 2020/0087304 A1 | 3/2020 | Grice et al. |

FOREIGN PATENT DOCUMENTS

| | | |
|---|---|---|
| WO | WO-2010074588 A2 | 7/2010 |
| WO | WO-2013078771 A1 | 6/2013 |
| WO | WO-2015179559 A2 | 11/2015 |
| WO | WO-2016014975 A2 | 1/2016 |
| WO | WO-2017087854 A1 | 5/2017 |
| WO | WO-2017087858 A1 | 5/2017 |
| WO | WO-2017087863 A1 | 5/2017 |
| WO | WO-2017096315 A1 | 6/2017 |
| WO | WO-2018217805 A1 | 11/2018 |
| WO | WO-2018217809 A1 | 11/2018 |

OTHER PUBLICATIONS

Baggelaar et al. Development of an activity-based probe and in silico design reveal highly selective inhibitors for diacylglycerol lipase—α in brain. Angew Chem Int Ed Engl 52(46):12081-12085 (2013).
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
Horig et al. From bench to clinic and back: Perspective on the 1st IQPC Translational Research conference. J Transl Med 2(1):44 (2004).
Hsu et al. Development and Optimization of Piperidyl-1,2,3-Triazole Ureas as Selective Chemical Probes of Endocannabinoid Biosynthesis. J Med Chem 56:8257-8269 (2013).
Hsu et al. Discovery and optimization of piperidyl-1,2,3-triazole ureas as potent, selective, and in vivo-active inhibitors of α/β—hydrolase domain containing 6 (ABHD6). J Med Chem 56:8270-8279 (2012).

(Continued)

*Primary Examiner* — Timothy R Rozof
(74) *Attorney, Agent, or Firm* — Wilson Sonsini Goodrich & Rosati

(57) ABSTRACT

Provided herein are pyrazole compounds and pharmaceutical compositions comprising said compounds. The subject compounds and compositions are useful as modulators of monoacylglycerol lipase (MAGL). Furthermore, the subject compounds and compositions are useful for the treatment of pain.

12 Claims, No Drawings

(56) References Cited

OTHER PUBLICATIONS

Hsu et al. Supporting Information for Development and Optimization of Piperidyl-1,2,3-Triazole Ureas as Selective Chemical Probes of Endocannabinoid Biosynthesis. J Med Chem 56:8257-8269, S1-S18 (2013).

Janssen et al. Discovery of glycine sulfonamides as dual inhibitors of sn-1-diacylglycerol lipase α and α/β—hydrolase domain 6. J Med Chem 57(15):6610-6622 (2014).

Kohnz et al. Chemical approaches to therapeutically target the metabolism and signaling of the endocannabinoid 2-AG and eicosanoids. Chem Soc Rev 43(19):6859-6869 (2014).

Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).

Long et al. Selective blockade of 2-arachidonoylglycerol hydrolysis produces cannabinoid behavioral effects. Nat Chem Biol. 5(1):37-44 (2009).

Lysenko et al. Monoacylglycerol lipase inhibitor JZL184 improves behavior and neural properties in Ts65Dn mice, a model of down syndrome. PLoS One 9(12):e114521 (2013).

Morren et al. The filaricidal derivatives of 1-methylpiperazine. Bulletin des Societes Chimiques Belges 59(3-4):228-237 (1950).

Mulvihill et al. Therapeutic potential of monoacylglycerol lipase inhibitors. Life Sci 92(8-9):492-497 (2013).

Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).

Ogasawara et al. Rapid and profound rewiring of brain lipid signaling networks by acute diacylglycerol lipase inhibition. PNAS USA 113(1):26-33 (2016).

Otrubova et al. Discovery libraries targeting the major enzyme classes: the serine hydrolases. Bioorg Med Chem Lett 24(16):3807-3813 (2014).

PCT/US2015/031834 International Search Report and Written Opinion dated Apr. 20, 2016.

PCT/US2016/062862 International Search Report and Written Opinion dated Jan. 27, 2017.

PCT/US2016/062868 International Search Report and Written Opinion dated Jan. 30, 2017.

PCT/US2016/062873 International Search Report and Written Opinion dated Jan. 27, 2017.

PCT/US2016/064844 International Search Report and Written Opinion dated Feb. 15, 2017.

PCT/US2018/033959 International Search Report and Written Opinion dated Jul. 23, 2018.

PCT/US2018/033964 International Search Report and Written Opinion dated Sep. 13, 2018.

PCT/US2018/033964 Invitation to Pay Additional Fees dated Jul. 20, 2018.

Schafer et al. Failure is an option: learning from unsuccessful proof-of-concept trials. Drug Discov Today 13(21-22):913-916 (2008).

U.S. Appl. No. 15/315,998 Office Action dated Nov. 2, 2017.

U.S. Appl. No. 15/778,207 Office Action dated Jun. 6, 2019.

Van Den Nieuwendijk et al. Synthesis of Eight 1-Deoxynojirimycin Isomers from a Single Chiral Cyanohydrin. Eur JOC 18:3437-3446 (2012).

Van Den Nieuwendijk et al. Synthesis of L-altro-1-deoxynojirimycin, D-allo-1-deoxynojirimycin, and D-galacto-1-deoxynojirimycin from a single chiral cyanohydrin. Org lett 12(17):3957-3959 (2010).

Van Der Wel et al. A natural substrate-based fluorescence assay for inhibitor screening on diacylglycerol lipase α. J Lipid Res 56(4):927-935 (2015).

* cited by examiner

PYRAZOLE MAGL INHIBITORS

CROSS-REFERENCE

This application is a continuation of U.S. application Ser. No. 16/615,747, filed Nov. 21, 2019, which is a US National Stage entry of PCT application PCT/US2018/33959 filed May 22, 2018, claims the benefit of U.S. Provisional Application No. 62/510,213, filed on May 23, 2017, which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. Fatty acid amide hydrolase (FAAH) is another enzyme responsible for hydrolyzing endocannabinoids such as anandamide.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound of Formula (I):

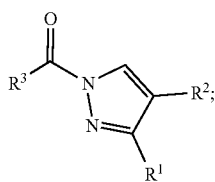

Formula (I)

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;

$R^3$ is

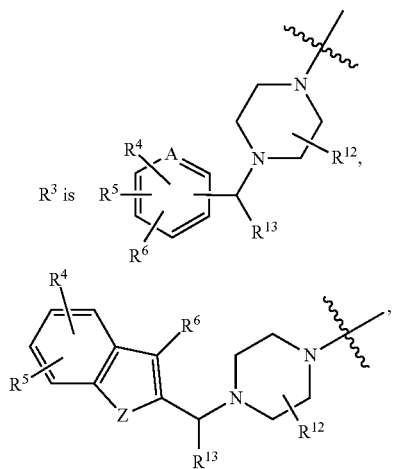

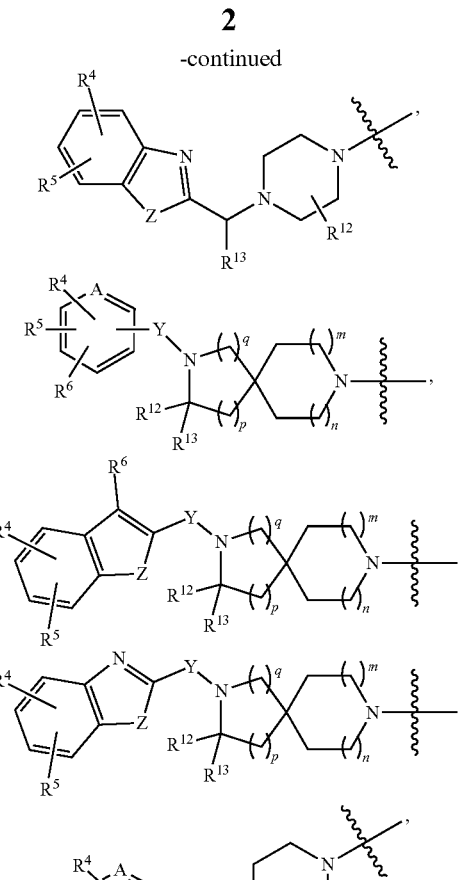

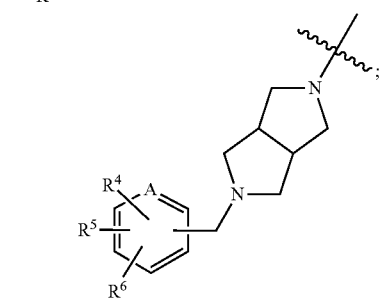

A is N or C(H);
X is —O—, —N(R$^{16}$)—, or —CH$_2$N(R$^{16}$)CH$_2$—;
Y is —CH$_2$— or —C(O)—;
Z is —S—, —O—, or —N(R$^{18}$)—;
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{3-9}$cycloalkyl, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{3-8}$cycloalkyl, $C_{2-9}$heterocycloalkyl, —C$_{1-6}$alkyl-C$_{2-9}$heterocycloalkyl, $C_{6-10}$aryl, or $C_{1-9}$heteroaryl are optionally substituted with 1 or 2 R$^{14}$;

$R^5$ is H, halogen, $C_{1-6}$alkyl, $C_{1-6}$haloalkyl, $C_{1-6}$haloalkoxy, or phenyl;

$R^6$ is H, halogen or $C_{1-6}$alkyl;

$R^7$ is H, $C_{1-6}$alkyl, $C_{1-6}$haloalkyl, —$C_{1-6}$alkyl-OH, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)OH, —C(O)NR$^8$R$^9$, —SO$_2$—$C_{1-6}$alkyl, and —N(R$^{17}$)C(O)—$C_{1-6}$alkyl;

$R^{15}$ is H or $C_{1-6}$alkyl;

$R^{16}$ is H, $C_{1-6}$alkyl, —C(O)—$C_{1-6}$alkyl, —$C_{1-6}$alkyl-OH, or —CH$_2$CO$_2$H;

$R^{17}$ is H or $C_{1-6}$alkyl;

$R^{18}$ is H or $C_{1-6}$alkyl;

v is 0 or 1;

n is 0 or 1;

m is 0 or 1;

p is 0, 1, or 2; and q is 0, 1 or 2;

or a solvate, hydrate, tautomer, N-oxide, stereoisomer, or pharmaceutically acceptable salt thereof.

In another aspect is a compound of Formula (I'):

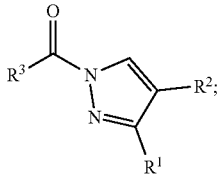

Formula (I')

wherein:

$R^1$ is —C(O)OR$^{15}$ or —C(O)NR$^{10}$R$^{11}$;

$R^2$ is H, halogen, $C_{1-6}$alkyl, or $C_{1-6}$haloalkyl;

$R^3$ is

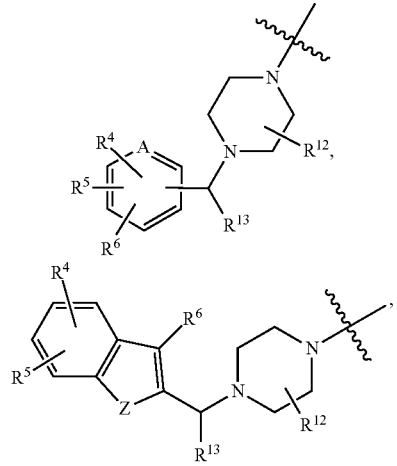

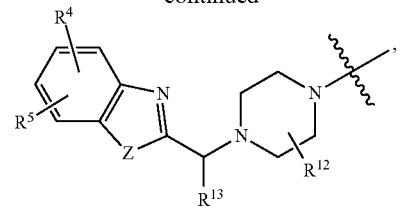

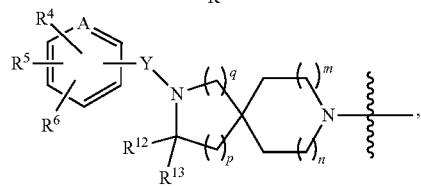

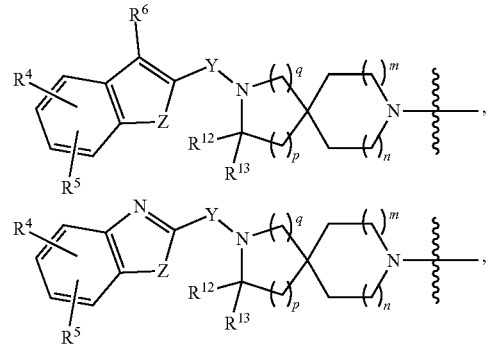

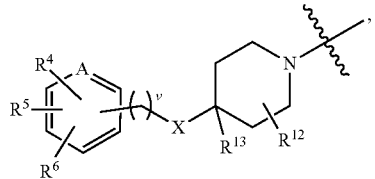

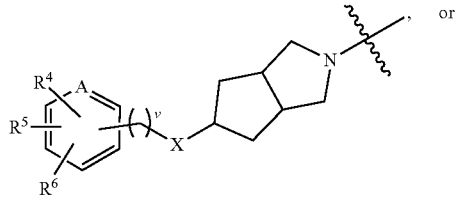

A is N or C(H);

X is —O—, —N(R$^{16}$)—, or —CH$_2$N(R$^{16}$)CH$_2$—;

Y is —CH$_2$— or —C(O)—;

Z is —S—, —O—, or —N(R$^{18}$)—;

$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —$C_{1-6}$alkyl-$C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^{14}$;

R⁵ is H, halogen, C₁₋₆alkyl, C₁₋₆haloalkyl, C₁₋₆haloalkoxy, or phenyl;
R⁶ is H, halogen or C₁₋₆alkyl;
R⁷ is H, C₁₋₆ alkyl, C₁₋₆haloalkyl, C₂₋₉heterocycloalkyl, C₆₋₁₀aryl, or C₁₋₉heteroaryl, wherein C₂₋₉heterocycloalkyl, C₆₋₁₀aryl, or C₁₋₉heteroaryl are optionally substituted with 1 or 2 R¹⁴;
each R⁸ and each R⁹ are independently selected from H and C₁₋₆alkyl; or R⁸ and R⁹ together with the nitrogen to which they are attached are combined to form a heterocycloalkyl ring;
R¹⁰ and R¹¹ are each independently H or C₁₋₆ alkyl;
R¹² is H, halogen, or C₁₋₆alkyl;
R¹³ is H or C₁₋₆alkyl;
each R¹⁴ is independently selected from halogen, —OH, C₁₋₆ alkyl, C₁₋₆haloalkyl, C₁₋₆alkoxy, —C₁₋₆alkyl-OH, C₃₋₈ cycloalkyl, —C(O)NR⁸R⁹, —SO₂—C₁₋₆ alkyl, and —N(R¹⁷)C(O)—C₁₋₆ alkyl;
R¹⁵ is H or C₁₋₆alkyl;
R¹⁶ is H, C₁₋₆alkyl, —C(O)—C₁₋₆alkyl, or —CH₂CO₂H;
R¹⁷ is H or C₁₋₆alkyl;
R¹⁸ is H or C₁₋₆alkyl;
v is 0 or 1;
n is 0 or 1;
m is 0 or 1;
p is 0, 1, or 2; and
q is 0, 1 or 2;
or a solvate, hydrate, tautomer, N-oxide, stereoisomer, or pharmaceutically acceptable salt thereof.

In some embodiments is a compound of Formula (I) or (I'), or a solvate, hydrate, tautomer, N-oxide, stereoisomer, or pharmaceutically acceptable salt thereof, wherein R³ is

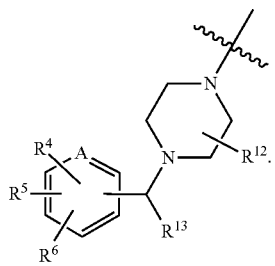

In another embodiment is a compound of Formula (I) or (I'), or a solvate, hydrate, tautomer, N-oxide, stereoisomer, or pharmaceutically acceptable salt thereof, wherein A is C(H). In another embodiment is a compound of Formula (I) or (I'), or a solvate, hydrate, tautomer, N-oxide, stereoisomer, or pharmaceutically acceptable salt thereof, wherein A is N. In another embodiment is a compound of Formula (I) or (I'), or a solvate, hydrate, tautomer, N-oxide, stereoisomer, or pharmaceutically acceptable salt thereof, wherein R⁶ is H. In another embodiment is a compound of Formula (I) or (I'), or a solvate, hydrate, tautomer, N-oxide, stereoisomer, or pharmaceutically acceptable salt thereof, wherein R³ is

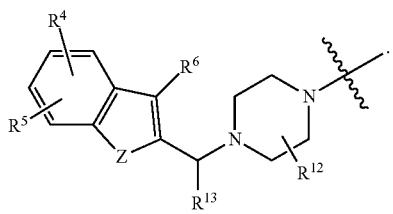

In another embodiment is a compound of Formula (I) or (I'), or a solvate, hydrate, tautomer, N-oxide, stereoisomer, or pharmaceutically acceptable salt thereof, wherein R³ is

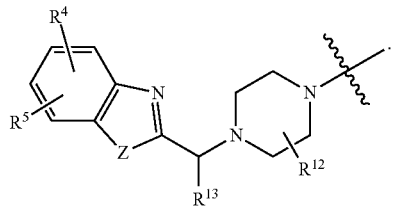

In another embodiment is a compound of Formula (I) or (I'), or a solvate, hydrate, tautomer, N-oxide, stereoisomer, or pharmaceutically acceptable salt thereof, wherein Z is —S—. In another embodiment is a compound of Formula (I) or (I'), or a solvate, hydrate, tautomer, N-oxide, stereoisomer, or pharmaceutically acceptable salt thereof, wherein Z is —N(H)—. In another embodiment is a compound of Formula (I) or (I'), or a solvate, hydrate, tautomer, N-oxide, stereoisomer, or pharmaceutically acceptable salt thereof, wherein R³ is

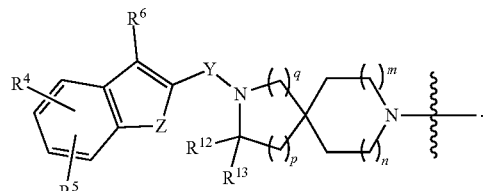

In another embodiment is a compound of Formula (I) or (I'), or a solvate, hydrate, tautomer, N-oxide, stereoisomer, or pharmaceutically acceptable salt thereof, wherein Z is —S—. In another embodiment is a compound of Formula (I) or (I'), or a solvate, hydrate, tautomer, N-oxide, stereoisomer, or pharmaceutically acceptable salt thereof, wherein R³ is

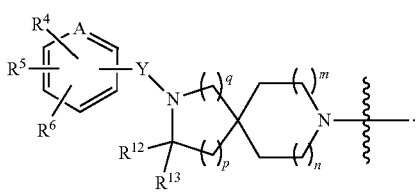

In another embodiment is a compound of Formula (I) or (I'), or a solvate, hydrate, tautomer, N-oxide, stereoisomer, or pharmaceutically acceptable salt thereof, wherein m is 1, n is 1, q is 1, and p is 1. In another embodiment is a compound of Formula (I) or (I'), or a solvate, hydrate, tautomer, N-oxide, stereoisomer, or pharmaceutically acceptable salt thereof, wherein m is 0, n is 1, q is 2, and p is 1. In another embodiment is a compound of Formula (I) or (I'), or a solvate, hydrate, tautomer, N-oxide, stereoisomer, or pharmaceutically acceptable salt thereof, wherein m is 1, n is 1, q is 0, and p is 2. In another embodiment is a compound of Formula (I) or (I'), or a solvate, hydrate, tautomer, N-oxide, stereoisomer, or pharmaceutically acceptable salt thereof, wherein m is 1, n is 1, q is 1, and p is 0. In another embodiment is a compound of Formula (I) or (I'), or a solvate, hydrate, tautomer, N-oxide, stereoisomer, or pharmaceutically acceptable salt thereof, wherein Y is —CH$_2$—. In another embodiment is a compound of Formula (I) or (I'), or a solvate, hydrate, tautomer, N-oxide, stereoisomer, or pharmaceutically acceptable salt thereof, wherein Y is —C(O)—. In another embodiment is a compound of Formula (I) or (I'), or a solvate, hydrate, tautomer, N-oxide, stereoisomer, or pharmaceutically acceptable salt thereof, wherein R$^{13}$ is H. In another embodiment is a compound of Formula (I) or (I'), or a solvate, hydrate, tautomer, N-oxide, stereoisomer, or pharmaceutically acceptable salt thereof, wherein R$^{12}$ is H. In another embodiment is a compound of Formula (I) or (I'), or a solvate, hydrate, tautomer, N-oxide, stereoisomer, or pharmaceutically acceptable salt thereof, wherein R$^3$ is

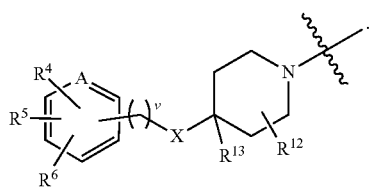

In another embodiment is a compound of Formula (I) or (I'), or a solvate, hydrate, tautomer, N-oxide, stereoisomer, or pharmaceutically acceptable salt thereof, wherein R$^{13}$ is H. In another embodiment is a compound of Formula (I) or (I'), or a solvate, hydrate, tautomer, N-oxide, stereoisomer, or pharmaceutically acceptable salt thereof, wherein R$^{13}$ is —CH$_3$. In another embodiment is a compound of Formula (I) or (I'), or a solvate, hydrate, tautomer, N-oxide, stereoisomer, or pharmaceutically acceptable salt thereof, wherein R$^{12}$ is H. In another embodiment is a compound of Formula (I) or (I'), or a solvate, hydrate, tautomer, N-oxide, stereoisomer, or pharmaceutically acceptable salt thereof, wherein R$^3$ is

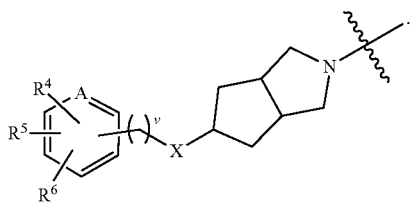

In another embodiment is a compound of Formula (I) or (I'), or a solvate, hydrate, tautomer, N-oxide, stereoisomer, or pharmaceutically acceptable salt thereof, wherein v is 0. In another embodiment is a compound of Formula (I) or (I'), or a solvate, hydrate, tautomer, N-oxide, stereoisomer, or pharmaceutically acceptable salt thereof, wherein v is 1. In another embodiment is a compound of Formula (I) or (I'), or a solvate, hydrate, tautomer, N-oxide, stereoisomer, or pharmaceutically acceptable salt thereof, wherein X is —O—. In another embodiment is a compound of Formula (I) or (I'), or a solvate, hydrate, tautomer, N-oxide, stereoisomer, or pharmaceutically acceptable salt thereof, wherein X is —N(CH$_3$)—. In another embodiment is a compound of Formula (I) or (I'), or a solvate, hydrate, tautomer, N-oxide, stereoisomer, or pharmaceutically acceptable salt thereof, wherein X is —CH$_2$N(CH$_3$)CH$_2$—. In another embodiment is a compound of Formula (I) or (I'), or a solvate, hydrate, tautomer, N-oxide, stereoisomer, or pharmaceutically acceptable salt thereof, wherein R$^3$ is

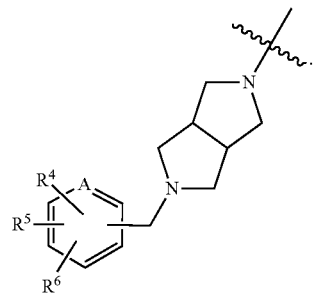

In another embodiment is a compound of Formula (I) or (I'), or a solvate, hydrate, tautomer, N-oxide, stereoisomer, or pharmaceutically acceptable salt thereof, wherein A is C(H). In another embodiment is a compound of Formula (I) or (I'), or a solvate, hydrate, tautomer, N-oxide, stereoisomer, or pharmaceutically acceptable salt thereof, wherein A is N. In another embodiment is a compound of Formula (I) or (I'), or a solvate, hydrate, tautomer, N-oxide, stereoisomer, or pharmaceutically acceptable salt thereof, wherein R$^6$ is H. In another embodiment is a compound of Formula (I) or (I'), or a solvate, hydrate, tautomer, N-oxide, stereoisomer, or pharmaceutically acceptable salt thereof, wherein R$^4$ is halogen, —OR$^7$, C$_{1-6}$ alkyl, C$_{2-6}$alkynyl, C$_{1-6}$haloalkyl, —C(O)NR$^8$R$^9$, C$_{2-9}$heterocycloalkyl, C$_{6-10}$aryl, or C$_{1-9}$heteroaryl, wherein C$_{2-9}$heterocycloalkyl, —C$_{1-6}$alkyl-C$_{2-9}$heterocycloalkyl, C$_{6-10}$aryl, or C$_{1-9}$heteroaryl are optionally substituted with 1 or 2 R$^{14}$. In another embodiment is a compound of Formula (I) or (I'), or a solvate, hydrate, tautomer, N-oxide, stereoisomer, or pharmaceutically acceptable salt thereof, wherein R$^4$ is halogen, —OR$^7$, C$_{1-6}$haloalkyl, C$_{2-9}$heterocycloalkyl, C$_{6-10}$aryl, or C$_{1-6}$heteroaryl, wherein C$_{2-9}$heterocycloalkyl, C$_{6-10}$-aryl, or C$_{1-9}$heteroaryl are optionally substituted with 1 or 2 R$^{14}$. In another embodiment is a compound of Formula (I) or (I'), or a solvate, hydrate, tautomer, N-oxide, stereoisomer, or pharmaceutically acceptable salt thereof, wherein R$^4$ is halogen. In another embodiment is a compound of Formula (I) or (I'), or a solvate, hydrate, tautomer, N-oxide, stereoisomer, or pharmaceutically acceptable salt thereof, wherein R$^4$ is —Cl. In another embodiment is a compound of Formula (I) or (I'), or a solvate, hydrate, tautomer, N-oxide, stereoisomer, or pharmaceutically acceptable salt thereof, wherein R$^4$ is C$_{1-6}$haloalkyl. In another embodiment is a compound of Formula (I) or (I'), or a solvate, hydrate, tautomer, N-oxide, stereoisomer, or pharmaceutically acceptable salt thereof, wherein R$^4$ is —CF$_3$. In another embodiment is a compound of Formula (I) or (I'), or a solvate, hydrate, tautomer, N-oxide, stereoisomer, or pharmaceutically acceptable salt thereof, wherein R$^4$ is —OR$^7$. In another embodiment is a compound of Formula (I) or (I'), or a solvate, hydrate, tautomer, N-oxide, stereoisomer, or pharmaceutically acceptable salt thereof, wherein R$^7$ is C$_{1-6}$haloalkyl, C$_{6-10}$aryl, or C$_{1-9}$heteroaryl, wherein C$_{6-10}$aryl or C$_{1-9}$heteroaryl are optionally substituted with 1 or 2 R$^{14}$. In another embodiment is a compound of Formula (I) or (I'), or a solvate, hydrate, tautomer, N-oxide, stereoisomer, or pharmaceutically acceptable salt thereof, wherein R$^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (I) or (I'), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (I) or (I'), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (I) or (I'), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (I) or (I'), or a solvate, hydrate, tautomer, N-oxide, stereoisomer, or pharmaceutically acceptable salt thereof, wherein $R^4$ is

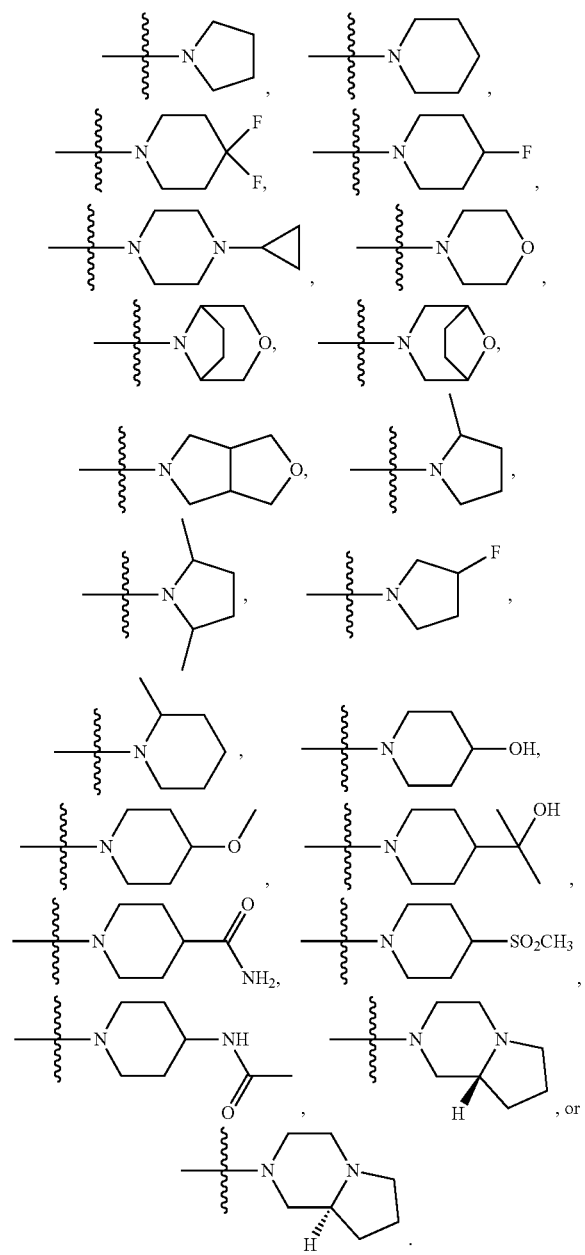

In another embodiment is a compound of Formula (I) or (I'), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^4$. In another embodiment is a compound of Formula (I) or (I'), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (I) or (I'), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (I) or (I'), or a solvate, hydrate, tautomer, N-oxide, stereoisomer, or pharmaceutically acceptable salt thereof, wherein $R^4$ is

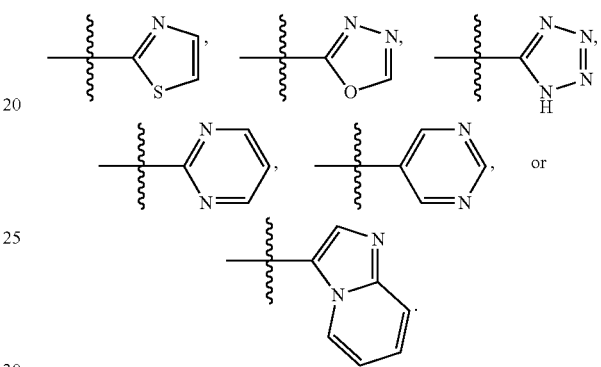

In another embodiment is a compound of Formula (I) or (I'), or a solvate, hydrate, tautomer, N-oxide, stereoisomer, or pharmaceutically acceptable salt thereof, wherein $R^5$ is H, halogen, $C_{1-6}$ alkyl, $C_{1-6}$haloalkyl, or $C_{1-6}$haloalkoxy. In another embodiment is a compound of Formula (I) or (I'), or a solvate, hydrate, tautomer, N-oxide, stereoisomer, or pharmaceutically acceptable salt thereof, wherein $R^5$ is H. In another embodiment is a compound of Formula (I) or (I'), or a solvate, hydrate, tautomer, N-oxide, stereoisomer, or pharmaceutically acceptable salt thereof, wherein $R^5$ is halogen. In another embodiment is a compound of Formula (I) or (I'), or a solvate, hydrate, tautomer, N-oxide, stereoisomer, or pharmaceutically acceptable salt thereof, wherein $R^5$ is —Cl. In another embodiment is a compound of Formula (I) or (I'), or a solvate, hydrate, tautomer, N-oxide, stereoisomer, or pharmaceutically acceptable salt thereof, wherein $R^5$ is $C_{1-6}$haloalkyl. In another embodiment is a compound of Formula (I) or (I'), or a solvate, hydrate, tautomer, N-oxide, stereoisomer, or pharmaceutically acceptable salt thereof, wherein $R^5$ is —$CF_3$. In another embodiment is a compound of Formula (I) or (I'), or a solvate, hydrate, tautomer, N-oxide, stereoisomer, or pharmaceutically acceptable salt thereof, wherein $R^2$ is H. In another embodiment is a compound of Formula (I) or (I'), or a solvate, hydrate, tautomer, N-oxide, stereoisomer, or pharmaceutically acceptable salt thereof, wherein $R^2$ is halogen. In another embodiment is a compound of Formula (I) or (I'), or a solvate, hydrate, tautomer, N-oxide, stereoisomer, or pharmaceutically acceptable salt thereof, wherein $R^2$ is $C_{1-6}$alkyl. In another embodiment is a compound of Formula (I) or (I'), or a solvate, hydrate, tautomer, N-oxide, stereoisomer, or pharmaceutically acceptable salt thereof, wherein $R^1$ is —C(O)O$R^{15}$. In another embodiment is a compound of Formula (I) or (I'), or a solvate, hydrate, tautomer, N-oxide, stereoisomer, or pharmaceutically acceptable salt thereof, wherein $R^{15}$ is H. In another embodiment is a compound of Formula (I) or (I'), or a solvate, hydrate, tautomer, N-oxide, stereoisomer, or pharmaceutically acceptable salt thereof, wherein $R^1$ is —C(O)$NR^{10}R^{11}$. In another embodiment is a compound of Formula (I) or (I'), or a solvate, hydrate, tautomer, N-oxide, stereoisomer, or pharmaceutically acceptable salt thereof, wherein $R^{10}$ and $R^{11}$ are each H.

In another embodiment is a pharmaceutical composition comprising a compound of Formula (I) or (I') described herein, or a solvate, hydrate, tautomer, N-oxide, or a pharmaceutically acceptable salt thereof, and at least one pharmaceutically acceptable excipient.

In another embodiment is a method of treating pain in a patient in need thereof, comprising administering to the patient a therapeutically effective amount of a compound of Formula (I) or (I') described herein, or a solvate, hydrate, tautomer, N-oxide, or a pharmaceutically acceptable salt thereof. In another embodiment is a method of treating chronic pain in a patient in need thereof, comprising administering to the patient a therapeutically effective amount of a compound of Formula (I) or (I') described herein, or a solvate, hydrate, tautomer, N-oxide, or a pharmaceutically acceptable salt thereof. In another embodiment is a method of treating inflammatory pain in a patient in need thereof, comprising administering to the patient a therapeutically effective amount of a compound of Formula (I) or (I') described herein, or a solvate, hydrate, tautomer, N-oxide, or a pharmaceutically acceptable salt thereof.

In another embodiment is a method of treating migraine in a patient in need thereof, comprising administering to the patient a therapeutically effective amount of a compound of Formula (I) or (I') described herein, or a solvate, hydrate, tautomer, N-oxide, or a pharmaceutically acceptable salt thereof.

In another embodiment is a method of treating scleroderma in a patient in need thereof comprising administering a therapeutically effective amount of a compound of Formula (I) or (I') herein, or a solvate, hydrate, tautomer, N-oxide, or a pharmaceutically acceptable salt thereof.

In another embodiment is a method of treating nonalcoholic fatty liver disease (NASH) in a patient in need thereof comprising administering a therapeutically effective amount of a compound of Formula (I) or (I') described herein, or a solvate, hydrate, tautomer, N-oxide, or a pharmaceutically acceptable salt thereof.

DETAILED DESCRIPTION OF THE INVENTION

This disclosure is directed, at least in part, to modulators or inhibitors of MAGL. For example, provided herein are compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$SR^a$, —OC(O)—$R^f$, —N$(R^a)_2$, —C(O)$R^a$, —C(O)O$R^a$, —C(O)N$(R^a)_2$, —N$(R^a)$C(O)O$R^f$, —OC(O)—NR$^a$R$^f$, —N$(R^a)$C(O)$R^f$, —N$(R^a)$S(O)$_t$R$^f$ (where t is 1 or 2), —S(O)$_t$O$R^a$ (where t is 1 or 2), —S(O)$_t$R$^f$ (where t is 1 or 2) and —S(O)$_t$N$(R^a)_2$ (where t is 1 or 2) where each IV is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkoxy" refers to a radical bonded through an oxygen atom of the formula O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$SR^a$, —OC(O)—$R^f$, —$N(R^a)_2$, —C(O)$R^a$, —C(O)O$R^a$, —C(O)N$(R^a)_2$, —N$(R^a)$C(O)O$R^f$, —OC(O)—NR$^a$R$^f$, —N$(R^a)$C(O)$R^f$, —N$(R^a)$S(O)$_t$R$^f$ (where t is 1 or 2), —S(O)$_t$OR$^a$ (where t is 1 or 2), —S(O)$_t$R$^f$ (where t is 1 or 2) and —S(O)$_t$N$(R^a)_2$ (where t is 1 or 2) where each IV is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OC(O)—$R^f$, —$N(R^a)_2$, —C(O)$R^a$, —C(O)O$R^a$, —C(O)N$(R^a)_2$, —N$(R^a)$C(O)O$R^f$, —OC(O)—NR$^a$R$^f$, —N$(R^a)$C(O)$R^f$, —N$(R^a)$S(O)$_t$R$^f$ (where t is 1 or 2), —S(O)$_t$OR$^a$ (where t is 1 or 2), —S(O)$_t$R$^f$ (where t is 1 or 2) and —S(O)$_t$N$(R^a)_2$ (where t is 1 or 2) where each IV is independently hydrogen, alkyl, haloalkyl, cycloalkyl, aryl, aralkyl, heterocycloalkyl, heteroaryl or heteroarylalkyl, and each R$^f$ is independently alkyl, haloalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—O$R^a$, —$R^b$—OC(O)—$R^a$, —$R^b$—OC(O)—O$R^a$, —$R^b$—OC(O)—N$(R^a)_2$, —$R^b$—N$(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N$(R^a)$C(O)O$R^a$, —$R^b$—N$(R^a)$C(O)$R^a$, —$R^b$—N$(R^a)$S(O)$_t$R$^a$ (where t is 1 or 2), —$R^b$—S(O)$_t$OR$^a$ (where t is 1 or 2), —$R^b$—S(O)$_t$R$^a$ (where t is 1 or 2) and —$R^b$—S(O)$_t$N$(R^a)_2$ (where t is 1 or 2), where each R$^a$ is independently hydrogen, alkyl, haloalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Aryloxy" refers to a radical bonded through an oxygen atom of the formula O-aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula O-aralkyl, where aralkyl is as defined above.

"Aralkenyl" refers to a radical of the formula R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—OC(O)—$R^a$, —$R^b$—OC(O)—O$R^a$, —$R^b$—OC(O)—N$(R^a)_2$, —$R^b$—N$(R^a)_2$, —$R^b$—C(O)$R^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each IV is independently hydrogen, alkyl, haloalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each IV is independently hydrogen, alkyl, haloalkyl, cycloalkyl, cycloalkylalkyl, aryl, aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula O-heteroaryl, where heteroaryl is as defined above.

"Heteroarylalkyl" refers to a radical of the formula R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

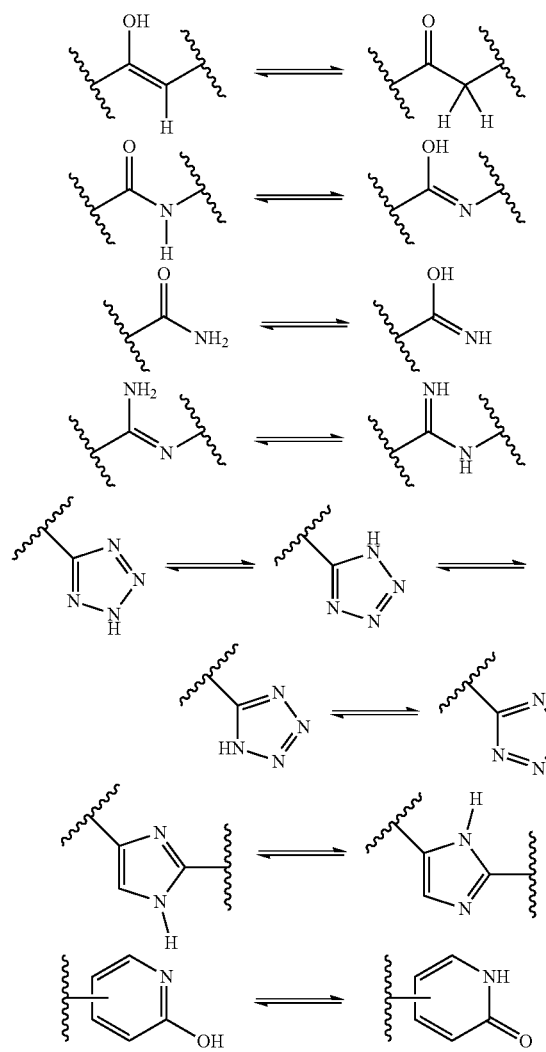

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (I'), (Ia), (Ib), (Ic), (Id), (Ie), (If), (Ig), (Ih), or (Ii) described herein which are modulators of MAGL. In some embodiments, the compounds are inhibitors of MAGL. In some embodiments, the compounds of Formula (I), (I'), (Ia), (Ib), (Ic), (Id), (Ie), (If), (Ig), (Ih), or (Ii) described herein, and compositions comprising these compounds, are useful for the treatment of pain, migraine, scleroderma, or nonalcoholic fatty liver disease (NASH).

In some embodiments is a compound of Formula (I):

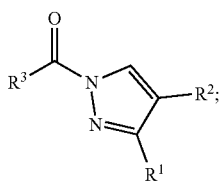

Formula (I)

wherein:

$R^1$ is —C(O)OR$^{15}$ or —C(O)NR$^{10}$R$^{11}$;

$R^2$ is H, halogen, $C_{1-6}$alkyl, or $C_{1-6}$haloalkyl;

$R^3$ is

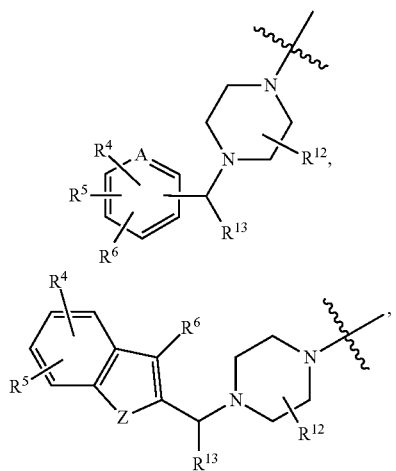

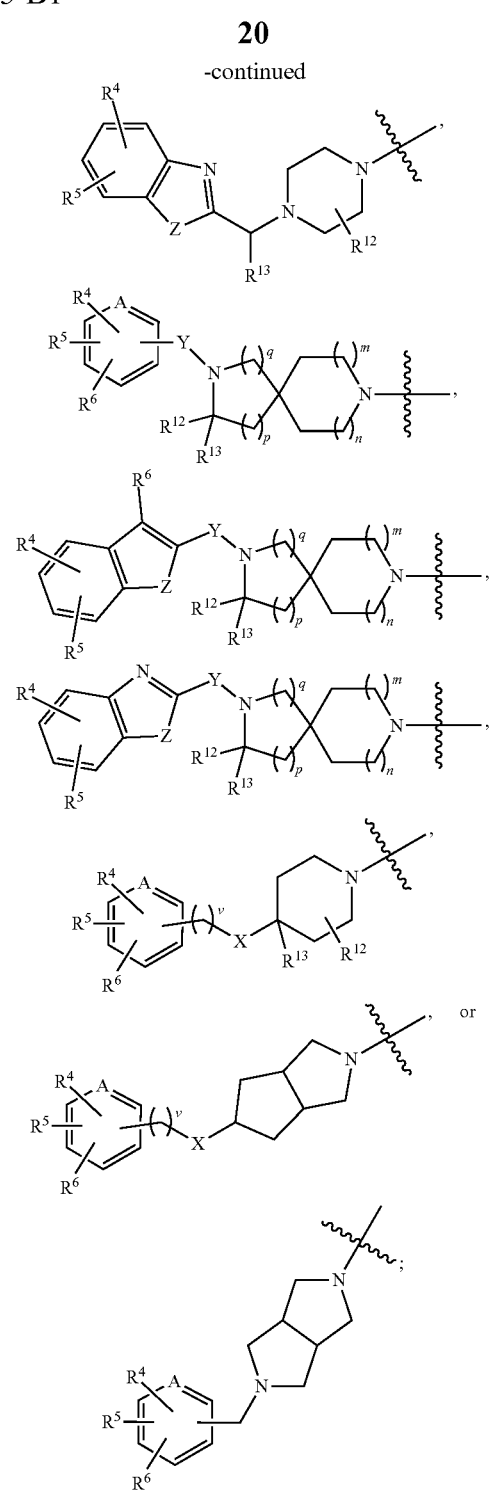

A is N or C(H);
X is —O—, —N(R$^{16}$)—, or —CH$_2$N(R$^{16}$)CH$_2$—;
Y is —CH$_2$— or —C(O)—;
Z is —S—, —O—, or —N(R$^{18}$)—;
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{3-8}$cycloalkyl, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{3-8}$cycloalkyl, $C_{2-9}$heterocycloalkyl, —C$_{1-6}$alkyl-C$_{2-9}$heterocycloalkyl, $C_{6-10}$aryl, or $C_{1-9}$heteroaryl are optionally substituted with 1 or 2 R$^{14}$;

$R^5$ is H, halogen, $C_{1-6}$alkyl, $C_{1-6}$haloalkyl, $C_{1-6}$haloalkoxy, or phenyl;

$R^6$ is H, halogen or $C_{1-6}$alkyl;

$R^7$ is H, $C_{1-6}$alkyl, $C_{1-6}$haloalkyl, —$C_{1-6}$alkyl-OH, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)OH, —C(O)NR$^8$R$^9$, —SO$_2$—$C_{1-6}$alkyl, and —N(R$^{17}$)C(O)—$C_{1-6}$alkyl;

$R^{15}$ is H or $C_{1-6}$alkyl;

$R^{16}$ is H, $C_{1-6}$alkyl, —C(O)—$C_{1-6}$alkyl, —$C_{1-6}$alkyl-OH, or —CH$_2$CO$_2$H;

$R^{17}$ is H or $C_{1-6}$alkyl;

$R^{18}$ is H or $C_{1-6}$alkyl;

v is 0 or 1;

n is 0 or 1;

m is 0 or 1;

p is 0, 1, or 2; and q is 0, 1 or 2;

or a solvate, hydrate, tautomer, N-oxide, stereoisomer, or pharmaceutically acceptable salt thereof.

In another embodiment is a compound of Formula (I), wherein $R^1$ is —C(O)OR$^{15}$. In another embodiment is a compound of Formula (I), wherein $R^1$ is —C(O)OR$^{15}$ and $R^{15}$ is H. In another embodiment is a compound of Formula (I), wherein $R^1$ is —C(O)OR$^{15}$ and $R^{15}$ is $C_{1-6}$alkyl. In another embodiment is a compound of Formula (I), wherein $R^1$ is —C(O)OR$^{15}$ and $R^{15}$ is —CH$_3$. In another embodiment is a compound of Formula (I), wherein $R^1$ is —C(O)NR$^{10}$R$^{11}$. In another embodiment is a compound of Formula (I), wherein $R^1$ is —C(O)NR$^{10}$R$^{11}$, $R^{10}$ is H, and $R^{11}$ is H. In another embodiment is a compound of Formula (I), wherein $R^1$ is —C(O)NR$^{10}$R$^{11}$, $R^{10}$ is H, and $R^{11}$ is $C_{1-6}$ alkyl. In another embodiment is a compound of Formula (I), wherein $R^1$ is —C(O)NR$^{10}$R$^{11}$, $R^{10}$ is H, and $R^{11}$ is —CH$_3$. In another embodiment is a compound of Formula (I), wherein $R^1$ is —C(O)NR$^{10}$R$^{11}$, $R^{10}$ is $C_{1-6}$ alkyl, and $R^{11}$ is $C_{1-6}$alkyl. In another embodiment is a compound of Formula (I), wherein $R^1$ is —C(O)NR$^{10}$R$^{11}$, $R^{10}$ is —CH$_3$, and $R^{11}$ is —CH$_3$.

In another embodiment is a compound of Formula (I), wherein $R^2$ is H. In another embodiment is a compound of Formula (I), wherein $R^2$ is halogen. In another embodiment is a compound of Formula (I), wherein $R^2$ is —Cl. In another embodiment is a compound of Formula (I), wherein $R^2$ is $C_{1-6}$alkyl. In another embodiment is a compound of Formula (I), wherein $R^2$ is —CH$_3$. In another embodiment is a compound of Formula (I), wherein $R^2$ is $C_{1-6}$haloalkyl. In another embodiment is a compound of Formula (I), wherein $R^2$ is —CF$_3$.

In another embodiment is a compound of Formula (I), wherein $R^3$ is

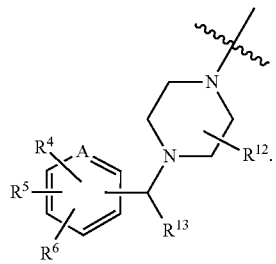

In another embodiment is a compound of Formula (I), wherein $R^3$ is

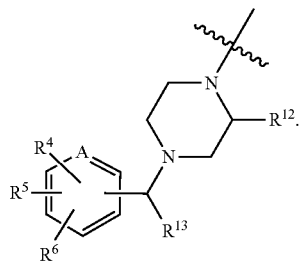

In another embodiment is a compound of Formula (I), wherein $R^3$ is

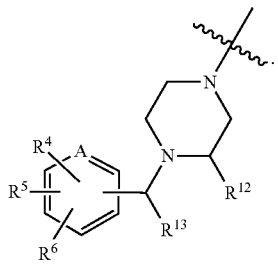

In another embodiment is a compound of Formula (I), wherein A is N. In another embodiment is a compound of Formula (I), wherein A is C(H). In another embodiment is a compound of Formula (I), wherein $R^3$ is

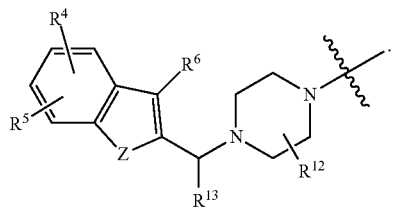

In another embodiment is a compound of Formula (I), wherein $R^3$ is

In another embodiment is a compound of Formula (I), wherein R³ is

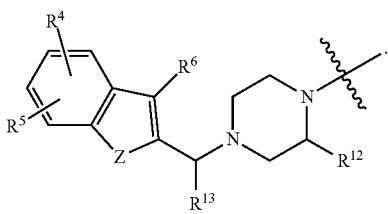

In another embodiment is a compound of Formula (I), wherein R³ is

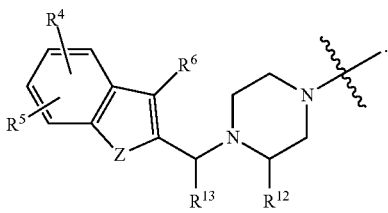

In another embodiment is a compound of Formula (I), wherein R³ is

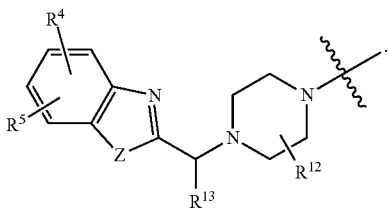

In another embodiment is a compound of Formula (I), wherein R³ is

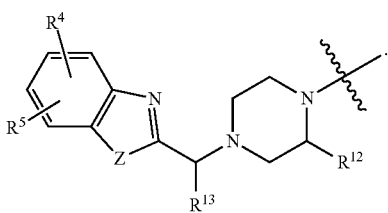

In another embodiment is a compound of Formula (I), wherein R³ is

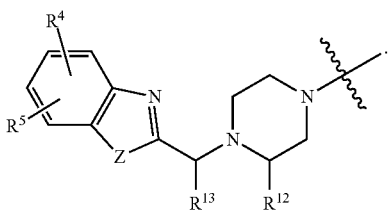

In another embodiment is a compound of Formula (I), wherein Z is —S—. In another embodiment is a compound of Formula (I), wherein Z is —O—. In another embodiment is a compound of Formula (I), wherein Z is —N($R^{18}$)—. In another embodiment is a compound of Formula (I), wherein Z is —N(H)—. In another embodiment is a compound of Formula (I), wherein Z is —N($CH_3$)—. In another embodiment is a compound of Formula (I), wherein $R^{12}$ is H and $R^3$ is H. In another embodiment is a compound of Formula (I), wherein $R^{12}$ is $C_{1-6}$ alkyl and $R^3$ is H. In another embodiment is a compound of Formula (I), wherein $R^{12}$ is —$CH_3$ and $R^{13}$ is H. In another embodiment is a compound of Formula (I), wherein $R^{12}$ is H and $R^3$ is $C_{1-6}$alkyl. In another embodiment is a compound of Formula (I), wherein $R^2$ is H and $R^3$ is —$CH_3$. In another embodiment is a compound of Formula (I), wherein $R^{12}$ is $C_{1-6}$alkyl and $R^{13}$ is $C_{1-6}$alkyl. In another embodiment is a compound of Formula (I), wherein $R^2$ is —$CH_3$ and $R^{13}$ is —$CH_3$.

In another embodiment is a compound of Formula (I), wherein R³ is

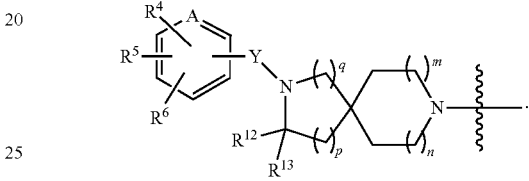

In another embodiment is a compound of Formula (I), wherein A is N. In another embodiment is a compound of Formula (I), wherein A is C(H). In another embodiment is a compound of Formula (I), wherein R³ is

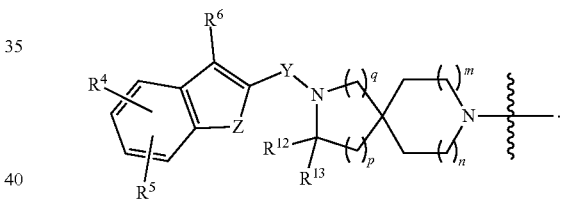

In another embodiment is a compound of Formula (I), wherein R³ is

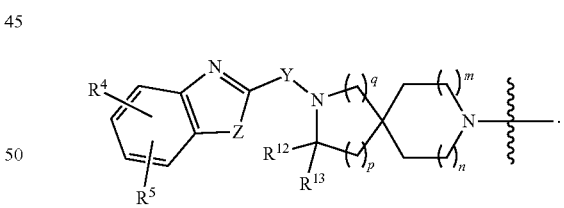

In another embodiment is a compound of Formula (I), wherein Z is —S—. In another embodiment is a compound of Formula (I), wherein Z is —O—. In another embodiment is a compound of Formula (I), wherein Z is —N($R^{18}$)—. In another embodiment is a compound of Formula (I), wherein Z is —N(H)—. In another embodiment is a compound of Formula (I), wherein Z is —N($CH_3$)—. In another embodiment is a compound of Formula (I), wherein Y is —$CH_2$—. In another embodiment is a compound of Formula (I), wherein Y is —C(O)—. In another embodiment is a compound of Formula (I), or a solvate, hydrate, tautomer, N-oxide, stereoisomer, or pharmaceutically acceptable salt thereof, wherein m is 1, n is 1, q is 1, and p is 1. In another embodiment is a compound of Formula (I), or a solvate, hydrate, tautomer, N-oxide, stereoisomer, or pharmaceutically acceptable salt thereof, wherein m is 0, n is 1, q is 2, and p is 1. In another embodiment is a compound of Formula (I), or a solvate, hydrate, tautomer, N-oxide, stereoisomer, or pharmaceutically acceptable salt thereof, wherein m is 1, n is 1, q is 0, and p is 2. In another embodiment is a compound of Formula (I), or a solvate, hydrate, tautomer, N-oxide, stereoisomer, or pharmaceutically acceptable salt thereof, wherein m is 1, n is 1, q is 1, and p is 0. In another embodiment is a compound of Formula (I), or a solvate, hydrate, tautomer, N-oxide, stereoisomer, or pharmaceutically acceptable salt thereof, wherein m is 0, n is 0, q is 2, and p is 1. In another embodiment is a compound of Formula (I), wherein $R^{12}$ is H and $R^{13}$ is H. In another embodiment is a compound of Formula (I), wherein $R^2$ is $C_{1-6}$alkyl and $R^3$ is H. In another embodiment is a compound of Formula (I), wherein $R^2$ is —$CH_3$ and $R^3$ is H. In another embodiment is a compound of Formula (I), wherein $R^{12}$ is H and $R^{13}$ is $C_{1-6}$alkyl. In another embodiment is a compound of Formula (I), wherein $R^{12}$ is H and $R^{13}$ is —$CH_3$. In another embodiment is a compound of Formula (I), wherein $R^2$ is $C_{1-6}$alkyl and $R^{13}$ is $C_{1-6}$alkyl. In another embodiment is a compound of Formula (I), wherein $R^2$ is —$CH_3$ and $R^3$ is —$CH_3$.

In another embodiment is a compound of Formula (I), wherein $R^3$ is

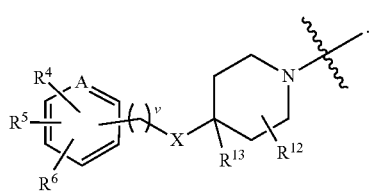

In another embodiment is a compound of Formula (I), wherein $R^{12}$ is H. In another embodiment is a compound of Formula (I), wherein $R^2$ is halogen. In another embodiment is a compound of Formula (I), wherein $R^{12}$ is F. In another embodiment is a compound of Formula (I), wherein $R^{12}$ is $C_{1-6}$alkyl. In another embodiment is a compound of Formula (I), wherein $R^{12}$ is —$CH_3$. In another embodiment is a compound of Formula (I), wherein $R^{12}$ is H and $R^3$ is H. In another embodiment is a compound of Formula (I), wherein $R^2$ is $C_{1-6}$alkyl and $R^3$ is H. In another embodiment is a compound of Formula (I), wherein $R^2$ is —$CH_3$ and $R^3$ is H. In another embodiment is a compound of Formula (I), wherein $R^{12}$ is H and $R^{13}$ is $C_{1-6}$alkyl. In another embodiment is a compound of Formula (I), wherein $R^{12}$ is H and $R^{13}$ is —$CH_3$. In another embodiment is a compound of Formula (I), wherein $R^2$ is $C_{1-6}$alkyl and $R^{13}$ is $C_{1-6}$alkyl. In another embodiment is a compound of Formula (I), wherein $R^2$ is —$CH_3$ and $R^3$ is —$CH_3$. In another embodiment is a compound of Formula (I), wherein $R^3$ is

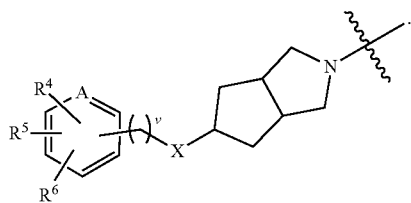

In another embodiment is a compound of Formula (I), wherein X is —O—. In another embodiment is a compound of Formula (I), wherein X is —N($R^{16}$)—. In another embodiment is a compound of Formula (I), wherein X is —N(H)—. In another embodiment is a compound of Formula (I), wherein X is —N($CH_3$)—. In another embodiment is a compound of Formula (I), wherein X is —N($R^{16}$)— and $R^6$ is —$C_{1-6}$ alkyl-OH. In another embodiment is a compound of Formula (I), wherein X is —$CH_2$N($R^{16}$)$CH_2$—. In another embodiment is a compound of Formula (I), wherein X is —$CH_2$N(H)$CH_2$—. In another embodiment is a compound of Formula (I), wherein X is —$CH_2$N($CH_3$)$CH_2$—. In another embodiment is a compound of Formula (I), wherein A is N. In another embodiment is a compound of Formula (I), wherein A is C(H). In another embodiment is a compound of Formula (I), wherein v is 0. In another embodiment is a compound of Formula (I), wherein v is 1. In another embodiment is a compound of Formula (I), wherein $R^3$ is

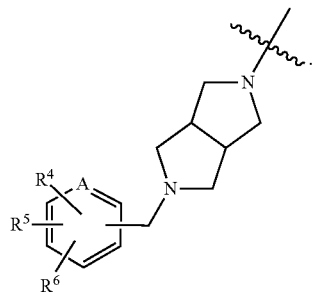

In another embodiment is a compound of Formula (I), or a solvate, hydrate, tautomer, N-oxide, stereoisomer, or pharmaceutically acceptable salt thereof, wherein $R^4$ is halogen, —$OR^7$, $C_{1-6}$alkyl, $C_{2-6}$ alkynyl, $C_{1-6}$haloalkyl, —C(O)$NR^8R^9$, $C_{3-8}$cycloalkyl, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen, —$OR^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen. In another embodiment is a compound of Formula (I), or a solvate, hydrate, tautomer, N-oxide, stereoisomer, or pharmaceutically acceptable salt thereof, wherein $R^4$ is —Cl. In another embodiment is a compound of Formula (I), or a solvate, hydrate, tautomer, N-oxide, stereoisomer, or pharmaceutically acceptable salt thereof, wherein $R^4$ is $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —$CF_3$. In another embodiment is a compound of Formula (I), or a solvate, hydrate, tautomer, N-oxide, stereoisomer, or pharmaceutically acceptable salt thereof, wherein $R^4$ is —$OR^7$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, —$C_{1-6}$alkyl-OH, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is —$C_{1-6}$ alkyl-OH. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (I), or a solvate, hydrate, tautomer, N-oxide, stereoisomer, or pharmaceutically acceptable salt thereof, wherein $R^4$ is $C_{3-8}$cycloalkyl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{3-8}$cycloalkyl. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is

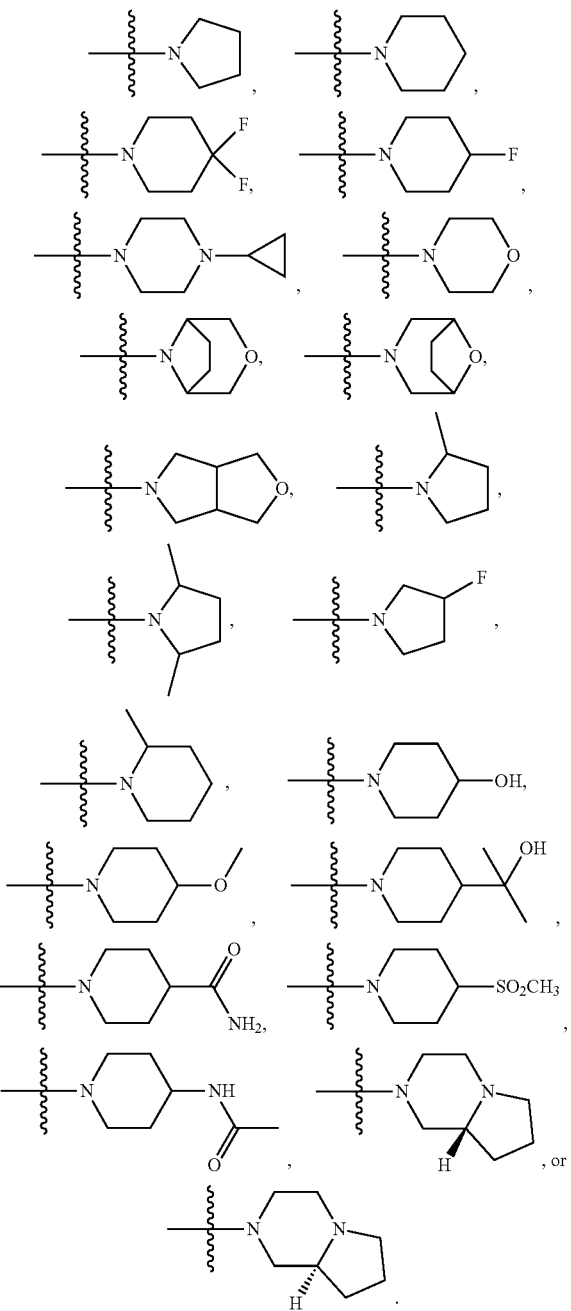

In another embodiment is a compound of Formula (I), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (I), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is

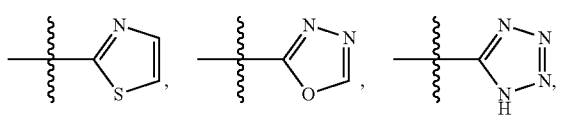

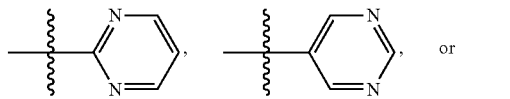

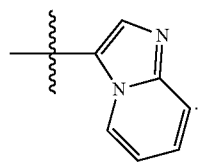

In another embodiment is a compound of Formula (I), wherein $R^5$ is H, halogen, $C_{1-6}$alkyl, $C_{1-6}$haloalkyl, $C_{1-6}$haloalkoxy. In another embodiment is a compound of Formula (I), wherein $R^5$ is H. In another embodiment is a compound of Formula (I), wherein $R^5$ is halogen. In another embodiment is a compound of Formula (I), wherein $R^5$ is —Cl. In another embodiment is a compound of Formula (I), wherein $R^5$ is —F. In another embodiment is a compound of Formula (I), wherein $R^5$ is $C_{1-6}$alkyl. In another embodiment is a compound of Formula (I), wherein $R^5$ is —CH$_3$. In another embodiment is a compound of Formula (I), wherein $R^5$ is $C_{1-6}$haloalkyl. In another embodiment is a compound of Formula (I), wherein $R^5$ is —CF$_3$. In another embodiment is a compound of Formula (I), wherein $R^5$ is $C_{1-6}$haloalkoxy. In another embodiment is a compound of Formula (I), wherein $R^5$ is —OCF$_3$.

In another embodiment is a compound of Formula (I), wherein $R^6$ is H. In another embodiment is a compound of Formula (I), wherein $R^6$ is halogen. In another embodiment is a compound of Formula (I), wherein $R^6$ is —Cl. In another embodiment is a compound of Formula (I), wherein $R^6$ is —F. In another embodiment is a compound of Formula (I), wherein $R^6$ is $C_{1-6}$alkyl. In another embodiment is a compound of Formula (I), wherein $R^6$ is —CH$_3$.

In some embodiments is a compound of Formula (I'):

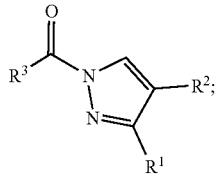

Formula (I')

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;

$R^3$ is

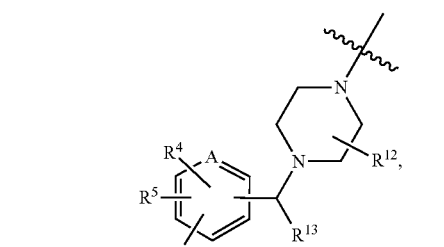

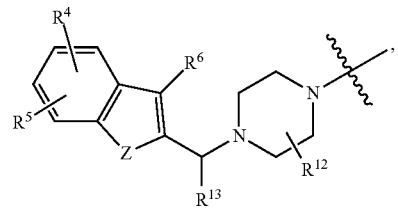

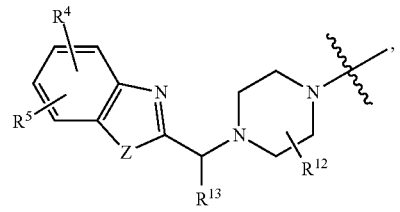

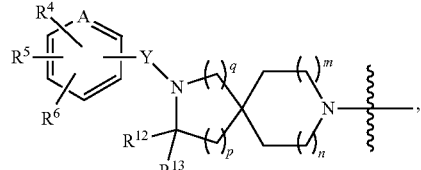

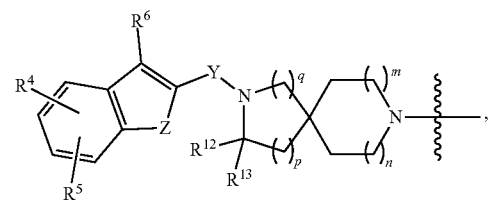

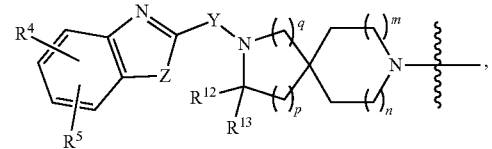

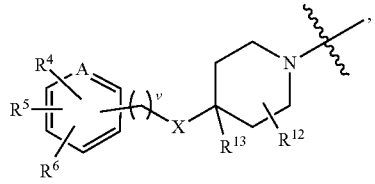

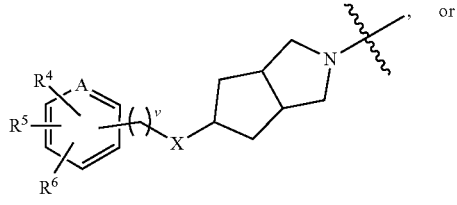

-continued

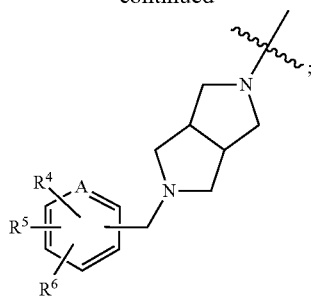

A is N or C(H);
X is —O—, —N(R$^{16}$)—, or —CH$_2$N(R$^{16}$)CH$_2$—;
Y is —CH$_2$— or —C(O)—;
Z is —S—, —O—, or —N(R$^{18}$)—;
R$^4$ is H, halogen, —OR$^7$, C$_{1-6}$alkyl, C$_{2-6}$alkenyl, C$_{2-6}$alkynyl, C$_{1-6}$haloalkyl, —C(O)NR$^8$R$^9$, C$_{2-9}$heterocycloalkyl, —C$_{1-6}$alkyl-C$_{2-9}$heterocycloalkyl, C$_{6-10}$aryl, or C$_{1-9}$heteroaryl, wherein C$_{2-9}$heterocycloalkyl, —C$_{1-6}$alkyl-C$_{2-9}$heterocycloalkyl, C$_{6-10}$aryl, or C$_{1-9}$heteroaryl are optionally substituted with 1 or 2 R$^4$;
R$^5$ is H, halogen, C$_{1-6}$alkyl, C$_{1-6}$haloalkyl, C$_{1-6}$haloalkoxy, or phenyl;
R$^6$ is H, halogen or C$_{1-6}$alkyl;
R$^7$ is H, C$_{1-6}$ alkyl, C$_{1-6}$haloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^{14}$;
each R$^8$ and each R$^9$ are independently selected from H and C$_{1-6}$alkyl; or R$^8$ and R$^9$ together with the nitrogen to which they are attached are combined to form a heterocycloalkyl ring;
R$^{10}$ and R$^{11}$ are each independently H or C$_{1-6}$ alkyl;
R$^{12}$ is H, halogen, or C$_{1-6}$alkyl;
R$^{13}$ is H or C$_{1-6}$alkyl;
each R$^{14}$ is independently selected from halogen, —OH, C$_{1-6}$ alkyl, C$_{1-6}$haloalkyl, C$_{1-6}$alkoxy, —C$_{1-6}$alkyl-OH, C$_{3-8}$ cycloalkyl, —C(O)NR$^8$R$^9$, —SO$_2$—C$_{1-6}$ alkyl, and —N(R$^{17}$)C(O)—C$_{1-6}$ alkyl;
R$^{15}$ is H or C$_{1-6}$alkyl;
R$^{16}$ is H, C$_{1-6}$alkyl, —C(O)—C$_{1-6}$alkyl, or —CH$_2$CO$_2$H;
R$^{17}$ is H or C$_{1-6}$alkyl;
R$^{18}$ is H or C$_{1-6}$alkyl;
v is 0 or 1;
n is 0 or 1;
m is 0 or 1;
p is 0, 1, or 2; and
q is 0, 1 or 2;
or a solvate, hydrate, tautomer, N-oxide, stereoisomer, or pharmaceutically acceptable salt thereof.

In another embodiment is a compound of Formula (I'), wherein R$^1$ is —C(O)OR$^{15}$. In another embodiment is a compound of Formula (I'), wherein R$^1$ is —C(O)OR$^{15}$ and R$^{15}$ is H. In another embodiment is a compound of Formula (I'), wherein R$^1$ is —C(O)OR$^{15}$ and R$^{15}$ is C$_{1-6}$alkyl. In another embodiment is a compound of Formula (I'), wherein R$^1$ is —C(O)OR$^{15}$ and R$^{15}$ is —CH$_3$. In another embodiment is a compound of Formula (I'), wherein R$^1$ is —C(O)NR$^{10}$R$^{11}$. In another embodiment is a compound of Formula (I'), wherein R$^1$ is —C(O)NR$^{10}$R$^{11}$, R$^{10}$ is H, and R$^{11}$ is H. In another embodiment is a compound of Formula (I'), wherein R$^1$ is —C(O)NR$^{10}$R$^{11}$ R$^{10}$ is H, and R$^{11}$ is C$_{1-6}$ alkyl. In another embodiment is a compound of Formula (I'), wherein R$^1$ is —C(O)NR$^{10}$R$^{11}$, R$^{10}$ is H, and R$^{11}$ is —CH$_3$. In another embodiment is a compound of Formula (I'), wherein R$^1$ is —C(O)NR$^{10}$R$^{11}$, is C$_{1-6}$ alkyl, and R$^{11}$ is C$_{1-6}$alkyl. In another embodiment is a compound of Formula (I'), wherein R$^1$ is —C(O)NR$^{10}$R$^{11}$, is —CH$_3$, and R$^{11}$ is —CH$_3$.

In another embodiment is a compound of Formula (I'), wherein R$^2$ is H. In another embodiment is a compound of Formula (I'), wherein R$^2$ is halogen. In another embodiment is a compound of Formula (I'), wherein R$^2$ is —Cl. In another embodiment is a compound of Formula (I'), wherein R$^2$ is C$_{1-6}$alkyl. In another embodiment is a compound of Formula (I'), wherein R$^2$ is —CH$_3$. In another embodiment is a compound of Formula (I'), wherein R$^2$ is C$_{1-6}$haloalkyl. In another embodiment is a compound of Formula (I'), wherein R$^2$ is —CF$_3$.

In another embodiment is a compound of Formula (I'), wherein R$^3$ is

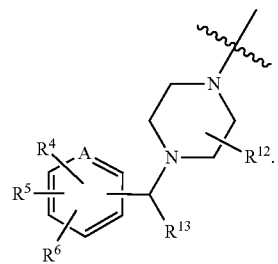

In another embodiment is a compound of Formula (I'), wherein R$^3$ is

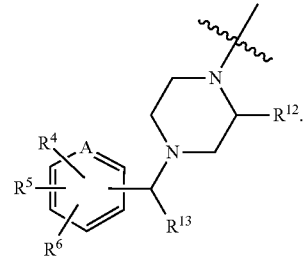

In another embodiment is a compound of Formula (I'), wherein R$^3$ is

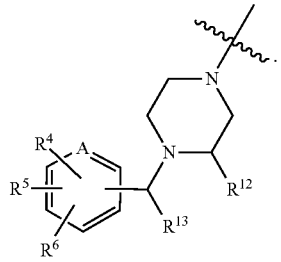

In another embodiment is a compound of Formula (I'), wherein A is N. In another embodiment is a compound of Formula (I'), wherein A is C(H). In another embodiment is a compound of Formula (I'), wherein R$^3$ is

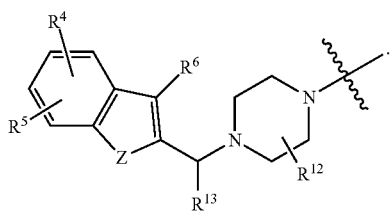

In another embodiment is a compound of Formula (I'), wherein R³ is

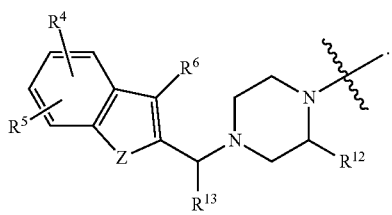

In another embodiment is a compound of Formula (I'), wherein R³ is

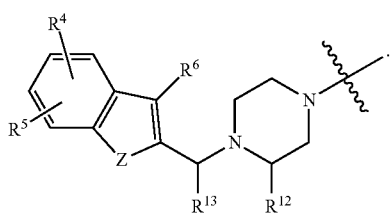

In another embodiment is a compound of Formula (I'), wherein R³ is

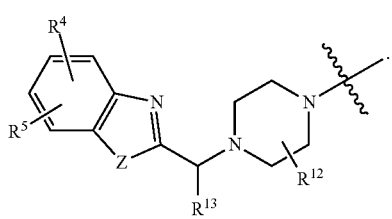

In another embodiment is a compound of Formula (I'), wherein R³ is

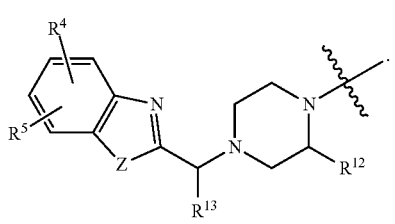

In another embodiment is a compound of Formula (I'), wherein R³ is

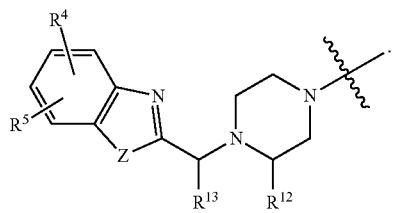

In another embodiment is a compound of Formula (I'), wherein Z is —S—. In another embodiment is a compound of Formula (I'), wherein Z is —O—. In another embodiment is a compound of Formula (I'), wherein Z is —N(R$^{18}$)—. In another embodiment is a compound of Formula (I'), wherein Z is —N(H)—. In another embodiment is a compound of Formula (I'), wherein Z is —N(CH$_3$)—. In another embodiment is a compound of Formula (I'), wherein R$^{12}$ is H and R³ is H. In another embodiment is a compound of Formula (I'), wherein R² is C$_{1-6}$ alkyl and R$^{13}$ is H. In another embodiment is a compound of Formula (I'), wherein R² is —CH$_3$ and R³ is H. In another embodiment is a compound of Formula (I'), wherein R$^{12}$ is H and R$^{13}$ is C$_{1-6}$alkyl. In another embodiment is a compound of Formula (I'), wherein R$^{12}$ is H and R$^{13}$ is —CH$_3$. In another embodiment is a compound of Formula (I'), wherein R$^{12}$ is C$_{1-6}$alkyl and R³ is C$_{1-6}$alkyl. In another embodiment is a compound of Formula (I'), wherein R$^{12}$ is —CH$_3$ and R$^{13}$ is —CH$_3$.

In another embodiment is a compound of Formula (I'), wherein R³ is

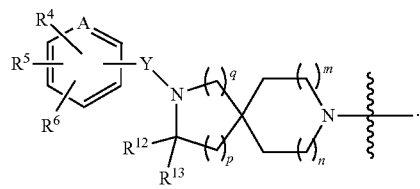

In another embodiment is a compound of Formula (I'), wherein A is N. In another embodiment is a compound of Formula (I'), wherein A is C(H). In another embodiment is a compound of Formula (I'), wherein R³ is

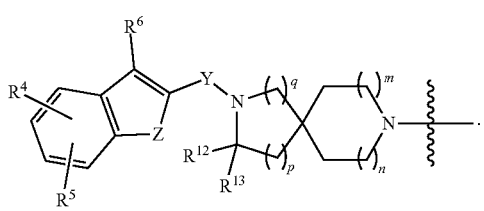

In another embodiment is a compound of Formula (I'), wherein R³ is

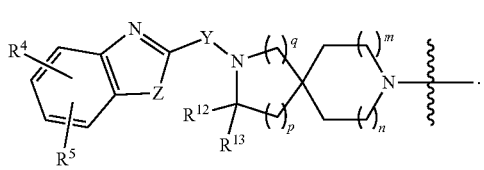

In another embodiment is a compound of Formula (I'), wherein Z is —S—. In another embodiment is a compound of Formula (I'), wherein Z is —O—. In another embodiment is a compound of Formula (I'), wherein Z is —N(R$^{18}$)—. In another embodiment is a compound of Formula (I'), wherein Z is —N(H)—. In another embodiment is a compound of Formula (I'), wherein Z is —N(CH$_3$)—. In another embodiment is a compound of Formula (I'), wherein Y is —CH$_2$—. In another embodiment is a compound of Formula (I'), wherein Y is —C(O)—. In another embodiment is a compound of Formula (I'), or a solvate, hydrate, tautomer, N-oxide, stereoisomer, or pharmaceutically acceptable salt thereof, wherein m is 1, n is 1, q is 1, and p is 1. In another embodiment is a compound of Formula (I'), or a solvate, hydrate, tautomer, N-oxide, stereoisomer, or pharmaceutically acceptable salt thereof, wherein m is 0, n is 1, q is 2, and p is 1. In another embodiment is a compound of Formula (I'), or a solvate, hydrate, tautomer, N-oxide, stereoisomer, or pharmaceutically acceptable salt thereof, wherein m is 1, n is 1, q is 0, and p is 2. In another embodiment is a compound of Formula (I'), or a solvate, hydrate, tautomer, N-oxide, stereoisomer, or pharmaceutically acceptable salt thereof, wherein m is 1, n is 1, q is 1, and p is 0. In another embodiment is a compound of Formula (I'), or a solvate, hydrate, tautomer, N-oxide, stereoisomer, or pharmaceutically acceptable salt thereof, wherein m is 0, n is 0, q is 2, and p is 1. In another embodiment is a compound of Formula (I'), wherein R$^{12}$ is H and R$^{13}$ is H. In another embodiment is a compound of Formula (I'), wherein R$^2$ is C$_{1-6}$alkyl and R$^{13}$ is H. In another embodiment is a compound of Formula (I'), wherein R$^2$ is —CH$_3$ and R$^3$ is H. In another embodiment is a compound of Formula (I'), wherein R$^{12}$ is H and R$^3$ is C$_{1-6}$alkyl. In another embodiment is a compound of Formula (I'), wherein R$^{12}$ is H and R$^3$ is —CH$_3$. In another embodiment is a compound of Formula (I'), wherein R$^{12}$ is C$_{1-6}$alkyl and R$^3$ is C$_{1-6}$alkyl. In another embodiment is a compound of Formula (I'), wherein R$^{12}$ is —CH$_3$ and R$^{13}$ is —CH$_3$.

In another embodiment is a compound of Formula (I'), wherein R$^3$ is

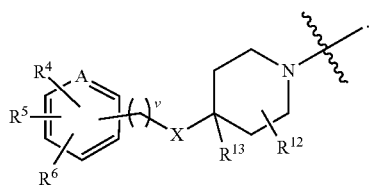

In another embodiment is a compound of Formula (I'), wherein R$^{12}$ is H. In another embodiment is a compound of Formula (I'), wherein R$^{12}$ is halogen. In another embodiment is a compound of Formula (I'), wherein R$^{12}$ is F. In another embodiment is a compound of Formula (I'), wherein R$^2$ is C$_{1-6}$alkyl. In another embodiment is a compound of Formula (I'), wherein R$^2$ is —CH$_3$. In another embodiment is a compound of Formula (I'), wherein R$^{12}$ is H and R$^3$ is H. In another embodiment is a compound of Formula (I'), wherein R$^{12}$ is C$_{1-6}$alkyl and R$^3$ is H. In another embodiment is a compound of Formula (I'), wherein R$^2$ is —CH$_3$ and R$^{13}$ is H. In another embodiment is a compound of Formula (I'), wherein R$^{12}$ is H and R$^{13}$ is C$_{1-6}$alkyl. In another embodiment is a compound of Formula (I'), wherein R$^{12}$ is H and R$^3$ is —CH$_3$. In another embodiment is a compound of Formula (I'), wherein R$^{12}$ is C$_{1-6}$alkyl and R$^{13}$ is C$_{1-6}$alkyl.

In another embodiment is a compound of Formula (I'), wherein R$^{12}$ is —CH$_3$ and R$^{13}$ is —CH$_3$. In another embodiment is a compound of Formula (I'), wherein R$^3$ is

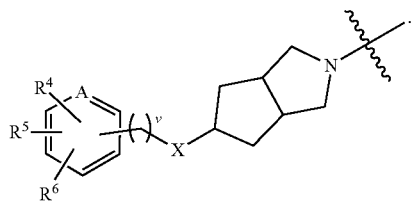

In another embodiment is a compound of Formula (I'), wherein X is —O—. In another embodiment is a compound of Formula (I'), wherein X is —N(R$^{16}$)—. In another embodiment is a compound of Formula (I'), wherein X is —N(H)—. In another embodiment is a compound of Formula (I'), wherein X is —N(CH$_3$)—. In another embodiment is a compound of Formula (I'), wherein X is —CH$_2$N(R$^{16}$)CH$_2$—. In another embodiment is a compound of Formula (I'), wherein X is —CH$_2$N(H)CH$_2$—. In another embodiment is a compound of Formula (I'), wherein X is —CH$_2$N(CH$_3$)CH$_2$—. In another embodiment is a compound of Formula (I'), wherein A is N. In another embodiment is a compound of Formula (I'), wherein A is C(H). In another embodiment is a compound of Formula (I'), wherein v is 0. In another embodiment is a compound of Formula (I'), wherein v is 1. In another embodiment is a compound of Formula (I'), wherein R$^3$ is

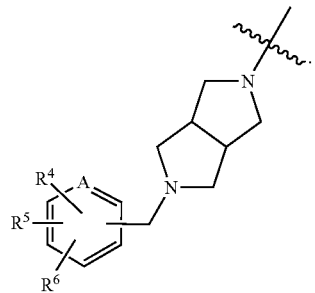

In another embodiment is a compound of Formula (I'), or a solvate, hydrate, tautomer, N-oxide, stereoisomer, or pharmaceutically acceptable salt thereof, wherein R$^4$ is halogen, —OR$^7$, C$_{1-6}$alkyl, C$_{2-6}$ alkynyl, C$_{1-6}$haloalkyl, —C(O)NR$^8$R$^9$, C$_{2-9}$heterocycloalkyl, C$_{6-10}$aryl, or C$_{1-9}$heteroaryl, wherein C$_{2-9}$heterocycloalkyl, —C$_{1-6}$alkyl-C$_{2-9}$heterocycloalkyl, C$_{6-10}$aryl, or C$_{1-9}$heteroaryl are optionally substituted with 1 or 2 R$^{14}$. In another embodiment is a compound of Formula (I'), or a solvate, hydrate, tautomer, N-oxide, stereoisomer, or pharmaceutically acceptable salt thereof, wherein R$^4$ is halogen, —OR$^7$, C$_{1-6}$haloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^4$. In another embodiment is a compound of Formula (I'), or a solvate, hydrate, tautomer, N-oxide, stereoisomer, or pharmaceutically acceptable salt thereof, wherein R$^4$ is halogen. In another embodiment is a compound of Formula (I'), or a solvate, hydrate, tautomer, N-oxide, stereoisomer, or pharmaceutically acceptable salt thereof, wherein R$^4$ is —Cl. In another embodiment is a compound of Formula (I'), or a solvate, hydrate, tautomer, N-oxide, stereoisomer, or pharmaceutically acceptable salt thereof, wherein $R^4$ is $C_{1-6}$haloalkyl. In another embodiment is a compound of Formula (I'), or a solvate, hydrate, tautomer, N-oxide, stereoisomer, or pharmaceutically acceptable salt thereof, wherein $R^4$ is —$CF_3$. In another embodiment is a compound of Formula (I'), or a solvate, hydrate, tautomer, N-oxide, stereoisomer, or pharmaceutically acceptable salt thereof, wherein $R^4$ is —$OR^7$. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (I'), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (I'), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (I'), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (I'), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (I'), or a solvate, hydrate, tautomer, N-oxide, stereoisomer, or pharmaceutically acceptable salt thereof, wherein $R^4$ is

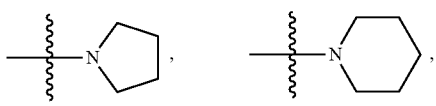

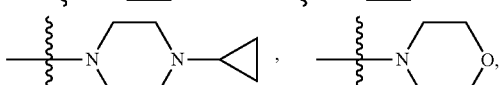

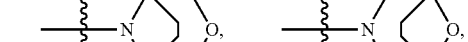


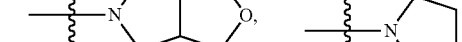

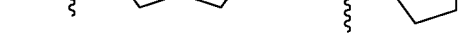

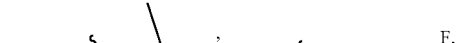

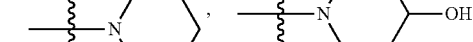

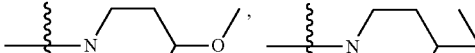

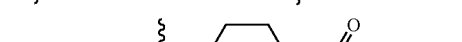

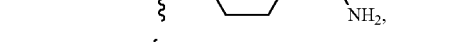

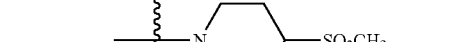

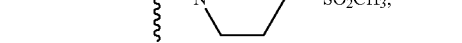

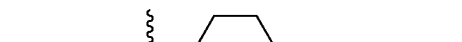

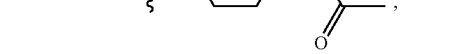

In another embodiment is a compound of Formula (I'), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (I'), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (I'), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (I'), or a solvate, hydrate, tautomer, N-oxide, stereoisomer, or pharmaceutically acceptable salt thereof, wherein $R^4$ is

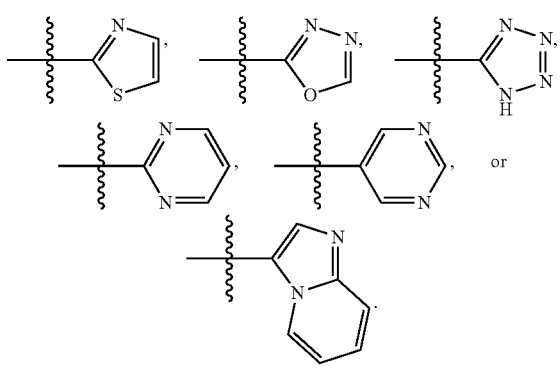

In another embodiment is a compound of Formula (I'), wherein $R^5$ is H, halogen, $C_{1-6}$alkyl, $C_{1-6}$haloalkyl, $C_{1-6}$haloalkoxy. In another embodiment is a compound of Formula (I'), wherein $R^5$ is H. In another embodiment is a compound of Formula (I'), wherein $R^5$ is halogen. In another embodiment is a compound of Formula (I'), wherein $R^5$ is —Cl. In another embodiment is a compound of Formula (I'), wherein $R^5$ is —F. In another embodiment is a compound of Formula (I'), wherein $R^5$ is $C_{1-6}$alkyl. In another embodiment is a compound of Formula (I'), wherein $R^5$ is —CH$_3$. In another embodiment is a compound of Formula (I'), wherein $R^5$ is $C_{1-6}$haloalkyl. In another embodiment is a compound of Formula (I'), wherein $R^5$ is —CF$_3$. In another embodiment is a compound of Formula (I'), wherein $R^5$ is $C_{1-6}$haloalkoxy. In another embodiment is a compound of Formula (I'), wherein $R^5$ is —OCF$_3$.

In another embodiment is a compound of Formula (I'), wherein $R^6$ is H. In another embodiment is a compound of Formula (I'), wherein $R^6$ is halogen. In another embodiment is a compound of Formula (I'), wherein $R^6$ is —Cl. In another embodiment is a compound of Formula (I'), wherein $R^6$ is —F. In another embodiment is a compound of Formula (I'), wherein $R^6$ is $C_{1-6}$alkyl. In another embodiment is a compound of Formula (I'), wherein $R^6$ is —CH$_3$.

In another embodiment is a compound of Formula (I) having the structure of Formula (Ia):

Formula (Ia)

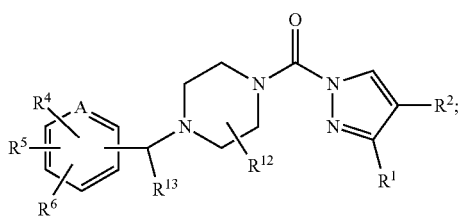

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;
A is N or C(H);
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —$C_{1-6}$alkyl-$C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 R$^{14}$;

$R^5$ is H, halogen, $C_{1-6}$alkyl, $C_{1-6}$haloalkyl, $C_{1-6}$haloalkoxy, or phenyl;
$R^6$ is H, halogen or $C_{1-6}$alkyl;
$R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 R$^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{10}$ and $R^{11}$ are each independently H or $C_{1-6}$ alkyl;
$R^{12}$ is H, halogen, or $C_{1-6}$alkyl;
$R^{13}$ is H or $C_{1-6}$alkyl;
each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)NR$^8$R$^9$, —SO$_2$—$C_{1-6}$ alkyl, and —N(R$^{17}$)C(O)—$C_{1-6}$ alkyl;
$R^{15}$ is H or $C_{1-6}$alkyl; and
$R^{17}$ is H or $C_{1-6}$alkyl;
or a solvate, hydrate, tautomer, N-oxide, stereoisomer, or pharmaceutically acceptable salt thereof.

In another embodiment is a compound of Formula (I), wherein $R^3$ is

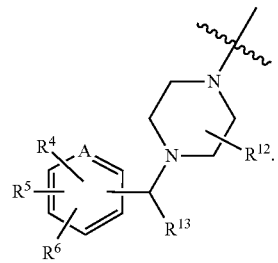

In another embodiment is a compound of Formula (I), wherein $R^3$ is

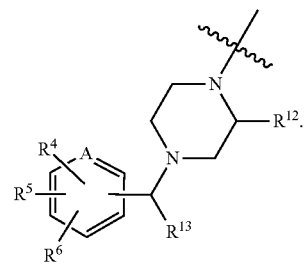

In another embodiment is a compound of Formula (I), wherein $R^3$ is

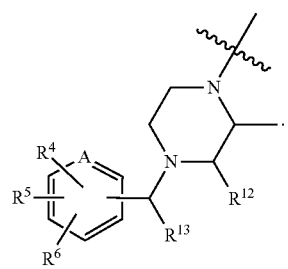

In another embodiment is a compound of Formula (Ia), wherein $R^1$ is —C(O)OR$^{15}$. In another embodiment is a compound of Formula (Ia), wherein $R^1$ is —C(O)OR$^{15}$ and $R^{15}$ is H. In another embodiment is a compound of Formula (Ia), wherein $R^1$ is —C(O)OR$^{15}$ and $R^{15}$ is $C_{1-6}$alkyl. In another embodiment is a compound of Formula (Ia), wherein $R^1$ is —C(O)OR$^{15}$ and $R^{15}$ is —CH$_3$. In another embodiment is a compound of Formula (Ia), wherein $R^1$ is —C(O)NR$^{10}$R$^{11}$. In another embodiment is a compound of Formula (Ia), wherein $R^1$ is —C(O)NR$^{10}$R$^{11}$, $R^{10}$ is H, and $R^{11}$ is H. In another embodiment is a compound of Formula (Ia), wherein $R^1$ is —C(O)NR$^1$ is H, and $R^{11}$ is $C_{1-6}$ alkyl. In another embodiment is a compound of Formula (Ia), wherein $R^1$ is —C(O)NR$^{10}$R$^{11}$, $R^{10}$ is H, and $R^{11}$ is —CH$_3$. In another embodiment is a compound of Formula (Ia), wherein $R^1$ is —C(O)NR$^{10}$R$^{11}$, is $C_{1-6}$ alkyl, and $R^{11}$ is $C_{1-6}$alkyl. In another embodiment is a compound of Formula (Ia), wherein $R^1$ is —C(O) $R^{10}$ is —CH$_3$, and $R^{11}$ is —CH$_3$.

In another embodiment is a compound of Formula (Ia), wherein $R^2$ is H. In another embodiment is a compound of Formula (Ia), wherein $R^2$ is halogen. In another embodiment is a compound of Formula (Ia), wherein $R^2$ is —Cl. In another embodiment is a compound of Formula (Ia), wherein $R^2$ is $C_{1-6}$alkyl. In another embodiment is a compound of Formula (Ia), wherein $R^2$ is —CH$_3$. In another embodiment is a compound of Formula (Ia), wherein $R^2$ is $C_{1-6}$haloalkyl. In another embodiment is a compound of Formula (Ia), wherein $R^2$ is —CF$_3$.

In another embodiment is a compound of Formula (Ia), wherein $R^{12}$ is H. In another embodiment is a compound of Formula (Ia), wherein $R^{12}$ is halogen. In another embodiment is a compound of Formula (Ia), wherein $R^{12}$ is F. In another embodiment is a compound of Formula (Ia), wherein $R^2$ is $C_{1-6}$alkyl. In another embodiment is a compound of Formula (Ia), wherein $R^{12}$ is —CH$_3$. In another embodiment is a compound of Formula (Ia), wherein $R^{13}$ is H. In another embodiment is a compound of Formula (Ia), wherein $R^{13}$ is $C_{1-6}$alkyl. In another embodiment is a compound of Formula (Ia), wherein $R^{13}$ is —CH$_3$. In another embodiment is a compound of Formula (Ia), wherein $R^{12}$ is H and $R^{13}$ is H. In another embodiment is a compound of Formula (Ia), wherein $R^{12}$ is H and $R^{13}$ is $C_{1-6}$alkyl. In another embodiment is a compound of Formula (Ia), wherein $R^{12}$ is H and $R^{13}$ is —CH$_3$. In another embodiment is a compound of Formula (Ia), wherein $R^2$ is $C_{1-6}$alkyl and $R^{13}$ is H. In another embodiment is a compound of Formula (Ia), wherein $R^{12}$ is —CH$_3$ and $R^{13}$ is H. In another embodiment is a compound of Formula (Ia), wherein $R^{12}$ is $C_{1-6}$alkyl and $R^{13}$ is $C_{1-6}$alkyl. In another embodiment is a compound of Formula (Ia), wherein $R^2$ is —CH$_3$ and $R^{13}$ is —CH$_3$.

In another embodiment is a compound of Formula (Ia), wherein A is C(H). In another embodiment is a compound of Formula (Ia), wherein A is N.

In another embodiment is a compound of Formula (Ia), or a solvate, hydrate, tautomer, N-oxide, stereoisomer, or pharmaceutically acceptable salt thereof, wherein $R^4$ is halogen, —OR$^7$, $C_{1-6}$alkyl, $C_{2-6}$ alkynyl, $C_{1-6}$haloalkyl, —C(O) NR$^8$R$^9$, $C_{2-9}$heterocycloalkyl, $C_{6-10}$aryl, or $C_{1-9}$heteroaryl, wherein $C_{2-9}$heterocycloalkyl, —C$_{1-6}$alkyl-C$_{2-9}$heterocycloalkyk $C_{6-10}$aryl, or $C_{1-9}$heteroaryl are optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is halogen, —OR$^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 R$^4$. In another embodiment is a compound of Formula (Ia), or a solvate, hydrate, tautomer, N-oxide, stereoisomer, or pharmaceutically acceptable salt thereof, wherein $R^4$ is halogen. In another embodiment is a compound of Formula (Ia), or a solvate, hydrate, tautomer, N-oxide, stereoisomer, or pharmaceutically acceptable salt thereof, wherein $R^4$ is —Cl. In another embodiment is a compound of Formula (Ia), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^4$ is —CF$_3$. In another embodiment is a compound of Formula (Ia), or a solvate, hydrate, tautomer, N-oxide, stereoisomer, or pharmaceutically acceptable salt thereof, wherein $R^4$ is —OR$^7$. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is —CF$_3$. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is $C_{6-10}$aryl or $C_{1-9}$heteroaryl, wherein $C_{6-10}$aryl or $C_{1-9}$heteroaryl are optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —CF$_3$. In another embodiment is a compound of Formula (Ia), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 R$^4$. In another embodiment is a compound of Formula (Ia), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ia), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ia), or a solvate, hydrate, tautomer, N-oxide, stereoisomer, or pharmaceutically acceptable salt thereof, wherein $R^4$ is

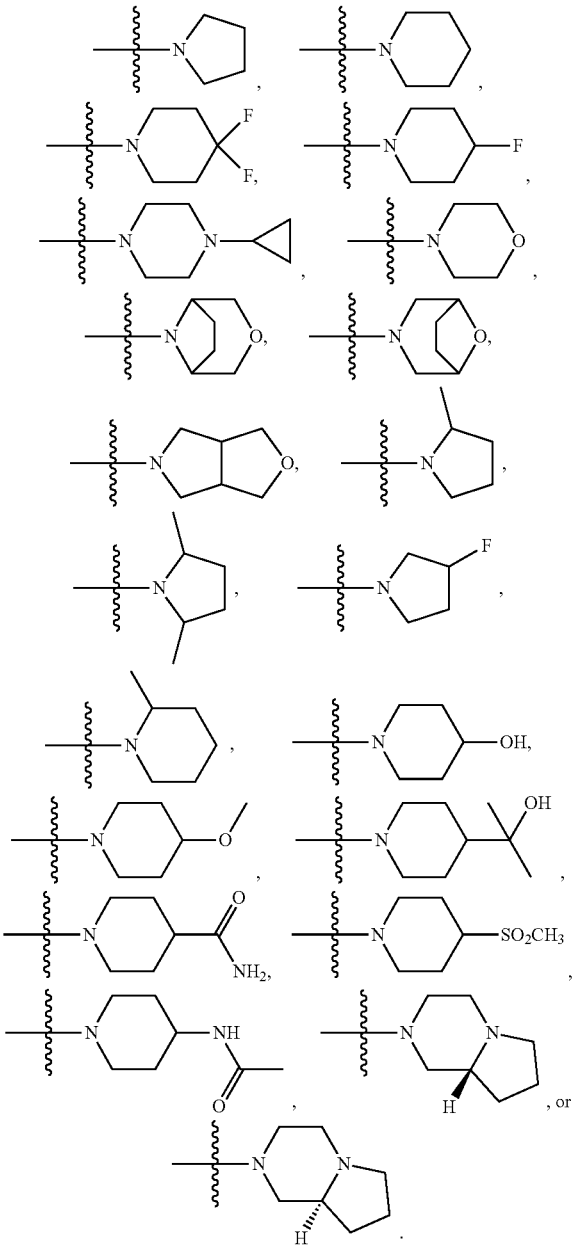

In another embodiment is a compound of Formula (Ia), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ia), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ia), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ia), or a solvate, hydrate, tautomer, N-oxide, stereoisomer, or pharmaceutically acceptable salt thereof, wherein $R^4$ is

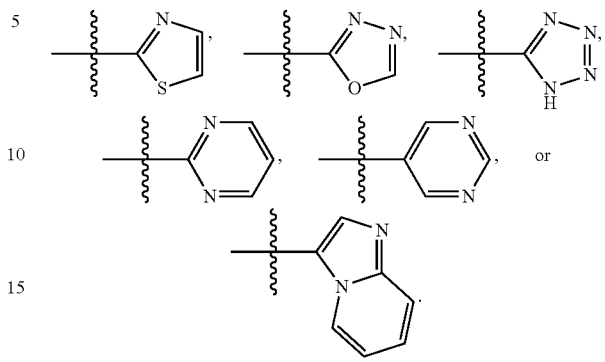

In another embodiment is a compound of Formula (Ia), wherein $R^5$ is H, halogen, $C_{1-6}$alkyl, $C_{1-6}$haloalkyl, $C_{1-6}$haloalkoxy. In another embodiment is a compound of Formula (Ia), wherein $R^5$ is H. In another embodiment is a compound of Formula (Ia), wherein $R^5$ is halogen. In another embodiment is a compound of Formula (Ia), wherein $R^5$ is —Cl. In another embodiment is a compound of Formula (Ia), wherein $R^5$ is —F. In another embodiment is a compound of Formula (Ia), wherein $R^5$ is $C_{1-6}$alkyl. In another embodiment is a compound of Formula (Ia), wherein $R^5$ is —CH$_3$. In another embodiment is a compound of Formula (Ia), wherein $R^5$ is $C_{1-6}$haloalkyl. In another embodiment is a compound of Formula (Ia), wherein $R^5$ is —CF$_3$. In another embodiment is a compound of Formula (Ia), wherein $R^5$ is $C_{1-6}$haloalkoxy. In another embodiment is a compound of Formula (Ia), wherein $R^5$ is —OCF$_3$.

In another embodiment is a compound of Formula (Ia), wherein $R^6$ is H. In another embodiment is a compound of Formula (Ia), wherein $R^6$ is halogen. In another embodiment is a compound of Formula (Ia), wherein $R^6$ is —Cl. In another embodiment is a compound of Formula (Ia), wherein $R^6$ is —F. In another embodiment is a compound of Formula (Ia), wherein $R^6$ is $C_{1-6}$alkyl. In another embodiment is a compound of Formula (Ia), wherein $R^6$ is —CH$_3$.

In another embodiment is a compound of Formula (I) having the structure of Formula (%)

Formula (Ib)

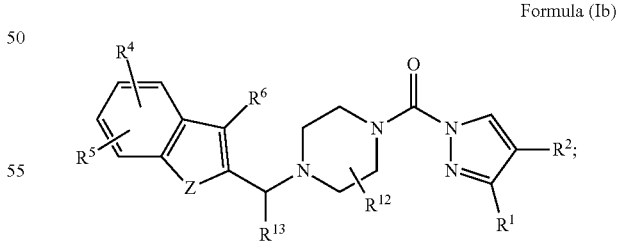

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;
Z is —S—, —O—, or —N(R$^{18}$)—;
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{2-9}$heterocycloalkyl, —C$_{1-6}$alkyl-C$_{2-9}$heterocycloalkyl, C$_{6-10}$aryl, C$_{1-9}$heteroaryl are optionally substituted with 1 or 2 R$^4$;

R$^5$ is H, halogen, C$_{1-6}$alkyl, C$_{1-6}$haloalkyl, C$_{1-6}$haloalkoxy, or phenyl;

R$^6$ is H, halogen or C$_{1-6}$alkyl;

R$^7$ is H, C$_{1-6}$ alkyl, C$_{1-6}$haloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^{14}$; each R$^8$ and each R$^9$ are independently selected from H and C$_{1-6}$alkyl; or R$^8$ and R$^9$ together with the nitrogen to which they are attached are combined to form a heterocycloalkyl ring;

R$^{10}$ and R$^{11}$ are each independently H or C$_{1-6}$ alkyl;

R$^{12}$ is H, halogen, or C$_{1-6}$alkyl;

R$^{13}$ is H or C$_{1-6}$alkyl;

each R$^{14}$ is independently selected from halogen, —OH, C$_{1-6}$ alkyl, C$_{1-6}$haloalkyl, C$_{1-6}$alkoxy, —C$_{1-6}$alkyl-OH, C$_{3-8}$ cycloalkyl, —C(O)NR$^8$R$^9$, —SO$_2$—C$_{1-6}$ alkyl, and —N(R$^{17}$)C(O)—C$_{1-6}$ alkyl;

R$^{15}$ is H or C$_{1-6}$alkyl;

R$^{17}$ is H or C$_{1-6}$alkyl; and

R$^{18}$ is H or C$_{1-6}$alkyl;

or a solvate, hydrate, tautomer, N-oxide, stereoisomer, or pharmaceutically acceptable salt thereof.

In another embodiment is a compound of Formula (Ib), wherein R$^3$ is

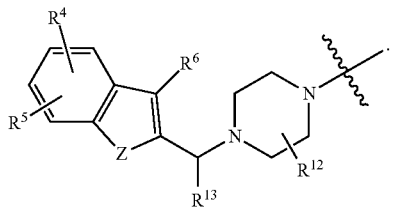

In another embodiment is a compound of Formula (Ib), wherein R$^3$ is

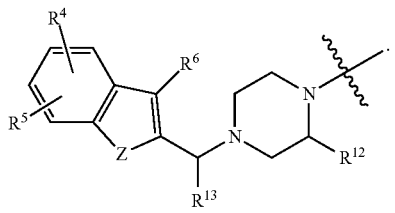

In another embodiment is a compound of Formula (Ib), wherein R$^3$ is

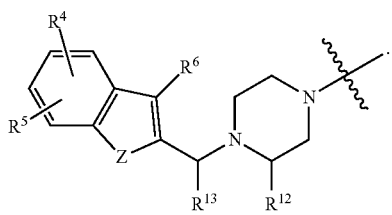

In another embodiment is a compound of Formula (Ib), wherein R$^1$ is —C(O)OR$^{15}$. In another embodiment is a compound of Formula (Ib), wherein R$^1$ is —C(O)OR$^{15}$ and R$^{15}$ is H. In another embodiment is a compound of Formula (Ib), wherein R$^1$ is —C(O)OR$^{15}$ and R$^{15}$ is C$_{1-6}$alkyl. In another embodiment is a compound of Formula (Ib), wherein R$^1$ is —C(O)OR$^{15}$ and R$^{15}$ is —CH$_3$. In another embodiment is a compound of Formula (Ib), wherein R$^1$ is —C(O)NR$^{10}$R$^{11}$. In another embodiment is a compound of Formula (Ib), wherein R$^1$ is —C(O)NR$^1$ is H, and R$^{11}$ is H. In another embodiment is a compound of Formula (Ib), wherein R$^1$ is —C(O)NR$^{10}$R$^{11}$ is H, and R$^{11}$ is C$_{1-6}$ alkyl. In another embodiment is a compound of Formula (Ib), wherein R$^1$ is —C(O)NR$^{10}$R$^{11}$, R$^{10}$ is H, and R$^{11}$ is —CH$_3$. In another embodiment is a compound of Formula (Ib), wherein R$^1$ is —C(O)NR$^{10}$R$^{11}$, is C$_{1-6}$ alkyl, and R$^{11}$ is C$_{1-6}$alkyl. In another embodiment is a compound of Formula (Ib), wherein R$^1$ is —C(O)NR$^{10}$R$^{11}$, R$^{10}$ is —CH$_3$, and R$^{11}$ is —CH$_3$.

In another embodiment is a compound of Formula (Ib), wherein R$^2$ is H. In another embodiment is a compound of Formula (Ib), wherein R$^2$ is halogen. In another embodiment is a compound of Formula (Ib), wherein R$^2$ is —Cl. In another embodiment is a compound of Formula (Ib), wherein R$^2$ is C$_{1-6}$alkyl. In another embodiment is a compound of Formula (Ib), wherein R$^2$ is —CH$_3$. In another embodiment is a compound of Formula (Ib), wherein R$^2$ is C$_{1-6}$haloalkyl. In another embodiment is a compound of Formula (Ib), wherein R$^2$ is —CF$_3$.

In another embodiment is a compound of Formula (Ib), wherein R$^{12}$ is H. In another embodiment is a compound of Formula (Ib), wherein R$^2$ is halogen. In another embodiment is a compound of Formula (Ib), wherein R$^2$ is F. In another embodiment is a compound of Formula (Ib), wherein R$^{12}$ is C$_{1-6}$alkyl. In another embodiment is a compound of Formula (Ib), wherein R$^{12}$ is —CH$_3$. In another embodiment is a compound of Formula (Ib), wherein R$^{13}$ is H. In another embodiment is a compound of Formula (Ib), wherein R$^{13}$ is C$_{1-6}$alkyl. In another embodiment is a compound of Formula (Ib), wherein R$^{13}$ is —CH$_3$. In another embodiment is a compound of Formula (Ib), wherein R$^{12}$ is H and R$^{13}$ is H. In another embodiment is a compound of Formula (Ib), wherein R$^{12}$ is H and R$^{13}$ is C$_{1-6}$alkyl. In another embodiment is a compound of Formula (Ib), wherein R$^{12}$ is H and R$^{13}$ is —CH$_3$. In another embodiment is a compound of Formula (Ib), wherein R$^{12}$ is C$_{1-6}$ alkyl and R$^{13}$ is H. In another embodiment is a compound of Formula (Ib), wherein R$^{12}$ is —CH$_3$ and R$^{13}$ is H. In another embodiment is a compound of Formula (Ib), wherein R$^{12}$ is C$_{1-6}$alkyl and R$^{13}$ is C$_{1-6}$alkyl. In another embodiment is a compound of Formula (Ib), wherein R$^{12}$ is —CH$_3$ and R$^{13}$ is —CH$_3$.

In another embodiment is a compound of Formula (Ib), wherein Z is —S—. In another embodiment is a compound of Formula (Ib), wherein Z is —O—. In another embodiment is a compound of Formula (Ib), wherein Z is —N(R$^{18}$)—. In another embodiment is a compound of Formula (Ib), wherein Z is —N(H)—. In another embodiment is a compound of Formula (Ib), wherein Z is —N(CH$_3$)—.

In another embodiment is a compound of Formula (Ib), or a solvate, hydrate, tautomer, N-oxide, stereoisomer, or pharmaceutically acceptable salt thereof, wherein R$^4$ is halogen, —OR$^7$, C$_{1-6}$alkyl, C$_{2-6}$ alkynyl, C$_{1-6}$haloalkyl, —C(O)NR$^8$R$^9$, C$_{2-9}$heterocycloalkyl, C$_{6-10}$aryl, or C$_{1-9}$heteroaryl, wherein C$_{2-9}$heterocycloalkyl, —C$_{1-6}$alkyl-C$_{2-9}$heterocycloalkyl, C$_{6-10}$aryl, C$_{1-9}$heteroaryl are optionally substituted with 1 or 2 R$^{14}$. In another embodiment is a compound of Formula (Ib), or a solvate, hydrate, tautomer, N-oxide, stereoisomer, or pharmaceutically acceptable salt thereof, wherein R$^4$ is halogen, —OR$^7$, C$_{1-6}$haloalkyl, C$_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is halogen. In another embodiment is a compound of Formula (Ib), or a solvate, hydrate, tautomer, N-oxide, stereoisomer, or pharmaceutically acceptable salt thereof, wherein $R^4$ is —Cl. In another embodiment is a compound of Formula (Ib), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ib), or a solvate, hydrate, tautomer, N-oxide, stereoisomer, or pharmaceutically acceptable salt thereof, wherein $R^4$ is —$CF_3$. In another embodiment is a compound of Formula (Ib), or a solvate, hydrate, tautomer, N-oxide, stereoisomer, or pharmaceutically acceptable salt thereof, wherein $R^4$ is —$OR^7$. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ib), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (Ib), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (Ib), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ib), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (Ib), or a solvate, hydrate, tautomer, N-oxide, stereoisomer, or pharmaceutically acceptable salt thereof, wherein $R^4$ is

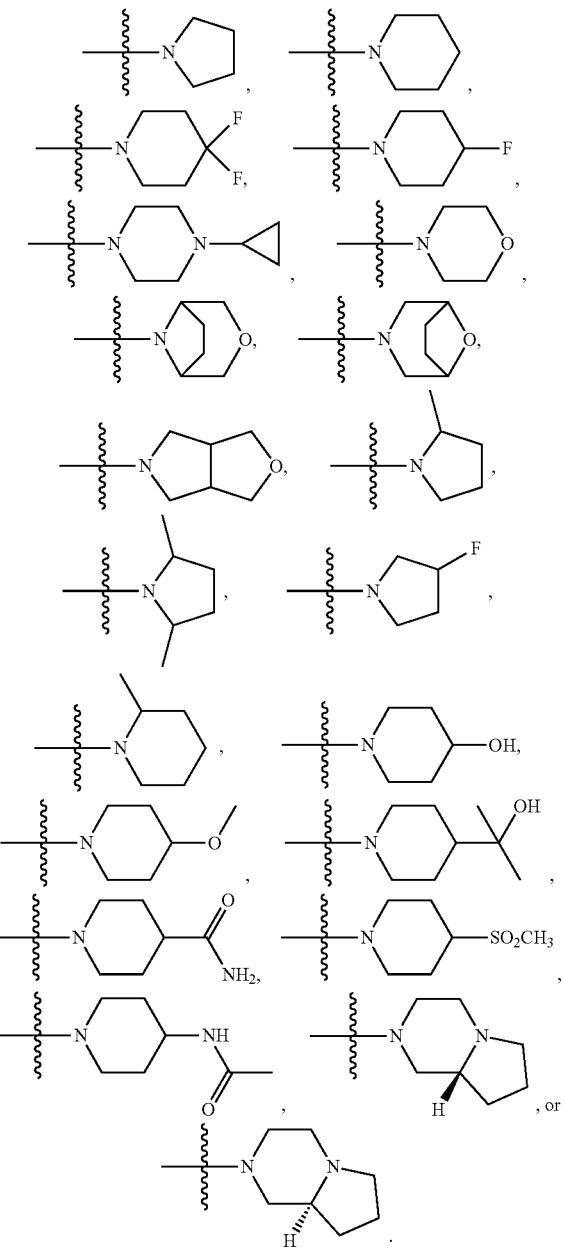

In another embodiment is a compound of Formula (Ib), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ib), or a solvate, hydrate, tautomer, N-oxide, stereoisomer, or pharmaceutically acceptable salt thereof, wherein R$^4$ is C$_{2-9}$heteroaryl substituted with 1 or 2 R$^4$. In another embodiment is a compound of Formula (Ib), or a solvate, hydrate, tautomer, N-oxide, stereoisomer, or pharmaceutically acceptable salt thereof, wherein R$^4$ is

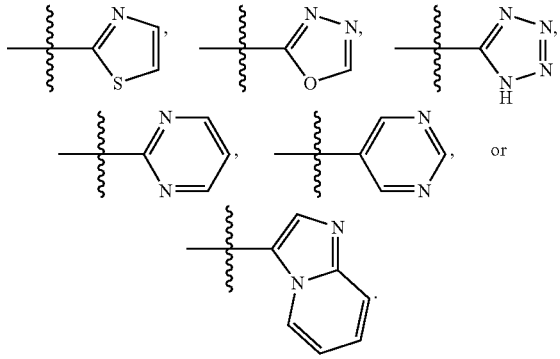

In another embodiment is a compound of Formula (Ib), wherein R$^5$ is H, halogen, C$_{1-6}$alkyl, C$_{1-6}$haloalkyl, C$_{1-6}$haloalkoxy. In another embodiment is a compound of Formula (Ib), wherein R$^5$ is H. In another embodiment is a compound of Formula (Ib), wherein R$^5$ is halogen. In another embodiment is a compound of Formula (Ib), wherein R$^5$ is —Cl. In another embodiment is a compound of Formula (Ib), wherein R$^5$ is —F. In another embodiment is a compound of Formula (Ib), wherein R$^5$ is C$_{1-6}$alkyl. In another embodiment is a compound of Formula (Ib), wherein R$^5$ is —CH$_3$. In another embodiment is a compound of Formula (Ib), wherein R$^5$ is C$_{1-6}$haloalkyl. In another embodiment is a compound of Formula (Ib), wherein R$^5$ is —CF$_3$. In another embodiment is a compound of Formula (Ib), wherein R$^5$ is C$_{1-6}$haloalkoxy. In another embodiment is a compound of Formula (Ib), wherein R$^5$ is —OCF$_3$.

In another embodiment is a compound of Formula (Ib), wherein R$^6$ is H. In another embodiment is a compound of Formula (Ib), wherein R$^6$ is halogen. In another embodiment is a compound of Formula (Ib), wherein R$^6$ is —Cl. In another embodiment is a compound of Formula (Ib), wherein R$^6$ is —F. In another embodiment is a compound of Formula (Ib), wherein R$^6$ is C$_{1-6}$alkyl. In another embodiment is a compound of Formula (Ib), wherein R$^6$ is —CH$_3$.

In another embodiment is a compound of Formula (I) having the structure of Formula (Ic):

Formula (Ic)

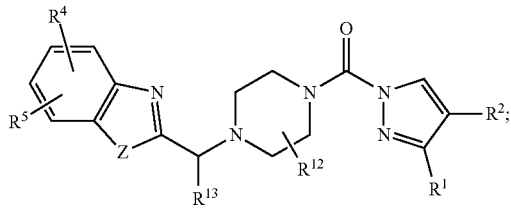

wherein:
R$^1$ is —C(O)OR$^{15}$ or —C(O)NR$^{10}$R$^{11}$;
R$^2$ is H, halogen, C$_{1-6}$alkyl, or C$_{1-6}$haloalkyl;
Z is —S—, —O—, or —N(R$^{18}$)—;
R$^4$ is H, halogen, —OR$^7$, C$_{1-6}$alkyl, C$_{2-6}$alkenyl, C$_{2-6}$alkynyl, C$_{1-6}$haloalkyl, —C(O)NR$^8$R$^9$, C$_{2-9}$heterocycloalkyl, —C$_{1-6}$alkyl-C$_{2-9}$heterocycloalkyl, C$_{6-10}$aryl, or C$_{1-9}$heteroaryl, wherein C$_{2-9}$heterocycloalkyl, —C$_{1-6}$alkyl-C$_{2-9}$heterocycloalkyl, C$_{6-10}$aryl, or C$_{1-9}$heteroaryl are optionally substituted with 1 or 2 R$^4$;

R$^5$ is H, halogen, C$_{1-6}$alkyl, C$_{1-6}$haloalkyl, C$_{1-6}$haloalkoxy, or phenyl;
R$^7$ is H, C$_{1-6}$ alkyl, C$_{1-6}$haloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^{14}$;
each R$^8$ and each R$^9$ are independently selected from H and C$_{1-6}$alkyl; or R$^8$ and R$^9$ together with the nitrogen to which they are attached are combined to form a heterocycloalkyl ring;
R$^{10}$ and R$^{11}$ are each independently H or C$_{1-6}$ alkyl;
R$^{12}$ is H, halogen, or C$_{1-6}$alkyl;
R$^{13}$ is H or C$_{1-6}$alkyl;
each R$^{14}$ is independently selected from halogen, —OH, C$_{1-6}$ alkyl, C$_{1-6}$haloalkyl, C$_{1-6}$alkoxy, —C$_{1-6}$alkyl-OH, C$_{3-8}$ cycloalkyl, —C(O)NR$^8$R$^9$, —SO$_2$—C$_{1-6}$ alkyl, and —N(R$^{17}$)C(O)—C$_{1-6}$ alkyl;
R$^{15}$ is H or C$_{1-6}$alkyl;
R$^{17}$ is H or C$_{1-6}$alkyl; and
R$^{18}$ is H or C$_{1-6}$alkyl;
or a solvate, hydrate, tautomer, N-oxide, stereoisomer, or pharmaceutically acceptable salt thereof.

In another embodiment is a compound of Formula (Ic), wherein R$^3$ is

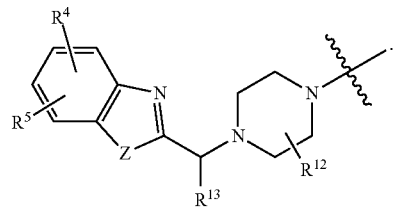

In another embodiment is a compound of Formula (Ic), wherein R$^3$ is

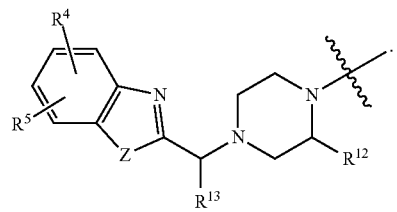

In another embodiment is a compound of Formula (Ic), wherein R$^3$ is

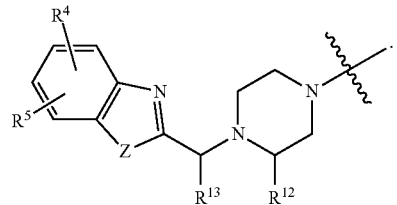

In another embodiment is a compound of Formula (Ic), wherein $R^1$ is —C(O)O$R^{15}$. In another embodiment is a compound of Formula (Ic), wherein $R^1$ is —C(O)O$R^{15}$ and $R^{15}$ is H. In another embodiment is a compound of Formula (Ic), wherein $R^1$ is —C(O)O$R^{15}$ and $R^{15}$ is $C_{1-6}$alkyl. In another embodiment is a compound of Formula (Ic), wherein $R^1$ is —C(O)O$R^{15}$ and $R^{15}$ is —CH$_3$. In another embodiment is a compound of Formula (Ic), wherein $R^1$ is —C(O)N$R^{10}R^{11}$. In another embodiment is a compound of Formula (Ic), wherein $R^1$ is —C(O)N$R^{10}R^{11}$, $R^{10}$ is H, and $R^{11}$ is H. In another embodiment is a compound of Formula (Ic), wherein $R^1$ is —C(O)N$R^{10}R^{11}$, $R^{10}$ is H, and $R^{11}$ is $C_{1-6}$alkyl. In another embodiment is a compound of Formula (Ic), wherein $R^1$ is —C(O)N$R^{10}R^{11}$, $R^{10}$ is H, and $R^{11}$ is —CH$_3$. In another embodiment is a compound of Formula (Ic), wherein $R^1$ is —C(O)N$R^{10}R^{11}$, $R^{10}$ is $C_{1-6}$ alkyl, and $R^{11}$ is $C_{1-6}$alkyl. In another embodiment is a compound of Formula (Ic), wherein $R^1$ is —C(O)N$R^{10}R^{11}$, $R^{10}$ is —CH$_3$, and $R^{11}$ is —CH$_3$.

In another embodiment is a compound of Formula (Ic), wherein $R^2$ is H. In another embodiment is a compound of Formula (Ic), wherein $R^2$ is halogen. In another embodiment is a compound of Formula (Ic), wherein $R^2$ is —Cl. In another embodiment is a compound of Formula (Ic), wherein $R^2$ is $C_{1-6}$alkyl. In another embodiment is a compound of Formula (Ic), wherein $R^2$ is —CH$_3$. In another embodiment is a compound of Formula (Ic), wherein $R^2$ is $C_{1-6}$haloalkyl. In another embodiment is a compound of Formula (Ic), wherein $R^2$ is —CF$_3$.

In another embodiment is a compound of Formula (Ic), wherein $R^{18}$ is H. In another embodiment is a compound of Formula (Ic), wherein $R^{18}$ is halogen. In another embodiment is a compound of Formula (Ic), wherein $R^{18}$ is F. In another embodiment is a compound of Formula (Ic), wherein $R^2$ is $C_{1-6}$alkyl. In another embodiment is a compound of Formula (Ic), wherein $R^{12}$ is —CH$_3$. In another embodiment is a compound of Formula (Ic), wherein $R^3$ is H. In another embodiment is a compound of Formula (Ic), wherein $R^{13}$ is $C_{1-6}$alkyl. In another embodiment is a compound of Formula (Ic), wherein $R^{13}$ is —CH$_3$. In another embodiment is a compound of Formula (Ic), wherein $R^{12}$ is H and $R^{13}$ is H. In another embodiment is a compound of Formula (Ic), wherein $R^{12}$ is H and $R^3$ is $C_{1-6}$alkyl. In another embodiment is a compound of Formula (Ic), wherein $R^{12}$ is H and $R^{13}$ is —CH$_3$. In another embodiment is a compound of Formula (Ic), wherein $R^{12}$ is $C_{1-6}$alkyl and $R^{13}$ is H. In another embodiment is a compound of Formula (Ic), wherein $R^{12}$ is —CH$_3$ and $R^{13}$ is H. In another embodiment is a compound of Formula (Ic), wherein $R^{12}$ is $C_{1-6}$alkyl and $R^{13}$ is $C_{1-6}$alkyl. In another embodiment is a compound of Formula (Ic), wherein $R^{12}$ is —CH$_3$ and $R^{13}$ is —CH$_3$.

In another embodiment is a compound of Formula (Ic), wherein Z is —S—. In another embodiment is a compound of Formula (Ic), wherein Z is —O—. In another embodiment is a compound of Formula (Ic), wherein Z is —N($R^{18}$)—. In another embodiment is a compound of Formula (Ic), wherein Z is —N(H)—. In another embodiment is a compound of Formula (Ic), wherein Z is —N(CH$_3$)—.

In another embodiment is a compound of Formula (Ic), or a solvate, hydrate, tautomer, N-oxide, stereoisomer, or pharmaceutically acceptable salt thereof, wherein $R^4$ is halogen, —O$R^7$, $C_{1-6}$alkyl, $C_{2-6}$ alkynyl, $C_{1-6}$haloalkyl, —C(O)N$R^8R^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyk $C_{6-10}$aryl, or $C_{1-9}$heteroaryl are optionally substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is halogen, —O$R^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^4$. In another embodiment is a compound of Formula (Ic), or a solvate, hydrate, tautomer, N-oxide, stereoisomer, or pharmaceutically acceptable salt thereof, wherein $R^4$ is halogen. In another embodiment is a compound of Formula (Ic), or a solvate, hydrate, tautomer, N-oxide, stereoisomer, or pharmaceutically acceptable salt thereof, wherein $R^4$ is —Cl. In another embodiment is a compound of Formula (Ic), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ic), or a solvate, hydrate, tautomer, N-oxide, stereoisomer, or pharmaceutically acceptable salt thereof, wherein $R^4$ is —CF$_3$. In another embodiment is a compound of Formula (Ic), or a solvate, hydrate, tautomer, N-oxide, stereoisomer, or pharmaceutically acceptable salt thereof, wherein $R^4$ is —O$R^7$. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is $C_{1-6}$haloalkyl. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is —CF$_3$. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ic), or a solvate, hydrate, tautomer, N-oxide, stereoisomer, or pharmaceutically acceptable salt thereof, wherein $R^4$ is —O$R^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —CF$_3$. In another embodiment is a compound of Formula (Ic), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (Ic), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ic), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (Ic), or a solvate, hydrate, tautomer, N-oxide, stereoisomer, or pharmaceutically acceptable salt thereof, wherein $R^4$ is

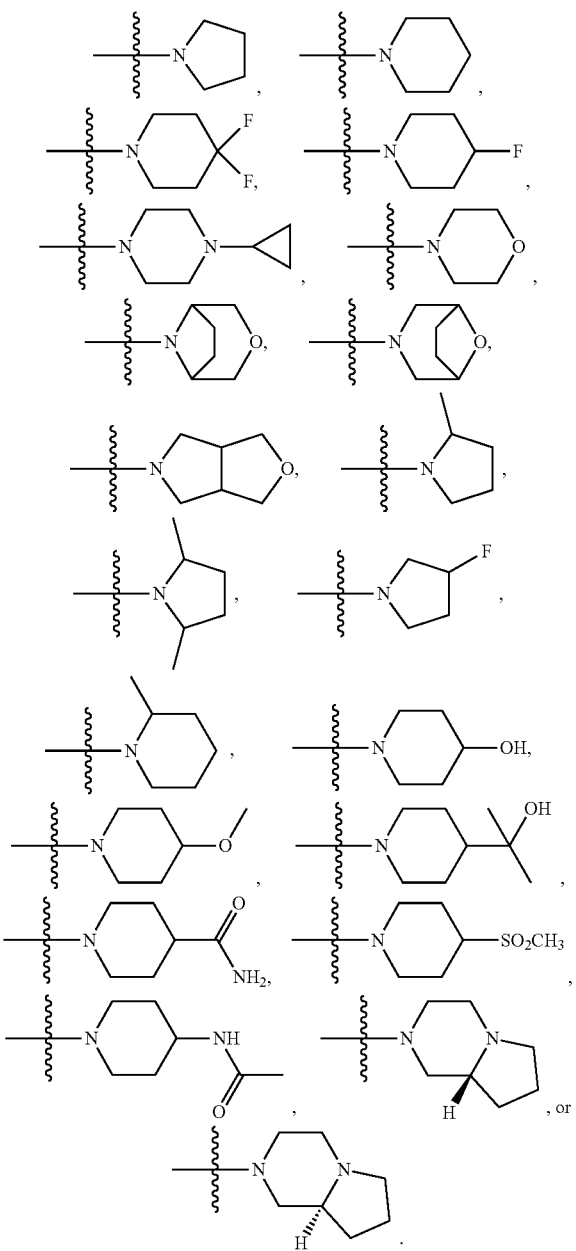

In another embodiment is a compound of Formula (Ic), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ic), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (Ic), or a solvate, hydrate, tautomer, N-oxide, stereoisomer, or pharmaceutically acceptable salt thereof, wherein $R^4$ is

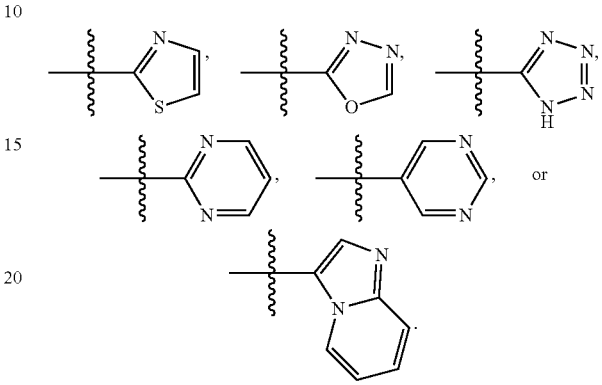

In another embodiment is a compound of Formula (Ic), wherein $R^5$ is H, halogen, $C_{1-6}$alkyl, $C_{1-6}$haloalkyl, $C_{1-6}$haloalkoxy. In another embodiment is a compound of Formula (Ic), wherein $R^5$ is H. In another embodiment is a compound of Formula (Ic), wherein $R^5$ is halogen. In another embodiment is a compound of Formula (Ic), wherein $R^5$ is —Cl. In another embodiment is a compound of Formula (Ic), wherein $R^5$ is —F. In another embodiment is a compound of Formula (Ic), wherein $R^5$ is $C_{1-6}$alkyl. In another embodiment is a compound of Formula (Ic), wherein $R^5$ is —CH$_3$. In another embodiment is a compound of Formula (Ic), wherein $R^5$ is $C_{1-6}$haloalkyl. In another embodiment is a compound of Formula (Ic), wherein $R^5$ is —CF$_3$. In another embodiment is a compound of Formula (Ic), wherein $R^5$ is $C_{1-6}$haloalkoxy. In another embodiment is a compound of Formula (Ic), wherein $R^5$ is —OCF$_3$.

In another embodiment is a compound of Formula (I) having the structure of Formula (Id):

Formula (Id)

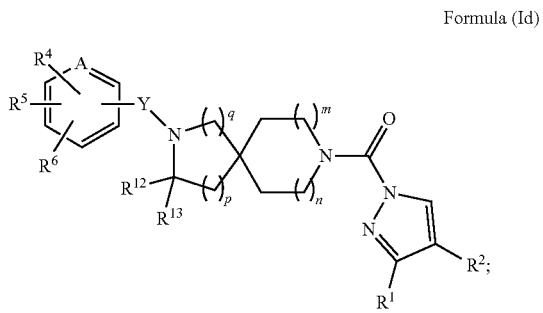

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;
A is N or C(H);
Y is —CH$_2$— or —C(O)—;
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^4$;

$R^5$ is H, halogen, $C_{1-6}$alkyl, $C_{1-6}$haloalkyl, $C_{1-6}$haloalkoxy, or phenyl;

$R^6$ is H, halogen or $C_{1-6}$alkyl;

$R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)NR$^8$R$^9$, —SO$_2$—$C_{1-6}$ alkyl, and —N(R$^{17}$)C(O)—$C_{1-6}$ alkyl;

$R^{15}$ is H or $C_{1-6}$alkyl;

$R^{17}$ is H or $C_{1-6}$alkyl;

n is 0 or 1;

m is 0 or 1;

p is 0, 1, or 2; and q is 0, 1 or 2;

or a solvate, hydrate, tautomer, N-oxide, stereoisomer, or pharmaceutically acceptable salt thereof.

In another embodiment is a compound of Formula (Id), wherein $R^1$ is —C(O)OR$^{15}$. In another embodiment is a compound of Formula (Id), wherein $R^1$ is —C(O)OR$^{15}$ and $R^{15}$ is H. In another embodiment is a compound of Formula (Id), wherein $R^1$ is —C(O)OR$^{15}$ and $R^{15}$ is $C_{1-6}$alkyl. In another embodiment is a compound of Formula (Id), wherein $R^1$ is —C(O)OR$^{15}$ and $R^{15}$ is —CH$_3$. In another embodiment is a compound of Formula (Id), wherein $R^1$ is —C(O)NR$^{10}$R$^{11}$. In another embodiment is a compound of Formula (Id), wherein $R^1$ is —C(O)NR$^{10}$R$^{11}$, $R^{10}$ is H, and $R^{11}$ is H. In another embodiment is a compound of Formula (Id), wherein $R^1$ is —C(O)NR$^{10}$R$^{11}$, $R^{10}$ is H, and $R^{11}$ is $C_{1-6}$alkyl. In another embodiment is a compound of Formula (Id), wherein $R^1$ is —C(O)NR$^{10}$R$^{11}$, $R^{10}$ is H, and $R^{11}$ is —CH$_3$. In another embodiment is a compound of Formula (Id), wherein $R^1$ is —C(O)NR$^{10}$R$^{11}$, $R^{10}$ is $C_{1-6}$ alkyl, and $R^{11}$ is $C_{1-6}$alkyl. In another embodiment is a compound of Formula (Id), wherein $R^1$ is —C(O)NR$^{10}$R$^{11}$, $R^{10}$ is —CH$_3$, and $R^{11}$ is —CH$_3$.

In another embodiment is a compound of Formula (Id), wherein $R^2$ is H. In another embodiment is a compound of Formula (Id), wherein $R^2$ is halogen. In another embodiment is a compound of Formula (Id), wherein $R^2$ is —Cl. In another embodiment is a compound of Formula (Id), wherein $R^2$ is $C_{1-6}$alkyl. In another embodiment is a compound of Formula (Id), wherein $R^2$ is —CH$_3$. In another embodiment is a compound of Formula (Id), wherein $R^2$ is $C_{1-6}$haloalkyl. In another embodiment is a compound of Formula (Id), wherein $R^2$ is —CF$_3$.

In another embodiment is a compound of Formula (Id), wherein $R^{12}$ is H. In another embodiment is a compound of Formula (Id), wherein $R^2$ is halogen. In another embodiment is a compound of Formula (Id), wherein $R^2$ is F. In another embodiment is a compound of Formula (Id), wherein $R^{12}$ is $C_{1-6}$alkyl. In another embodiment is a compound of Formula (Id), wherein $R^{12}$ is —CH$_3$. In another embodiment is a compound of Formula (Id), wherein $R^3$ is H. In another embodiment is a compound of Formula (Id), wherein $R^3$ is $C_{1-6}$alkyl. In another embodiment is a compound of Formula (Id), wherein $R^3$ is —CH$_3$. In another embodiment is a compound of Formula (Id), wherein $R^{12}$ is H and $R^{13}$ is H. In another embodiment is a compound of Formula (Id), wherein $R^{12}$ is H and $R^{13}$ is $C_{1-6}$alkyl. In another embodiment is a compound of Formula (Id), wherein $R^{12}$ is H and $R^{13}$ is —CH$_3$. In another embodiment is a compound of Formula (Id), wherein $R^{12}$ is $C_{1-6}$ alkyl and $R^{13}$ is H. In another embodiment is a compound of Formula (Id), wherein $R^{12}$ is —CH$_3$ and $R^{13}$ is H. In another embodiment is a compound of Formula (Id), wherein $R^{12}$ is $C_{1-6}$alkyl and $R^{13}$ is $C_{1-6}$alkyl. In another embodiment is a compound of Formula (Id), wherein $R^{12}$ is —CH$_3$ and $R^{13}$ is —CH$_3$.

In another embodiment is a compound of Formula (Id), wherein A is C(H). In another embodiment is a compound of Formula (Id), wherein A is N.

In another embodiment is a compound of Formula (Id), wherein Y is —CH$_2$—. In another embodiment is a compound of Formula (Id), wherein Y is —C(O)—.

In another embodiment is a compound of Formula (Id), or a solvate, hydrate, tautomer, N-oxide, stereoisomer, or pharmaceutically acceptable salt thereof, wherein m is 1, n is 1, q is 1, and p is 1. In another embodiment is a compound of Formula (Id), or a solvate, hydrate, tautomer, N-oxide, stereoisomer, or pharmaceutically acceptable salt thereof, wherein m is 0, n is 1, q is 2, and p is 1. In another embodiment is a compound of Formula (Id), or a solvate, hydrate, tautomer, N-oxide, stereoisomer, or pharmaceutically acceptable salt thereof, wherein m is 1, n is 1, q is 0, and p is 2. In another embodiment is a compound of Formula (Id), or a solvate, hydrate, tautomer, N-oxide, stereoisomer, or pharmaceutically acceptable salt thereof, wherein m is 1, n is 1, q is 1, and p is 0. In another embodiment is a compound of Formula (Id), or a solvate, hydrate, tautomer, N-oxide, stereoisomer, or pharmaceutically acceptable salt thereof, wherein m is 0, n is 0, q is 2, and p is 1.

In another embodiment is a compound of Formula (Id), or a solvate, hydrate, tautomer, N-oxide, stereoisomer, or pharmaceutically acceptable salt thereof, wherein $R^4$ is halogen, —OR$^7$, $C_{1-6}$alkyl, $C_{2-6}$ alkynyl, $C_{1-6}$haloalkyl, —C(O)NR$^8$R$^9$, $C_{2-9}$heterocycloalkyl, $C_{6-10}$aryl, or $C_{1-6}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 R$^{14}$. In another embodiment is a compound of Formula (Id), or a solvate, hydrate, tautomer, N-oxide, stereoisomer, or pharmaceutically acceptable salt thereof, wherein $R^4$ is halogen, —OR$^7$, $C_{1-6}$haloalkyl, $C_{2-9}$heterocycloalkyl, $C_{6-10}$aryl, or $C_{1-9}$heteroaryl, wherein $C_{2-9}$heterocycloalky, $C_{6-10}$aryl, or $C_{1-9}$heteroaryl are optionally substituted with 1 or 2 R$^{14}$. In another embodiment is a compound of Formula (Id), or a solvate, hydrate, tautomer, N-oxide, stereoisomer, or pharmaceutically acceptable salt thereof, wherein $R^4$ is halogen. In another embodiment is a compound of Formula (Id), or a solvate, hydrate, tautomer, N-oxide, stereoisomer, or pharmaceutically acceptable salt thereof, wherein $R^4$ is —Cl. In another embodiment is a compound of Formula (Id), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^4$ is —CF$_3$. In another embodiment is a compound of Formula (Id), or a solvate, hydrate, tautomer, N-oxide, stereoisomer, or pharmaceutically acceptable salt thereof, wherein $R^4$ is —OR$^7$. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (Id), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (Id), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Id), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (Id), or a solvate, hydrate, tautomer, N-oxide, stereoisomer, or pharmaceutically acceptable salt thereof, wherein $R^4$ is

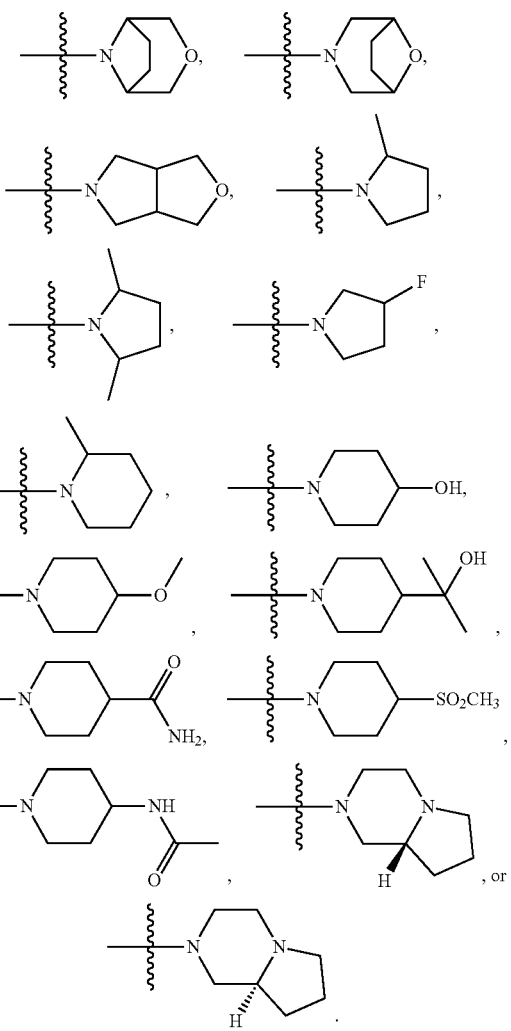

In another embodiment is a compound of Formula (Id), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Id), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (Id), or a solvate, hydrate, tautomer, N-oxide, stereoisomer, or pharmaceutically acceptable salt thereof, wherein $R^4$ is

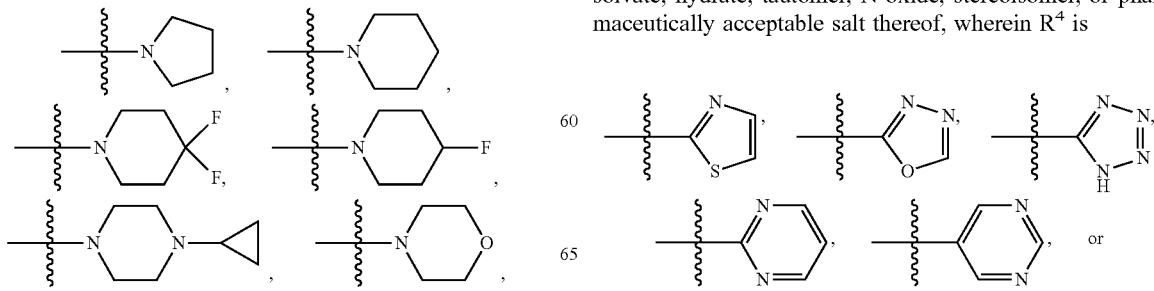

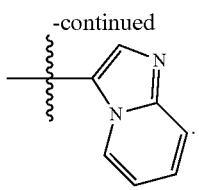

In another embodiment is a compound of Formula (Id), wherein $R^5$ is H, halogen, $C_{1-6}$alkyl, $C_{1-6}$haloalkyl, $C_{1-6}$haloalkoxy. In another embodiment is a compound of Formula (Id), wherein $R^5$ is H. In another embodiment is a compound of Formula (Id), wherein $R^5$ is halogen. In another embodiment is a compound of Formula (Id), wherein $R^5$ is —Cl. In another embodiment is a compound of Formula (Id), wherein $R^5$ is —F. In another embodiment is a compound of Formula (Id), wherein $R^5$ is $C_{1-6}$alkyl. In another embodiment is a compound of Formula (Id), wherein $R^5$ is —$CH_3$. In another embodiment is a compound of Formula (Id), wherein $R^5$ is $C_{1-6}$haloalkyl. In another embodiment is a compound of Formula (Id), wherein $R^5$ is —$CF_3$. In another embodiment is a compound of Formula (Id), wherein $R^5$ is $C_{1-6}$haloalkoxy. In another embodiment is a compound of Formula (Id), wherein $R^5$ is —$OCF_3$.

In another embodiment is a compound of Formula (Id), wherein $R^6$ is H. In another embodiment is a compound of Formula (Id), wherein $R^6$ is halogen. In another embodiment is a compound of Formula (Id), wherein $R^6$ is —Cl. In another embodiment is a compound of Formula (Id), wherein $R^6$ is —F. In another embodiment is a compound of Formula (Id), wherein $R^6$ is $C_{1-6}$alkyl. In another embodiment is a compound of Formula (Id), wherein $R^6$ is —$CH_3$.

In another embodiment is a compound of Formula (I) having the structure of Formula (Ie):

Formula (Ie)

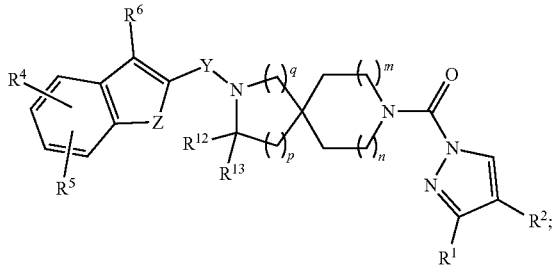

wherein:

$R^1$ is —$C(O)OR^{15}$ or —$C(O)NR^{10}R^{11}$;

$R^2$ is H, halogen, $C_{1-6}$alkyl, or $C_{1-6}$haloalkyl;

Y is —$CH_2$— or —$C(O)$—;

Z is —S—, —O—, or —$N(R^{18})$—;

$R^4$ is H, halogen, —$OR^7$, $C_{1-6}$alkyl, $C_{2-6}$alkenyl, $C_{2-6}$alkynyl, $C_{1-6}$haloalkyl, —$C(O)NR^8R^9$, 9heterocycloalkyl, —$C_{1-6}$alkyl-$C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^{14}$;

$R^5$ is H, halogen, $C_{1-6}$alkyl, $C_{1-6}$haloalkyl, $C_{1-6}$haloalkoxy, or phenyl;

$R^6$ is H, halogen or $C_{1-6}$alkyl;

$R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —$C(O)NR^8R^9$, —$SO_2$—$C_{1-6}$ alkyl, and —$N(R^{17})C(O)$—$C_{1-6}$ alkyl;

$R^{15}$ is H or $C_{1-6}$alkyl;

$R^{17}$ is H or $C_{1-6}$alkyl;

$R^{18}$ is H or $C_{1-6}$alkyl;

n is 0 or 1;

m is 0 or 1;

p is 0, 1, or 2; and q is 0, 1 or 2;

or a solvate, hydrate, tautomer, N-oxide, stereoisomer, or pharmaceutically acceptable salt thereof.

In another embodiment is a compound of Formula (Ie), wherein $R^1$ is —$C(O)OR^{15}$. In another embodiment is a compound of Formula (Ie), wherein $R^1$ is —$C(O)OR^{15}$ and $R^{15}$ is H. In another embodiment is a compound of Formula (Ie), wherein $R^1$ is —$C(O)OR^{15}$ and $R^{15}$ is $C_{1-6}$alkyl. In another embodiment is a compound of Formula (Ie), wherein $R^1$ is —$C(O)OR^{15}$ and $R^{15}$ is —$CH_3$. In another embodiment is a compound of Formula (Ie), wherein $R^1$ is —$C(O)NR^{10}R^{11}$. In another embodiment is a compound of Formula (Ie), wherein $R^1$ is —$C(O) NR^{10}R^{11}$, $R^{10}$ is H, and $R^{11}$ is H. In another embodiment is a compound of Formula (Ie), wherein $R^1$ is —$C(O) NR^{10}R^{11}$, $R^{10}$ is H, and $R^{11}$ is $C_{1-6}$ alkyl. In another embodiment is a compound of Formula (Ie), wherein $R^1$ is —$C(O)NR^{10}R^{11}$, $R^{10}$ is H, and $R^{11}$ is —$CH_3$. In another embodiment is a compound of Formula (Ie), wherein $R^1$ is —$C(O)NR^{10}R^{11}$, $R^{10}$ is $C_{1-6}$ alkyl, and $R^{11}$ is $C_{1-6}$alkyl. In another embodiment is a compound of Formula (Ie), wherein $R^1$ is —$C(O) NR^{10}R^{11}$, $R^{10}$ is —$CH_3$, and $R^{11}$ is —$CH_3$.

In another embodiment is a compound of Formula (Ie), wherein $R^2$ is H. In another embodiment is a compound of Formula (Ie), wherein $R^2$ is halogen. In another embodiment is a compound of Formula (Ie), wherein $R^2$ is —Cl. In another embodiment is a compound of Formula (Ie), wherein $R^2$ is $C_{1-6}$alkyl. In another embodiment is a compound of Formula (Ie), wherein $R^2$ is —$CH_3$. In another embodiment is a compound of Formula (Ie), wherein $R^2$ is $C_{1-6}$haloalkyl. In another embodiment is a compound of Formula (Ie), wherein $R^2$ is —$CF_3$.

In another embodiment is a compound of Formula (Ie), wherein $R^{12}$ is H. In another embodiment is a compound of Formula (Ie), wherein $R^{12}$ is halogen. In another embodiment is a compound of Formula (Ie), wherein $R^{12}$ is F. In another embodiment is a compound of Formula (Ie), wherein $R^2$ is $C_{1-6}$alkyl. In another embodiment is a compound of Formula (Ie), wherein $R^{12}$ is —$CH_3$. In another embodiment is a compound of Formula (Ie), wherein $R^3$ is H. In another embodiment is a compound of Formula (Ie), wherein $R^{13}$ is $C_{1-6}$alkyl. In another embodiment is a compound of Formula (Ie), wherein $R^{13}$ is —$CH_3$. In another embodiment is a compound of Formula (Ie), wherein $R^{12}$ is H and $R^3$ is H. In another embodiment is a compound of Formula (Ie), wherein $R^{12}$ is H and $R^3$ is $C_{1-6}$alkyl. In another embodiment is a compound of Formula (Ie), wherein $R^{12}$ is H and $R^3$ is —$CH_3$. In another embodiment is a compound of Formula (Ie), wherein $R^2$ is $C_{1-6}$alkyl and $R^{13}$ is H. In another embodiment is a compound of Formula (Ie), wherein $R^{12}$ is —$CH_3$ and $R^{13}$ is H. In another embodiment is a compound of Formula (Ie), wherein $R^{12}$ is $C_{1-6}$alkyl and $R^{13}$ is $C_{1-6}$alkyl. In another embodiment is a compound of Formula (Ie), wherein $R^2$ is —$CH_3$ and $R^3$ is —$CH_3$.

In another embodiment is a compound of Formula (Ie), wherein Y is —$CH_2$—. In another embodiment is a compound of Formula (Ie), wherein Y is —C(O)—.

In another embodiment is a compound of Formula (Ie), wherein Z is —S—. In another embodiment is a compound of Formula (Ie), wherein Z is —O—. In another embodiment is a compound of Formula (Ie), wherein Z is —N($R^{18}$)—. In another embodiment is a compound of Formula (Ie), wherein Z is —N(H)—. In another embodiment is a compound of Formula (Ie), wherein Z is —N($CH_3$)—.

In another embodiment is a compound of Formula (Ie), or a solvate, hydrate, tautomer, N-oxide, stereoisomer, or pharmaceutically acceptable salt thereof, wherein m is 1, n is 1, q is 1, and p is 1. In another embodiment is a compound of Formula (Ie), or a solvate, hydrate, tautomer, N-oxide, stereoisomer, or pharmaceutically acceptable salt thereof, wherein m is 0, n is 1, q is 2, and p is 1. In another embodiment is a compound of Formula (Ie), or a solvate, hydrate, tautomer, N-oxide, stereoisomer, or pharmaceutically acceptable salt thereof, wherein m is 1, n is 1, q is 0, and p is 2. In another embodiment is a compound of Formula (Ie), or a solvate, hydrate, tautomer, N-oxide, stereoisomer, or pharmaceutically acceptable salt thereof, wherein m is 1, n is 1, q is 1, and p is 0. In another embodiment is a compound of Formula (Ie), or a solvate, hydrate, tautomer, N-oxide, stereoisomer, or pharmaceutically acceptable salt thereof, wherein m is 0, n is 0, q is 2, and p is 1.

In another embodiment is a compound of Formula (Ie), or a solvate, hydrate, tautomer, N-oxide, stereoisomer, or pharmaceutically acceptable salt thereof, wherein $R^4$ is halogen, —$OR^7$, $C_{1-6}$alkyl, $C_{2-6}$ alkynyl, $C_{1-6}$haloalkyl, —C(O)$NR^8R^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is halogen, —$OR^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^4$. In another embodiment is a compound of Formula (Ie), or a solvate, hydrate, tautomer, N-oxide, stereoisomer, or pharmaceutically acceptable salt thereof, wherein $R^4$ is halogen. In another embodiment is a compound of Formula (Ie), or a solvate, hydrate, tautomer, N-oxide, stereoisomer, or pharmaceutically acceptable salt thereof, wherein $R^4$ is —Cl. In another embodiment is a compound of Formula (Ie), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ie), or a solvate, hydrate, tautomer, N-oxide, stereoisomer, or pharmaceutically acceptable salt thereof, wherein $R^4$ is —$CF_3$. In another embodiment is a compound of Formula (Ie), or a solvate, hydrate, tautomer, N-oxide, stereoisomer, or pharmaceutically acceptable salt thereof, wherein $R^4$ is —$OR^7$. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (Ie), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (Ie), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ie), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (Ie), or a solvate, hydrate, tautomer, N-oxide, stereoisomer, or pharmaceutically acceptable salt thereof, wherein $R^4$ is

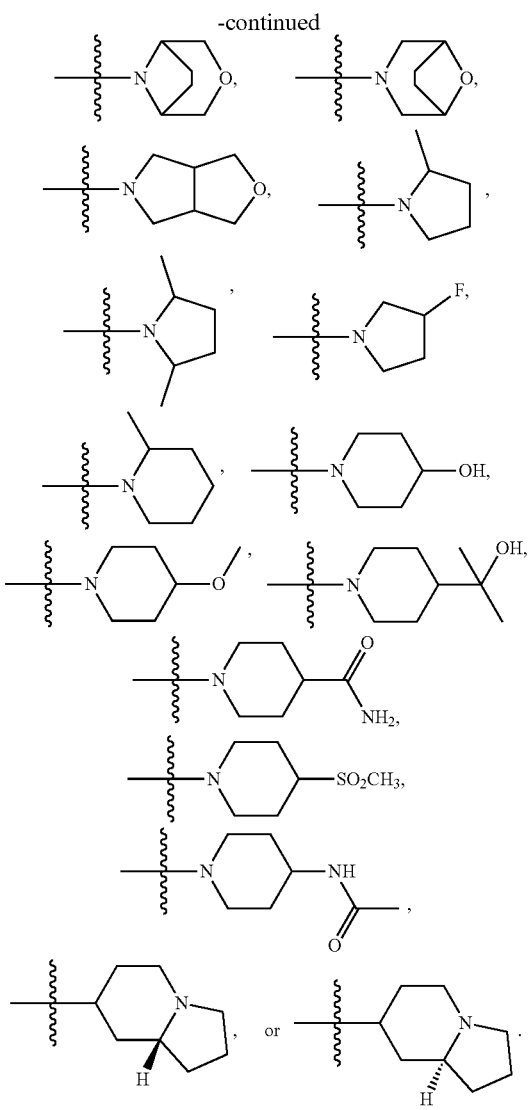

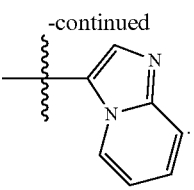

In another embodiment is a compound of Formula (Ie), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ie), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (Ie), or a solvate, hydrate, tautomer, N-oxide, stereoisomer, or pharmaceutically acceptable salt thereof, wherein $R^4$ is

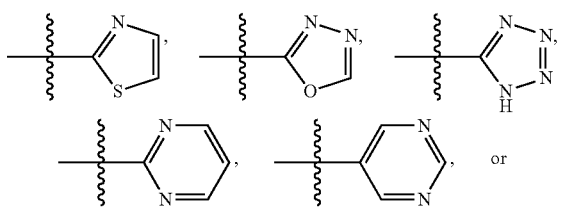

In another embodiment is a compound of Formula (Ie), wherein $R^5$ is H, halogen, $C_{1-6}$alkyl, $C_{1-6}$haloalkyl, $C_{1-6}$haloalkoxy. In another embodiment is a compound of Formula (Ie), wherein $R^5$ is H. In another embodiment is a compound of Formula (Ie), wherein $R^5$ is halogen. In another embodiment is a compound of Formula (Ie), wherein $R^5$ is —Cl. In another embodiment is a compound of Formula (Ie), wherein $R^5$ is —F. In another embodiment is a compound of Formula (Ie), wherein $R^5$ is $C_{1-6}$alkyl. In another embodiment is a compound of Formula (Ie), wherein $R^5$ is —CH$_3$. In another embodiment is a compound of Formula (Ie), wherein $R^5$ is $C_{1-6}$haloalkyl. In another embodiment is a compound of Formula (Ie), wherein $R^5$ is —CF$_3$. In another embodiment is a compound of Formula (Ie), wherein $R^5$ is $C_{1-6}$haloalkoxy. In another embodiment is a compound of Formula (Ie), wherein $R^5$ is —OCF$_3$.

In another embodiment is a compound of Formula (Ie), wherein $R^6$ is H. In another embodiment is a compound of Formula (Ie), wherein $R^6$ is halogen. In another embodiment is a compound of Formula (Ie), wherein $R^6$ is —Cl. In another embodiment is a compound of Formula (Ie), wherein $R^6$ is —F. In another embodiment is a compound of Formula (Ie), wherein $R^6$ is $C_{1-6}$alkyl. In another embodiment is a compound of Formula (Ie), wherein $R^6$ is —CH$_3$.

In another embodiment is a compound of Formula (I) having the structure of Formula (If):

Formula (If)

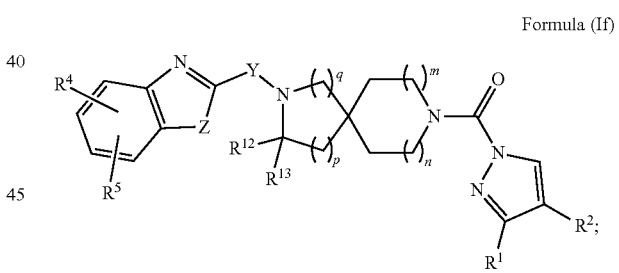

wherein:
 $R^1$ is —C(O)OR$^{15}$ or —C(O)NR$^{10}$R$^{11}$;
 $R^2$ is H, halogen, $C_{1-6}$alkyl, or $C_{1-6}$haloalkyl;
 Y is —CH$_2$— or —C(O)—;
 Z is —S—, —O—, or —N(R$^{18}$)—;
 $R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{2-9}$heterocycloalkyl, —C$_{1-6}$alkyl-C$_{2-9}$heterocycloalkyl, $C_{6-10}$aryl, or $C_{1-9}$heteroaryl are optionally substituted with 1 or 2 $R^4$;
 $R^5$ is H, halogen, $C_{1-6}$alkyl, $C_{1-6}$haloalkyl, $C_{1-6}$haloalkoxy, or phenyl;
 $R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)NR$^8$R$^9$, —SO$_2$—C$_{1-6}$ alkyl, and —N(R$^{17}$)C(O)—C$_{1-6}$ alkyl;

$R^{15}$ is H or $C_{1-6}$alkyl;

$R^{17}$ is H or $C_{1-6}$alkyl;

$R^{18}$ is H or $C_{1-6}$alkyl;

n is 0 or 1;

m is 0 or 1;

p is 0, 1, or 2; and q is 0, 1 or 2;

or a solvate, hydrate, tautomer, N-oxide, stereoisomer, or pharmaceutically acceptable salt thereof.

In another embodiment is a compound of Formula (If), wherein $R^1$ is —C(O)OR$^{15}$. In another embodiment is a compound of Formula (If), wherein $R^1$ is —C(O)OR$^{15}$ and $R^{15}$ is H. In another embodiment is a compound of Formula (If), wherein $R^1$ is —C(O)OR$^{15}$ and $R^{15}$ is $C_{1-6}$alkyl. In another embodiment is a compound of Formula (If), wherein $R^1$ is —C(O)OR$^{15}$ and $R^{15}$ is —CH$_3$. In another embodiment is a compound of Formula (If), wherein $R^1$ is —C(O)NR$^{10}$R$^{11}$. In another embodiment is a compound of Formula (If), wherein $R^1$ is —C(O) NR$^{10}$R$^{11}$, $R^{10}$ is H, and $R^{11}$ is H. In another embodiment is a compound of Formula (If), wherein $R^1$ is —C(O) NR$^{10}$R$^{11}$, $R^{10}$ is H, and $R^{11}$ is $C_{1-6}$ alkyl. In another embodiment is a compound of Formula (If), wherein $R^1$ is —C(O)NR$^{10}$R$^{11}$, $R^{10}$ is H, and $R^{11}$ is —CH$_3$. In another embodiment is a compound of Formula (If), wherein $R^1$ is —C(O)NR$^{10}$R$^{11}$, $R^{10}$ is $C_{1-6}$ alkyl, and $R^{11}$ is $C_{1-6}$alkyl. In another embodiment is a compound of Formula (If), wherein $R^1$ is —C(O)NR$^{10}$R$^{11}$, $R^{10}$ is —CH$_3$, and $R^{11}$ is —CH$_3$.

In another embodiment is a compound of Formula (If), wherein $R^2$ is H. In another embodiment is a compound of Formula (If), wherein $R^2$ is halogen. In another embodiment is a compound of Formula (If), wherein $R^2$ is —Cl. In another embodiment is a compound of Formula (If), wherein $R^2$ is $C_{1-6}$alkyl. In another embodiment is a compound of Formula (If), wherein $R^2$ is —CH$_3$. In another embodiment is a compound of Formula (If), wherein $R^2$ is $C_{1-6}$haloalkyl. In another embodiment is a compound of Formula (If), wherein $R^2$ is —CF$_3$.

In another embodiment is a compound of Formula (If), wherein $R^{12}$ is H. In another embodiment is a compound of Formula (If), wherein $R^{12}$ is halogen. In another embodiment is a compound of Formula (If), wherein $R^2$ is F. In another embodiment is a compound of Formula (If), wherein $R^2$ is $C_{1-6}$alkyl. In another embodiment is a compound of Formula (If), wherein $R^{12}$ is —CH$_3$. In another embodiment is a compound of Formula (If), wherein $R^{13}$ is H. In another embodiment is a compound of Formula (If), wherein $R^{13}$ is $C_{1-6}$alkyl. In another embodiment is a compound of Formula (If), wherein $R^3$ is —CH$_3$. In another embodiment is a compound of Formula (If), wherein $R^{12}$ is H and $R^{13}$ is H. In another embodiment is a compound of Formula (If), wherein $R^{12}$ is H and $R^3$ is $C_{1-6}$alkyl. In another embodiment is a compound of Formula (If), wherein $R^2$ is H and $R^3$ is —CH$_3$. In another embodiment is a compound of Formula (If), wherein $R^{12}$ is $C_{1-6}$alkyl and $R^{13}$ is H. In another embodiment is a compound of Formula (If), wherein $R^2$ is —CH$_3$ and $R^{13}$ is H. In another embodiment is a compound of Formula (If), wherein $R^2$ is $C_{1-6}$alkyl and $R^{13}$ is $C_{1-6}$alkyl. In another embodiment is a compound of Formula (If), wherein $R^2$ is —CH$_3$ and $R^{13}$ is —CH$_3$.

In another embodiment is a compound of Formula (If), wherein Y is —CH$_2$—. In another embodiment is a compound of Formula (If), wherein Y is —C(O)—.

In another embodiment is a compound of Formula (If), wherein Z is —S—. In another embodiment is a compound of Formula (If), wherein Z is —O—. In another embodiment is a compound of Formula (If), wherein Z is —N(R$^{18}$)—. In another embodiment is a compound of Formula (If), wherein Z is —N(H)—. In another embodiment is a compound of Formula (If), wherein Z is —N(CH$_3$)—.

In another embodiment is a compound of Formula (If), or a solvate, hydrate, tautomer, N-oxide, stereoisomer, or pharmaceutically acceptable salt thereof, wherein m is 1, n is 1, q is 1, and p is 1. In another embodiment is a compound of Formula (If), or a solvate, hydrate, tautomer, N-oxide, stereoisomer, or pharmaceutically acceptable salt thereof, wherein m is 0, n is 1, q is 2, and p is 1. In another embodiment is a compound of Formula (If), or a solvate, hydrate, tautomer, N-oxide, stereoisomer, or pharmaceutically acceptable salt thereof, wherein m is 1, n is 1, q is 0, and p is 2. In another embodiment is a compound of Formula (If), or a solvate, hydrate, tautomer, N-oxide, stereoisomer, or pharmaceutically acceptable salt thereof, wherein m is 1, n is 1, q is 1, and p is 0. In another embodiment is a compound of Formula (If), or a solvate, hydrate, tautomer, N-oxide, stereoisomer, or pharmaceutically acceptable salt thereof, wherein m is 0, n is 0, q is 2, and p is 1.

In another embodiment is a compound of Formula (If), or a solvate, hydrate, tautomer, N-oxide, stereoisomer, or pharmaceutically acceptable salt thereof, wherein $R^4$ is halogen, —OR$^7$, $C_{1-6}$alkyl, $C_{2-6}$ alkynyl, $C_{1-6}$haloalkyl, —C(O)NR$^8$R$^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocloalkyk $C_{6-10}$aryl, or $C_{1-9}$heteroaryl are optionally substituted with 1 or 2 R$^{14}$. In another embodiment is a compound of Formula (If), or a solvate, hydrate, tautomer, N-oxide, stereoisomer, or pharmaceutically acceptable salt thereof, wherein $R^4$ is halogen, —OR$^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 R$^{14}$. In another embodiment is a compound of Formula (If), or a solvate, hydrate, tautomer, N-oxide, stereoisomer, or pharmaceutically acceptable salt thereof, wherein $R^4$ is halogen. In another embodiment is a compound of Formula (If), or a solvate, hydrate, tautomer, N-oxide, stereoisomer, or pharmaceutically acceptable salt thereof, wherein $R^4$ is —Cl. In another embodiment is a compound of Formula (If), or a solvate, hydrate, tautomer, N-oxide, stereoisomer, or pharmaceutically acceptable salt thereof, wherein $R^4$ is $C_{1-6}$haloalkyl. In another embodiment is a compound of Formula (If), or a solvate, hydrate, tautomer, N-oxide, stereoisomer, or pharmaceutically acceptable salt thereof, wherein $R^4$ is —CF$_3$. In another embodiment is a compound of Formula (If), or a solvate, hydrate, tautomer, N-oxide, stereoisomer, or pharmaceutically acceptable salt thereof, wherein $R^4$ is —OR$^7$. In another embodiment is a compound of Formula (If), or a solvate, hydrate, tautomer, N-oxide, stereoisomer, or pharmaceutically acceptable salt thereof, wherein $R^4$ is —OR$^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 R$^{14}$. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (If), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (If), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (If), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (If), or a solvate, hydrate, tautomer, N-oxide, stereoisomer, or pharmaceutically acceptable salt thereof, wherein $R^4$ is

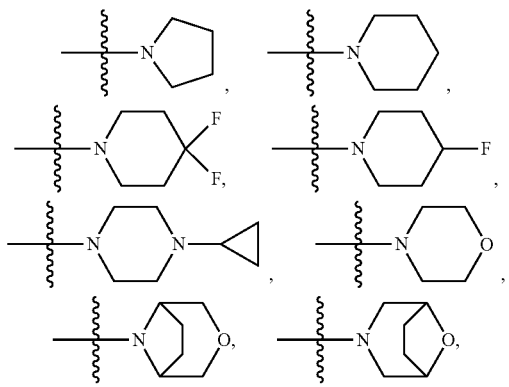

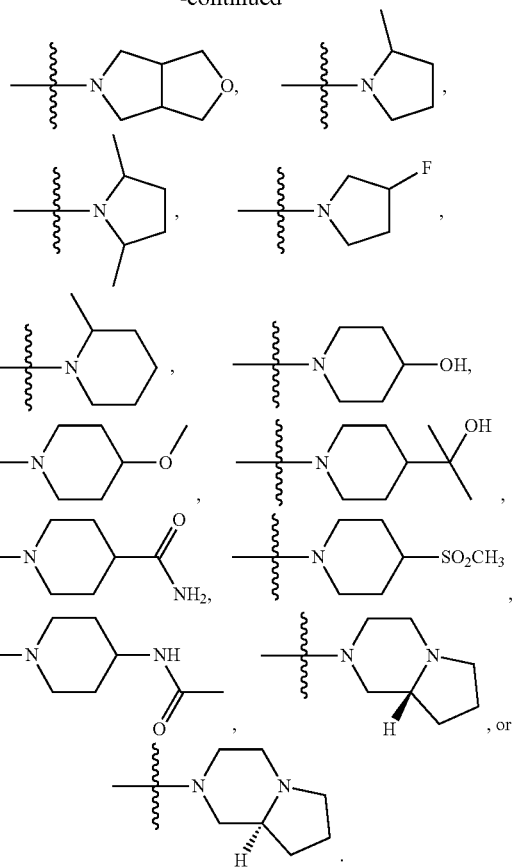

In another embodiment is a compound of Formula (If), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (If), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (If), or a solvate, hydrate, tautomer, N-oxide, stereoisomer, or pharmaceutically acceptable salt thereof, wherein $R^4$ is

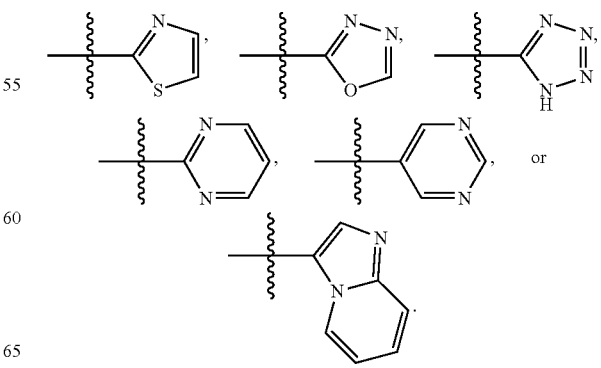

In another embodiment is a compound of Formula (If), wherein $R^5$ is H, halogen, $C_{1-6}$alkyl, $C_{1-6}$haloalkyl, $C_{1-6}$haloalkoxy. In another embodiment is a compound of Formula (If), wherein $R^5$ is H. In another embodiment is a compound of Formula (If), wherein $R^5$ is halogen. In another embodiment is a compound of Formula (If), wherein $R^5$ is —Cl. In another embodiment is a compound of Formula (If), wherein $R^5$ is —F. In another embodiment is a compound of Formula (If), wherein $R^5$ is $C_{1-6}$alkyl. In another embodiment is a compound of Formula (If), wherein $R^5$ is —CH$_3$. In another embodiment is a compound of Formula (If), wherein $R^5$ is $C_{1-6}$haloalkyl. In another embodiment is a compound of Formula (If), wherein $R^5$ is —CF$_3$. In another embodiment is a compound of Formula (If), wherein $R^5$ is $C_{1-6}$haloalkoxy. In another embodiment is a compound of Formula (If), wherein $R^5$ is —OCF$_3$.

In another embodiment is a compound of Formula (I) having the structure of Formula (Ig):

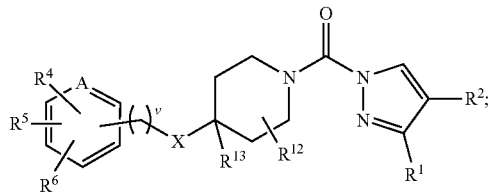

Formula (Ig)

wherein:

$R^1$ is —C(O)OR$^{15}$ or —C(O)NR$^{10}$R$^{11}$;

$R^2$ is H, halogen, $C_{1-6}$alkyl, or $C_{1-6}$haloalkyl;

A is N or C(H);

X is —O—, —N(R$^{16}$)—, or —CH$_2$N(R$^{16}$)CH$_2$—;

$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —$C_{1-6}$alkyl-$C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^4$;

$R^5$ is H, halogen, $C_{1-6}$alkyl, $C_{1-6}$haloalkyl, $C_{1-6}$haloalkoxy, or phenyl;

$R^6$ is H, halogen or $C_{1-6}$alkyl;

$R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ and $R^{11}$ are each independently H or $C_{1-6}$ alkyl;

$R^{12}$ is H, halogen, or $C_{1-6}$alkyl;

$R^{13}$ is H or $C_{1-6}$alkyl;

each $R^{14}$ is independently selected from halogen, —OH, $C_{1-6}$ alkyl, $C_{1-6}$haloalkyl, $C_{1-6}$alkoxy, —$C_{1-6}$alkyl-OH, $C_{3-8}$ cycloalkyl, —C(O)NR$^8$R$^9$, —SO$_2$—$C_{1-6}$ alkyl, and —N(R$^{17}$)C(O)—$C_{1-6}$ alkyl;

$R^{15}$ is H or $C_{1-6}$alkyl;

$R^{16}$ is H, $C_{1-6}$alkyl, —C(O)—$C_{1-6}$alkyl, or —CH$_2$CO$_2$H;

$R^{17}$ is H or $C_{1-6}$alkyl; and v is 0 or 1;

or a solvate, hydrate, tautomer, N-oxide, stereoisomer, or pharmaceutically acceptable salt thereof.

In another embodiment is a compound of Formula (Ig), wherein $R^1$ is —C(O)OR$^{15}$. In another embodiment is a compound of Formula (Ig), wherein $R^1$ is —C(O)OR$^{15}$ and $R^{15}$ is H. In another embodiment is a compound of Formula (Ig), wherein $R^1$ is —C(O)OR$^{15}$ and $R^{15}$ is $C_{1-6}$alkyl. In another embodiment is a compound of Formula (Ig), wherein $R^1$ is —C(O)OR$^{15}$ and $R^{15}$ is —CH$_3$. In another embodiment is a compound of Formula (Ig), wherein $R^1$ is —C(O)NR$^{10}$R$^{11}$. In another embodiment is a compound of Formula (Ig), wherein $R^1$ is —C(O)NR$^{10}$R$^{11}$, $R^{10}$ is H, and $R^{11}$ is H. In another embodiment is a compound of Formula (Ig), wherein $R^1$ is —C(O)NR$^{10}$R$^{11}$, $R^{10}$ is H, and $R^{11}$ is $C_{1-6}$ alkyl. In another embodiment is a compound of Formula (Ig), wherein $R^1$ is —C(O)NR$^{10}$R$^{11}$, $R^{10}$ is H, and $R^{11}$ is —CH$_3$. In another embodiment is a compound of Formula (Ig), wherein $R^1$ is —C(O)NR$^{10}$R$^{11}$, $R^{10}$ is $C_{1-6}$ alkyl, and $R^{11}$ is $C_{1-6}$alkyl. In another embodiment is a compound of Formula (Ig), wherein $R^1$ is —C(O)NR$^{10}$R$^{11}$, $R^{10}$ is —CH$_3$, and $R^{11}$ is —CH$_3$.

In another embodiment is a compound of Formula (Ig), wherein $R^2$ is H. In another embodiment is a compound of Formula (Ig), wherein $R^2$ is halogen. In another embodiment is a compound of Formula (Ig), wherein $R^2$ is —Cl. In another embodiment is a compound of Formula (Ig), wherein $R^2$ is $C_{1-6}$alkyl. In another embodiment is a compound of Formula (Ig), wherein $R^2$ is —CH$_3$. In another embodiment is a compound of Formula (Ig), wherein $R^2$ is $C_{1-6}$haloalkyl. In another embodiment is a compound of Formula (Ig), wherein $R^2$ is —CF$_3$.

In another embodiment is a compound of Formula (Ig), wherein $R^{12}$ is H. In another embodiment is a compound of Formula (Ig), wherein $R^2$ is halogen. In another embodiment is a compound of Formula (Ig), wherein $R^{12}$ is F. In another embodiment is a compound of Formula (Ig), wherein $R^{12}$ is $C_{1-6}$alkyl. In another embodiment is a compound of Formula (Ig), wherein $R^{12}$ is —CH$_3$. In another embodiment is a compound of Formula (Ig), wherein $R^{13}$ is H. In another embodiment is a compound of Formula (Ig), wherein $R^{13}$ is $C_{1-6}$alkyl. In another embodiment is a compound of Formula (Ig), wherein $R^{13}$ is —CH$_3$. In another embodiment is a compound of Formula (Ig), wherein $R^{12}$ is H and $R^{13}$ is H. In another embodiment is a compound of Formula (Ig), wherein $R^{12}$ is H and $R^{13}$ is $C_{1-6}$alkyl. In another embodiment is a compound of Formula (Ig), wherein $R^{12}$ is H and $R^{13}$ is —CH$_3$. In another embodiment is a compound of Formula (Ig), wherein $R^{12}$ is $C_{1-6}$ alkyl and $R^{13}$ is H. In another embodiment is a compound of Formula (Ig), wherein $R^{12}$ is —CH$_3$ and $R^{13}$ is H. In another embodiment is a compound of Formula (Ig), wherein $R^{12}$ is $C_{1-6}$alkyl and $R^{13}$ is $C_{1-6}$alkyl. In another embodiment is a compound of Formula (Ig), wherein $R^{12}$ is —CH$_3$ and $R^{13}$ is —CH$_3$.

In another embodiment is a compound of Formula (Ig), wherein A is N. In another embodiment is a compound of Formula (Ig), wherein A is C(H).

In another embodiment is a compound of Formula (Ig), wherein X is —O—. In another embodiment is a compound of Formula (Ig), wherein X is —N(R$^{16}$)—. In another embodiment is a compound of Formula (Ig), wherein X is —N(H)—. In another embodiment is a compound of Formula (Ig), wherein X is —N(CH$_3$)—. In another embodiment is a compound of Formula (Ig), wherein X is —CH$_2$N(R$^{16}$)CH$_2$—. In another embodiment is a compound of Formula (Ig), wherein X is —CH$_2$N(H)CH$_2$—. In another embodiment is a compound of Formula (Ig), wherein X is —CH$_2$N(CH$_3$)CH$_2$—.

In another embodiment is a compound of Formula (Ig), wherein v is 0. In another embodiment is a compound of Formula (Ig), wherein v is 1.

In another embodiment is a compound of Formula (Ig), or a solvate, hydrate, tautomer, N-oxide, stereoisomer, or pharmaceutically acceptable salt thereof, wherein $R^4$ is halogen, —$OR^7$, $C_{1-6}$alkyl, $C_{2-6}$ alkynyl, $C_{1-6}$haloalkyl, —C(O)$NR^8R^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is halogen, —$OR^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^4$. In another embodiment is a compound of Formula (Ig), or a solvate, hydrate, tautomer, N-oxide, stereoisomer, or pharmaceutically acceptable salt thereof, wherein $R^4$ is halogen. In another embodiment is a compound of Formula (Ig), or a solvate, hydrate, tautomer, N-oxide, stereoisomer, or pharmaceutically acceptable salt thereof, wherein $R^4$ is —Cl. In another embodiment is a compound of Formula (Ig), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ig), or a solvate, hydrate, tautomer, N-oxide, stereoisomer, or pharmaceutically acceptable salt thereof, wherein $R^4$ is —$CF_3$. In another embodiment is a compound of Formula (Ig), or a solvate, hydrate, tautomer, N-oxide, stereoisomer, or pharmaceutically acceptable salt thereof, wherein $R^4$ is —$OR^7$. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is $C_{1-6}$haloalkyl. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is —$CF_3$. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is $C_{6-10}$aryl or $C_{1-9}$heteroaryl, wherein $C_{6-10}$aryl or $C_{1-9}$heteroaryl are optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —$CF_3$. In another embodiment is a compound of Formula (Ig), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^4$. In another embodiment is a compound of Formula (Ig), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ig), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^4$. In another embodiment is a compound of Formula (Ig), or a solvate, hydrate, tautomer, N-oxide, stereoisomer, or pharmaceutically acceptable salt thereof, wherein $R^4$ is

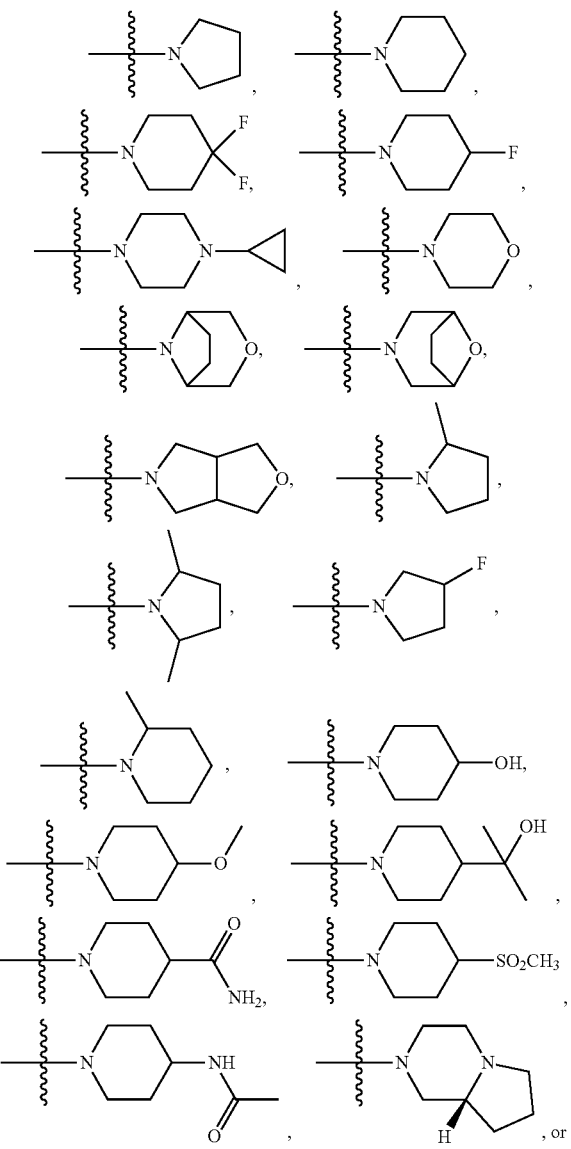

-continued

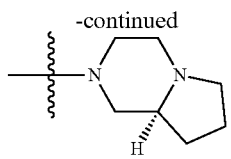

In another embodiment is a compound of Formula (Ig), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ig), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (Ig), or a solvate, hydrate, tautomer, N-oxide, stereoisomer, or pharmaceutically acceptable salt thereof, wherein $R^4$ is

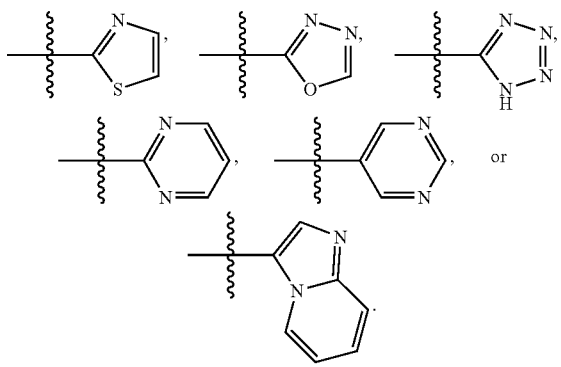

In another embodiment is a compound of Formula (Ig), wherein $R^5$ is H, halogen, $C_{1-6}$alkyl, $C_{1-6}$haloalkyl, $C_{1-6}$haloalkoxy. In another embodiment is a compound of Formula (Ig), wherein $R^5$ is H. In another embodiment is a compound of Formula (Ig), wherein $R^5$ is halogen. In another embodiment is a compound of Formula (Ig), wherein $R^5$ is —Cl. In another embodiment is a compound of Formula (Ig), wherein $R^5$ is —F. In another embodiment is a compound of Formula (Ig), wherein $R^5$ is $C_{1-6}$alkyl. In another embodiment is a compound of Formula (Ig), wherein $R^5$ is —CH$_3$. In another embodiment is a compound of Formula (Ig), wherein $R^5$ is $C_{1-6}$haloalkyl. In another embodiment is a compound of Formula (Ig), wherein $R^5$ is —CF$_3$. In another embodiment is a compound of Formula (Ig), wherein $R^5$ is $C_{1-6}$haloalkoxy. In another embodiment is a compound of Formula (Ig), wherein $R^5$ is —OCF$_3$.

In another embodiment is a compound of Formula (Ig), wherein $R^6$ is H. In another embodiment is a compound of Formula (Ig), wherein $R^6$ is halogen. In another embodiment is a compound of Formula (Ig), wherein $R^6$ is —Cl. In another embodiment is a compound of Formula (Ig), wherein $R^6$ is —F. In another embodiment is a compound of Formula (Ig), wherein $R^6$ is $C_{1-6}$alkyl. In another embodiment is a compound of Formula (Ig), wherein $R^6$ is —CH$_3$.

In another embodiment is a compound of Formula (I) having the structure of Formula (Ih):

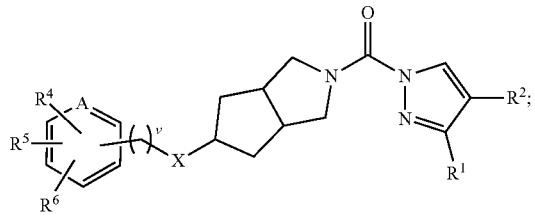

Formula (Ih)

wherein:
$R^1$ is —C(O)OR$^{15}$ or —C(O)NR$^{10}$R$^{11}$;
$R^2$ is H, halogen, $C_{1-6}$alkyl, or $C_{1-6}$haloalkyl;
A is N or C(H);
X is —O—, —N(R$^{16}$)—, or —CH$_2$N(R$^{16}$)CH$_2$—;
$R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{2-9}$heterocycloalkyl, —C$_{1-6}$alkyl-C$_{2-9}$heterocycloalkyl, $C_{6-10}$aryl, or $C_{1-9}$heteroaryl are optionally substituted with 1 or 2 $R^4$;
$R^5$ is H, halogen, $C_{1-6}$alkyl, $C_{1-6}$haloalkyl, $C_{1-6}$haloalkoxy, or phenyl;
$R^6$ is H, halogen or $C_{1-6}$alkyl;
$R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{10}$ and $R^{11}$ are each independently H or $C_{1-6}$ alkyl;
each $R^{14}$ is independently selected from halogen, —OH, $C_{1-6}$ alkyl, $C_{1-6}$haloalkyl, $C_{1-6}$alkoxy, —C$_{1-6}$alkyl-OH, $C_{3-8}$ cycloalkyl, —C(O)NR$^8$R$^9$, —SO$_2$—C$_{1-6}$ alkyl, and —N(R$^{17}$)C(O)—C$_{1-6}$ alkyl;
$R^{15}$ is H or $C_{1-6}$alkyl;
$R^{16}$ is H, $C_{1-6}$alkyl, —C(O)—C$_{1-6}$alkyl, or —CH$_2$CO$_2$H;
$R^{17}$ is H or $C_{1-6}$alkyl; and
v is 0 or 1;
or a solvate, hydrate, tautomer, N-oxide, stereoisomer, or pharmaceutically acceptable salt thereof.

In another embodiment is a compound of Formula (Ih), wherein $R^1$ is —C(O)OR$^{15}$. In another embodiment is a compound of Formula (Ih), wherein $R^1$ is —C(O)OR$^{15}$ and $R^{15}$ is H. In another embodiment is a compound of Formula (Ih), wherein $R^1$ is —C(O)OR$^{15}$ and $R^{15}$ is $C_{1-6}$alkyl. In another embodiment is a compound of Formula (Ih), wherein $R^1$ is —C(O)OR$^{15}$ and $R^{15}$ is —CH$_3$. In another embodiment is a compound of Formula (Ih), wherein $R^1$ is —C(O)NR$^{10}$R$^{11}$. In another embodiment is a compound of Formula (Ih), wherein $R^1$ is —C(O)NR$^{10}$R$^{11}$-10 is H, and $R^{11}$ is H. In another embodiment is a compound of Formula (Ih), wherein $R^1$ is —C(O)NR$^{10}$R$^{11}$-10 is H, and $R^{11}$ is $C_{1-6}$ alkyl. In another embodiment is a compound of Formula (Ih), wherein $R^1$ is —C(O)NR$^{10}$R$^{11}$, $R^{10}$ is H, and $R^{11}$ is —CH$_3$. In another embodiment is a compound of Formula (Ih), wherein $R^1$ is —C(O) NR$^{10}$R$^{11}$, $R^{10}$ is $C_{1-6}$ alkyl, and $R^{11}$ is $C_{1-6}$alkyl. In another embodiment is a compound of Formula (Ih), wherein $R^1$ is —C(O) NR$^{10}$R$^{11}$, $R^{10}$ is —CH$_3$, and $R^{11}$ is —CH$_3$.

In another embodiment is a compound of Formula (Ih), wherein $R^2$ is H. In another embodiment is a compound of Formula (Ih), wherein $R^2$ is halogen. In another embodiment is a compound of Formula (Ih), wherein $R^2$ is —Cl. In another embodiment is a compound of Formula (Ih), wherein $R^2$ is $C_{1-6}$alkyl. In another embodiment is a compound of Formula (Ih), wherein $R^2$ is —CH$_3$. In another embodiment is a compound of Formula (Ih), wherein $R^2$ is $C_{1-6}$haloalkyl. In another embodiment is a compound of Formula (Ih), wherein $R^2$ is —CF$_3$.

In another embodiment is a compound of Formula (Ih), wherein A is N. In another embodiment is a compound of Formula (Ih), wherein A is C(H).

In another embodiment is a compound of Formula (Ih), wherein X is —O—. In another embodiment is a compound of Formula (Ih), wherein X is —N(R$^{16}$)—. In another embodiment is a compound of Formula (Ih), wherein X is —N(H)—. In another embodiment is a compound of Formula (Ih), wherein X is —N(CH$_3$)—. In another embodiment is a compound of Formula (Ih), wherein X is —CH$_2$N(R$^{16}$)CH$_2$—. In another embodiment is a compound of Formula (Ih), wherein X is —CH$_2$N(H)CH$_2$—. In another embodiment is a compound of Formula (Ih), wherein X is —CH$_2$N(CH$_3$)CH$_2$—.

In another embodiment is a compound of Formula (Ih), wherein v is 0. In another embodiment is a compound of Formula (Ih), wherein v is 1.

In another embodiment is a compound of Formula (Ih), or a solvate, hydrate, tautomer, N-oxide, stereoisomer, or pharmaceutically acceptable salt thereof, wherein $R^4$ is halogen, —OR$^7$, $C_{1-6}$alkyl, $C_{2-6}$ alkynyl, $C_{1-6}$haloalkyl, —C(O)NR$^8$R$^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 R$^{14}$. In another embodiment is a compound of Formula (Ih), or a solvate, hydrate, tautomer, N-oxide, stereoisomer, or pharmaceutically acceptable salt thereof, wherein $R^4$ is halogen, —OR$^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 R$^4$. In another embodiment is a compound of Formula (Ih), or a solvate, hydrate, tautomer, N-oxide, stereoisomer, or pharmaceutically acceptable salt thereof, wherein $R^4$ is halogen. In another embodiment is a compound of Formula (Ih), or a solvate, hydrate, tautomer, N-oxide, stereoisomer, or pharmaceutically acceptable salt thereof, wherein $R^4$ is —Cl. In another embodiment is a compound of Formula (Ih), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ih), or a solvate, hydrate, tautomer, N-oxide, stereoisomer, or pharmaceutically acceptable salt thereof, wherein $R^4$ is —CF$_3$. In another embodiment is a compound of Formula (Ih), or a solvate, hydrate, tautomer, N-oxide, stereoisomer, or pharmaceutically acceptable salt thereof, wherein $R^4$ is —OR$^7$. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 R$^{14}$. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is $C_{1-6}$haloalkyl. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is —CF$_3$. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is $C_{6-10}$aryl or $C_{1-9}$heteroaryl, wherein $C_{6-10}$aryl or $C_{1-9}$heteroaryl are optionally substituted with 1 or 2 R$^{14}$. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ih), or a solvate, hydrate, tautomer, N-oxide, stereoisomer, or pharmaceutically acceptable salt thereof, wherein $R^4$ is —OR$^7$ and R$^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —CF$_3$. In another embodiment is a compound of Formula (Ih), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 R$^{14}$. In another embodiment is a compound of Formula (Ih), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ih), or a solvate, hydrate, tautomer, N-oxide, stereoisomer, or pharmaceutically acceptable salt thereof, wherein $R^4$ is $C_{2-9}$heterocycloalkyl substituted with 1 or 2 R$^{14}$. In another embodiment is a compound of Formula (Ih), or a solvate, hydrate, tautomer, N-oxide, stereoisomer, or pharmaceutically acceptable salt thereof, wherein $R^4$ is -continued

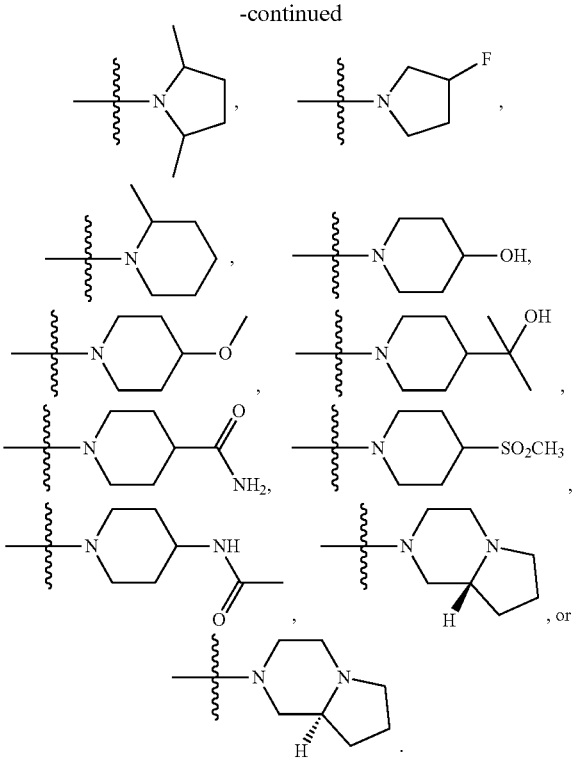

In another embodiment is a compound of Formula (Ih), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ih), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is

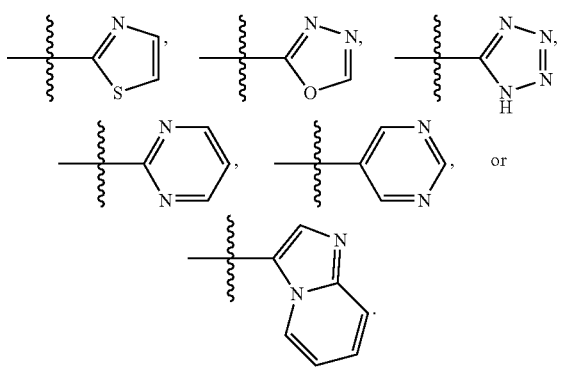

In another embodiment is a compound of Formula (Ih), wherein $R^5$ is H, halogen, $C_{1-6}$alkyl, $C_{1-6}$haloalkyl, $C_{1-6}$haloalkoxy. In another embodiment is a compound of Formula (Ih), wherein $R^5$ is H. In another embodiment is a compound of Formula (Ih), wherein $R^5$ is halogen. In another embodiment is a compound of Formula (Ih), wherein $R^5$ is —Cl. In another embodiment is a compound of Formula (Ih), wherein $R^5$ is —F. In another embodiment is a compound of Formula (Ih), wherein $R^5$ is $C_{1-6}$alkyl. In another embodiment is a compound of Formula (Ih), wherein $R^5$ is —CH$_3$. In another embodiment is a compound of Formula (Ih), wherein $R^5$ is $C_{1-6}$haloalkyl. In another embodiment is a compound of Formula (Ih), wherein $R^5$ is —CF$_3$. In another embodiment is a compound of Formula (Ih), wherein $R^5$ is $C_{1-6}$haloalkoxy. In another embodiment is a compound of Formula (Ih), wherein $R^5$ is —OCF$_3$.

In another embodiment is a compound of Formula (Ih), wherein $R^6$ is H. In another embodiment is a compound of Formula (Ih), wherein $R^6$ is halogen. In another embodiment is a compound of Formula (Ih), wherein $R^6$ is —Cl. In another embodiment is a compound of Formula (Ih), wherein $R^6$ is —F. In another embodiment is a compound of Formula (Ih), wherein $R^6$ is $C_{1-6}$alkyl. In another embodiment is a compound of Formula (Ih), wherein $R^6$ is —CH$_3$.

In another embodiment is a compound of Formula (I) having the structure of Formula (Ii):

Formula (Ii)

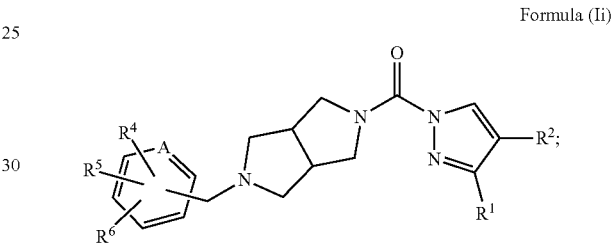

wherein:
  $R^1$ is —C(O)OR$^{15}$ or —C(O)NR$^{10}$R$^{11}$;
  $R^2$ is H, halogen, $C_{1-6}$alkyl, or $C_{1-6}$haloalkyl;
  A is N or C(H);
  $R^4$ is H, halogen, —OR$^7$, $C_{1-6}$alkyl, $C_{2-6}$alkenyl, $C_{2-6}$alkynyl, $C_{1-6}$haloalkyl, —C(O)NR$^8$R$^9$, $C_{2-9}$heterocycloalkyl, —C$_{1-6}$alkyl-C$_{2-9}$heterocycloalkyl, $C_{6-10}$aryl, or $C_{1-9}$heteroaryl, wherein $C_{2-9}$heterocycloalkyl, —C$_{1-6}$alkyl-C$_{2-9}$heterocycloalkyl, $C_{6-10}$aryl, or $C_{1-9}$heteroaryl are optionally substituted with 1 or 2 $R^4$;
  $R^5$ is H, halogen, $C_{1-6}$alkyl, $C_{1-6}$haloalkyl, $C_{1-6}$haloalkoxy, or phenyl;
  $R^6$ is H, halogen or $C_{1-6}$alkyl;
  $R^7$ is H, $C_{1-6}$ alkyl, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
  each $R^8$ and each $R^9$ are independently selected from H and $C_{1-6}$alkyl; or $R^8$ and $R^9$ together with the nitrogen to which they are attached are combined to form a heterocycloalkyl ring;
  $R^{10}$ and $R^{11}$ are each independently H or $C_{1-6}$ alkyl;
  each $R^{14}$ is independently selected from halogen, —OH, $C_{1-6}$ alkyl, $C_{1-6}$haloalkyl, $C_{1-6}$alkoxy, —C$_{1-6}$alkyl-OH, $C_{3-8}$ cycloalkyl, —C(O)NR$^8$R$^9$, —SO$_2$—C$_{1-6}$ alkyl, and —N(R$^{17}$)C(O)—C$_{1-6}$ alkyl;
  $R^{15}$ is H or $C_{1-6}$alkyl; and
  $R^{17}$ is H or $C_{1-6}$alkyl;
  or a solvate, hydrate, tautomer, N-oxide, stereoisomer, or pharmaceutically acceptable salt thereof.

In another embodiment is a compound of Formula (Ii), wherein $R^1$ is —C(O)OR$^{15}$. In another embodiment is a compound of Formula (Ii), wherein $R^1$ is —C(O)OR$^{15}$ and $R^{15}$ is H. In another embodiment is a compound of Formula (Ii), wherein $R^1$ is —C(O)OR$^{15}$ and $R^{15}$ is $C_{1-6}$alkyl. In another embodiment is a compound of Formula (Ii), wherein $R^1$ is —C(O)OR$^{15}$ and $R^{15}$ is —CH$_3$. In another embodiment is a compound of Formula (Ii), wherein $R^1$ is —C(O)NR$^{10}$R$^{11}$. In another embodiment is a compound of Formula (Ii), wherein $R^1$ is —C(O)NR$^{10}$R$^{11}$, $R^{10}$ is H, and $R^{11}$ is H. In another embodiment is a compound of Formula (Ii), wherein $R^1$ is —C(O)NR$^{10}$R$^{11}$, $R^{10}$ is H, and $R^{11}$ is $C_{1-6}$alkyl. In another embodiment is a compound of Formula (Ii), wherein $R^1$ is —C(O)NR$^{10}$R$^{11}$, $R^{10}$ is H, and $R^{11}$ is —CH$_3$. In another embodiment is a compound of Formula (Ii), wherein $R^1$ is —C(O)NR$^{10}$R$^{11}$, $R^{10}$ is $C_{1-6}$ alkyl, and $R^{11}$ is $C_{1-6}$alkyl. In another embodiment is a compound of Formula (Ii), wherein $R^1$ is —C(O)NR$^{10}$R$^{11}$, $R^{10}$ is —CH$_3$ and $R^{11}$ is —CH$_3$.

In another embodiment is a compound of Formula (Ii), wherein $R^2$ is H. In another embodiment is a compound of Formula (Ii), wherein $R^2$ is halogen. In another embodiment is a compound of Formula (Ii), wherein $R^2$ is —Cl. In another embodiment is a compound of Formula (Ii), wherein $R^2$ is $C_{1-6}$alkyl. In another embodiment is a compound of Formula (Ii), wherein $R^2$ is —CH$_3$. In another embodiment is a compound of Formula (Ii), wherein $R^2$ is $C_{1-6}$haloalkyl. In another embodiment is a compound of Formula (Ii), wherein $R^2$ is —CF$_3$.

In another embodiment is a compound of Formula (Ii), wherein A is N. In another embodiment is a compound of Formula (Ii), wherein A is C(H).

In another embodiment is a compound of Formula (Ii), or a solvate, hydrate, tautomer, N-oxide, stereoisomer, or pharmaceutically acceptable salt thereof, wherein $R^4$ is halogen, —OR$^7$, $C_{1-6}$alkyl, $C_{2-6}$alkynyl, $C_{1-6}$haloalkyl, —C(O)NR$^8$R$^9$, $C_{2-9}$heterocycloalkyl, $C_{6-10}$aryl, or $C_{1-9}$heteroaryl, wherein $C_{2-9}$heterocycloalkyl, —$C_{1-6}$alkyl-$C_{2-9}$heterocycloalkyl, $C_{6-10}$aryl, or $C_{1-9}$heteroaryl are optionally substituted with 1 or 2 R$^{14}$. In another embodiment is a compound of Formula (Ii), or a solvate, hydrate, tautomer, N-oxide, stereoisomer, or pharmaceutically acceptable salt thereof, wherein $R^4$ is halogen, —OR$^7$, $C_{1-6}$haloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 R$^4$. In another embodiment is a compound of Formula (Ii), or a solvate, hydrate, tautomer, N-oxide, stereoisomer, or pharmaceutically acceptable salt thereof, wherein $R^4$ is halogen. In another embodiment is a compound of Formula (Ii), or a solvate, hydrate, tautomer, N-oxide, stereoisomer, or pharmaceutically acceptable salt thereof, wherein $R^4$ is —Cl. In another embodiment is a compound of Formula (Ii), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ii), or a solvate, hydrate, tautomer, N-oxide, stereoisomer, or pharmaceutically acceptable salt thereof, wherein $R^4$ is —CF$_3$. In another embodiment is a compound of Formula (Ii), or a solvate, hydrate, tautomer, N-oxide, stereoisomer, or pharmaceutically acceptable salt thereof, wherein $R^4$ is —OR$^7$. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is $C_{1-6}$haloalkyl, $C_{6-10}$aryl, or $C_{1-9}$heteroaryl, wherein $C_{6-10}$aryl or $C_{1-9}$heteroaryl are optionally substituted with 1 or 2 R$^{14}$. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is $C_{1-6}$haloalkyl. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is —CF$_3$. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is $C_{6-10}$aryl or $C_{1-9}$heteroaryl, wherein $C_{6-10}$aryl or $C_{1-9}$heteroaryl are optionally substituted with 1 or 2 R$^{14}$. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are optionally substituted with halogen or $C_{1-6}$haloalkyl. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are unsubstituted. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with halogen or $C_{1-6}$haloalkyl. In another embodiment is a compound of Formula (Ii), or a solvate, hydrate, tautomer, N-oxide, stereoisomer, or pharmaceutically acceptable salt thereof, wherein $R^4$ is —OR$^7$ and $R^7$ is phenyl, pyridyl, pyrimidinyl, pyridizinyl, or pyrazinyl, wherein phenyl, pyridyl, pyrimidinyl, pyridizinyl, or pyrazinyl are substituted with —Cl or —CF$_3$. In another embodiment is a compound of Formula (Ii), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 R$^4$. In another embodiment is a compound of Formula (Ii), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ii), or a solvate, hydrate, tautomer, N-oxide, stereoisomer, or pharmaceutically acceptable salt thereof, wherein $R^4$ is $C_{2-9}$heterocycloalkyl substituted with 1 or 2 R$^4$. In another embodiment is a compound of Formula (Ii), or a solvate, hydrate, tautomer, N-oxide, stereoisomer, or pharmaceutically acceptable salt thereof, wherein $R^4$ is -continued

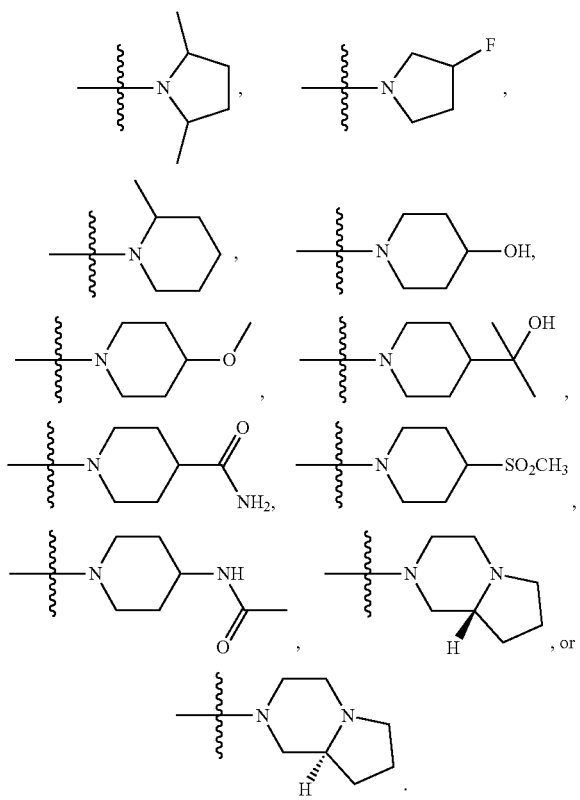

In another embodiment is a compound of Formula (Ii), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ii), or a solvate, hydrate, tautomer, N-oxide, stereoisomer, or pharmaceutically acceptable salt thereof, wherein $R^4$ is $C_{2-9}$heteroaryl substituted with 1 or 2 $R^4$. In another embodiment is a compound of Formula (Ii), or a solvate, hydrate, tautomer, N-oxide, stereoisomer, or pharmaceutically acceptable salt thereof, wherein $R^4$ is

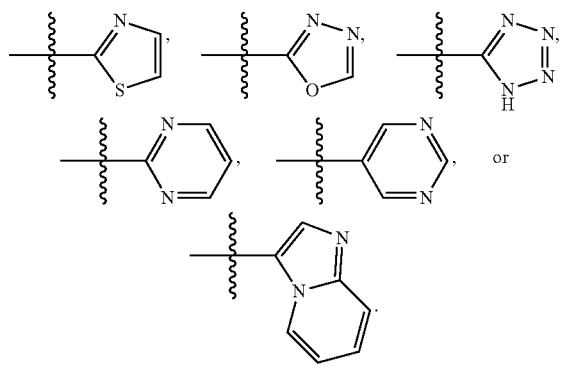

In another embodiment is a compound of Formula (Ii), wherein $R^5$ is H, halogen, $C_{1-6}$alkyl, $C_{1-6}$haloalkyl, $C_{1-6}$ haloalkoxy. In another embodiment is a compound of Formula (Ii), wherein $R^5$ is H. In another embodiment is a compound of Formula (Ii), wherein $R^5$ is halogen. In another embodiment is a compound of Formula (Ii), wherein $R^5$ is —Cl. In another embodiment is a compound of Formula (Ii), wherein $R^5$ is —F. In another embodiment is a compound of Formula (Ii), wherein $R^5$ is $C_{1-6}$alkyl. In another embodiment is a compound of Formula (Ii), wherein $R^5$ is —CH$_3$. In another embodiment is a compound of Formula (Ii), wherein $R^5$ is $C_{1-6}$haloalkyl. In another embodiment is a compound of Formula (Ii), wherein $R^5$ is —CF$_3$. In another embodiment is a compound of Formula (Ii), wherein $R^5$ is $C_{1-6}$haloalkoxy. In another embodiment is a compound of Formula (Ii), wherein $R^5$ is —OCF$_3$.

In another embodiment is a compound of Formula (Ii), wherein $R^6$ is H. In another embodiment is a compound of Formula (Ii), wherein $R^6$ is halogen. In another embodiment is a compound of Formula (Ii), wherein $R^6$ is —Cl. In another embodiment is a compound of Formula (Ii), wherein $R^6$ is —F. In another embodiment is a compound of Formula (Ii), wherein $R^6$ is $C_{1-6}$alkyl. In another embodiment is a compound of Formula (Ii), wherein $R^6$ is —CH$_3$.

Further embodiments provided herein include combinations of one or more of the particular embodiments set forth above.

In some embodiments, the compound disclosed herein is selected from examples 1-456.

In another embodiment is a compound having the structure:

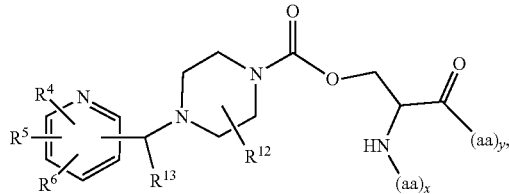

wherein $R^4$, $R^5$, $R^6$, $R^{12}$, and $R^{13}$ are defined as in Formula (Ia) described herein, and x and y are at least one amino acid (aa). In another embodiment is a compound having the structure:

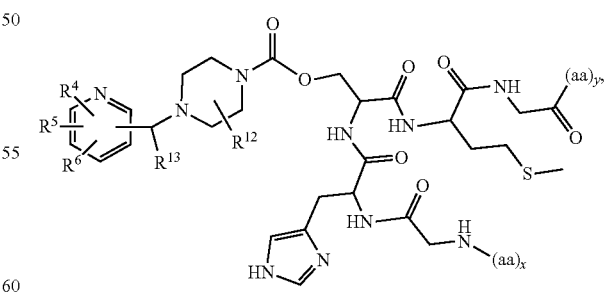

wherein $R^4$, $R^5$, $R^6$, $R^{12}$, and $R^{13}$ are defined as in Formula (Ia) described herein, and x and y are at least one amino acid (aa).

In another embodiment is a compound having the structure:

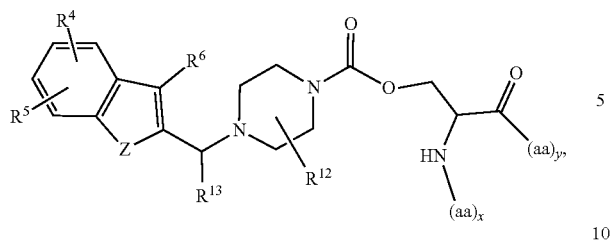

wherein $R^4$, $R^5$, $R^6$, $R^{12}$, $R^{13}$ and Z are defined as in Formula (Ib) described herein, and x and y are at least one amino acid (aa). In another embodiment is a compound having the structure:

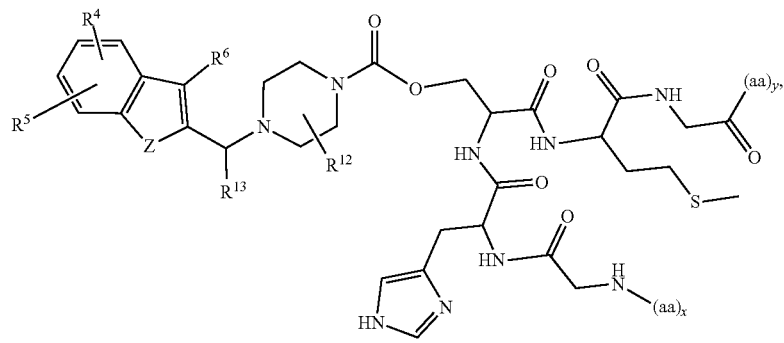

wherein $R^4$, $R^5$, $R^6$, $R^{12}$, $R^{13}$ and Z are defined as in Formula (Ib) described herein, and x and y are at least one amino acid (aa).

In another embodiment is a compound having the structure:

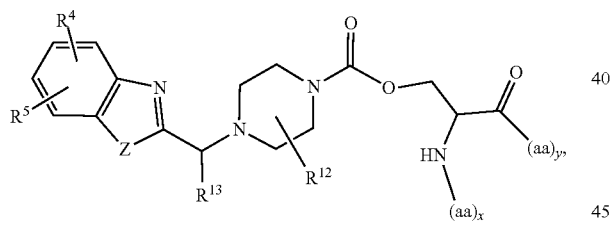

wherein $R^4$, $R^5$, $R^{12}$, $R^{13}$ and Z are defined as in Formula (Ic) described herein, and x and y are at least one amino acid (aa). In another embodiment is a compound having the structure:

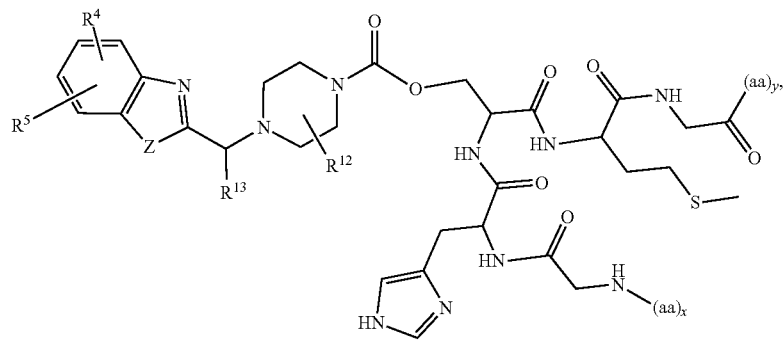

wherein $R^4$, $R^5$, $R^{12}$, $R^{13}$, and Z are defined as in Formula (Ic) described herein, and x and y are at least one amino acid (aa).

In another embodiment is a compound having the structure:

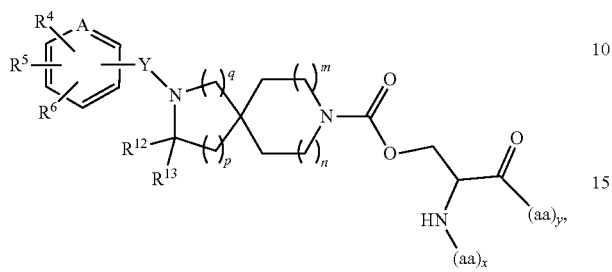

wherein $R^4$, $R^5$, $R^6$, $R^{12}$, $R^{13}$, A, Y, m, n, p, and q are defined as in Formula (Id) described herein, and x and y are at least one amino acid (aa). In another embodiment is a compound having the structure:

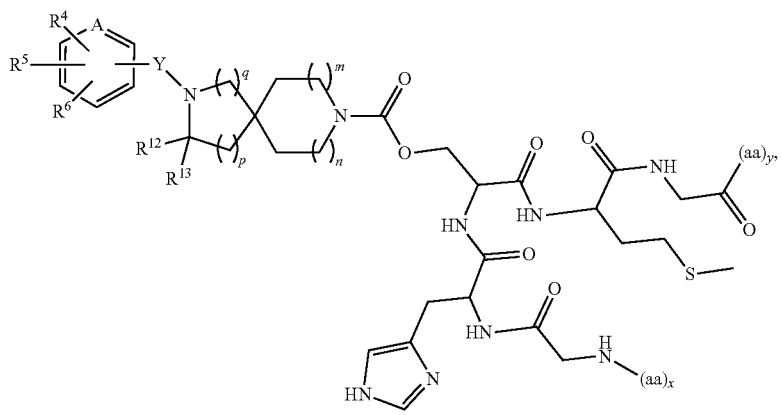

wherein $R^4$, $R^5$, $R^6$, $R^{12}$, $R^{13}$, A, Y, m, n, p, and q are defined as in Formula (Id) described herein, and x and y are at least one amino acid (aa).

In another embodiment is a compound having the structure:

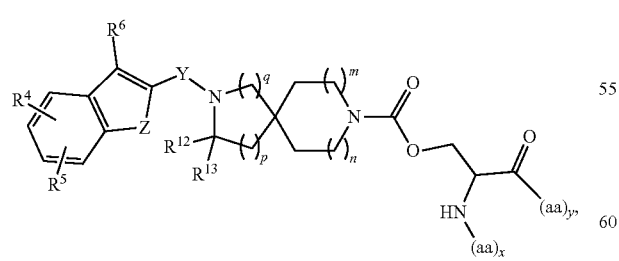

wherein $R^4$, $R^5$, $R^6$, $R^{12}$, $R^{13}$, Y, Z, m, n, p, and q are defined as in Formula (Ie) described herein, and x and y are at least one amino acid (aa). In another embodiment is a compound having the structure:

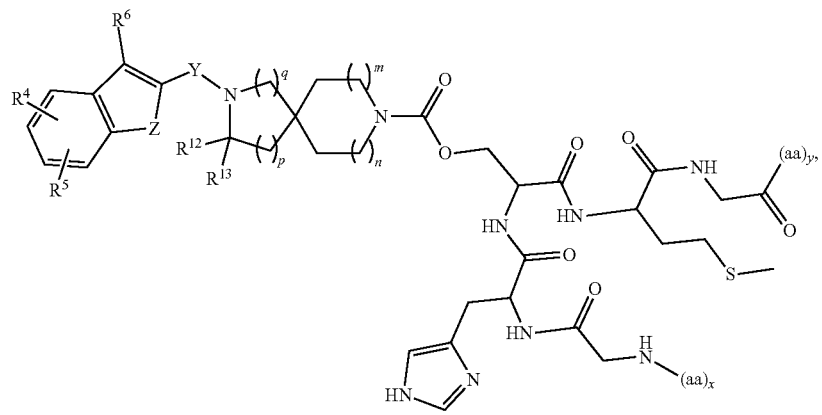

wherein $R^4$, $R^5$, $R^6$, $R^{12}$, $R^{13}$, Y, Z, m, n, p, and q are defined as in Formula (Ie) described herein, and x and y are at least one amino acid (aa).

In another embodiment is a compound having the structure:

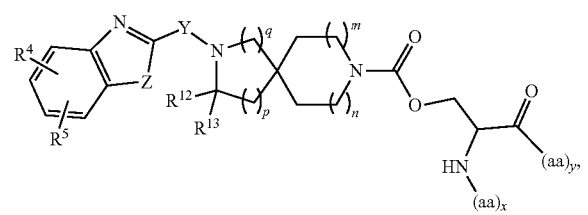

wherein $R^4$, $R^5$, $R^{12}$, $R^{13}$, Y, Z, m, n, p, and q are defined as in Formula (If) described herein, and x and y are at least one amino acid (aa). In another embodiment is a compound having the structure:

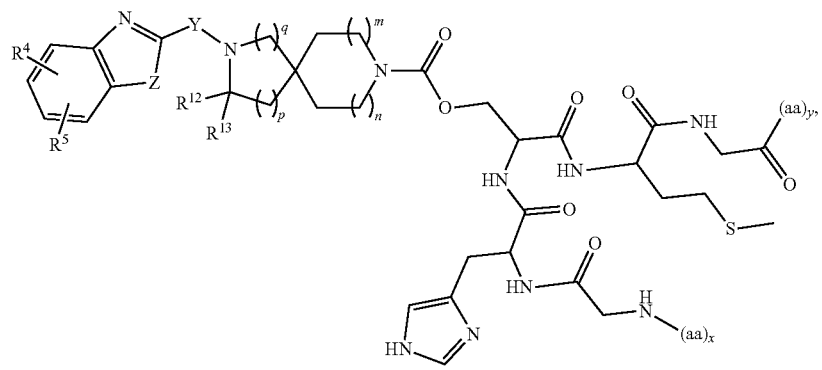

wherein $R^4$, $R^5$, $R^{12}$, $R^{13}$, Y, Z, m, n, p, and q are defined as in Formula (If) described herein, and x and y are at least one amino acid (aa).

In another embodiment is a compound having the structure:

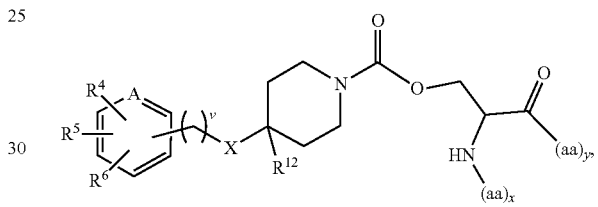

wherein $R^4$, $R^5$, $R^6$, $R^{12}$, A, X, and v are defined as in Formula (Ig) described herein, and x and y are at least one amino acid (aa). In another embodiment is a compound having the structure:

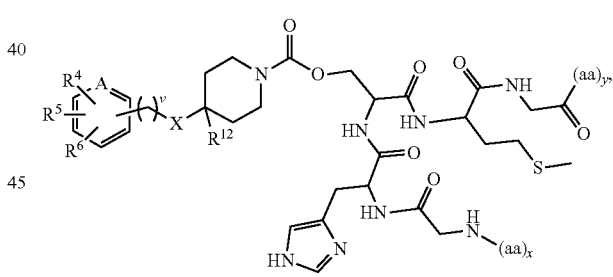

wherein R⁴, R⁵, R⁶, R¹², A, X, and v are defined as in Formula (Ig) described herein, and x and y are at least one amino acid (aa).

In another embodiment is a compound having the structure:

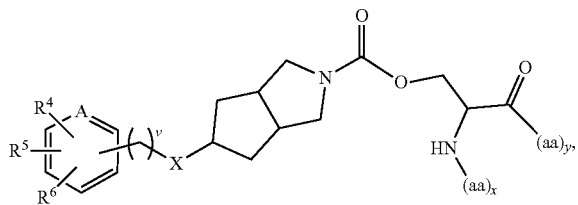

wherein R⁴, R⁵, R⁶, A, X, and v are defined as in Formula (Ih) described herein, and x and y are at least one amino acid (aa). In another embodiment is a compound having the structure:

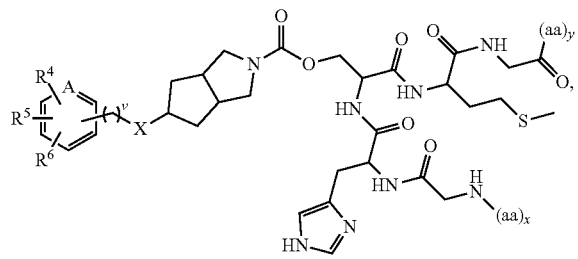

wherein R⁴, R⁵, R⁶, A, X, and v are defined as in Formula (Ih) described herein, and x and y are at least one amino acid (aa).

In another embodiment is a compound having the structure:

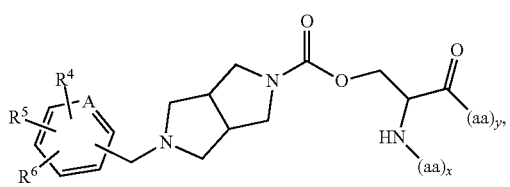

wherein R⁴, R⁵, and R⁶ are defined as in Formula (Ii) described herein, and x and y are at least one amino acid (aa). In another embodiment is a compound having the structure:

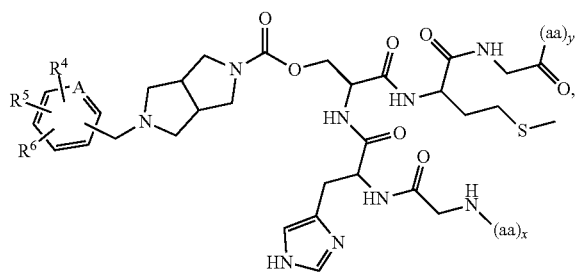

wherein R⁴, R⁵, and R⁶ are defined as in Formula (Ii) described herein, and x and y are at least one amino acid (aa).

Described herein are inhibitors of monoacylglycerol lipase (MAGL) having the structure of Formula (I), (I'), (Ia), (Ib), (Ic), (Id), (Ie), (If), (Ig), (Ih), or (Ii). In one embodiment, the inhibitors of MAGL are covalent inhibitors of MAGL, that is, the compounds of Formula (I), (I'), (Ia), (Ib), (Ic), (Id), (Ie), (If), (Ig), (Ih), or (Ii) react with a serine residue of MAGL to form a modified serine residue, comprising the staying group of Formula (I), (I'), (Ia), (Ib), (Ic), (Id), (Ie), (If), (Ig), (Ih), or (Ii); in such an embodiment, the leaving group of Formula (I), (I'), (Ia), (Ib), (Ic), (Id), (Ie), (If), (Ig), (Ih), or (Ii) is removed from the compound of Formula (I), (I'), (Ia), (Ib), (Ic), (Id), (Ie), (If), (Ig), (Ih), or (Ii). In a further embodiment, the covalent inhibitors of MAGL react irreversibly with a serine residue of MAGL to form the modified serine residue.

The staying group portion of the compounds of Formula (Ia) is

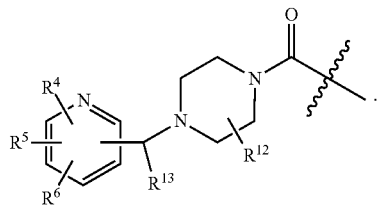

The staying group portion of the compounds of Formula (Ib) is

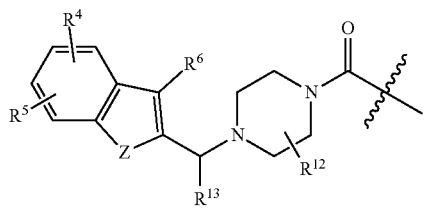

The staying group portion of the compounds of Formula (Ic) is

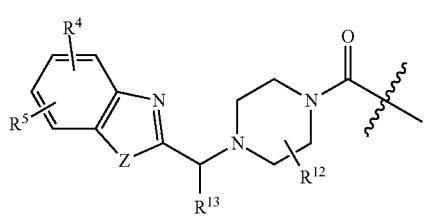

The staying group portion of the compounds of Formula (Id) is

The staying group portion of the compounds of Formula (Ie) is

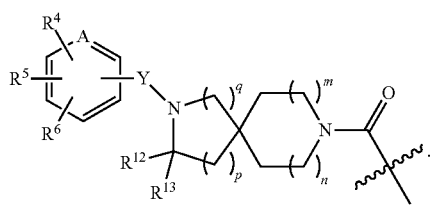

The staying group portion of the compounds of Formula (If) is

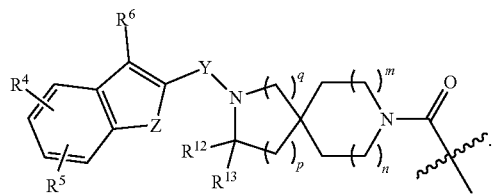

The staying group portion of the compounds of Formula (Ig) is

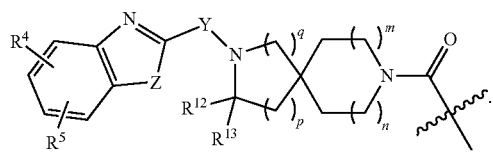

The staying group portion of the compounds of Formula (Ih) is

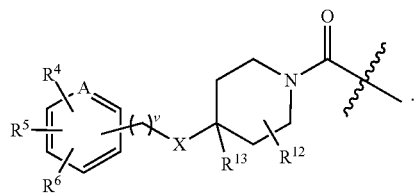

The staying group portion of the compounds of Formula (Ii) is

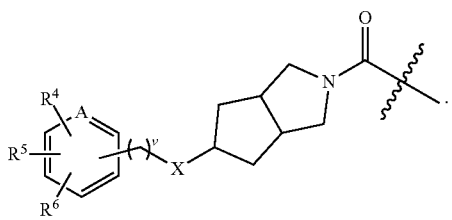

The leaving group portion of the compounds of Formula (I), (I'), (Ia), (Ib), (Ic), (Id), (Ie), (If), (Ig), (Ih), or (Ii) is:

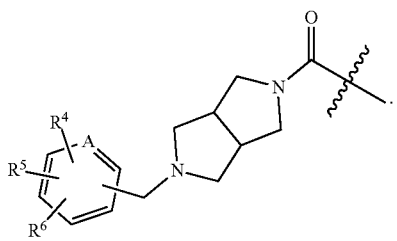

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$C$_1$, respectively. Compounds described herein, and pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

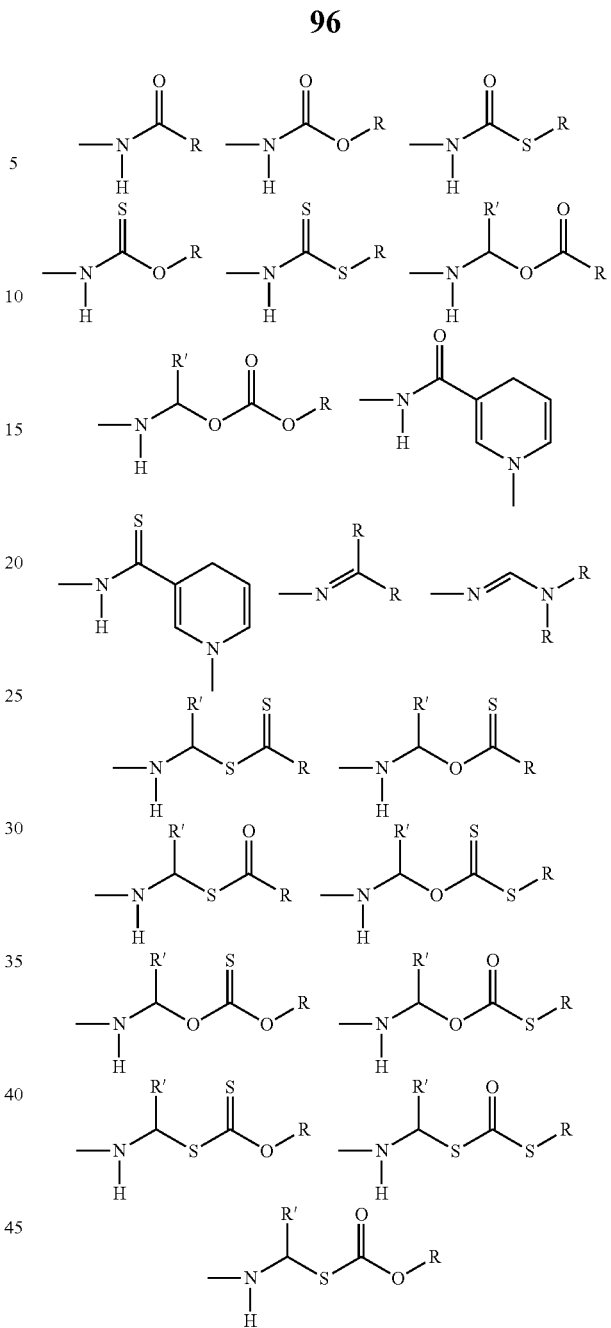

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (I'), (Ia), (Ib), (Ic), (Id), (Ie), (If), (Ig), (Ih), or (Ii) as described herein is administered as a pure chemical. In some embodiments, the compound of Formula (I), (I'), (Ia), (Ib), (Ic), (Id), (Ie), (If), (Ig), (Ih), or (Ii) described herein is combined with a pharmaceutically suitable or acceptable carrier (also referred herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (I'), (Ia), (Ib), (Ic), (Id), (Ie), (If), (Ig), (Ih), or (Ii) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. Another embodiment provides a pharmaceutical composition comprising a pharmaceutically acceptable excipient and a compound of Formula (Ia), or a pharmaceutically acceptable salt thereof. Another embodiment provides a pharmaceutical composition comprising a pharmaceutically acceptable excipient and a compound of Formula (Ib), or a pharmaceutically acceptable salt thereof. Another embodiment provides a pharmaceutical composition comprising a pharmaceutically acceptable excipient and a compound of Formula (Ic), or a pharmaceutically acceptable salt thereof. Another embodiment provides a pharmaceutical composition comprising a pharmaceutically acceptable excipient and a compound of Formula (Id), or a pharmaceutically acceptable salt thereof. Another embodiment provides a pharmaceutical composition comprising a pharmaceutically acceptable excipient and a compound of Formula (Ie), or a pharmaceutically acceptable salt thereof. Another embodiment provides a pharmaceutical composition comprising a pharmaceutically acceptable excipient and a compound of Formula (If), or a pharmaceutically acceptable salt thereof. Another embodiment provides a pharmaceutical composition comprising a pharmaceutically acceptable excipient and a compound of Formula (Ig), or a pharmaceutically acceptable salt thereof. Another embodiment provides a pharmaceutical composition comprising a pharmaceutically acceptable excipient and a compound of Formula (Ih), or a pharmaceutically acceptable salt thereof. Another embodiment provides a pharmaceutical composition comprising a pharmaceutically acceptable excipient and a compound of Formula (Ii), or a pharmaceutically acceptable salt thereof.

Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (Id), or a pharmaceutically acceptable salt thereof. Another embodiment provides a pharmaceutical composition consisting essentially of a pharmaceutically acceptable excipient and a compound of Formula (Ie), or a pharmaceutically acceptable salt thereof. Another embodiment provides a pharmaceutical composition consisting essentially of a pharmaceutically acceptable excipient and a compound of Formula (If), or a pharmaceutically acceptable salt thereof. Another embodiment provides a pharmaceutical composition consisting essentially of a pharmaceutically acceptable excipient and a compound of Formula (Ig), or a pharmaceutically acceptable salt thereof. Another embodiment provides a pharmaceutical composition consisting essentially of a pharmaceutically acceptable excipient and a compound of Formula (Ih), or a pharmaceutically acceptable salt thereof. Another embodiment provides a pharmaceutical composition consisting essentially of a pharmaceutically acceptable excipient and a compound of Formula (Ii), or a pharmaceutically acceptable salt thereof.

In certain embodiments, the compound of Formula (I), (I'), (Ia), (Ib), (Ic), (Id), (Ie), (If), (Ig), (Ih), or (Ii) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammoniumethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (I'), (Ia), (Ib), (Ic), (Id), (Ie), (If), (Ig), (Ih), or (Ii) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (I'), (Ia), (Ib), (Ic), (Id), (Ie), (If), (Ig), (Ih), or (Ii). In some embodiments, provided herein is a compound of Formula (I), (I'), (Ia), (Ib), (Ic), (Id), (Ie), (If), (Ig), (Ih), or (Ii) wherein the compound is a MAGL inhibitor. In some embodiments, provided herein is a compound of Formula (I), (I'), (Ia), (Ib), (Ic), (Id), (Ie), (If), (Ig), (Ih), or (Ii) wherein the compound is a selective MAGL inhibitor. The ability of compounds described herein to modulate or inhibit MAGL is evaluated by procedures known in the art and/or described herein. Another aspect of this disclosure provides methods of treating a disease associated with expression or activity of MAGL in a patient. In some embodiments, provided herein is a compound of Formula (I), (I'), (Ia), (Ib), (Ic), (Id), (Ie), (If), (Ig), (Ih), or (Ii) wherein the compound is selective in inhibiting MAGL as compared to inhibition of other serine hydrolases. In some embodiments, provided herein is a compound of Formula (I), (I'), (Ia), (Ib), (Ic), (Id), (Ie), (If), (Ig), (Ih), or (Ii) wherein the compound is 10, 100, or 1000 fold selective in inhibiting MAGL as compared to inhibition of other serine hydrolases.

In another embodiment is a method of treating pain in a patient, comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof, to a patient in need thereof to treat said pain. In another embodiment is a method of treating neuropathic pain in a patient, comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof, to a patient in need thereof to treat said neuropathic pain. In another embodiment is a method of treating inflammatory pain in a patient, comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof, to a patient in need thereof to treat said inflammatory pain. In another embodiment is a method of treating chronic pain in a patient, comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof, to a patient in need thereof to treat said chronic pain.

In another embodiment is a method of treating migraine in a patient in need thereof comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof.

In another embodiment is a method of treating scleroderma in a patient in need thereof comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof.

In another embodiment is a method of treating nonalcoholic fatty liver disease (NASH) in a patient in need thereof comprising administering a therapeutically effective amount of a compound of Formula (I), (I'), (Ia), (Ib), (Ic), (Id), (Ie), (If), (Ig), (Ih), or (Ii) described herein, or a solvate, hydrate, tautomer, N-oxide, or a pharmaceutically acceptable salt thereof.

In certain embodiments, a disclosed compound utilized by one or more of the foregoing methods is one of the generic, subgeneric, or specific compounds described herein, such as a compound of Formula (I), (I'), (Ia), (Ib), (Ic), (Id), (Ie), (If), (Ig), (Ih), or (Ii).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous, or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

In some embodiments, for contemplated treatment of pain, a disclosed compound is co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($C_1CH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 1-(4-(4-chlorobenzyl)piperazine-1-carbonyl)-1H-pyrazole-3-carboxylic Acid

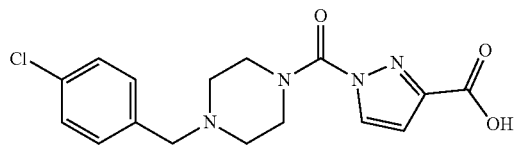 [SMILES: O=C(O)c1ccn(C(=O)N2CCN(Cc3ccc(Cl)cc3)CC2)n1]

Step 1: Preparation of di-t-butyl 1H-pyrazole-1,3-dicarboxylate

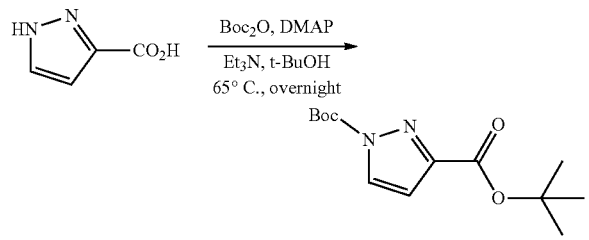

A flask was charged with 1H-pyrazole-3-carboxylic acid (5.00 g, 44.6 mmol, 1.00 equiv), t-butanol (50 mL), di-t-butyl dicarbonate (39.0 g, 179 mmol, 4.01 equiv), triethylamine (27.0 g, 268 mmol, 6.00 equiv) and DMAP (1.10 g, 9.00 mmol, 0.20 equiv). The resulting solution was stirred overnight at 65° C. and quenched with water (20 mL). The mixture was extracted with EtOAc (3×50 mL) and the organic layers were combined, washed with water (3×20 mL), dried over anhydrous sodium sulfate, filtered and concentrated under reduced pressure to provide 11.2 g (crude) of di-t-butyl 1H-pyrazole-1,3-dicarboxylate as a yellow oil. LCMS (ESI, m/z): 169 [M+H–Boc]$^+$.

Step 2: Preparation of t-butyl 1H-pyrazole-3-carboxylate

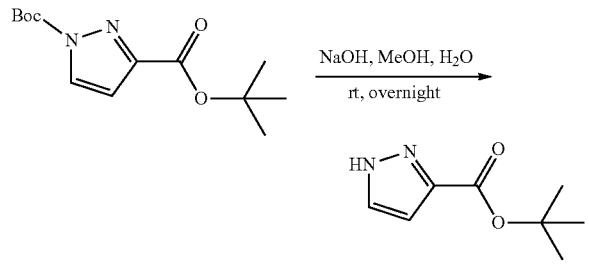

A flask was charged with 1,3-di-t-butyl 1H-pyrazole-1,3-dicarboxylate (5.00 g, 18.6 mmol, 1.00 equiv), MeOH (30 mL), NaOH (2.50 g, 62.5 mmol, 3.35 equiv) and water (5 mL). The resulting solution was stirred overnight at room temperature and quenched with water (10 mL). The mixture was extracted with EtOAc (3×30 mL) and the organic layers were combined, washed with water (3×10 mL), dried over anhydrous sodium sulfate, filtered and concentrated under reduced pressure to provide 3.05 g (crude) of t-butyl 1H-pyrazole-3-carboxylate as a yellow solid. LCMS (ESI, m/z): 169 [M+H]$^+$.

Step 3: Preparation of 4-(4-chlorobenzyl)piperazine-1-carbonyl Chloride

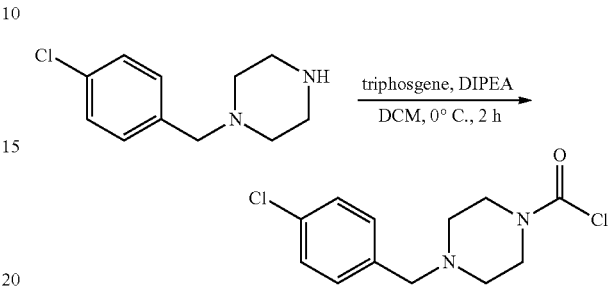

A flask was charged with triphosgene (210 mg, 1.00 mmol, 1.00 equiv), DCM (10 mL) and 1-[(4-chlorophenyl)methyl]piperazine (206 mg, 0.698 mmol, 0.70 equiv). DIPEA (516 mg, 3.99 mmol, 4.00 equiv) was added dropwise at 0° C. The resulting solution was stirred for 2 h at 0° C. and quenched with water (20 mL). The mixture was extracted with DCM (3×30 mL) and the organic layers were combined, washed with water (3×10 mL), dried over anhydrous sodium sulfate, filtered and concentrated under reduced pressure to provide 250 mg (crude) of 4-(4-chlorobenzyl)piperazine-1-carbonyl chloride as a yellow oil.

Step 4: Preparation of t-butyl 1-(4-(4-chlorobenzyl)piperazine-1-carbonyl)-1H-pyrazole-3-carboxylate

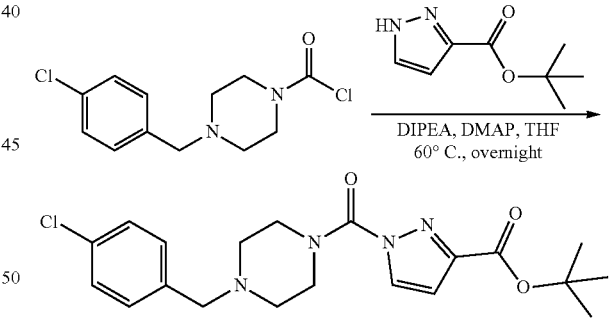

A flask was charged with 4-(4-chlorobenzyl)piperazine-1-carbonyl chloride (250 mg, 0.920 mmol, 1.00 equiv), THF (10 mL), t-butyl 1H-pyrazole-3-carboxylate (155 mg, 0.920 mmol, 1.01 equiv), DIPEA (237 mg, 1.83 mmol, 2.00 equiv) and DMAP (22.0 mg, 0.180 mmol, 0.20 equiv). The resulting solution was stirred overnight at 60° C. and quenched with water (5 mL). The mixture was extracted with EtOAc (3×30 mL) and the organic layers were combined, washed with water (3×10 mL), dried over anhydrous sodium sulfate, filtered and concentrated under reduced pressure. The residue was chromatographed on a silica gel column to provide 260 mg (70% yield) of t-butyl 1-(4-(4-chlorobenzyl)piperazine-1-carbonyl)-1H-pyrazole-3-carboxylate as a yellow oil. LCMS (ESI, m/z): 405 [M+H]$^+$.

Step 5: Preparation of 1-(4-(4-chlorobenzyl)piperazine-1-carbonyl)-1H-pyrazole-3-carboxylic Acid

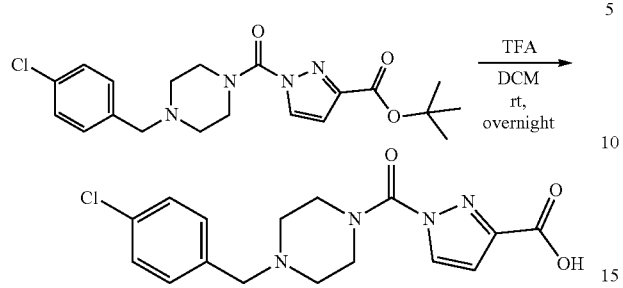

A flask was charged with t-butyl 1-(4-(4-chlorobenzyl)piperazine-1-carbonyl)-1H-pyrazole-3-carboxylate (260 mg, 0.861 mmol, 1.00 equiv), DCM (10 mL) and TFA (1 mL). The resulting solution was stirred overnight at room temperature and concentrated under reduced pressure. The crude product was purified by preparative HPLC to provide 66.6 mg (30% yield) of 1-(4-(4-chlorobenzyl)piperazine-1-carbonyl)-1H-pyrazole-3-carboxylic acid as a yellow solid. 41 NMR (400 MHz, CD$_3$OD) δ 8.08 (s, 1H), 7.34-7.39 (m, 4H), 6.75 (s, 1H), 3.68-4.14 (m, 4H), 3.52-3.77 (m, 2H), 2.47-2.70 (m, 4H). LCMS (ESI, m/z): 349 [M+H]$^+$.

Example 2: 1-(4-(3-phenoxybenzyl)piperazine-1-carbonyl)-1H-pyrazole-3-carboxylic Acid

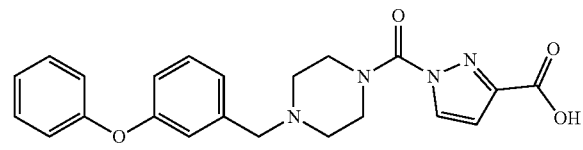 [SMILES: O=C(O)c1ccn(C(=O)N2CCN(Cc3cccc(Oc4ccccc4)c3)CC2)n1]

Step 1: Preparation of di-t-butyl 1H-pyrazole-1,3-dicarboxylate

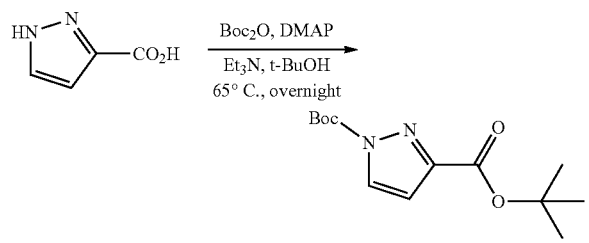

A flask was charged with 1H-pyrazole-3-carboxylic acid (5.00 g, 44.6 mmol, 1.00 equiv), t-butanol (50 mL), di-t-butyl dicarbonate (39.0 g, 179 mmol, 4.01 equiv), triethylamine (27.0 g, 268 mmol, 6.00 equiv) and DMAP (1.10 g, 9.00 mmol, 0.20 equiv). The resulting solution was stirred overnight at 65° C. and quenched with water (20 mL), as described in Example 1, Step 1 to provide 11.2 g (crude) of di-t-butyl 1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

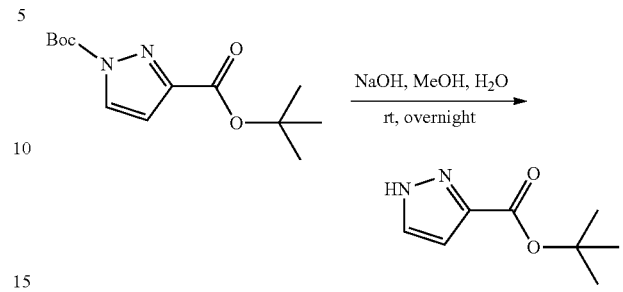

A flask was charged with 1,3-di-t-butyl 1H-pyrazole-1,3-dicarboxylate (5.00 g, 18.6 mmol, 1.00 equiv), MeOH (30 mL), NaOH (2.50 g, 62.5 mmol, 3.35 equiv) and water (5 mL). The resulting solution was stirred overnight at room temperature and quenched with water (10 mL), as described in Example 1, Step 2 to provide 3.05 g (crude) of t-butyl 1H-pyrazole-3-carboxylate as a yellow solid. LCMS (ESI, m/z): 169 [M+H]$^+$.

Step 3: Preparation of t-butyl 4-(3-phenoxybenzyl)piperazine-1-carboxylate

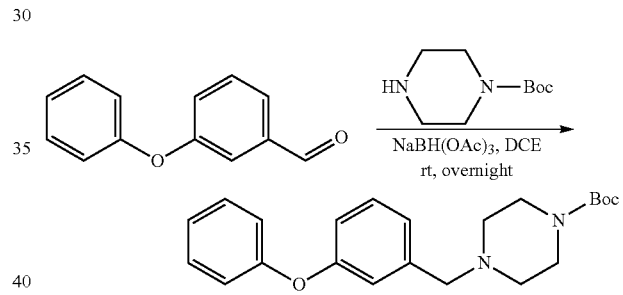

A flask was charged with 3-phenoxybenzaldehyde (5.00 g, 25.2 mmol, 1.00 equiv), t-butyl piperazine-1-carboxylate (4.25 g, 22.8 mmol, 0.90 equiv) and DCE (100 mL). The mixture was stirred for 1 h at room temperature, and then sodium triacetoxyborohydride (10.6 g, 50.0 mmol, 1.98 equiv) was added. The resulting solution was stirred overnight at room temperature and quenched with water (50 mL). The mixture was extracted with DCM (3×50 mL) and the organic layers were combined, washed with water (3×30 mL), dried over anhydrous sodium sulfate, filtered and concentrated under reduced pressure. The residue was chromatographed on a silica gel column to provide 8.80 g (95% yield) of t-butyl 4-(3-phenoxybenzyl)piperazine-1-carboxylate as a yellow oil. LCMS (ESI, m/z): 369 [M+H]$^+$.

Step 4: Preparation of 1-(3-phenoxybenzyl)piperazine

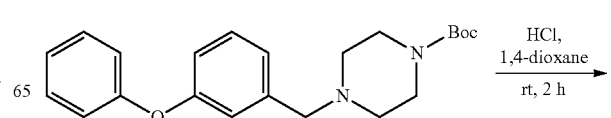

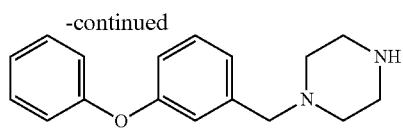

A flask was charged with t-butyl 4-(3-phenoxybenzyl) piperazine-1-carboxylate (8.80 g, 23.9 mmol, 1.00 equiv), 1,4-dioxane (50 mL) and concentrated hydrochloric acid (5 mL). The resulting solution was stirred for 2 h at room temperature and concentrated under reduced pressure to provide 6.03 g (crude) of 1-(3-phenoxybenzyl)piperazine as a white solid. LCMS (ESI, m/z): 269 [M+H]$^+$.

Step 5: Preparation of 4-(3-phenoxybenzyl)piperazine-1-carbonyl Chloride

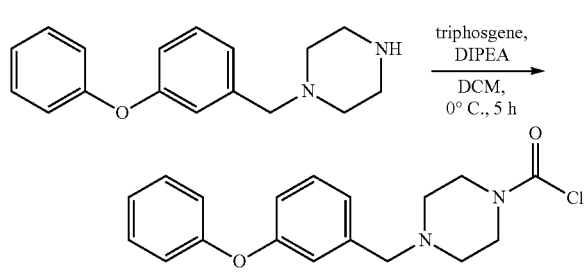

A flask was charged with 1-(3-phenoxybenzyl)piperazine (200 mg, 0.751 mmol, 1.00 equiv), DCM (10.0 mL) and triphosgene (135 mg, 0.451 mmol, 0.70 equiv). DIPEA (388 mg, 3.00 mmol, 4.00 equiv) was added dropwise at 0° C. The resulting solution was stirred for 5 h at 0° C. and quenched with water (20 mL). The mixture was extracted with DCM (3×30 mL) and the organic layers were combined, washed with water (3×10 mL), dried over anhydrous sodium sulfate, filtered and concentrated under reduced pressure as described in Example 1, Step 3 to provide 217 mg (crude) of 4-[(3-phenoxyphenyl)methyl]piperazine-1-carbonyl chloride as a yellow oil.

Step 6: Preparation of t-butyl 1-(4-(3-phenoxybenzyl)piperazine-1-carbonyl)-1H-pyrazole-3-carboxylate

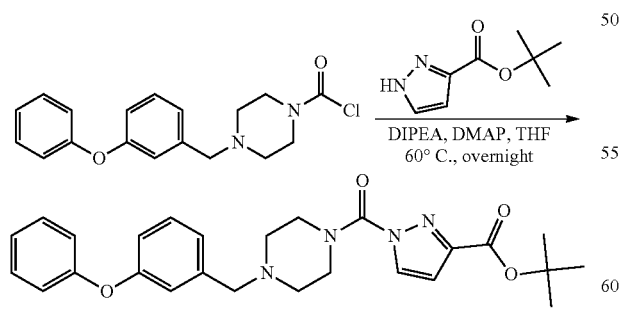

A flask was charged with 4-[(3-phenoxyphenyl)methyl] piperazine-1-carbonyl chloride (217 mg, 0.661 mmol, 1.00 equiv), THF (10 mL), t-butyl 1H-pyrazole-3-carboxylate (110 mg, 0.652 mmol, 1.00 equiv), DMAP (16.2 mg, 0.131 mmol, 0.20 equiv) and DIPEA (169 mg, 1.31 mmol, 2.00 equiv). The resulting solution was stirred overnight at 60° C. and quenched with water (20 mL). The mixture was extracted with EtOAc (3×30 mL) and the organic layers were combined, washed with water (3×10 mL), dried over anhydrous sodium sulfate, filtered and concentrated under reduced pressure, as described in Example 1, Step 4. The residue was chromatographed on a silica gel column to provide 120 mg (40% yield) of t-butyl 1-(4-(3-phenoxybenzyl)piperazine-1-carbonyl)-1H-pyrazole-3-carboxylate as a yellow oil. LCMS (ESI, m/z): 463 [M+H]$^+$.

Step 7: Preparation of 1-(4-(3-phenoxybenzyl)piperazine-1-carbonyl)-1H-pyrazole-3-carboxylic Acid

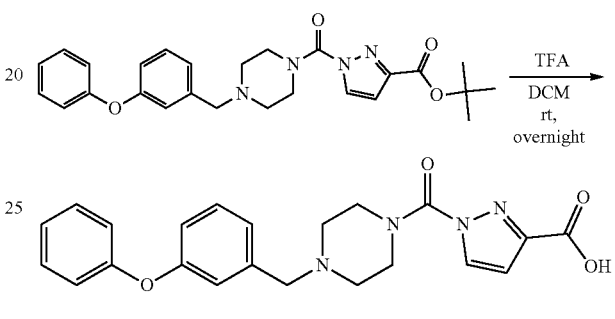

A flask was charged with t-butyl 1-(4-(3-phenoxybenzyl) piperazine-1-carbonyl)-1H-pyrazole-3-carboxylate (120 mg, 0.261 mmol, 1.00 equiv), DCM (5 mL) and TFA (1 mL). The resulting mixture was stirred overnight at room temperature and concentrated under reduced pressure, as described in Example 1, Step 5. The crude product was purified by preparative HPLC to provide 81.6 mg (77% yield) of 1-(4-(3-phenoxybenzyl)piperazine-1-carbonyl)-1H-pyrazole-3-carboxylic acid as a white powder. $^1$H NMR: (400 MHz, CD$_3$OD) δ 8.15 (s, 1H), 7.33-7.48 (m, 3H), 7.11-7.27 (m, 2H), 7.06-7.11 (s, 1H), 6.99-7.06 (m, 2H), 6.90-6.99 (m, 1H), 6.75-6.90 (m, 1H), 3.82-4.13 (s, 4H), 3.70-3.82 (d, J=8.2 Hz, 2H), 2.60-2.93 (s, 4H). LCMS (ESI, m/z): 407 [M+H]$^+$.

Example 3: 1-(4-(2-Morpholino-4-(trifluoromethyl) benzyl)piperazine-1-carbonyl)-1H-pyrazole-3-carboxylic Acid

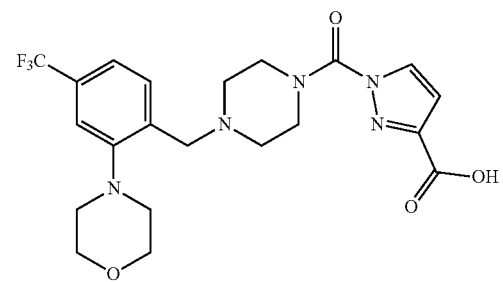 [SMILES: O=C(O)c1ccn(C(=O)N2CCN(Cc3ccc(C(F)(F)F)cc3N3CCOCC3)CC2)n1]

Step 1: Preparation of di-t-butyl 1H-pyrazole-1,3-dicarboxylate

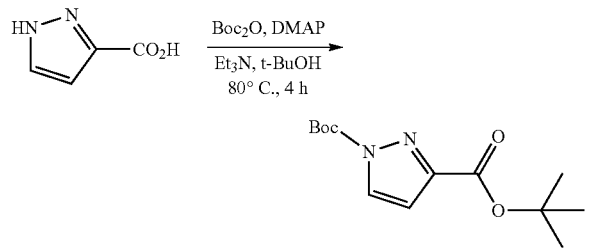

A flask was charged with 1H-pyrazole-3-carboxylic acid (10.0 g, 89.2 mmol, 1.00 equiv), DMAP (2.15 g, 17.6 mmol, 0.20 equiv), triethylamine (27.0 g, 267 mmol, 3.00 equiv), di-t-butyl dicarbonate (80.0 g, 366 mmol, 4.00 equiv), and t-butanol (100 mL), as described in Example 1, Step 1. The resulting solution was stirred for 4 h at 80° C. and concentrated under reduced pressure to provide 25.0 g (crude) of 1,3-di-t-butyl 1H-pyrazole-1,3-dicarboxylate as a red oil. LCMS (ESI, m/z): 269 [M+H]⁺.

Step 2: Preparation of t-butyl 1H-pyrazole-3-carboxylate

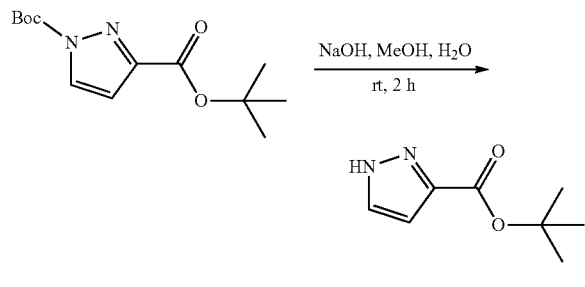

A flask was charged with 1,3-di-t-butyl 1H-pyrazole-1,3-dicarboxylate (25.0 g, 93.2 mmol, 1.00 equiv), NaOH (5.60 g, 140 mmol, 1.50 equiv), water (80 mL) and MeOH (240 mL). The resulting solution was stirred for 2 h at room temperature and concentrated under reduced pressure, as described in Example 1, Step 2. The residue was chromatographed on a silica gel column to provide 10.0 g (64% yield) of t-butyl 1H-pyrazole-3-carboxylate as a white solid. LCMS (ESI, m/z): 169 [M+H]⁺.

Step 3: Preparation of 2-morpholino-4-(trifluoromethyl)benzaldehyde

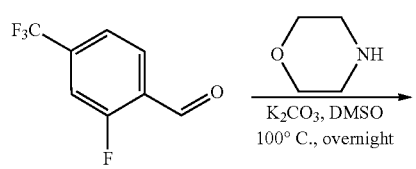

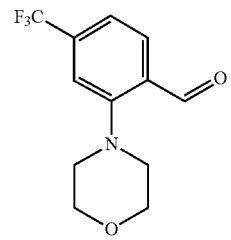

A flask was charged with 2-fluoro-4-(trifluoromethyl) benzaldehyde (3.00 g, 15.6 mmol, 1.00 equiv), potassium carbonate (8.62 g, 62.4 mmol, 4.00 equiv), morpholine (2.72 g, 31.2 mmol, 2.00 equiv), and DMSO (40 mL) under nitrogen. The resulting solution was stirred overnight at 100° C. and then quenched with water (50 mL). The resulting mixture was extracted with EtOAc (3×50 mL) and the organic layers were combined, washed with brine (100 mL), dried over anhydrous sodium sulfate, filtered and concentrated under reduced pressure. The residue was to provide 1.86 g (46% yield) of 2-(morpholin-4-yl)-4-(trifluoromethyl)benzaldehyde as a yellow solid. LCMS (ESI, m/z):260 [M+H]⁺.

Step 4: Preparation of t-butyl 4-(2-morpholino-4-(trifluoromethyl)benzyl)piperazine-1-carboxylate

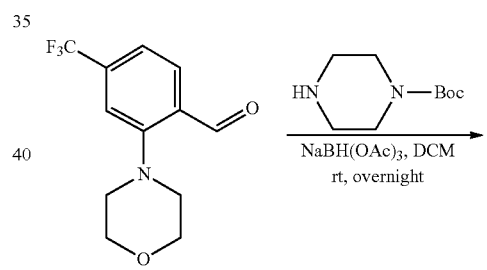

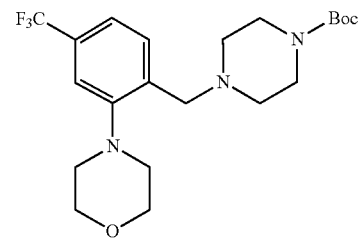

A flask was charged with 2-(morpholin-4-yl)-4-(trifluoromethyl)benzaldehyde (0.600 g, 2.31 mmol, 1.00 equiv), t-butyl piperazine-1-carboxylate (0.646 g, 3.47 mmol, 1.50 equiv), and DCM (20 mL). The mixture was stirred for 2 h at room temperature. Sodium triacetoxyborohydride (1.96 g, 9.23 mmol, 4.00 equiv) was added, as described in Example 2, Step 3. The residue was chromatographed to provide 0.920 g (93% yield) of t-butyl 4-(2-morpholino-4-(trifluoromethyl)benzyl)piperazine-1-carboxylate as a yellow oil. LCMS (ESI, m/z): 430 [M+H]⁺.

Step 5: Preparation of 4-(2-(piperazin-1-ylmethyl)-5-(trifluoromethyl)phenyl)morpholine

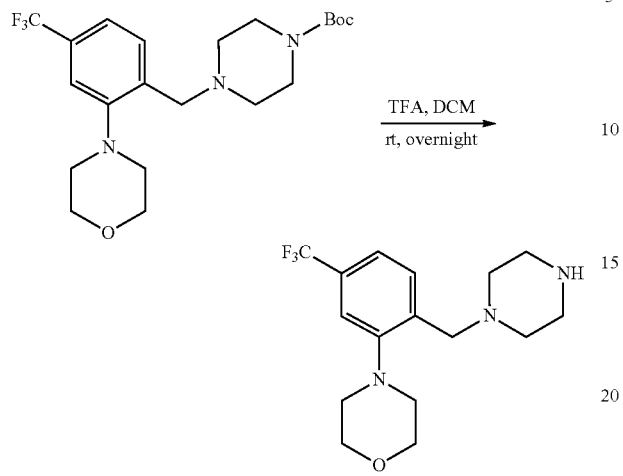

A 250-mL round-bottom flask was charged with t-butyl 4-(2-morpholino-4-(trifluoromethyl)benzyl)piperazine-1-carboxylate (920 mg, 2.14 mmol, 1.00 equiv), trifluoroacetic acid (10 mL), and DCM (30 mL), as described in Example 1, Step 5 to provide 700 mg (99% yield) of 4-(2-(piperazin-1-ylmethyl)-5-(trifluoromethyl)phenyl)morpholine as a brown oil. LCMS (ESI, m/z): 330 [M+H]$^+$.

Step 6: Preparation of 4-(2-morpholino-4-(trifluoromethyl)benzyl)piperazine-1-carbonyl Chloride

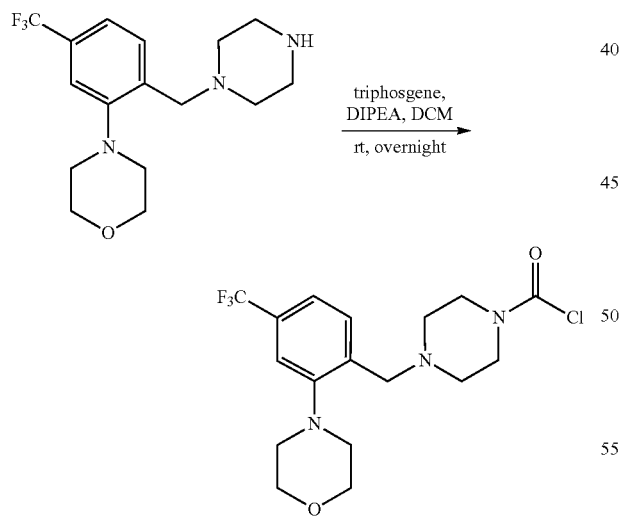

A flask was charged with triphosgene (226 mg, 0.760 mmol, 0.50 equiv), DCM (10 mL). 4-(2-(Piperazin-1-ylmethyl)-5-(trifluoromethyl)phenyl)morpholine (500 mg, 1.52 mmol, 1.00 equiv) and DIPEA (588 mg, 4.56 mmol, 3.00 equiv) were added at 0° C. as described in Example 1, Step 3 to provide 500 mg (84% yield) of 4-(2-morpholino-4-(trifluoromethyl)benzyl)piperazine-1-carbonyl chloride as a yellow oil. LCMS (ESI, m/z): 392 [M+H]$^+$.

Step 7: Preparation of t-butyl 1-(4-(2-morpholino-4-(trifluoromethyl)benzyl)piperazine-1-carbonyl)-1H-pyrazole-3-carboxylate

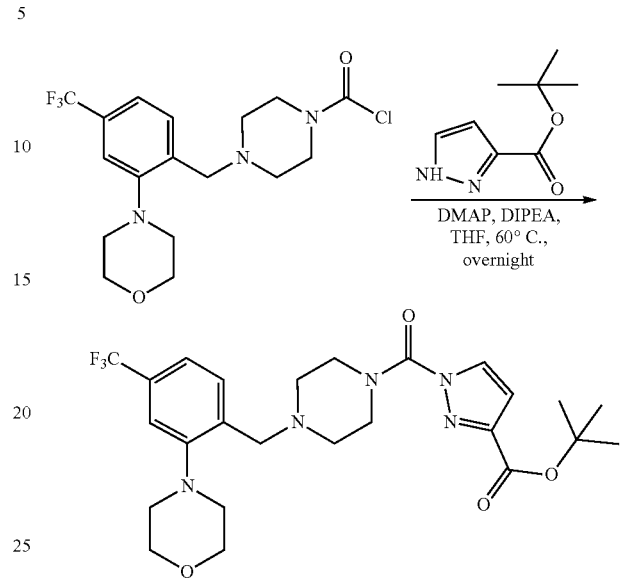

A flask was charged with 4-(2-morpholino-4-(trifluoromethyl)benzyl)piperazine-1-carbonyl chloride (400 mg, 1.02 mmol, 1.00 equiv), t-butyl 1H-pyrazole-3-carboxylate (190 mg, 1.13 mmol, 1.10 equiv), DMAP (62.0 mg, 0.510 mmol, 0.50 equiv), DIPEA (396 mg, 3.07 mmol, 3.00 equiv), THF (10 mL) as described in Example 1, Step 4. The residue was chromatographed to provide 300 mg (56% yield) of t-butyl 1-(4-(2-morpholino-4-(trifluoromethyl)benzyl)piperazine-1-carbonyl)-1H-pyrazole-3-carboxylate as a white solid. LCMS (ESI, m/z): 524 [M+H]$^+$.

Step 8: Preparation of 1-(4-(2-morpholino-4-(trifluoromethyl)benzyl)piperazine-1-carbonyl)-1H-pyrazole-3-carboxylic Acid

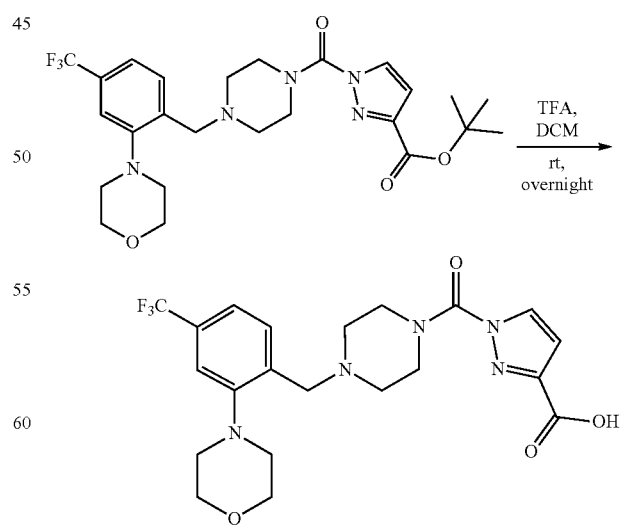

A flask was charged with t-butyl 1-(4-(2-morpholino-4-(trifluoromethyl)benzyl)piperazine-1-carbonyl)-1H-pyrazole-3-carboxylate (140 mg, 0.270 mmol, 1.00 equiv), TFA (1 mL), and DCM (10 mL) as described in Example 1, Step 5 to provide the crude product (250 mg). The residue was purified by preparative HPLC to provide 78.2 mg (63% yield) of 1-(4-(2-morpholino-4-(trifluoromethyl)benzyl)piperazine-1-carbonyl)-1H-pyrazole-3-carboxylic acid as a white solid. 41 NMR (400 MHz, Methanol-d₄) □□ 8.14 (d, J=2.6 Hz, 1H), 7.73 (d, J=8.2 Hz, 1H), 7.41-7.42 (m, 2H), 6.83 (d, J=2.6 Hz, 1H), 3.81-3.88 (m, 10H), 3.01-3.02 (m, 4H), 2.71 (br, 4H). LCMS (ESI, m/z): 468 [M+H]⁺.

Example 4: 1-(4-Methyl-4-(methyl(2-morpholino-4-(trifluoromethyl)benzyl)amino)piperidine-1-carbonyl)-1H-pyrazole-3-carboxylic Acid

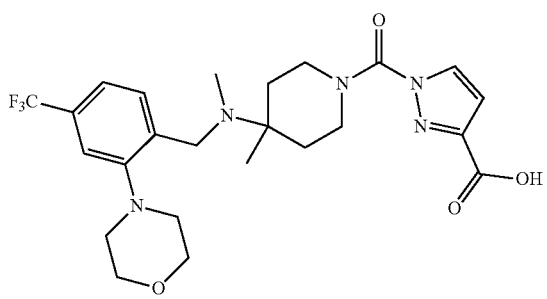 [SMILES: CN(Cc1ccc(C(F)(F)F)cc1N1CCOCC1)C1(C)CCN(C(=O)n2ccc(C(=O)O)n2)CC1]

Step 1: Preparation of di-t-butyl 1H-pyrazole-1,3-dicarboxylate

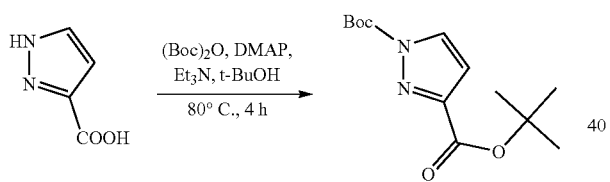

A flask was charged with 1H-pyrazole-3-carboxylic acid (10.0 g, 89.2 mmol, 1.00 equiv), DMAP (2.15 g, 17.6 mmol, 0.20 equiv), triethylamine (27.0 g, 267 mmol, 3.00 equiv), di-t-butyl dicarbonate (80.0 g, 366 mmol, 4.00 equiv) in t-butanol (100 mL) as described in Example 1, Step 1 to provide 25.0 g (crude) of 1,3-di-t-butyl 1H-pyrazole-1,3-dicarboxylate as a red oil. LCMS (ESI, m/z): 269 [M+H]⁺.

Step 2: Preparation of t-butyl 1H-pyrazole-3-carboxylate

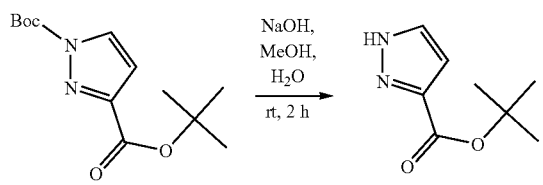 [SMILES: CC(C)(C)OC(=O)c1ccn(C(=O)OC(C)(C)C)n1 ; CC(C)(C)OC(=O)c1cc[nH]n1]

A flask was charged with 1,3-di-t-butyl 1H-pyrazole-1,3-dicarboxylate (25.0 g, 93.2 mmol, 1.00 equiv), NaOH (5.60 g, 140 mmol, 1.50 equiv) in water (80 mL) and MeOH (240 mL) as described in Example 1, Step 2 to provide 10.0 g (64% yield) of t-butyl 1H-pyrazole-3-carboxylate as a white solid. LCMS (ESI, m/z): 169 [M+H]⁺.

Step 3: Preparation of 3-(t-butyl) 1-(4-nitrophenyl) 1H-pyrazole-1,3-dicarboxylate

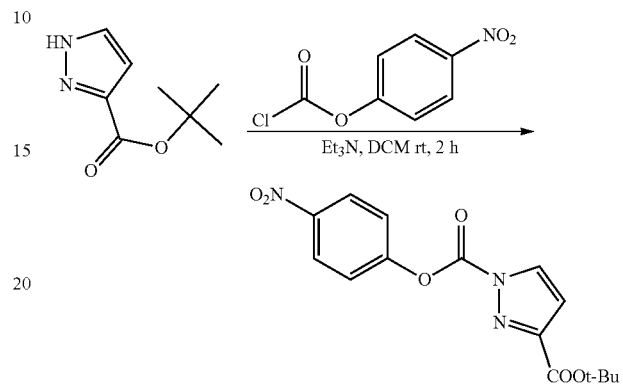

A flask was charged with t-butyl 1H-pyrazole-3-carboxylate (2.42 g, 14.4 mmol, 1.00 equiv), DCM (20 mL), 4-nitrophenyl chloroformate (2.90 g, 14.4 mmol, 1.00 equiv), and triethylamine (4.36 g, 43.1 mmol, 3.00 equiv). The resulting solution was stirred for 3 h at room temperature and concentrated under reduced pressure to provide 4.80 g (crude) of 3-(t-butyl) 1-(4-nitrophenyl) 1H-pyrazole-1,3-dicarboxylate as a yellow oil. LCMS (ESI, m/z): 334 [M+H]⁺.

Step 4: Preparation of 2-morpholino-4-(trifluoromethyl)benzaldehyde

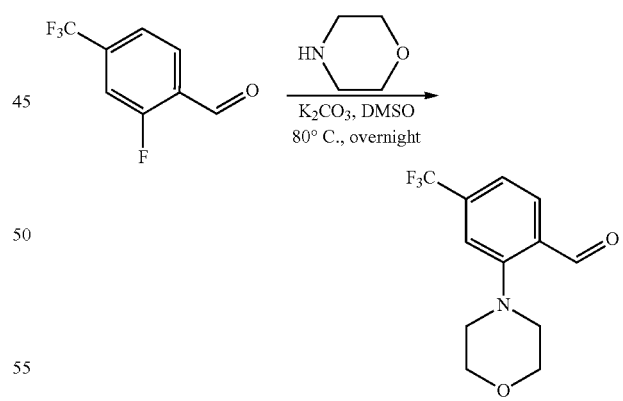

A flask was charged with 2-fluoro-4-(trifluoromethyl)benzaldehyde (5.00 g, 26.0 mmol, 1.00 equiv), potassium carbonate (10.8 g, 78.1 mmol, 3.00 equiv), morpholine (6.79 g, 78.0 mmol, 3.00 equiv), and DMSO (50 mL) under nitrogen. The resulting solution was stirred overnight at 80° C. and quenched with water (50 mL) as described in Example 3, Step 3 to provide 4.00 g (59% yield) of 2-morpholino-4-(trifluoromethyl)benzaldehyde as a yellow solid. LCMS (ESI, m/z): 260 [M+H]⁺.

Step 5: Preparation of t-butyl 4-methyl-4-((2-morpholino-4-(trifluoromethyl)benzyl)amino)piperidine-1-carboxylate

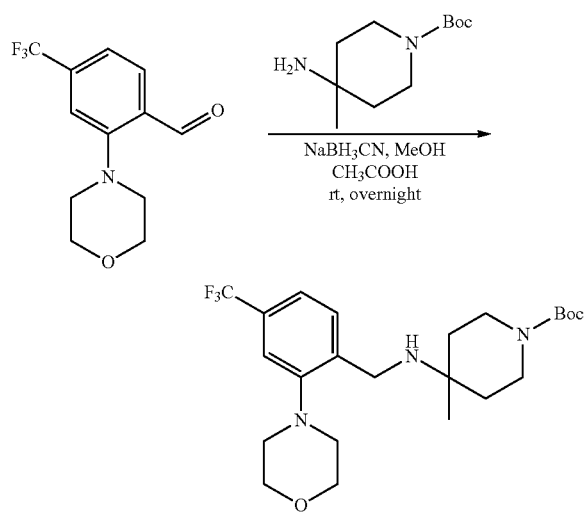

A 100-mL round-bottom flask was charged with 2-morpholino-4-(trifluoromethyl)benzaldehyde (2.50 g, 9.64 mmol, 1.00 equiv), MeOH (25 mL), AcOH (1.70 g, 28.3 mmol, 3.00 equiv), and t-butyl 4-amino-4-methylpiperidine-1-carboxylate (2.46 g, 11.5 mmol, 1.20 equiv). The resulting solution was stirred for 30 min at room temperature. Sodium cyanoborohydride (1.78 g, 28.3 mmol, 3.00 equiv) was added. The resulting solution was stirred overnight at room temperature and quenched with water (30 mL). The resulting solution was extracted with DCM (3×30 mL) and the organic layers were combined, washed with brine (2×30 mL), dried over anhydrous sodium sulfate, filtered and concentrated under reduced pressure. The residue was chromatographed on a silica gel column to yield 3.51 g (80% yield) of t-butyl 4-methyl-442-morpholino-4-(trifluoromethyl)benzyl)amino)piperidine-1-carboxylate as a yellow oil. LCMS (ESI, m/z): 458 [M+H]$^+$.

Step 6: Preparation of t-butyl 4-methyl-4-(methyl (2-morpholino-4-(trifluoromethyl)benzyl)amino) piperidine-1-carboxylate

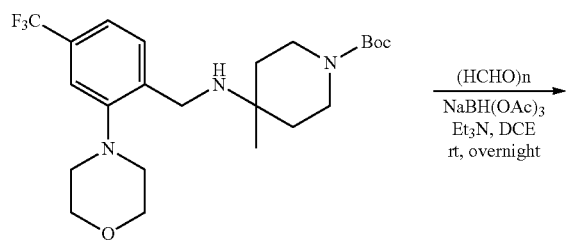

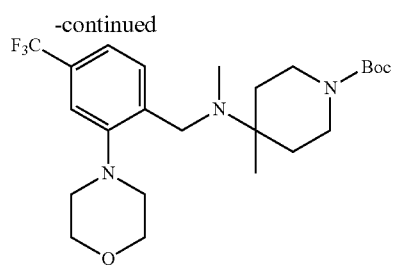

A 100-mL round-bottom flask was charged with t-butyl 4-methyl-4-((2-morpholino-4-(trifluoromethyl)benzylamino)piperidine-1-carboxylate (3.51 g, 7.67 mmol, 1.00 equiv), paraformaldehyde (2.30 g, 76.7 mmol, 10.0 equiv), triethylamine (2.30 g, 22.7 mmol, 3.00 equiv), and DCE (30 mL). The resulting solution was stirred for 30 min at room temperature. Sodium triacetoxyborohydride (4.80 g, 22.6 mmol, 3.00 equiv) was added. The resulting solution was stirred overnight at room temperature and quenched with water (30 mL) as described in Example 2, Step 3 to yield 3.39 g (94% yield) of t-butyl 4-methyl-4-(methyl(2-morpholino-4-(trifluoromethyl)benzyl)amino)piperidine-1-carboxylate as a yellow oil. LCMS (ESI, m/z): 472 [M+H]$^+$.

Step 7: Preparation of t-butyl 4-methyl-4-(methyl (2-morpholino-4-(trifluoromethyl)benzyl)amino) piperidine-1-carboxylate

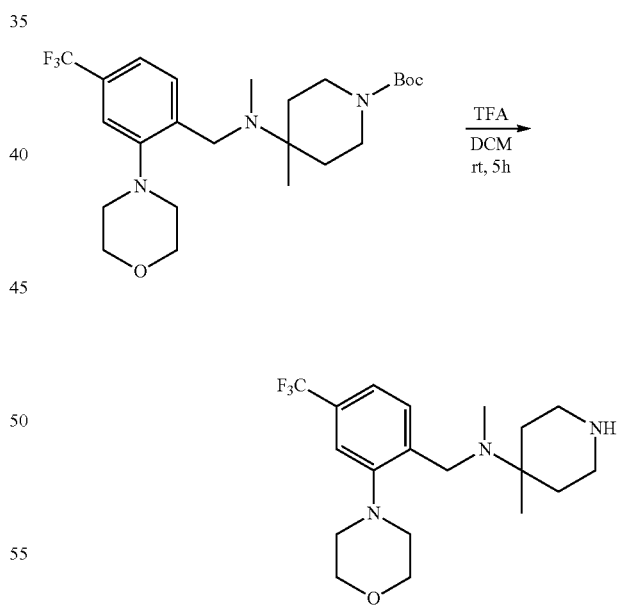

A flask was charged with t-butyl 4-methyl-4-(methyl(2-morpholino-4-(trifluoromethyl)benzyl)amino)piperidine-1-carboxylate (3.39 g, 7.19 mmol, 1.00 equiv), DCM (20 mL), and TFA (5 mL) as described in Example 1, Step 5 to yield 3.50 g (crude) of t-butyl 4-methyl-4-(methyl(2-morpholino-4-(trifluoromethyl)benzyl)amino)piperidine-1-carboxylate as a white solid. LCMS (ESI, m/z): 372 [M+H]$^+$.

Step 8: Preparation of t-butyl 1-(4-methyl-4-(methyl(2-morpholino-4-(trifluoromethyl)benzyl)amino)piperidine-1-carbonyl)-1H-pyrazole-3-carboxylate

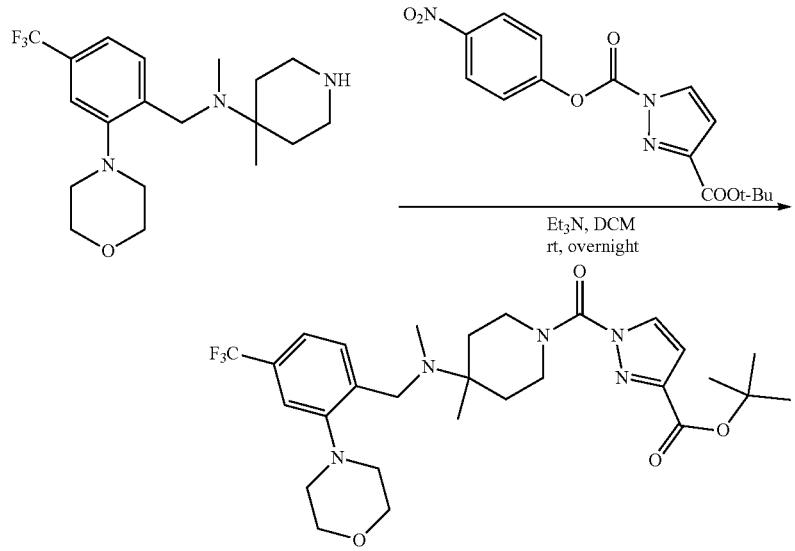

A flask was charged with 3-t-butyl 1-(4-nitrophenyl) 1H-pyrazole-1,3-dicarboxylate (3.50 g, 9.43 mmol, 1.00 equiv), DCM (20 mL), t-butyl 4-methyl-4-(methyl(2-morpholino-4-(trifluoromethyl)benzyl)amino)piperidine-1-carboxylate (6.28 g, 18.7 mmol, 2.00 equiv), and triethylamine (2.86 g, 28.3 mmol, 3.00 equiv), as described in Example 4, Step 3 to provide 4.58 g (80% yield) of t-butyl 1-(4-methyl-4-(methyl(2-morpholino-4-(trifluoromethyl)benzyl)amino)piperidine-1-carbonyl)-1H-pyrazole-3-carboxylate as a yellow oil. LCMS (ESI, m/z): 566 [M+H]$^+$.

Step 9: Preparation of 1-(4-methyl-4-(methyl(2-morpholino-4-(trifluoromethyl)benzyl)amino)piperidine-1-carbonyl)-1H-pyrazole-3-carboxylic Acid

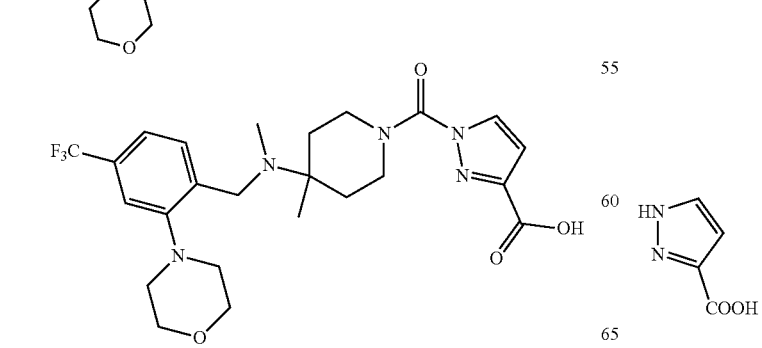

A flask was charged with t-butyl 1-(4-methyl-4-(methyl(2-morpholino-4-(trifluoromethyl)benzyl)amino)piperidine-1-carbonyl)-1H-pyrazole-1-carbonyl)-1H-pyrazole-3-carboxylate (4.58 g, 8.10 mmol, 1.00 equiv), DCM (50 mL), and TFA (10 mL), as described in Example 1, Step 5. The crude product (3.50 g) was purified by preparative HPLC to provide 694.3 mg (17% yield) of 1-(4-methyl-4-(methyl(2-morpholino-4-(trifluoromethyl)benzyl)amino)piperidine-1-carbonyl)-1H-pyrazole-3-carboxylic acid as a white solid. $^1$H NMR (300 MHz, Methanol-d$_4$) δ 8.08 (d, J=2.6 Hz, 1H), 7.84 d, J=8.4 Hz, 1H), 7.49-7.52 (m, 2H), 6.78 (d, J=2.6 Hz, 1H), 4.12-4.25 (m, 4H), 3.84-3.87 (m, 4H), 3.54-3.65 (m, 2H), 2.93-3.07 (m, 4H), 2.41 (br, 3H), 2.11-2.16 (m, 2H), 2.03-2.10 (m, 2H), 1.41 (br, 3H). LCMS (ESI, m/z): 510 [M+H]$^+$.

Example 5: 1-(4-(2-(1H-Tetrazol-5-yl)-4-(trifluoromethyl)benzyl)piperazine-1-carbonyl)-1H-pyrazole-3-carboxylic Acid

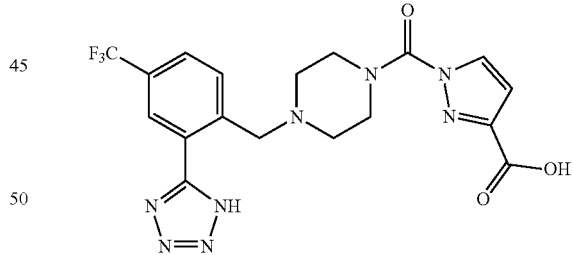

Step 1: Preparation of di-t-butyl 1H-pyrazole-1,3-dicarboxylate

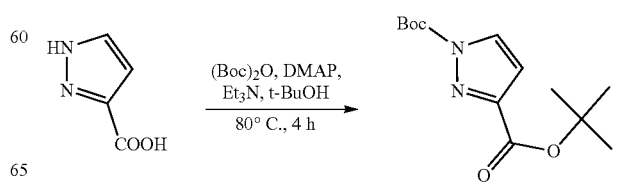

A flask was charged with 1H-pyrazole-3-carboxylic acid (10.0 g, 89.2 mmol, 1.00 equiv), 4-dimethylaminopyridine (2.15 g, 17.6 mmol, 0.20 equiv), triethylamine (27.0 g, 267 mmol, 3.00 equiv), di-t-butyl dicarbonate (80.0 g, 366 mmol, 4.00 equiv) in t-butanol (100 mL) as described in Example 1, Step 1 to provide 25.0 g (crude) of 1,3-di-t-butyl 1H-pyrazole-1,3-dicarboxylate as a red oil. LCMS (ESI, m/z): 269 [M+H]⁺.

Step 2: Preparation of t-butyl 1H-pyrazole-3-carboxylate

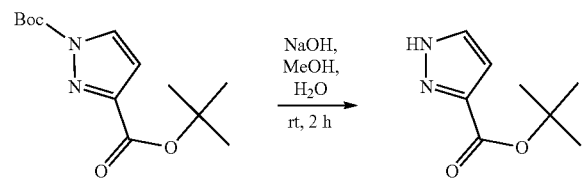 [SMILES: CC(C)(C)OC(=O)c1ccn(C(=O)OC(C)(C)C)n1 ; CC(C)(C)OC(=O)c1cc[nH]n1]

A flask was charged with 1,3-di-t-butyl 1H-pyrazole-1,3-dicarboxylate (25.0 g, 93.2 mmol, 1.00 equiv), NaOH (5.60 g, 140 mmol, 1.50 equiv) in water (80 mL) and MeOH (240 mL), as described in Example 1, Step 2 to provide 10.0 g (64% yield) of t-butyl 1H-pyrazole-3-carboxylate as a white solid. LCMS (ESI, m/z): 169 [M+H]⁺.

Step 3: Preparation of t-butyl 4-(2-bromo-4-(trifluoromethyl)benzyl)piperazine-1-carboxylate

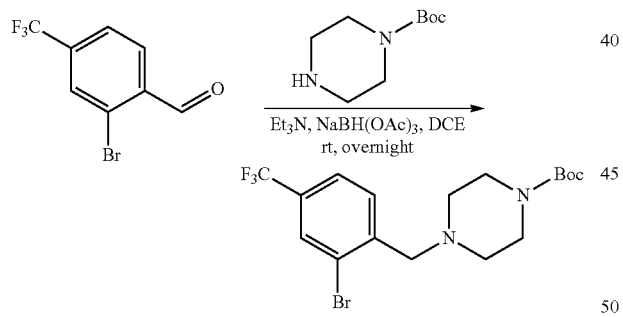

A flask was charged with 2-bromo-4-(trifluoromethyl)benzaldehyde (500 mg, 1.98 mmol, 1.00 equiv), triethylamine (600 mg, 5.93 mmol, 3.00 equiv), t-butyl piperazine-1-carboxylate (443 mg, 2.38 mmol, 1.20 equiv) in DCE (10 mL). The resulting solution was stirred for 0.5 h at room temperature. Sodium triacetoxyborohydride (1.26 g, 5.94 mmol, 3.00 equiv) was added. The resulting solution was stirred overnight at room temperature and quenched with water (10 mL), as described in Example 2, Step 3. The residue was chromatographed to provide 680 mg (81% yield) of t-butyl 4-(2-bromo-4-(trifluoromethyl)benzyl)piperazine-1-carboxylate as a white solid. LCMS (ESI, m/z): 423 [M+H]⁺.

Step 4: Preparation of t-butyl 4-(2-cyano-4-(trifluoromethyl)benzyl)piperazine-1-carboxylate

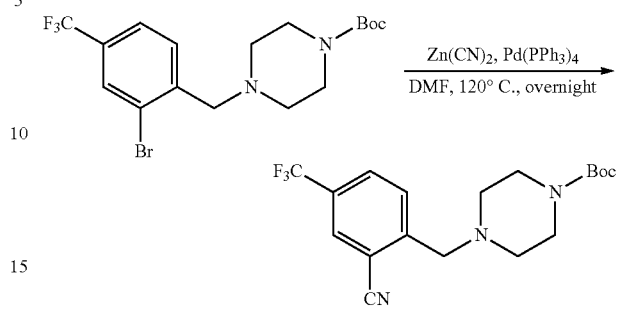

A flask was charged with t-butyl 4-(2-bromo-4-(trifluoromethyl)benzyl)piperazine-1-carboxylate (680 mg, 1.61 mmol, 1.00 equiv), zinc cyanide (374 mg, 3.22 mmol, 2.00 equiv), tetrakis(triphenylphosphine)palladium (170 mg, 0.150 mmol, 0.10 equiv) in DMF (10 mL) under nitrogen. The resulting solution was stirred overnight at 120° C. and quenched with water (10 mL). The resulting solution was extracted with EtOAc (3×30 mL) and the organic layers were combined, washed with brine (2×30 mL), dried over anhydrous sodium sulfate, filtered and concentrated under reduced pressure. The residue was chromatographed to provide 230 mg (39% yield) of t-butyl 4-(2-cyano-4-(trifluoromethyl)benzyl)piperazine-1-carboxylate as a white solid. LCMS (ESI, m/z): 370 [M+H]⁺.

Step 5: Preparation of t-butyl 4-(2-(1H-tetrazol-5-yl)-4-(trifluoromethyl)benzyl)piperazine-1-carboxylate

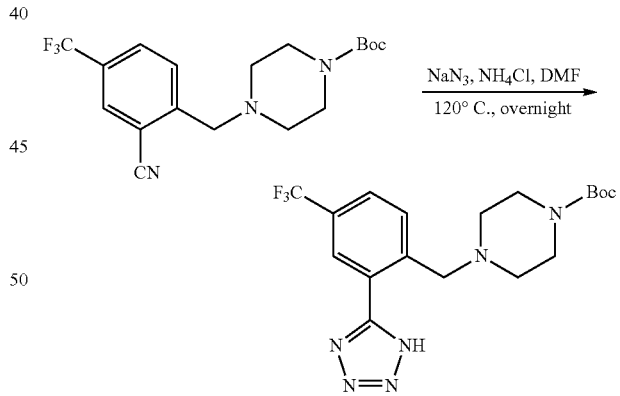

A flask was charged with t-butyl 4-(2-cyano-4-(trifluoromethyl)benzyl)piperazine-1-carboxylate (230 mg, 0.620 mmol, 1.00 equiv), sodium azide (203 mg, 3.12 mmol, 5.00 equiv), ammonium chloride (198 mg, 3.70 mmol, 6.00 equiv) in DMF (10 mL). The resulting solution was stirred overnight at 120° C. and quenched with water (10 mL). The resulting solution was extracted with EtOAc (3×30 mL) and the organic layers were combined, washed with brine (2×20 mL), dried over anhydrous sodium sulfate, filtered and concentrated under reduced pressure. The residue was chromatographed to provide 140 mg (55% yield) of t-butyl 4-(2-(1H-tetrazol-5-yl)-4-(trifluoromethyl)benzyl)piperazine-1-carboxylate as a white solid. LCMS (ESI, m/z): 413 [M+H]⁺.

Step 6: Preparation of 1-(2-(1H-tetrazol-5-yl)-4-(trifluoromethyl)benzyl)piperazine

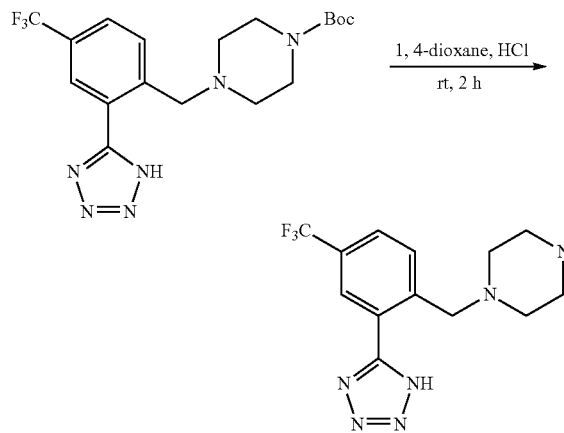

A flask was charged with t-butyl 4-(2-(1H-tetrazol-5-yl)-4-(trifluoromethyl)benzyl)piperazine-1-carboxylate (140 mg, 0.340 mmol, 1.00 equiv), 1,4-dioxane (10 mL), concentrated hydrochloric acid (3 mL), as described in Example 2, Step 4 to provide 130 mg (crude) of 1-(2-(1H-tetrazol-5-yl)-4-(trifluoromethyl)benzyl)piperazine as a white solid. LCMS (ESI, m/z): 313 [M+H]⁺.

Step 7: Preparation of t-butyl 1-(4-(2-(1H-tetrazol-5-yl)-4-(trifluoromethyl)benzyl)piperazine-1-carbonyl)-1H-pyrazole-3-carboxylate

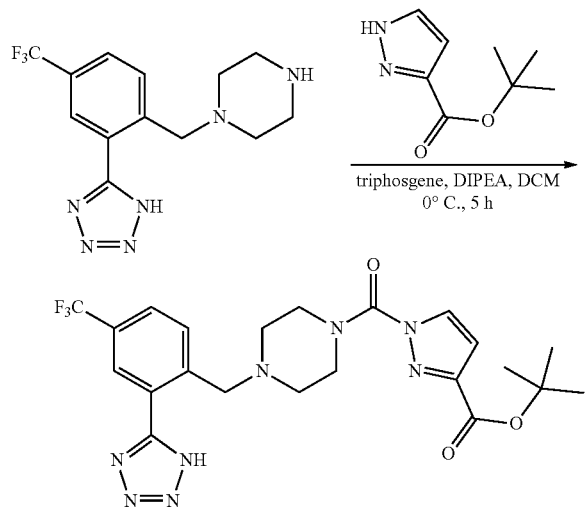

A flask was charged with triphosgene (38.0 mg, 0.130 mmol, 0.40 equiv), t-butyl 1H-pyrazole-3-carboxylate (70.0 mg, 0.420 mmol, 1.30 equiv) in DCM (10 mL) under nitrogen. DIPEA (122 mg, 0.960 mmol, 3.00 equiv) was added dropwise at 0° C. The resulting solution was stirred for 2 h at 0° C. 1-(2-(1H-Tetrazol-5-yl)-4-(trifluoromethyl) benzyl)piperazine (100 mg, 0.320 mmol, 1.00 equiv) was added as described in Example 1, Step 3 to provide 90.0 mg (55% yield) of t-butyl 1-(4-(2-(1H-tetrazol-5-yl)-4-(trifluoromethyl)benzyl)piperazine-1-carbonyl)-1H-pyrazole-3-carboxylate as a white solid. LCMS (ESI, m/z): 507 [M+H]⁺.

Step 8: Preparation of 1-(4-(2-(1H-tetrazol-5-yl)-4-(trifluoromethyl)benzyl)piperazine-1-carbonyl)-1H-pyrazole-3-carboxylic Acid

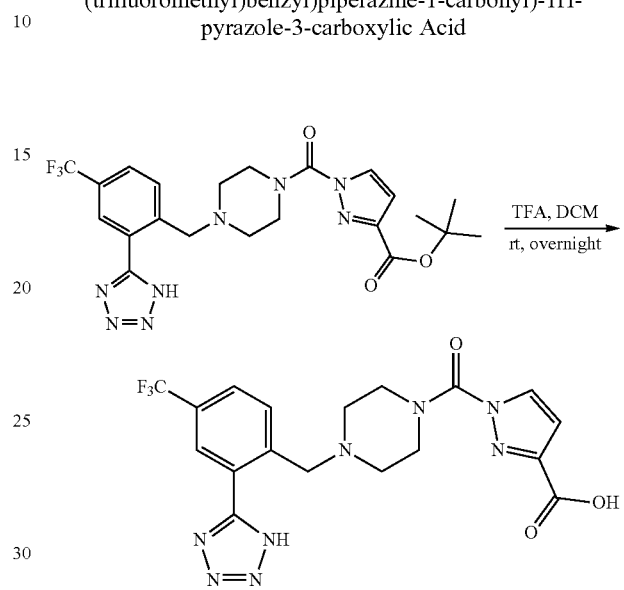

A flask was charged with t-butyl 1-(4-(2-(1H-tetrazol-5-yl)-4-(trifluoromethyl)benzyl)piperazine-1-carbonyl)-1H-pyrazole-3-carboxylate (90.0 mg, 0.180 mmol, 1.00 equiv), and TFA (3 mL) in DCM (10 mL), as described in Example 1, Step 5 to provide the crude product (100 mg), which was purified by preparative HPLC. Purification resulted in 22.3 mg (28% yield) of 1-(4-(2-(1H-tetrazol-5-yl)-4-(trifluoromethyl)benzyl)piperazine-1-carbonyl)-1H-pyrazole-3-carboxylic acid as a white solid. ¹H NMR (300 MHz, Methanol-d₄) δ 8.30 (s, 1H), 8.14 (d, J=2.7 Hz, 1H), 7.76-7.87 (m, 2H), 6.78 (d, J=2.7 Hz, 1H), 4.44 (s, 2H), 4.18 (br, 4H), 3.24 (br, 4H). LCMS (ESI, m/z): 451 [M+H]⁺.

Example 6: 1-(4-(2-(4-Cyclopropylpiperazin-1-yl)-4-(trifluoromethyl)benzyl)piperazine-1-carbonyl)-1H-pyrazole-3-carboxylic Acid

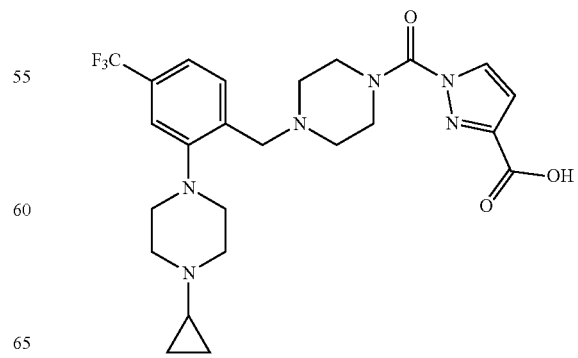

Step 1: Preparation of 2-(4-cyclopropylpiperazin-1-yl)-4-(trifluoromethyl)benzaldehyde

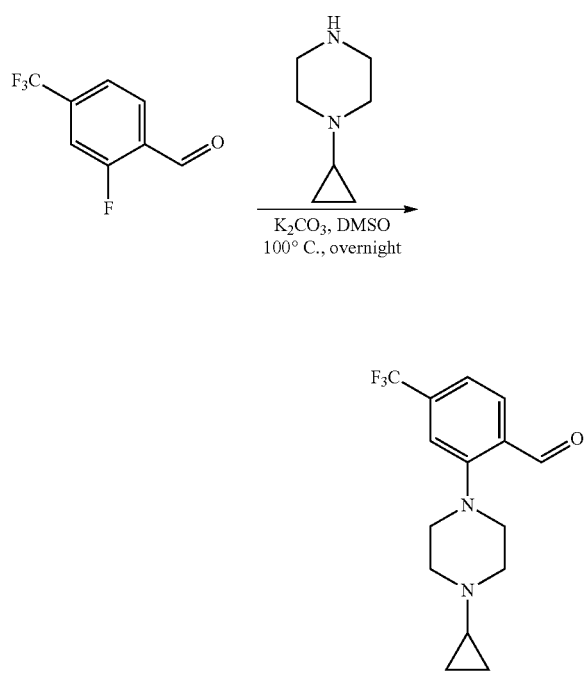

A flask was charged with 2-fluoro-4-(trifluoromethyl) benzaldehyde (400 mg, 2.08 mmol, 1.00 equiv), DMSO (10 mL), potassium carbonate (861 mg, 6.24 mmol, 3.00 equiv), and 1-cyclopropylpiperazine (524 mg, 4.16 mmol, 2.00 equiv) under nitrogen, as described in Example 3, Step 3 to provide the crude product. The residue was chromatographed to provide 460 mg (74% yield) of 2-(4-cyclopropylpiperazin-1-yl)-4-(trifluoromethyl)benzaldehyde as a yellow oil. LCMS (ESI, m/z): 299 [M+H]$^+$.

Step 2: Preparation of di-t-butyl 1H-pyrazole-1,3-dicarboxylate

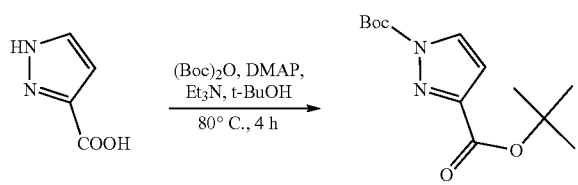 [SMILES: O=C(O)c1cc[nH]n1 ; CC(C)(C)OC(=O)c1ccn(C(=O)OC(C)(C)C)n1]

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), and t-butanol (100 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]$^+$.

Step 3: Preparation of t-butyl 1H-pyrazole-3-carboxylate

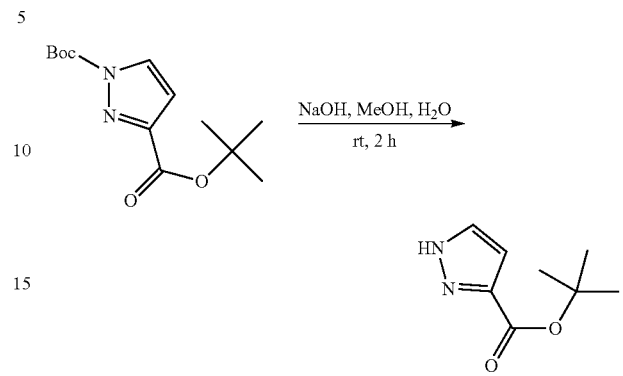

A flask was charged with 1,3-di-t-butyl 1H-pyrazole-1,3-dicarboxylate (25.0 g, 93.3 mmol, 1.00 equiv), NaOH (5.60 g, 140 mmol, 1.50 equiv), water (80 mL), and MeOH (240 mL), as described in Example 1, Step 2 provide the crude product. The residue was chromatographed to provide 10.0 g (64% yield) of t-butyl 1H-pyrazole-3-carboxylate as a white solid. LCMS (ESI, m/z): 169 [M+H]$^+$.

Step 4: Preparation of t-butyl 1-(4-benzylpiperazine-1-carbonyl)-1H-pyrazole-3-carboxylate

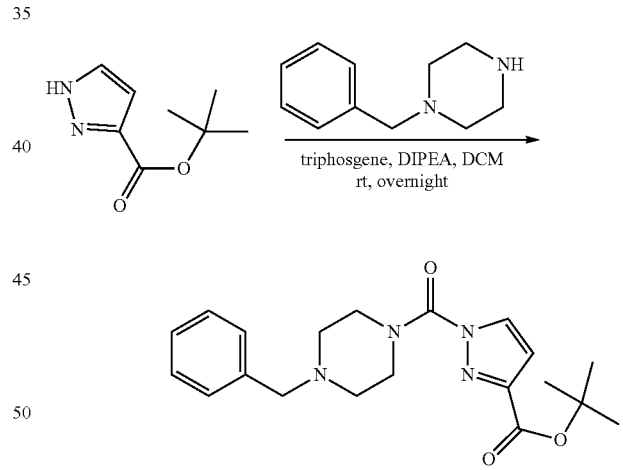

A flask was charged with triphosgene (1.24 g, 4.18 mmol, 0.70 equiv) and DCM (20 mL). t-Butyl 1H-pyrazole-3-carboxylate (1.00 g, 5.95 mmol, 1.00 equiv) was added at 0° C. DIPEA (3.07 g, 23.8 mmol, 4.00 equiv) was added at 0° C. The mixture was stirred at room temperature for 2 h at 0° C. 1-Benzylpiperazine (1.26 g, 7.15 mmol, 1.20 equiv) was added at 0° C., as described in Example 1, Step 3 to provide the crude product. The residue was chromatographed to provide 1.35 g (61% yield) of t-butyl 1-(4-benzylpiperazine-1-carbonyl)-1H-pyrazole-3-carboxylate as a yellow oil. LCMS (ESI, m/z): 371 [M+H]$^+$.

Step 5: Preparation of t-butyl 1-(piperazine-1-carbonyl)-1H-pyrazole-3-carboxylate

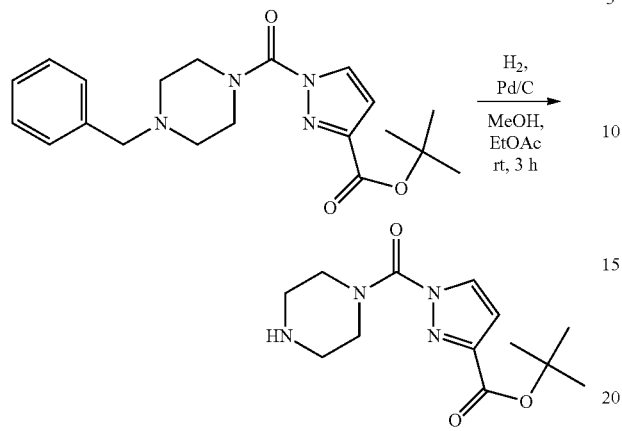

A flask was charged with t-butyl 1-(4-benzylpiperazine-1-carbonyl)-1H-pyrazole-3-carboxylate (1.00 g, 2.70 mmol, 1.00 equiv), MeOH (10 mL), EtOAc (10 mL), and palladium-on-carbon (0.400 g). Hydrogen was introduced. The resulting solution was stirred for 3 h at room temperature and the catalysts were filtered out. The filtrate was concentrated under reduced pressure to provide 0.690 g (crude) of t-butyl 1-(piperazine-1-carbonyl)-1H-pyrazole-3-carboxylate as a colorless oil. LCMS (ESI, m/z): 281 [M+H]$^+$.

Step 6: Preparation of t-butyl 1-(4-(2-(4-cyclopropylpiperazin-1-yl)-4-(trifluoromethyl)benzyl)piperazine-1-carbonyl)-1H-pyrazole-3-carboxylate

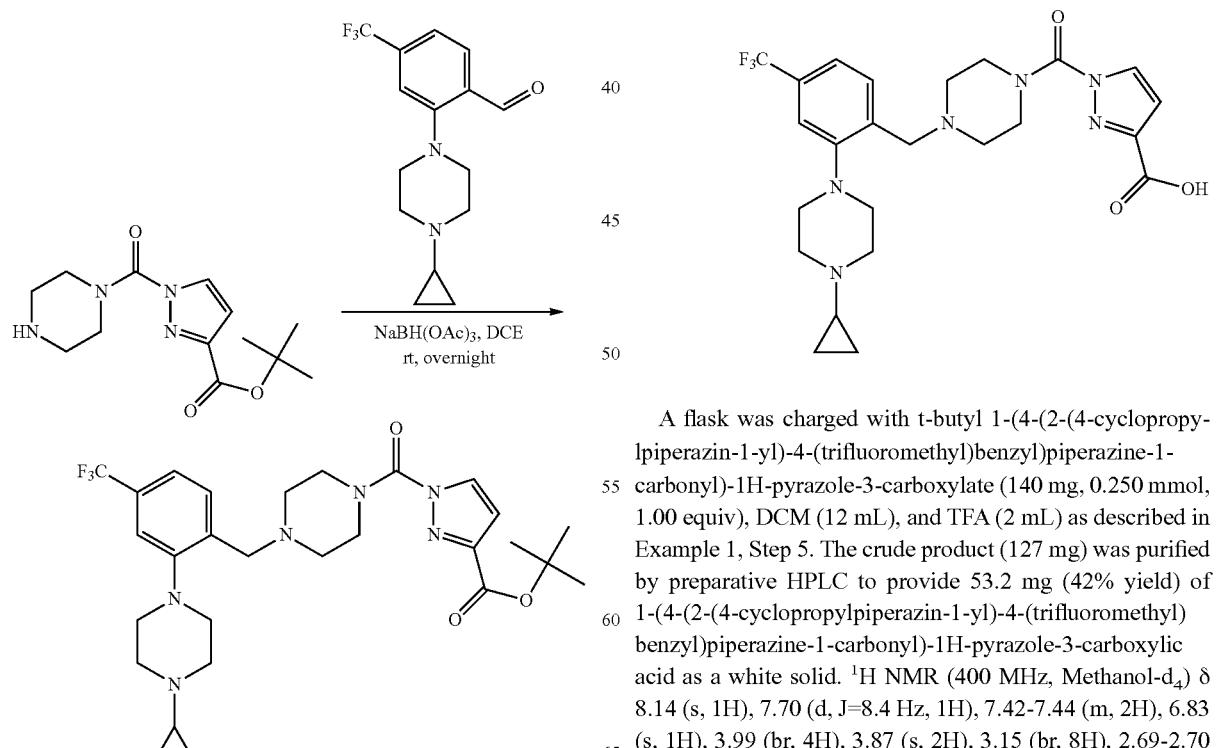

A flask was charged with 2-(4-cyclopropylpiperazin-1-yl)-4-(trifluoromethyl)benzaldehyde (92.2 mg, 0.309 mmol, 1.00 equiv), t-butyl 1-[(piperazin-1-yl)carbonyl]-1H-pyrazole-3-carboxylate (130 mg, 0.464 mmol, 1.50 equiv), DCE (10 mL). The resulting solution was stirred for 1 h at room temperature. Sodium triacetoxyborohydride (262 mg, 1.24 mmol, 4.00 equiv) was added, as described in Example 2, Step 3 to provide the crude product. The residue was chromatographed to provide 140 mg (81% yield) of t-butyl 1-(4-(2-(4-cyclopropylpiperazin-1-yl)-4-(trifluoromethyl)benzyl)piperazine-1-carbonyl)-1H-pyrazole-3-carboxylate as a yellow oil. LCMS (ESI, m/z): 563 [M+H]$^+$.

Step 7: Preparation of 1-(4-(2-(4-cyclopropylpiperazin-1-yl)-4-(trifluoromethyl)benzyl)piperazine-1-carbonyl)-1H-pyrazole-3-carboxylic Acid

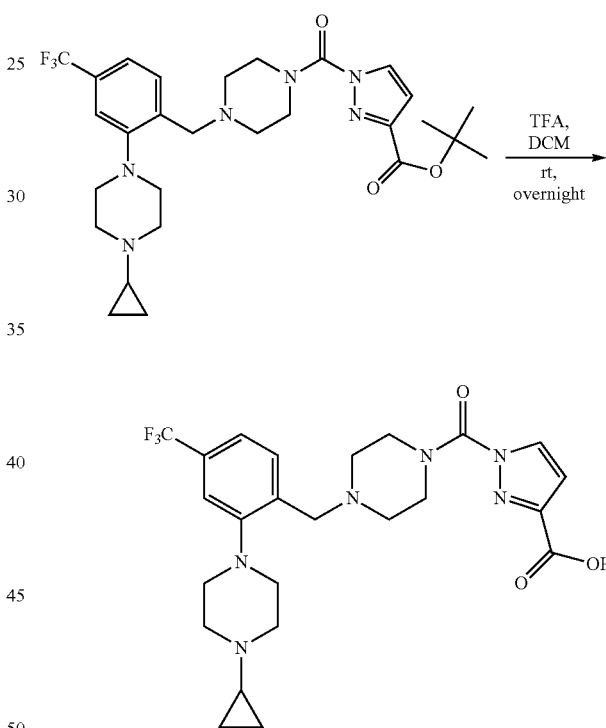

A flask was charged with t-butyl 1-(4-(2-(4-cyclopropylpiperazin-1-yl)-4-(trifluoromethyl)benzyl)piperazine-1-carbonyl)-1H-pyrazole-3-carboxylate (140 mg, 0.250 mmol, 1.00 equiv), DCM (12 mL), and TFA (2 mL) as described in Example 1, Step 5. The crude product (127 mg) was purified by preparative HPLC to provide 53.2 mg (42% yield) of 1-(4-(2-(4-cyclopropylpiperazin-1-yl)-4-(trifluoromethyl)benzyl)piperazine-1-carbonyl)-1H-pyrazole-3-carboxylic acid as a white solid. $^1$H NMR (400 MHz, Methanol-d$_4$) δ 8.14 (s, 1H), 7.70 (d, J=8.4 Hz, 1H), 7.42-7.44 (m, 2H), 6.83 (s, 1H), 3.99 (br, 4H), 3.87 (s, 2H), 3.15 (br, 8H), 2.69-2.70 (m, 4H), 2.28-2.34 (m, 1H), 0.65-0.84 (m, 4H). LCMS (ESI, m/z): 507 [M+H]$^+$.

129

Example 7: 1-(4-(3-(Pyrrolidin-1-yl)-4-(trifluoromethyl)benzyl)piperazine-1-carbonyl)-1H-pyrazole-3-carboxylic Acid

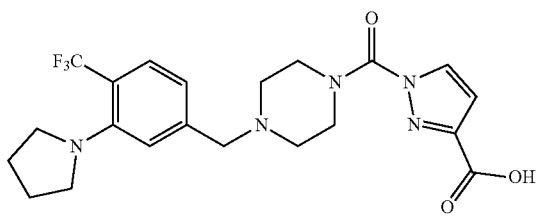 [SMILES: O=C(O)c1ccn(C(=O)N2CCN(Cc3ccc(C(F)(F)F)c(N4CCCC4)c3)CC2)n1]

Step 1: Preparation of 3-(pyrrolidin-1-yl)-4-(trifluoromethyl)benzaldehyde

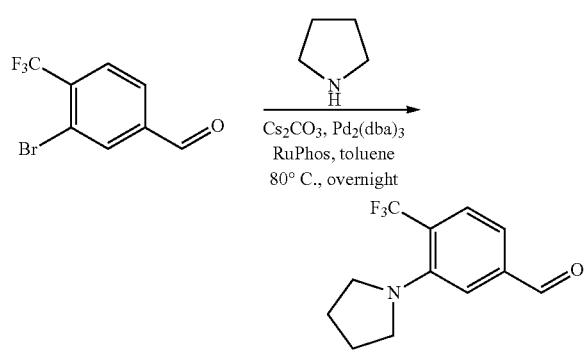

A flask was charged with 3-bromo-4-(trifluoromethyl)benzaldehyde (380 mg, 1.50 mmol, 1.00 equiv), pyrrolidine (160 mg, 2.25 mmol, 1.50 equiv), tris(dibenzylideneacetone)dipalladium (77.6 mg, 0.0750 mmol, 0.05 equiv), dicyclohexylphosphino-2',6'-di-i-propoxy-1,1'-biphenyl (52.5 mg, 0.110 mmol, 0.07 equiv), cesium carbonate (978 mg, 3.00 mmol, 3.00 equiv) and toluene (10 mL) under $N_2$ atmosphere. The resulting solution was stirred overnight at 80° C. and quenched with water (20 mL). The mixture was extracted with DCM (3×30 mL) and the organic layers were combined, washed with water (3×10 mL), dried over anhydrous sodium sulfate, filtered and concentrated under reduced pressure. The residue was chromatographed to provide 84.0 mg (23% yield) of 3-(pyrrolidin-1-yl)-4-(trifluoromethyl)benzaldehyde as a yellow oil. LCMS (ESI, m/z): 244 [M+H]+.

Step 2: Preparation of di-t-butyl 1H-pyrazole-1,3-dicarboxylate

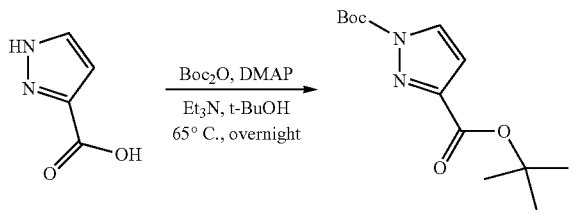 [SMILES: O=C(O)c1cc[nH]n1 ; CC(C)(C)OC(=O)c1ccn(C(=O)OC(C)(C)C)n1]

130

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL) as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]+.

Step 3: Preparation of t-butyl 1H-pyrazole-3-carboxylate

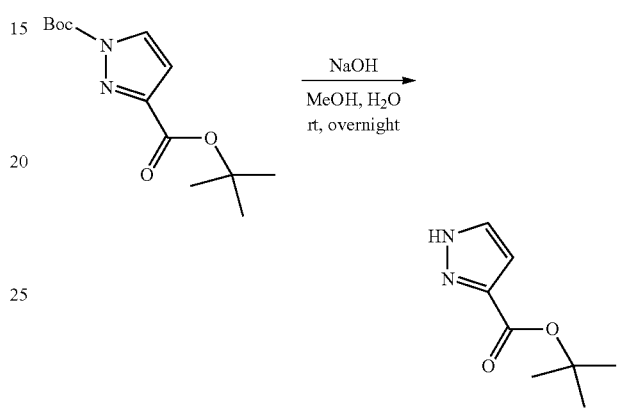

A flask was charged with 1,3-di-t-butyl-1H-pyrazole-1,3-dicarboxylate (20.0 g, 74.6 mmol, 1.00 equiv), MeOH (80 mL), NaOH (10.0 g, 250 mmol, 3.35 equiv) and water (40 mL), as described in Example 1, Step 2 to provide 6.70 g (crude) of t-butyl-1H-pyrazole-3-carboxylate as a yellow solid. LCMS (ESI, m/z): 169 [M+H]+.

Step 4: Preparation of t-butyl 1-(4-benzylpiperazine-1-carbonyl)-1H-pyrazole-3-carboxylate

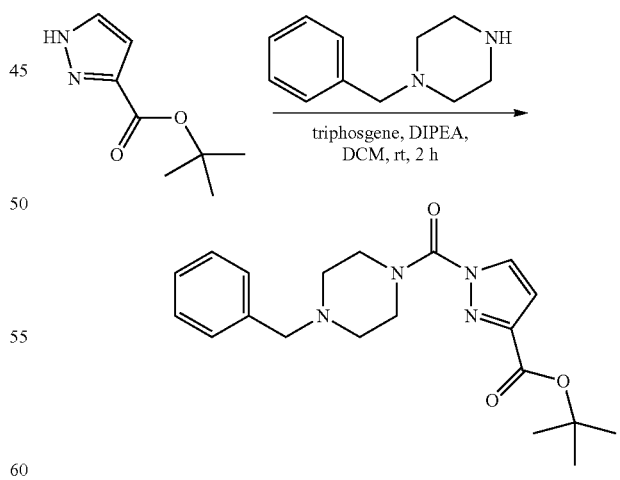

A flask was charged with t-butyl 1H-pyrazole-3-carboxylate (1.68 g, 10.0 mmol, 1.00 equiv), triphosgene (1.49 g, 5.00 mmol, 0.50 equiv) and DCM (20 mL). DIPEA (3.87 g, 30.0 mmol, 3.00 equiv) was then added dropwise at 0° C. The resulting solution was stirred for 2 h at room temperature. Then 1-benzylpiperazine (1.76 g, 10.0 mmol, 1.00 equiv) was added as described in Example 1, Step 3 to provide the crude product. The residue was chromatographed to provide 2.20 g (59% yield) of t-butyl 1-[(4-benzylpiperazin-1-yl)carbonyl]-1H-pyrazole-3-carboxylate as a yellow oil. LCMS (ESI, m/z): 371 [M+H]+.

Step 5: Preparation of t-butyl 1-(piperazine-1-carbonyl)-1H-pyrazole-3-carboxylate

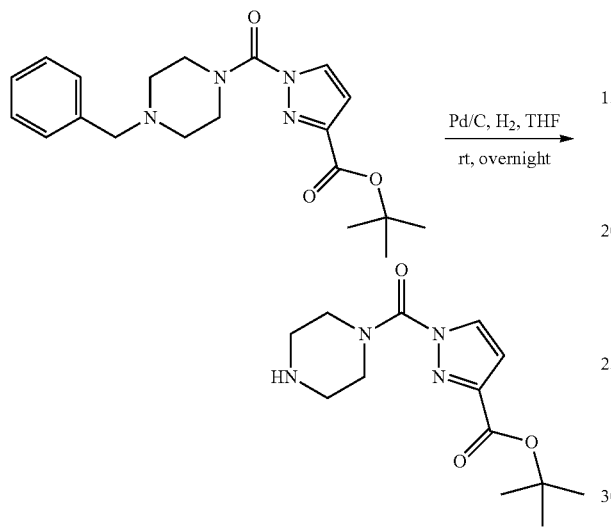

A flask was charged with t-butyl 1-[(4-benzylpiperazin-1-yl)carbonyl]-1H-pyrazole-3-carboxylate (2.20 g, 5.94 mmol, 1.00 equiv), palladium-on-carbon (200 mg) and THF (20 mL) under hydrogen, as described in Example 6, Step 2 to provide 1.37 g (crude) of t-butyl 1-[(piperazin-1-yl)carbonyl]-1H-pyrazole-3-carboxylate as a white solid. LCMS (ESI, m/z): 281 [M+H]+.

Step 6: Preparation of t-butyl 1-(4-(3-(pyrrolidin-1-yl)-4-(trifluoromethyl)benzyl)piperazine-1-carbonyl)-1H-pyrazole-3-carboxylate

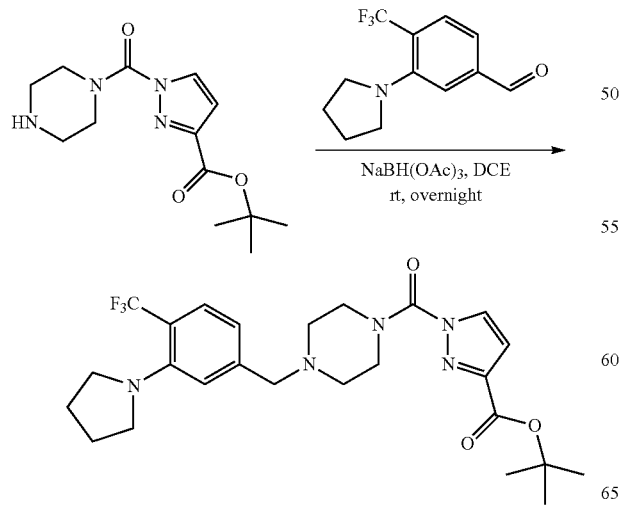

A flask was charged with 3-(pyrrolidin-1-yl)-4-(trifluoromethyl)benzaldehyde (84.0 mg, 0.350 mmol, 1.00 equiv), t-butyl 1-[(piperazin-1-yl)carbonyl]-1H-pyrazole-3-carboxylate (106 mg, 0.380 mmol, 1.10 equiv) and DCE (10 mL). The resulting solution was stirred for 1 hour at room temperature and sodium triacetoxyborohydride (148 mg, 0.700 mmol, 2.00 equiv) was added, as described in Example 2, Step 3 to provide the crude product. The residue was chromatographed to provide 83.0 mg (47% yield) of t-butyl 1-(4-(3-(pyrrolidin-1-yl)-4-(trifluoromethyl)benzyl)piperazine-1-carbonyl)-1H-pyrazole-3-carboxylate as a white oil. LCMS (ESI, m/z): 508 [M+H]+.

Step 7: Preparation of 1-(4-(3-(pyrrolidin-1-yl)-4-(trifluoromethyl)benzyl)piperazine-1-carbonyl)-1H-pyrazole-3-carboxylic Acid

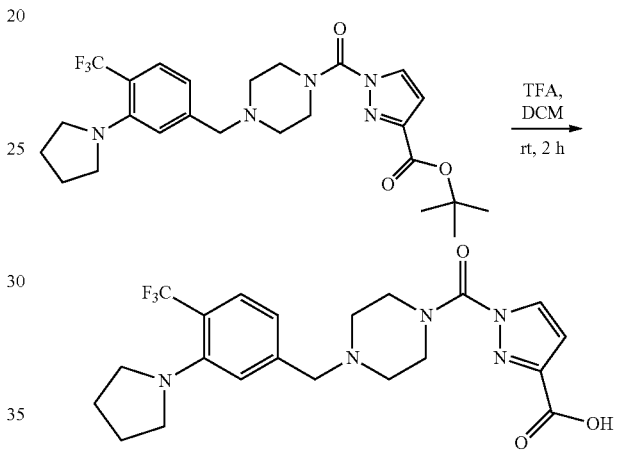

A flask was charged with t-butyl 1-(4-(3-(pyrrolidin-1-yl)-4-(trifluoromethyl)benzyl)piperazine-1-carbonyl)-1H-pyrazole-3-carboxylate (83.0 mg, 0.160 mmol, 1.00 equiv), TFA (1 mL) and DCM (4 mL), as described in Example 1, Step 5. The crude product was purified by preparative HPLC to provide 32.0 mg (43% yield) of 1-(4-(3-(pyrrolidin-1-yl)-4-(trifluoromethyl)benzyl)piperazine-1-carbonyl)-1H-pyrazole-3-carboxylic acid as a white solid. $^1$H NMR (300 MHz, Methanol-$d_4$) δ 8.08-8.15 (m, 1H), 7.45-7.56 (m, 1H), 7.13 (s, 1H), 6.73-6.94 (m, 2H), 3.71-3.94 (m, 6H), 3.26-3.34 (m, 4H), 2.71-2.87 (m, 4H), 1.74-2.01 (m, 4H). LCMS (ESI, m/z): 452 [M+H]+.

Example 8: 1-(4-(3-(Thiazol-2-yl)-4-(trifluoromethyl)benzyl)piperazine-1-carbonyl)-1H-pyrazole-3-carboxylic Acid

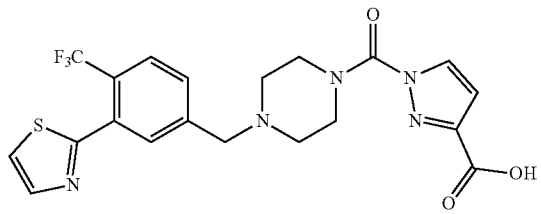 [SMILES: O=C(O)c1ccn(C(=O)N2CCN(Cc3ccc(C(F)(F)F)c(-c4nccs4)c3)CC2)n1]

Step 1: Preparation of di-t-butyl 1H-pyrazole-1,3-dicarboxylate

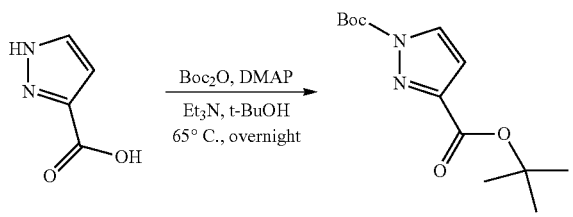 [SMILES: O=C(O)c1cc[nH]n1 ; CC(C)(C)OC(=O)c1ccn(C(=O)OC(C)(C)C)n1]

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL) as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

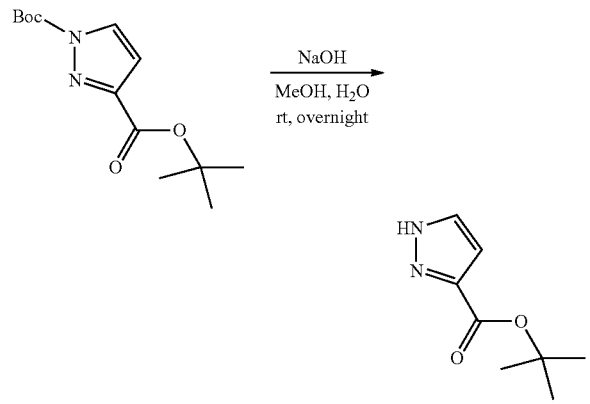

A flask was charged with 1,3-di-t-butyl-1H-pyrazole-1,3-dicarboxylate (20.0 g, 74.6 mmol, 1.00 equiv), MeOH (80 mL), NaOH (10.0 g, 250 mmol, 3.35 equiv) and water (40 mL), as described in Example 1, Step 2 to provide 6.70 g (crude) of t-butyl-1H-pyrazole-3-carboxylate as a yellow solid. LCMS (ESI, m/z): 169 [M+H]$^+$.

Step 3: Preparation of t-butyl 4-(3-bromo-4-(trifluoromethyl)benzyl)piperazine-1-carboxylate

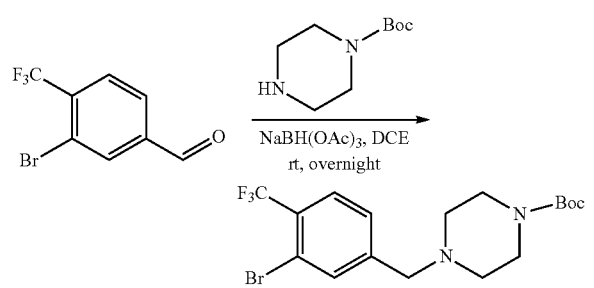

A flask was charged with 3-bromo-4-(trifluoromethyl)benzaldehyde (1.80 g, 7.11 mmol, 1.10 equiv), t-butyl piperazine-1-carboxylate (1.20 g, 6.44 mmol, 1.00 equiv) and DCE (50 mL). The resulting solution was stirred for 2 h at room temperature. Then sodium triacetoxyborohydride (2.74 g, 12.9 mmol, 2.00 equiv) was added, as described in Example 2, Step 3 to provide the crude product. The residue was chromatographed to provide 1.52 g (56% yield) of t-butyl 4-(3-bromo-4-(trifluoromethyl)benzyl)piperazine-1-carboxylate as a white solid. LCMS (ESI, m/z): 423 [M+H]$^+$.

Step 4: Preparation of t-butyl 4-(3-(thiazol-2-yl)-4-(trifluoromethyl)benzyl)piperazine-1-carboxylate

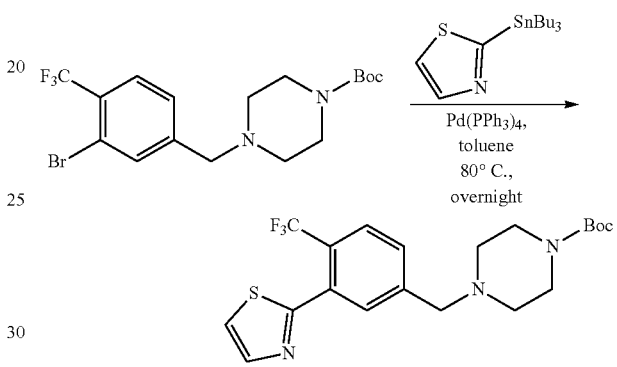

A flask was charged with t-butyl 4-(3-bromo-4-(trifluoromethyl)benzyl)piperazine-1-carboxylate (423 mg, 1.00 mmol, 1.00 equiv), 2-(tributylstannyl)-1,3-thiazole (374 mg, 1.00 mmol, 1.20 equiv), tetrakis(triphenylphosphine)palladium (115 mg, 0.100 mmol, 0.10 equiv) and toluene (10 mL) under nitrogen. The resulting solution was stirred overnight at 80° C. and diluted with water (10 mL). The mixture was extracted with ethyl acetate (3×30 mL) and the organic layers were combined, washed with brine (3×10 mL) and dried over anhydrous sodium sulfate, filtered and concentrated under reduced pressure. The residue was chromatographed to provide 188 mg (44% yield) of t-butyl 4-(3-(thiazol-2-yl)-4-(trifluoromethyl)benzyl)piperazine-1-carboxylate as a yellow solid. LCMS (ESI, m/z): 428 [M+H]$^+$.

Step 5: Preparation of 2-(5-(piperazin-1-ylmethyl)-2-(trifluoromethyl)phenyl)thiazole

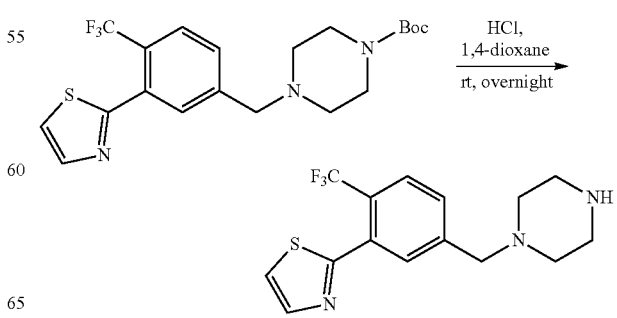

A flask was charged with t-butyl 4-(3-(thiazol-2-yl)-4-(trifluoromethyl)benzyl)piperazine-1-carboxylate (188 mg, 0.440 mmol, 1.00 equiv), HCl (1 mL) and 1,4-dioxane (4 mL), as described in Example 2, Step 4 to provide 144 mg (crude) of 2-(5-(piperazin-1-ylmethyl)-2-(trifluoromethyl)phenyl)thiazole as a white solid. LCMS (ESI, m/z): 328 [M+H]⁺.

Step 6: Preparation of t-butyl 1-(4-(3-(thiazol-2-yl)-4-(trifluoromethyl)benzyl)piperazine-1-carbonyl)-1H-pyrazole-3-carboxylate

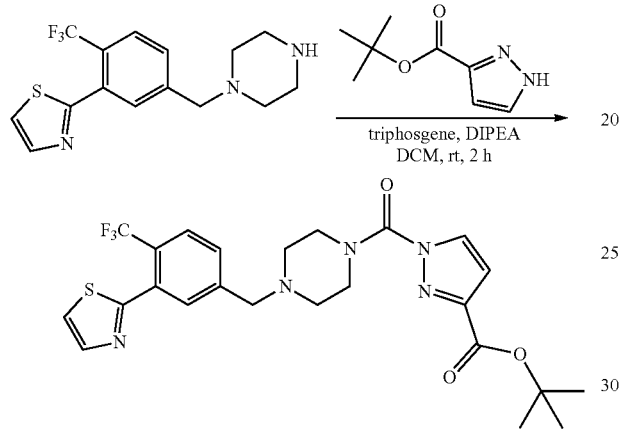

A flask was charged with t-butyl-1H-pyrazole-3-carboxylate (74.0 mg, 0.440 mmol, 1.00 equiv), triphosgene (65.0 mg, 0.220 mmol, 0.50 equiv) and DCM (10 mL). Then DIPEA (170 mg, 1.32 mmol, 3.00 equiv) was added at 0° C. and the resulting solution was stirred for 2 h at room temperature. Then 2-(5-(piperazin-1-ylmethyl)-2-(trifluoromethyl)phenyl)thiazole (144 mg, 0.440 mmol, 1.00 equiv) was added, as described in Example 1, Step 3 to provide the crude product. The residue was chromatographed to provide 119 mg (52% yield) of t-butyl 1-(4-(3-(thiazol-2-yl)-4-(trifluoromethyl)benzyl)piperazine-1-carbonyl)-1H-pyrazole-3-carboxylate as a colorless oil. LCMS (ESI, m/z): 522 [M+H]⁺.

Step 7: Preparation of 1-(4-(3-(thiazol-2-yl)-4-(trifluoromethyl)benzyl)piperazine-1-carbonyl)-1H-pyrazole-3-carboxylic Acid

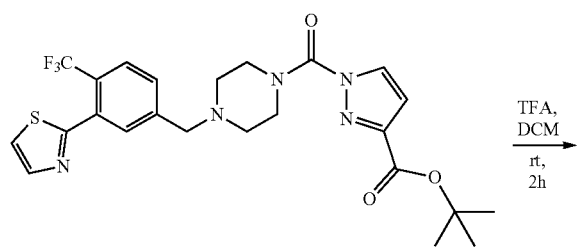

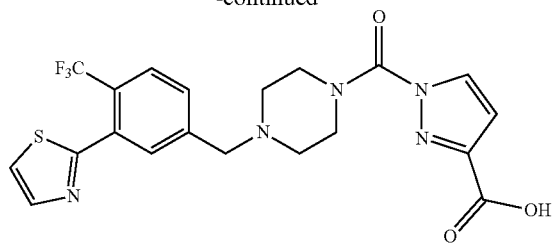

A flask was charged with t-butyl 1-(4-(3-(thiazol-2-yl)-4-(trifluoromethyl)benzyl)piperazine-1-carbonyl)-1H-pyrazole-3-carboxylate (119 mg, 0.231 mmol, 1.00 equiv), TFA (1 mL) and DCM (4 mL), as described in Example 1 Step 5 to provide the crude product. The crude product was purified by preparative HPLC to provide 31.2 mg (29% yield) of 1-(4-(3-(thiazol-2-yl)-4-(trifluoromethyl)benzyl)piperazine-1-carbonyl)-1H-pyrazole-3-carboxylic acid as a white solid. ¹H NMR (300 MHz, Methanol-$d_4$) δ 8.13 (s, 1H), 7.70-7.90 (m, 5H), 6.80-6.85 (m, 1H), 3.70-3.90 (m, 6H), 2.60-2.70 (m, 4H). LCMS (ESI, m/z): 466 [M+H]⁺.

Example 9: 1-(4-(3-(1,3,4-oxadiazol-2-yl)-4-(trifluoromethyl)benzyl)piperazine-1-carbonyl)-1H-pyrazole-3-carboxylic Acid

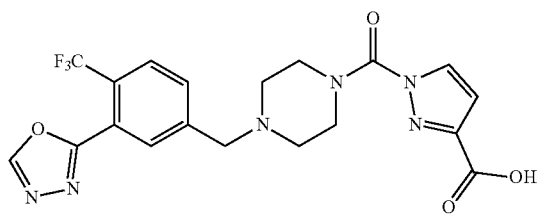 [SMILES: O=C(O)c1ccn(C(=O)N2CCN(Cc3ccc(C(F)(F)F)c(-c4nnco4)c3)CC2)n1]

Step 1: Preparation of t-butyl 4-(3-bromo-4-(trifluoromethyl)benzyl)piperazine-1-carboxylate

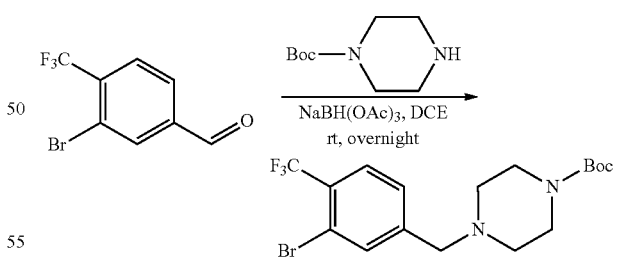

A flask was charged with t-butyl piperazine-1-carboxylate (0.800 g, 4.30 mmol, 1.00 equiv), 3-bromo-4-(trifluoromethyl)benzaldehyde (1.20 g, 4.74 mmol, 1.10 equiv) and DCE (20 mL). The resulting solution was stirred for 2 h at room temperature and sodium triacetoxyborohydride (1.83 g, 8.63 mmol, 2.00 equiv) was added, as described in Example 2, Step 3. The residue was chromatographed to provide 1.56 g (86% yield) of t-butyl 4-(3-(methoxycarbonyl)-4-(trifluoromethyl)benzyl)piperazine-1-carboxylate as a white solid. LCMS (ESI, m/z): 423 [M+H]⁺.

Step 2: Preparation of t-butyl 4-(3-(methoxycarbonyl)-4-(trifluoromethyl)benzyl)piperazine-1-carboxylate

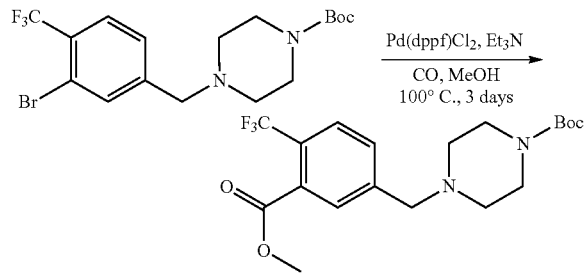

A pressure tank reactor was charged with t-butyl 4-(3-(methoxycarbonyl)-4-(trifluoromethyl)benzyl)piperazine-1-carboxylate (600 mg, 1.42 mmol, 1.00 equiv), [1,1'-bis(diphenylphosphino)ferrocene]dichloropalladium(II) (203 mg, 0.280 mmol, 0.20 equiv), triethylamine (421 mg, 4.16 mmol, 3.00 equiv) and MeOH (10 mL). The resulting solution was stirred for 3 days at 100° C. under carbon monoxide atmosphere (10 atm) and quenched with water (20 mL). The mixture was extracted with DCM (3×30 mL) and the organic layers were combined, washed with water (3×10 mL), dried over anhydrous sodium sulfate, filtered and concentrated under reduced pressure. The residue was chromatographed to provide 560 mg (98% yield) of t-butyl 4-(3-(methoxycarbonyl)-4-(trifluoromethyl)benzyl)piperazine-1-carboxylate as a yellow oil. LCMS (ESI, m/z): 403 [M+H]$^+$.

Step 3: Preparation of t-butyl 4-(3-(hydrazinecarbonyl)-4-(trifluoromethyl)benzyl)piperazine-1-carboxylate

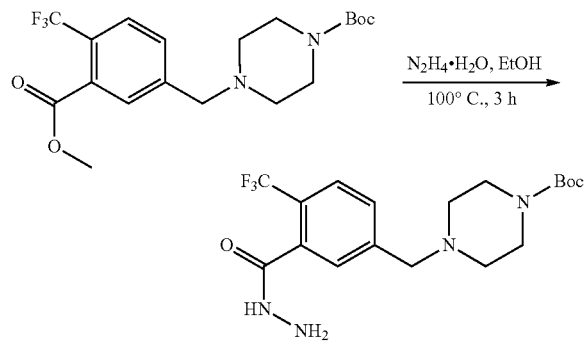

A 50-mL round-bottom flask was charged with t-butyl 4-(3-(methoxycarbonyl)-4-(trifluoromethyl)benzyl)piperazine-1-carboxylate (560 mg, 1.39 mmol, 1.00 equiv), hydrazine hydrate (209 mg, 4.17 mmol, 3.00 equiv) and EtOH (10 mL). The resulting solution was stirred for 3 h at 100° C. and concentrated under reduced pressure to provide 560 mg (crude) of t-butyl 4-(3-(hydrazinecarbonyl)-4-(trifluoromethyl)benzyl)piperazine-1-carboxylate as a yellow oil. LCMS (ESI, m/z): 403 [M+H]$^+$.

Step 4: Preparation of t-butyl 4-(3-(1,3,4-oxadiazol-2-yl)-4-(trifluoromethyl)benzyl)piperazine-1-carboxylate

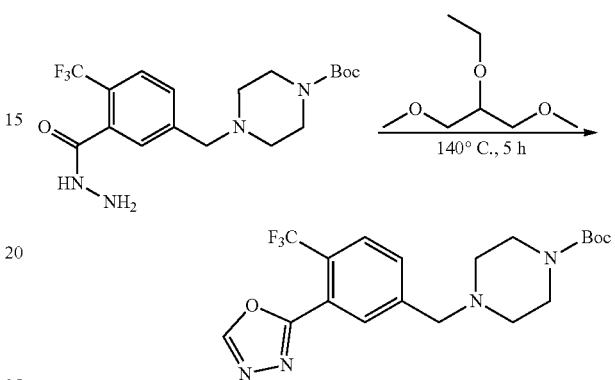

A flask was charged with t-butyl 4-(3-(hydrazinecarbonyl)-4-(trifluoromethyl)benzyl)piperazine-1-carboxylate (560 mg, 1.34 mmol, 1.00 equiv) and triethoxymethane (10 mL). The resulting solution was stirred for 5 h at 140° C. and concentrated under reduced pressure. The residue was chromatographed to provide 540 mg (94% yield) of t-butyl 4-(3-(1,3,4-oxadiazol-2-yl)-4-(trifluoromethyl)benzyl)piperazine-1-carboxylate as a yellow oil. LCMS (ESI, m/z): 413 [M+H]$^+$.

Step 5: Preparation of 2-(5-(piperazin-1-ylmethyl)-2-(trifluoromethyl)phenyl)-1,3,4-oxadiazole

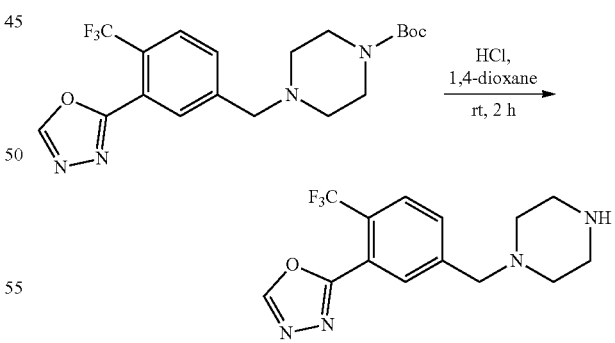

A flask was charged with t-butyl 4-(3-(1,3,4-oxadiazol-2-yl)-4-(trifluoromethyl)benzyl)piperazine-1-carboxylate (540 mg, 1.26 mmol, 1.00 equiv), HCl (3 mL) and 1,4-dioxane (10 mL), as described in Example 2, Step 4 to provide 409 mg (crude) of 2-((5-(piperazin-1-ylmethyl)-2-(trifluoromethyl)phenyl)-1,3,4-oxadiazole as a white solid. LCMS (ESI, m/z): 313 [M+H]$^+$.

Step 6: Preparation of t-butyl 1-(4-(3-(1,3,4-oxadiazol-2-yl)-4-(trifluoromethyl)benzyl)piperazine-1-carbonyl)-1H-pyrazole-3-carboxylate

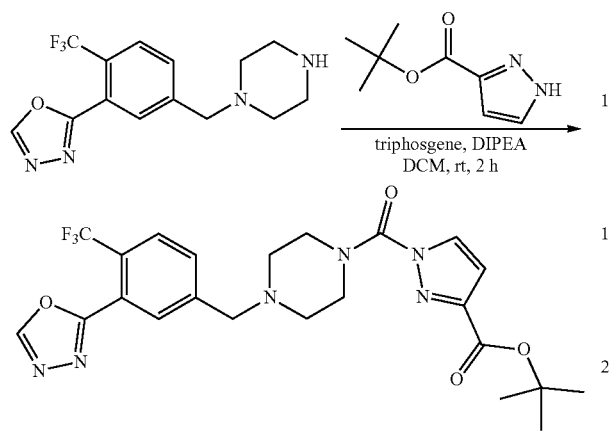

A flask was charged with 2-(5-(piperazin-1-ylmethyl)-2-(trifluoromethyl)phenyl)-1,3,4-oxadiazole (264 mg, 1.57 mmol, 1.20 equiv), triphosgene (235 mg, 0.790 mmol, 0.60 equiv) and DCM (10 mL). Then DIPEA (676 mg, 5.23 mmol, 4.00 equiv) was added dropwise at 0° C. and the resulting solution was stirred for 2 h at room temperature. Then t-butyl 1H-pyrazole-3-carboxylate (409 mg, 1.31 mmol, 1.00 equiv) was added, as described in Example 1, Step 3. The residue was chromatographed to provide 302 mg (46% yield) of t-butyl 1-(4-(3-(1,3,4-oxadiazol-2-yl)-4-(trifluoromethyl)benzyl)piperazine-1-carbonyl)-1H-pyrazole-3-carboxylate as a yellow solid. LCMS (ESI, m/z): 507 [M+H]$^+$.

Step 7: Preparation of 1-(4-(3-(1,3,4-oxadiazol-2-yl)-4-(trifluoromethyl)benzyl)piperazine-1-carbonyl)-1H-pyrazole-3-carboxylic Acid

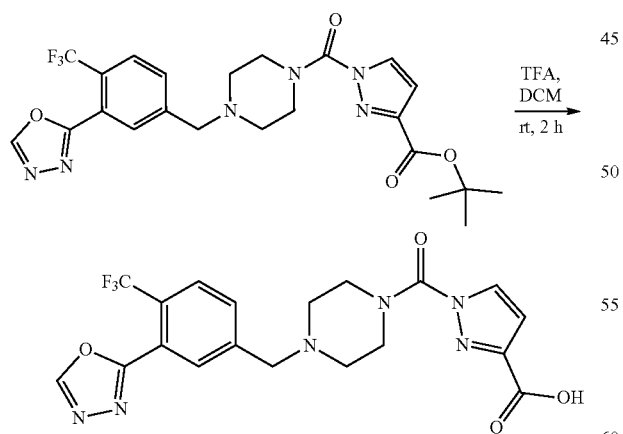

A flask was charged with t-butyl 1-(4-(3-(1,3,4-oxadiazol-2-yl)-4-(trifluoromethyl)benzyl)piperazine-1-carbonyl)-1H-pyrazole-3-carboxylate (302 mg, 0.600 mmol, 1.00 equiv), TFA (1 mL) and DCM (4 mL), as described in Example 1, Step 5. The crude product was purified by preparative HPLC to provide 60.3 mg (22% yield) of 1-(4-(3-(1,3,4-oxadiazol-2-yl)-4-(trifluoromethyl)benzyl)piperazine-1-carbonyl)-1H-pyrazole-3-carboxylic acid as a white solid. $^1$H NMR (300 MHz, Methanol-d$_4$) δ 9.14 (s, 1H), 8.08-8.15 (m, 1H), 8.06 (s, 1H), 7.88-7.99 (m, 1H), 7.76-7.88 (m, 1H), 6.74-6.87 (m, 1H), 3.89 (s, 3H), 3.69-3.78 (m, 2H), 2.54-2.67 (m, 4H). LCMS (ESI, m/z): 451 [M+H]$^+$.

Example 10: 1-(4-methyl-4-(methyl(2-(thiazol-2-yl)-4-(trifluoromethyl)benzyl)amino)piperidine-1-carbonyl)-1H-pyrazole-3-carboxylic Acid

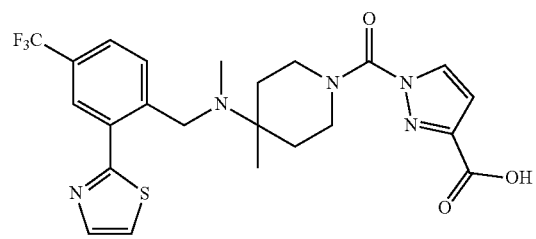 [SMILES: CN(Cc1ccc(C(F)(F)F)cc1-c1nccs1)C1(C)CCN(C(=O)n2ccc(C(=O)O)n2)CC1]

Step 1: Preparation of di-t-butyl 1H-pyrazole-1,3-dicarboxylate

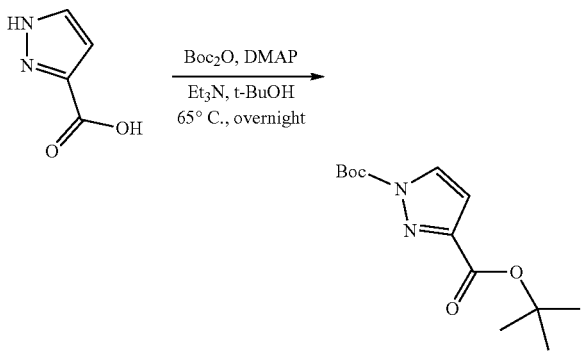

A flask was charged with 1H-pyrazole-3-carboxylic acid (10.0 g, 89.2 mmol, 1.00 equiv), DMAP (2.15 g, 17.6 mmol, 0.20 equiv), triethylamine (27.0 g, 267 mmol, 3.00 equiv), di-t-butyl dicarbonate (80.0 g, 366 mmol, 4.00 equiv) in t-butanol (100 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]$^+$.

Step 2: Preparation of t-butyl 1H-pyrazole-3-carboxylate

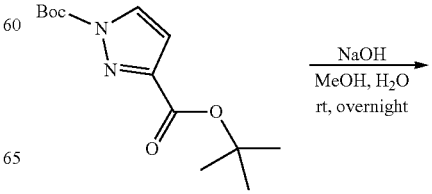

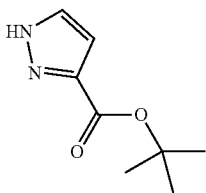

A flask was charged with 1,3-di-t-butyl 1H-pyrazole-1,3-dicarboxylate (25.0 g, 93.2 mmol, 1.00 equiv), NaOH (5.60 g, 140 mmol, 1.50 equiv) in water (80 mL) and MeOH (240 mL), as described in Example 1, Step 2 to provide 10.0 g (64% yield) of t-butyl 1H-pyrazole-3-carboxylate as a white solid. LCMS (ESI, m/z): 169 [M+H]+.

Step 3: Preparation of 3-(t-butyl) 1-(4-nitrophenyl) 1H-pyrazole-1,3-dicarboxylate

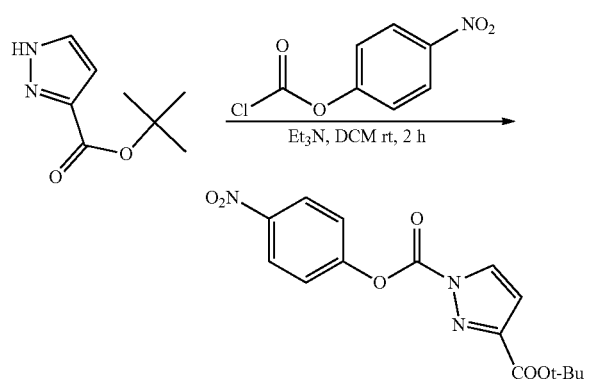

A flask was charged with 4-nitrophenyl chloroformate (448 mg, 2.22 mmol, 1.05 equiv), t-butyl 1H-pyrazole-3-carboxylate (356 mg, 2.12 mmol, 1.00 equiv), DCM (5 mL), and triethylamine (642 mg, 6.34 mmol, 3.00 equiv), as described in Example 4, Step 3 to provide 500 mg (crude) of 3-t-butyl 1-(4-nitrophenyl) 1H-pyrazole-1,3-dicarboxylate as a yellow oil. LCMS (ESI, m/z): 334 [M+H]+.

Step 4: Preparation of t-butyl 4-((2-bromo-4-(trifluoromethyl)benzyl)amino)-4-methylpiperidine-1-carboxylate

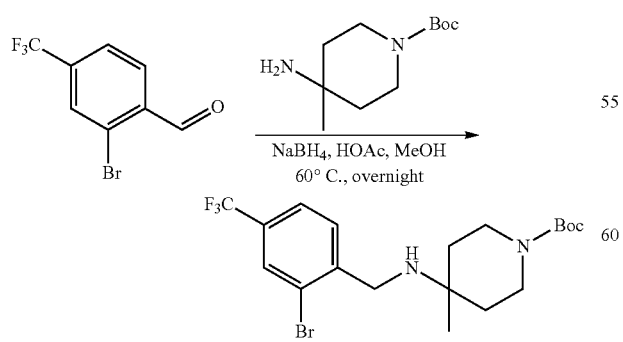

A flask was charged with 2-bromo-4-(trifluoromethyl)benzaldehyde (970 mg, 3.83 mmol, 1.00 equiv), t-butyl 4-amino-4-methylpiperidine-1-carboxylate (1.07 g, 4.99 mmol, 1.30 equiv), MeOH (10 mL), and AcOH (696 mg, 11.6 mmol, 3.00 equiv). The resulting solution was stirred for 1 h at 60° C. Sodium borohydride (441 mg, 11.6 mmol, 3.00 equiv) was added. The residue was chromatographed to provide 1.41 g (81% yield) of t-butyl 4-((2-bromo-4-(trifluoromethyl)benzyl)amino)-4-methylpiperidine-1-carboxylate as a yellow oil. LCMS (ESI, m/z): 451 [M+H]+.

Step 5: Preparation of t-butyl 4-((2-bromo-4-(trifluoromethyl)benzyl)(methyl)amino)-4-methylpiperidine-1-carboxylate

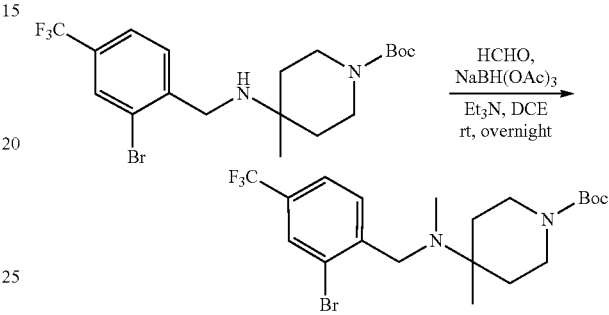

A flask was charged with t-butyl 4-((2-bromo-4-(trifluoromethyl)benzyl)amino)-4-methylpiperidine-1-carboxylate (1.41 g, 3.12 mmol, 1.00 equiv), paraformaldehyde (939 mg, 31.2 mmol, 10.0 equiv), triethylamine (948 mg, 9.36 mmol, 3.00 equiv), and DCE (20 mL). The resulting solution was stirred for 1 h at room temperature. Sodium triacetoxyborohydride (1.99 g, 9.36 mmol, 3.00 equiv) was added as described in Example 2, Step 3. The residue was chromatographed to provide 1.10 g (76% yield) of t-butyl 4-((2-bromo-4-(trifluoromethyl)benzyl)(methyl)amino)-4-methylpiperidine-1-carboxylate as a yellow oil. LCMS (ESI, m/z): 465 [M+H]+.

Step 6: Preparation of t-butyl 4-methyl-4-(methyl (2-(thiazol-2-yl)-4-(trifluoromethyl)benzyl)amino) piperidine-1-carboxylate

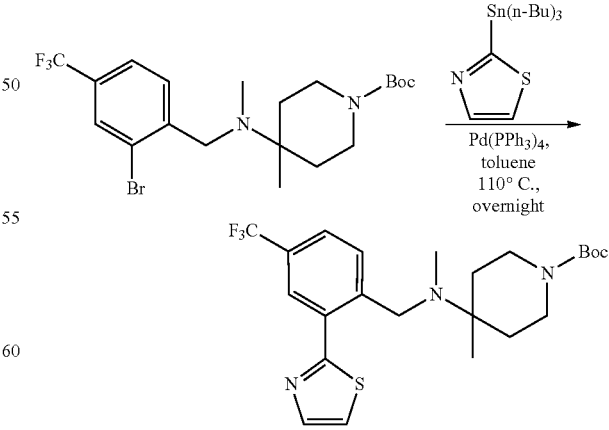

A flask was charged with t-butyl 4-((2-bromo-4-(trifluoromethyl)benzyl)(methyl)amino)-4-methylpiperidine-1-carboxylate (417 mg, 0.899 mmol, 1.00 equiv), 2-(tributylstannyl)-1,3-thiazole (506 mg, 1.35 mmol, 1.50 equiv), tetrakis(triphenylphosphine)palladium (104 mg, 0.0899 mmol, 0.10 equiv), and toluene (10 mL). The resulting solution was stirred overnight at 110° C. and quenched with water (10 mL), as described in Example 8, Step 4. The residue was chromatographed to provide 400 mg (95% yield) of t-butyl 4-methyl-4-(methyl(2-(thiazol-2-yl)-4-(trifluoromethyl)benzyl)amino)piperidine-1-carboxylate as a yellow oil. LCMS (ESI, m/z): 470 [M+H]⁺.

Step 7: Preparation of N,4-dimethyl-N-(2-(thiazol-2-yl)-4-(trifluoromethyl)benzyl)piperidin-4-amine

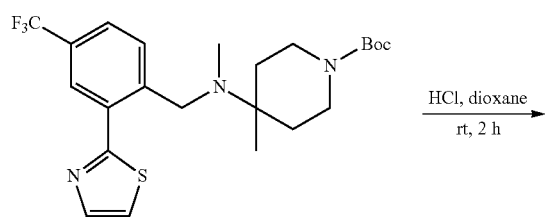

A flask was charged with t-butyl 4-methyl-4-(methyl(2-(thiazol-2-yl)-4-(trifluoromethyl)benzyl)amino)piperidine-1-carboxylate (495 mg, 1.05 mmol, 1.00 equiv), 1,4-dioxane (5 mL), concentrated HCl (1 mL), as described in Example 2, Step 4 to provide 500 mg (crude) of N,4-dimethyl-N-(2-(thiazol-2-yl)-4-(trifluoromethyl)benzyl)piperidin-4-amine as a yellow oil. LCMS (ESI, m/z): 370 [M+H]⁺.

Step 8: Preparation of t-butyl 1-(4-methyl-4-(methyl(2-(thiazol-2-yl)-4-(trifluoromethyl)benzyl)amino)piperidine-1-carbonyl)-1H-pyrazole-3-carboxylate

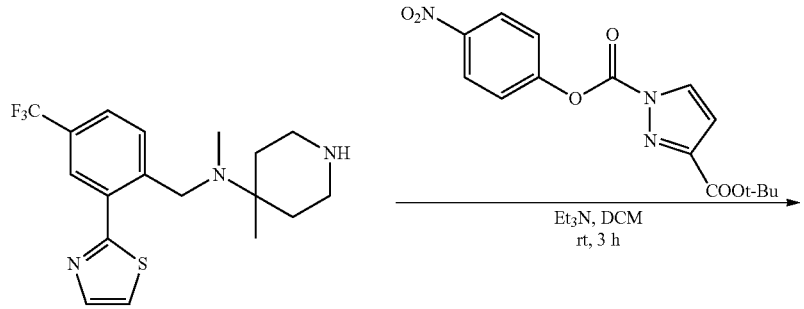

A flask was charged with 3-t-butyl 1-(4-nitrophenyl) 1H-pyrazole-1,3-dicarboxylate (708 mg, 2.12 mmol, 2.00 equiv), N,4-dimethyl-N-(2-(thiazol-2-yl)-4-(trifluoromethyl)benzyl)piperidin-4-amine (391 mg, 1.06 mmol, 1.00 equiv), DCM (10 mL), and triethylamine (321 mg, 3.17 mmol, 3.00 equiv). The resulting solution was stirred for 3 h at room temperature and quenched with water (10 mL), as described in Example 4, Step 3. The residue was chromatographed to provide 560 mg (94% yield) of t-butyl 1-(4-methyl-4-(methyl(2-(thiazol-2-yl)-4-(trifluoromethyl)benzyl)amino)piperidine-1-carbonyl)-1H-pyrazole-3-carboxylate as a yellow oil. LCMS (ESI, m/z): 564 [M+H]⁺.

Step 9: Preparation of 1-(4-methyl-4-(methyl(2-(thiazol-2-yl)-4-(trifluoromethyl)benzyl)amino)piperidine-1-carbonyl)-1H-pyrazole-3-carboxylic Acid

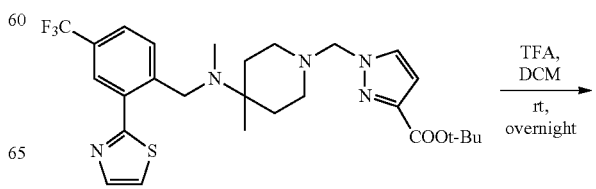

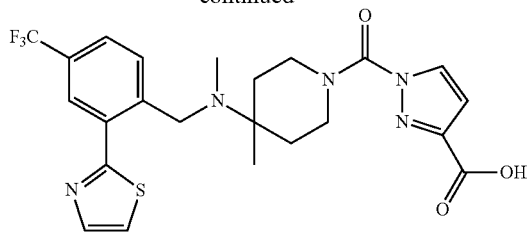

A flask was charged with t-butyl 1-(4-methyl-4-(methyl (2-(thiazol-2-yl)-4-(trifluoromethyl)benzyl)amino)piperidine-1-carbonyl)-1H-pyrazole-3-carboxylate (560 mg, 0.990 mmol, 1.00 equiv), DCM (10 mL), and TFA (2 mL), as described in Example 1, Step 5. The crude product (400 mg) was purified by preparative HPLC to provide 132.0 mg (26% yield) of 1-(4-methyl-4-(methyl(2-(thiazol-2-yl)-4-(trifluoromethyl)benzyl)amino)piperidine-1-carbonyl)-1H-pyrazole-3-carboxylic acid as a white solid. $^1$H NMR (400 MHz, Methanol-$d_4$) δ 8.00-8.10 (m, 4H), 7.84-7.88 (m, 2H), 6.80 (d, J=2.7 Hz, 1H), 4.20-4.30 (m, 4H), 3.62 (br, 2H), 2.38 (br, 3H), 2.14 (br, 2H), 1.91 (br, 2H), 1.36 (br, 3H). LCMS (ESI, m/z): 508 [M+H]$^+$.

Example 11: 1-(4-(4-Chloro-2-(pyrrolidin-1-yl)phenoxy)piperidine-1-carbonyl)-1H-pyrazole-3-carboxylic Acid

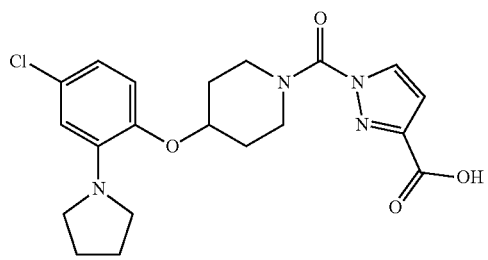 [SMILES: O=C(O)c1ccn(C(=O)N2CCC(Oc3ccc(Cl)cc3N3CCCC3)CC2)n1]

Step 1: Preparation of di-t-butyl 1H-pyrazole-1,3-dicarboxylate

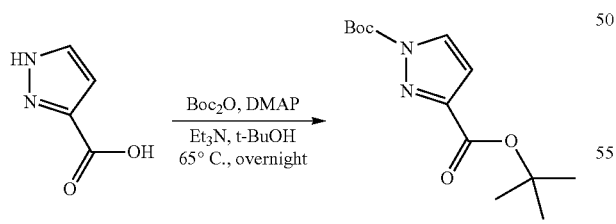

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL), as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

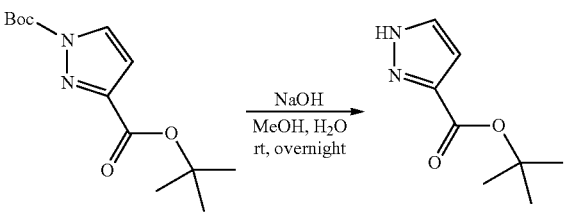 [SMILES: CC(C)(C)OC(=O)c1ccn(C(=O)OC(C)(C)C)n1 ; "NaOH" ; CC(C)(C)OC(=O)c1cc[nH]n1]

A flask was charged with 1,3-di-t-butyl-1H-pyrazole-1,3-dicarboxylate (20.0 g, 74.6 mmol, 1.00 equiv), MeOH (80 mL), NaOH (10.0 g, 250 mmol, 3.35 equiv) and water (40 mL). The resulting solution was stirred overnight at room temperature and quenched by water (40 mL), as described in Example 1, Step 2 to provide 6.70 g (crude) of t-butyl-1H-pyrazole-3-carboxylate as a yellow solid. LCMS (ESI, m/z): 169 [M+H]$^+$.

Step 3: Preparation of t-butyl 4-((methylsulfonyl)oxy)piperidine-1-carboxylate

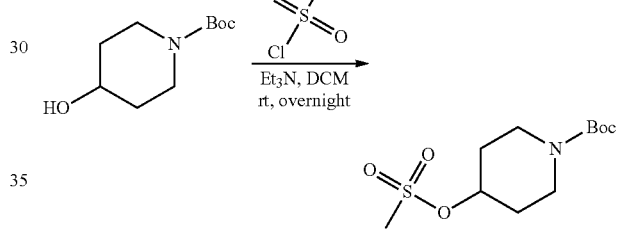

A flask was charged with t-butyl 4-hydroxypiperidine-1-carboxylate (1.00 g, 4.97 mmol, 1.00 equiv), DCM (20 mL), methanesulfonyl chloride (629 mg, 5.47 mmol, 1.10 equiv). Triethylamine (1.51 g, 14.9 mmol, 3.00 equiv) was added dropwise at 0° C. The resulting solution was stirred overnight at room temperature and concentrated under reduced pressure to provide 1.29 g (crude) of t-butyl 4-(methanesulfonyloxy)piperidine-1-carboxylate as a white solid. LCMS (ESI, m/z): 280 [M+H]$^+$.

Step 4: Preparation of t-butyl 4-(2-bromo-4-chlorophenoxy)piperidine-1-carboxylate

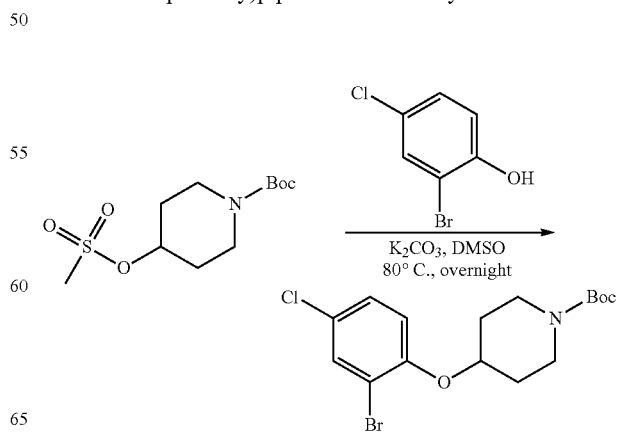

A flask was charged with 2-bromo-4-chlorophenol (367 mg, 1.77 mmol, 1.10 equiv), DMSO (15 mL), t-butyl 4-(methanesulfonyloxy)piperidine-1-carboxylate (450 mg, 1.61 mmol, 1.00 equiv) and potassium carbonate (667 mg, 4.83 mmol, 3.00 equiv). The resulting solution was stirred overnight at 80° C. and quenched with water (30 mL). The mixture was extracted with EtOAc (3×50 mL) and the organic layers were combined, washed with water (3×20 mL), dried over anhydrous sodium sulfate, filtered and concentrated under reduced pressure. The residue was chromatographed to provide 400 mg (64% yield) of t-butyl 4-(2-bromo-4-chlorophenoxy)piperidine-1-carboxylate as a yellow oil. LCMS (ESI, m/z): 390 [M+H]+.

Step 5: Preparation of t-butyl 4-(4-chloro-2-(pyrrolidin-1-yl)phenoxy)piperidine-1-carboxylate

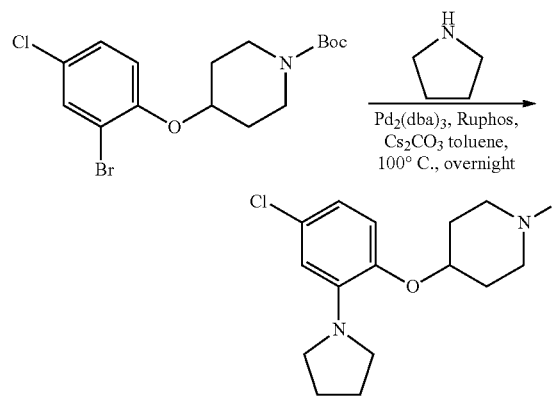

A flask was charged with t-butyl 4-(2-bromo-4-chlorophenoxy)piperidine-1-carboxylate (400 mg, 1.02 mmol, 1.00 equiv), toluene (15 mL), pyrrolidine (109 mg, 1.53 mmol, 1.50 equiv), cesium carbonate (665 mg, 2.04 mmol, 2.00 equiv), tris(dibenylideneacetone)dipalladium-chloroform (52.8 mg, 0.0510 mmol, 0.05 equiv) and dicyclohexylphosphino-2',6'-di-i-propoxy-1,1'-biphenyl (35.7 mg, 0.0714 mmol, 0.07 equiv), as described in Example 7, Step 1. The residue was chromatographed to provide 220 mg (56% yield) of t-butyl 4-(4-chloro-2-(pyrrolidin-1-yl)phenoxy)piperidine-1-carboxylate as a yellow oil. LCMS (ESI, m/z): 381 [M+H]+.

Step 6: Preparation of 4-(4-chloro-2-(pyrrolidin-1-yl)phenoxy)piperidine

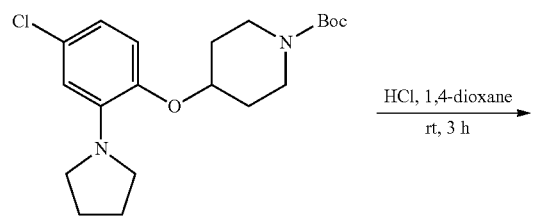

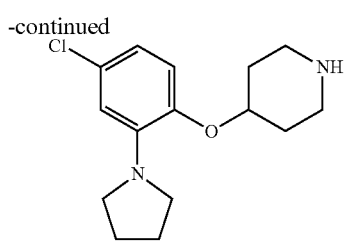

A flask was charged with t-butyl 4-(4-chloro-2-(pyrrolidin-1-yl)phenoxy)piperidine-1-carboxylate (220 mg, 0.582 mmol, 1.00 equiv), 1,4-dioxane (10 mL) and HCl (2 mL), as described in Example 2, Step 4 to provide 150 mg (crude) of 4-(4-chloro-2-(pyrrolidin-1-yl)phenoxy)piperidine as a yellow oil. LCMS (ESI, m/z): 281 [M+H]+.

Step 7: Preparation of 4-(4-chloro-2-(pyrrolidin-1-yl)phenoxy)piperidine-1-carbonyl Chloride

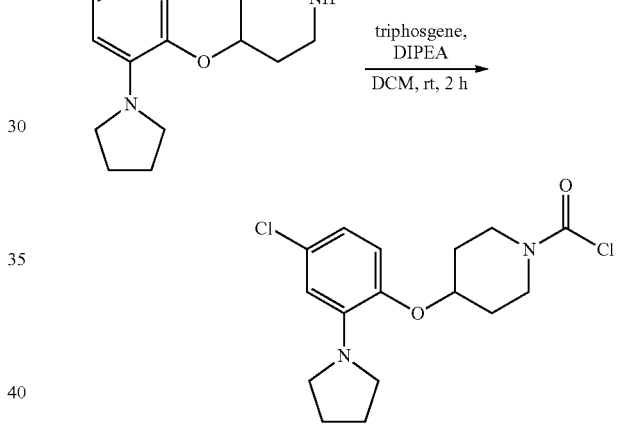

A flask was charged with 4-(4-chloro-2-(pyrrolidin-1-yl)phenoxy)piperidine (150 mg, 0.532 mmol, 1.00 equiv), DCM (10 mL) and triphosgene (79.3 mg, 0.266 mmol, 0.50 equiv). DMAP (207 mg, 1.60 mmol, 3.00 equiv) was added dropwise at 0° C., as described in Example 1, Step 3 to provide 183 mg (crude) of 4-(4-chloro-2-(pyrrolidin-1-yl)phenoxy)piperidine-1-carbonyl chloride as a yellow oil.

Step 8: Preparation of t-butyl 1-(4-(4-chloro-2-(pyrrolidin-1-yl)phenoxy)piperidine-1-carbonyl)-1H-pyrazole-3-carboxylate

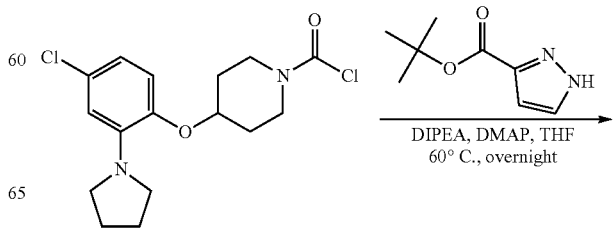

-continued

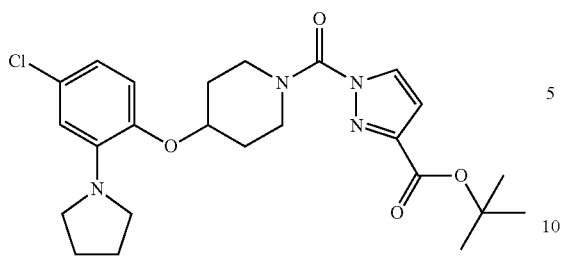

A flask was charged with 4-(4-chloro-2-(pyrrolidin-1-yl)phenoxy)piperidine-1-carbonyl chloride (183 mg, 0.530 mmol, 1.00 equiv), THF (10 mL), t-butyl 1H-pyrazole-3-carboxylate (89.7 mg, 0.530 mmol, 1.00 equiv), DIPEA (138 mg, 1.07 mmol, 2.00 equiv) and DMAP (13.1 mg, 0.107 mmol, 0.20 equiv). The resulting solution was stirred overnight at 60° C. and quenched by water (20 mL), as described in Example 1, Step 4. The residue was chromatographed to provide 135 mg (53% yield) of t-butyl 1-(4-(4-chloro-2-(pyrrolidin-1-yl)phenoxy)piperidine-1-carbonyl)-1H-pyrazole-3-carboxylate as a yellow oil. LCMS (ESI, m/z): 475 [M+H]⁺.

Step 9: Preparation of 1-(4-(4-chloro-2-(pyrrolidin-1-yl)phenoxy)piperidine-1-carbonyl)-1H-pyrazole-3-carboxylic Acid

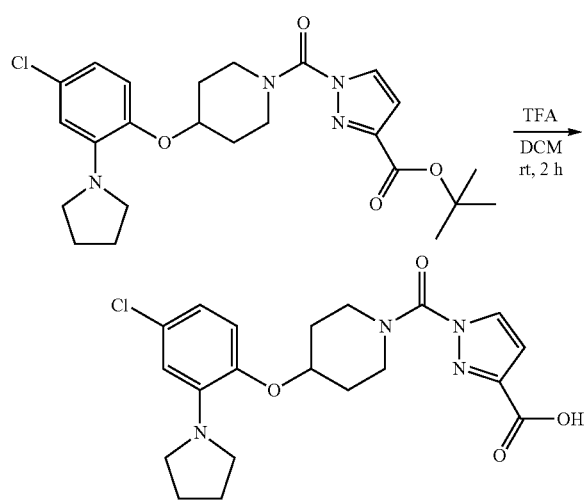

A flask was charged with t-butyl 1-(4-(4-chloro-2-(pyrrolidin-1-yl)phenoxy)piperidine-1-carbonyl)-1H-pyrazole-3-carboxylate (135 mg, 0.282 mmol, 1.00 equiv), DCM (5 mL) and TFA (1 mL), as described in Example 1, Step 5. The crude product was purified by preparative HPLC to provide 12.6 mg (11% yield) of 1-(4-(4-chloro-2-(pyrrolidin-1-yl)phenoxy)piperidine-1-carbonyl)-1H-pyrazole-3-carboxylic acid as a yellow solid. ¹H NMR: (300 MHz, Methanol-d₄) δ 8.12 (s, 1H), 6.87-6.95 (m, 1H), 6.82 (m, 1H), 6.66-6.75 (m, 2H), 4.60 (m, 1H), 3.92-4.11 (m, 2H), 3.60-3.80 (m, 2H), 3.32 (m, 2H), 3.29 (m, 2H), 2.00-2.20 (m, 2H), 1.80-2.00 (m, 6H). LCMS (ESI, m/z): 419 [M+H]⁺.

Example 12: 1-(4-(2-(4-Methoxypiperidin-1-yl)-4-(trifluoromethyl)benzyl)piperazine-1-carbonyl)-1H-pyrazole-3-carboxylic Acid

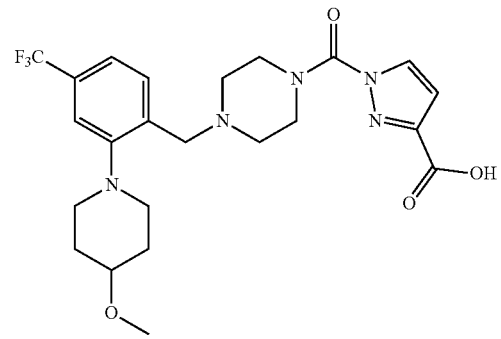 [SMILES: COC1CCN(c2cc(C(F)(F)F)ccc2CN2CCN(C(=O)n3ccc(C(=O)O)n3)CC2)CC1]

Step 1: Preparation of di-t-butyl 1H-pyrazole-1,3-dicarboxylate

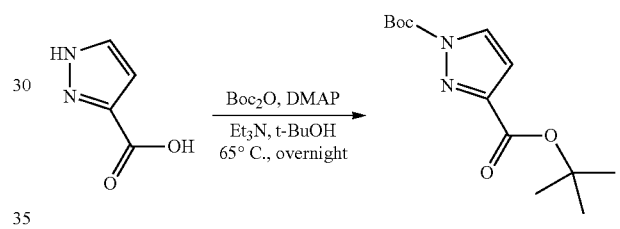

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]⁺.

Step 2: Preparation of t-butyl 1H-pyrazole-3-carboxylate

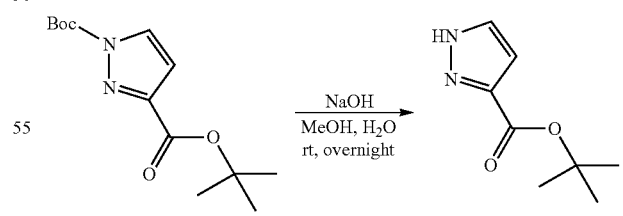

A flask was charged with 1,3-di-t-butyl 1H-pyrazole-1,3-dicarboxylate (25.0 g, 93.3 mmol, 1.00 equiv), NaOH (5.60 g, 140 mmol, 1.50 equiv), water (80 mL), and MeOH (240 mL), as described in Example 1, Step 2. The residue was chromatographed on a silica gel column to provide 10.0 g (64% yield) of t-butyl 1H-pyrazole-3-carboxylate as a white solid. LCMS (ESI, m/z): 169 [M+H]⁺.

Step 3: Preparation of t-butyl 4-(2-bromo-4-(trifluoromethyl)benzyl)piperazine-1-carboxylate

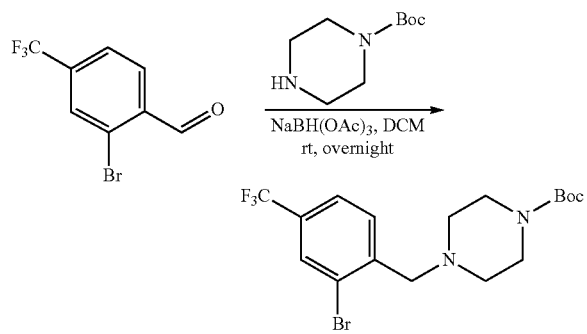

A flask was charged with 2-bromo-4-(trifluoromethyl) benzaldehyde (2.00 g, 7.90 mmol, 1.00 equiv), t-butyl piperazine-1-carboxylate (2.94 g, 15.8 mmol, 2.00 equiv), and DCM (30 mL). The mixture was stirred for 1 h at room temperature. Sodium triacetoxyborohydride (6.70 g, 31.6 mmol, 4.00 equiv) was added, as described in Example 2, Step 3. The residue was chromatographed to provide 3.25 g (97% yield) of t-butyl 4-(2-bromo-4-(trifluoromethyl)benzyl)piperazine-1-carboxylate as a colorless oil. LCMS (ESI, m/z): 423 [M+H]$^+$.

Step 4: Preparation of t-butyl 4-(2-(4-methoxypiperidin-1-yl)-4-(trifluoromethyl)benzyl)piperazine-1-carboxylate

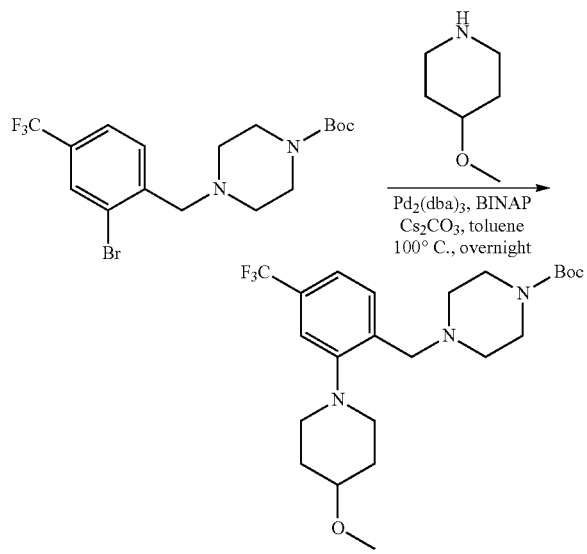

A flask was charged with t-butyl 4-(2-bromo-4-(trifluoromethyl)benzyl)piperazine-1-carboxylate (0.500 g, 1.18 mmol, 1.00 equiv), 4-methoxypiperidine (0.271 g, 2.36 mmol, 2.00 equiv), tris(dibenzylideneacetone)dipalladium (0.162 g, 0.177 mmol, 0.15 equiv), 2,2'-bis(diphenylphosphino)-1,1'-binaphthyl (0.331 g, 0.531 mmol, 0.45 equiv), cesium carbonate (1.73 g, 5.31 mmol, 4.50 equiv), and toluene (15 mL) under nitrogen. The resulting solution was stirred overnight at 100° C. and then quenched with water (30 mL). The resulting solution was extracted with DCM (3×50 mL) and the organic layers were combined, washed with brine (1x 50 mL), dried over anhydrous sodium sulfate, filtered and concentrated under reduced pressure. The residue was chromatographed on a silica gel column to provide 0.200 g (37% yield) of t-butyl 4-(2-(4-methoxypiperidin-1-yl)-4-(trifluoromethyl)benzyl)piperazine-1-carboxylate as a yellow oil. LCMS (ESI, m/z): 458 [M+H]$^+$.

Step 5: Preparation of 1-(2-(4-methoxypiperidin-1-yl)-4-(trifluoromethyl)benzyl)piperazine

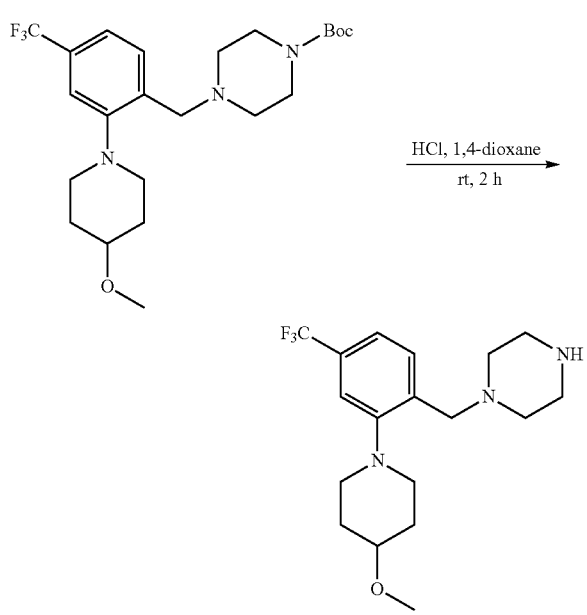

A flask was charged with t-butyl 4-(2-(4-methoxypiperidin-1-yl)-4-(trifluoromethyl)benzyl)piperazine-1-carboxylate (200 mg, 0.438 mmol, 1.00 equiv), 1,4-dioxane (5 mL), and concentrated HCl (1 mL), as described in Example 2, Step 4 to provide 210 mg (crude) of 1-(2-(4-methoxypiperidin-1-yl)-4-(trifluoromethyl)benzyl)piperazine as a yellow oil. LCMS (ESI, m/z): 358 [M+H]$^+$.

Step 6: Preparation of t-butyl 1-(4-(2-(4-methoxypiperidin-1-yl)-4-(trifluoromethyl)benzyl)piperazine-1-carbonyl)-1H-pyrazole-3-carboxylate

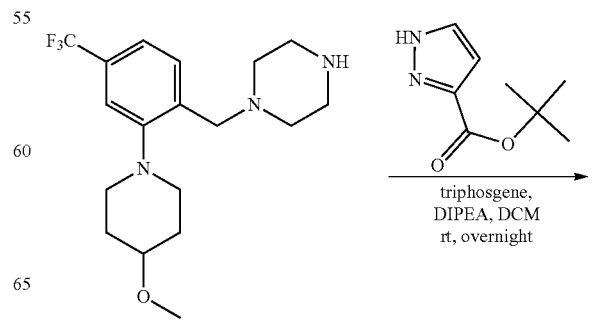

153

-continued

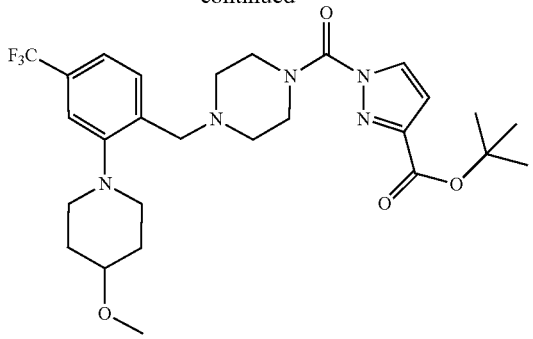

A flask was charged with triphosgene (90.9 mg, 0.306 mmol, 0.70 equiv), and DCM (10 mL). t-Butyl 1H-pyrazole-3-carboxylate (147 mg, 0.874 mmol, 2.00 equiv) was added at 0° C. DIPEA (283 mg, 2.19 mmol, 5.00 equiv) was added at 0° C. The mixture was stirred for 2 h at room temperature. 1-(2-(4-Methoxypiperidin-1-yl)-4-(trifluoromethyl)benzyl)piperazine (156 mg, 0.437 mmol, 1.00 equiv) was added. The resulting solution was stirred overnight at room temperature and then quenched with water (15 mL), as described in Example 1, Step 3 to provide 220 mg (92% yield) of t-butyl 1-(4-(2-(4-methoxypiperidin-1-yl)-4-(trifluoromethyl)benzyl)piperazine-1-carbonyl)-1H-pyrazole-3-carboxylate as a yellow oil. LCMS (ESI, m/z): 552 [M+H]+.

Step 7: Preparation of 1-(4-(2-(4-methoxypiperidin-1-yl)-4-(trifluoromethyl)benzyl)piperazine-1-carbonyl)-1H-pyrazole-3-carboxylic Acid

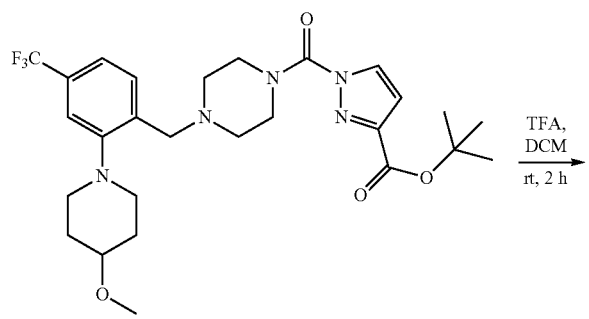

A flask was charged with t-butyl 1-(4-(2-(4-methoxypiperidin-1-yl)-4-(trifluoromethyl)benzyl)piperazine-1-carbonyl)-1H-pyrazole-3-carboxylate (220 mg, 0.400 mmol, 1.00 equiv), DCM (5 mL), and TFA (2 mL), as described in Example 1, Step 5. The crude product (195 mg) was purified by preparative HPLC to provide 68.4 mg (35% yield) of

154

1-(4-(2-(4-methoxypiperidin-1-yl)-4-(trifluoromethyl)benzyl)piperazine-1-carbonyl)-1H-pyrazole-3-carboxylic acid as a white solid. $^1$H NMR (400 MHz, Methanol-$d_4$) δ 8.14 (s, 1H), 7.69 (d, J=7.6 Hz, 1H), 7.36-7.38 (m, 2H), 6.83 (s, 1H), 3.70-3.99 (m, 6H), 3.39-3.48 (m, 4H), 3.12-3.15 (m, 2H), 2.66-2.82 (m, 6H), 2.05-2.08 (m, 2H), 1.69-1.77 (m, 2H). LCMS (ESI, m/z): 496 [M+H]+.

Example 13: 1-(4-(3-Chloro-2-(pyrrolidin-1-yl)phenoxy)piperidine-1-carbonyl)-1H-pyrazole-3-carboxylic Acid

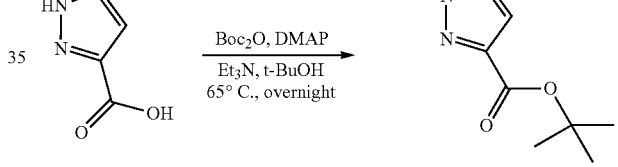

Step 1: Preparation of di-t-butyl 1H-pyrazole-1,3-dicarboxylate

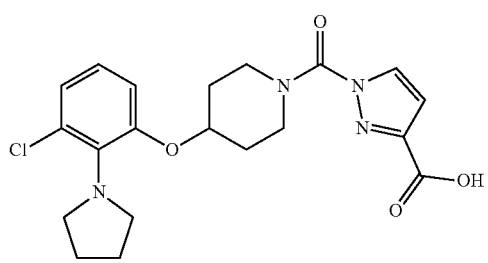 [SMILES: O=C(O)c1ccn(C(=O)N2CCC(Oc3cccc(Cl)c3N3CCCC3)CC2)n1]

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL), as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]+.

Step 2: Preparation of t-butyl 1H-pyrazole-3-carboxylate

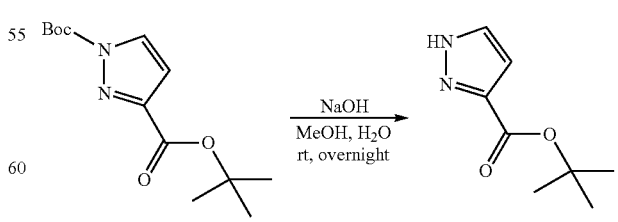

A flask was charged with 1,3-di-t-butyl-1H-pyrazole-1,3-dicarboxylate (20.0 g, 74.6 mmol, 1.00 equiv), MeOH (80 mL), NaOH (10.0 g, 250 mmol, 3.35 equiv) and water (40 mL). The resulting solution was stirred overnight at room temperature and quenched by water (40 mL), as described in Example 1, Step 2 to provide 6.70 g (crude) of t-butyl-1H-pyrazole-3-carboxylate as a yellow solid. LCMS (ESI, m/z): 169 [M+H]$^+$.

Step 3: Preparation of t-butyl 4-((methylsulfonyl)oxy)piperidine-1-carboxylate

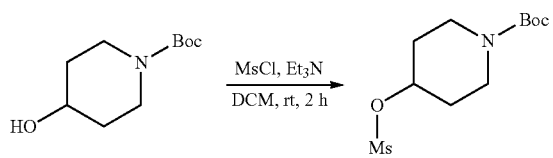 [SMILES: CC(C)(C)OC(=O)N1CCC(O)CC1 ; CC(C)(C)OC(=O)N1CCC(OS(C)(=O)=O)CC1]

A flask was charged with t-butyl 4-hydroxypiperidine-1-carboxylate (2.00 g, 9.94 mmol, 1.00 equiv), triethylamine (3.01 g, 29.8 mmol, 3.00 equiv) and DCM (30 mL). Then methanesulfonyl chloride (1.71 g, 14.9 mmol, 1.50 equiv) was added dropwise at 0° C. The resulting solution was stirred for 2 h at room temperature and quenched by water (30 mL), as described in Example 11, Step 3 to provide 2.50 g (crude) of t-butyl 4-((methylsulfonyl)oxy)piperidine-1-carboxylate as a white solid.

Step 4: Preparation of t-butyl 4-(3-chloro-2-nitrophenoxy)piperidine-1-carboxylate

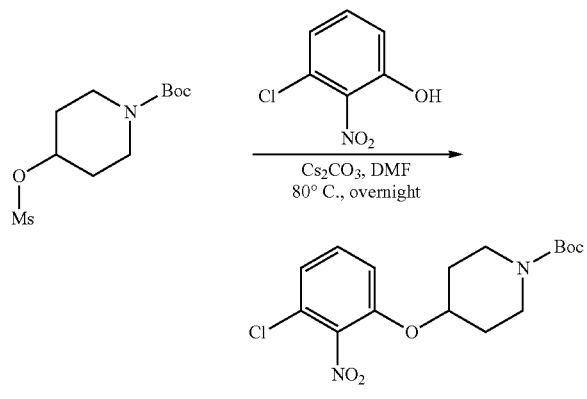

A vial was charged with 3-chloro-2-nitrophenol (0.500 g, 2.88 mmol, 1.00 equiv), t-butyl 4-((methylsulfonyl)oxy)piperidine-1-carboxylate (0.804 g, 2.88 mmol, 1.00 equiv), cesium carbonate (1.88 g, 5.77 mmol, 2.00 equiv) and DMF (15 mL). The resulting solution was stirred overnight at 80° C. and quenched with water (10 mL). The mixture was extracted with DCM (3×20 mL) and the organic layers were combined, washed with water (3×10 mL), dried over anhydrous sodium sulfate, filtered and concentrated under reduced pressure. The residue was chromatographed on a silica gel column to provide 0.714 g (69% yield) of t-butyl 4-(3-chloro-2-nitrophenoxy)piperidine-1-carboxylate as a white solid. LCMS (ESI, m/z): 357 [M+H]$^+$.

Step 5: Preparation of t-butyl 4-(2-amino-3-chlorophenoxy)piperidine-1-carboxylate

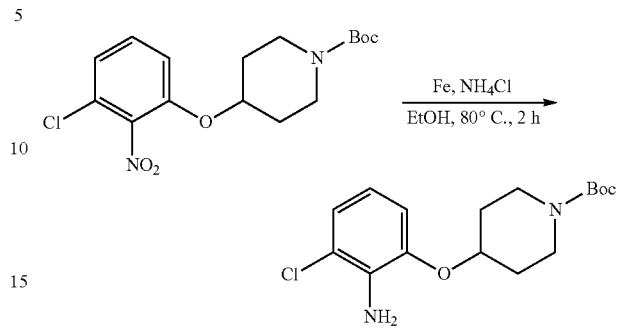

A vial was charged with t-butyl 4-(3-chloro-2-nitrophenoxy)piperidine-1-carboxylate (0.400 g, 1.12 mmol, 1.00 equiv), iron (0.628 g, 11.2 mmol, 10.00 equiv), ammonium chloride (1.21 g, 22.6 mmol, 20.00 equiv) and EtOH (15 mL). The resulting solution was stirred for 2 h at 80° C. and quenched with water (10 mL). The mixture was extracted with DCM (3×20 mL) and the organic layers were combined, washed with water (3×10 mL), dried over anhydrous sodium sulfate, filtered and concentrated under reduced pressure. The residue was chromatographed on a silica gel column to provide 0.327 g (89% yield) of t-butyl 4-(2-amino-3-chlorophenoxy)piperidine-1-carboxylate as a white solid. LCMS (ESI, m/z): 327 [M+H]$^+$.

Step 6: Preparation of t-butyl 4-(3-chloro-2-(pyrrolidin-1-yl)phenoxy)piperidine-1-carboxylate

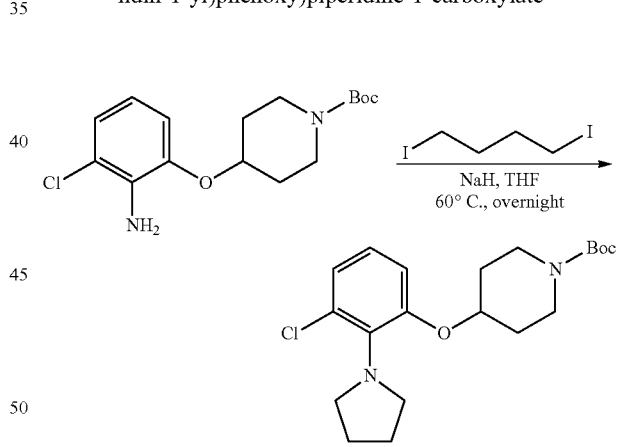

A vial was charged with t-butyl 4-(2-amino-3-chlorophenoxy)piperidine-1-carboxylate (327 mg, 1.00 mmol, 1.00 equiv), 1,4-diiodobutane (324 mg, 1.05 mmol, 1.50 equiv) and THF (15 mL). Sodium hydride (486 mg, 20.3 mmol, 3.00 equiv) was added dropwise at 0° C. The resulting solution was stirred overnight at 60° C. and quenched with water (10 mL). The mixture was extracted with DCM (3×20 mL) and the organic layers were combined, washed with water (3×10 mL), dried over anhydrous sodium sulfate, filtered and concentrated under reduced pressure. The residue was chromatographed on a silica gel column to provide 270 mg (71% yield) of t-butyl 4-(3-chloro-2-(pyrrolidin-1-yl)phenoxy)piperidine-1-carboxylate as a white solid. LCMS (ESI, m/z): 381 [M+H]$^+$.

Step 7: Preparation of 4-(3-chloro-2-(pyrrolidin-1-yl)phenoxy)piperidine

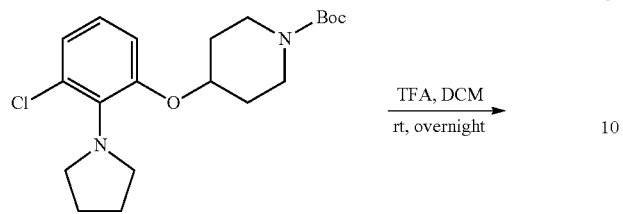

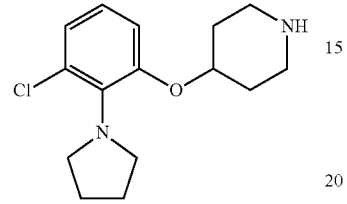

A vial was charged with t-butyl 4-(3-chloro-2-(pyrrolidin-1-yl)phenoxy)piperidine-1-carboxylate (270 mg, 0.710 mmol, 1.00 equiv), TFA (1 mL) and DCM (5 mL), as described in Example 1, Step 5 to provide 200 mg (crude) of 4-(3-chloro-2-(pyrrolidin-1-yl)phenoxy)piperidine as a white solid. LCMS (ESI, m/z): 281 [M+H]$^+$.

Step 8: Preparation of t-butyl 1-(4-(3-chloro-2-(pyrrolidin-1-yl)phenoxy)piperidine-1-carbonyl)-1H-pyrazole-3-carboxylate

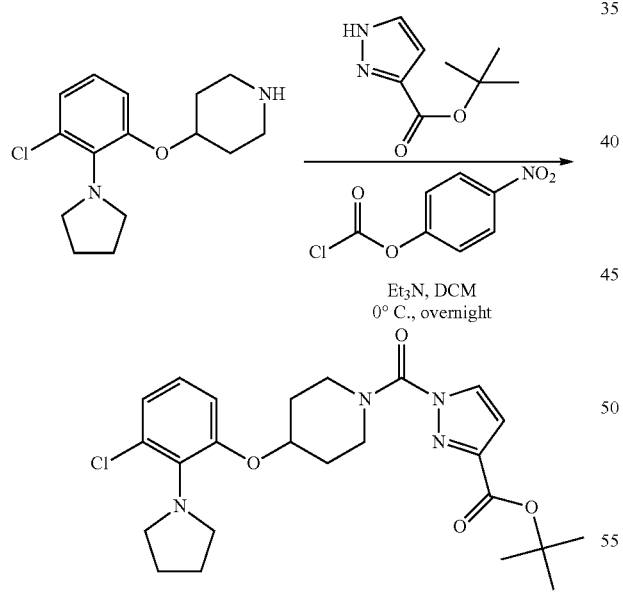

A vial was charged with t-butyl 1H-pyrazole-3-carboxylate (120 mg, 0.710 mmol, 1.00 equiv), triethylamine (287 mg, 2.84 mmol, 4.00 equiv) and DCM (15 mL). 4-Nitrophenyl chloroformate (174 mg, 0.860 mmol, 1.20 equiv) was added dropwise at 0° C. The resulting solution was stirred for 2 h at room temperature. Then 4-(3-chloro-2-(pyrrolidin-1-yl)phenoxy)piperidine (200 mg, 0.710 mmol, 1.00 equiv) was added. The resulting solution was stirred overnight at room temperature and quenched with water (10 mL), as described in Example 4, Step 3. The residue was chromatographed on a silica gel column to provide 180 mg (53% yield) of t-butyl 1-(4-(3-chloro-2-(pyrrolidin-1-yl)phenoxy)piperidine-1-carbonyl)-1H-pyrazole-3-carboxylate as a white solid. LCMS (ESI, m/z): 475 [M+H]$^+$.

Step 9: Preparation of 1-(4-(3-chloro-2-(pyrrolidin-1-yl)phenoxy)piperidine-1-carbonyl)-1H-pyrazole-3-carboxylic Acid

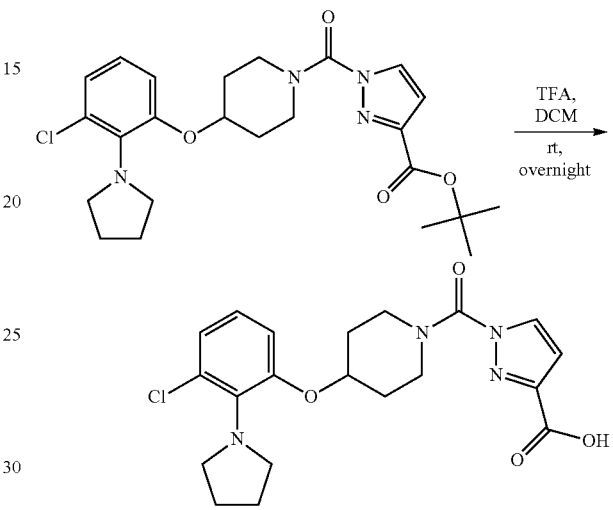

A vial was charged with t-butyl 1-(4-(3-chloro-2-(pyrrolidin-1-yl)phenoxy)piperidine-1-carbonyl)-1H-pyrazole-3-carboxylate (180 mg, 0.380 mmol, 1.00 equiv), TFA (1 mL) and DCM (5 mL). The resulting solution was stirred for 2 h at room temperature and concentrated under reduced pressure. The crude product was dissolved in saturated NaHCO$_3$ solution (10 mL) and extracted with DCM (3×20 mL). The organic layers were combined, washed with brine (10 mL), dried over anhydrous sodium sulfate, filtered and concentrated under reduced pressure. The crude product was purified by preparative HPLC to provide 65.1 mg (41% yield) of 1-(4-(3-chloro-2-(pyrrolidin-1-yl)phenoxy)piperidine-1-carbonyl)-1H-pyrazole-3-carboxylic acid as a white solid. $^1$H NMR (400 MHz, Methanol-d$_4$) δ 7.92-8.22 (m, 1H), 6.88-7.12 (m, 3H), 6.58-6.85 (m, 1H), 4.66-4.75 (m, 1H), 3.61-4.20 (m, 4H), 3.18-3.29 (m, 4H), 2.04-2.25 (m, 2H), 1.77-2.02 (m, 6H). LCMS (ESI, m/z): 419 [M+H]$^+$.

Example 14: 1-(4-(4-Carbamoyl-3-(trifluoromethyl)benzyl)piperazine-1-carbonyl)-1H-pyrazole-3-carboxylic Acid

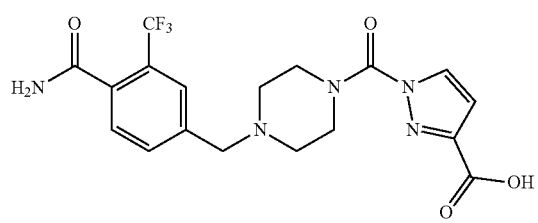 [SMILES: NC(=O)c1ccc(CN2CCN(C(=O)n3ccc(C(=O)O)n3)CC2)cc1C(F)(F)F]

Step 1: Preparation of di-t-butyl 1H-pyrazole-1,3-dicarboxylate

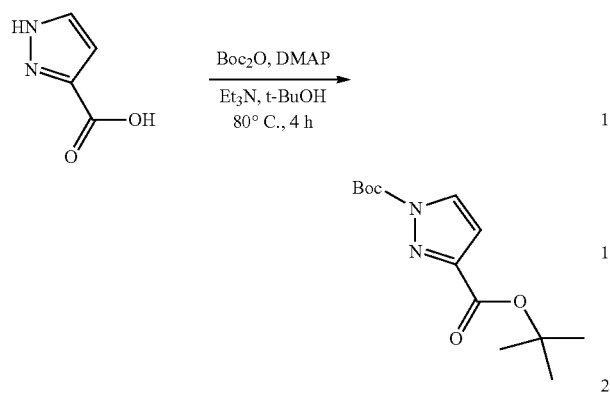

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]+.

Step 2: Preparation of t-butyl 1H-pyrazole-3-carboxylate

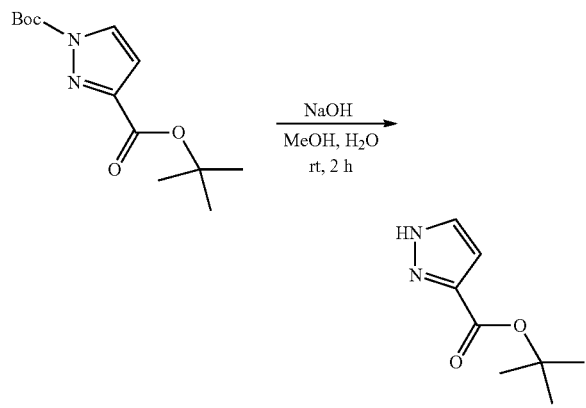

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed to provide 10.0 g (64% yield) of t-butyl 1H-pyrazole-3-carboxylate as a white solid. LCMS (ESI, m/z): 169 [M+H]+.

Step 3: Preparation of 3-(t-butyl) 1-(4-nitrophenyl) 1H-pyrazole-1,3-dicarboxylate

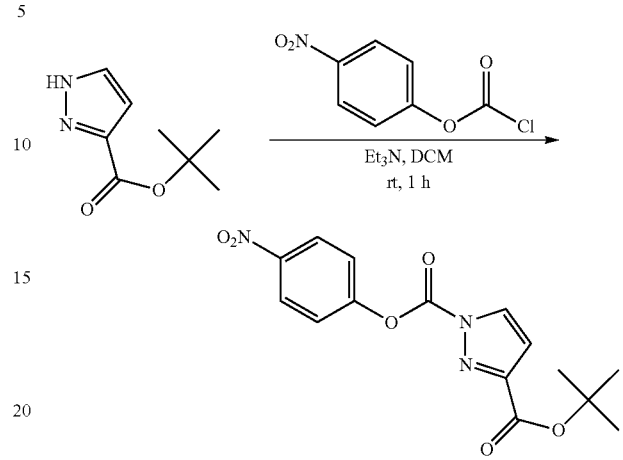

A flask was charged with t-butyl 1H-pyrazole-3-carboxylate (2.00 g, 11.9 mmol, 1.00 equiv), 4-nitrophenyl chloroformate (2.87 g, 14.2 mmol, 1.20 equiv), triethylamine (3.61 g, 35.7 mmol, 3.00 equiv), and DCM (20 mL), as described in Example 4, Step 3 to provide 3.90 g (crude) of 3-t-butyl 1-(4-nitrophenyl) 1H-pyrazole-1,3-dicarboxylate as a yellow solid. LCMS (ESI, m/z): 334 [M+H]+.

Step 4: Preparation of methyl 4-formyl-2-(trifluoromethyl)benzoate

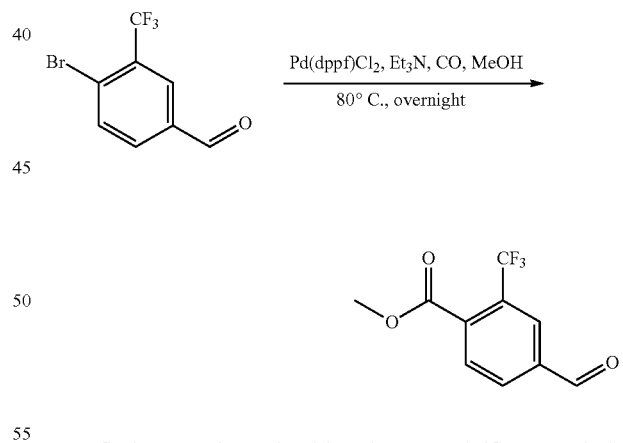

A flask was charged with 4-bromo-3-(trifluoromethyl)benzaldehyde (1.61 g, 6.36 mmol, 1.00 equiv), 1,1'-bis(diphenylphosphino)ferrocenepalladium dichloride (0.466 g, 0.636 mmol, 0.10 equiv), triethylamine (1.93 g, 19.1 mmol, 3.00 equiv), and MeOH (15 mL). Carbon monoxide (10 atm) was introduced. The resulting solution was stirred overnight at 80° C. and then quenched with water (30 mL), as described in Example 9, Step 2. The residue was chromatographed to provide 1.00 g (68% yield) of methyl 4-formyl-2-(trifluoromethyl)benzoate as a yellow oil.

Step 5: Preparation of t-butyl 4-(4-(methoxycarbonyl)-3-(trifluoromethyl)benzyl)piperazine-1-carboxylate

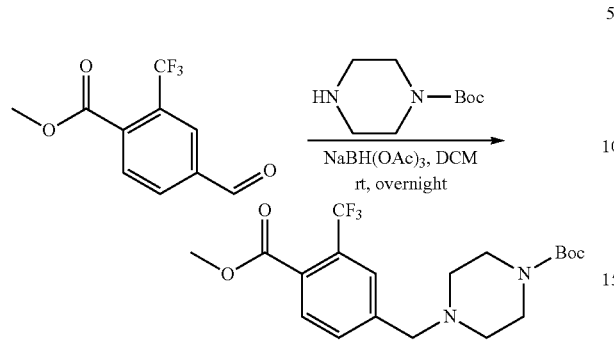

A flask was charged with methyl 4-formyl-2-(trifluoromethyl)benzoate (0.800 g, 3.45 mmol, 1.00 equiv), t-butyl piperazine-1-carboxylate (0.962 g, 5.17 mmol, 1.50 equiv), and DCM (15 mL). The mixture was stirred for 2 h at room temperature. Sodium triacetoxyborohydride (2.93 g, 13.8 mmol, 4.00 equiv) was added. The resulting solution was stirred overnight at room temperature and then quenched with water (30 mL), as described in Example 2, Step 3. The residue was chromatographed to provide 1.26 g (91% yield) of t-butyl 4-(4-(methoxycarbonyl)-3-(trifluoromethyl)benzyl)piperazine-1-carboxylate as a yellow oil. LCMS (ESI, m/z): 403 [M+H]$^+$.

Step 6: Preparation of 4-((4-(t-butoxycarbonyl)piperazin-1-yl)methyl)-2-(trifluoromethyl)benzoic Acid

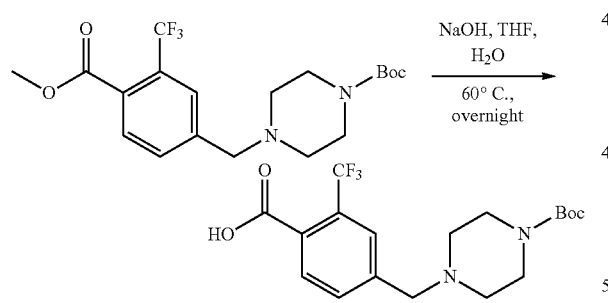

A flask was charged with t-butyl 4-(4-(methoxycarbonyl)-3-(trifluoromethyl)benzyl)piperazine-1-carboxylate (1.21 g, 3.01 mmol, 1.00 equiv), THF (10 mL), water (2 mL), and NaOH (2.41 g, 60.2 mmol, 20.00 equiv). The resulting solution was stirred overnight at 60° C. The pH of the solution was adjusted to 6 with HCl (1M). The resulting solution was extracted with DCM (3×80 mL). The organic layers were combined, washed with brine (100 mL), dried over anhydrous sodium sulfate, filtered and concentrated under reduced pressure to provide 1.40 g (crude) of 4-((4-(t-butoxycarbonyl)piperazin-1-yl)methyl)-2-(trifluoromethyl)benzoic acid as a white solid. LCMS (ESI, m/z): 389 [M+H]$^+$.

Step 7: Preparation of t-butyl 4-(4-carbamoyl-3-(trifluoromethyl)benzyl)piperazine-1-carboxylate

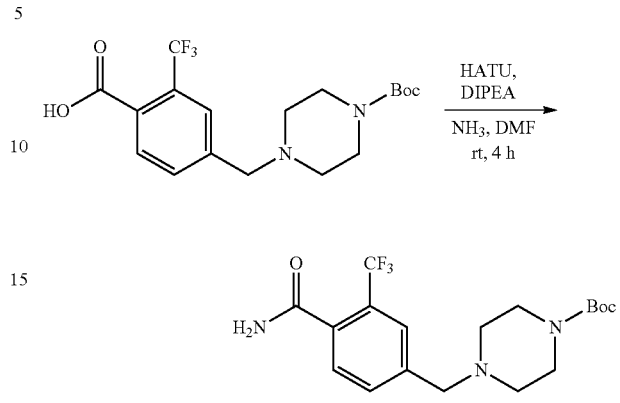

A flask was charged with 4-((4-(t-butoxycarbonyl)piperazin-1-yl)methyl)-2-(trifluoromethyl)benzoic acid (1.24 g, 3.19 mmol, 1.00 equiv), N,N,N',N'-tetramethyl-O-(7-azabenzotriazol-1-yl)uronium hexafluorophospate (2.43 g, 6.39 mmol, 2.00 equiv), DIPEA (1.24 g, 12.8 mmol, 4.00 equiv), DMF (10 mL), and ammonia (0.5 M in 1,4-dioxane solution, 63.8 ml, 31.9 mmol, 10.00 equiv). The resulting solution was stirred overnight at room temperature and then concentrated under reduced pressure. The residue was chromatographed on a silica gel column to provide 1.00 g (81% yield) of t-butyl 4-(4-carbamoyl-3-(trifluoromethyl)benzyl)piperazine-1-carboxylate as a white solid. LCMS (ESI, m/z): 388 [M+H]$^+$.

Step 8: Preparation of 4-(piperazin-1-ylmethyl)-2-(trifluoromethyl)benzamide

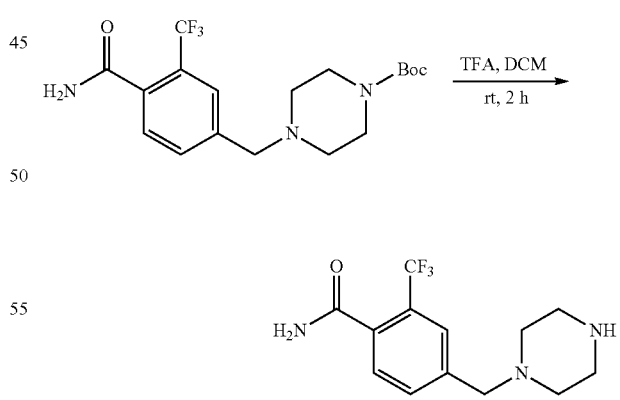

A flask was charged t-butyl 4-(4-carbamoyl-3-(trifluoromethyl)benzyl)piperazine-1-carboxylate (520 mg, 1.34 mmol, 1.00 equiv), DCM (10 mL), and TFA (3 mL), as described in Example 1, Step 5 to provide 550 mg (crude) of 4-(piperazin-1-ylmethyl)-2-(trifluoromethyl)benzamide as a yellow oil. LCMS (ESI, m/z): 288 [M+H]$^+$.

Step 9: Preparation of t-butyl 1-(4-(4-carbamoyl-3-(trifluoromethyl)benzyl)piperazine-1-carbonyl)-1H-pyrazole-3-carboxylate

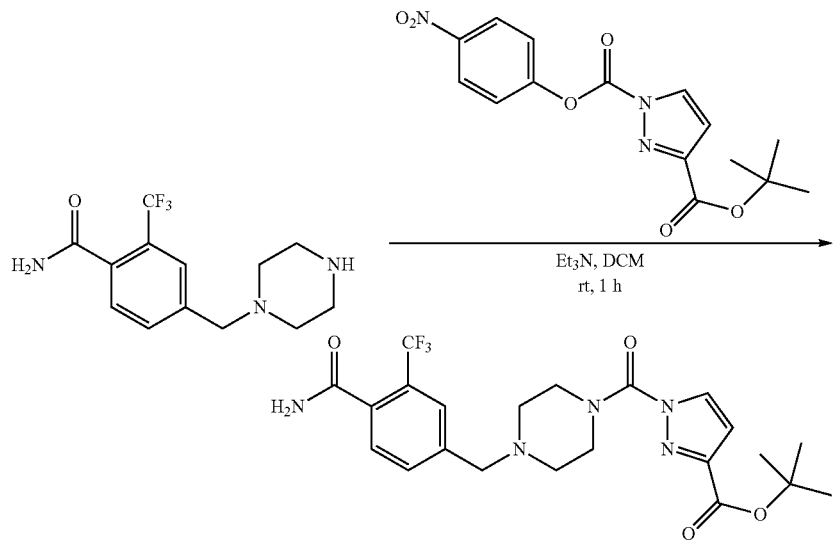

A flask was charged with 4-(piperazin-1-ylmethyl)-2-(trifluoromethyl)benzamide (185 mg, 0.645 mmol, 1.00 equiv), 3-t-butyl 1-(4-nitrophenyl) 1H-pyrazole-1,3-dicarboxylate (322 mg, 0.968 mmol, 1.50 equiv), DCM (10 mL), and triethylamine (261 mg, 2.58 mmol, 4.00 equiv), as described in Example 4, Step 3. The residue was chromatographed on a silica gel column to provide 200 mg (67% yield) of t-butyl 1-(4-(4-carbamoyl-3-(trifluoromethyl)benzyl)piperazine-1-carbonyl)-1H-pyrazole-3-carboxylate as a yellow oil. LCMS (ESI, m/z): 466 [M+H]$^+$.

Step 10: Preparation of 1-(4-(4-carbamoyl-3-(trifluoromethyl)benzyl)piperazine-1-carbonyl)-1H-pyrazole-3-carboxylic Acid

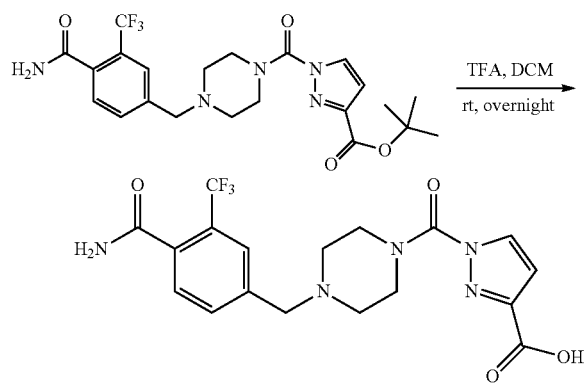

A flask was charged with t-butyl 1-(4-(4-carbamoyl-3-(trifluoromethyl)benzyl)piperazine-1-carbonyl)-1H-pyrazole-3-carboxylate (200 mg, 0.430 mmol, 1.00 equiv), DCM (15 mL), TFA (4 mL) as described in Example 1, Step 5. The crude product (280 mg) was purified by preparative HPLC to provide 25.6 mg (14% yield) of 1-(4-(4-carbamoyl-3-(trifluoromethyl)benzyl)piperazine-1-carbonyl)-1H-pyrazole-3-carboxylic acid as a white solid. $^1$H NMR (300 MHz, Methanol-d$_4$) δ 8.14 (d, J=2.7 Hz, 1H), 7.80 (s, 1H), 7.70 (d, J=8.1 Hz, 1H), 7.57 (d, J=7.8 Hz, 1H), 6.83 (d, J=2.7 Hz, 1H), 3.87 (br, 4H), 3.72 (s, 2H), 2.63-2.64 (m, 4H). LCMS (ESI, m/z): 424 [M−H]$^-$.

Example 15: 1-(trans-5-((2-Chlorobenzyl)oxy)octahydrocyclopenta[c]pyrrole-2-carbonyl)-1H-pyrazole-3-carboxylic Acid

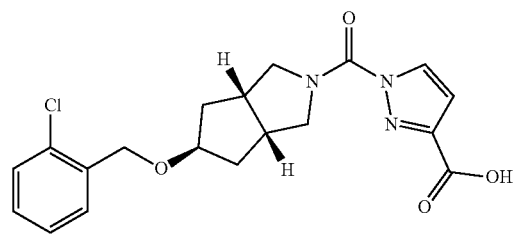 [SMILES: O=C(O)c1ccn(C(=O)N2C[C@H]3C[C@H](OCc4ccccc4Cl)C[C@H]3C2)n1]

Step 1: Preparation of di-t-butyl 1H-pyrazole-1,3-dicarboxylate

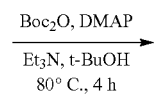

Boc$_2$O, DMAP

Et$_3$N, t-BuOH
80° C., 4 h

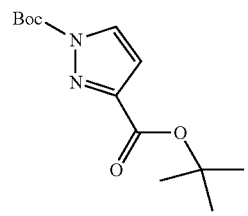

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]+.

Step 2: Preparation of t-butyl 1H-pyrazole-3-carboxylate

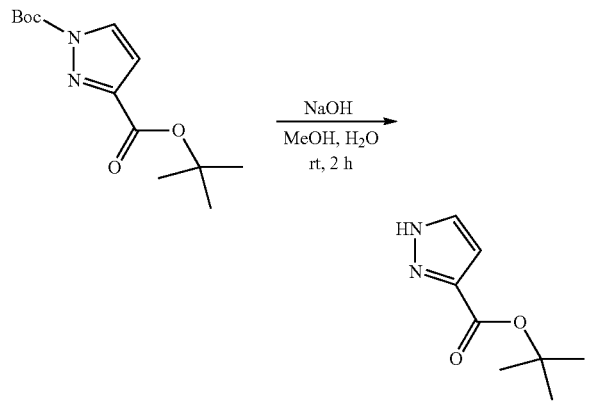

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed to provide 10.0 g (64% yield) of t-butyl 1H-pyrazole-3-carboxylate as a white solid. LCMS (ESI, m/z): 169 [M+H]$^+$.

Step 3: Preparation of 3-(t-butyl) 1-(4-nitrophenyl) 1H-pyrazole-1,3-dicarboxylate

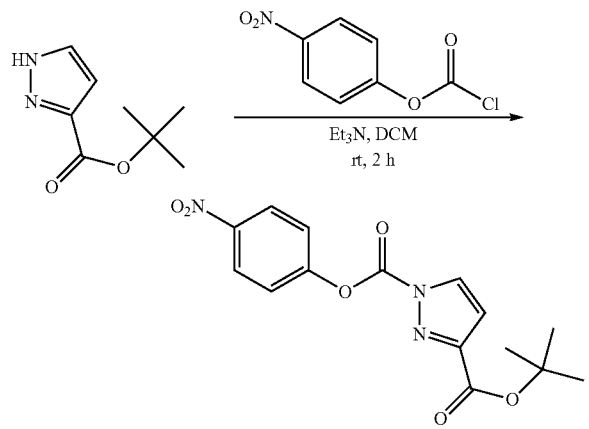

A flask was charged with t-butyl 1H-pyrazole-3-carboxylate (225 mg, 1.34 mmol, 1.00 equiv), DCM (10 mL), and triethylamine (406 mg, 4.01 mmol, 3.00 equiv). 4-Nitrophenyl chloroformate (296 mg, 1.47 mmol, 1.10 equiv) was added at 0° C., as described in Example 4, Step 3 to provide 500 mg (crude) of 3-(t-butyl) 1-(4-nitrophenyl) 1H-pyrazole-1,3-dicarboxylate as a yellow solid. LCMS (ESI, m/z): 334 [M+H]$^+$.

Step 4: Preparation of t-butyl trans-5-hydroxyhexahydrocyclopenta[c]pyrrole-2(1H)-carboxylate

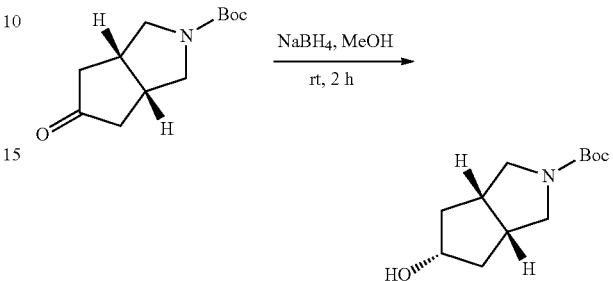

A flask was charged with t-butyl (3aR,6aS)-5-oxohexahydrocyclopenta[c]pyrrole-2(1H)-carboxylate (1.00 g, 4.44 mmol, 1.00 equiv) and MeOH (15 mL). Sodium borohydride (0.507 g, 13.4 mmol, 3.00 equiv) was added at 0° C. The resulting solution was stirred for 2 h at room temperature and quenched with water (20 mL). The resulting solution was extracted with DCM (3×30 mL) and the organic layers were combined, washed with brine (1×50 mL), dried over anhydrous sodium sulfate, filtered and concentrated under reduced pressure to provide 0.950 g (94% yield) of t-butyl trans-5-hydroxyhexahydrocyclopenta[c]pyrrole-2 (1H)-carboxylate as a yellow oil. LCMS (ESI, m/z): 228 [M+H]$^+$.

Step 5: Preparation of t-butyl trans-5-((4-nitrobenzoyl)oxy)hexahydrocyclopenta[c]pyrrole-2(1H)-carboxylate

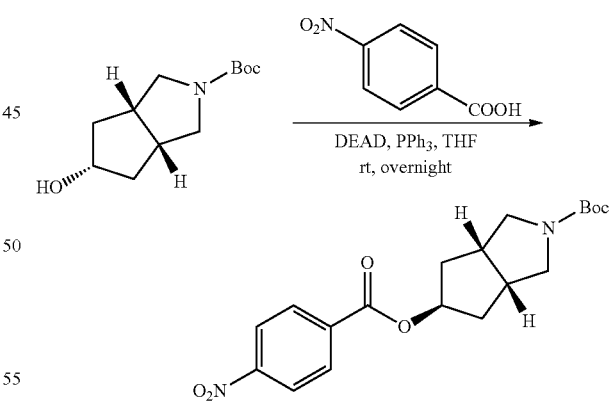

A flask was charged with t-butyl trans-5-hydroxyhexahydrocyclopenta[c]pyrrole-2(1H)-carboxylate (0.500 g, 2.20 mmol, 1.00 equiv), 4-nitrobenzoic acid (0.735 g, 4.40 mmol, 2.00 equiv), triphenylphosphine (1.15 g, 4.40 mmol, 2.00 equiv), and THF (10 mL) under nitrogen. Diethyl azodicarboxylate (0.766 g, 4.40 mmol, 2.00 equiv) was added at 0° C. The resulting solution was stirred overnight at room temperature and quenched with water (20 mL). The resulting solution was extracted with DCM (3×30 mL) and the organic layers were combined, washed with brine (1×50 mL), dried over anhydrous sodium sulfate, filtered and concentrated under reduced pressure. The residue was chromatographed to provide 0.540 g (65% yield) of t-butyl trans-5-((4-nitrobenzoyl)oxy)hexahydrocyclopenta[c]pyrrole-2(1H)-carboxylate as a white solid. LCMS (ESI, m/z): 377 [M+H]$^+$.

Step 6: Preparation of t-butyl trans-5-hydroxyhexahydrocyclopenta[c]pyrrole-2(1H)-carboxylate

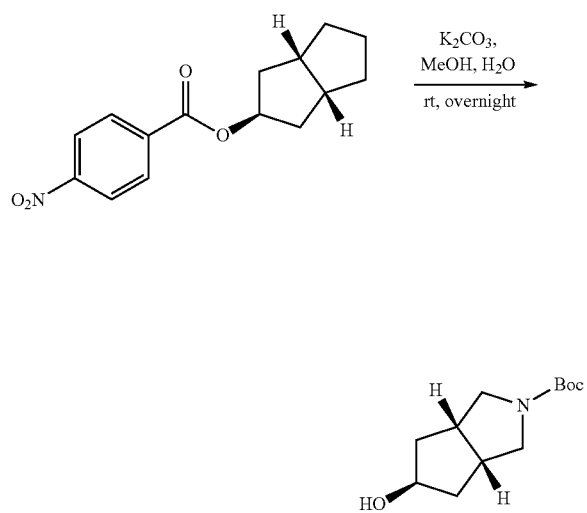

A flask was charged with t-butyl trans-5-((4-nitrobenzoyl)oxy)hexahydrocyclopenta[c]pyrrole-2(1H)-carboxylate (540 mg, 1.43 mmol, 1.00 equiv), potassium carbonate (396 mg, 2.87 mmol, 2.00 equiv), MeOH (15 mL), and water (5 mL). The resulting solution was stirred overnight at room temperature and quenched with water (15 mL). The resulting solution was extracted with DCM (3×30 mL) and the organic layers were combined, washed with brine (1×50 mL), dried over anhydrous sodium sulfate, filtered and concentrated under reduced pressure. The residue was chromatographed to provide 270 mg (83% yield) of t-butyl trans-5-hydroxyhexahydrocyclopenta[c]pyrrole-2(1H)-carboxylate as a white solid. LCMS (ESI, m/z): 228 [M+H]$^+$.

Step 7: Preparation of t-butyl trans-5-((2-chlorobenzyl)oxy)hexahydrocyclopenta[c]pyrrole-2(1H)-carboxylate

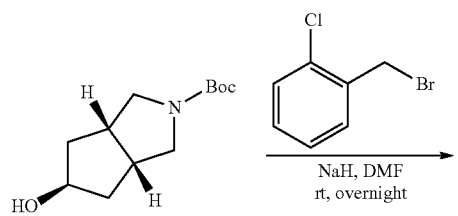

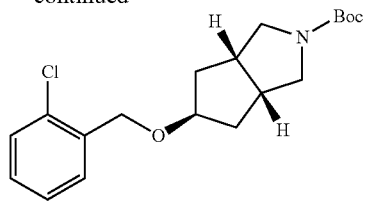

A flask was charged with t-butyl trans-5-hydroxyhexahydrocyclopenta[c]pyrrole-2(1H)-carboxylate (270 mg, 1.19 mmol, 1.00 equiv), and DMF (10 mL). Sodium hydride (95.2 mg, 60% in mineral oil, 2.38 mmol, 2.00 equiv) was added at 0° C. The mixture was stirred for 20 min at room temperature. 1-(Bromomethyl)-2-chlorobenzene (291 mg, 1.42 mmol, 1.20 equiv) was added. The resulting solution was stirred overnight at room temperature and quenched with water (15 mL). The resulting solution was extracted with EtOAc (3×20 mL) and the organic layers were combined, washed with brine (1×30 mL), dried over anhydrous sodium sulfate, filtered and concentrated under reduced pressure. The residue was chromatographed on a silica gel column to provide 380 mg (91% yield) of t-butyl trans-5-(2-chlorobenzyl)oxy)hexahydrocyclopenta[c]pyrrole-2(1H)-carboxylate as a yellow oil. LCMS (ESI, m/z): 352 [M+H]$^+$.

Step 8: Preparation of trans-5((2-chlorobenzyl)oxy)octahydrocyclopenta[c]pyrrole

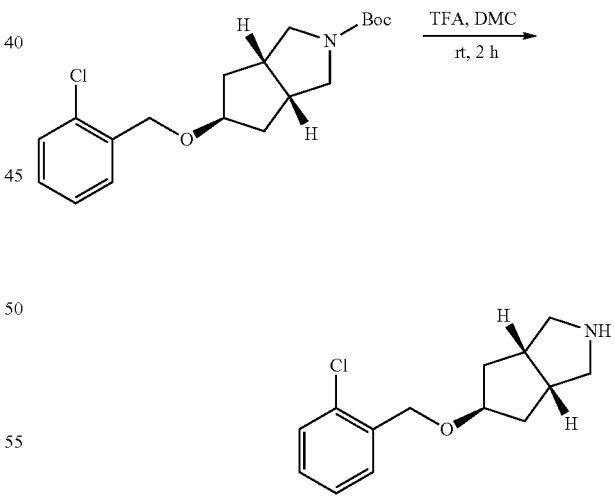

A flask was charged with t-butyl trans-5-(2-chlorobenzyl)oxy)hexahydrocyclopenta[c]pyrrole-2(1H)-carboxylate (380 mg, 1.08 mmol, 1.00 equiv), DCM (10 mL), and TFA (2 mL), as described in Example 1, Step 5 to provide 450 mg (crude) of trans-5((2-chlorobenzyl)oxy)octahydrocyclopenta[c]pyrrole as a yellow oil. LCMS (ESI, m/z): 252 [M+H]$^+$.

Step 9: Preparation of t-butyl 1-(trans-5-((2-chlorobenzyl)oxy)octahydrocyclopenta[c]pyrrole-2-carbonyl)-1H-pyrazole-3-carboxylate

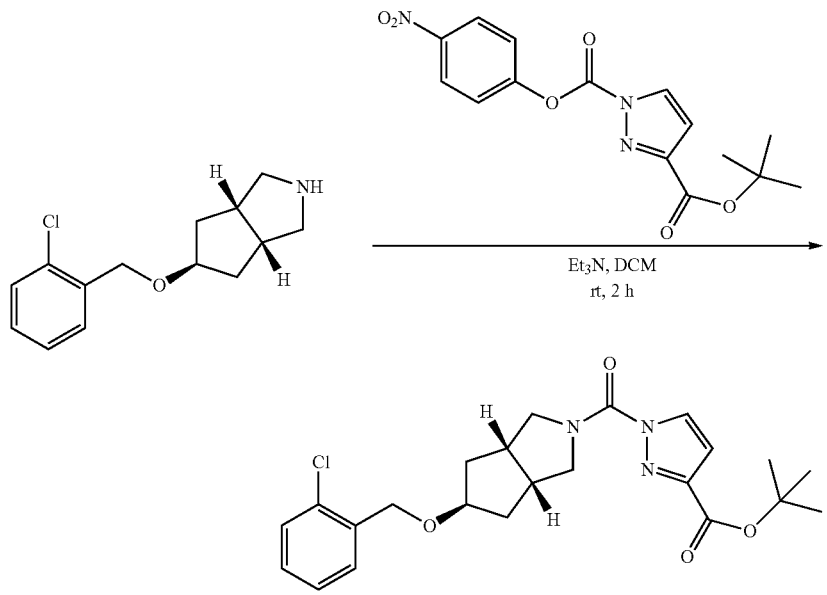

A flask was charged with trans-5-((2-chlorobenzyl)oxy)octahydrocyclopenta[c]pyrrole (260 mg, 1.03 mmol, 1.00 equiv), 3-(t-butyl) 1-(4-nitrophenyl) 1H-pyrazole-1,3-dicarboxylate (448 mg, 1.34 mmol, 1.30 equiv), triethylamine (314 mg, 3.10 mmol, 3.00 equiv), and DCM (10 mL), as described in Example 4, Step 3. The residue was chromatographed on a silica gel column to provide 340 mg (74% yield) of t-butyl 1-(trans-5-((2-chlorobenzyl)oxy)octahydrocyclopenta[c]pyrrole-2-carbonyl)-1H-pyrazole-3-carboxylate as a colorless oil. LCMS (ESI, m/z): 446 [M+H]$^+$.

Step 10: Preparation of 1-(trans-5-((2-chlorobenzyl)oxy)octahydrocyclopenta[c]pyrrole-2-carbonyl)-1H-pyrazole-3-carboxylic Acid

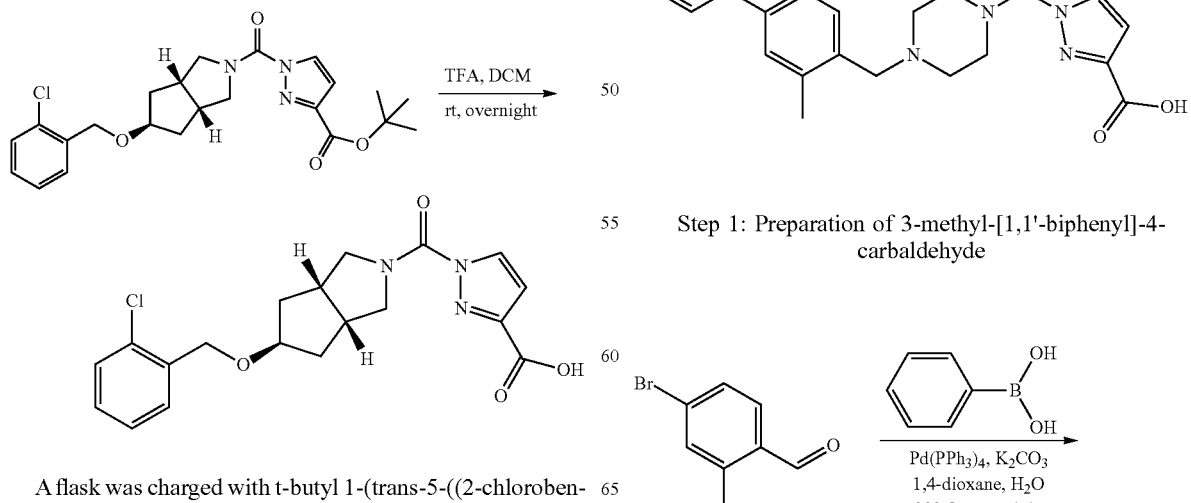

A flask was charged with t-butyl 1-(trans-5-((2-chlorobenzyl)oxy)octahydrocyclopenta[c]pyrrole-2-carbonyl)-1H-pyrazole-3-carboxylate (210 mg, 0.470 mmol, 1.00 equiv), DCM (10 mL), and TFA (2 mL). The resulting solution was stirred overnight at room temperature and concentrated under reduced pressure, as described in Example 1, Step 5 to provide 66.2 mg (36% yield) of 1-(trans-5-((2-chlorobenzyl)oxy)octahydrocyclopenta[c]pyrrole-2-carbonyl)-1H-pyrazole-3-carboxylic acid as a white solid. $^1$H NMR (300 MHz, Methanol-d$_4$) δ 8.14 (d, J=2.7 Hz, 1H), 7.47-7.50 (m, 1H), 7.32-7.38 (m, 1H), 7.23-7.30 (m, 2H), 6.74 (d, J=2.7 Hz, 1H), 4.56 (s, 2H), 4.23-4.29 (m, 1H), 3.40-4.20 (m, 4H), 2.92 (br, 2H), 2.10-2.16 (m, 2H), 1.76-1.84 (m, 2H). LCMS (ESI, m/z): 412 [M+Na]$^+$.

Example 16: 1-(4-((3-Methyl-[1,1'-biphenyl]-4-yl)methyl)piperazine-1-carbonyl)-1H-pyrazole-3-carboxylic acid

Step 1: Preparation of 3-methyl-[1,1'-biphenyl]-4-carbaldehyde

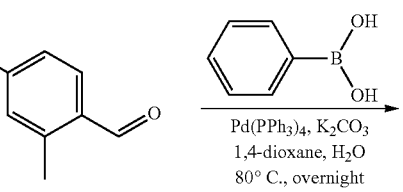

-continued

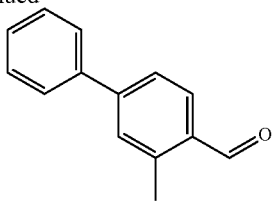

A flask was charged with 4-bromo-2-methylbenzaldehyde (5.00 g, 25.1 mmol, 1.00 equiv), phenylboronic acid (3.98 g, 32.6 mmol, 1.30 equiv), tetrakis(triphenylphosphine)palladium (2.90 g, 2.51 mmol, 0.10 equiv), potassium carbonate (10.4 g, 75.3 mmol, 3.00 equiv), 1,4-dioxane (200 mL), and water (40 mL) under nitrogen. The resulting solution was stirred overnight at 80° C. and then quenched with water (250 mL). The resulting solution was extracted with DCM (3×250 mL) and the organic layers were combined, washed with brine (2×150 mL), dried over anhydrous sodium sulfate, filtered and concentrated under reduced pressure. The residue was chromatographed on a silica gel column to provide 4.79 g (97% yield) of 3-methyl-[1,1'-biphenyl]-4-carbaldehyde as a colorless oil. LCMS (ESI, m/z): 197 [M+H]+.

Step 2: Preparation of t-butyl 4-((3-methyl-[1,1'-biphenyl]-4-yl)methyl)piperazine-1-carboxylate

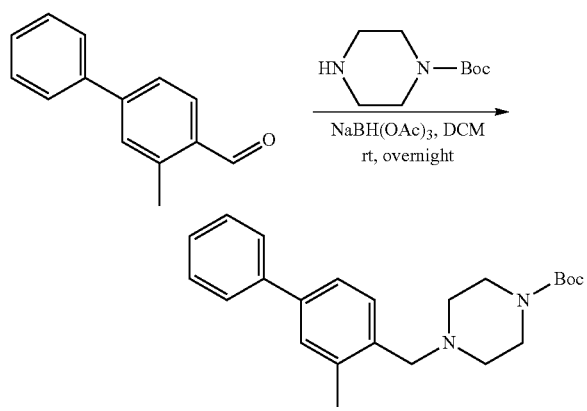

A flask was charged with 3-methyl-[1,1'-biphenyl]-4-carbaldehyde (0.700 g, 3.57 mmol, 1.00 equiv), t-butyl piperazine-1-carboxylate (0.797 g, 4.28 mmol, 1.20 equiv), and DCM (20 mL). The mixture was stirred for 1 h at room temperature. Sodium triacetoxyborohydride (2.27 g, 10.7 mmol, 3.00 equiv) was added. The resulting solution was stirred overnight at room temperature and quenched with water (30 mL), as described in Example 2, Step 3. The residue was chromatographed on a silica gel column to provide 1.00 g (76% yield) of t-butyl 4-((3-methyl-[1,1'-biphenyl]-4-yl)methyl)piperazine-1-carboxylate as a yellow oil. LCMS (ESI, m/z): 367 [M+H]+.

Step 3: Preparation of 1-((3-methyl-[1,1'-biphenyl]-4-yl)methyl)piperazine

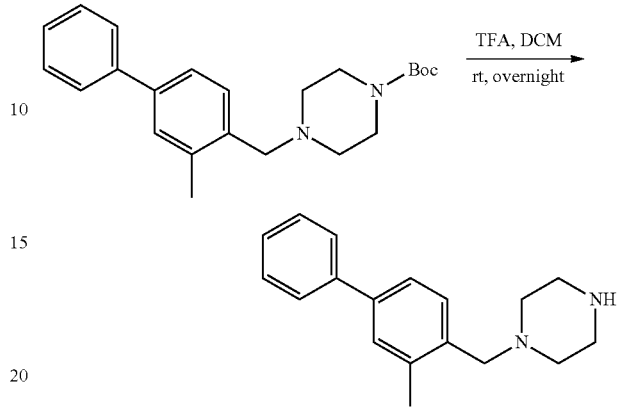

A flask was charged with t-butyl 4-((3-methyl-[1,1'-biphenyl]-4-yl)methyl)piperazine-1-carboxylate (300 mg, 0.820 mmol, 1.00 equiv), DCM (8 mL), and TFA (3 mL), as described in Example 1, Step 5 to provide 218 mg (crude) of 1-((3-methyl-[1,1'-biphenyl]-4-yl)methyl)piperazine as a yellow oil. LCMS (ESI, m/z): 267 [M+H]+.

Step 4: Preparation of di-t-butyl 1H-pyrazole-1,3-dicarboxylate

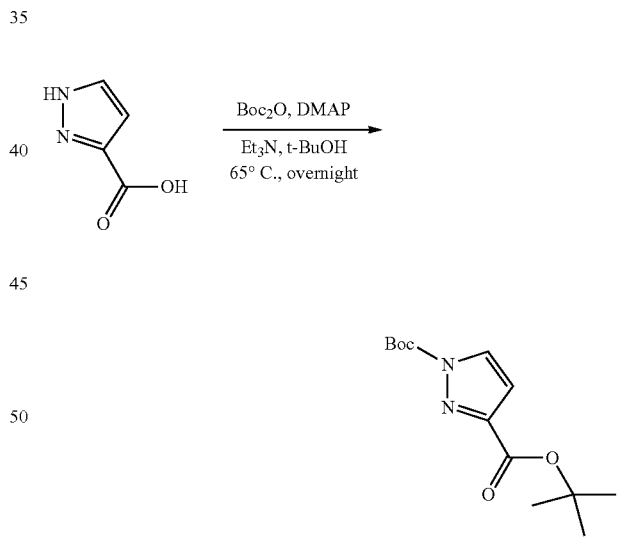

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]+.

Step 5: Preparation of t-butyl 1H-pyrazole-3-carboxylate

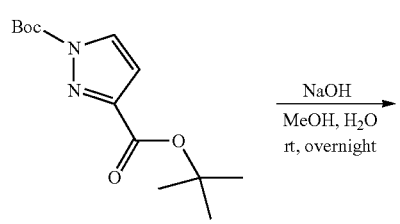

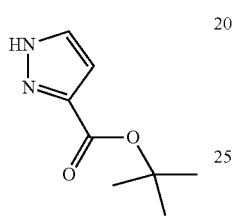

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed to provide 10.0 g (64% yield) of t-butyl 1H-pyrazole-3-carboxylate as a white solid. LCMS (ESI, m/z): 169 [M+H]$^+$.

Step 6: Preparation of 3-(t-butyl) 1-(4-nitrophenyl) 1H-pyrazole-1,3-dicarboxylate

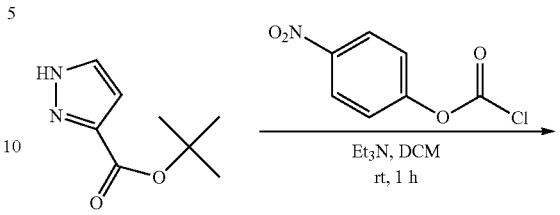

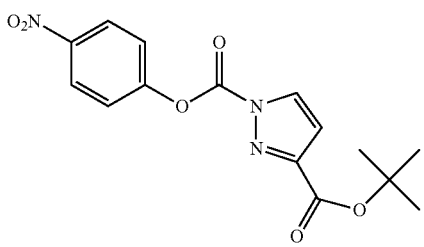

A flask was charged with t-butyl 1H-pyrazole-3-carboxylate (2.00 g, 11.9 mmol, 1.00 equiv), 4-nitrophenyl chloroformate (2.87 g, 14.2 mmol, 1.20 equiv), triethylamine (3.61 g, 35.7 mmol, 3.00 equiv), and DCM (20 mL), as described in Example 4, Step 3 to provide 4.50 g (crude) of 3-(t-butyl) 1-(4-nitrophenyl) 1H-pyrazole-1,3-dicarboxylate as a yellow solid. LCMS (ESI, m/z): 334 [M+H]$^+$.

Step 7: Preparation of t-butyl 1-(4-((3-methyl-[1,1'-biphenyl]-4-yl)methyl)piperazine-1-carbonyl)-1H-pyrazole-3-carboxylate

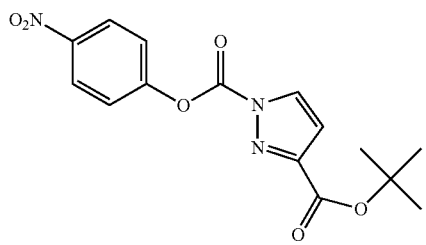 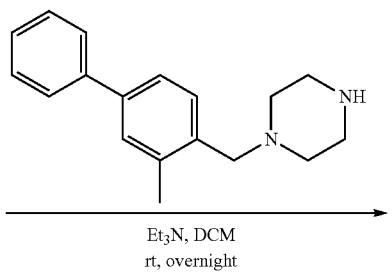

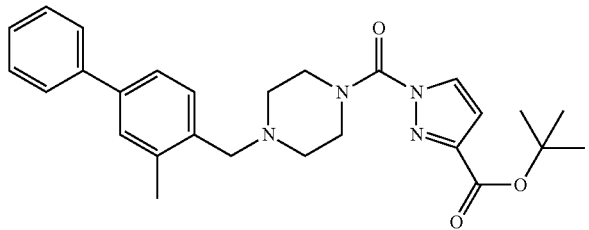

A flask was charged with of 3-(t-butyl) 1-(4-nitrophenyl) 1H-pyrazole-1,3-dicarboxylate (218 mg, 0.820 mmol, 1.00 equiv), 1-((3-methyl-[1,1'-biphenyl]-4-yl)methyl)piperazine (410 mg, 1.23 mmol, 1.50 equiv), DCM (5 mL), and triethylamine (331 mg, 3.27 mmol, 4.00 equiv), as described in Example 4, Step 3. The residue was chromatographed on a silica gel column to provide 200 mg (53% yield) of t-butyl 1-(4-((3-methyl-[1,1'-biphenyl]-4-yl)methyl)piperazine-1-carbonyl)-1H-pyrazole-3-carboxylate as a yellow oil. LCMS (ESI, m/z): 461 [M+H]$^+$.

Step 8: Preparation of 1-(4-((3-methyl-[1,1'-biphenyl]-4-yl)methyl)piperazine-1-carbonyl)-1H-pyrazole-3-carboxylic Acid

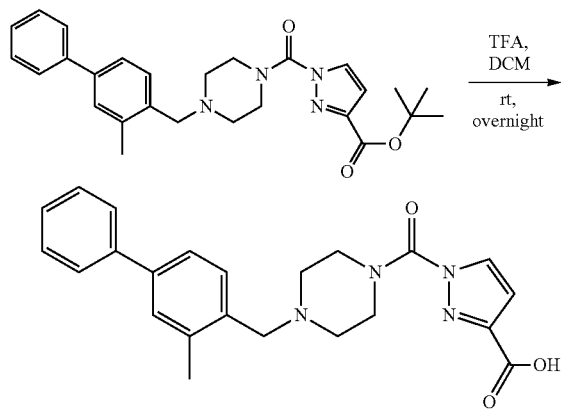

A flask was charged with t-butyl 1-(4-((3-methyl-[1,1'-biphenyl]-4-yl)methyl)piperazine-1-carbonyl)-1H-pyrazole-3-carboxylate (200 mg, 0.430 mmol, 1.00 equiv), DCM (5 mL), and TFA (2 mL). The resulting solution was stirred overnight at room temperature and concentrated under reduced pressure. The crude product was dissolved in saturated NaHCO$_3$ solution (10 mL) and extracted with DCM (3×20 mL), as described in Example 1, Step 5 to provide 87.1 mg (50% yield) of 1-(4-((3-methyl-[1,1'-biphenyl]-4-yl)methyl)piperazine-1-carbonyl)-1H-pyrazole-3-carboxylic acid as a white solid. $^1$H NMR (300 MHz, Methanol-d$_4$) δ 8.12 (d, J=2.4 Hz, 1H), 7.59 (d, J=7.2 Hz, 2H), 7.29-7.46 (m, 6H), 6.81 (d, J=2.4 Hz, 1H), 3.97 (br, 4H), 3.74 (s, 2H), 2.76 (br, 4H), 2.48 (s, 3H). LCMS (ESI, m/z): 405 [M+H]$^+$.

Example 17: 1-(5-(4-Morpholino-2-(trifluoromethyl)benzyl)octahydropyrrolo[3,4-c]pyrrole-2-carbonyl)-1H-pyrazole-3-carboxamide

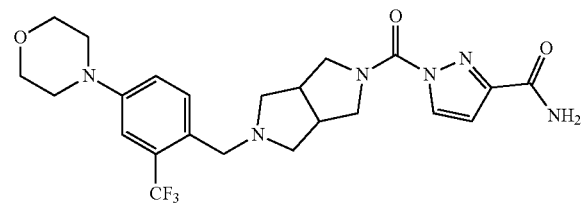 [SMILES: NC(=O)c1ccn(C(=O)N2CC3CN(Cc4ccc(N5CCOCC5)cc4C(F)(F)F)CC3C2)n1]

Step 1: Preparation of 4-morpholino-2-(trifluoromethyl)benzaldehyde

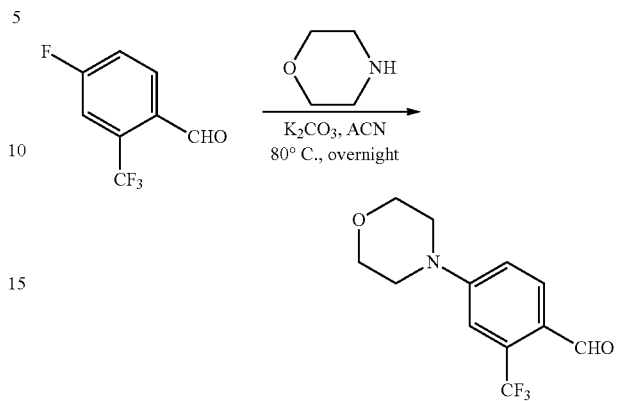

A flask was charged ACN (100 mL), morpholine (4.50 g, 51.7 mmol, 1.00 equiv), 4-fluoro-2-(trifluoromethyl)benzaldehyde (10.0 g, 51.7 mmol, 1.00 equiv) and potassium carbonate (14.0 g, 101 mmol, 2.00 equiv) under nitrogen. The resulting solution was stirred overnight at 80° C. and quenched with water (150 mL). The mixture was extracted with DCM (3×50 mL) and the organic layers were combined, washed with water (3×50 mL), dried over anhydrous sodium sulfate, filtered and concentrated under reduced pressure. The residue was chromatographed on a silica gel column to provide 10.0 g (75% yield) of 4-morpholino-2-(trifluoromethyl)benzaldehyde as a yellow solid. LCMS (ESI, m/z): 260 [M+H]$^+$.

Step 2: Preparation of t-butyl 5-(4-morpholino-2-(trifluoromethyl)benzyl)hexahydropyrrolo[3,4-c]pyrrole-2(1H)-carboxylate

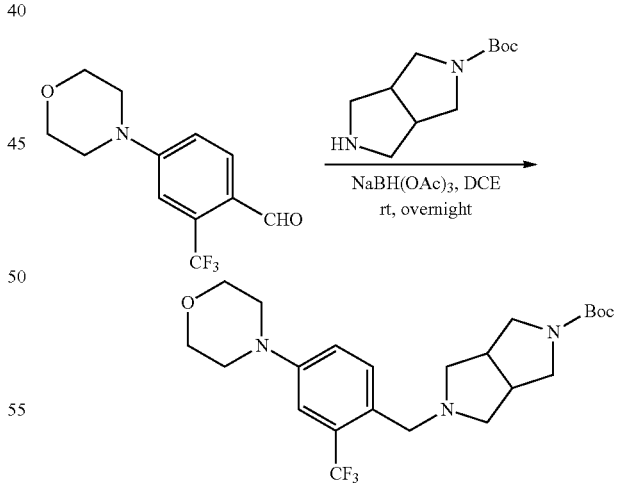

A flask was charged with 4-morpholino-2-(trifluoromethyl)benzaldehyde (5.00 g, 19.3 mmol, 1.00 equiv), t-butyl octahydropyrrolo[3,4-c]pyrrole-2-carboxylate (4.10 g, 19.3 mmol, 1.00 equiv) and DCE (100 mL). The mixture was stirred for 2 h at room temperature, then sodium triacetoxyborohydride (8.20 g, 38.7 mmol, 2.00 equiv) was added, as described in Example 2, Step 3. The residue was chromatographed on a silica gel column to provide 6.00 g (68% yield)

of t-butyl 5-(4-morpholino-2-(trifluoromethyl)benzyl)hexahydropyrrolo[3,4-c]pyrrole-2(1H)-carboxylate as a light yellow oil. LCMS (ESI, m/z): 456 [M+H]+.

Step 3: Preparation of 4-(4-((hexahydropyrrolo[3,4-c]pyrrol-2(1H)-yl)methyl)-3-(trifluoromethyl)phenyl)morpholine

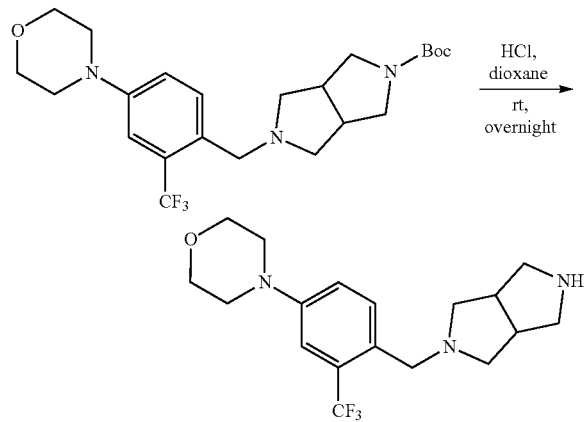

A flask was charged with t-butyl 5-(4-morpholino-2-(trifluoromethyl)benzyl)hexahydropyrrolo[3,4-c]pyrrole-2(1H)-carboxylate (6.00 g, 13.2 mmol, 1.00 equiv), 1,4-dioxane (100 mL) and concentrated HCl (20 mL), as described in Example 2, Step 4 to provide 4.00 g (crude) of 4-(4-((hexahydropyrrolo[3,4-c]pyrrol-2(1H)-yl)methyl)-3-(trifluoromethyl)phenyl)morpholine as a pink solid. LCMS (ESI, m/z): 356 [M+H]+.

Step 4: Preparation of 5-(4-morpholino-2-(trifluoromethyl)benzyl)hexahydropyrrolo[3,4-c]pyrrole-2(1H)-carbonyl Chloride

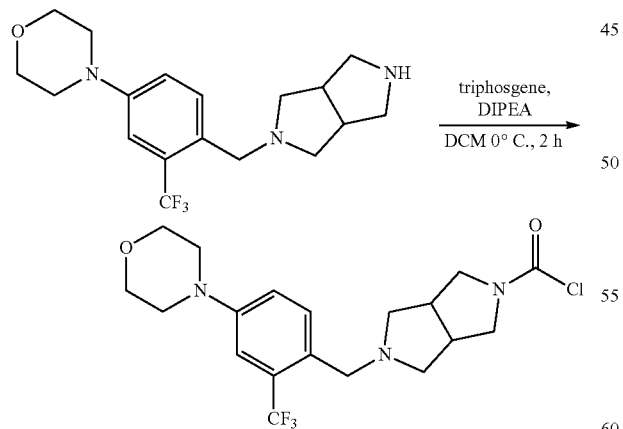

A flask was charged with 4-(4-((hexahydropyrrolo[3,4-c]pyrrol-2(1H)-yl)methyl)-3-(trifluoromethyl)phenyl)morpholine (1.00 g, 2.81 mmol, 1.00 equiv), DCM (10 mL) and triphosgene (0.335 g, 1.14 mmol, 0.40 equiv). DIPEA (1.09 g, 8.45 mmol, 3.00 equiv) was added dropwise at 0° C. The resulting solution was stirred for 2 h at 0° C. and quenched with water (5 mL), as described in Example 1, Step 3 to provide 1.12 g (crude) of 5-(4-morpholino-2-(trifluoromethyl)benzyl)hexahydropyrrolo[3,4-c]pyrrole-2(1H)-carbonyl chloride as a yellow oil.

Step 5: Preparation of 1-(5-(4-morpholino-2-(trifluoromethyl)benzyl)octahydropyrrolo[3,4-c]pyrrole-2-carbonyl)-1H-pyrazole-3-carboxamide

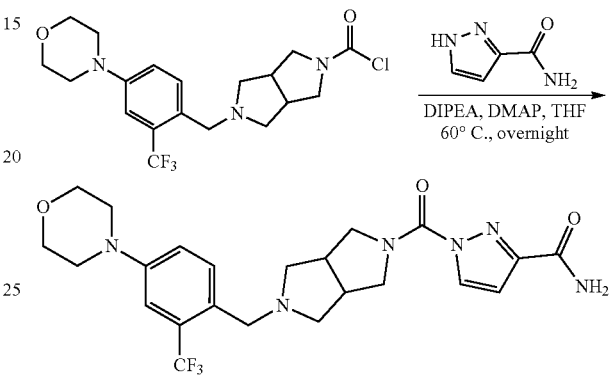

A was charged with 5-(4-morpholino-2-(trifluoromethyl)benzyl)hexahydropyrrolo[3,4-c]pyrrole-2(1H)-carbonyl chloride (235 mg, 0.560 mmol, 1.00 equiv), 1H-pyrazole-3-carboxamide (62.0 mg, 0.560 mmol, 1.00 equiv), DIPEA (147 mg, 1.14 mmol, 2.00 equiv), DMAP (14.0 mg, 0.110 mmol, 0.20 equiv) and THF (10 mL). The resulting solution was stirred overnight at 60° C. and quenched with water (10 mL), as described in Example 1, Step 4. The crude product was purified by preparative HPLC to provide 35.8 mg (13% yield) of 1-(5-(4-morpholino-2-(trifluoromethyl)benzyl)octahydropyrrolo[3,4-c]pyrrole-2-carbonyl)-1H-pyrazole-3-carboxamide as a yellow oil. $^1$H NMR (300 MHz, Chloroform-d) δ 8.30 (d, J=2.6 Hz, 1H), 7.50-7.60 (m, 1H), 6.80-7.20 (m, 3H), 6.60-6.80 (brm 1H), 5.56-5.70 (br, 1H), 4.00-4.30 (m, 2H), 3.60-3.90 (m, 8H), 3.18-2.26 (m, 4H), 2.80-3.00 (m, 2H), 2.50-2.76 (m, 4H). LCMS (ESI, m/z): 493 [M+H]+.

Example 18: 1-(4-(3-(Pyridin-3-yloxy)benzyl)piperazine-1-carbonyl)-1H-pyrazole-3-carboxylic acid

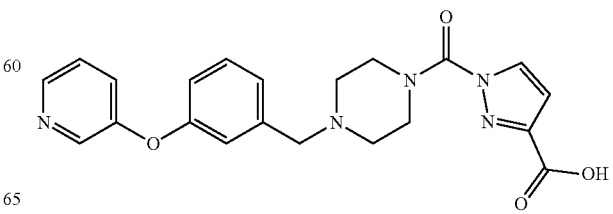

Step 1: Preparation of di-t-butyl 1H-pyrazole-1,3-dicarboxylate

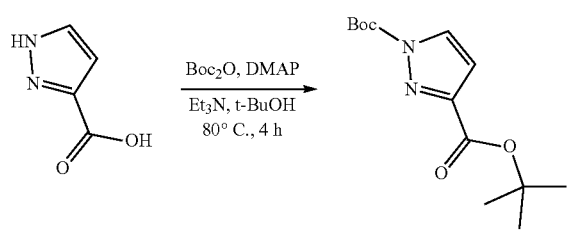 [SMILES: O=C(O)c1cc[nH]n1 ; CC(C)(C)OC(=O)c1ccn(C(=O)OC(C)(C)C)n1]

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]+.

Step 2: Preparation of t-butyl 1H-pyrazole-3-carboxylate

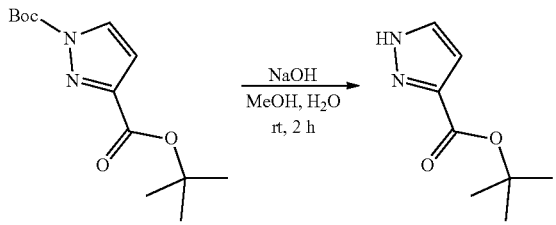 [SMILES: CC(C)(C)OC(=O)c1ccn(C(=O)OC(C)(C)C)n1 ; "NaOH" ; CC(C)(C)OC(=O)c1cc[nH]n1]

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed to provide 10.0 g (64% yield) of t-butyl 1H-pyrazole-3-carboxylate as a white solid. LCMS (ESI, m/z): 169 [M+H]+.

Step 3: Preparation of 3-(t-butyl) 1-(4-nitrophenyl) 1H-pyrazole-1,3-dicarboxylate

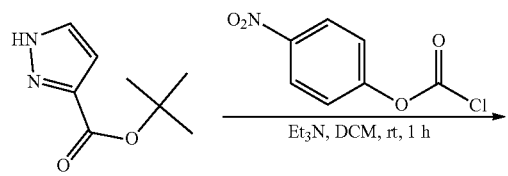

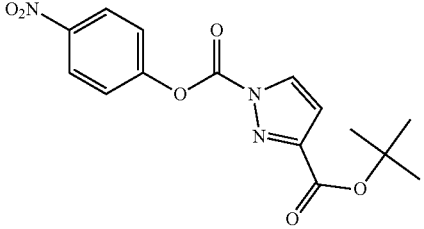

A flask was charged with t-butyl 1H-pyrazole-3-carboxylate (2.00 g, 11.9 mmol, 1.00 equiv), 4-nitrophenyl chloroformate (2.87 g, 14.2 mmol, 1.20 equiv), triethylamine (3.61 g, 35.7 mmol, 3.00 equiv), and DCM (20 mL), as described in Example 4, Step 3 to provide 3.90 g (crude) of 3-t-butyl 1-(4-nitrophenyl) 1H-pyrazole-1,3-dicarboxylate as a yellow solid. LCMS (ESI, m/z): 334 [M+H]+.

Step 4: Preparation of 3-(pyridin-3-yloxy)benzaldehyde

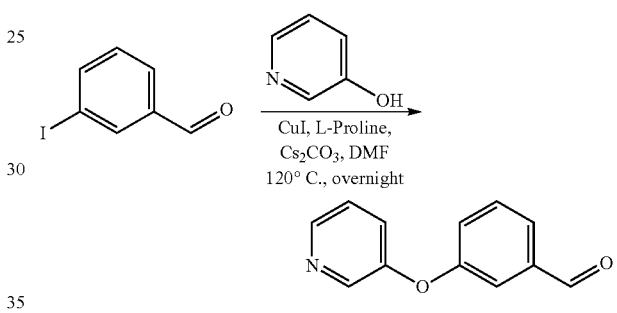

A flask was charged with 3-iodobenzaldehyde (0.928 g, 4.00 mmol, 1.00 equiv), copper(I) iodide (0.152 g, 0.800 mmol, 0.20 equiv), L-proline (0.184 g, 1.60 mmol, 0.40 equiv), cesium carbonate (3.91 g, 12.0 mmol, 3.00 equiv), pyridin-3-ol (0.570 g, 6.00 mmol, 1.50 equiv), and DMF (15 mL) under nitrogen. The resulting solution was stirred overnight at 120° C. and then quenched with water (15 mL). The resulting solution was extracted with EtOAc (3×20 mL) and the organic layers were combined, washed with brine (20 mL), dried over anhydrous sodium sulfate, filtered and concentrated under reduced pressure. The residue was chromatographed on a silica gel column to provide 0.160 g (20% yield) of 3-(pyridin-3-yloxy)benzaldehyde as a yellow oil. LCMS (ESI, m/z): 200 [M+H]+.

Step 5: Preparation of t-butyl 4-(3-(pyridin-3-yloxy)benzyl)piperazine-1-carboxylate

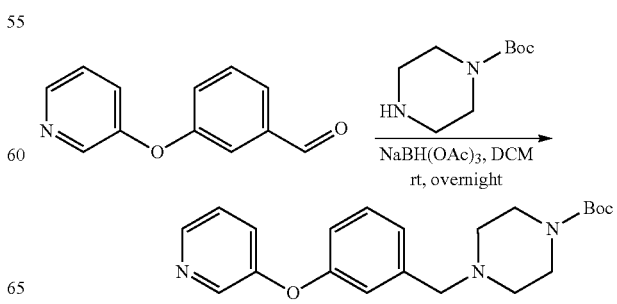

A flask was charged with 3-(pyridin-3-yloxy)benzaldehyde (160 mg, 0.800 mmol, 1.00 equiv), t-butyl piperazine-1-carboxylate (179 mg, 0.960 mmol, 1.20 equiv), and DCM (15 mL). The mixture was stirred for 2 h at room temperature. Sodium triacetoxyborohydride (678 mg, 3.20 mmol, 4.00 equiv) was added. The resulting solution was stirred overnight at room temperature and then quenched with water (20 mL), as described in Example 2, Step 3. The residue was chromatographed to provide 270 mg (91% yield) of t-butyl 4-(3-(pyridin-3-yloxy)benzyl)piperazine-1-carboxylate as a brown oil.

Step 6: Preparation of 1-(3-(pyridin-3-yloxy)benzyl)piperazine

A flask was charged with t-butyl 4-(3-(pyridin-3-yloxy)benzyl)piperazine-1-carboxylate (270 mg, 0.730 mmol, 1.00 equiv), DCM (15 mL), and TFA (3 mL), as described in Example 1, Step 5 to provide 197 mg (quantitative) of 1-(3-(pyridin-3-yloxy)benzyl)piperazine as a yellow oil. LCMS (ESI, m/z): 270 [M+H]$^+$.

Step 7: Preparation of t-butyl 1-(4-(3-(pyridin-3-yloxy)benzyl)piperazine-1-carbonyl)-1H-pyrazole-3-carboxylate A flask was charged with 1-(3-(pyridin-3-yloxy)benzyl)piperazine (197 mg, 0.730 mmol, 1.00 equiv), 3-t-butyl 1-(4-nitrophenyl) 1H-pyrazole-1,3-dicarboxylate (340 mg, 1.02 mmol, 1.40 equiv), DCM (15 mL), and triethylamine (222 mg, 2.19 mmol, 3.00 equiv). The resulting solution was stirred overnight at room temperature and then quenched with water (20 mL), as described in Example 4, Step 3. The residue was chromatographed to provide 200 mg (59% yield) of t-butyl 1-(4-(3-(pyridin-3-yl oxy)benzyl)piperazine-1-carbonyl)-1H-pyrazole-3-carboxylate as a yellow oil. LCMS (ESI, m/z): 464 [M+H]$^+$.

Step 8: Preparation of 1-(4-(3-(pyridin-3-yloxy)benzyl)piperazine-1-carbonyl)-1H-pyrazole-3-carboxylic Acid

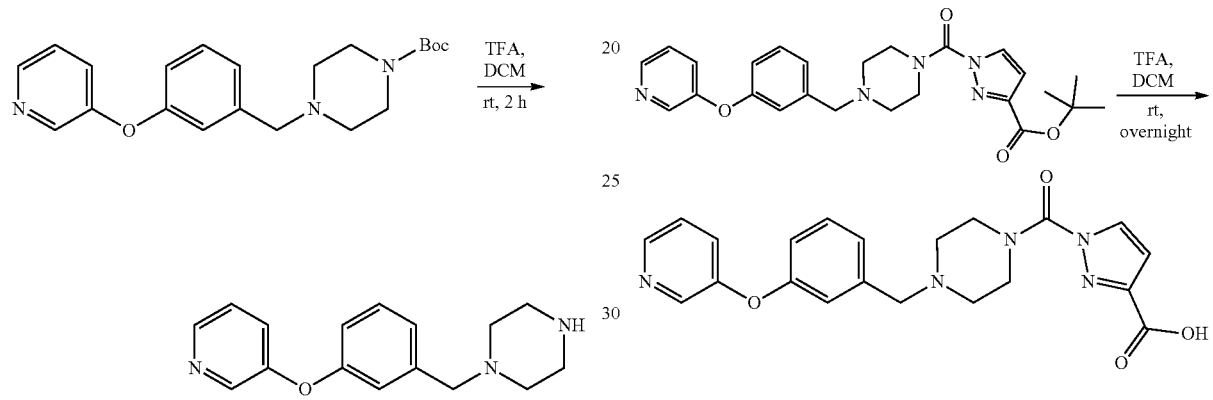

A flask was charged with t-butyl 1-(4-(3-(pyridin-3-yloxy)benzyl)piperazine-1-carbonyl)-1H-pyrazole-3-carboxylate (200 mg, 0.430 mmol, 1.00 equiv), DCM (15 mL), and TFA (3 mL), as described in Example 1, Step 5. The crude product (200 mg) was purified by preparative HPLC to provide 17.9 mg (10% yield) of 1-(4-(3-(pyridin-3-yloxy)benzyl)piperazine-1-carbonyl)-1H-pyrazole-3-carboxylic acid as a white solid. $^1$H NMR (300 MHz, Methanol-d$_4$) δ 8.28-8.30 (m, 2H), 8.06 (d, J=2.7 Hz, 1H), 7.36-7.44 (m, 3H), 7.20-7.22 (m, 1H), 7.11-7.12 (m, 1H), 6.96-7.00 (m, 1H), 6.74 (d, J=2.7 Hz, 1H), 3.86 (br, 4H), 3.60 (s, 2H), 2.57-2.60 (m, 4H). LCMS (ESI, m/z): 408 [M+H]$^+$.

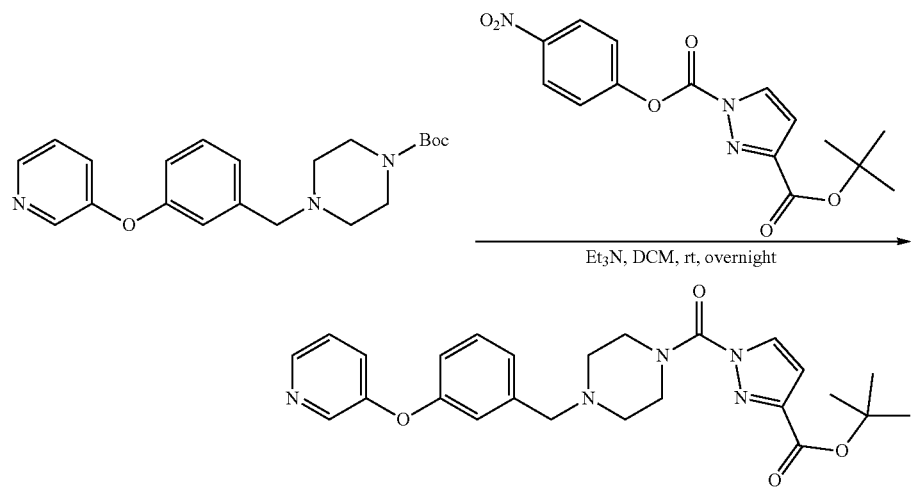

Example 19: 1-(4-(3-Chloro-5-(4-chlorophenoxy)benzyl)piperazine-1-carbonyl)-1H-pyrazole-3-carboxylic Acid

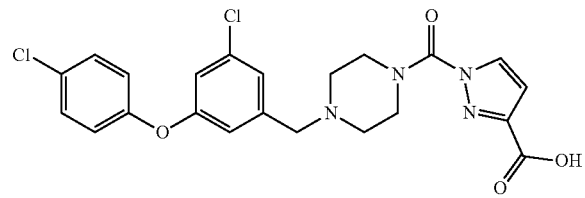 [SMILES: O=C(O)c1ccn(C(=O)N2CCN(Cc3cc(Cl)cc(Oc4ccc(Cl)cc4)c3)CC2)n1]

Step 1: Preparation of bis(4-chlorophenyl)iodonium tetrafluoroborate

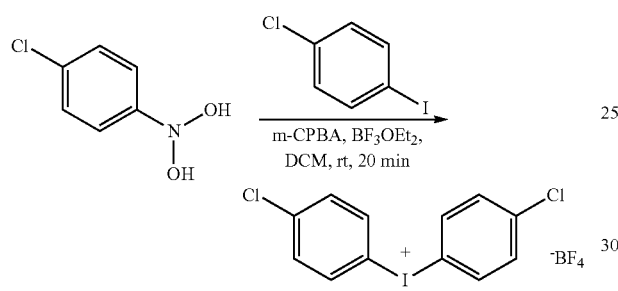

A flask was charged with m-chloroperoxybenzoic acid (1.60 g, 9.27 mmol, 1.10 equiv), DCM (10 mL), boron trifluoride ether complex (3.58 g, 25.2 mmol, 3.00 equiv) and 1-chloro-4-iodobenzene (2.00 g, 8.39 mmol, 1.00 equiv). The resulting solution was stirred for 0.5 h at room temperature. Then (4-chlorophenyl)boronic acid (1.44 g, 9.22 mmol, 1.10 equiv) was added at 0° C. The resulting solution was stirred for 20 min at room temperature and concentrated under reduced pressure. The crude was triturated to provide 3.00 g (78% yield) of bis(4-chlorophenyl)iodonium tetrafluoroborate as a white solid. LCMS (ESI, m/z): 349 [M-BF4]+.

Step 2: Preparation of di-t-butyl 1H-pyrazole-1,3-dicarboxylate

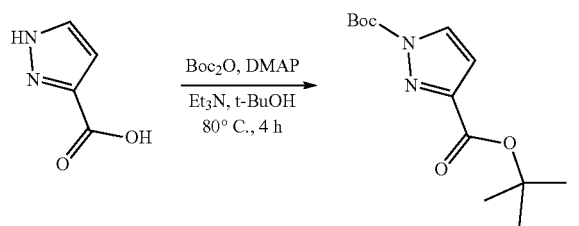 [SMILES: O=C(O)c1cc[nH]n1 ; CC(C)(C)OC(=O)c1ccn(C(=O)OC(C)(C)C)n1]

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]+.

Step 3: Preparation of t-butyl 1H-pyrazole-3-carboxylate

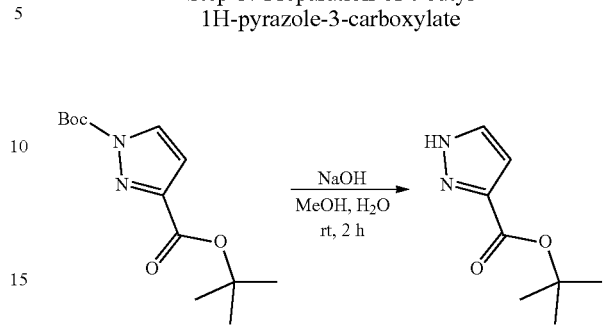

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed to provide 10.0 g (64% yield) of t-butyl 1H-pyrazole-3-carboxylate as a white solid. LCMS (ESI, m/z): 169 [M+H]+.

Step 4: Preparation of 3-(t-butyl) 1-(4-nitrophenyl) 1H-pyrazole-1,3-dicarboxylate

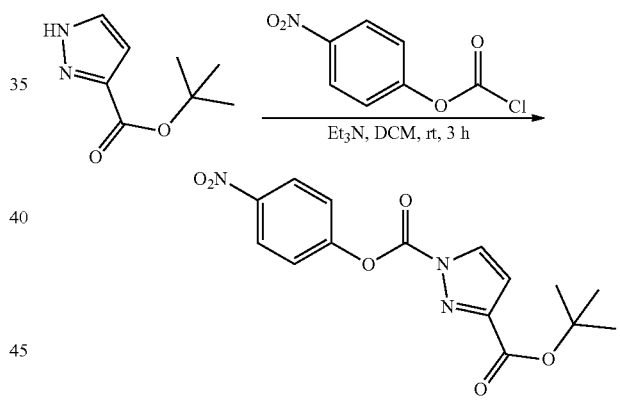

A flask was charged with t-butyl 1H-pyrazole-3-carboxylate (208 mg, 1.24 mmol, 1.00 equiv), DCM (10 mL), 4-nitrophenyl chloroformate (264 mg, 1.30 mmol, 1.05 equiv), and triethylamine (378 mg, 3.72 mmol, 3.00 equiv), as described in Example 4, Step 3 to provide 450 mg (crude) of 3-t-butyl 1-(4-nitrophenyl) 1H-pyrazole-1,3-dicarboxylate as a yellow oil. LCMS (ESI, m/z): 334 [M+H]+.

Step 5: Preparation of t-butyl 4-(3-chloro-5-hydroxybenzyl)piperazine-1-carboxylate

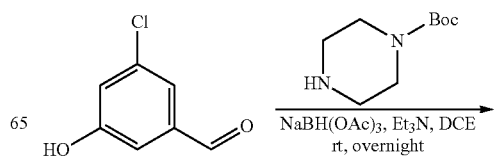

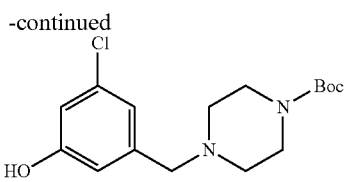

A flask was charged with 3-chloro-5-hydroxybenzaldehyde (300 mg, 1.92 mmol, 1.00 equiv), DCE (10 mL), t-butyl piperazine-1-carboxylate (536 mg, 2.88 mmol, 1.50 equiv), and triethylamine (582 mg, 5.76 mmol, 3.00 equiv). The resulting solution was stirred for 1 h at room temperature. Sodium triacetoxyborohydride (1.21 g, 5.76 mmol, 3.00 equiv) was added. The resulting solution was stirred overnight at room temperature and quenched with water (20 mL), as described in Example 2, Step 3. The residue was chromatographed to provide 460 mg (73% yield) of t-butyl 4-(3-chloro-5-hydroxybenzyl)piperazine-1-carboxylate as a white solid. LCMS (ESI, m/z): 327 [M+H]+.

Step 6: Preparation of t-butyl 4-(3-chloro-5-(4-chlorophenoxy)benzyl)piperazine-1-carboxylate

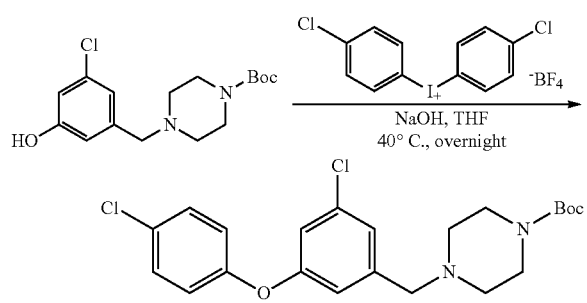

A 50-mL round-bottom flask was charged with t-butyl 4-(3-chloro-5-hydroxybenzyl)piperazine-1-carboxylate (300 mg, 0.920 mmol, 1.00 equiv), THF (10 mL), and NaOH (40.4 mg, 1.01 mmol, 1.10 equiv). The resulting solution was stirred for 15 min at 0° C. Then bis(4-chlorophenyl) iodanium tetrafluoroborate (440 mg, 1.01 mmol, 1.10 equiv) was added. The resulting solution was stirred overnight at 40° C. and quenched with water (10 mL). The mixture was extracted with EtOAc (3×10 mL) and the organic layers were combined, washed with brine (2×15 mL), dried over anhydrous sodium sulfate, filtered and concentrated under reduced pressure. The residue was chromatographed on a silica gel column to provide 100 mg (25% yield) of t-butyl 4-(3-chloro-5-(4-chlorophenoxy)benzyl)piperazine-1-carboxylate as a colorless oil. LCMS (ESI, m/z): 437 [M+H]+.

Step 7: Preparation of 1-(3-chloro-5-(4-chlorophenoxy)benzyl)piperazine

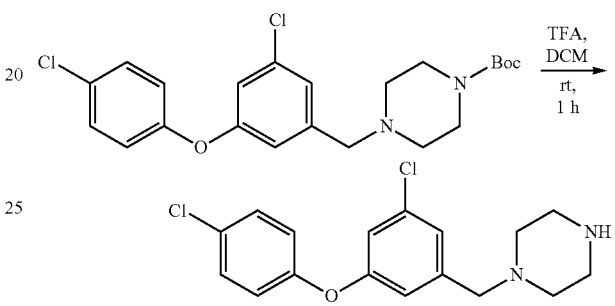

A flask was charged with t-butyl 4-(3-chloro-5-(4-chlorophenoxy)benzyl)piperazine-1-carboxylate (100 mg, 0.229 mmol, 1.00 equiv), DCM (5 mL), and TFA (1 mL), as described in Example 1, Step 5 to provide 80.0 mg (crude) of 1-(3-chloro-5-(4-chlorophenoxy)benzyl)piperazine as a yellow oil. LCMS (ESI, m/z): 337 [M+H]+.

Step 8: Preparation of t-butyl 1-(4-(3-chloro-5-(4-chlorophenoxy)benzyl)piperazine-1-carbonyl)-1H-pyrazole-3-carboxylate

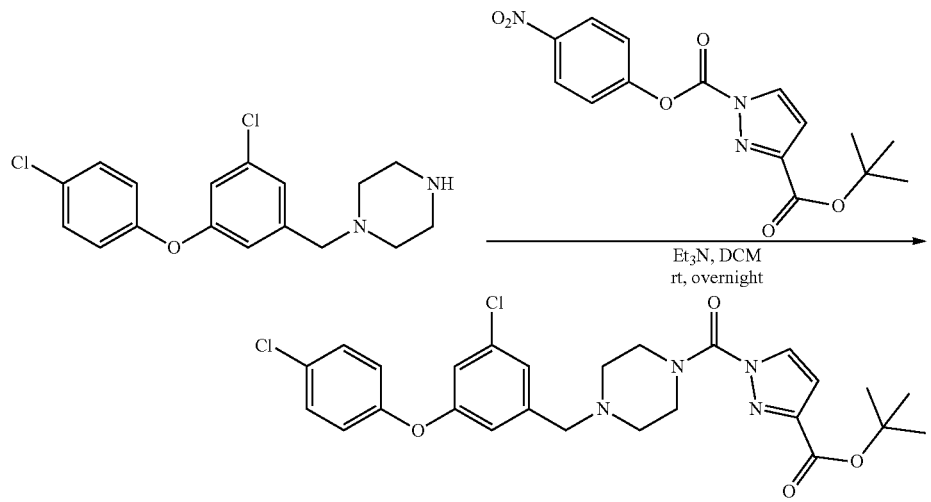

A flask was charged with 1-[[3-chloro-5-(4-chlorophenoxy)phenyl]methyl]piperazine (80.0 mg, 0.238 mmol, 1.00 equiv), DCM (10 mL), 3-t-butyl 1-(4-nitrophenyl) 1H-pyrazole-1,3-dicarboxylate (159 mg, 0.476 mmol, 2.00 equiv), and triethylamine (72.1 mg, 0.714 mmol, 3.00 equiv). The resulting solution was stirred overnight at room temperature and quenched with water (10 mL), as described in Example 4, Step 3. The residue was chromatographed to provide 100 mg (79% yield) of t-butyl 1-(4-(3-chloro-5-(4-chlorophenoxy)benzyl)piperazine-1-carbonyl)-1H-pyrazole-3-carboxylate as a yellow oil. LCMS (ESI, m/z): 531 [M+H]$^+$.

Step 9: Preparation of 1-(4-(3-chloro-5-(4-chlorophenoxy)benzyl)piperazine-1-carbonyl)-1H-pyrazole-3-carboxylic acid

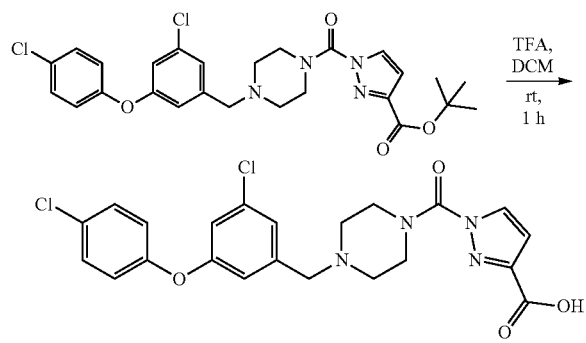

A flask was charged with t-butyl 1-(4-(3-chloro-5-(4-chlorophenoxy)benzyl)piperazine-1-carbonyl)-1H-pyrazole-3-carboxylate (70.0 mg, 0.132 mmol, 1.00 equiv), DCM (5 mL), and TFA (1 mL). The resulting solution was stirred overnight at room temperature and concentrated under reduced pressure. The crude product was dissolved in DCM (10 mL). The pH value of the solution was adjusted to 8 with saturated NaHCO$_3$ solution, as described in Example 1, Step 5. The crude product (200 mg) was purified by preparative HPLC to provide 15.4 mg (25% yield) of 1-(4-(3-chloro-5-(4-chlorophenoxy)benzyl)piperazine-1-carbonyl)-1H-pyrazole-3-carboxylic acid as a white solid. $^1$H NMR (300 MHz, Methanol-d$_4$) δ 8.14 (d, J=2.7 Hz, 1H), 7.35-7.43 (m, 2H), 7.19 (br, 1H), 7.02-7.06 (m, 2H), 6.93-6.97 (m, 1H), 6.92 (s, 1H), 6.82 (d, J=2.7 Hz, 1H), 3.86 (br, 4H), 3.60 (s, 2H), 2.57-2.67 (m, 4H). LCMS (ESI, m/z): 475 [M+H]$^+$.

Example 20: 4-Chloro-1-(5-(4-(imidazo[1,2-a]pyridin-3-yl)-2-(trifluoromethyl)benzyl)octahydropyrrolo[3,4-c]pyrrole-2-carbonyl)-1H-pyrazole-3-carboxylic Acid

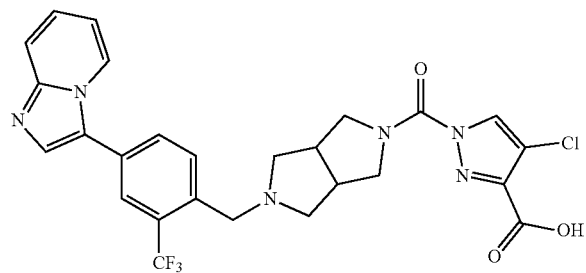 [SMILES: O=C(O)c1nn(C(=O)N2CC3CN(Cc4ccc(-c5cnc6ccccn56)cc4C(F)(F)F)CC3C2)cc1Cl]

Step 1: Preparation of t-butyl 4-chloro-1H-pyrazole-3-carboxylate

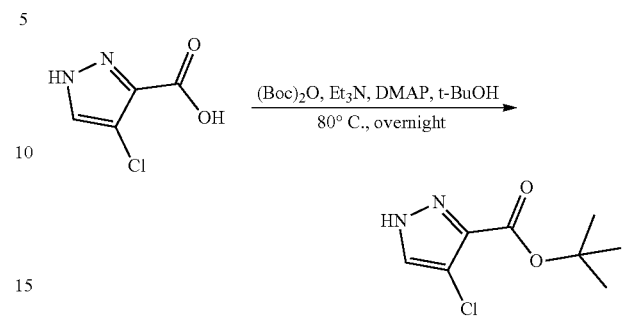

A flask was charged with 4-chloro-1H-pyrazole-3-carboxylic acid (2.00 g, 13.6 mmol, 1.00 equiv), di-t-butyl dicarbonate (11.9 g, 54.5 mmol, 4.00 equiv), DMAP (332 mg, 2.72 mmol, 0.20 equiv), triethylamine (4.12 g, 40.8 mmol, 3.00 equiv), t-BuOH (20 mL). The resulting solution was stirred overnight at 80° C. and quenched with water (50 mL), as described in Example 1, Step 1. The residue was chromatographed to provide 260 mg (9% yield) of t-butyl 4-chloro-1H-pyrazole-3-carboxylate as a yellow solid. LCMS (ESI, m/z): 203 [M+H]$^+$.

Step 2: Preparation of 4-(4,4,5,5-tetramethyl-1,3,2-dioxaborolan-2-yl)-2-(trifluoromethyl)benzaldehyde

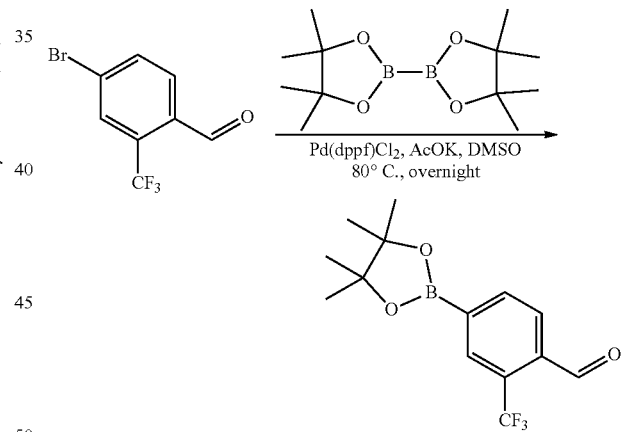

A flask was charged with 4-bromo-2-(trifluoromethyl)benzaldehyde (2.00 g, 7.90 mmol, 1.00 equiv), 1,1'-bis(diphenylphosphino)ferrocenepalladiumdichloride (578 mg, 0.790 mmol, 0.10 equiv), potassium acetate (2.32 g, 23.7 mmol, 3.00 equiv), DMSO (30 mL), 4,4,5,5-tetramethyl-2-(tetramethyl-1,3,2-dioxaborolan-2-yl)-1,3,2-dioxaborolane (2.40 g, 9.45 mmol, 1.20 equiv) under nitrogen. The resulting solution was stirred overnight at 80° C. and quenched with water (20 mL). The mixture was extracted with EtOAc (3×30 mL) and the organic layers were combined, washed with brine (3×30 mL), dried over anhydrous sodium sulfate, filtered and concentrated under reduced pressure. The residue was chromatographed to provide 2.00 g (84% yield) of 4-(4,4,5,5-tetramethyl-1,3,2-dioxaborolan-2-yl)-2-(trifluoromethyl)benzaldehyde as a white solid. LCMS (ESI, m/z): 301 [M+H]$^+$.

Step 3: Preparation of 4-(imidazo[1,2-a]pyridin-3-yl)-2-(trifluoromethyl)benzaldehyde

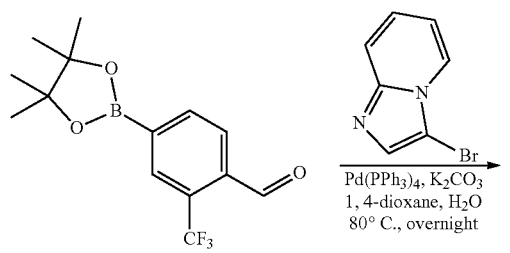

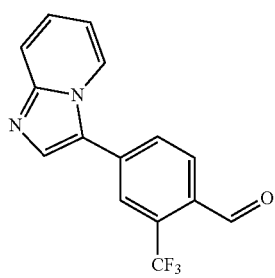

A flask was charged with 4-(tetramethyl-1,3,2-dioxaborolan-2-yl)-2-(trifluoromethyl)benzaldehyde (900 mg, 3.00 mmol, 1.00 equiv), 3-bromoimidazo[1,2-a]pyridine (886 mg, 4.50 mmol, 1.50 equiv), tetrakis(triphenylphosphine) palladium (173 mg, 0.151 mmol, 0.05 equiv), potassium carbonate (1.24 g, 8.97 mmol, 3.00 equiv), 1,4-dioxane (10 mL), and water (10 mL) under nitrogen. The resulting solution was stirred overnight at 80° C. and quenched with water (20 mL). The mixture was extracted with DCM (3×30 mL) and the organic layers were combined, washed with brine (3×30 mL), dried over anhydrous sodium sulfate, filtered and concentrated under reduced pressure. The residue was chromatographed to provide 740 mg (85% yield) of 4-(imidazo[1,2-a]pyridin-3-yl)-2-(trifluoromethyl)benzaldehyde as a yellow solid. LCMS (ESI, m/z): 291 [M+H]$^+$.

Step 4: Preparation of t-butyl 5-(4-(imidazo[1,2-a]pyridin-3-yl)-2-(trifluoromethyl)benzyl)hexahydropyrrolo[3,4-c]pyrrole-2(1H)-carboxylate

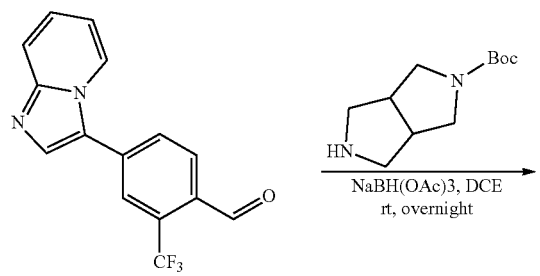

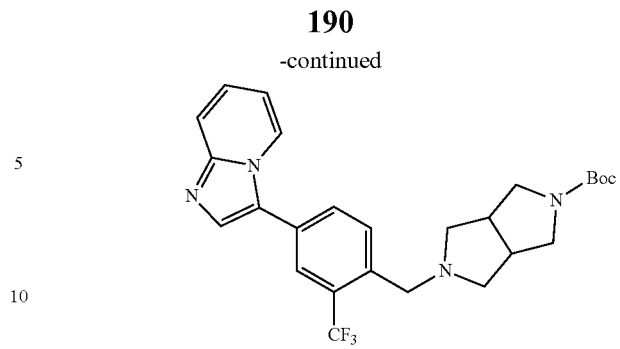

A flask was charged with 4-(imidazo[1,2-a]pyridin-3-yl)-2-(trifluoromethyl)benzaldehyde (290 mg, 1.00 mmol, 1.00 equiv), DCE (5 mL), and t-butyl octahydropyrrolo[3,4-c]pyrrole-2-carboxylate (233 mg, 1.10 mmol, 1.10 equiv). The resulting solution was stirred for 2 h at room temperature. Sodium triacetoxyborohydride (636 mg, 3.00 mmol, 3.00 equiv) was added, as described in Example 2, Step 3. The residue was chromatographed to provide 430 mg (88% yield) of t-butyl 5-(4-(imidazo[1,2-a]pyridin-3-yl)-2-(trifluoromethyl)benzyl)hexahydropyrrolo[3,4-c]pyrrole-2(1H)-carboxylate as a light yellow oil. LCMS (ESI, m/z): 487 [M+H]$^+$.

Step 5: Preparation of 3-(4-((hexahydropyrrolo[3,4-c]pyrrol-2(1H)-yl)methyl)-3-(trifluoromethyl)phenyl)imidazo[1,2-a]pyridine

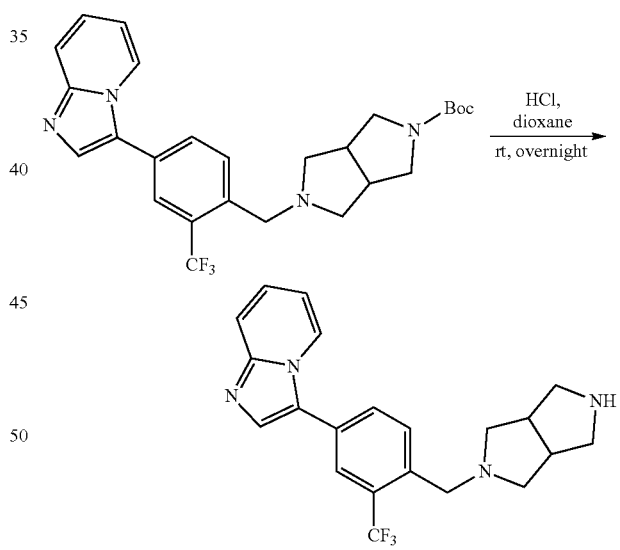

A flask was charged with t-butyl 5-(4-(imidazo[1,2-a]pyridin-3-yl)-2-(trifluoromethyl)benzyl)hexahydropyrrolo[3,4-c]pyrrole-2(1H)-carboxylate (430 mg, 0.881 mmol, 1.00 equiv), dioxane (6 mL), and concentrated HCl (1 mL), as described in Example 2, Step 4. The resulting solution was stirred overnight at room temperature and concentrated under reduced pressure to provide 341 mg (crude) of 3-(4-((hexahydropyrrolo[3,4-c]pyrrol-2(1H)-yl)methyl)-3-(trifluoromethyl)phenyl)imidazo[1,2-a]pyridine as a yellow oil. LCMS (ESI, m/z): 387 [M+H]$^+$.

191

Step 6: Preparation of t-butyl 4-chloro-1-(5-(4-(imi-dazo[1,2-a]pyridin-3-yl)-2-(trifluoromethyl)benzyl)octahydropyrrolo[3,4-c]pyrrole-2-carbonyl)-1H-pyrazole-3-carboxylate

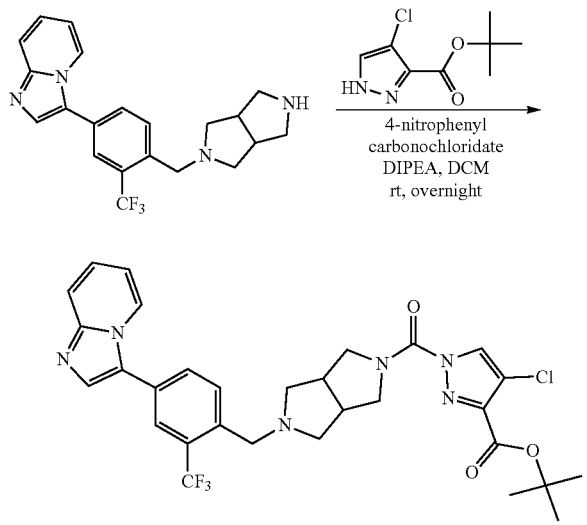

A flask was charged with 4-nitrophenyl carbonochloridate (212 mg, 1.05 mmol, 1.20 equiv), tert-butyl 4-chloro-1H-pyrazole-3-carboxylate (212 mg, 1.05 mmol, 1.20 equiv), and DCM (5 mL). DIPEA (340 mg, 2.64 mmol, 3.00 equiv) was added at 0° C. The resulting solution was stirred for 2 h at room temperature. 3-(4-((Hexahydropyrrolo[3,4-c]pyrrol-2(1H)-yl)methyl)-3-(trifluoromethyl)phenyl)imidazo[1,2-a]pyridine (340 mg, 0.881 mmol, 1.00 equiv) was added. The resulting solution was stirred overnight at room temperature and quenched with water (20 mL), as described in Example 1, Step 4. The residue was chromatographed on a silica gel column to provide 274 mg (51% yield) of t-butyl 4-chloro-1-(5-(4-(imidazo[1,2-a]pyridin-3-yl)-2-(trifluoromethyl)benzyl)octahydropyrrolo[3,4-c]pyrrole-2-carbonyl)-1H-pyrazole-3-carboxylate as a yellow oil. LCMS (ESI, m/z): 615 [M+H]⁺.

Step 7: Preparation of 4-chloro-1-(5-(4-(imidazo[1,2-a]pyridin-3-yl)-2-(trifluoromethyl)benzyl)octahydropyrrolo[3,4-c]pyrrole-2-carbonyl)-1H-pyrazole-3-carboxylic acid

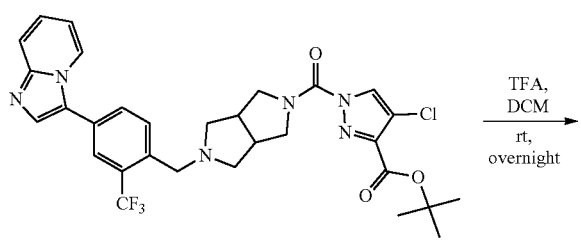

192

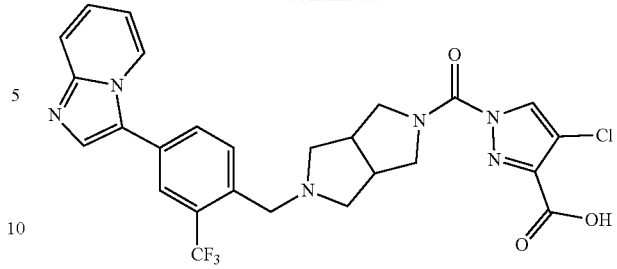

A flask was charged with t-butyl 4-chloro-1-(5-(4-(imidazo[1,2-a]pyridin-3-yl)-2-(trifluoromethyl)benzyl)octahydropyrrolo[3,4-c]pyrrole-2-carbonyl)-1H-pyrazole-3-carboxylate (274 mg, 0.45 mmol, 1.00 equiv), DCM (5 mL), and TFA (1 mL), as described in Example 1, Step 5. The crude product (301 mg) was purified by preparative HPLC to provide 101.1 mg (41% yield) of 4-chloro-1-(5-(4-(imidazo[1,2-a]pyridin-3-yl)-2-(trifluoromethyl)benzyl)octahydropyrrolo[3,4-c]pyrrole-2-carbonyl)-1H-pyrazole-3-carboxylic acid as a white solid. ¹H NMR (400 MHz, Chloroform-d) δ 8.23-8.29 (m, 2H), 7.92-8.02 (m, 2H), 7.75-7.79 (m, 3H), 7.27-7.32 (m, 1H), 6.93-7.00 (m, 1H), 3.86-4.37 (m, 4H), 3.72 (br, 2H), 2.62-3.04 (m, 5H), 2.40 (br, 1H). LCMS (ESI, m/z): 559 [M+H]⁺.

Example 21: 1-(2-(4-Chloro-3-ethoxybenzyl)-2,8-diazaspiro[4.5]decane-8-carbonyl)-1H-pyrazole-3-carboxylic Acid

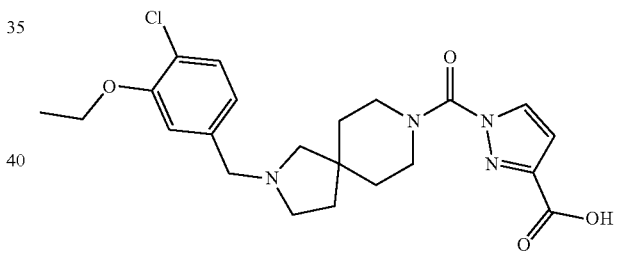

Step 1: Preparation of di-t-butyl 1H-pyrazole-1,3-dicarboxylate

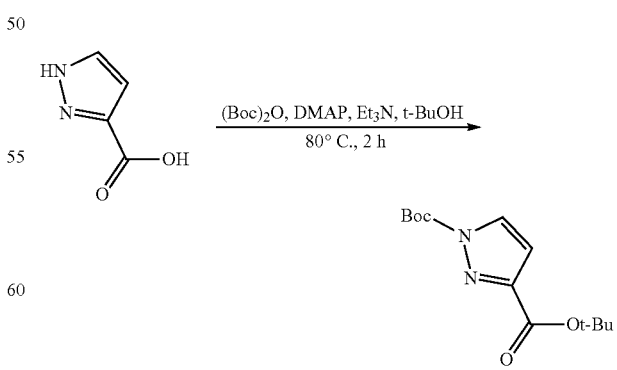

A flask was charged with 1H-pyrazole-3-carboxylic acid (22.4 g, 200 mmol, 1.00 equiv), t-butanol (100 mL), triethylamine (60.6 g, 599 mmol, 3.00 equiv), DMAP (4.88 g, 39.9 mmol, 0.20 equiv), and di-t-butyl dicarbonate (174 g, 797 mmol, 4.00 equiv). The resulting solution was stirred for 2 h at 80° C. and quenched with water (100 mL) as described in Example 1, Step 1 to provide 62.5 g (crude) of 1,3-di-t-butyl 1H-pyrazole-1,3-dicarboxylate as a brown oil. LCMS (ESI, m/z): 269 [M+H]+.

Step 2: Preparation of t-butyl 1H-pyrazole-3-carboxylate

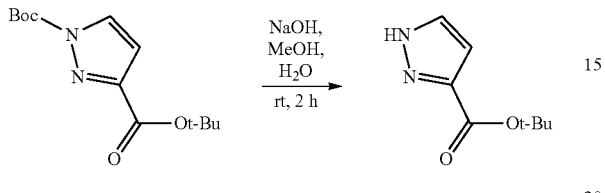

A flask was charged with 1,3-di-t-butyl 1H-pyrazole-1,3-dicarboxylate (62.5 g, 233 mmol, 1.00 equiv), MeOH (240 mL), water (80 mL), and sodium hydroxide (14.0 g, 350 mmol, 1.50 equiv). The resulting solution was stirred for 2 h at room temperature and concentrated under reduced pressure, as described in Example 1, Step 2. The residue was chromatographed on a silica gel column to provide 16.2 g (41% yield) of t-butyl 1H-pyrazole-3-carboxylate as a white solid. LCMS (ESI, m/z): 169 [M+H]+.

Step 3: Preparation of t-butyl 8-(3-(t-butoxycarbonyl)-1H-pyrazole-1-carbonyl)-2,8-diazaspiro[4.5]decane-2-carboxylate

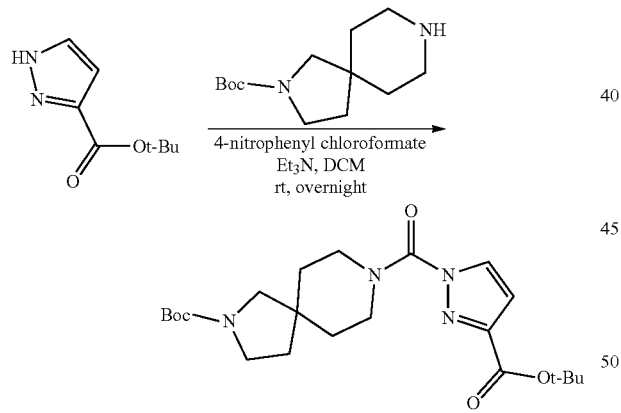

A flask was charged with t-butyl 1H-pyrazole-3-carboxylate (2.52 g, 15.0 mmol, 1.50 equiv), 4-nitrophenyl chloroformate (3.02 g, 15.0 mmol, 1.50 equiv), DCM (50 mL), and triethylamine (3.03 g, 29.9 mmol, 3.00 equiv). The resulting solution was stirred for 2 h at room temperature. t-Butyl 2,8-diazaspiro[4.5]decane-2-carboxylate (2.40 g, 9.99 mmol, 1.00 equiv) was added. The resulting solution was stirred overnight at room temperature and quenched with water (30 mL), as described in Example 4, Step 3. The residue was chromatographed on a silica gel column to provide 4.16 g (96% yield) of t-butyl 8-(3-(t-butoxycarbonyl)-1H-pyrazole-1-carbonyl)-2,8-diazaspiro[4.5]decane-2-carboxylate as a white solid. LCMS (ESI, m/z): 435 [M+H]+.

Step 4: Preparation of 1-(2,8-diazaspiro[4.5]decane-8-carbonyl)-1H-pyrazole-3-carboxylic acid

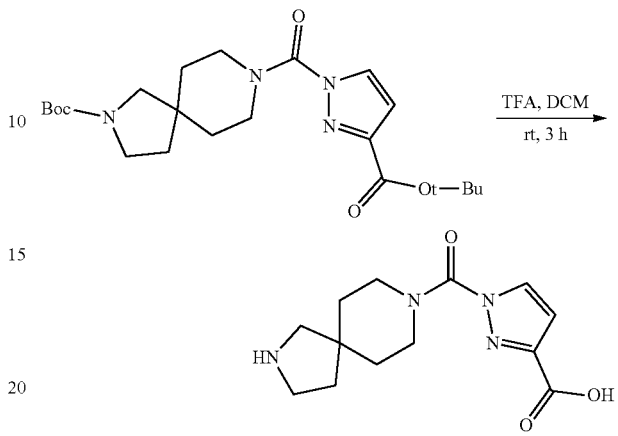

A flask was charged with t-butyl 8-(3-(t-butoxycarbonyl)-1H-pyrazole-1-carbonyl)-2,8-diazaspiro[4.5]decane-2-carboxylate (1740 mg, 4.00 mmol, 1.00 equiv), DCM (15 mL), and TFA (5 mL). The resulting solution was stirred for 3 h at room temperature and concentrated under reduced pressure to provide 1116 mg (quantitative) of 1-(2,8-diazaspiro[4.5]decane-8-carbonyl)-1H-pyrazole-3-carboxylic acid as a yellow oil. LCMS (ESI, m/z): 279 [M+H]+.

Step 5: Preparation of 4-chloro-3-ethoxybenzaldehyde

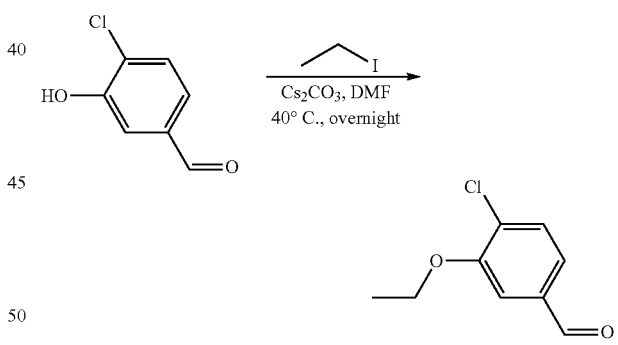

A flask was charged with 4-chloro-3-hydroxybenzaldehyde (785 mg, 5.01 mmol, 1.00 equiv), DMF (10 mL), iodoethane (1560 mg, 10.0 mmol, 2.00 equiv), and cesium carbonate (4890 mg, 15.0 mmol, 3.00 equiv). The resulting solution was stirred overnight at 40° C. and quenched with water (10 mL). The resulting solution was extracted with EtOAc (3×20 mL) and the organic layers were combined, washed with brine (2×20 mL), dried over anhydrous sodium sulfate, filtered and concentrated under reduced pressure. The residue was chromatographed on a silica gel column to provide 710 mg (77% yield) of 4-chloro-3-ethoxybenzaldehyde as a yellow oil. $^1$H NMR (300 MHz, Chloroform-d) δ 9.94 (s, 1H), 7.55 (d, J=7.8 Hz, 1H), 7.42 (s, 1H), 7.39 (d, J=7.8 Hz, 1H), 4.20 (m, 2H), 1.51 (t, J=6.9 Hz, 3H).

Step 6: Preparation of 1-(2-(4-chloro-3-ethoxybenzyl)-2,8-diazaspiro[4.5]decane-8-carbonyl)-1H-pyrazole-3-carboxylic Acid

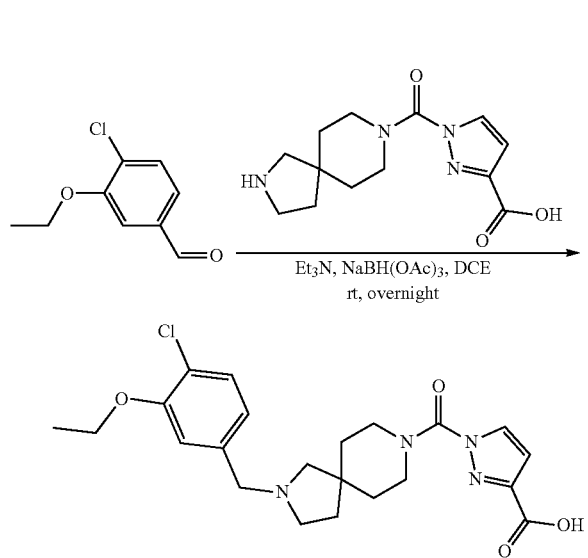

A flask was charged with 4-chloro-3-ethoxybenzaldehyde (92.5 mg, 0.501 mmol, 1.00 equiv) in DCE (10 mL), 1-(2,8-diazaspiro[4.5]decane-8-carbonyl)-1H-pyrazole-3-carboxylic acid (278 mg, 1.00 mmol, 2.00 equiv), and triethylamine (152 mg, 1.50 mmol, 3.00 equiv). The resulting solution was stirred for 2 h at room temperature. Sodium triacetoxyborohydride (318 mg, 1.50 mmol, 3.00 equiv) was added. The resulting solution was stirred overnight at room temperature and quenched with saturated NaHCO$_3$ solution (10 mL), as described in Example 2, Step 3. The crude product (500 mg) was purified by preparative HPLC to provide 92.9 mg (41% yield) of 1-(2-(4-chloro-3-ethoxybenzyl)-2,8-diazaspiro[4.5]decane-8-carbonyl)-1H-pyrazole-3-carboxylic acid as a white solid. $^1$H NMR (300 MHz, MeOH-4) δ 8.06 (d, J=2.7 Hz, 1H), 7.43 (d, J=8.1 Hz, 1H), 7.29 (d, J=2.1 Hz, 1H), 7.08-7.05 (m, 1H), 6.76 (d, J=2.7 Hz, 1H), 4.34 (s, 2H), 4.14-4.07 (m, 2H), 3.86-3.69 (m, 4H), 3.44 (t, J=6.9 Hz, 2H), 3.28 (s, 2H), 2.07 (t, J=4.2 Hz, 2H), 1.89-1.77 (m, 4H), 1.41 (t, J=6.9 Hz, 3H). LCMS (ESI, m/z): 447 [M+H]$^+$.

Example 22: 1-(1-(((6-(Trifluoromethyl)benzo[b]thiophen-2-yl)methyl)-1,8-diazaspiro[4.5]decane-8-carbonyl)-1H-pyrazole-3-carboxamide

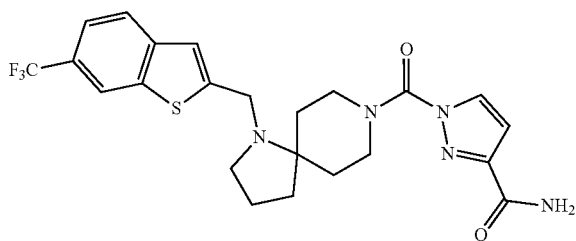 [SMILES: NC(=O)c1ccn(C(=O)N2CCC3(CCCN3Cc3cc4ccc(C(F)(F)F)cc4s3)CC2)n1]

Step 1: Preparation of 4-nitrophenyl 3-carbamoyl-1H-pyrazole-1-carboxylate

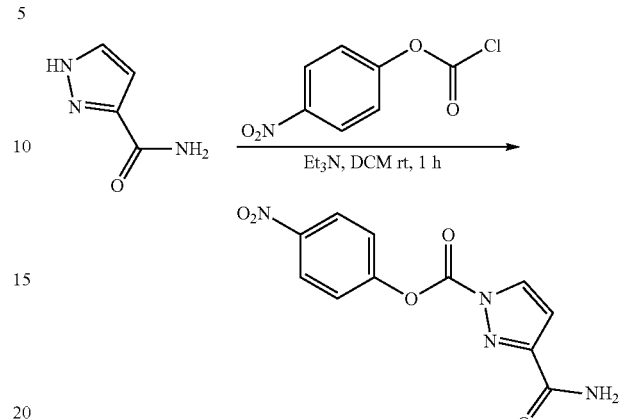

A flask was charged with 1H-pyrazole-3-carboxamide (73.4 mg, 0.660 mmol, 1.00 equiv), 4-nitrophenyl chloroformate (159 mg, 0.790 mmol, 1.20 equiv), DCM (10 mL), and triethylamine (200 mg, 1.98 mmol, 3.00 equiv), as described in Example 4, Step 3, to provide 182 mg (crude) of 4-nitrophenyl 3-carbamoyl-1H-pyrazole-1-carboxylate as a yellow oil. LCMS (ESI, m/z): 277 [M+H]$^+$.

Step 2: Preparation of t-butyl 1-(6-(trifluoromethyl)benzo[b]thiophene-2-carbonyl)-1,8-diazaspiro[4.5]decane-8-carboxylate

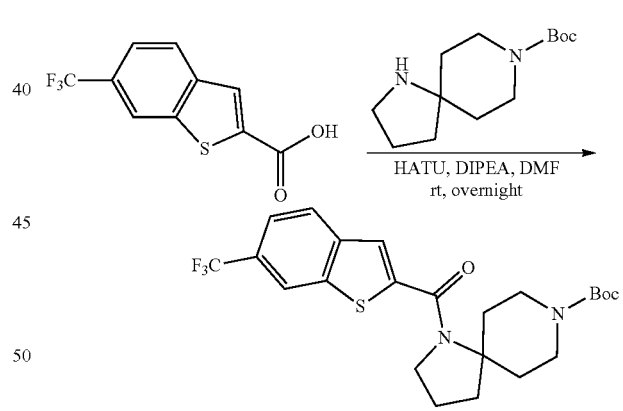

A flask was charged with 6-(trifluoromethyl)-1-benzothiophene-2-carboxylic acid (0.492 g, 2.00 mmol, 1.00 equiv), t-butyl 1,8-diazaspiro[4.5]decane-8-carboxylate (0.720 g, 3.00 mmol, 1.50 equiv), DMF (10 mL), N,N,N',N'-tetramethyl-O-(7-azabenzotriazol-1-yl)uronium (1.52 g, 4.00 mmol, 2.00 equiv), and DIPEA (0.774 g, 6.00 mmol, 3.00 equiv). The resulting solution was stirred overnight at room temperature and quenched with water (10 mL), as described in Example 14, Step 7. The residue was chromatographed on a silica gel column to provide 800 mg (85% yield) of t-butyl 1-(6-(trifluoromethyl)benzo[b]thiophene-2-carbonyl)-1,8-diazaspiro[4.5]decane-8-carboxylate as a yellow solid. LCMS (ESI, m/z): 469 [M+H]$^+$.

Step 3: Preparation of t-butyl 1-46-(trifluoromethyl) benzo[b]thiophen-2-yl)methyl)-1,8-diazaspiro[4.5] decane-8-carboxylate

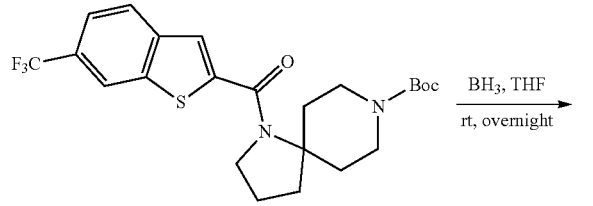

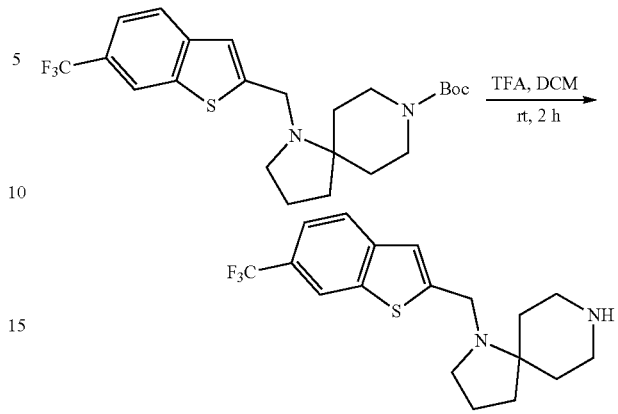

Step 4: Preparation of 1-((6-(trifluoromethyl)benzo [b]thiophen-2-yl)methyl)-1,8-diazaspiro[4.5]decane A flask was charged with t-butyl 1-((6-(trifluoromethyl) benzo[b]thiophen-2-yl)methyl)-1,8-diazaspiro[4.5]decane-8-carboxylate (200 mg, 0.440 mmol, 1.00 equiv), DCM (10 mL), and TFA (2 mL). The resulting solution was stirred for 2 h at room temperature and concentrated under reduced pressure to provide 156 mg (quantitative) of 1-((6-(trifluoromethyl)benzo[b]thiophen-2-yl)methyl)-1,8-diazaspiro [4.5]decane as a yellow oil. LCMS (ESI, m/z): 355 [M+H]+.

A flask was charged with t-butyl 1-(6-(trifluoromethyl) benzo[b]thiophene-2-carbonyl)-1,8-diazaspiro[4.5]decane-8-carboxylate (300 mg, 0.640 mmol, 1.00 equiv), THF (3 mL), and borane (1 M in THF solution, 2.56 ml, 2.56 mmol, 4.00 equiv). The resulting solution was stirred overnight at room temperature. MeOH (20 mL) was added and the resulting mixture was stirred at 60° C. for 1 h and quenched with water (20 mL). The resulting solution was extracted with DCM (3×30 mL) and the organic layers were combined, washed with brine (1×30 mL), dried over anhydrous sodium sulfate, filtered and concentrated under reduced pressure. The residue was chromatographed on a silica gel column to provide 200 mg (69% yield) of t-butyl 1-((6-(trifluoromethyl)benzo[b]thiophen-2-yl)methyl)-1,8-diaz-aspiro[4.5]decane-8-carboxylate as a colorless oil. LCMS (ESI, m/z): 455 [M+H]+.

Step 5: Preparation of 1-(1-((6-(trifluoromethyl) benzo[b]thiophen-2-yl)methyl)-1,8-diazaspiro[4.5] decane-8-carbonyl)-1H-pyrazole-3-carboxamide

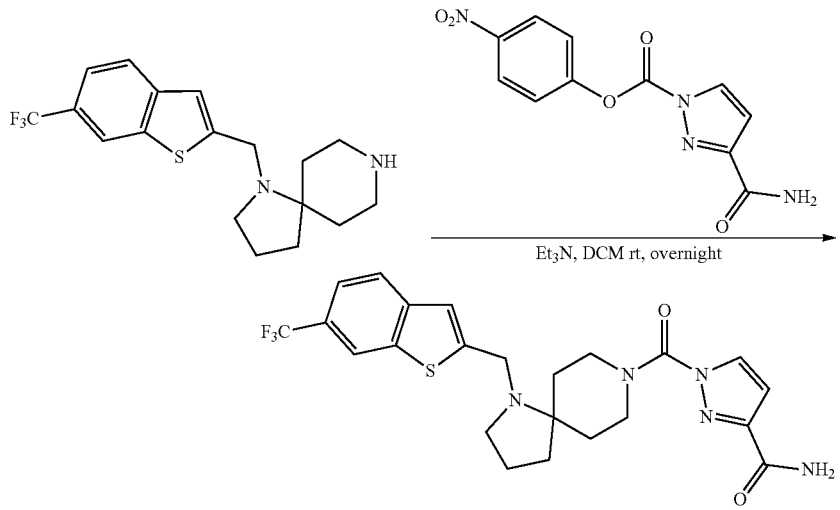

A flask was charged with 1-((6-(trifluoromethyl)benzo[b] thiophen-2-yl)methyl)-1,8-diazaspiro[4.5]decane (156 mg, 0.440 mmol, 1.00 equiv), 4-nitrophenyl 3-carbamoyl-1H-pyrazole-1-carboxylate (182 mg, 0.660 mmol, 1.50 equiv), DCM (10 mL), and triethylamine (133 mg, 1.32 mmol, 3.00 equiv). The resulting solution was stirred overnight at room temperature and then quenched with water (20 mL), as described in Example 4, Step 3. The crude product (200 mg) was purified by preparative HPLC to provide 80.6 mg (37% yield) of 1-[(1-[[6-(trifluoromethyl)-1-benzothiophen-2-yl] methyl]-1,8-diazaspiro[4.5]decan-8-yl)carbonyl]-1H-pyrazole-3-carboxamide as a white solid. $^1$H NMR (300 MHz, Chloroform-d) δ 8.09 (d, J=2.7 Hz, 1H), 8.04 (s, 1H), 7.74

(d, J=8.4 Hz, 1H), 7.53 (d, J=8.7 Hz, 1H), 7.20 (s, 1H), 6.91 (d, J=2.7 Hz, 1H), 6.64 (br, 1H), 5.47 (br, 1H), 4.60-4.47 (m, 2H), 3.96 (s, 2H), 3.15 (t, J=12.9 Hz, 2H), 2.85 (t, J=6.3 Hz, 2H), 2.01-1.78 (m, 6H), 1.62-1.57 (m, 2H). LCMS (ESI, m/z): 492 [M+H]$^+$.

Example 23: 1-(trans-5-(3-(Pyrimidin-5-yl)phenoxy) octahydrocyclopenta[c]pyrrole-2-carbonyl)-1H-pyrazole-3-carboxylic Acid

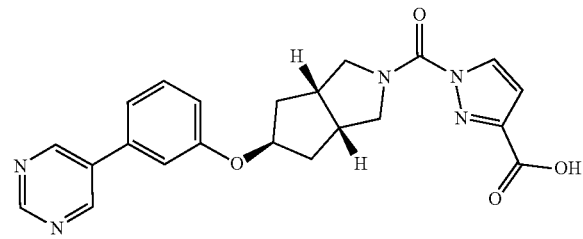 [SMILES: O=C(O)c1ccn(C(=O)N2C[C@H]3C[C@H](Oc4cccc(-c5cncnc5)c4)C[C@H]3C2)n1]

Step 1: Preparation of di-t-butyl 1H-pyrazole-1,3-dicarboxylate

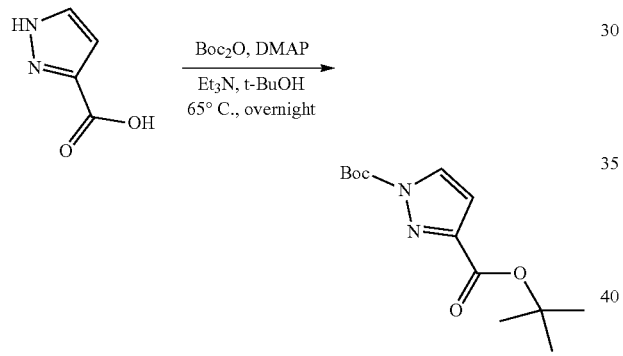

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL). The resulting solution was stirred overnight at 65° C. and quenched by water (200 mL), as described in Example 1, Step 1, to provide 20.0 g (crude) of 1,3-di-t-butyl-1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

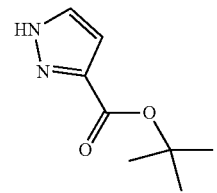

A flask was charged with 1,3-di-t-butyl-1H-pyrazole-1,3-dicarboxylate (20.0 g, 74.6 mmol, 1.00 equiv), MeOH (80 mL), sodium hydroxide (10.0 g, 250 mmol, 3.35 equiv) and water (40 mL). The resulting solution was stirred overnight at room temperature and quenched with water (40 mL), as described in Example 1, Step 2, to provide 6.70 g (crude) of t-butyl-1H-pyrazole-3-carboxylate as a yellow solid. LCMS (ESI, m/z): 169 [M+H]$^+$.

Step 3: Preparation of 3-(t-butyl) 1-(4-nitrophenyl) 1H-pyrazole-1,3-dicarboxylate A flask was charged with t-butyl 1H-pyrazole-3-carboxylate (1.68 g, 9.99 mmol, 1.00 equiv), DCM (20 mL) and triethylamine (3.03 g, 29.9 mmol, 3.00 equiv). 4-Nitrophenyl chloroformate (2.42 g, 12.0 mmol, 1.20 equiv) was added at 0° C. as described in Example 4, Step 3, to provide 3.33 g (crude) of 3-t-butyl 1-(4-nitrophenyl) 1H-pyrazole-1,3-dicarboxylate as a yellow solid.

Step 4: Preparation of t-butyl (3aR,5r,6aS)-5-hydroxyhexahydrocyclopenta[c]pyrrole-2(1H)-carboxylate A flask was charged with t-butyl (3aR,6aS)-5-oxohexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure. The resulting mixture was diluted with water (40 mL), extracted with EtOAc (3×50 mL) and the organic layers were combined, washed with water (3×20 mL), dried over anhydrous sodium sulfate, filtered and concentrated under reduced pressure as described in Example 15, Step 4, to provide 3.01 g (crude) of t-butyl (3aR,5r,6aS)-5-hydroxyhexahydrocyclopenta[c]pyrrole-2 (1H)-carboxylate as a white solid. LCMS (ESI, m/z): 228 [M+H]+.

Step 5: Preparation of t-butyl (3aR,5r,6aS)-5-((methylsulfonyl)oxy)hexahydrocyclopenta[c]pyrrole-2(1H)-carboxylate

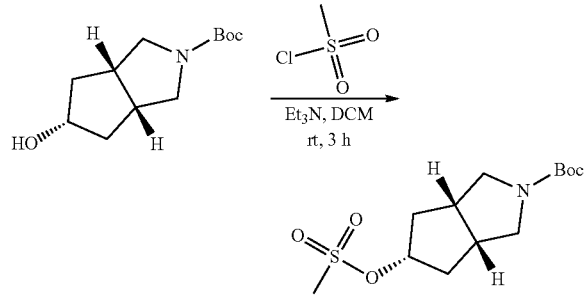

A flask was charged with t-butyl (3aR,5r,6aS)-5-hydroxyhexahydrocyclopenta[c]pyrrole-2(1H)-carboxylate (1.00 g, 4.40 mmol, 1.00 equiv), DCM (20 mL) and triethylamine (1.34 g, 13.2 mmol, 3.00 equiv). Methanesulfonyl chloride (0.608 g, 5.28 mmol, 1.20 equiv) was added dropwise at 0° C. as described in Example 11, Step 3 to provide 1.34 g (crude) of t-butyl (3aR,5r,6aS)-5-((methylsulfonyl)oxy)hexahydrocyclopenta[c]pyrrole-2(1H)-carboxylate as a yellow oil. LCMS (ESI, m/z): 306 [M+H]+.

Step 6: Preparation of 3-(pyrimidin-5-yl)phenol

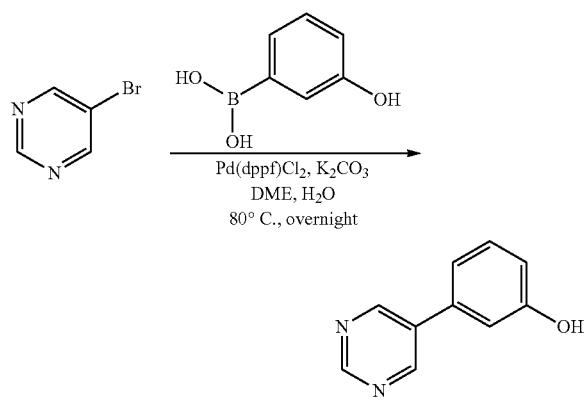

A vial was charged with 5-bromopyrimidine (1.58 g, 10.0 mmol, 1.00 equiv), (3-hydroxyphenyl)boronic acid (2.07 g, 15.0 mmol, 1.50 equiv), 1,1'-bis(diphenylphosphino)ferrocenepalladiumdichloride (0.731 g, 1.00 mmol, 0.10 equiv), potassium carbonate (4.14 g, 30.0 mmol, 3.00 equiv), eth-ylene glycol dimethyl ether (16 mL) and water (4 mL). The resulting solution was stirred overnight at 80° C. and quenched with water (20 mL). The mixture was extracted with EtOAc (3×20 mL) and the organic layers were combined, washed with water (3×20 mL), dried over anhydrous sodium sulfate, filtered and concentrated under reduced pressure. The residue was chromatographed on a silica gel column (1/1) to provide 1.27 g (74% yield) of 3-(pyrimidin-5-yl)phenol as a yellow solid. LCMS (ESI, m/z): 173 [M+H]+.

Step 7: Preparation of t-butyl (3aR,5s,6aS)-5-(3-(pyrimidin-5-yl)phenoxy)hexahydrocyclopenta[c]pyrrole-2(1H)-carboxylate

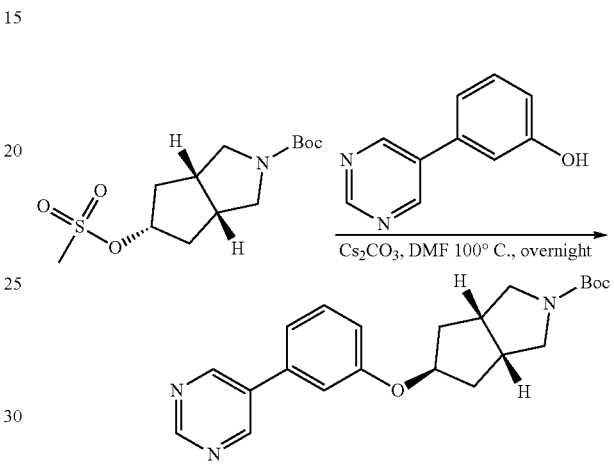

A vial was charged with 3-(pyrimidin-5-yl)phenol (206 mg, 1.20 mmol, 1.00 equiv), t-butyl (3aR,5r,6aS)-5-(methanesulfonyloxy)-octahydrocyclopenta[c]pyrrole-2-carboxylate (366 mg, 1.20 mmol, 1.00 equiv), cesium carbonate (782 mg, 2.40 mmol, 2.00 equiv) and DMF (15 mL). The resulting solution was stirred overnight at 100° C. and quenched by water (10 mL), as described in Example 13, Step 4. The residue was chromatographed on a silica gel column to provide 320 mg (70% yield) of t-butyl (3aR,5s,6aS)-5-(3-(pyrimidin-5-yl)phenoxy)hexahydrocyclopenta[c]pyrrole-2(1H)-carboxylate as a yellow oil. LCMS (ESI, m/z): 382 [M+H]+.

Step 8: Preparation of (3aR,5s,6aS)-5-(3-(pyrimidin-5-yl)phenoxy)octahydrocyclopenta[c]pyrrole

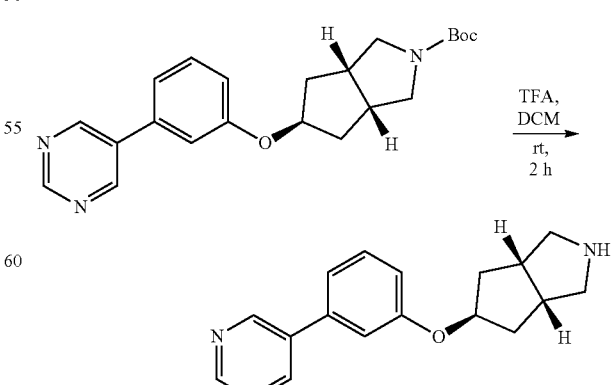

A vial was charged with t-butyl (3aR,5s,6aS)-5-(3-(pyrimidin-5-yl)phenoxy)hexahydrocyclopenta[c]pyrrole-2(1H)-carboxylate (200 mg, 0.520 mmol, 1.00 equiv), TFA (2 mL) and DCM (5 mL). The resulting solution was stirred for 2 h at room temperature and concentrated under reduced pressure, as described in Example 1, Step 5, to provide 147 mg (quantitative) of (3aR,5s,6aS)-5-(3-(pyrimidin-5-yl)phenoxy)octahydrocyclopenta[c]pyrrole as a yellow oil. LCMS (ESI, m/z): 282 [M+H]⁺.

Step 9: Preparation of t-butyl 1-(trans-5-(3-(pyrimidin-5-yl)phenoxy)octahydrocyclopenta[c]pyrrole-2-carbonyl)-1H-pyrazole-3-carboxylate

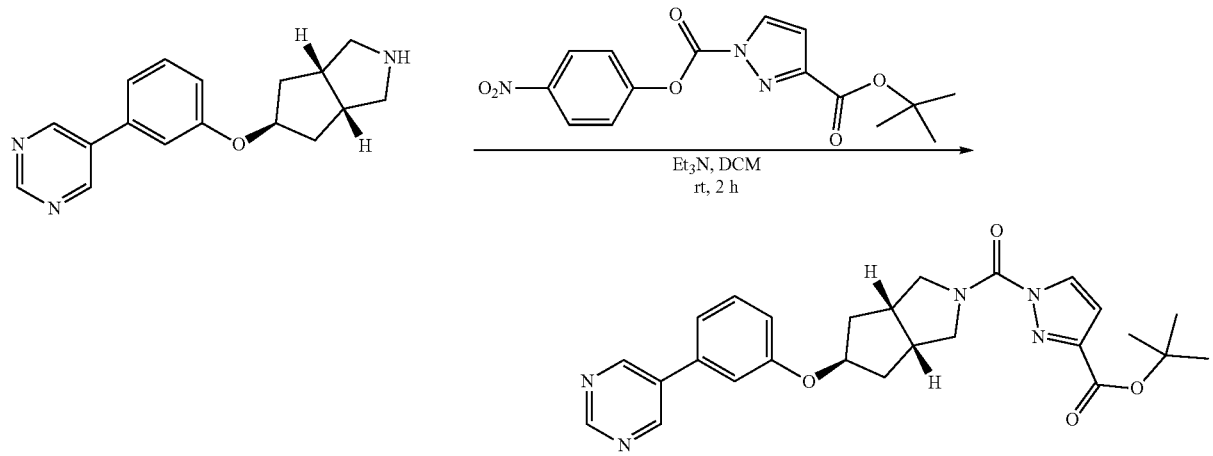

A vial was charged with (3aR,5s,6aS)-5-(3-(pyrimidin-5-yl)phenoxy)octahydrocyclopenta[c]pyrrole (147 mg, 0.520 mmol, 1.00 equiv), triethylamine (263 mg, 2.60 mmol, 5.00 equiv), 3-t-butyl 1-(4-nitrophenyl) 1H-pyrazole-1,3-dicarboxylate (260 mg, 0.780 mmol, 1.50 equiv) and DCM (15 mL). The resulting solution was stirred for 2 h at room temperature as described in Example 4, Step 3. The residue was chromatographed on a silica gel column to provide 166 mg (67% yield) of t-butyl 1-(trans-5-(3-(pyrimidin-5-yl)phenoxy)octahydrocyclopenta[c]pyrrole-2-carbonyl)-1H-pyrazole-3-carboxylate as a white solid. LCMS (ESI, m/z): 476 [M+H]⁺.

Step 10: Preparation of 1-(trans-5-(3-(pyrimidin-5-yl)phenoxy)octahydrocyclopenta[c]pyrrole-2-carbonyl)-1H-pyrazole-3-carboxylic acid

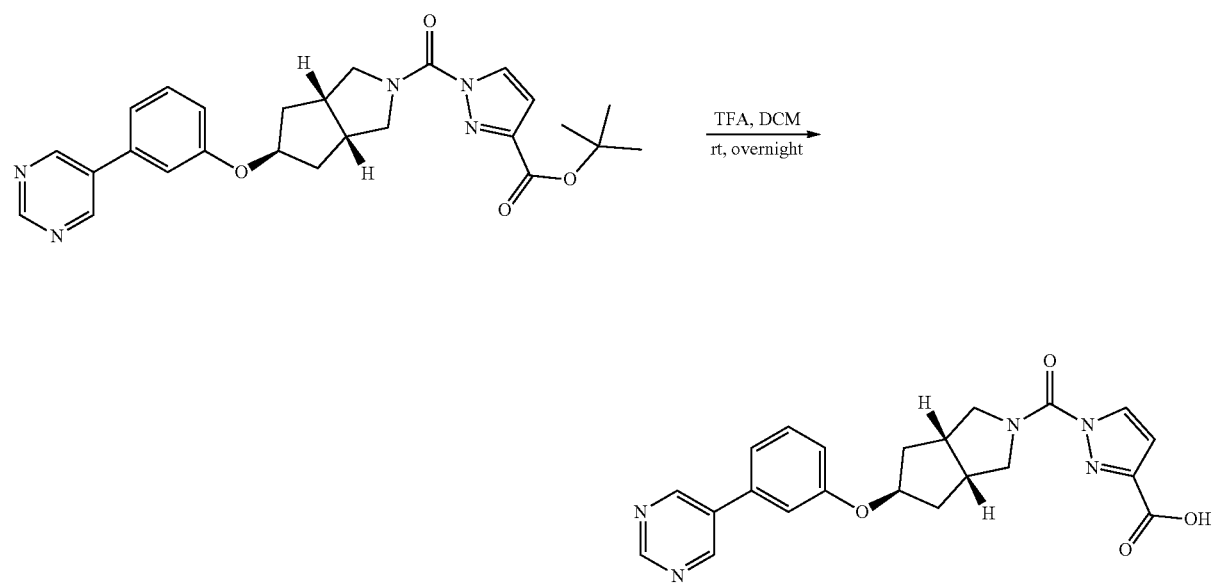

A vial was charged with t-butyl 1-((3aR,5s,6aS)-5-(3-(pyrimidin-5-yl)phenoxy)octahydrocyclopenta[c]pyrrole-2-carbonyl)-1H-pyrazole-3-carboxylate (166 mg, 0.350 mmol, 1.00 equiv), TFA (2 mL) and DCM (5 mL). The resulting solution was stirred overnight at room temperature and concentrated under reduced pressure as described in Example 1, Step 5. The crude product was purified by preparative HPLC to provide 82.1 mg (56% yield) of 1-(trans-5-(3-(pyrimidin-5-yl)phenoxy)octahydrocyclopenta[c]pyrrole-2-carbonyl)-1H-pyrazole-3-carboxylic acid as a white solid. $^1$H NMR: (300 MHz, MeOH-d$_4$) δ 9.14 (s, 1H), 9.05 (s, 2H), 8.17 (d, J=9.3 Hz, 1H), 7.43 (t, J=8.0 Hz, 1H), 7.27-7.18 (m, 2H), 7.08-6.98 (m, 1H), 6.80 (d, J=2.7 Hz, 1H), 5.17-5.08 (m, 1H), 4.35-3.51 (m, 4H), 3.08-2.88 (m, 2H), 2.28-2.15 (m, 2H), 2.08-1.92 (m, 2H). LCMS (ESI, m/z): 420 [M+H]$^+$.

Example 24: 1-((2S,4S)-2-Methyl-4-(methyl(3-(trifluoromethyl)benzyl)amino)piperidine-1-carbonyl)-1H-pyrazole-3-carboxamide

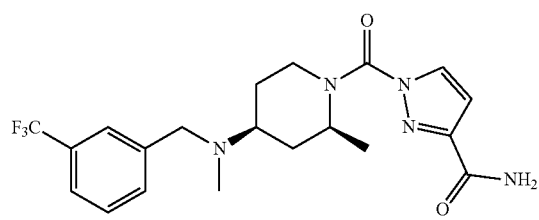 [SMILES: C[C@H]1C[C@@H](N(C)Cc2cccc(C(F)(F)F)c2)CCN1C(=O)n1ccc(C(N)=O)n1]

Step 1: Preparation of t-butyl (2S,4S)-4-hydroxy-2-methylpiperidine-1-carboxylate and t-butyl (2S,4R)-4-hydroxy-2-methylpiperidine-1-carboxylate

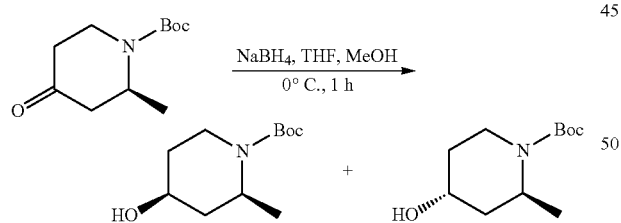

A flask was charged with t-butyl (2S)-2-methyl-4-oxopiperidine-1-carboxylate (10.0 g, 46.9 mmol, 1.00 equiv), and THF (36 mL). Sodium borohydride (1.07 g, 28.2 mmol, 0.60 equiv) and MeOH (12 mL) were added dropwise at 0° C. The resulting solution was stirred for 1 h at 0° C. and quenched with water (50 mL), as described in Example 15, Step 4. The crude product (11.0 g) was purified by preparative HPLC to provide 4.90 g (49% yield) of t-butyl (2S,4S)-4-hydroxy-2-methylpiperidine-1-carboxylate as a yellow oil (LCMS (ESI, m/z): 216 [M+H]$^+$) and 4.10 g (41% yield) of t-butyl (2S,4R)-4-hydroxy-2-methylpiperidine-1-carboxylate as a white solid LCMS (ESI, m/z): 216 [M+H]$^+$.

Step 2: Preparation of t-butyl (2S,4R)-2-methyl-4-((methylsulfonyl)oxy)piperidine-1-carboxylate

A flask was charged with t-butyl (2S,4R)-4-hydroxy-2-methylpiperidine-1-carboxylate (600 mg, 2.79 mmol, 1.00 equiv), DCM (15 mL), and triethylamine (845 mg, 8.35 mmol, 3.00 equiv). Methanesulfonyl chloride (417 mg, 3.63 mmol, 1.30 equiv) was added dropwise at 0° C. as described in Example 11, Step 3, to provide 817 mg (crude) of t-butyl (2S,4R)-2-methyl-4-((methylsulfonyl)oxy)piperidine-1-carboxylate as a yellow oil. LCMS (ESI, m/z): 294 [M+H]$^+$.

Step 3: Preparation of t-butyl (2S,4S)-2-methyl-4-(methylamino)piperidine-1-carboxylate

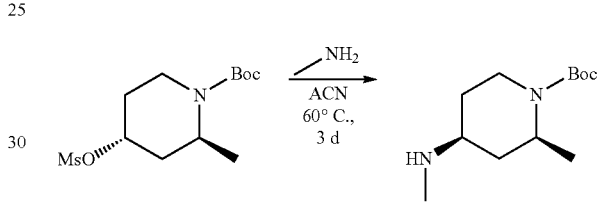

A flask was charged with t-butyl (2S,4R)-4-(methanesulfonyloxy)-2-methylpiperidine-1-carboxylate (817 mg, 2.78 mmol, 1.00 equiv), ACN (10 mL), and methylamine (2.2 mL, 27.8 mmol, 10.0 equiv, 40% in water). The resulting solution was stirred for 3 days at 60° C. and concentrated under reduced pressure. The residue was chromatographed on a silica gel column to provide 420 mg (66% yield) of t-butyl (2S,4S)-2-methyl-4-(methylamino)piperidine-1-carboxylate as a yellow oil. LCMS (ESI, m/z): 229 [M+H]$^+$.

Step 4: Preparation of t-butyl (2S,4S)-2-methyl-4-(methyl(3-(trifluoromethyl)benzyl)amino)piperidine-1-carboxylate

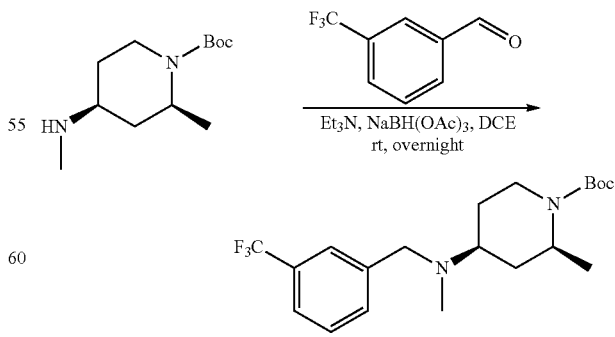

A flask was charged with 3-(trifluoromethyl)benzaldehyde (264 mg, 1.52 mmol, 1.00 equiv), t-butyl (2S,4S)-2-methyl-4-(methylamino)piperidine-1-carboxylate (380 mg, 1.66 mmol, 1.10 equiv), DCE (10 mL), and triethylamine (460 mg, 4.55 mmol, 3.00 equiv). The resulting solution was stirred for 1 h at room temperature. Sodium triacetoxyborohydride (967 mg, 4.56 mmol, 3.00 equiv) was added as described in Example 2, Step 3, to provide the crude product. The residue was chromatographed on a silica gel column to provide 400 mg (68% yield) of t-butyl (2S,4S)-2-methyl-4-(methyl(3-(trifluoromethyl)benzyl)amino)piperidine-1-carboxylate as a yellow oil. LCMS (ESI, m/z): 387 [M+H]⁺.

Step 5: Preparation of (2S,4S)—N,2-dimethyl-N-(3-(trifluoromethyl)benzyl)piperidin-4-amine

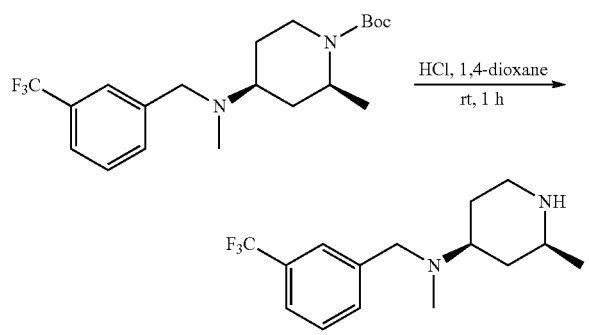

A flask was charged with t-butyl (2S,4S)-2-methyl-4-(methyl(3-(trifluoromethyl)benzyl)amino)piperidine-1-carboxylate (400 mg, 1.04 mmol, 1.00 equiv), 1,4-dioxane (10 mL), and concentrated hydrochloric acid (2.5 mL). The resulting solution was stirred for 1 h at room temperature and concentrated under reduced pressure to yield 296 mg (quantitative) of (2S,4S)—N,2-dimethyl-N-(3-(trifluoromethyl)benzyl)piperidin-4-amine as a yellow oil. LCMS (ESI, m/z): 287 [M+H]⁺.

Step 6: Preparation of (2S,4S)-2-methyl-4-(methyl(3-(trifluoromethyl)benzyl)amino)piperidine-1-carbonyl chloride

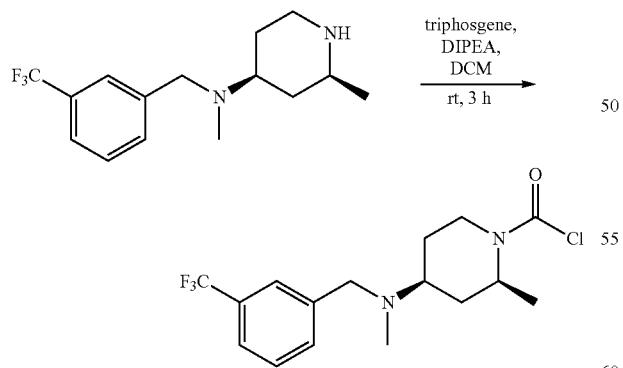

A flask was charged with (2S,4S)—N,2-dimethyl-N-(3-(trifluoromethyl)benzyl)piperidin-4-amine (296 mg, 1.03 mmol, 1.00 equiv), DCM (10 mL), and triphosgene (154 mg, 0.520 mmol, 0.50 equiv) under nitrogen. DIPEA (402 mg, 3.12 mmol, 3.00 equiv) was added dropwise at 0° C. The resulting solution was stirred for 3 h at room temperature and quenched with water (10 mL), as described in Example 1, Step 3 to provide 362 mg (crude) of (2S,4S)-2-methyl-4-(methyl(3-(trifluoromethyl)benzyl)amino)piperidine-1-carbonyl chloride as a yellow oil. LCMS (ESI, m/z): 349 [M+H]⁺.

Step 7: Preparation of 1-((2S,4S)-2-methyl-4-(methyl(3-(trifluoromethyl)benzyl)amino)piperidine-1-carbonyl)-1H-pyrazole-3-carboxamide

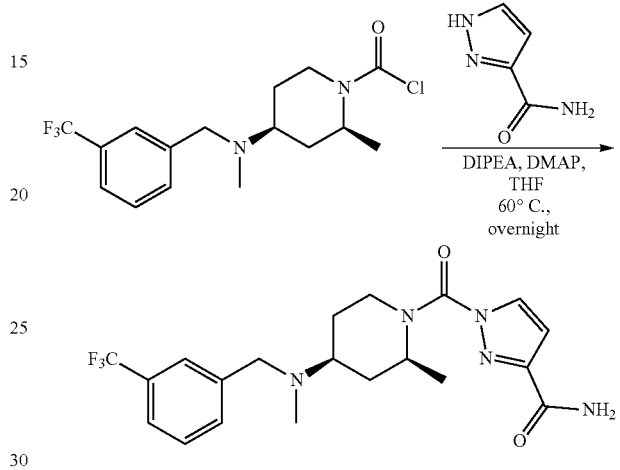

A flask was charged with (2S,4S)-2-methyl-4-(methyl(3-(trifluoromethyl)benzyl)amino)piperidine-1-carbonyl chloride (181 mg, 0.520 mmol, 1.00 equiv), 1H-pyrazole-3-carboxamide (86.6 mg, 0.780 mmol, 1.50 equiv), THF (10 mL), DMAP (12.7 mg, 0.104 mmol, 0.20 equiv), and DIPEA (201 mg, 1.56 mmol, 3.00 equiv). The resulting solution was stirred overnight at 60° C. and quenched with water (10 mL), as described in Example 1, Step 4. The crude product (300 mg) was purified by preparative HPLC to provide 54.6 mg (25% yield) of 1-((2S,4S)-2-methyl-4-(methyl(3-(trifluoromethyl)benzyl)amino)piperidine-1-carbonyl)-1H-pyrazole-3-carboxamide as a white semi-solid. ¹H NMR (300 MHz, Chloroform-d) δ 8.09 (d, J=2.7 Hz, 1H), 7.60 (s, 1H), 7.53-7.51 (m, 2H), 7.46-7.41 (m, 1H), 6.90 (d, J=2.7 Hz, 1H), 6.68 (br, 1H), 5.61 (br, 1H), 4.32-4.21 (m, 1H), 4.14-4.07 (m, 1H), 3.64 (br, 2H), 3.52-3.42 (m, 1H), 2.82 (br, 1H), 2.20 (s, 3H), 2.07-2.03 (m, 2H), 1.83-1.73 (m, 2H), 1.48 (d, J=6.3 Hz, 3H). LCMS (ESI, m/z): 424 [M+H]⁺.

Example 25: 1-(trans-5-(3-(Oxazol-2-yl)phenoxy)octahydrocyclopenta[c]pyrrole-2-carbonyl)-1H-pyrazole-3-carboxylic Acid

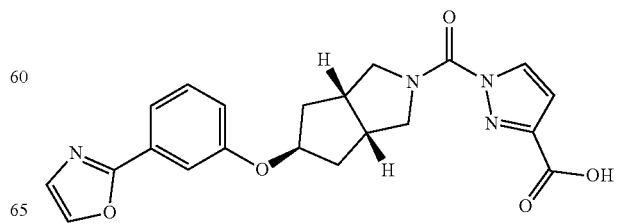

Step 1: Preparation of di-t-butyl 1H-pyrazole-1,3-dicarboxylate

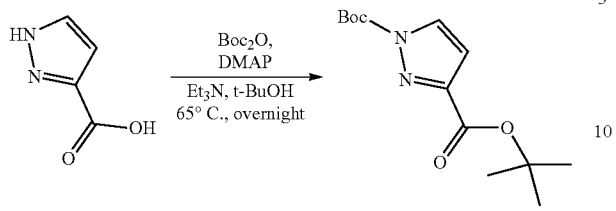

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL). The resulting solution was stirred overnight at 65° C. and quenched by water (200 mL), as described in Example 1, Step 1 to provide 20.0 g (crude) of di-t-butyl 1H-pyrazole-1,3-dicarboxylate as a yellow oil. LCMS (ESI, m/z): 169 [M+H-Boc]+.

Step 2: Preparation of t-butyl 1H-pyrazole-3-carboxylate

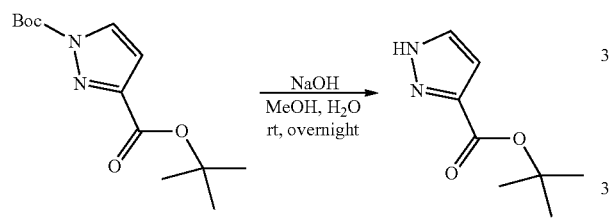

A flask was charged with di-t-butyl 1H-pyrazole-1,3-dicarboxylate (20.0 g, 74.6 mmol, 1.00 equiv), MeOH (80 mL), sodium hydroxide (10.0 g, 250 mmol, 3.35 equiv) and water (40 mL). The resulting solution was stirred overnight at room temperature and quenched by water (40 mL), as described in Example 1, Step 2 to provide 6.70 g (crude) of t-butyl 1H-pyrazole-3-carboxylate as a yellow solid. LCMS (ESI, m/z): 169 [M+H]+.

Step 3: Preparation of 3-(t-butyl) 1-(4-nitrophenyl) 1H-pyrazole-1,3-dicarboxylate

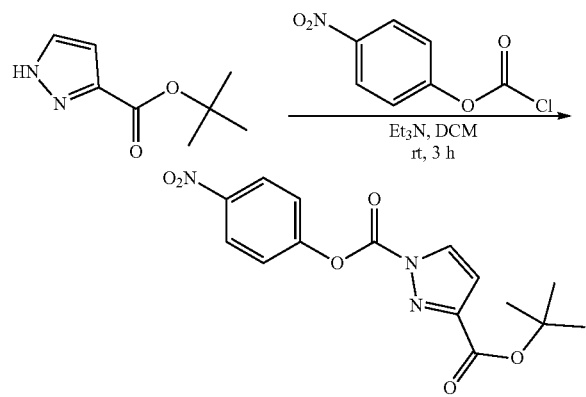

A flask was charged with t-butyl 1H-pyrazole-3-carboxylate (1.68 g, 9.99 mmol, 1.00 equiv), DCM (20 mL) and triethylamine (3.03 g, 29.9 mmol, 3.00 equiv). 4-Nitrophenyl chloroformate (2.42 g, 12.0 mmol, 1.20 equiv) was added at 0° C. The resulting solution was stirred for 3 h at room temperature and concentrated under reduced pressure as described in Example 4, Step 3 to provide 3.33 g (crude) of 3-(t-butyl) 1-(4-nitrophenyl) 1H-pyrazole-1,3-dicarboxylate as a yellow solid.

Step 4: Preparation of t-butyl (3aR,5r,6aS)-5-hydroxyhexahydrocyclopenta[c]pyrrole-2(1H)-carboxylate

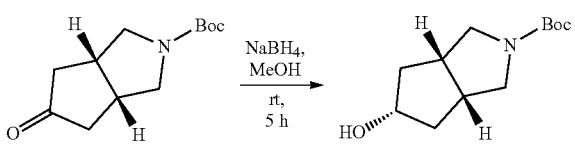 [SMILES: CC(C)(C)OC(=O)N1C[C@H]2CC(=O)C[C@H]2C1 ; CC(C)(C)OC(=O)N1C[C@H]2C[C@@H](O)C[C@H]2C1]

A flask was charged with (3aR,6aS)-t-butyl 5-oxo-hexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure, as described in Example 15, Step 4 to provide 3.01 g (crude) of t-butyl (3aR,5r,6aS)-5-hydroxyhexahydrocyclopenta[c]pyrrole-2(1H)-carboxylate as a white solid. LCMS (ESI, m/z): 228 [M+H]+.

Step 5: Preparation of t-butyl (3aR,5r,6aS)-5-((methylsulfonyl)oxy)hexahydrocyclopenta[c]pyrrole-2(1H)-carboxylate

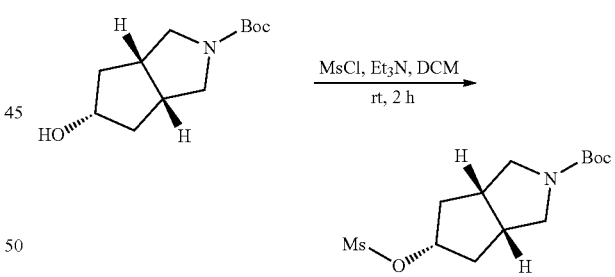

A vial was charged with t-butyl (3aR,5r,6aS)-5-hydroxyhexahydrocyclopenta[c]pyrrole-2(1H)-carboxylate (200 mg, 0.881 mmol, 1.00 equiv), triethylamine (267 mg, 2.64 mmol, 3.00 equiv) and DCM (15 mL). Methanesulfonyl chloride (152 mg, 1.32 mmol, 1.50 equiv) was added dropwise at 0° C. The resulting solution was stirred for 2 h at room temperature. The mixture was quenched by water (10 mL), extracted with DCM (3×20 mL) and the organic layers were combined, washed with brine (10 mL), dried over anhydrous sodium sulfate, filtered and concentrated under reduced pressure as described in Example 11, Step 3 to provide 268 mg (crude) of t-butyl (3aR,5r,6aS)-5-((methylsulfonyl)oxy)hexahydrocyclopenta[c]pyrrole-2(1H)-carboxylate as a yellow oil.

Step 6: Preparation of 3-(oxazol-2-yl)phenol

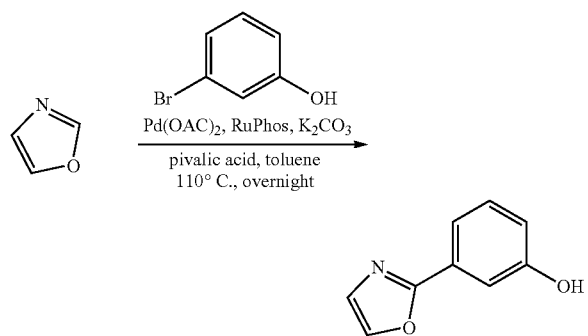

A flask was charged with 1,3-oxazole (1.00 g, 14.5 mmol, 1.00 equiv), 3-bromophenol (1.25 g, 7.25 mmol, 0.50 equiv), potassium carbonate (6.00 g, 43.5 mmol, 3.00 equiv), pivalic acid (0.592 g, 5.80 mmol, 0.40 equiv) and toluene (100 mL). Palladium(II) acetate (0.326 g, 1.45 mmol, 0.10 equiv) and 2-dicyclohexylphosphino-2',6'-di-i-propoxy-1,1'-biphenyl (1.35 g, 2.90 mmol, 0.20 equiv) were added under nitrogen atmosphere. The resulting solution was stirred overnight at 110° C. The mixture was quenched by water (20 mL), extracted with EtOAc (3×50 mL) and the organic layers were combined, washed with brine (3×30 mL), dried over anhydrous sodium sulfate, filtered and concentrated under reduced pressure. The residue was chromatographed on a silica gel column to provide 0.220 g (9% yield) of 3-(oxazol-2-yl)phenol as a yellow oil. LCMS (ESI, m/z): 162 [M+H]⁺.

Step 7: Preparation of t-butyl (3aR,5s,6aS)-5-(3-(oxazol-2-yl)phenoxy)hexahydrocyclopenta[c]pyrrole-2(1H)-carboxylate

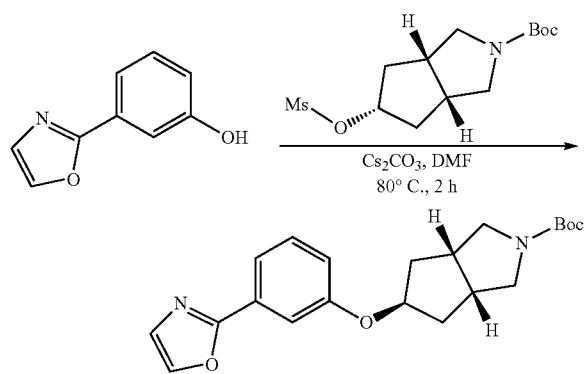

A vial was charged with 3-(oxazol-2-yl)phenol (142 mg, 0.88 mmol, 1.00 equiv), cesium carbonate (860 mg, 2.63 mmol, 3.00 equiv), t-butyl (3aR,5r,6aS)-5-((methylsulfonyl)oxy)hexahydrocyclopenta[c]pyrrole-2(1H)-carboxylate (268 mg, 0.881 mmol, 1.00 equiv) and DMF (15 mL). The resulting solution was stirred for 2 h at 80° C. The mixture was quenched by water (10 mL), extracted with EtOAc (3×20 mL) and the organic layers were combined, washed with brine (2×20 mL), dried over anhydrous sodium sulfate, filtered and concentrated under reduced pressure, as described in Example 13, Step 4. The residue was chromatographed on a silica gel column to provide 105 mg (32% yield) of t-butyl (3aR,5s,6aS)-5-(3-(oxazol-2-yl)phenoxy)hexahydrocyclopenta[c]pyrrole-2(1H)-carboxylate as a yellow oil. LCMS (ESI, m/z): 371 [M+H]⁺.

Step 8: Preparation of 2-(3-(((3aR,5s,6aS)-octahydrocyclopenta[c]pyrrol-5-yl)oxy)phenyl)oxazole

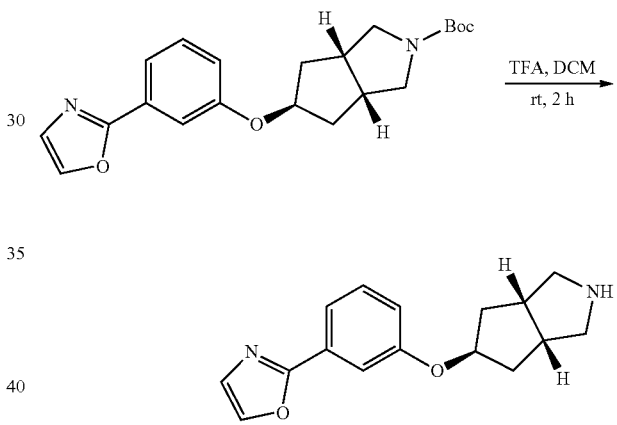

A vial was charged with t-butyl (3aR,5s,6aS)-5-(3-(oxazol-2-yl)phenoxy)hexahydrocyclopenta[c]pyrrole-2(1H)-carboxylate (105 mg, 0.284 mmol, 1.00 equiv), TFA (2 mL) and DCM (10 mL), as described in Example 1, Step 5 to provide 76.6 mg (quantitative) of 2-(3-(((3aR,5s,6aS)-octahydrocyclopenta[c]pyrrol-5-yl)oxy)phenyl)oxazole as a yellow oil. LCMS (ESI, m/z): 271 [M+H]⁺.

Step 9: Preparation of t-butyl 1-((3aR,5s,6aS)-5-(3-(oxazol-2-yl)phenoxy)octahydrocyclopenta[c]pyrrole-2-carbonyl)-1H-pyrazole-3-carboxylate

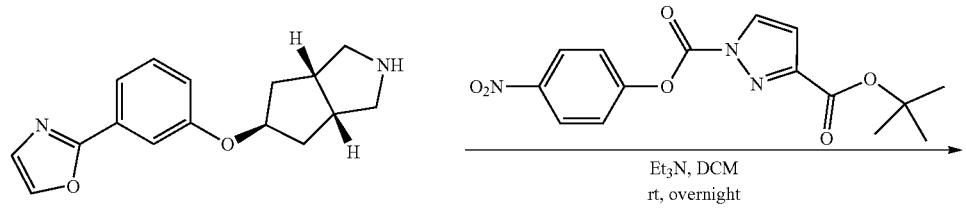

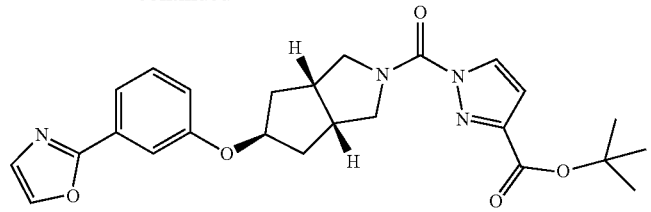

A vial was charged with 2-(3-(((3aR,5s,6aS)-octahydro-cyclopenta[c]pyrrol-5-yl)oxy)phenyl)oxazole (76.6 mg, 0.284 mmol, 1.00 equiv), triethylamine (115 mg, 1.14 mmol, 4.00 equiv), 3-(t-butyl) 1-(4-nitrophenyl) 1H-pyrazole-1,3-dicarboxylate (142 mg, 0.426 mmol, 1.50 equiv) and DCM (15 mL). The resulting solution was stirred overnight at room temperature. The mixture was quenched by water (10 mL), extracted with DCM (3×20 mL) and the organic layers were combined, washed with brine (10 mL), dried over anhydrous sodium sulfate, filtered and concentrated under reduced pressure, as described in Example 4, Step 3. The residue was chromatographed on a silica gel column to provide 108 mg (82% yield) of t-butyl 1-((3aR,5s,6aS)-5-(3-(oxazol-2-yl)phenoxy)octahydrocyclopenta[c]pyrrole-2-carbonyl)-1H-pyrazole-3-carboxylate as a yellow oil. LCMS (ESI, m/z): 465 [M+H]⁺.

Step 10: Preparation of 1-(trans-5-(3-(oxazol-2-yl)phenoxy)octahydrocyclopenta[c]pyrrole-2-carbonyl)-1H-pyrazole-3-carboxylic acid

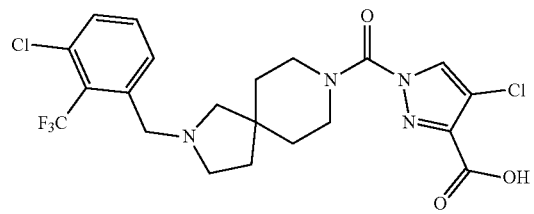 [SMILES: O=C(O)c1nn(C(=O)N2CCC3(CCN(Cc4cccc(Cl)c4C(F)(F)F)C3)CC2)cc1Cl]

A vial was charged with t-butyl 1-((3aR,5s,6aS)-5-(3-(oxazol-2-yl)phenoxy)octahydrocyclopenta[c]pyrrole-2-carbonyl)-1H-pyrazole-3-carboxylate (108 mg, 0.232 mmol, 1.00 equiv), TFA (2 mL) and DCM (10 mL). The resulting solution was stirred for 2 h at room temperature and concentrated under reduced pressure as described in Example 1, Step 5. The crude product was purified by preparative HPLC to provide 71.0 mg (75% yield) of 1-(trans-5-(3-(oxazol-2-yl)phenoxy)octahydrocyclopenta[c]pyrrole-2-carbonyl)-1H-pyrazole-3-carboxylic acid as a white solid. $^1$H NMR: (300 MHz, MeOH-d₄) δ 8.17 (d, J=2.7 Hz, 1H), 8.02-7.95 (m, 1H), 7.67-7.56 (m, 1H), 7.56-7.49 (m, 1H), 7.45-7.37 (m, 1H), 7.31-7.27 (m, 1H), 7.10-6.99 (m, 1H), 6.76 (d, J=2.7 Hz, 1H), 5.14-5.05 (m, 1H), 4.30-3.82 (br, 3H), 3.82-3.57 (br, 1H), 3.11-2.84 (br, 2H), 2.30-2.11 (m, 2H), 2.11-1.89 (m, 2H). LCMS (ESI, m/z): 409 [M+H]⁺.

Example 26: 4-Chloro-1-(2-(3-chloro-2-(trifluoromethyl)benzyl)-2,8-diazaspiro[4.5]decane-8-carbonyl)-1H-pyrazole-3-carboxylic Acid

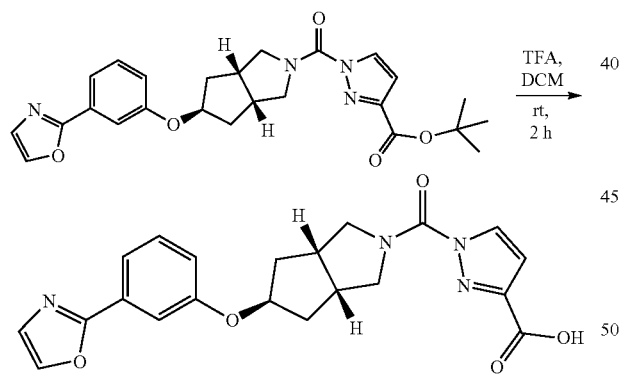

Step 1: Preparation of 3-chloro-2-(trifluoromethyl)benzaldehyde

A flask was charged with 1-bromo-3-chloro-2-(trifluoromethyl)benzene (500 mg, 1.94 mmol, 1.00 equiv) and THF (20 mL) under nitrogen. n-Butyllithium (0.93 mL, 2.32 mmol, 1.20 equiv, 2.5M in hexane) was added dropwise at −78° C. The resulting solution was stirred for 2 h at −78° C. DMF (10 mL) was added. The resulting solution was stirred for 2 h at −78° C. and quenched with water (20 mL). The mixture was extracted with EtOAc (3×20 mL) and the organic layers were combined, washed with brine (2×25 mL), dried over anhydrous sodium sulfate, filtered and concentrated under reduced pressure. The residue was chromatographed on a silica gel column to provide 130 mg (32% yield) of 3-chloro-2-(trifluoromethyl)benzaldehyde as a yellow oil. LCMS (ESI, m/z): 209 [M+H]⁺.

Step 2: Preparation of t-butyl 4-chloro-1H-pyrazole-3-carboxylate

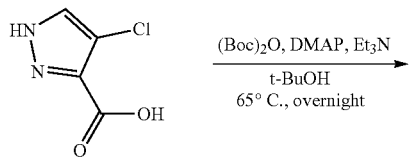

A flask was charged with 4-chloro-1H-pyrazole-3-carboxylic acid (4.00 g, 27.4 mmol, 1.00 equiv), t-butanol (50 mL), di-t-butyl dicarbonate (21.5 g, 98.6 mmol, 3.60 equiv), DMAP (468 mg, 3.83 mmol, 0.14 equiv), and triethylamine (8.30 g, 82.2 mmol, 3.00 equiv). The resulting solution was stirred overnight at 65° C. and quenched with water (50 mL), as described in Example 1, Step 1. The residue was chromatographed on a silica gel column to provide 520 mg (9% yield) of t-butyl 4-chloro-1H-pyrazole-3-carboxylate as a yellow solid. LCMS (ESI, m/z): 203 [M+H]$^+$.

Step 3: Preparation of t-butyl 8-(3-(t-butoxycarbonyl)-4-chloro-1H-pyrazole-1-carbonyl)-2,8-diazaspiro[4.5]decane-2-carboxylate

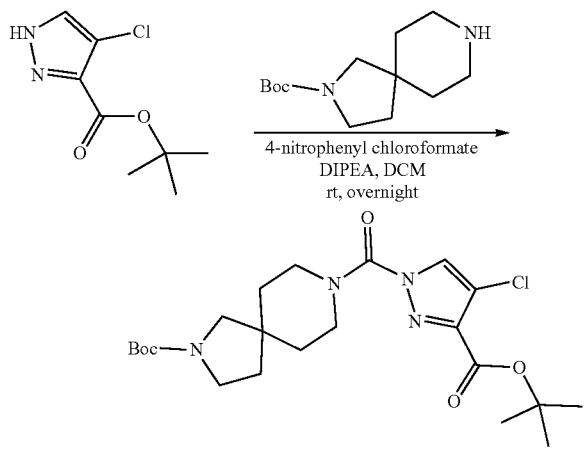 [SMILES: CC(C)(C)OC(=O)c1n[nH]cc1Cl ; CC(C)(C)OC(=O)N1CCC2(CCNCC2)C1 ; CC(C)(C)OC(=O)c1nn(C(=O)N2CCC3(CCN(C(=O)OC(C)(C)C)C3)CC2)cc1Cl]

A flask was charged with t-butyl 4-chloro-1H-pyrazole-3-carboxylate (355 mg, 1.75 mmol, 1.20 equiv), DCM (20 mL), 4-nitrophenyl chloroformate (442 mg, 2.19 mmol, 1.50 equiv), and DIPEA (565 mg, 4.38 mmol, 3.00 equiv). The resulting solution was stirred for 3 h at room temperature. t-Butyl 2,8-diazaspiro[4.5]decane-2-carboxylate (350 mg, 1.46 mmol, 1.00 equiv) was added. The resulting solution was stirred overnight at room temperature and quenched with water (20 mL). The mixture was extracted with DCM (3×20 mL) and the organic layers were combined, washed with brine (2×25 mL), dried over anhydrous sodium sulfate, filtered and concentrated under reduced pressure. The residue was chromatographed on a silica gel to provide 650 mg (95% yield) of t-butyl 8-(3-(t-butoxycarbonyl)-4-chloro-1H-pyrazole-1-carbonyl)-2,8-diazaspiro[4.5]decane-2-carboxylate as a yellow oil. LCMS (ESI, m/z): 469 [M+H]$^+$.

Step 4: Preparation of 4-chloro-1-(2,8-diazaspiro[4.5]decane-8-carbonyl)-1H-pyrazole-3-carboxylic Acid

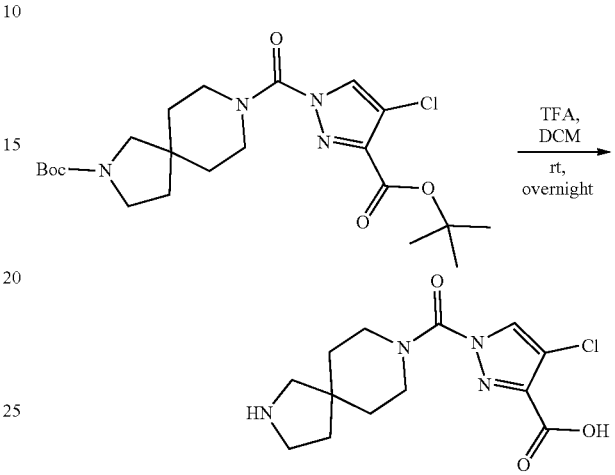

A flask was charged with t-butyl 8-(3-(t-butoxycarbonyl)-4-chloro-1H-pyrazole-1-carbonyl)-2,8-diazaspiro[4.5]decane-2-carboxylate (650 mg, 1.39 mmol, 1.00 equiv), DCM (10 mL), and TFA (3 mL) as described in Example 1, Step 5 to provide 433 mg (quantitative) of 4-chloro-1-(2,8-diazaspiro[4.5]decane-8-carbonyl)-1H-pyrazole-3-carboxylic acid as a yellow oil. LCMS (ESI, m/z): 313 [M+H]$^+$.

Step 5: Preparation of 4-chloro-1-(2-(3-chloro-2-(trifluoromethyl)benzyl)-2,8-diazaspiro[4.5]decane-8-carbonyl)-1H-pyrazole-3-carboxylic Acid

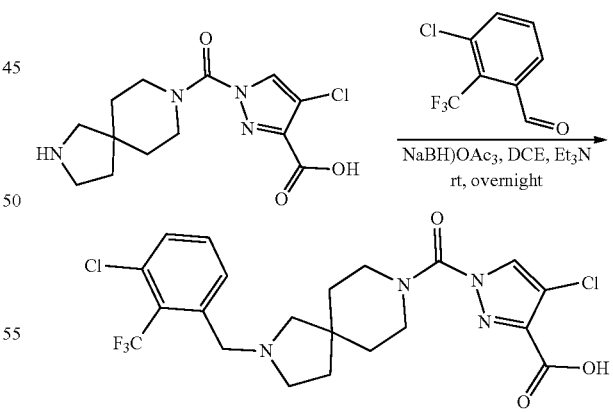

A flask was charged with 3-chloro-2-(trifluoromethyl) benzaldehyde (77.8 mg, 0.374 mmol, 1.00 equiv), DCE (20 mL), 4-chloro-1-(2,8-diazaspiro[4.5]decane-8-carbonyl)-1H-pyrazole-3-carboxylic acid (140 mg, 0.449 mmol, 1.20 equiv), and triethylamine (113 mg, 1.12 mmol, 3.00 equiv). The resulting solution was stirred for 1 h at room temperature. Sodium triacetoxyborohydride (238 mg, 1.12 mmol, 3.00 equiv) was added. The resulting solution was stirred overnight at room temperature and quenched with saturated NaHCO₃ solution (20 mL), as described in Example 2, Step 3. The crude product (200 mg) was purified by preparative HPLC to provide 10.8 mg (6% yield) of 4-chloro-1-(2-(3-chloro-2-(trifluoromethyl)benzyl)-2,8-diazaspiro[4.5]decane-8-carbonyl)-1H-pyrazole-3-carboxylic acid as a white solid. ¹H NMR (300 MHz, MeOH-d₄) δ 8.13 (s, 1H), 7.90-7.88 (m, 1H), 7.82-7.80 (m, 1H), 7.57-7.52 (m, 1H), 4.26 (br, 2H), 3.93-3.79 (m, 2H), 3.69-3.57 (m, 2H), 3.14-3.07 (m, 2H), 2.99-2.84 (m, 2H), 1.94 (t, J=7.2 Hz, 2H), 1.84-1.72 (m, 4H). LCMS (ESI, m/z): 505 [M+H]⁺.

Example 27: 1-(4-((3-Chloro-5-(4-chlorophenoxy)benzyl)oxy)piperidine-1-carbonyl)-1H-pyrazole-3-carboxylic Acid

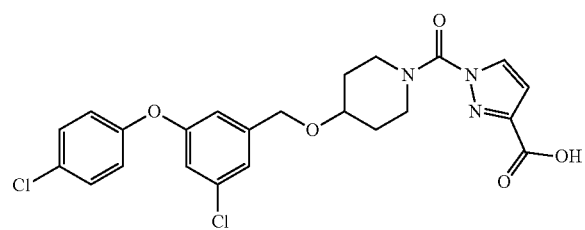 [SMILES: O=C(O)c1ccn(C(=O)N2CCC(OCc3cc(Cl)cc(Oc4ccc(Cl)cc4)c3)CC2)n1]

Step 1: Preparation of di-t-butyl 1H-pyrazole-1,3-dicarboxylate

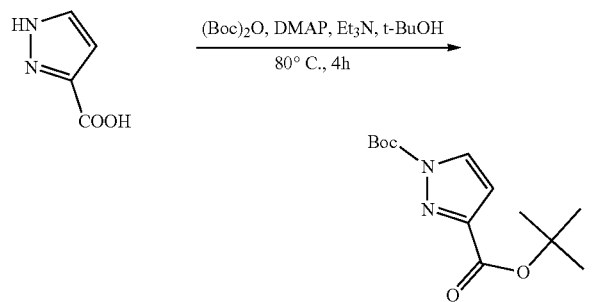

A flask was charged with 1H-pyrazole-3-carboxylic acid (10.0 g, 89.3 mmol, 1.00 equiv), DMAP (2.18 g, 17.9 mmol, 0.20 equiv), triethylamine (27.1 g, 268 mmol, 3.00 equiv), di-t-butyl dicarbonate (77.8 g, 357 mmol, 4.00 equiv), and t-butanol (100 mL). The resulting solution was stirred for 4 h at 80° C. and quenched with water (50 mL), as described in Example 1, Step 1 to provide 25.0 g (crude) of 1,3-di-t-butyl 1H-pyrazole-1,3-dicarboxylate as a red oil. LCMS (ESI, m/z): 269 [M+H]⁺.

Step 2: Preparation of t-butyl 1H-pyrazole-3-carboxylate

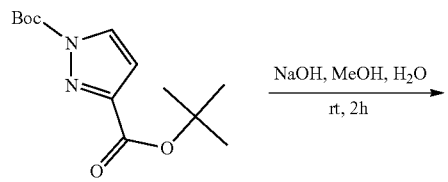

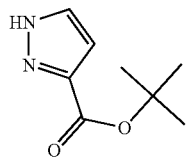

A flask was charged with 1,3-di-t-butyl 1H-pyrazole-1,3-dicarboxylate (25.0 g, 93.3 mmol, 1.00 equiv), sodium hydroxide (5.60 g, 140 mmol, 1.50 equiv), water (80 mL), and MeOH (240 mL). The resulting solution was stirred for 2 h at room temperature and quenched with water (30 mL), as described in Example 1, Step 2. The residue was chromatographed on a silica gel column to provide 10.0 g (64% yield) of t-butyl 1H-pyrazole-3-carboxylate as a white solid. LCMS (ESI, m/z): 169 [M+H]⁺.

Step 3: Preparation of 3-(t-butyl) 1-(4-nitrophenyl) 1H-pyrazole-1,3-dicarboxylate

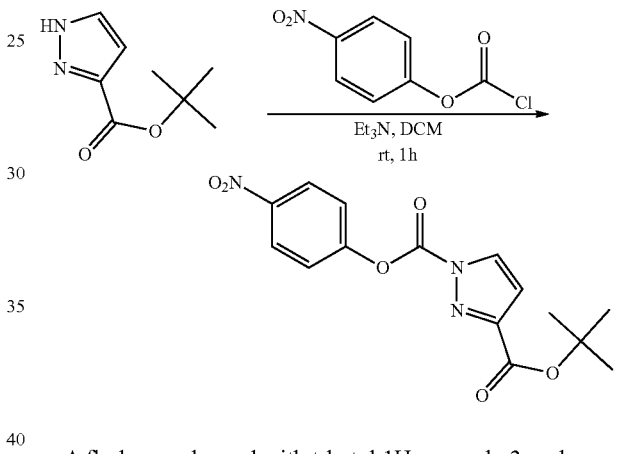

A flask was charged with t-butyl 1H-pyrazole-3-carboxylate (2.00 g, 11.9 mmol, 1.00 equiv), 4-nitrophenyl chloroformate (2.87 g, 14.2 mmol, 1.20 equiv), triethylamine (3.61 g, 35.7 mmol, 3.00 equiv), and DCM (20 mL). The resulting solution was stirred for 1 h at room temperature and concentrated under reduced pressure to provide 3.90 g (crude) of 3-t-butyl 1-(4-nitrophenyl) 1H-pyrazole-1,3-dicarboxylate as a yellow solid. LCMS (ESI, m/z): 334 [M+H]⁺.

Step 4: Preparation of bis(4-chlorophenyl)iodonium tetrafluoroborate

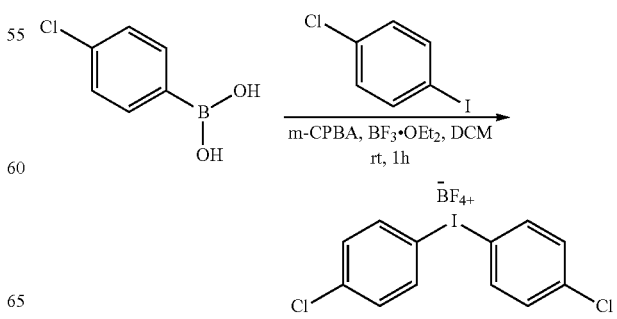

A flask was charged with m-CPBA (3.18 g, 18.4 mmol, 1.10 equiv), and DCM (25 mL). Boron trifluoride ether complex (7.16 g, 50.4 mmol, 3.00 equiv) and 1-chloro-4-iodobenzene (4.00 g, 16.8 mmol, 1.00 equiv) were added at 0° C. The resulting solution was stirred for 0.5 h at room temperature. (4-Chlorophenyl)boronic acid (2.89 g, 18.5 mmol, 1.10 equiv) was added at 0° C., as described in Example 19, Step 1. The resulting solution was stirred for 0.5 h at room temperature and concentrated under reduced pressure. The crude product was triturated with ethyl ether to provide 5.50 g (75% yield) of bis(4-chlorophenyl)iodonium tetrafluoroborate as a white solid. LCMS (ESI, m/z): 349 [M-BF$_4$]$^+$.

Step 5: Preparation of
3-chloro-5-(4-chlorophenoxy)benzaldehyde

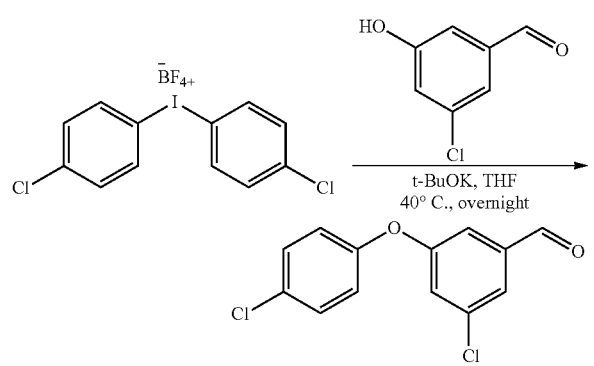

A flask was charged with potassium t-butoxide (0.840 g, 7.50 mmol, 1.50 equiv) and THF (20 mL). 3-Chloro-5-hydroxybenzaldehyde (780 mg, 5.00 mmol, 1.00 equiv) was added at 0° C. and the reaction was stirred for 20 min. Bis(4-chlorophenyl)iodonium tetrafluoroborate (2.62 g, 6.00 mmol, 1.20 equiv) was added at 0° C. The resulting solution was stirred overnight at 40° C. and quenched with water (20 mL). The mixture was extracted with DCM (3×40 mL) and the organic layers were combined, washed with brine (30 mL), dried over anhydrous sodium sulfate, filtered and concentrated under reduced pressure. The residue was chromatographed on a silica gel column to provide 300 mg (19% yield) of 3-chloro-5-(4-chlorophenoxy)benzaldehyde as a colorless oil. LCMS (ESI, m/z): 267 [M+H]$^+$.

Step 6: Preparation of
(3-chloro-5-(4-chlorophenoxy)phenyl)MeOH

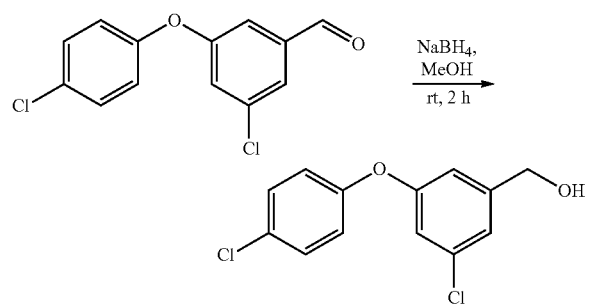

A flask was charged with 3-chloro-5-(4-chlorophenoxy) benzaldehyde (310 mg, 1.16 mmol, 1.00 equiv), MeOH (15 mL), and sodium borohydride (129 mg, 3.41 mmol, 3.00 equiv). The resulting solution was stirred for 2 h at room temperature then quenched with water (20 mL), as described in Example 15, Step 4 to provide 303 mg (97% yield) of (3-chloro-5-(4-chlorophenoxy)phenyl)MeOH as a colorless oil. LCMS (ESI, m/z): 269 [M+H]$^+$.

Step 7: Preparation of 1-(bromomethyl)-3-chloro-5-
(4-chlorophenoxy)benzene

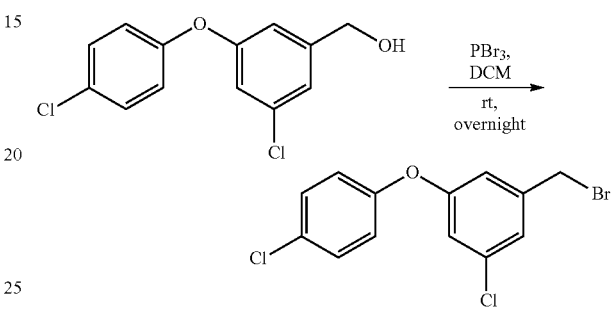

A flask was charged with (3-chloro-5-(4-chlorophenoxy) phenyl)MeOH (303 mg, 1.13 mmol, 1.00 equiv), and DCM (15 mL). Phosphorus tribromide (610 mg, 2.25 mmol, 2.00 equiv) was added at 0° C. The resulting solution was stirred overnight at room temperature then quenched with water (20 mL). The resulting solution was extracted with DCM (3×40 mL) and the organic layers were combined, washed with brine (30 mL), dried over anhydrous sodium sulfate, filtered and concentrated under reduced pressure to provide 200 mg (54% yield) of 1-(bromomethyl)-3-chloro-5-(4-chlorophenoxy)benzene as a yellow oil. LCMS (ESI, m/z): 331 [M+H]$^+$.

Step 8: Preparation of t-butyl 4-((3-chloro-5-(4-chlorophenoxy)benzyl)oxy)piperidine-1-carboxylate

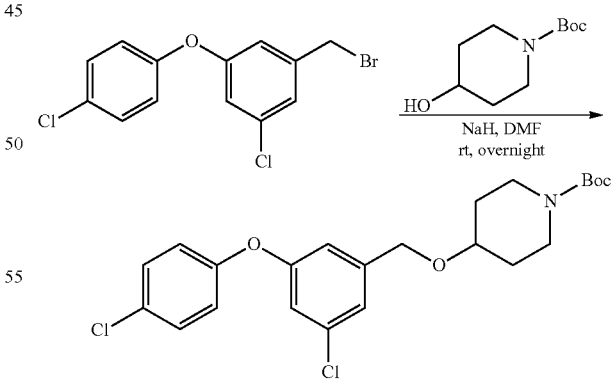

A flask was charged with t-butyl 4-hydroxypiperidine-1-carboxylate (183 mg, 0.910 mmol, 1.50 equiv) and DMF (5 mL). Sodium hydride (72.8 mg, 60% in mineral oil, 1.82 mmol, 3.00 equiv) was added at 0° C. The mixture was stirred at 0° C. for 5 min. 1-(Bromomethyl)-3-chloro-5-(4-chlorophenoxy)benzene (200 mg, 0.606 mmol, 1.00 equiv) was added at 0° C. The resulting solution was stirred overnight at room temperature and then quenched with water (10 mL), as described in Example 15, Step 7. The residue was chromatographed on a silica gel column to provide 150 mg (55% yield) of t-butyl 4-((3-chloro-5-(4-chlorophenoxy)benzyl)oxy)piperidine-1-carboxylate as a yellow oil. LCMS (ESI, m/z): 452 [M+H]$^+$.

Step 9: Preparation of 4-((3-chloro-5-(4-chlorophenoxy)benzyl)oxy)piperidine

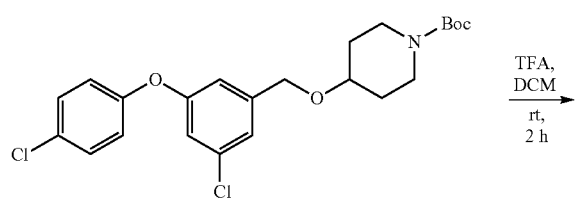

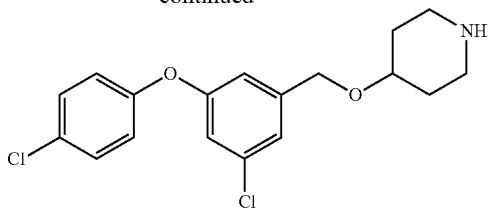

A flask was charged with t-butyl 4-((3-chloro-5-(4-chlorophenoxy)benzyl)oxy)piperidine-1-carboxylate (150 mg, 0.330 mmol, 1.00 equiv), DCM (10 mL), and TFA (3 mL). The resulting solution was stirred for 2 h at room temperature and concentrated under reduced pressure to provide 117 mg (quantitative) of 4-((3-chloro-5-(4-chlorophenoxy)benzyl)oxy)piperidine as a yellow oil. LCMS (ESI, m/z): 352 [M+H]$^+$.

Step 10: Preparation of t-butyl 1-(4-((3-chloro-5-(4-chlorophenoxy)benzyl)oxy)piperidine-1-carbonyl)-1H-pyrazole-3-carboxylate

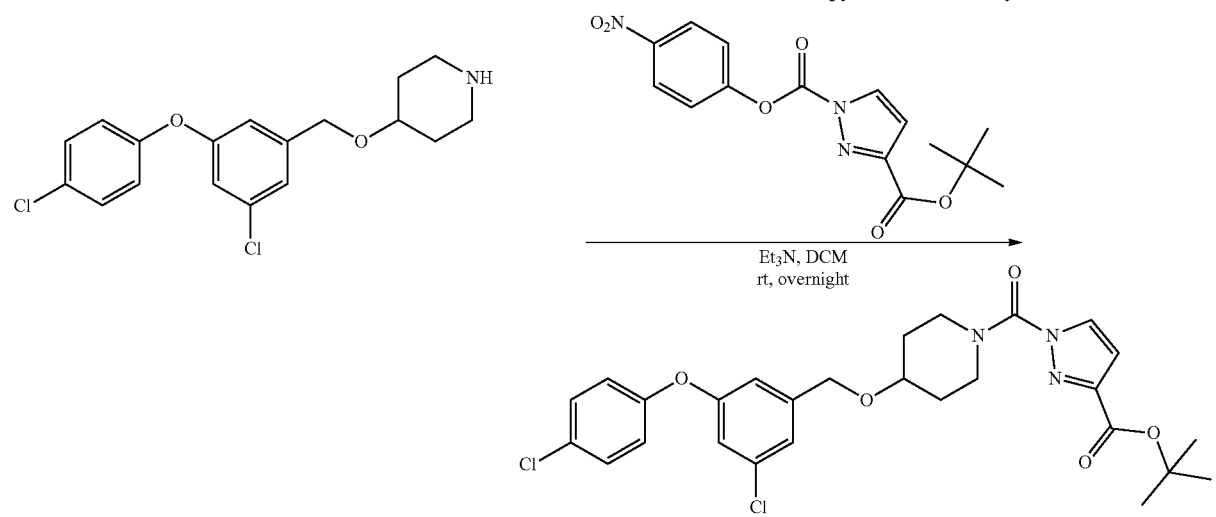

A flask was charged with 4-((3-chloro-5-(4-chlorophenoxy)benzyl)oxy)piperidine (117 mg, 0.330 mmol, 1.00 equiv), 3-t-butyl 1-(4-nitrophenyl) 1H-pyrazole-1,3-dicarboxylate (166 mg, 0.500 equiv, 1.50 equiv), DCM (10 mL), and triethylamine (100 mg, 0.990 mmol, 3.00 equiv). The resulting solution was stirred overnight at room temperature and quenched with water (10 mL), as described in Example 4, Step 3. The residue was chromatographed on a silica gel column to provide 160 mg (88% yield) of t-butyl 1-(4-((3-chloro-5-(4-chlorophenoxy)benzyl)oxy)piperidine-1-carbonyl)-1H-pyrazole-3-carboxylate as a yellow oil. LCMS (ESI, m/z): 546 [M+H]$^+$.

Step 11: Preparation of 1-(4-((3-chloro-5-(4-chlorophenoxy)benzyl)oxy)piperidine-1-carbonyl)-1H-pyrazole-3-carboxylic Acid

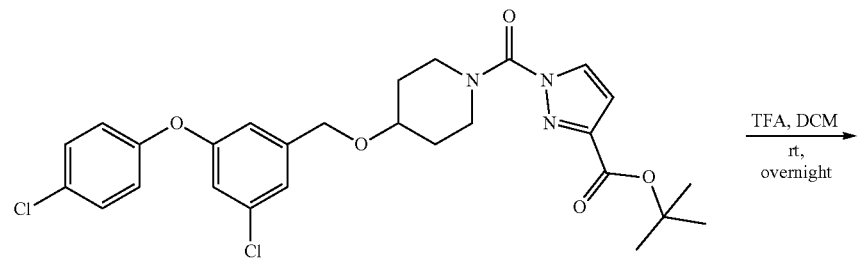

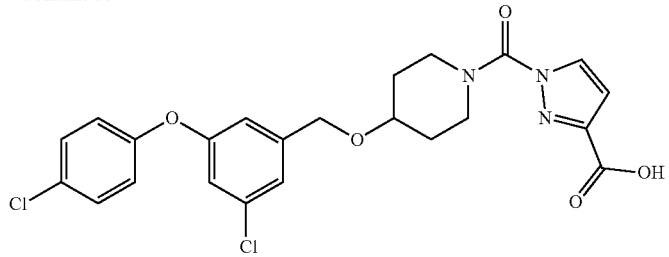

A flask was charged with t-butyl 1-(4-((3-chloro-5-(4-chlorophenoxy)benzyl)oxy)piperidine-1-carbonyl)-1H-pyrazole-3-carboxylate (160 mg, 0.290 mmol, 1.00 equiv), DCM (10 mL), and TFA (3 mL), as described in Example 1, Step 5. The crude product (200 mg) was purified by preparative HPLC to provide 60.7 mg (42% yield) of 1-(4-((3-chloro-5-(4-chlorophenoxy)benzyl)oxy)piperidine-1-carbonyl)-1H-pyrazole-3-carboxylic acid as a yellow oil. $^1$H NMR (300 MHz, MeOH-d$_4$) δ 8.05 (d, J=2.7 Hz, 1H), 7.41-7.35 (m, 2H), 7.15 (s, 1H), 7.04-6.99 (m, 2H), 6.92-6.89 (m, 2H), 6.76 (d, J=2.7 Hz, 1H), 4.55 (s, 2H), 4.00 (br, 2H), 3.76-3.71 (m, 1H), 3.70-3.54 (m, 2H), 2.03-1.96 (m, 2H), 1.79-1.68 (m, 2H). LCMS (ESI, m/z): 490 [M+H]$^+$.

Example 28: 1-(trans-5-((3-Chloro-2-(trifluoromethyl)benzyl)oxy)octahydrocyclopenta[c]pyrrole-2-carbonyl)-1H-pyrazole-3-carboxylic Acid

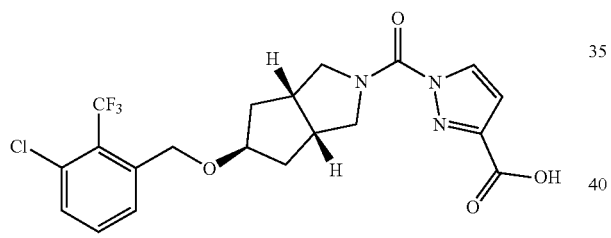

Step 1: Preparation of di-t-butyl 1H-pyrazole-1,3-dicarboxylate

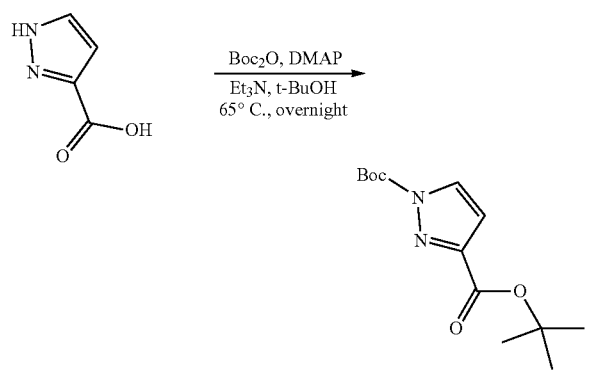

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL). The resulting solution was stirred overnight at 65° C. and quenched by water (200 mL) as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

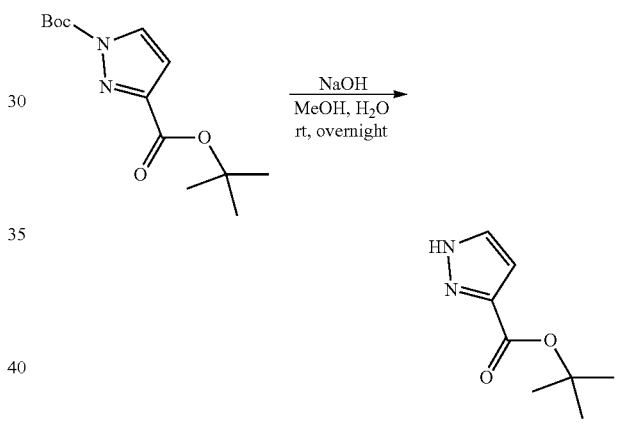

A flask was charged with 1,3-di-t-butyl-1H-pyrazole-1,3-dicarboxylate (20.0 g, 74.6 mmol, 1.00 equiv), MeOH (80 mL), sodium hydroxide (10.0 g, 250 mmol, 3.35 equiv) and water (40 mL). The resulting solution was stirred overnight at room temperature and quenched by water (40 mL), as described in Example 1, Step 2 to provide 6.70 g (crude) of t-butyl-1H-pyrazole-3-carboxylate as a yellow solid. LCMS (ESI, m/z): 169 [M+H]$^+$.

Step 3: Preparation of 3-(t-butyl) 1-(4-nitrophenyl) 1H-pyrazole-1,3-dicarboxylate

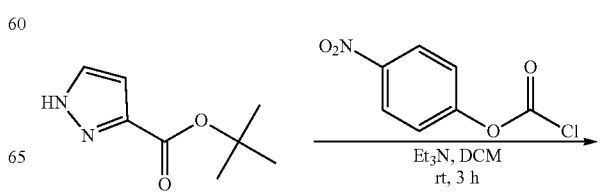

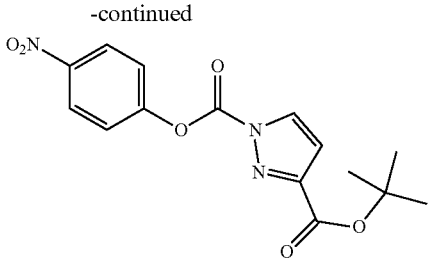

A flask was charged with t-butyl 1H-pyrazole-3-carboxylate (1.68 g, 9.99 mmol, 1.00 equiv), DCM (20 mL) and triethylamine (3.03 g, 29.9 mmol, 3.00 equiv). 4-Nitrophenyl chloroformate (2.42 g, 12.0 mmol, 1.20 equiv) was added at 0° C.), as described in Example 4, Step 3 to provide 3.33 g (crude) of 3-t-butyl 1-(4-nitrophenyl) 1H-pyrazole-1,3-dicarboxylate as a yellow solid.

Step 4: Preparation of t-butyl (3aR,5r,6aS)-5-hydroxyhexahydrocyclopenta[c]pyrrole-2(1H)-carboxylate

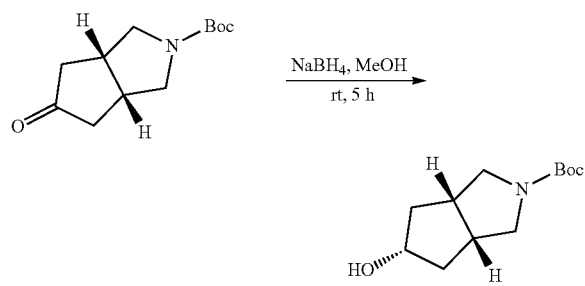

A flask was charged with (3aR,6aS)-t-butyl 5-oxo-hexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure as described in Example 15, Step 4 to provide 3.01 g (crude) of t-butyl (3aR,5r,6aS)-5-hydroxyhexahydrocyclopenta[c]pyrrole-2(1H)-carboxylate as a white solid. LCMS (ESI, m/z): 228 [M+H]$^+$.

Step 5: Preparation of t-butyl (3aR,5s,6aS)-5-((4-nitrobenzoyl)oxy)hexahydrocyclopenta[c]pyrrole-2(1H)-carboxylate

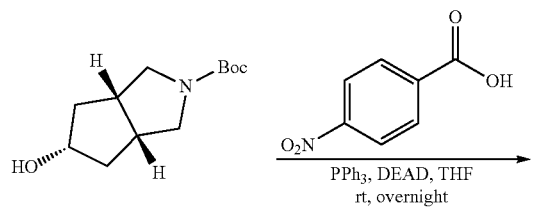

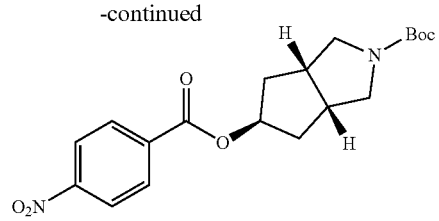

A flask was charged with t-butyl (3aR,5r,6aS)-5-hydroxyhexahydrocyclopenta[c]pyrrole-2(1H)-carboxylate (2.27 g, 9.99 mmol, 1.00 equiv), 4-nitrobenzoic acid (6.68 g, 40.0 mmol, 4.00 equiv), triphenylphosphine (10.5 g, 40.0 mmol, 4.00 equiv), and THF (30 mL). Diethyl azodicarboxylate (6.96 g, 40.0 mmol, 4.00 equiv) was added dropwise at 0° C. The resulting solution was stirred overnight at room temperature under nitrogen atmosphere and quenched by water (50 mL), as described in Example 15, Step 5. The residue was chromatographed on a silica gel column to provide 2.36 g (62% yield) of t-butyl (3aR,5s,6aS)-5-(4-nitrobenzoyl)oxy)hexahydrocyclopenta[c]pyrrole-2(1H)-carboxylate as a white solid. LCMS (ESI, m/z): 377 [M+H]$^+$.

Step 6: Preparation of t-butyl (3aR,5s,6aS)-5-hydroxyhexahydrocyclopenta[c]pyrrole-2(1H)-carboxylate

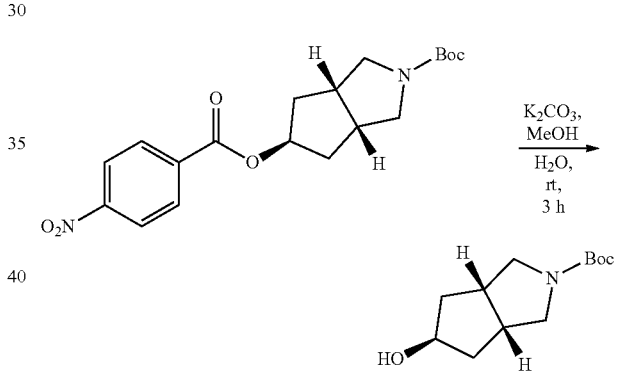

A flask was charged with t-butyl (3aR,5s,6aS)-5-(4-nitrobenzoyl)oxy)hexahydrocyclopenta[c]pyrrole-2(1H)-carboxylate (2.36 g, 6.27 mmol, 1.00 equiv), MeOH (30 mL), potassium carbonate (2.60 g, 18.8 mmol, 3.00 equiv) and water (5 mL). The resulting solution was stirred for 3 h at room temperature and concentrated under reduced pressure as described in Example 15, Step 6 to provide 1.31 g (crude) of (3aR,5s,6aS)-5-hydroxyhexahydrocyclopenta[c]pyrrole-2(1H)-carboxylate as a white solid. LCMS (ESI, m/z): 228 [M+H]$^+$.

Step 7: Preparation of 1-(bromomethyl)-3-methyl-2-(trifluoromethyl)benzene

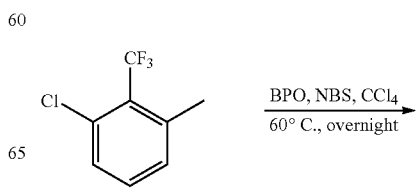

227
-continued

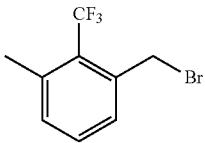

A vial was charged with 1-chloro-3-methyl-2-(trifluoromethyl)benzene (800 mg, 4.11 mmol, 1.00 equiv), dibenzoyl peroxide (264 mg, 1.03 mmol, 0.250 equiv), 1-bromo-2,5-pyrrolidinedione (956 mg, 5.37 mmol, 1.30 equiv) and carbon tetrachloride (15 mL). The resulting solution was stirred overnight at 60° C. and quenched by water (20 mL). The mixture was extracted with EtOAc (3×20 mL) and the organic layers were combined, washed with water (3×20 mL), dried over anhydrous sodium sulfate, filtered and concentrated under reduced pressure. The residue was chromatographed on a silica gel column to provide 400 mg (36% yield) of 1-(bromomethyl)-3-methyl-2-(trifluoromethyl) benzene as a yellow oil. ¹H NMR (300 MHz, Chloroform-d) δ 7.60-7.38 (m, 3H), 4.67 (br, 2H).

Step 8: Preparation of t-butyl (3aR,5s,6aS)-5-((3-chloro-2-(trifluoromethyl)benzyl)oxy)hexahydrocyclopenta[c]pyrrole-2(1H)-carboxylate

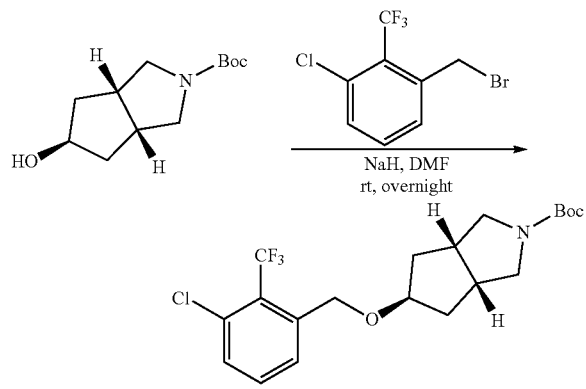

A flask was charged with t-butyl (3aR,5s,6aS)-5-hydroxy-octahydrocyclopenta[c]pyrrole-2-carboxylate (227 mg, 1.00 mmol, 1.00 equiv) and DMF (15 mL). Then sodium hydride (60% in oil, 80.0 mg, 2.00 mmol, 2.00 equiv) was added at 0° C. The resulting solution was stirred for 0.5 h at room temperature. Then 1-(bromomethyl)-3-methyl-2-(trifluoromethyl)benzene (228 mg, 0.830 mmol, 0.800 equiv) was added. The resulting solution was stirred overnight at room temperature and quenched by water (20 mL), as described in Example 15, Step 7. The residue was chromatographed on a silica gel column to provide 85.0 mg (24% yield) of t-butyl (3aR,5s,6aS)-5-((3-chloro-2-(trifluoromethyl)benzyl)oxy) hexahydrocyclopenta[c]pyrrole-2(1H)-carboxylate as a yellow oil. LCMS (ESI, m/z): 420 [M+H]⁺.

Step 9: Preparation of (3aR,5s,6aS)-5-((3-chloro-2-(trifluoromethyl)benzyl)oxy)octahydrocyclopenta[c]pyrrole

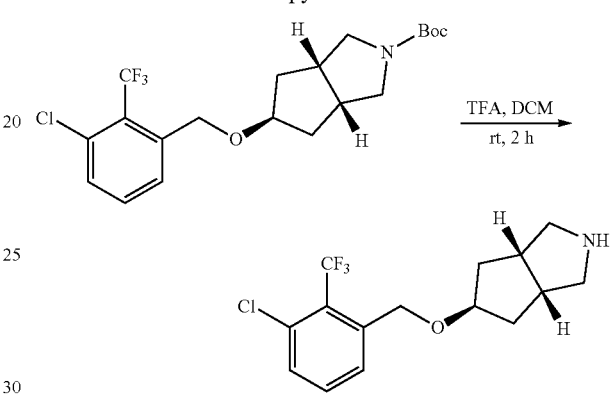

A flask was charged with t-butyl (3aR,5s,6aS)-5-((3-chloro-2-(trifluoromethyl)benzyl)oxy)hexahydrocyclopenta[c]pyrrole-2(1H)-carboxylate (85.0 mg, 0.200 mmol, 1.00 equiv), TFA (2 mL) and DCM (5 mL). The resulting solution was stirred for 2 h at room temperature and concentrated under reduced pressure. This resulted in 65.0 mg (quantitative) of (3aR,5s,6aS)-5-((3-chloro-2-(trifluoromethyl)benzyl)oxy)octahydrocyclopenta[c]pyrrole as a yellow solid. LCMS (ESI, m/z): 320 [M+H]⁺.

Step 10: Preparation of t-butyl 1-(3aR,5s,6aS)-5-((3-chloro-2-(trifluoromethyl)benzyl)oxy)octahydrocyclopenta[c]pyrrole-2-carbonyl)-1H-pyrazole-3-carboxylate

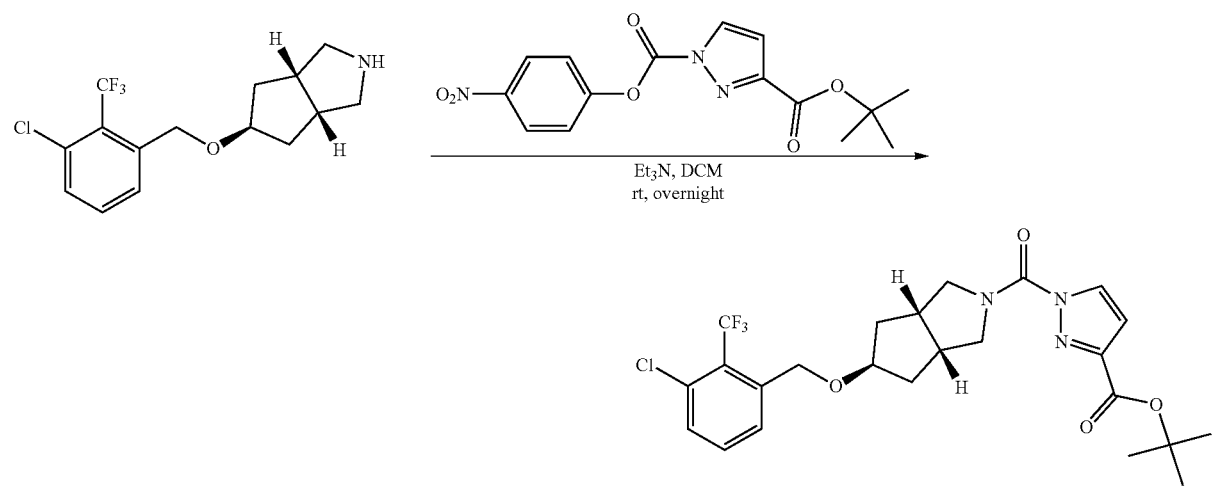

229

A vial was charged with (3aR,5s,6aS)-5-((3-chloro-2-(trifluoromethyl)benzyl)oxy)octahydrocyclopenta[c]pyrrole (65.0 mg, 0.200 mmol, 1.00 equiv), triethylamine (124 mg, 1.23 mmol, 6.00 equiv), 3-t-butyl 1-(4-nitrophenyl) 1H-pyrazole-1,3-dicarboxylate (99.9 mg, 0.300 mmol, 1.50 equiv) and DCM (15 mL). The resulting solution was stirred overnight at room temperature. The mixture was quenched by water (10 mL) as described in Example 4, Step 3. The residue was chromatographed on a silica gel column to provide 50.0 mg (48% yield) of t-butyl 1-((3aR,5s,6aS)-5-((3-chloro-2-(trifluoromethyl)benzyl)oxy)octahydrocyclopenta[c]pyrrole-2-carbonyl)-1H-pyrazole-3-carboxylate as a yellow oil. LCMS (ESI, m/z): 514 [M+H]⁺.

Step 11: Preparation of 1-(trans-5-((3-chloro-2-(trifluoromethyl)benzyl)oxy)octahydrocyclopenta[c]pyrrole-2-carbonyl)-1H-pyrazole-3-carboxylic Acid

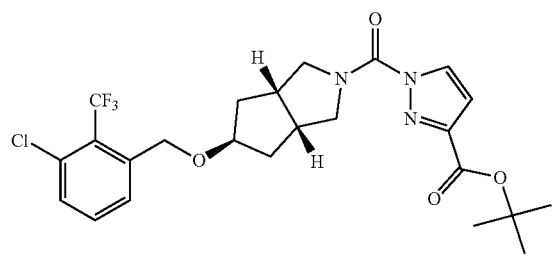

A vial was charged with t-butyl 1-((3aR,5s,6a5)-5-(3-chloro-2-(trifluoromethyl)benzyloxy)-octahydrocyclopenta[c]pyrrole-2-carbonyl)-1H-pyrazole-3-carboxylate (50.0 mg, 0.100 mmol, 1.00 equiv), TFA (2 mL) and DCM (5 mL). The resulting solution was stirred for 2 h at room temperature and concentrated under reduced pressure as described in Example 1, Step 5. The crude product was purified by preparative HPLC to provide 30.3 mg (68% yield) of 1-(trans-5-((3-chloro-2-(trifluoromethyl)benzyl)oxy)octahydrocyclopenta[c]pyrrole-2-carbonyl)-1H-pyrazole-3-carboxylic acid as a white solid. $^1$H NMR (400 MHz, MeOH-d$_4$) δ 8.15 (d, J=4.0 Hz, 1H), 7.67-7.61 (m, 1H), 7.55-7.48 (m, 2H), 6.74 (d, J=2.8 Hz, 1H), 4.64 (d, J=2.0 Hz, 2H), 4.25-4.19 (m, 1H), 4.15-3.48 (m, 4H), 2.90 (br, 2H), 2.15-2.05 (m, 2H), 1.85-1.75 (m, 2H). LCMS (ESI, m/z): 458 [M+H]⁺.

Example 29: 1-(trans-5-(2-(1H-Pyrazol-1-yl)phenoxy)octahydrocyclopenta[c]pyrrole-2-carbonyl)-1H-pyrazole-3-carboxylic Acid

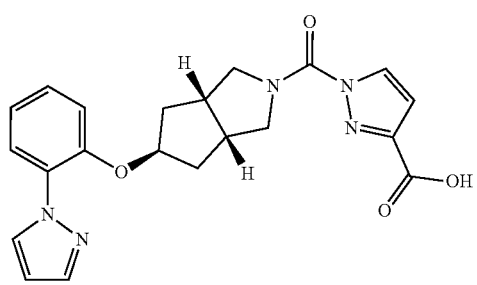 [SMILES: O=C(O)c1ccn(C(=O)N2C[C@H]3C[C@H](Oc4ccccc4-n4cccn4)C[C@H]3C2)n1]

230

Step 1: Preparation of di-t-butyl 1H-pyrazole-1,3-dicarboxylate

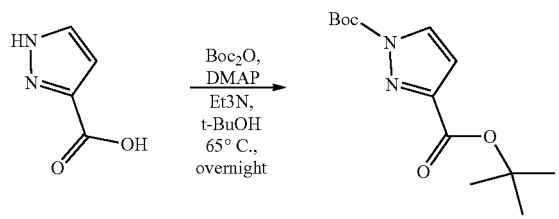

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL). The resulting solution was stirred overnight at 65° C. and quenched by water (200 mL), as described in Example 1, Step 1 to provide 20.0 g (crude) of 1,3-di-t-butyl-1H-pyrazole-1,3-dicarboxylate as a yellow oil. LCMS (ESI, m/z): 169 [M+H-Boc]⁺.

Step 2: Preparation of t-butyl 1H-pyrazole-3-carboxylate

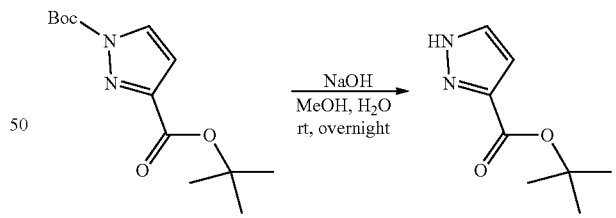

A flask was charged with 1,3-di-t-butyl-1H-pyrazole-1,3-dicarboxylate (20.0 g, 74.6 mmol, 1.00 equiv), MeOH (80 mL), sodium hydroxide (10.0 g, 250 mmol, 3.35 equiv) and water (40 mL). The resulting solution was stirred overnight at room temperature and quenched by water (40 mL), as described in Example 1, Step 2 to provide 6.70 g (crude) of t-butyl-1H-pyrazole-3-carboxylate as a yellow solid. LCMS (ESI, m/z): 169 [M+H]⁺.

Step 3: Preparation of 3-(t-butyl) 1-(4-nitrophenyl) 1H-pyrazole-1,3-dicarboxylate

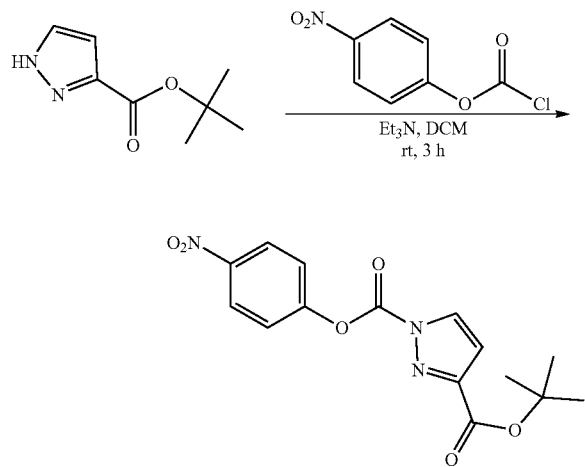

A flask was charged with N-(1H-pyrazol-3-yl)methanesulfonamide (1.68 g, 9.99 mmol, 1.00 equiv), DCM (20 mL) and triethylamine (3.03 g, 29.9 mmol, 3.00 equiv). 4-Nitrophenyl chloroformate (2.42 g, 12.0 mmol, 1.20 equiv) was added at 0° C. The resulting solution was stirred for 3 h at room temperature and concentrated under reduced pressure to provide 3.33 g (crude) of 3-(t-butyl) 1-(4-nitrophenyl) 1H-pyrazole-1,3-dicarboxylate as a yellow solid.

Step 4: Preparation of 2-(1H-pyrazol-1-yl)phenol

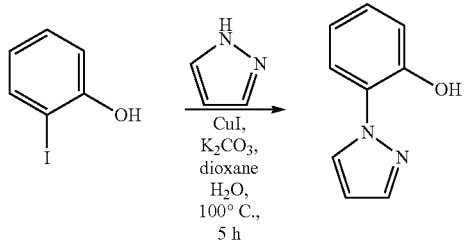 [SMILES: Oc1ccccc1I ; c1cn[nH]c1 ; Oc1ccccc1-n1cccn1]

A vial was charged with 2-iodophenol (2.00 g, 9.09 mmol, 1.00 equiv), 1H-pyrazole (0.741 g, 10.9 mmol, 1.20 equiv), potassium carbonate (3.15 g, 22.8 mmol, 2.50 equiv), copper (I) iodide (433 mg, 2.27 mmol, 0.25 equiv), dioxane (8 mL) and water (8 mL) under $N_2$ atmosphere. The resulting solution was stirred for 5 h at 100° C. and quenched by water (20 mL). The mixture was extracted with EtOAc (3×20 mL) and the organic layers were combined, washed with water (3×20 mL), dried over anhydrous sodium sulfate, filtered and concentrated under reduced pressure. The residue was chromatographed on a silica gel column to provide 700 mg (48% yield) of 2-(1H-pyrazol-1-yl)phenol as a light yellow oil. LCMS (ESI, m/z): 161 [M+H]$^+$.

Step 5: Preparation of t-butyl (3aR,5r,6aS)-5-hydroxyhexahydrocyclopenta[c]pyrrole-2(1H)-carboxylate

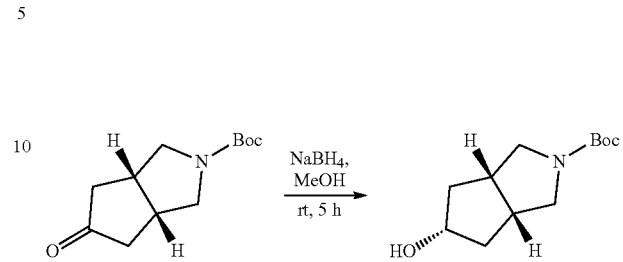

A flask was charged with (3aR,6aS)-t-butyl 5-oxo-hexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure as described in Example 15, Step 4 to provide 3.01 g (crude) of t-butyl (3aR,5r,6aS)-5-hydroxyhexahydrocyclopenta[c]pyrrole-2(1H)-carboxylate as a white solid. LCMS (ESI, m/z): 228 [M+H]$^+$.

Step 6: Preparation of t-butyl (3aR,5r,6aS)-5-((methylsulfonyl)oxy)hexahydrocyclopenta[c]pyrrole-2(1H)-carboxylate

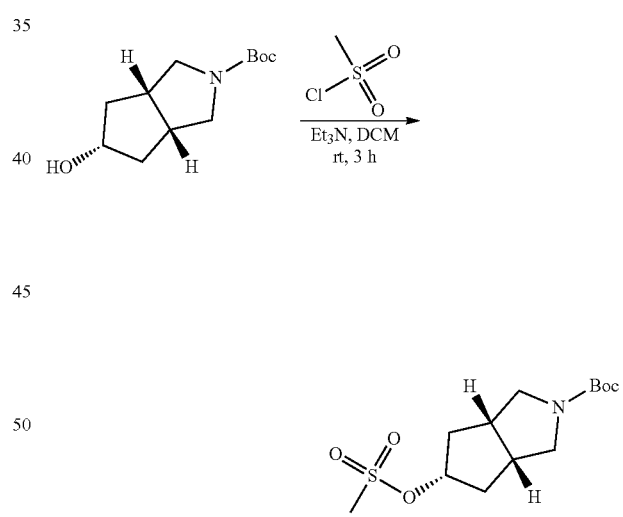

A flask was charged with t-butyl (3aR,5r,6aS)-5-hydroxyhexahydrocyclopenta[c]pyrrole-2(1H)-carboxylate (1.00 g, 4.40 mmol, 1.00 equiv), DCM (20 mL) and triethylamine (1.34 g, 13.2 mmol, 3.00 equiv). Methanesulfonyl chloride (0.608 g, 5.28 mmol, 1.20 equiv) was added dropwise at 0° C. The resulting solution was stirred for 3 h at room temperature and concentrated under reduced pressure to provide 1.34 g (crude) of t-butyl (3aR,5r,6aS)-5-((methylsulfonyl)oxy)hexahydrocyclopenta[c]pyrrole-2(1H)-carboxylate as a yellow oil. LCMS (ESI, m/z): 306 [M+H]$^+$.

Step 7: Preparation of t-butyl (3aR,5s,6aS)-5-(2-(1H-pyrazol-1-yl)phenoxy)hexahydrocyclopenta[c]pyrrole-2(1H)-carboxylate

Step 8: Preparation of (3aR,5s,6aS)-5-(2-(1H-pyrazol-1-yl)phenoxy)octahydrocyclopenta[c]pyrrole

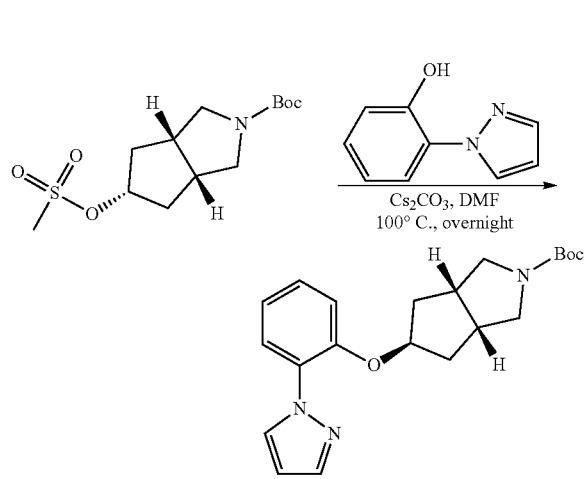

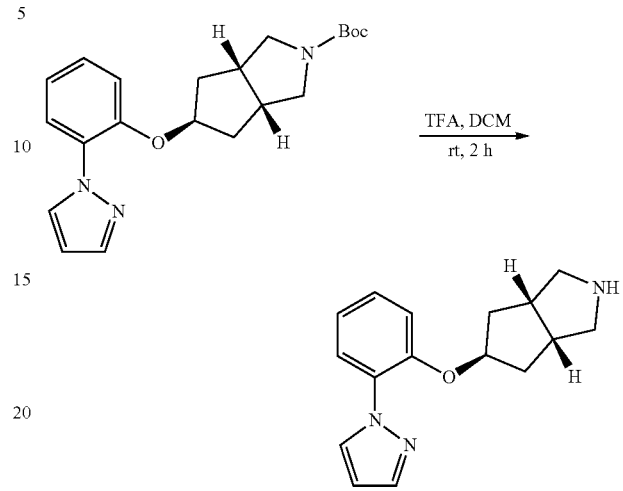

A vial was charged with 2-(1H-pyrazol-1-yl)phenol (160 mg, 1.00 mmol, 1.00 equiv), (3aR,5r,6aS)-t-butyl 5-(methylsulfonyloxy)-hexahydrocyclopenta[c]pyrrole-2(1H)-carboxylate (305 mg, 1.00 mmol, 1.00 equiv), potassium carbonate (652 mg, 2.00 mmol, 2.00 equiv) and DMF (15 mL). The resulting solution was stirred overnight at 100° C. and quenched by water (20 mL), as described in Example 13, Step 4. The residue was chromatographed on a silica gel column to provide 313 mg (85% yield) of t-butyl (3aR,5s,6aS)-5-(2-(1H-pyrazol-1-yl)phenoxy)hexahydrocyclopenta[c]pyrrole-2(1H)-carboxylate as a light yellow oil. LCMS (ESI, m/z): 370 [M+H]$^+$.

A flask was charged with t-butyl (3aR,5s,6aS)-5-(2-(1H-pyrazol-1-yl)phenoxy)hexahydrocyclopenta[c]pyrrole-2(1H)-carboxylate (313 mg, 0.850 mmol, 1.00 equiv), TFA (2 mL) and DCM (5 mL). The resulting solution was stirred for 2 h at room temperature and concentrated under reduced pressure, as described in Example 1, Step 5, providing 228 mg (quantitative) of (3aR,5s,6aS)-5-(2-(1H-pyrazol-1-yl)phenoxy)octahydrocyclopenta[c]pyrrole as a light yellow oil. LCMS (ESI, m/z): 270 [M+H]$^+$.

Step 9: Preparation of t-butyl 1-((3aR,5s,6aS)-5-(2-(1H-pyrazol-1-yl)phenoxy)octahydrocyclopenta[c]pyrrole-2-carbonyl)-1H-pyrazole-3-carboxylate

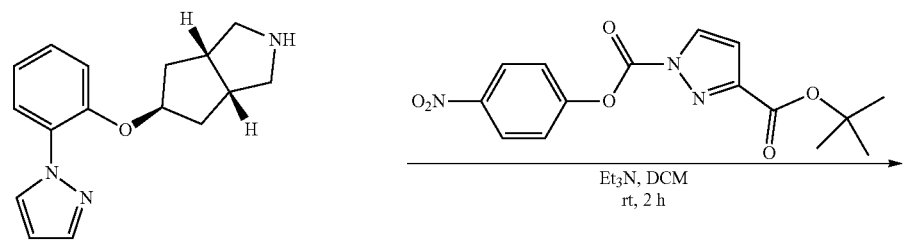

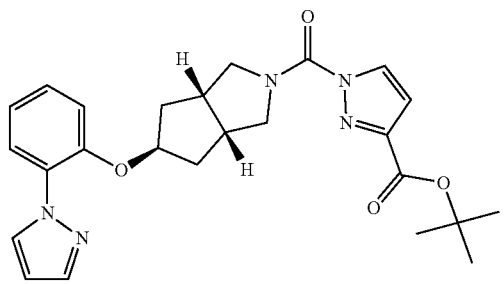

A vial was charged with (3aR,5s,6aS)-5-(2-(1H-pyrazol-1-yl)phenoxy)-octahydrocyclopenta[c]pyrrole (228 mg, 0.850 mmol, 1.00 equiv), triethylamine (429 mg, 4.25 mmol, 5.00 equiv), 3-(t-butyl) 1-(4-nitrophenyl) 1H-pyrazole-1,3-dicarboxylate (426 mg, 1.28 mmol, 1.50 equiv) and DCM (15 mL). The resulting solution was stirred for 2 h at room temperature. The mixture was quenched by water (10 mL), extracted with DCM (3×20 mL) and the organic layers were combined, washed with brine (2×20 mL), dried over anhydrous sodium sulfate, filtered and concentrated under reduced pressure, as described in Example 4, Step 3. The residue was chromatographed on a silica gel column to provide 295 mg (75% yield) of t-butyl 1-((3aR,5s,6aS)-5-(2-(1H-pyrazol-1-yl)phenoxy)octahydrocyclopenta[c]pyrrole-2-carbonyl)-1H-pyrazole-3-carboxylate as a colorless oil. LCMS (ESI, m/z):464 [M+H]$^+$.

Step 10: Preparation of 1-(trans-5-(2-(1H-pyrazol-1-yl)phenoxy)octahydrocyclopenta[c]pyrrole-2-carbonyl)-1H-pyrazole-3-carboxylic Acid

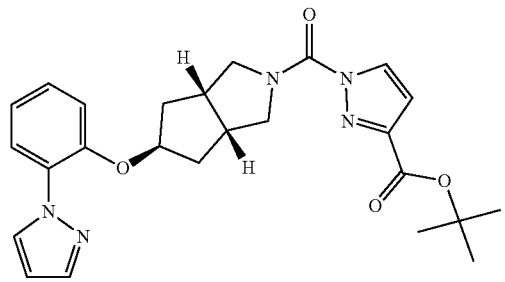

A vial was charged with t-butyl 1-((3aR,5s,6aS)-5-(2-(1H-pyrazol-1-yl)phenoxy)octahydrocyclopenta[c]pyrrole-2-carbonyl)-1H-pyrazole-3-carboxylate (166 mg, 0.360 mmol, 1.00 equiv), TFA (2 mL) and DCM (5 mL). The resulting solution was stirred for 2 h at room temperature and concentrated under reduced pressure. The crude product was dissolved in saturated NaHCO$_3$ solution (10 mL) and extracted with DCM (3×20 mL). The organic layers were combined, washed with brine (10 mL), dried over anhydrous sodium sulfate, filtered and concentrated under reduced pressure, as described in Example 1, Step 5. The crude product was purified by preparative HPLC to provide 61.2 mg (42% yield) of 1-(trans-5-(2-(1H-pyrazol-1-yl)phenoxy)octahydrocyclopenta[c]pyrrole-2-carbonyl)-1H-pyrazole-3-carboxylic acid as a white solid. $^1$H NMR: (300 MHz, MeOH-d$_4$) δ 8.25 (d, J=2.7 Hz, 1H), 8.14 (d, J=2.1 Hz, 1H), 7.71 (d, J=1.8 Hz, 1H), 7.57-7.54 (m, 1H), 7.41-7.33 (m, 1H), 7.24-7.19 (m, 1H), 7.12-7.05 (m, 1H), 6.79 (d, J=2.7 Hz, 1H), 6.50 (t, J=2.1 Hz, 1H), 5.13-5.08 (m, 1H), 4.35-3.41 (m, 4H), 2.82 (br, 2H), 2.21-2.11 (m, 2H), 2.01-1.89 (m, 2H). LCMS (ESI, m/z):430 [M+Na]$^+$.

Example 30: 1-(trans-5-(3-(Pyrimidin-4-yl)phenoxy) octahydrocyclopenta[c]pyrrole-2-carbonyl)-1H-pyrazole-3-carboxylic Acid

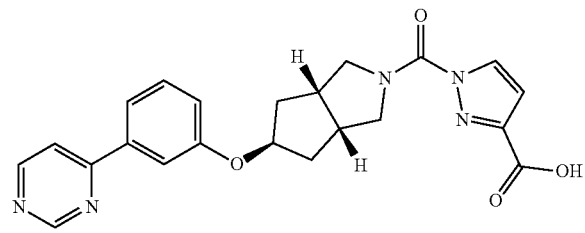 [SMILES: O=C(O)c1ccn(C(=O)N2C[C@H]3C[C@H](Oc4cccc(-c5ccncn5)c4)C[C@H]3C2)n1]

Step 1: Preparation of di-t-butyl 1H-pyrazole-1,3-dicarboxylate

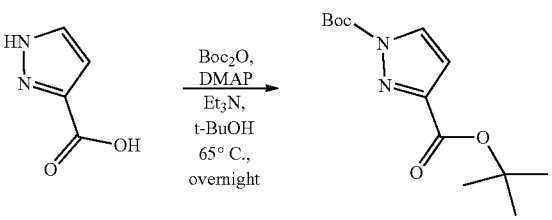

A flask was charged with 1H-pyrazole-3-carboxylic acid (20.0 g, 179 mmol, 1.00 equiv), di-t-butyl dicarbonate (158 g, 714 mmol, 4.00 equiv), DMAP (4.35 g, 35.7 mmol, 0.20 equiv), triethylamine (54.1 g, 536 mmol, 3.00 equiv) and t-butanol (200 mL). The resulting solution was stirred overnight at 65° C. and quenched by water (200 mL) as described in Example 1, Step 1 to provide 20.0 g (crude) of di-t-butyl 1H-pyrazole-1,3-dicarboxylate as a yellow oil. LCMS (ESI, m/z): 169 [M+H-Boc]$^+$.

Step 2: Preparation of t-butyl 1H-pyrazole-3-carboxylate

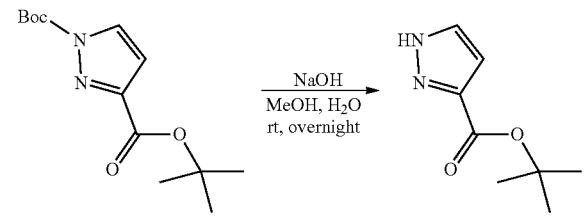 [SMILES: CC(C)(C)OC(=O)c1ccn(C(=O)OC(C)(C)C)n1 ; "NaOH" ; CC(C)(C)OC(=O)c1cc[nH]n1]

A flask was charged with di-t-butyl 1H-pyrazole-1,3-dicarboxylate (20.0 g, 74.6 mmol, 1.00 equiv), MeOH (80 mL), sodium hydroxide (10.0 g, 250 mmol, 3.35 equiv) and water (40 mL). The resulting solution was stirred overnight at room temperature and quenched by water (40 mL) as described in Example 1, Step 2 to provide 6.70 g (crude) of t-butyl-1H-pyrazole-3-carboxylate as a yellow solid. LCMS (ESI, m/z): 169 [M+H]$^+$.

Step 3: Preparation of 3-(t-butyl) 1-(4-nitrophenyl) 1H-pyrazole-1,3-dicarboxylate

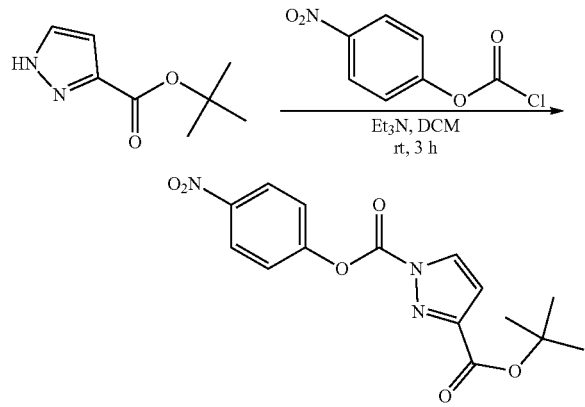

A flask was charged with t-butyl 1H-pyrazole-3-carboxylate (1.68 g, 9.99 mmol, 1.00 equiv), DCM (20 mL) and triethylamine (3.03 g, 29.9 mmol, 3.00 equiv). 4-Nitrophenyl chloroformate (2.42 g, 12.0 mmol, 1.20 equiv) was added at 0° C. The resulting solution was stirred for 3 h at room temperature and concentrated under reduced pressure as described in Example 4, Step 3 to provide 3.33 g (crude) of 3-(t-butyl) 1-(4-nitrophenyl) 1H-pyrazole-1,3-dicarboxylate as a yellow solid.

Step 4: Preparation of t-butyl (3aR,5r,6aS)-5-hydroxyhexahydrocyclopenta[c]pyrrole-2(1H)-carboxylate

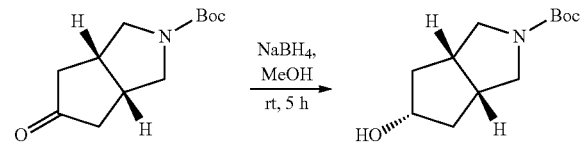 [SMILES: CC(C)(C)OC(=O)N1C[C@H]2CC(=O)C[C@H]2C1 ; CC(C)(C)OC(=O)N1C[C@H]2C[C@@H](O)C[C@H]2C1]

A flask was charged with t-butyl (3aR,6aS)-5-oxohexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure. The resulting mixture was diluted with water (40 mL), extracted with EtOAc (3×50 mL) and the organic layers were combined, washed with water (3×20 mL), dried over anhydrous sodium sulfate, filtered and concentrated under reduced pressure as described in Example 15, Step 4 to provide 3.01 g (crude) of t-butyl (3aR,5r,6aS)-5-hydroxyhexahydrocyclopenta[c]pyrrole-2(1H)-carboxylate as a white solid. LCMS (ESI, m/z): 228 [M+H]$^+$.

Step 5: Preparation of t-butyl (3aR,5r,6aS)-5-((methylsulfonyl)oxy)hexahydrocyclopenta[c]pyrrole-2(1H)-carboxylate

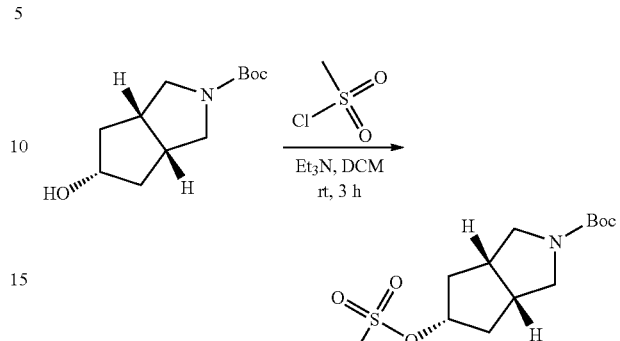

A flask was charged with t-butyl (3aR,5r,6aS)-5-hydroxyhexahydrocyclopenta[c]pyrrole-2(1H)-carboxylate (1.00 g, 4.40 mmol, 1.00 equiv), DCM (20 mL) and triethylamine (1.34 g, 13.2 mmol, 3.00 equiv). Methanesulfonyl chloride (0.608 g, 5.28 mmol, 1.20 equiv) was added dropwise at 0° C. The resulting solution was stirred for 3 h at room temperature and concentrated under reduced pressure as described in Example 4, Step 3 to provide 1.34 g (crude) of t-butyl (3aR,5r,6aS)-5-((methylsulfonyl)oxy)hexahydrocyclopenta[c]pyrrole-2(1H)-carboxylate as a yellow oil. LCMS (ESI, m/z): 306 [M+H]$^+$.

Step 6: Preparation of 4-(3-bromophenyl)pyrimidine

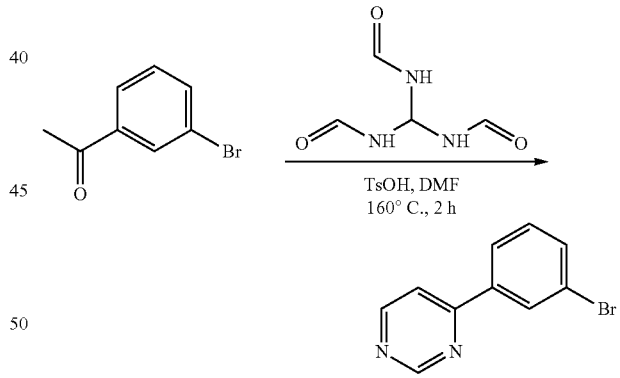

A vial was charged with N-(diformamidomethyl)formamide (1.45 g, 9.99 mmol, 1.00 equiv), 1-(3-bromophenyl)ethan-1-one (4.00 g, 20.10 mmol, 2.00 equiv), 4-methylbenzenesulfonic acid (172 mg, 1.00 mmol, 0.05 equiv) and DMF (10 mL). The resulting solution was stirred for 2 h at 160° C. and quenched by water (10 mL). The mixture was extracted with EtOAc (3×30 mL) and the organic layers were combined, washed with brine (2×10 mL), dried over anhydrous sodium sulfate, filtered and concentrated under reduced pressure. The residue was chromatographed on a silica gel column to provide 1.05 g (45% yield) of 4-(3-bromophenyl)pyrimidine as a white solid. LCMS (ESI, m/z): 235 [M+H]$^+$.

Step 7: Preparation of 3-(pyrimidin-4-yl)phenol

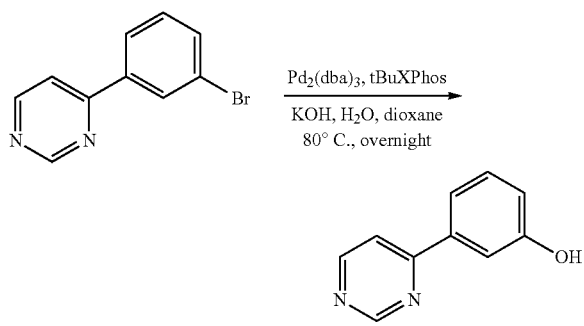

A vial was charged with 4-(3-bromophenyl)pyrimidine (940 mg, 4.00 mmol, 1.00 equiv), 2-di-t-butylphosphino-2', 4',6'-tri-i-propyl-1,1'-biphenyl (339 mg, 0.800 mmol, 0.20 equiv), potassium hydroxide (896 mg, 16.0 mmol, 4.00 equiv), tris(dibenzylideneacetone)dipalladium (414 mg, 0.450 mmol, 0.10 equiv), dioxane (10 mL) and water (10 mL) under $N_2$ atmosphere. The resulting solution was stirred overnight at 80° C. and quenched by water (10 mL). The mixture was extracted with EtOAc (3×30 mL) and the organic layers were combined, washed with water (3×10 mL), dried over anhydrous sodium sulfate, filtered and concentrated under reduced pressure. The residue was chromatographed on a silica gel column to provide 460 mg (67% yield) of 3-(pyrimidin-4-yl)phenol as a yellow solid. LCMS (ESI, m/z): 173 [M+H]$^+$.

Step 8: Preparation of t-butyl (3aR,5s,6aS)-5-(3-(pyrimidin-4-yl)phenoxy)hexahydrocyclopenta[c]pyrrole-2(1H)-carboxylate

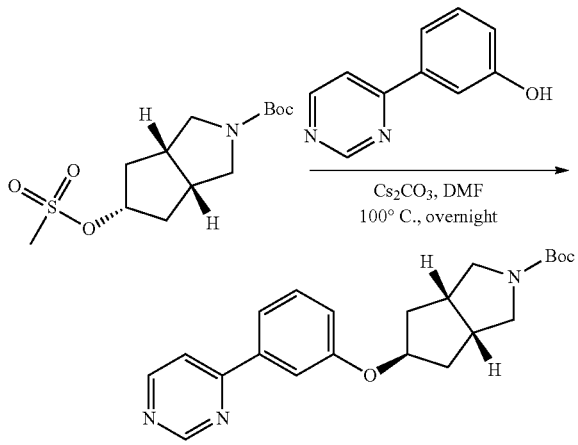

A flask was charged with 3-(pyrimidin-4-yl)phenol (172 mg, 1.00 mmol, 1.00 equiv), t-butyl (3aR,5r,6aS)-5-((methylsulfonyl)oxy)hexahydrocyclopenta[c]pyrrole-2(1H)-carboxylate (305 mg, 1.00 mmol, 1.00 equiv), cesium carbonate (978 mg, 3.00 mmol, 3.00 equiv) and DMF (15 mL). The resulting solution was stirred overnight at 100° C. and quenched by water (40 mL) as described in Example 13, Step 4. The residue was chromatographed on a silica gel column to provide 263 mg (69% yield) of t-butyl (3aR,5 s,6aS)-5-(3-(pyrimidin-4-yl)phenoxy)hexahydrocyclopenta[c]pyrrole-2(1H)-carboxylate as a colorless oil. LCMS (ESI, m/z): 382 [M+H]$^+$.

Step 9: Preparation of (3aR,5s,6aS)-5-(3-(pyrimidin-4-yl)phenoxy)octahydrocyclopenta[c]pyrrole

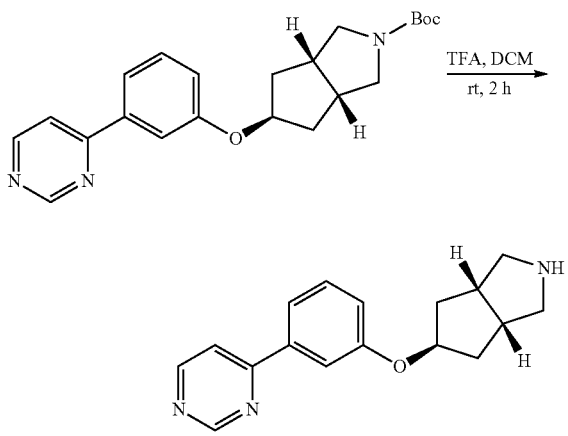

A flask was charged with t-butyl (3aR,5s,6aS)-5-(3-(pyrimidin-4-yl)phenoxy)hexahydrocyclopenta[c]pyrrole-2 (1H)-carboxylate (263 mg, 0.690 mmol, 1.00 equiv), TFA (2 mL) and DCM (10 mL). The resulting solution was stirred for 2 h at room temperature and concentrated under reduced pressure as described in Example 1, Step 5 to provide 267 mg (quantitative) of (3aR,5s,6aS)-5-(3-(pyrimidin-4-yl)phenoxy)octahydrocyclopenta[c]pyrrole as a light yellow oil. LCMS (ESI, m/z): 282 [M+H]$^+$.

Step 10: Preparation of t-butyl 1-((3aR,5s,6aS)-5-(3-(pyrimidin-4-yl)phenoxy)octahydrocyclopenta[c]pyrrole-2-carbonyl)-1H-pyrazole-3-carboxylate

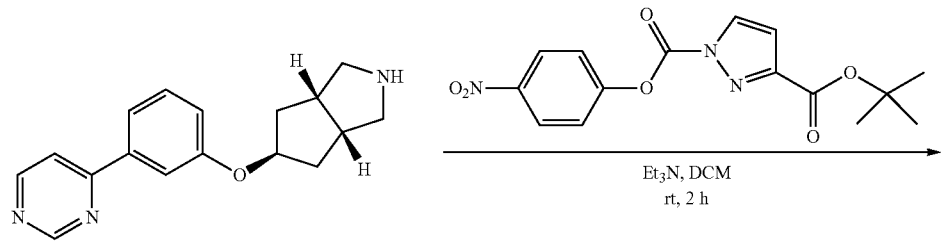

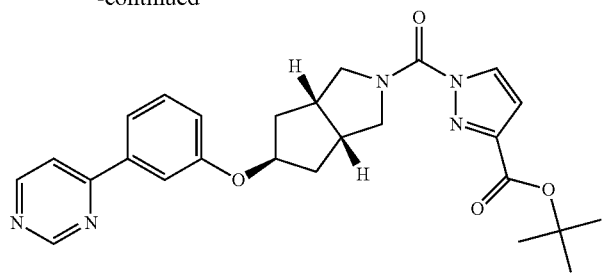

A vial was charged with (3aR,5s,6aS)-5-(3-(pyrimidin-4-yl)phenoxy)octahydrocyclopenta[c]pyrrole (267 mg, 0.950 mmol, 1.00 equiv), triethylamine (576 mg, 5.70 mmol, 6.00 equiv), 3-(t-butyl) 1-(4-nitrophenyl) 1H-pyrazole-1,3-dicarboxylate (476 mg, 1.43 mmol, 1.50 equiv) and DCM (15 mL). The resulting solution was stirred overnight at room temperature. The mixture was quenched by water (10 mL), extracted with DCM (3×20 mL) and the organic layers were combined, washed with brine (2×20 mL), dried over anhydrous sodium sulfate, filtered and concentrated under reduced pressure as described in Example 4, Step 3. The residue was chromatographed on a silica gel column to provide 302 mg (67% yield) of t-butyl 1-((3aR,5s,6aS)-5-(3-(pyrimidin-4-yl)phenoxy)octahydrocyclopenta[c]pyrrole-2-carbonyl)-1H-pyrazole-3-carboxylate as a colorless oil. LCMS (ESI, m/z): 476 [M+H]+.

Step 11: Preparation of 1-(trans-5-(3-(pyrimidin-4-yl)phenoxy)octahydrocyclopenta[c]pyrrole-2-carbonyl)-1H-pyrazole-3-carboxylic Acid

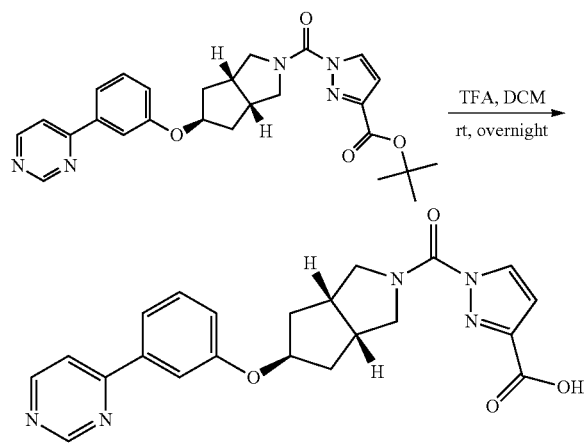

A vial was charged with t-butyl 1-((3aR,5s,6aS)-5-(3-(pyrimidin-4-yl)phenoxy)-octahydrocyclopenta[c]pyrrole-2-carbonyl)-1H-pyrazole-3-carboxylate (238 mg, 0.500 mmol, 1.00 equiv), TFA (2 mL) and DCM (5 mL). The resulting solution was stirred for 2 h at room temperature and concentrated under reduced pressure as described in Example 1, Step 5. The crude product was purified by preparative HPLC to provide 131.3 mg (63% yield) of 1-(trans-5-(3-(pyrimidin-4-yl)phenoxy)octahydrocyclopenta[c]pyrrole-2-carbonyl)-1H-pyrazole-3-carboxylic acid as a white solid. 1H NMR: (400 MHz, MeOH-d4) δ 9.16 (s, 1H), 8.78-8.72 (m, 1H), 8.18-8.12 (d, J=2.8 Hz, 1H), 8.01-7.91 (m, 1H), 7.72-7.65 (m, 2H), 7.44-7.37 (m, 1H), 7.12-7.08 (m, 1H), 6.78-6.72 (d, J=2.4 Hz, 1H), 5.12-5.08 (m, 1H), 4.28-3.61 (m, 4H), 2.98 (br, 2H), 2.25-2.11 (m, 2H), 2.09-1.95 (m, 2H). LCMS (ESI, m/z): 420 [M+H]+.

Example 31: 1-(2-(3-(Pyrimidin-5-yloxy)benzyl)-2,8-diazaspiro[4.5]decane-8-carbonyl)-1H-pyrazole-3-carboxylic Acid

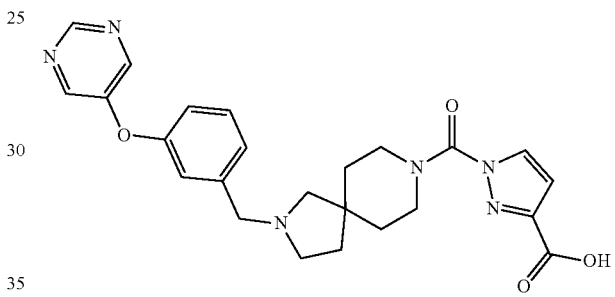

Step 1: Preparation of 3-(pyrimidin-5-yloxy)benzaldehyde

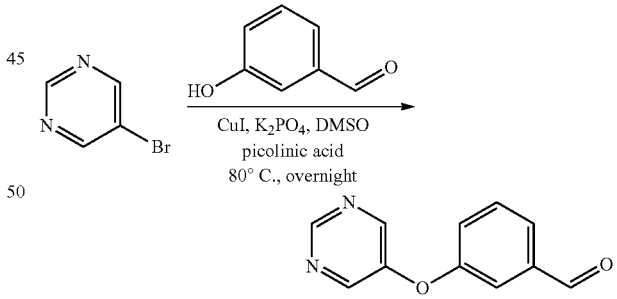

A vial was charged with 5-bromopyrimidine (500 mg, 3.14 mmol, 1.00 equiv), copper(I) iodide (30.0 mg, 0.160 mmol, 0.05 equiv), picolinic acid (38.9 mg, 0.320 mmol, 0.10 equiv), 3-hydroxybenzaldehyde (463 mg, 3.79 mmol, 1.20 equiv), potassiumphosphatetribasic (1.30 g, 6.13 mmol, 2.00 equiv), and DMSO (15 mL). The resulting solution was stirred overnight at 80° C. and quenched with water (20 mL). The resulting solution was extracted with EtOAc (3×20 mL) and the organic layers were combined, washed with brine (2×20 mL), dried over anhydrous sodium sulfate, filtered and concentrated under reduced pressure. The residue was chromatographed on a silica gel column to provide 130 mg (21% yield) of 3-(pyrimidin-5-yloxy)benzaldehyde as a yellow oil. LCMS (ESI, m/z): 201 [M+H]+.

Step 2: Preparation of t-butyl 8-(3-(t-butoxycarbonyl)-1H-pyrazole-1-carbonyl)-2,8-diazaspiro[4.5]decane-2-carboxylate

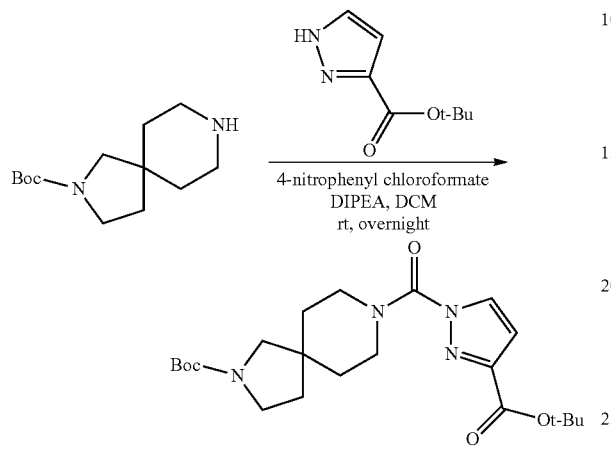

A flask was charged with t-butyl 1H-pyrazole-3-carboxylate (3.15 g, 18.8 mmol, 1.50 equiv), DCM (20 mL), 4-nitrophenyl chloroformate (3.80 g, 18.8 mmol, 1.50 equiv), and DIPEA (4.83 g, 37.5 mmol, 3.00 equiv). The resulting solution was stirred for 3 h at room temperature. t-Butyl 2,8-diazaspiro[4.5]decane-2-carboxylate (3.00 g, 12.5 mmol, 1.00 equiv) was added. The resulting solution was stirred overnight at room temperature and quenched with water (20 mL). The mixture was extracted with DCM (3×20 mL) and the organic layers were combined, washed with brine (2×25 mL), dried over anhydrous sodium sulfate, filtered and concentrated under reduced pressure. The residue was chromatographed on a silica gel column to provide 4.00 g (74% yield) of t-butyl 8-(3-(t-butoxycarbonyl)-1H-pyrazole-1-carbonyl)-2,8-diazaspiro[4.5]decane-2-carboxylate as a light yellow solid. LCMS (ESI, m/z): 435 [M+H]+.

Step 3: Preparation of 1-(2,8-diazaspiro[4.5]decane-8-carbonyl)-1H-pyrazole-3-carboxylic acid

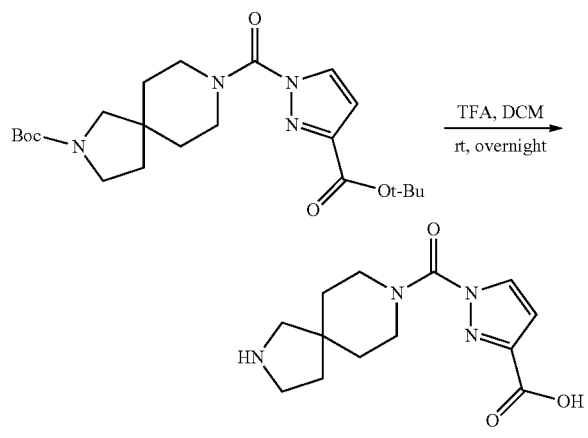

A flask was charged with t-butyl 8-(3-(t-butoxycarbonyl)-1H-pyrazole-1-carbonyl)-2,8-diazaspiro[4.5]decane-2-carboxylate (380 mg, 0.870 mmol, 1.00 equiv), DCM (10 mL), and TFA (3 mL), as described in Example 1, Step 5. The resulting solution was stirred overnight at room temperature and concentrated under reduced pressure to provide 242 mg (quantitative) of 1-(2,8-diazaspiro[4.5]decane-8-carbonyl)-1H-pyrazole-3-carboxylic acid as a yellow oil. LCMS (ESI, m/z): 279 [M+H]+.

Step 4: Preparation of 1-(2-(3-(pyrimidin-5-yloxy)benzyl)-2,8-diazaspiro[4.5]decane-8-carbonyl)-1H-pyrazole-3-carboxylic Acid

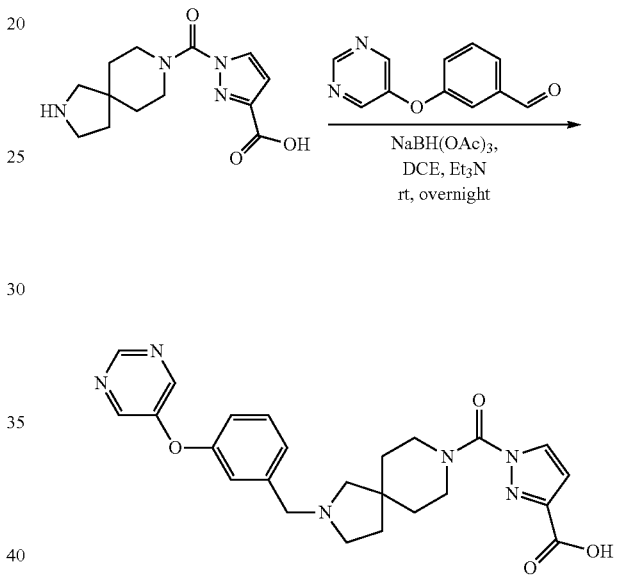

A flask was charged with 3-(pyrimidin-5-yloxy)benzaldehyde (130 mg, 0.650 mmol, 1.00 equiv), 1-(2,8-diazaspiro[4.5]decane-8-carbonyl)-1H-pyrazole-3-carboxylic acid (217 mg, 0.780 mmol, 1.20 equiv), triethylamine (196 mg, 1.94 mmol, 3.00 equiv), and DCE (10 mL). The mixture was stirred for 0.5 h at room temperature. Sodium triacetoxyborohydride (413 mg, 1.95 mmol, 3.00 equiv) was added. The resulting solution was stirred overnight at room temperature and quenched with saturated NaHCO$_3$ solution (20 mL), as described in Example 2, Step 3 to provide the crude product. The crude product (400 mg) was purified by preparative HPLC to provide 30.7 mg (10% yield) of 1-(2-(3-(pyrimidin-5-yloxy)benzyl)-2,8-diazaspiro[4.5]decane-8-carbonyl)-1H-pyrazole-3-carboxylic acid as a white solid. $^1$H NMR (300 MHz, MeOH-d$_4$) δ 8.90 (s, 1H), 8.54 (d, J=6.0 Hz, 2H), 8.03 (d, J=2.7 Hz, 1H), 7.50 (m, 1H), 7.39 (d, J=7.5 Hz, 1H), 7.34 (s, 1H), 7.21-7.18 (m, 1H), 6.72 (d, J=2.7 Hz, 1H), 4.26 (s, 2H), 3.83-3.65 (m, 4H), 3.33-3.28 (m, 2H), 3.15 (s, 2H), 2.01 (t, J=7.2 Hz, 2H), 1.82-1.72 (m, 4H). LCMS (ESI, m/z): 463 [M+H]+.

245

Example 32: 1-(1-(3-(1H-pyrazol-1-yl)-5-(Trifluoromethyl)benzyl)-1,8-diazaspiro[4.5]decane-8-carbonyl)-1H-pyrazole-3-carboxylic Acid

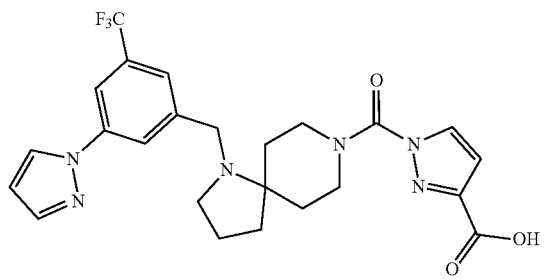 [SMILES: O=C(O)c1ccn(C(=O)N2CCC3(CCCN3Cc3cc(-n4cccn4)cc(C(F)(F)F)c3)CC2)n1]

Step 1: Preparation of 3-(t-butyl) 1-(4-nitrophenyl) 1H-pyrazole-1,3-dicarboxylate

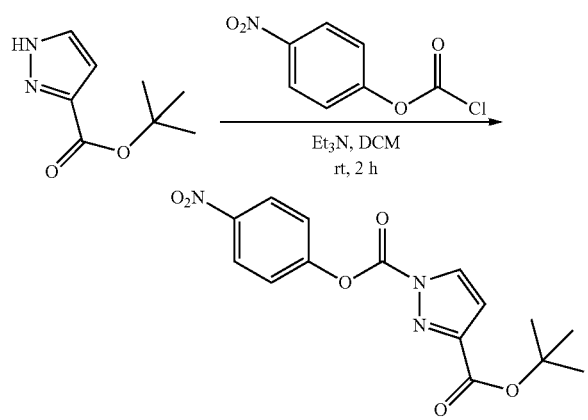

A flask was charged with t-butyl 1H-pyrazole-3-carboxylate (70.0 mg, 0.420 mmol, 1.00 equiv), DCM (10 mL), triethylamine (126 mg, 1.25 mmol, 3.00 equiv). 4-Nitrophenyl carbonochloridate (92.1 mg, 0.460 mmol, 1.10 equiv) was added at 0° C. The resulting solution was stirred for 2 h at room temperature and concentrated under reduced pressure as described in Example 4, Step 3 to provide 137 mg (crude) of 3-(t-butyl) 1-(4-nitrophenyl) 1H-pyrazole-1,3-dicarboxylate as a yellow oil. LCMS (ESI, m/z): 334 [M+H]$^+$.

Step 2: Preparation of t-butyl 1-(3-bromo-5-(trifluoromethyl)benzyl)-1,8-diazaspiro[4.5]decane-8-carboxylate

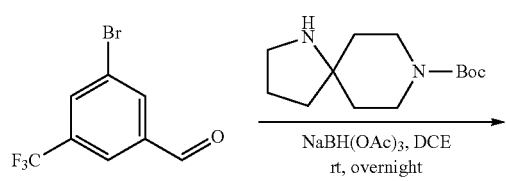

246

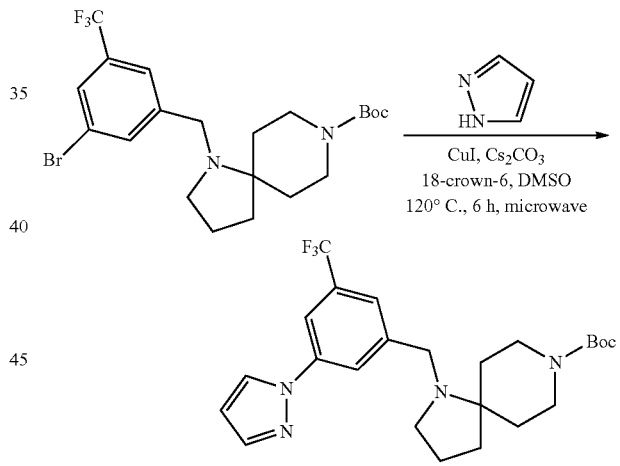

A flask was charged with 3-bromo-5-(trifluoromethyl)benzaldehyde (0.504 g, 1.99 mmol, 1.00 equiv), t-butyl 1,8-diazaspiro[4.5]decane-8-carboxylate (0.576 g, 2.40 mmol, 1.20 equiv) and DCE (20 mL). The mixture was stirred for 1 h at room temperature. Sodium triacetoxyborohydride (1.27 g, 5.99 mmol, 3.00 equiv) was added. The resulting solution was stirred overnight at room temperature and quenched with water (20 mL), as described in Example 2, Step 3. The residue was chromatographed on a silica gel column to provide 0.790 g (83% yield) of t-butyl 1-(3-bromo-5-(trifluoromethyl)benzyl)-1,8-diazaspiro[4.5]decane-8-carboxylate as a yellow oil. LCMS (ESI, m/z): 477 [M+H]$^+$.

Step 3: Preparation of t-butyl 1-(3-(1H-pyrazol-1-yl)-5-(trifluoromethyl)benzyl)-1,8-diazaspiro[4.5]decane-8-carboxylate A microwave tube was charged with t-butyl 1-(3-bromo-5-(trifluoromethyl)benzyl)-1,8-diazaspiro[4.5]decane-8-carboxylate (0.600 g, 1.26 mmol, 1.00 equiv), 1H-pyrazole (0.128 g, 1.88 mmol, 1.50 equiv), copper(I) iodide (0.0479 g, 0.250 mmol, 0.20 equiv), cesium carbonate (1.23 g, 3.78 mmol, 3.00 equiv), 1,4,7,10,13,16-hexaoxacyclooctadecane (0.0333 g, 0.130 mmol, 0.10 equiv), and dimethyl sulfoxide (10 mL) under nitrogen. The resulting solution was stirred for 6 h at 120° C. under microwave and quenched with water (20 mL). The resulting solution was extracted with EtOAc (3×30 mL) and the organic layers were combined, washed with brine (1×50 mL), dried over anhydrous sodium sulfate, filtered and concentrated under reduced pressure. The residue was chromatographed on a silica gel column to provide 0.100 g (17% yield) of t-butyl 1-(3-(1H-pyrazol-1-yl)-5-(trifluoromethyl)benzyl)-1,8-diazaspiro[4.5]decane-8-carboxylate as a yellow oil. LCMS (ESI, m/z): 465 [M+H]$^+$.

Step 4: Preparation of 1-(3-(1H-pyrazol-1-yl)-5-(trifluoromethyl)benzyl)-1,8-diazaspiro[4.5]decane

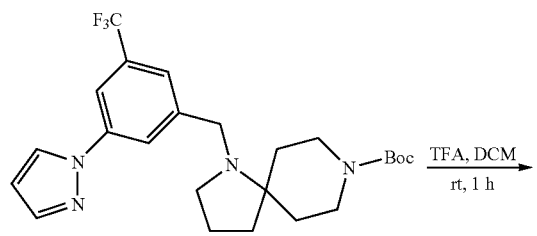

A flask was charged with t-butyl 1-[[3-(1H-pyrazol-1-yl)-5-(trifluoromethyl)phenyl]methyl]-1,8-diazaspiro[4.5]decane-8-carboxylate (100 mg, 0.220 mmol, 1.00 equiv), DCM (15 mL), and TFA (1 mL). The resulting solution was stirred for 1 h at room temperature and concentrated under reduced pressure to provide 78.4 mg (quantitative) of 1-(3-(1H-pyrazol-1-yl)-5-(trifluoromethyl)benzyl)-1,8-diazaspiro[4.5]decane as a yellow oil. LCMS (ESI, m/z): 365 [M+H]$^+$.

Step 5: Preparation of t-butyl 1-(1-(3-(1H-pyrazol-1-yl)-5-(trifluoromethyl)benzyl)-1,8-diazaspiro[4.5]decane-8-carbonyl)-1H-pyrazole-3-carboxylate

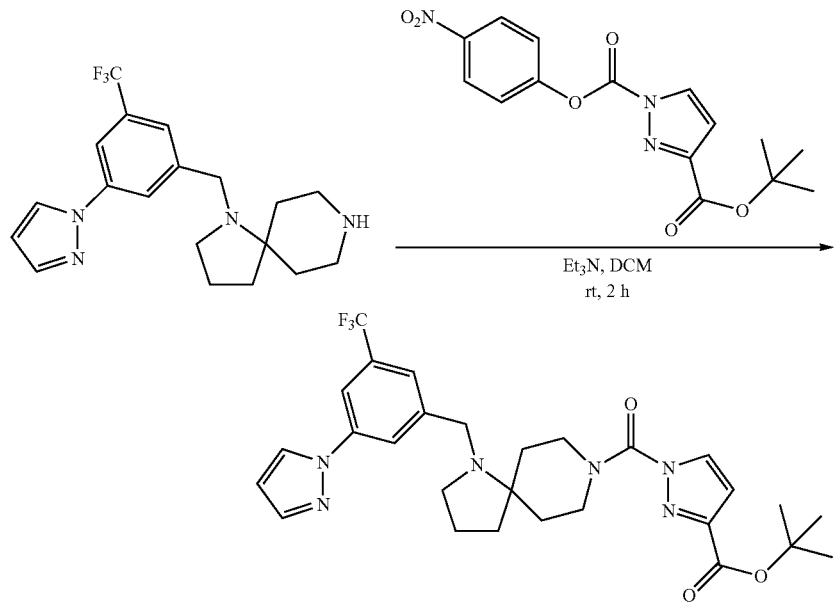

A flask was charged with 1-(3-(1H-pyrazol-1-yl)-5-(trifluoromethyl)benzyl)-1,8-diazaspiro[4.5]decane (78.4 mg, 0.220 mmol, 1.00 equiv), 3-(t-butyl) 1-(4-nitrophenyl) 1H-pyrazole-1,3-dicarboxylate (108 mg, 0.320 mmol, 1.50 equiv), triethylamine (65.3 mg, 0.650 mmol, 3.00 equiv), and DCM (10 mL). The resulting solution was stirred for 2 h at room temperature and quenched with water (15 mL), as described in Example 4, Step 3. The residue was chromatographed on a silica gel column to provide 96.0 mg (80% yield) of t-butyl 1-(1-(3-(1H-pyrazol-1-yl)-5-(trifluoromethyl)benzyl)-1,8-diazaspiro[4.5]decane-8-carbonyl)-1H-pyrazole-3-carboxylate as a yellow oil. LCMS (ESI, m/z): 559 [M+H]$^+$.

Step 6: Preparation of 1-(1-(3-(1H-pyrazol-1-yl)-5-(trifluoromethyl)benzyl)-1,8-diazaspiro[4.5]decane-8-carbonyl)-1H-pyrazole-3-carboxylic acid

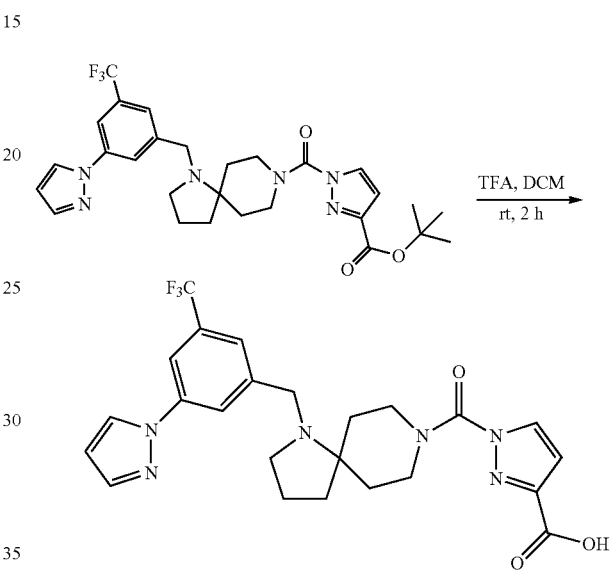

A flask was charged with t-butyl 1-(1-(3-(1H-pyrazol-1-yl)-5-(trifluoromethyl)benzyl)-1,8-diazaspiro[4.5]decane-8-carbonyl)-1H-pyrazole-3-carboxylate (96.0 mg, 0.170 mmol, 1.00 equiv), DCM (7 mL), and TFA (1 mL). The resulting solution was stirred for 2 h at room temperature and concentrated under reduced pressure. The crude product was dissolved in DCM (15 mL). The pH value of the solution was adjusted to 8 with saturated NaHCO$_3$ solution. The mixture was extracted with DCM (3×20 mL) and the organic layers were combined, washed with brine (2×15 mL), dried over anhydrous sodium sulfate, filtered and concentrated under reduced pressure, as described in Example 1, Step 5. The crude product (230 mg) was purified by preparative HPLC to provide 46.1 mg (53% yield) of 1-(1-(3-(1H-pyrazol-1-yl)-5-(trifluoromethyl)benzyl)-1,8-diazaspiro[4.5]decane-8-carbonyl)-1H-pyrazole-3-carboxylic acid as a white solid. $^1$H NMR (400 MHz, MeOH-d$_4$) δ 8.41 (d, J=2.4 Hz, 1H), 8.18 (s, 1H), 8.13-8.11 (m, 2H), 7.79-7.74 (m, 2H), 6.82 (d, J=2.4 Hz, 1H), 6.60 (s, 1H), 4.63 (br, 2H), 4.19 (s, 2H), 3.33-3.20 (m, 2H), 3.10-3.08 (m, 2H), 2.24-2.15 (m, 4H), 2.04-1.99 (m, 2H), 1.79-1.76 (m, 2H). LCMS (ESI, m/z): 503 [M+H]$^+$.

Example 33: 4-Chloro-1-((2S)-2-methyl-4-(methyl (2-(pyrrolidin-1-yl)-4-(trifluoromethyl)benzyl) amino)piperidine-1-carbonyl)-1H-pyrazole-3-carboxylic acid

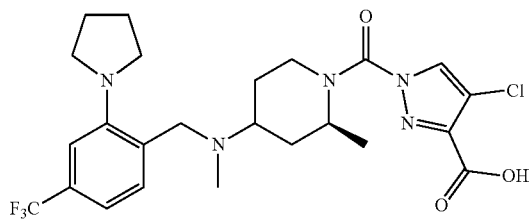 [SMILES: C[C@H]1CC(N(C)Cc2ccc(C(F)(F)F)cc2N2CCCC2)CCN1C(=O)n1cc(Cl)c(C(=O)O)n1]

Step 1: Preparation t-butyl 4-chloro-1H-pyrazole-3-carboxylate

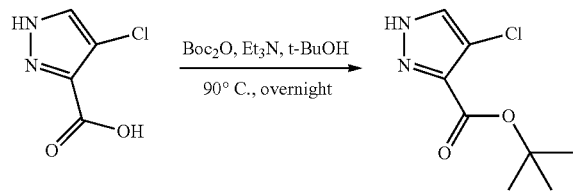

A flask was charged with 4-chloro-1H-pyrazole-3-carboxylic acid (1.60 g, 10.9 mmol, 1.00 equiv), t-butanol (100 mL), di-t-butyl dicarbonate (9.50 g, 43.6 mmol, 4.00 equiv), triethylamine (3.30 g, 32.7 mmol, 3.00 equiv). The resulting solution was stirred overnight at 90° C. and quenched with water (100 mL), as described in Example 1, Step 1. The residue was chromatographed on a silica gel column to provide 800 mg (36% yield) of t-butyl 4-chloro-1H-pyrazole-3-carboxylate as a yellow solid. LCMS (ESI, m/z): 405 [2M+H]$^+$.

Step 2: Preparation of t-butyl (2S)-2-methyl-4-(methylamino)piperidine-1-carboxylate

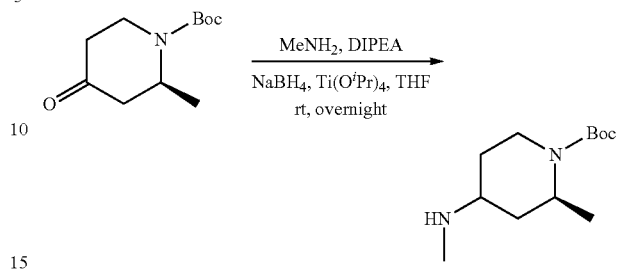

A flask was charged with t-butyl (2S)-2-methyl-4-oxopiperidine-1-carboxylate (300 mg, 1.41 mmol, 1.00 equiv), methylamine (5.00 mL, 2.82 mmol, 2.00 equiv, 2 M in THF), DIPEA (545 mg, 4.23 mmol, 3.00 equiv), and titanium tetraisopropoxide (4 mL). The mixture was stirred for 1 h at room temperature. Sodiumtetrahydroborate (54.0 mg, 1.41 mmol, 1.00 equiv) was added. The resulting solution was stirred overnight at room temperature and quenched with water (30 mL). The mixture was extracted with DCM (3×50 mL) and the organic layers were combined, washed with brine (3×30 mL), dried over anhydrous sodium sulfate, filtered and concentrated under reduced pressure. The residue was chromatographed on a silica gel column to provide 250 mg (78% yield) of t-butyl (2S)-2-methyl-4-(methylamino)piperidine-1-carboxylate as a yellow oil. LCMS (ESI, m/z): 229 [M+H]$^+$.

Step 3: Preparation of 2-(pyrrolidin-1-yl)-4-(trifluoromethyl)benzaldehyde

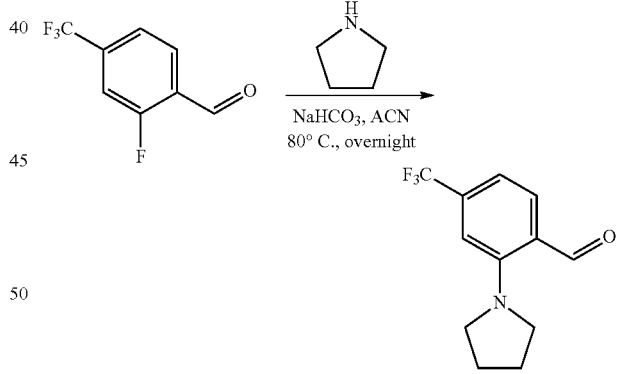

A flask was charged with 2-fluoro-4-(trifluoromethyl) benzaldehyde (4.00 g, 20.8 mmol, 1.00 equiv), ACN (15 mL), pyrrolidine (2.21 g, 31.0 mmol, 1.50 equiv), and sodium bicarbonate (4.37 g, 52.0 mmol, 2.50 equiv). The resulting solution was stirred overnight at 80° C. and quenched with water (30 mL). The resulting solution was extracted with EtOAc (3×50 mL) and the organic layers were combined, washed with brine (3×30 mL), dried over anhydrous sodium sulfate, filtered and concentrated under reduced pressure. The residue was chromatographed on a silica gel column to provide 2.20 g (43% yield) of 2-(pyrrolidin-1-yl)-4-(trifluoromethyl)benzaldehyde as a yellow oil. LCMS (ESI, m/z): 244 [M+H]$^+$.

Step 4: Preparation of t-butyl (2S)-2-methyl-4-(methyl(2-(pyrrolidin-1-yl)-4-(trifluoromethyl)benzyl)amino)piperidine-1-carboxylate

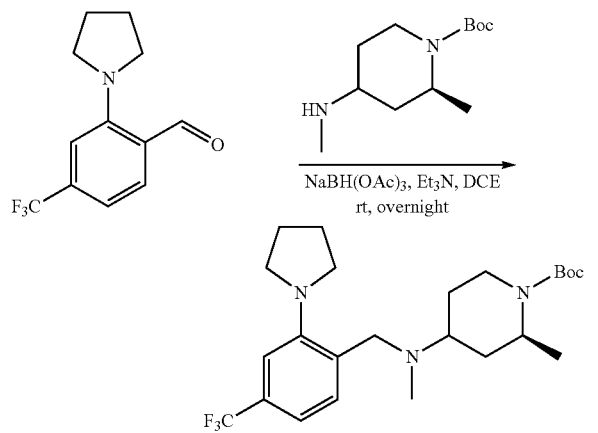

A flask was charged with 2-(pyrrolidin-1-yl)-4-(trifluoromethyl)benzaldehyde (200 mg, 0.820 mmol, 1.00 equiv), DCE (10 mL), t-butyl (2S)-2-methyl-4-(methylamino)piperidine-1-carboxylate (225 mg, 0.990 mmol, 1.20 equiv), triethylamine (249 mg, 2.46 mmol, 3.00 equiv). The mixture was stirred for 1 h at room temperature. Sodium triacetoxyborohydride (523 mg, 2.46 mmol, 3.00 equiv) was added. The resulting solution was stirred overnight at room temperature and quenched with water (30 mL), as described in Example 2, Step 3. The residue was chromatographed on a silica gel column to provide 300 mg (80% yield) of t-butyl (2S)-2-methyl-4-(methyl(2-(pyrrolidin-1-yl)-4-(trifluoromethyl)benzyl)amino)piperidine-1-carboxylate as a yellow oil. LCMS (ESI, m/z): 456 [M+H]$^+$.

Step 5: Preparation of (2S)—N,2-dimethyl-N-(2-(pyrrolidin-1-yl)-4-(trifluoromethyl)benzyl)piperidin-4-amine

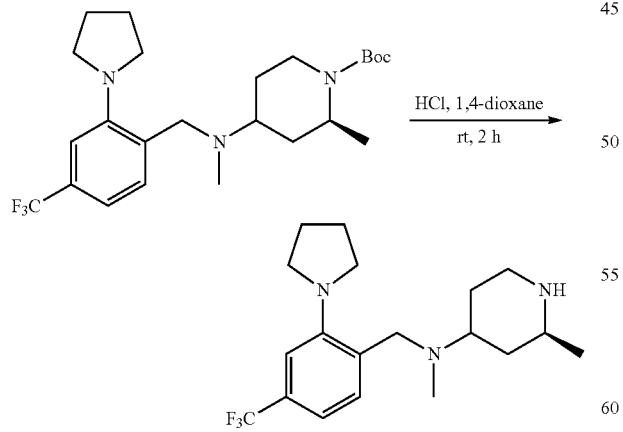

A flask was charged with t-butyl (2S)-2-methyl-4-(methyl (2-(pyrrolidin-1-yl)-4-(trifluoromethyl)benzyl)amino)piperidine-1-carboxylate (300 mg, 0.660 mmol, 1.00 equiv), 1,4-dioxane (8 mL), and concentrated hydrochloric acid (2 mL). The resulting solution was stirred for 2 h at room temperature and concentrated under reduced pressure. The crude product was dissolved in 1M NaOH solution (30 mL) and extracted with DCM (3×50 mL). The organic layers were combined, washed with brine (10 mL), dried over anhydrous sodium sulfate, filtered and concentrated under reduced pressure as described in Example 2, Step 4 to provide 200 mg (85% yield) of (2S)—N,2-dimethyl-N-(2-(pyrrolidin-1-yl)-4-(trifluoromethyl)benzyl)piperidin-4-amine as a yellow oil. LCMS (ESI, m/z): 356 [M+H]$^+$.

Step 6: Preparation of (2S)-2-methyl-4-(methyl(2-(pyrrolidin-1-yl)-4-(trifluoromethyl)benzyl)amino)piperidine-1-carbonyl Chloride

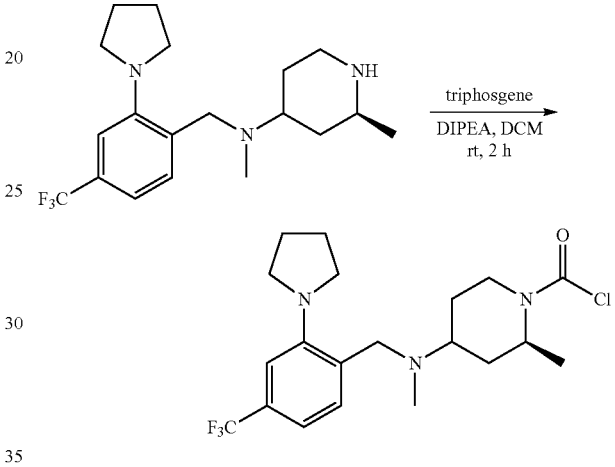

A flask was charged with (2S)—N,2-dimethyl-N-(2-(pyrrolidin-1-yl)-4-(trifluoromethyl)benzyl)piperidin-4-amine (200 mg, 0.560 mmol, 1.00 equiv), DCM (5 mL), and triphosgene (84.0 mg, 0.280 mmol, 0.50 equiv). DIPEA (218 mg, 1.68 mmol, 3.00 equiv) was added at 0° C. The resulting solution was stirred for 2 h at room temperature and concentrated under reduced pressure as described in Example 1, Step 3 to provide 234 mg (crude) of (2S)-2-methyl-4-(methyl(2-(pyrrolidin-1-yl)-4-(trifluoromethyl)benzyl)amino)piperidine-1-carbonyl chloride as a yellow oil. LCMS (ESI, m/z): 418 [M+H]$^+$.

Step 7: Preparation of t-butyl 4-chloro-1-((2S)-2-methyl-4-(methyl(2-(pyrrolidin-1-yl)-4-(trifluoromethyl)benzyl)amino)piperidine-1-carbonyl)-1H-pyrazole-3-carboxylate

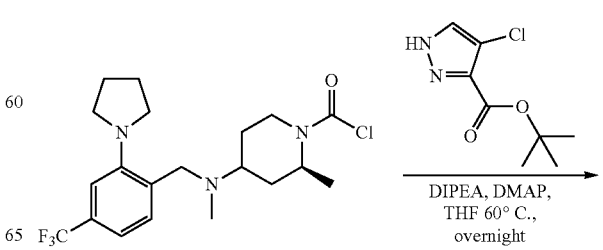

253

-continued

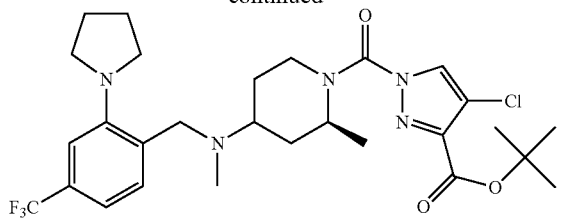

A flask was charged with (2S)-2-methyl-4-(methyl(2-(pyrrolidin-1-yl)-4-(trifluoromethyl)benzyl)amino)piperidine-1-carbonyl chloride (150 mg, 0.360 mmol, 1.00 equiv), THF (5 mL), t-butyl 4-chloro-1H-pyrazole-3-carboxylate (87.0 mg, 0.430 mmol, 1.20 equiv), DMAP (9.00 mg, 0.0700 mmol, 0.20 equiv), DIPEA (201 mg, 1.08 mmol, 3.00 equiv). The resulting solution was stirred overnight at 60° C. and quenched with water (10 mL), extracted with DCM (3×20 mL) and the organic layers were combined, washed with brine (2×20 mL), dried over anhydrous sodium sulfate, filtered and concentrated under reduced pressure, as described in Example 1, Step 4. The residue was chromatographed on a silica gel column to provide 100 mg (48% yield) of t-butyl 4-chloro-1-((2S)-2-methyl-4-(methyl(2-(pyrrolidin-1-yl)-4-(trifluoromethyl)benzyl)amino)piperidine-1-carbonyl)-1H-pyrazole-3-carboxylate as a yellow oil. LCMS (ESI, m/z): 584 [M+H]$^+$.

Step 8: Preparation of 4-chloro-1-((2S)-2-methyl-4-(methyl(2-(pyrrolidin-1-yl)-4-(trifluoromethyl)benzyl)amino)piperidine-1-carbonyl)-1H-pyrazole-3-carboxylic Acid

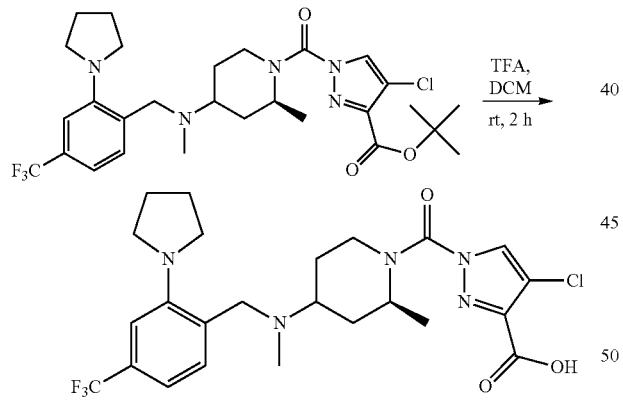

A flask was charged with 4-chloro-1-((2S)-2-methyl-4-(methyl(2-(pyrrolidin-1-yl)-4-(trifluoromethyl)benzyl)amino)piperidine-1-carbonyl)-1H-pyrazole-3-carboxylate (100 mg, 0.170 mmol, 1.00 equiv), DCM (3 mL), and TFA (1 mL). The resulting solution was stirred for 2 h at room temperature and concentrated under reduced pressure. The crude product was dissolved in DCM (20 mL). The pH value of the solution was adjusted to 8 with saturated NaHCO$_3$ solution. The mixture was extracted with DCM (3×50 mL) and the organic layers were combined, washed with brine (2×20 mL), dried over anhydrous sodium sulfate, filtered and concentrated under reduced pressure, as

254 described in Example 1, Step 5. The crude product (150 mg) was purified by preparative HPLC to provide 8.70 mg (10% yield) of 4-chloro-1-((2S)-2-methyl-4-(methyl(2-(pyrrolidin-1-yl)-4-(trifluoromethyl)benzyl)amino)piperidine-1-carbonyl)-1H-pyrazole-3-carboxylic acid as a white solid. $^1$H NMR (400 MHz, MeOH-d$_4$) δ 8.21 (s, 1H), 7.68 (d, J=8.0 Hz, 1H), 7.52 (s, 1H), 7.40 (d, J=7.6 Hz, 1H), 5.11 (br, 1H), 4.58-4.43 (m, 3H), 4.27-3.41 (m, 2H), 3.36-3.19 (m, 4H), 2.73-2.71 (m, 3H), 2.20-1.89 (m, 8H), 1.45-1.35 (m, 3H). LCMS (ESI, m/z): 528 [M+H]$^+$.

Example 34: 1-(trans-5-((3-Cyclopentylbenzyl)oxy)octahydrocyclopenta[c]pyrrole-2-carbonyl)-1H-pyrazole-3-carboxylic Acid

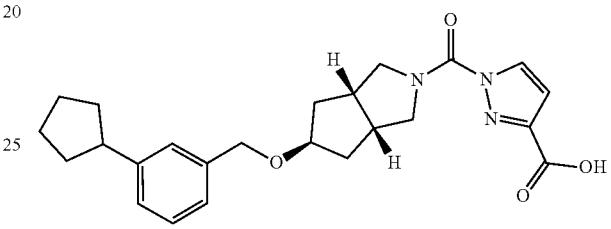

Step 1: Preparation of (3-(cyclopent-1-en-1-yl)phenyl) methanol

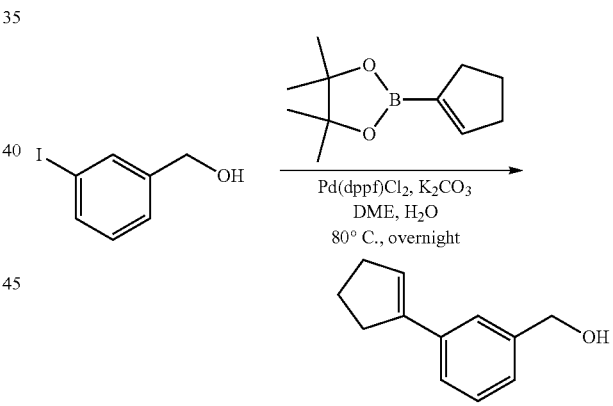

A vial was charged with 2-(cyclopent-1-en-1-yl)-4,4,5,5-tetramethyl-1,3,2-dioxaborolane (747 mg, 3.85 mmol, 1.50 equiv), (3-iodophenyl)MeOH (600 mg, 2.56 mmol, 1.00 equiv), 1,1'-bis(diphenylphosphino)ferrocenepalladiumdichloride (365 mg, 0.500 mmol, 0.20 equiv), potassium carbonate (704 mg, 5.09 mmol, 2.00 equiv), ethylene glycol dimethyl ether (16 mL) and water (4 mL). The resulting solution was stirred overnight at 80° C. and quenched by water (20 mL). The mixture was extracted with EtOAc (3×20 mL) and the organic layers were combined, washed with water (3×20 mL), dried over anhydrous sodium sulfate, filtered and concentrated under reduced pressure, as described in Example 23, Step 6. The residue was chromatographed on a silica gel column to provide 350 mg (78% yield) of (3-(cyclopent-1-en-1-yl)phenyl)MeOH as a yellow oil. LCMS (ESI, m/z): 175 [M+H]$^+$.

Step 2: Preparation of (3-cyclopentylphenyl) methanol

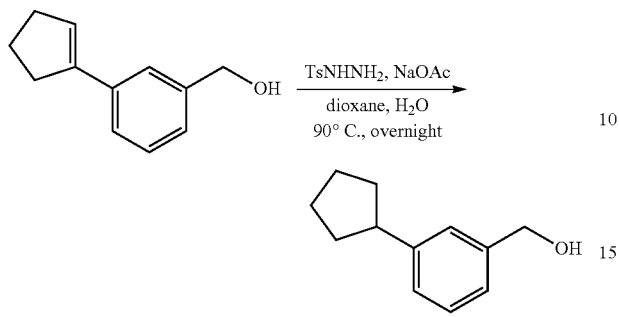

A vial was charged with (3-(cyclopent-1-en-1-yl)phenyl) methanol (0.525 g, 3.01 mmol, 1.00 equiv), 4-methylbenzenesulfonohydrazide (1.12 g, 6.02 mmol, 2.00 equiv), sodiumacetateanhydrous (0.738 g, 9.00 mmol, 3.00 equiv), dioxane (8 mL) and water (2 mL) under $N_2$ atmosphere. The resulting solution was stirred overnight at 90° C. and quenched by water (20 mL). The mixture was extracted with EtOAc (3×20 mL) and the organic layers were combined, washed with water (3×20 mL), dried over anhydrous sodium sulfate, filtered and concentrated under reduced pressure. The residue was chromatographed on a silica gel column to provide 0.130 g (24% yield) of (3-cyclopentylphenyl) methanol as a yellow oil.

Step 3: Preparation of 1-(bromomethyl)-3-cyclopentylbenzene

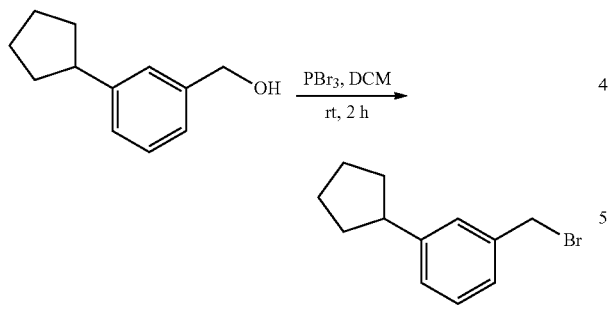

A vial was charged with (3-cyclopentylphenyl) methanol (0.130 g, 0.740 mmol, 1.00 equiv) and DCM (15 mL). Tribromophosphine (1.00 g, 3.69 mmol, 5.00 equiv) was then added dropwise at 0° C. The resulting solution was stirred for 2 h at room temperature and quenched by water (20 mL), as described in Example 27, Step 7. The residue was chromatographed on a silica gel column to provide 0.095 g (54% yield) of 1-(bromomethyl)-3-cyclopentylbenzene as a yellow oil.

Step 4: Preparation of t-butyl (3aR,5r,6aS)-5-hydroxyhexahydrocyclopenta[c]pyrrole-2(1H)-carboxylate

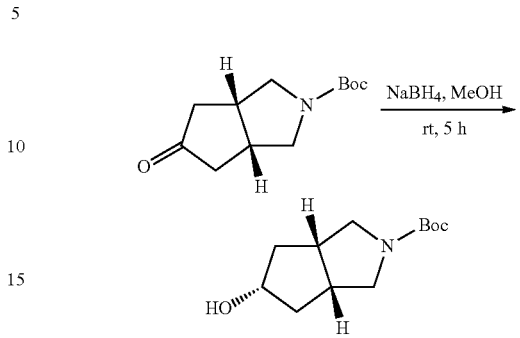

A flask was charged with (3aR,6aS)-t-butyl 5-oxo-hexahydrocyclopenta[c]pyrrole-2(1H)-carboxylate (3.00 g, 13.3 mmol, 1.00 equiv), MeOH (20 mL) and sodium borohydride (0.760 g, 20.1 mmol, 1.50 equiv). The resulting solution was stirred for 5 h at room temperature and concentrated under reduced pressure. The resulting mixture was diluted with water (40 mL), extracted with EtOAc (3×50 mL) and the organic layers were combined, washed with water (3×20 mL), dried over anhydrous sodium sulfate, filtered and concentrated under reduced pressure as described in Example 15, Step 4 to provide 3.01 g (crude) of t-butyl (3aR,5r,6aS)-5-hydroxyhexahydrocyclopenta[c]pyrrole-2 (1H)-carboxylate as a white solid. LCMS (ESI, m/z): 228 $[M+H]^+$.

Step 5: Preparation of t-butyl (3aR,5s,6aS)-5-((4-nitrobenzoyl)oxy)hexahydrocyclopenta[c]pyrrole-2 (1H)-carboxylate

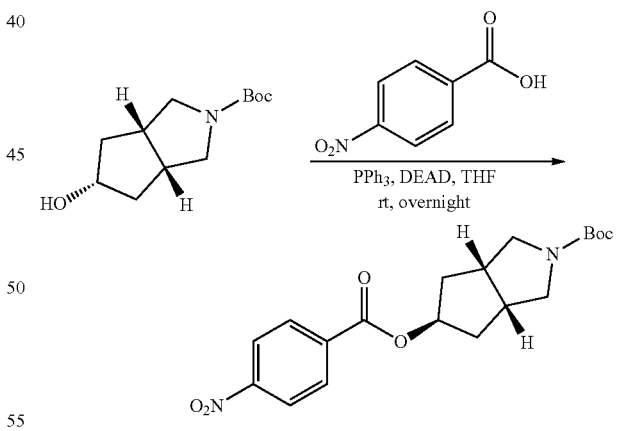

A flask was charged with t-butyl (3aR,5r,6aS)-5-hydroxyhexahydrocyclopenta[c]pyrrole-2(1H)-carboxylate (2.27 g, 9.99 mmol, 1.00 equiv), 4-nitrobenzoic acid (6.68 g, 40.0 mmol, 4.00 equiv), triphenylphosphine (10.5 g, 40.0 mmol, 4.00 equiv) and THF (30 mL). Diethyl azodicarboxylate (6.96 g, 40.0 mmol, 4.00 equiv) was added dropwise at 0° C. The resulting solution was stirred overnight at room temperature under nitrogen atmosphere and quenched by water (50 mL), as described in Example 15, Step 5. The residue was chromatographed on a silica gel column to provide 2.36 g (62% yield) of t-butyl (3aR,5s,6aS)-5-(4- nitrobenzoyl)oxy)hexahydrocyclopenta[c]pyrrole-2(1H)-carboxylate as a white solid. LCMS (ESI, m/z): 377 [M+H]⁺.

Step 6: Preparation of t-butyl (3aR,5s,6aS)-5-hydroxyhexahydrocyclopenta[c]pyrrole-2(1H)-carboxylate

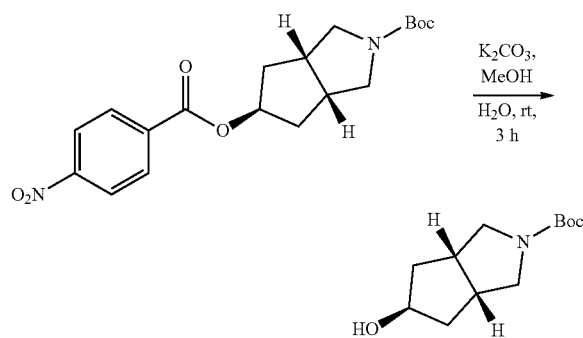

A flask was charged with t-butyl (3aR,5s,6aS)-5-(4-nitrobenzoyl)oxy)hexahydrocyclopenta[c]pyrrole-2(1H)-carboxylate (2.36 g, 6.27 mmol, 1.00 equiv), MeOH (30 mL), potassium carbonate (2.60 g, 18.8 mmol, 3.00 equiv) and water (5 mL). The resulting solution was stirred for 3 h at room temperature and concentrated under reduced pressure. The reaction was then diluted with water (30 mL), extracted with EtOAc (3×50 mL) and the organic layers were combined, washed with water (3×20 mL), dried over anhydrous sodium sulfate, filtered and concentrated under reduced pressure as described in Example 3, Step 3 to provide 1.31 g (crude) of t-butyl (3aR,5s,6aS)-5-hydroxyhexahydrocyclopenta[c]pyrrole-2(1H)-carboxylate as a white solid. LCMS (ESI, m/z): 228 [M+H]⁺.

Step 7: Preparation of t-butyl (3aR,5s,6aS)-5-((3-cyclopentylbenzyHoxy)hexahydrocyclopenta[c]pyrrole-2(1H)-carboxylate

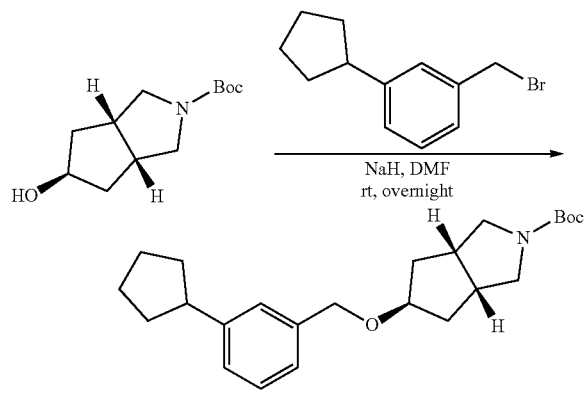

A flask was charged with t-butyl (3aR,5s,6aS)-5-hydroxyhexahydrocyclopenta[c]pyrrole-2(1H)-carboxylate (135 mg, 0.590 mmol, 1.50 equiv) and DMF (15 mL). Sodium hydride (60% in oil, 32.0 mg, 0.800 mmol, 2.00 equiv) was then added at 0° C. The resulting solution was stirred for 0.5 h at room temperature followed by addition of 1-(bromomethyl)-3-cyclopentylbenzene (95 mg, 0.400 mmol, 1.00 equiv). The resulting solution was stirred overnight at room temperature and quenched by water (20 mL) as described in Example 15, Step 7. The residue was chromatographed on a silica gel column to provide 135 mg (88% yield) of t-butyl (3aR,5s,6aS)-5-((3-cyclopentylbenzyl)oxy)hexahydrocyclopenta[c]pyrrole-2(1H)-carboxylate as a yellow oil. LCMS (ESI, m/z): 386 [M+H]⁺.

Step 8: Preparation of (3aR,5s,6aS)-5-((3-cyclopentylbenzyl)oxy)octahydrocyclopenta[c]pyrrole

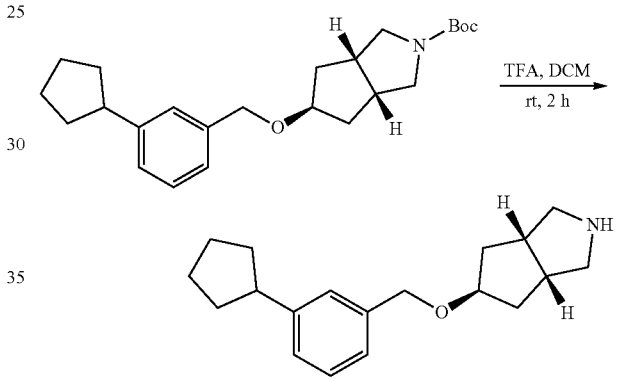

A flask was charged with t-butyl (3aR,5s,6aS)-5-(3-cyclopentylbenzyl)oxy)hexahydrocyclopenta[c]pyrrole-2(1H)-carboxylate (135 mg, 0.350 mmol, 1.00 equiv), TFA (2 mL) and DCM (5 mL). The resulting solution was stirred for 2 h at room temperature and concentrated under reduced pressure, as described in Example 1, Step 5 to provide. 100 mg (quantitative) of (3aR,5s,6aS)-5-((3-cyclopentylbenzyl)oxy)octahydrocyclopenta[c]pyrrole as a yellow oil. LCMS (ESI, m/z): 286 [M+H]⁺.

Step 9: Preparation of t-butyl 1-((3aR,5s,6aS)-54(3-cyclopentylbenzyl)oxy)octahydrocyclopenta[c]pyrrole-2-carbonyl)-1H-pyrazole-3-carboxylate

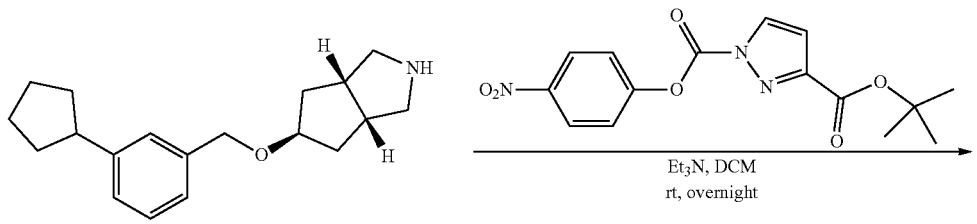

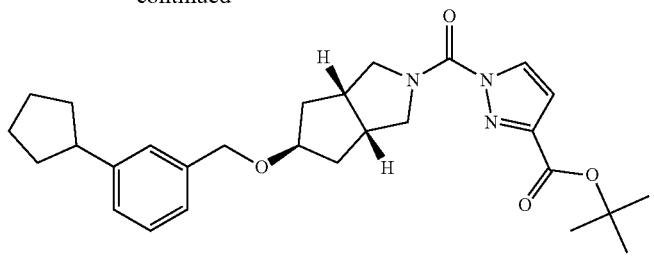

A vial was charged with (3aR,5s,6aS)-54(3-cyclopentylbenzyl)oxy)octahydrocyclopenta[c]pyrrole (100 mg, 0.350 mmol, 1.00 equiv), triethylamine (212 mg, 2.10 mmol, 6.00 equiv), 3-t-butyl 1-(4-nitrophenyl) 1H-pyrazole-1,3-dicarboxylate (175 mg, 0.525 mmol, 1.50 equiv) and DCM (15 mL). The resulting solution was stirred overnight at room temperature. The mixture was quenched by water (10 mL), extracted with DCM (3×20 mL) and the organic layers were combined, washed with brine (2×20 mL), dried over anhydrous sodium sulfate, filtered and concentrated under reduced pressure, as described in Example 4, Step 3. The residue was chromatographed on a silica gel column to provide 144 mg (86% yield) of t-butyl 1-((3aR,5s,6aS)-5-((3-cyclopentylbenzyl)oxy)octahydrocyclopenta[c]pyrrole-2-carbonyl)-1H-pyrazole-3-carboxylate as a yellow solid. LCMS (ESI, m/z): 480 [M+H]

Step 10: Preparation of 1-(trans-5-((3-cyclopentylbenzyl)oxy)octahydrocyclopenta[c]pyrrole-2-carbonyl)-1H-pyrazole-3-carboxylic Acid

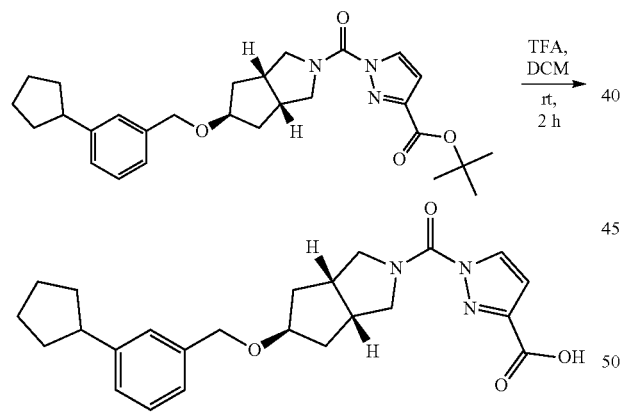

A vial was charged with t-butyl 1-((3aR,5s,6aS)-5-((3-cyclopentylbenzyl)oxy)octahydrocyclopenta[c]pyrrole-2-carbonyl)-1H-pyrazole-3-carboxylate (144 mg, 0.300 mmol, 1.00 equiv), TFA (2 mL) and DCM (5 mL). The resulting solution was stirred for 2 h at room temperature and concentrated under reduced pressure. The crude product was dissolved in saturated NaHCO₃ solution (10 mL) and extracted with DCM (3×20 mL). The organic layers were combined, washed with brine (10 mL), dried over anhydrous sodium sulfate, filtered and concentrated under reduced pressure as described in Example 1, Step 5. The crude product was purified by preparative HPLC to provide 47.6 mg (37% yield) of 1-(trans-5-((3-cyclopentylbenzyl)oxy)octahydrocyclopenta[c]pyrrole-2-carbonyl)-1H-pyrazole-3-carboxylic acid as a white solid. $^1$H NMR: (400 MHz, MeOH-d₄) δ 8.16 (s, 1H), 7.23-7.18 (m, 2H), 7.16-7.07 (m, 2H), 6.75 (d, J=2.8 Hz, 1H), 4.41 (s, 2H), 4.25-4.15 (m, 1H), 4.11-3.48 (m, 4H), 3.01-2.91 (m, 1H), 2.88 (br, 2H), 2.15-1.98 (m, 4H), 1.85-1.51 (m, 8H). LCMS (ESI, m/z): 424 [M+H]⁺.

Example 35: 4-(4-((5-(3-Carbamoyl-1H-pyrazole-1-carbonyl)hexahydropyrrolo[3,4-c]pyrrol-2(1H)-yl)methyl)-3-(trifluoromethyl)phenyl)tetrahydro-2H-pyran-4-carboxylic Acid

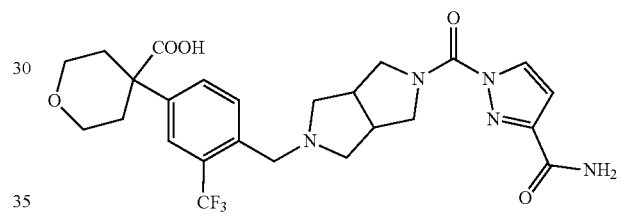

Step 1: Preparation of 4-nitrophenyl 3-carbamoyl-1H-pyrazole-1-carboxylate

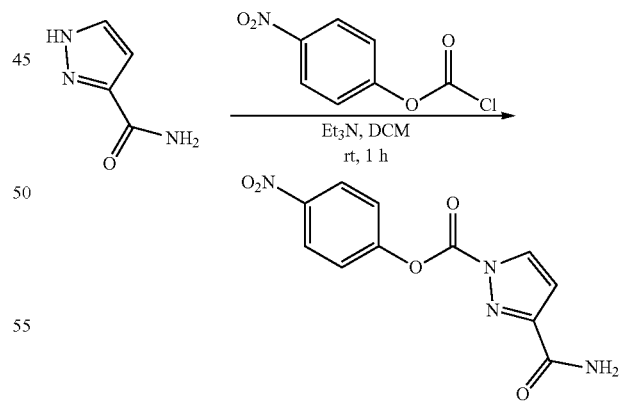

A flask was charged with 1H-pyrazole-3-carboxamide (64.0 mg, 0.580 mmol, 1.00 equiv), 4-nitrophenyl chloroformate (129 mg, 0.640 mmol, 1.10 equiv), triethylamine (176 mg, 1.74 mmol, 3.00 equiv), and DCM (10 mL). The resulting solution was stirred for 1 h at room temperature and concentrated under reduced pressure to provide 160 mg (crude) of 4-nitrophenyl 3-carbamoyl-1H-pyrazole-1-carboxylate as a yellow oil. LCMS (ESI, m/z): 277 [M+H]⁺.

Step 2: Preparation of potassium ((5-(tert-butoxycarbonyl)hexahydropyrrolo[3,4-c]pyrrol-2(1H)-yl)methyl)trifluoroborate

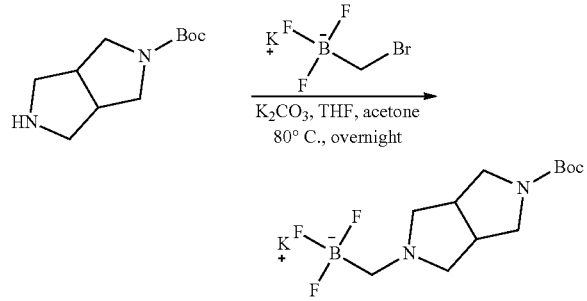

A flask was charged with tert-butyl octahydropyrrolo[3,4-c]pyrrole-2-carboxylate (1.20 g, 5.65 mmol, 1.00 equiv), potassium (bromomethyl)trifluoroboranuide (1.13 g, 5.63 mmol, 1.00 equiv), and THF (15 mL) under nitrogen. The mixture was stirred overnight at 80° C. and concentrated under reduced pressure. Potassium carbonate (0.781 g, 5.65 mmol, 1.00 equiv) and acetone (10 mL) were added. The resulting solution was stirred for 2 h at room temperature, dissolved in acetone (2×200 mL) and filtered. The filtrate was concentrated under reduced pressure to provide 1.40 g (75% yield) of potassium ((5-(tert-butoxycarbonyl)hexahydropyrrolo[3,4-c]pyrrol-2(1H)-yl)methyl)trifluoroborate as a yellow solid. LCMS (ESI, m/z): 293 [M-K]⁻.

Step 3: Preparation of t-butyl 2-(4-chloro-3-(trifluoromethyl)phenyl)acetate

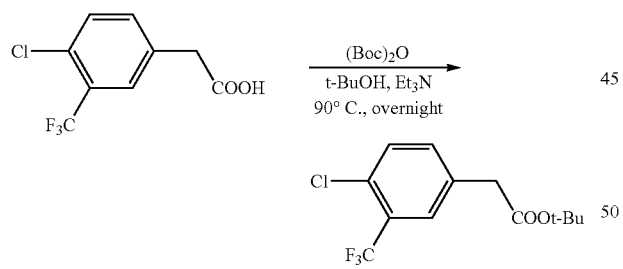

A flask was charged with 2-(4-chloro-3-(trifluoromethyl)phenyl)acetic acid (1.00 g, 4.19 mmol, 1.00 equiv), t-butanol (25 mL), triethylamine (1.27 g, 12.6 mmol, 3.00 equiv), and di-t-butyl dicarbonate (4.58 g, 20.9 mmol, 5.00 equiv). The resulting solution was stirred overnight at 90° C. and then quenched with water (25 mL), as described in Example 1, Step 1. The residue was chromatographed on a silica gel column to provide 0.810 g (66% yield) of t-butyl 2-(4-chloro-3-(trifluoromethyl)phenyl)acetate as a yellow oil. ¹H NMR (300 MHz, Chloroform-d) δ 7.60 (s, 1H), 7.48-7.40 (m, 2H), 3.56 (s, 2H), 1.45 (s, 9H).

Step 4: Preparation of t-butyl 4-(4-chloro-3-(trifluoromethyl)phenyl)tetrahydro-2H-pyran-4-carboxylate

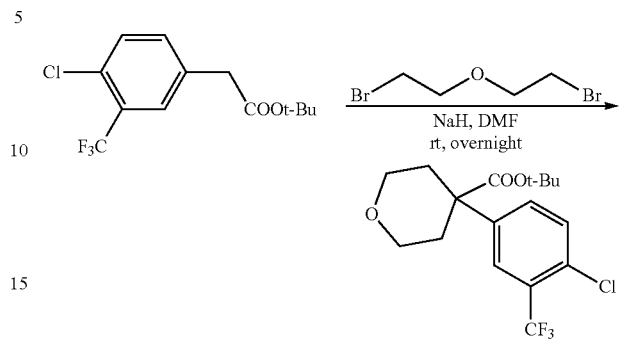

A flask was charged with t-butyl 2-(4-chloro-3-(trifluoromethyl)phenyl)acetate (500 mg, 1.70 mmol, 1.00 equiv) and DMF (10 mL). Sodium hydride (340 mg, 8.50 mmol, 5.00 equiv, 60% in mineral oil) was added at 0° C. 1-Bromo-2-(2-bromoethoxy)ethane (782 mg, 3.37 mmol, 2.00 equiv) was added. The resulting solution was stirred overnight at room temperature and then quenched with water (10 mL). The resulting mixture was extracted with EtOAc (3×15 mL) and the organic layers were combined, washed with brine (1×20 mL), dried over anhydrous sodium sulfate, filtered and concentrated under reduced pressure. The residue was chromatographed on a silica gel column to provide 190 mg (31% yield) of t-butyl 4-(4-chloro-3-(trifluoromethyl)phenyl)tetrahydro-2H-pyran-4-carboxylate as a yellow oil. ¹H NMR (300 MHz, Chloroform-d) δ 7.69 (s, 1H), 7.48 (br, 2H), 3.97-3.93 (m, 2H), 3.61-3.55 (m, 2H), 2.48-2.44 (m, 2H), 1.92-1.85 (m, 2H), 1.39 (s, 9H).

Step 5: Preparation of t-butyl 5-(4-(4-(t-butoxycarbonyl)tetrahydro-2H-pyran-4-yl)-2-(trifluoromethyl)benzyl)hexahydropyrrolo[3,4-c]pyrrole-2(1H)-carboxylate

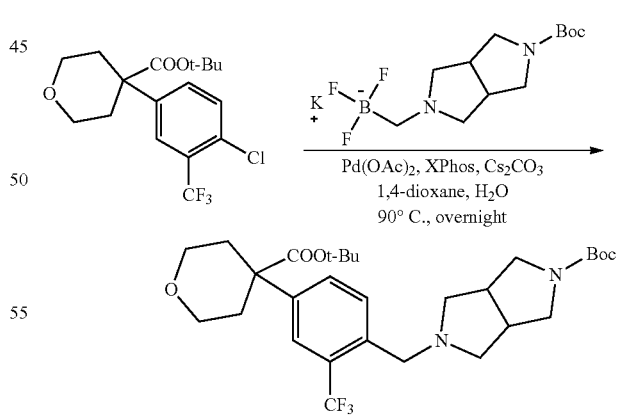

A flask was charged with t-butyl 4-(4-chloro-3-(trifluoromethyl)phenyl)tetrahydro-2H-pyran-4-carboxylate (364 mg, 1.00 mmol, 1.00 equiv), potassium ((5-(t-butoxycarbonyl)hexahydropyrrolo[3,4-c]pyrrol-2(1H)-yl)methyl)trifluoroborate (398 mg, 1.20 mmol, 1.20 equiv), palladium acetate (22.4 mg, 0.100 mmol, 0.10 equiv), 2-(dicyclohexylphosphino)-2',4',6'-triisopropylbiphenyl (95.0 mg, 0.200 mmol, 0.20 equiv), cesium carbonate (978 mg, 3.00 mmol, 3.00 equiv), 1,4-dioxane (10 mL), and water (2 mL) under nitrogen. The resulting solution was stirred overnight at 90° C. and then quenched with water (10 mL). The resulting mixture was extracted with DCM (3×15 mL) and the organic layers were combined, washed with brine (1×20 mL), dried over anhydrous sodium sulfate, filtered and concentrated under reduced pressure. The residue was chromatographed on a silica gel column to provide 250 mg (45% yield) of t-butyl 5-(4-(4-(t-butoxycarbonyl)tetrahydro-2H-pyran-4-yl)-2-(trifluoromethyl)benzyl)hexahydropyrrolo[3,4-c]pyrrole-2(1H)-carboxylate as a yellow oil. LCMS (ESI, m/z): 555 [M+H]⁺.

Step 6: Preparation of 4-(4-((hexahydropyrrolo[3,4-c]pyrrol-2(1H)-yl)methyl)-3-(trifluoromethyl)phenyl)tetrahydro-2H-pyran-4-carboxylic Acid

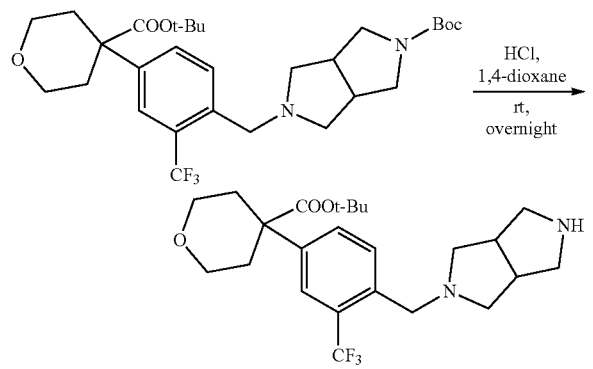

A flask was charged with t-butyl 5-(4-(4-(t-butoxycarbonyl)tetrahydro-2H-pyran-4-yl)-2-(trifluoromethyl)benzyl) hexahydropyrrolo[3,4-c]pyrrole-2(1H)-carboxylate (250 mg, 0.450 mmol, 1.00 equiv), concentrated hydrochloric acid (4 mL), and 1,4-dioxane (10 mL). The resulting solution was stirred overnight at room temperature and concentrated under reduced pressure as described in Example 2, Step 4 to provide 180 mg (quantitative) of 4-(4-((hexahydropyrrolo[3,4-c]pyrrol-2(1H)-yl)methyl)-3-(trifluoromethyl)phenyl)tetrahydro-2H-pyran-4-carboxylic acid as a yellow oil. LCMS (ESI, m/z): 399 [M+H]⁺.

Step 7: Preparation of 4-(4-((5-(3-carbamoyl-1H-pyrazole-1-carbonyl)hexahydropyrrolo[3,4-c]pyrrol-2(1H)-yl)methyl)-3-(trifluoromethyl)phenyl)tetrahydro-2H-pyran-4-carboxylic Acid

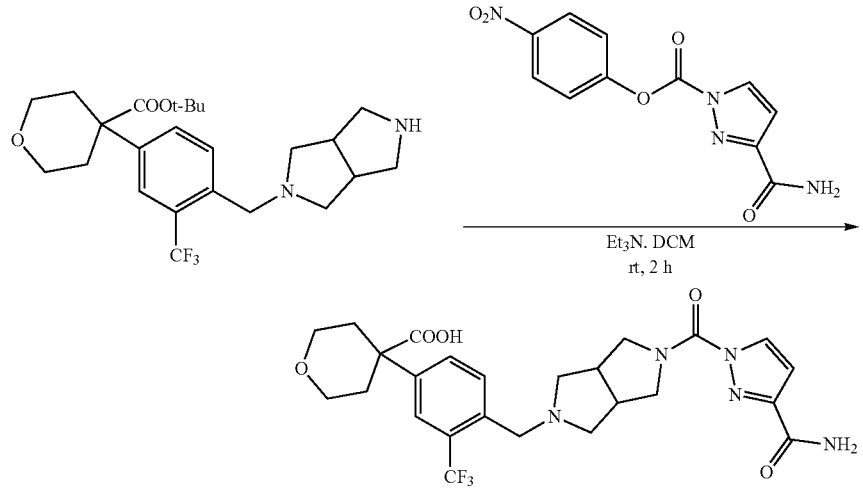

A flask was charged with 4-(4-((hexahydropyrrolo[3,4-c]pyrrol-2(1H)-yl)methyl)-3-(trifluoromethyl)phenyl)tetrahydro-2H-pyran-4-carboxylic acid (180 mg, 0.450 mmol, 1.00 equiv), 4-nitrophenyl 3-carbamoyl-1H-pyrazole-1-carboxylate (138 mg, 0.500 mmol, 1.10 equiv), triethylamine (137 mg, 1.35 mmol, 3.00 equiv), and DCM (10 mL). The resulting solution was stirred for 2 h at room temperature and then quenched with water (10 mL), as described in Example 4, Step 3. The crude product (300 mg) was purified by preparative HPLC to provide 126.1 mg (52% yield) of 4-(4-((5-(3-carbamoyl-1H-pyrazole-1-carbonyl)hexahydropyrrolo[3,4-c]pyrrol-2(1H)-yl)methyl)-3-(trifluoromethyl) phenyl)tetrahydro-2H-pyran-4-carboxylic acid as a white solid. ¹H NMR (300 MHz, Methanol-d₄) δ 8.30 (d, J=2.7 Hz, 1H), 7.77-7.72 (m, 2H), 7.67-7.65 (m, 1H), 6.88 (d, J=2.7 Hz, 1H), 4.23-3.83 (m, 8H), 3.65-3.56 (m, 2H), 2.98 (br, 2H), 2.74-2.67 (m, 4H), 2.55-2.51 (m, 2H), 1.94-1.87 (m, 2H). LCMS (ESI, m/z): 536 [M+H]⁺.

Example 36: 1-(4-((2-Hydroxy-2-methylpropyl)(3-(trifluoromethyl)benzyl)amino)piperidine-1-carbonyl)-1H-pyrazole-3-carboxamide

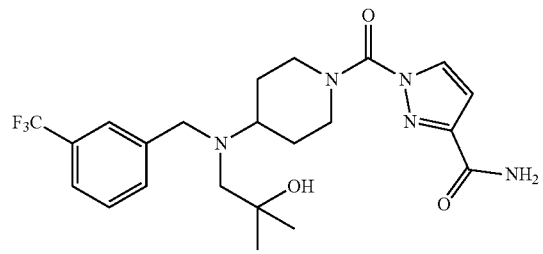 [SMILES: CC(C)(O)CN(Cc1cccc(C(F)(F)F)c1)C1CCN(C(=O)n2ccc(C(N)=O)n2)CC1]

Step 1: Preparation of t-butyl 4-((3-(trifluoromethyl)benzyl)amino)piperidine-1-carboxylate

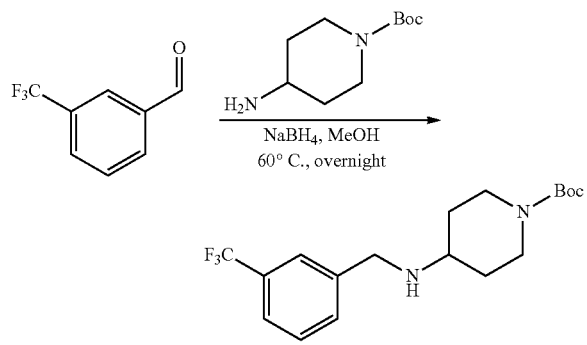 [SMILES: O=Cc1cccc(C(F)(F)F)c1 ; CC(C)(C)OC(=O)N1CCC(N)CC1 ; CC(C)(C)OC(=O)N1CCC(NCc2cccc(C(F)(F)F)c2)CC1]

A flask was charged with 3-(trifluoromethyl)benzaldehyde (522 mg, 3.00 mmol, 1.00 equiv), t-butyl 4-aminopiperidine-1-carboxylate (1.20 g, 6.00 mmol, 2.00 equiv), and MeOH (15 mL). The mixture was stirred for 4 h at 60° C. Sodium borohydride (456 mg, 12.0 mmol, 4.00 equiv) was added. The resulting solution was stirred overnight at 60° C. and quenched with water (20 mL), as described in Example 15, Step 4. The residue was chromatographed on a silica gel column to provide 0.800 g (74% yield) of t-butyl 4-((3-(trifluoromethyl)benzyl)amino)piperidine-1-carboxylate as a yellow oil. LCMS (ESI, m/z): 359 [M+H]$^+$.

Step 2: Preparation of t-butyl 4-((2-hydroxy-2-methylpropyl)(3-(trifluoromethyl)benzyl)amino)piperidine-1-carboxylate

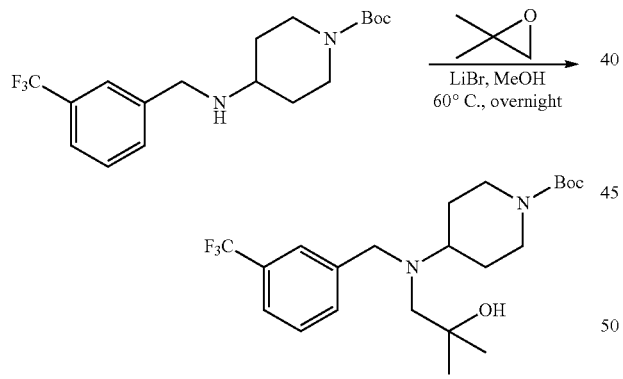

A flask was charged with t-butyl 4-((3-(trifluoromethyl)benzyl)amino)piperidine-1-carboxylate (358 mg, 1.00 mmol, 1.00 equiv), 2,2-dimethyloxirane (360 mg, 5.00 mmol, 5.00 equiv), MeOH (10 mL), and lithium bromide (258 mg, 3.00 mmol, 3.00 equiv). The resulting solution was stirred overnight at 60° C. and quenched with water (20 mL). The resulting mixture was extracted with DCM (3×30 mL) and the organic layers were combined, washed with brine (30 mL), dried over anhydrous sodium sulfate, filtered and concentrated under reduced pressure. The residue was chromatographed on a silica gel column to provide 230 mg (53% yield) of t-butyl 4-((2-hydroxy-2-methylpropyl)(3-(trifluoromethyl)benzyl)amino)piperidine-1-carboxylate as a yellow oil. LCMS (ESI, m/z): 431 [M+H]$^+$.

Step 3: Preparation of 2-methyl-1-(piperidin-4-yl(3-(trifluoromethyl)benzyl)amino)propan-2-ol

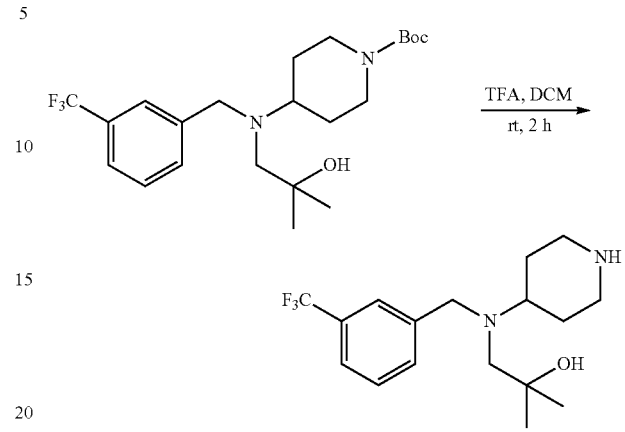

A flask was charged with t-butyl 4-((2-hydroxy-2-methylpropyl)(3-(trifluoromethyl)benzyl)amino)piperidine-1-carboxylate (215 mg, 0.500 mmol, 1.00 equiv), DCM (10 mL), and TFA (2 mL). The resulting solution was stirred for 2 h at room temperature and concentrated under reduced pressure, as described in Example 1, Step 5 to provide 165 mg (quantitative) of 2-methyl-1-(piperidin-4-yl(3-(trifluoromethyl)benzyl)amino)propan-2-ol as a yellow oil. LCMS (ESI, m/z): 331 [M+H]$^+$.

Step 4: Preparation of 4-((2-hydroxy-2-methylpropyl)(3-(trifluoromethyl)benzyl)amino)piperidine-1-carbonyl Chloride

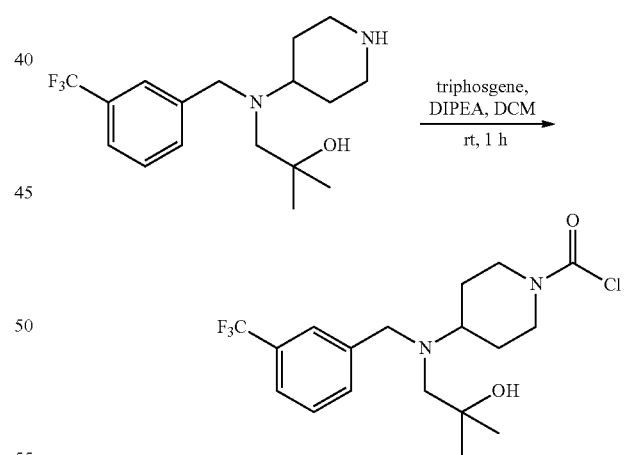

A flask was charged with triphosgene (104 mg, 0.350 mmol, 0.70 equiv) and DCM (10 mL). 2-Methyl-1-(piperidin-4-yl(3-(trifluoromethyl)benzyl)amino)propan-2-ol (165 mg, 0.500 mmol, 1.00 equiv) and DIPEA (258 mg, 2.00 mmol, 4.00 equiv) were added at 0° C. The resulting solution was stirred for 1 h at room temperature and quenched with water (20 mL), as described in Example 1, Step 3 to provide 196 mg (crude) of 4-((2-hydroxy-2-methylpropyl)(3-(trifluoromethyl)benzyl)amino)piperidine-1-carbonyl chloride as a brown oil. LCMS (ESI, m/z): 393 [M+H]$^+$.

Step 5: Preparation of 1-(4-((2-hydroxy-2-methyl-propyl)(3-(trifluoromethyl)benzyl)amino)piperidine-1-carbonyl)-1H-pyrazole-3-carboxamide

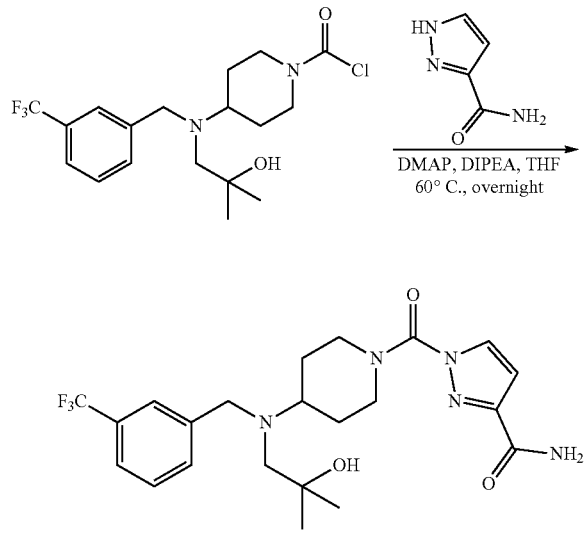

A flask was charged with 4-((2-hydroxy-2-methylpropyl)(3-(trifluoromethyl)benzyl)amino)piperidine-1-carbonyl chloride (196 mg, 0.500 mmol, 1.00 equiv), 1H-pyrazole-3-carboxamide (66.6 mg, 0.600 mmol, 1.20 equiv), THF (10 mL), DIPEA (258 mg, 2.00 mmol, 4.00 equiv), and DMAP (6.1 mg, 0.0500 mmol, 0.10 equiv) under nitrogen. The resulting solution was stirred overnight at 60° C. and then quenched with water (20 mL), as described in Example 1, Step 4. The crude product (280 mg) was purified by preparative HPLC to provide 106.9 mg (46% yield) of 1-(4-((2-hydroxy-2-methylpropyl)(3-(trifluoromethyl)benzyl)amino)piperidine-1-carbonyl)-1H-pyrazole-3-carboxamide as an off-white solid. $^1$HNMR (400 MHz, Methanol-d$_4$) δ 8.16 (d, J=2.4 Hz, 1H), 7.77 (s, 1H), 7.71 (d, J=7.2 Hz, 1H), 7.55-7.49 (m, 2H), 6.87 (d, J=2.4 Hz, 1H), 4.49-4.46 (m, 2H), 3.95 (s, 2H), 3.00-2.86 (m, 3H), 2.56 (s, 2H), 1.97-1.94 (m, 2H), 1.75-1.64 (m, 2H), 1.17 (s, 6H). LCMS (ESI, m/z): 468 [M+H]$^+$.

Example 37: 1-(4-(2-Chloro-3-(2-hydroxy-2-methylpropoxy)benzyl)piperazine-1-carbonyl)-1H-pyrazole-3-carboxamide

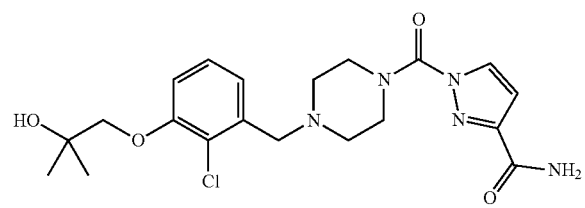 [SMILES: CC(C)(O)COc1cccc(CN2CCN(C(=O)n3ccc(C(N)=O)n3)CC2)c1Cl]

Step 1: Preparation of 2-chloro-3-(2-hydroxy-2-methylpropoxy)benzaldehyde

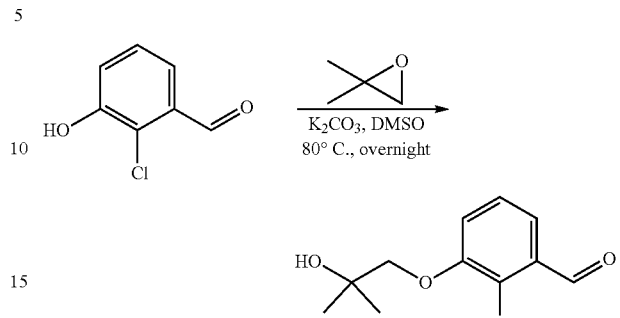

A flask was charged with 2-chloro-3-hydroxybenzaldehyde (0.624 g, 4.00 mmol, 1.00 equiv), 2,2-dimethyloxirane (0.576 g, 8.00 mol, 2.00 equiv), DMSO (10 mL), and potassium carbonate (1.66 g, 12.0 mmol, 3.00 equiv). The resulting solution was stirred overnight at 80° C. and quenched with water (30 mL). The resulting mixture was extracted with EtOAc (3×40 mL) and the organic layers were combined, washed with brine (30 mL), dried over anhydrous sodium sulfate, filtered and concentrated under reduced pressure. The residue was chromatographed to provide 550 mg (60% yield) of 2-chloro-3-(2-hydroxy-2-methylpropoxy)benzaldehyde as a colorless oil. LCMS (ESI, m/z): 229 [M+H]$^+$.

Step 2: Preparation of 4-nitrophenyl 3-carbamoyl-1H-pyrazole-1-carboxylate

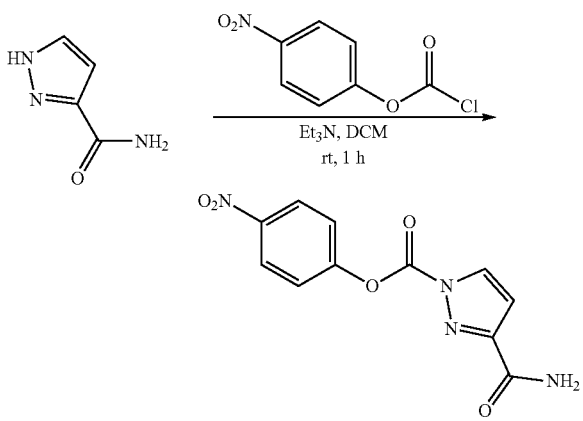

A flask was charged with 1H-pyrazole-3-carboxamide (0.555 g, 5.00 mmol, 1.00 equiv), 4-nitrophenyl chloroformate (1.21 g, 6.00 mmol, 1.20 equiv), DCM (20 mL), and triethylamine (1.51 g, 15.0 mmol, 3.00 equiv). The resulting solution was stirred for 1 h at room temperature and concentrated under reduced pressure to provide 1.38 g (crude) of 4-nitrophenyl 3-carbamoyl-1H-pyrazole-1-carboxylate as a yellow oil. LCMS (ESI, m/z): 277 [M+H]$^+$.

Step 3: Preparation of t-butyl 4-(3-carbamoyl-1H-pyrazole-1-carbonyl)piperazine-1-carboxylate

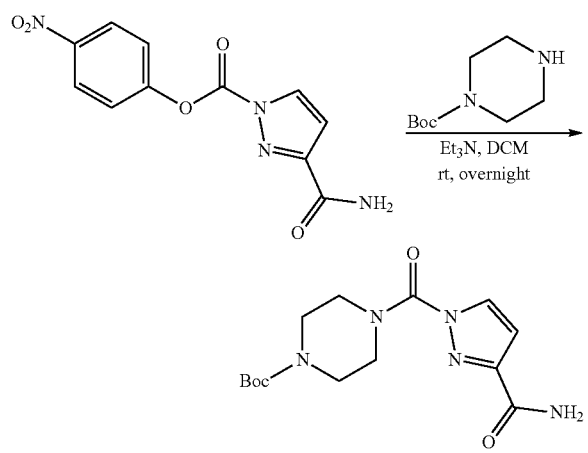

A flask was charged with 4-nitrophenyl 3-carbamoyl-1H-pyrazole-1-carboxylate (1.38 g, 5.00 mmol, 1.00 equiv), t-butyl piperazine-1-carboxylate (0.930 g, 5.00 mol, 1.00 equiv), DCM (15 mL), and triethylamine (1.51 g, 15.0 mmol, 3.00 equiv). The resulting solution was stirred overnight at room temperature and quenched with water (30 mL), as described in Example 4, Step 3. The residue was chromatographed on a silica gel column to provide 0.500 g (31% yield) of t-butyl 4-(3-carbamoyl-1H-pyrazole-1-carbonyl)piperazine-1-carboxylate as a white solid. LCMS (ESI, m/z): 324 [M+H]$^+$.

Step 4: Preparation of 1-(piperazine-1-carbonyl)-1H-pyrazole-3-carboxamide

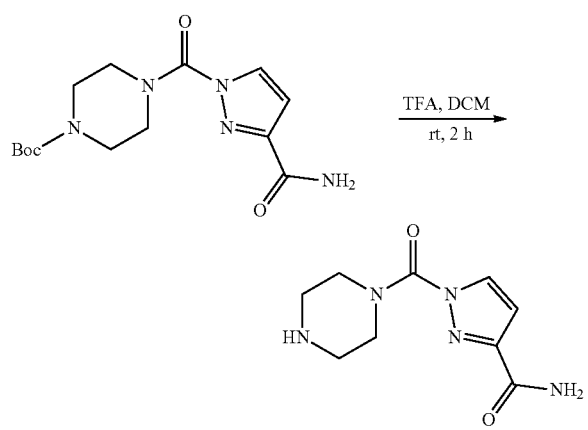

A flask was charged with t-butyl 4-(3-carbamoyl-1H-pyrazole-1-carbonyl)piperazine-1-carboxylate (150 mg, 0.460 mmol, 1.00 equiv), DCM (10 mL), and TFA (2 mL). The resulting solution was stirred for 2 h at room temperature and concentrated under reduced pressure as described in Example 1, Step 5 to provide 110 mg (quantitative) of 1-(piperazine-1-carbonyl)-1H-pyrazole-3-carboxamide as a yellow oil. LCMS (ESI, m/z): 224 [M+H]$^+$.

Step 5: Preparation of 1-(4-(2-chloro-3-(2-hydroxy-2-methylpropoxy)benzyl)piperazine-1-carbonyl)-1H-pyrazole-3-carboxamide

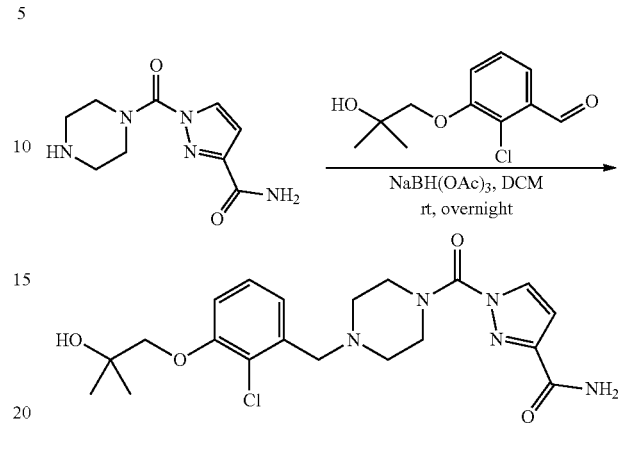

A flask was charged with 1-(piperazine-1-carbonyl)-1H-pyrazole-3-carboxamide (75.8 mg, 0.340 mmol, 1.20 equiv), 2-chloro-3-(2-hydroxy-2-methylpropoxy)benzaldehyde (64.7 mg, 0.280 mmol, 1.00 equiv), and DCM (15 mL). The mixture was stirred for 2 h at room temperature. Sodium triacetoxyborohydride (241 mg, 1.14 mmol, 4.00 equiv) was added. The resulting solution was stirred overnight at room temperature and then quenched with water (20 mL), as described in Example 2, Step 3. The crude product (200 mg) was purified by preparative HPLC to provide 52.7 mg (36% yield) of 1-(4-(2-chloro-3-(2-hydroxy-2-methylpropoxy)benzyl)piperazine-1-carbonyl)-1H-pyrazole-3-carboxamide as a white solid. $^1$H NMR (300 MHz, Chloroform-d) δ 8.09 (d, J=2.7 Hz, 1H), 7.25 (d, J=7.8 Hz, 1H), 7.12 (br, 1H), 6.90 (d, J=2.7 Hz, 1H), 6.86 (d, J=7.8 Hz, 1H), 6.65 (br, 1H), 5.47 (br, 1H), 3.85 (s, 6H), 3.71 (s, 2H), 2.65 (br, 4H), 2.40 (s, 1H), 1.39 (s, 6H). LCMS (ESI, m/z): 436 [M+H]$^+$.

Example 38: 1-(trans-5-((2-Chloro-3-(2-hydroxy-2-methylpropoxy)benzyl)oxy)octahydrocyclopenta[c]pyrrole-2-carbonyl)-1H-pyrazole-3-carboxylic Acid

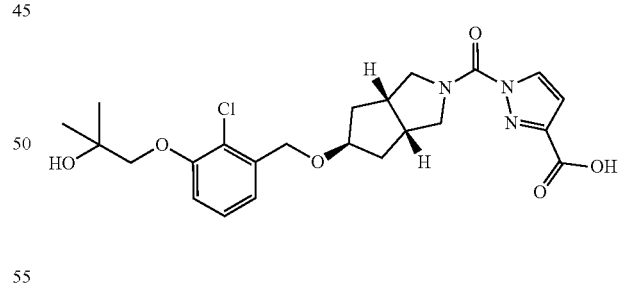

Step 1: Preparation of 3-(t-butyl) 1-(4-nitrophenyl) 1H-pyrazole-1,3-dicarboxylate

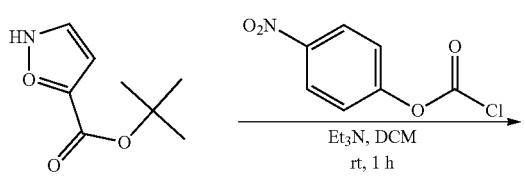

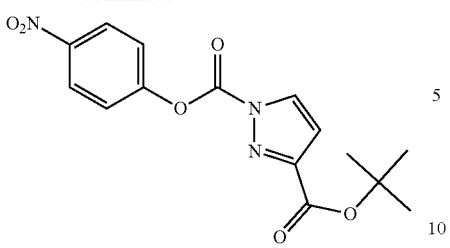

A flask was charged with t-butyl 1H-pyrazole-3-carboxylate (138 mg, 0.822 mmol, 1.00 equiv), 4-nitrophenyl carbonochloridate (198 mg, 0.986 mmol, 1.20 equiv), triethylamine (249 mg, 2.46 mmol, 3.00 equiv), and DCM (10 mL), as described in Example 4, Step 3. The resulting solution was stirred for 1 h at room temperature and concentrated under reduced pressure to provide 274 mg (crude) of 3-tert-butyl 1-(4-nitrophenyl) 1H-pyrazole-1,3-dicarboxylate as a yellow oil. LCMS (ESI, m/z): 334 [M+H]$^+$.

Step 2: Preparation of t-butyl (3aR,5r,6aS)-5-hydroxyhexahydrocyclopenta[c]pyrrole-2(1H)-carboxylate

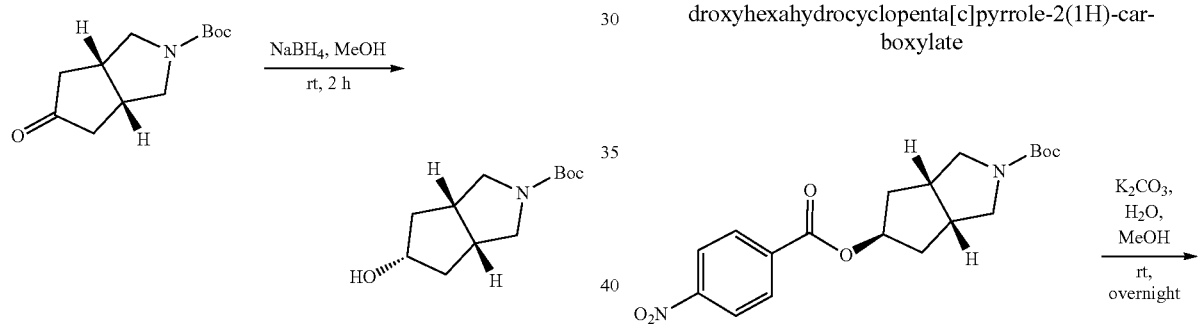

A flask was charged with t-butyl (3aR,6aS)-5-oxo-octahydrocyclopenta[c]pyrrole-2-carboxylate (1.00 g, 4.44 mmol, 1.00 equiv), and MeOH (15 mL). Sodium borohydride (0.507 g, 13.4 mmol, 3.00 equiv) was added at 0° C. The resulting solution was stirred for 2 h at room temperature and quenched with water (20 mL), as described in Example 15, Step 4 to provide 0.950 g (94% yield) of (3aR,5r,6aS)-tert-butyl 5-hydroxy-hexahydrocyclopenta[c]pyrrole-2(1H)-carboxylate as a yellow oil. LCMS (ESI, m/z): 228 [M+H]$^+$.

Step 3: Preparation of t-butyl (3aR,5s,6aS)-5-((4-nitrobenzoyl)oxy)hexahydrocyclopenta[c]pyrrole-2(1H)-carboxylate

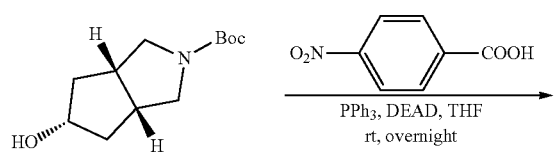

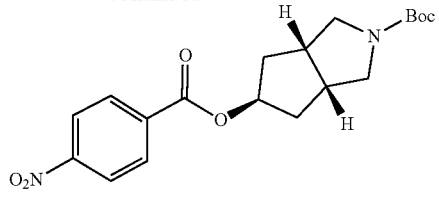

A flask was charged with (3aR,5r,6aS)-t-butyl 5-hydroxyhexahydrocyclopenta[c]pyrrole-2(1H)-carboxylate (2.00 g, 8.81 mmol, 1.00 equiv), 4-nitrobenzoic acid (1.470 g, 8.80 mmol, 2.00 equiv), triphenylphosphine (2.30 g, 8.80 mmol, 2.00 equiv), and THF (20 mL) under nitrogen. Diethyl azodicarboxylate (1.53 g, 8.80 mmol, 2.00 equiv) was added at 0° C. The resulting solution was stirred overnight at room temperature and quenched with water (40 mL), as described in Example 15, Step 5. The residue was chromatographed on a silica gel column to provide 1.8 g (54% yield) of t-butyl (3aR,5s,6aS)-5-(4-nitrobenzoyl)oxy)hexahydrocyclopenta[c]pyrrole-2(1H)-carboxylate as a white solid. LCMS (ESI, m/z): 377 [M+H]$^+$.

Step 4: Preparation of t-butyl (3aR,5s,6aS)-5-hydroxyhexahydrocyclopenta[c]pyrrole-2(1H)-carboxylate A flask was charged with t-butyl (3aR,5s,6aS)-5-(4-nitrobenzoyl)oxy)hexahydrocyclopenta[c]pyrrole-2(1H)-carboxylate (1.8 g, 4.79 mmol, 1.00 equiv), potassium carbonate (1.32 g, 9.58 mmol, 2.00 equiv), MeOH (30 mL), and water (10 mL). The resulting solution was stirred overnight at room temperature and quenched with water (30 mL), as described in Example 15, Step 6. The residue was chromatographed on a silica gel column to provide 900 mg (82% yield) of t-butyl (3aR,5s,6aS)-5-hydroxyhexahydrocyclopenta[c]pyrrole-2(1H)-carboxylate as a white solid. LCMS (ESI, m/z): 228 [M+H]$^+$.

Step 5: Preparation of t-butyl (3aR,5s,6aS)-5-((3-bromo-2-chlorobenzyl)oxy)hexahydrocyclopenta[c]pyrrole-2(1H)-carboxylate

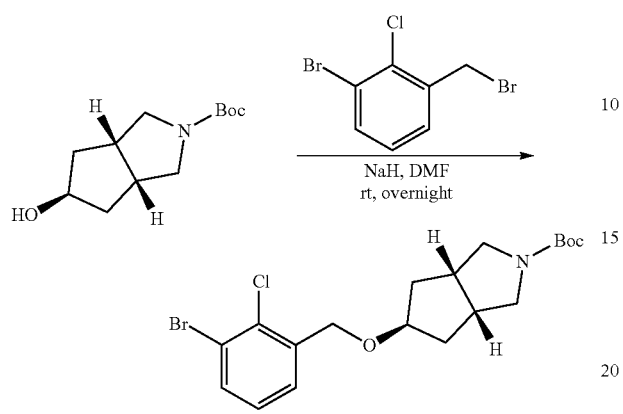

A flask was charged with t-butyl (3aR,5s,6aS)-5-hydroxyhexahydrocyclopenta[c]pyrrole-2(1H)-carboxylate (600 mg, 2.64 mmol, 1.00 equiv), 1-bromo-3-(bromomethyl)-2-chlorobenzene (820 mg, 2.91 mmol, 1.10 equiv), NaH (211 mg, 5.28 mmol, 2.00 equiv), and DMF (10 mL). The resulting solution was stirred overnight at room temperature and quenched with water (20 mL), as described in Example 15, Step 7. The residue was chromatographed on a silica gel column to provide 660 mg (60% yield) of t-butyl (3aR,5s,6aS)-5-(3-bromo-2-chlorobenzyl)oxy)hexahydrocyclopenta[c]pyrrole-2(1H)-carboxylate as a yellow solid. LCMS (ESI, m/z): 430 [M+H]$^+$.

Step 6: Preparation of t-butyl (3aR,5s,6aS)-5-((2-chloro-3-(4,4,5,5-tetramethyl-1,3,2-dioxaborolan-2-yl)benzyl)oxy)hexahydrocyclopenta[c]pyrrole-2(1H)-carboxylate

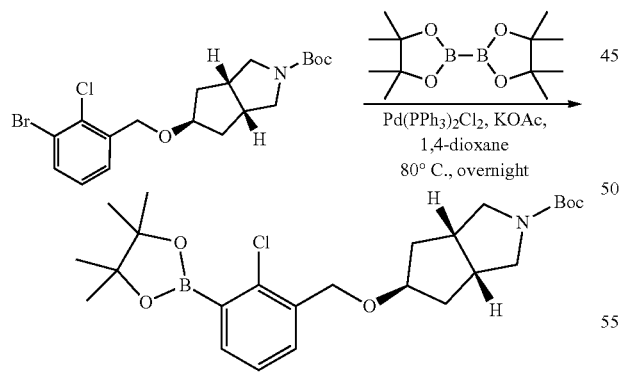

A flask was charged with t-butyl (3aR,5s,6aS)-5-(3-bromo-2-chlorobenzyl)oxy)hexahydrocyclopenta[c]pyrrole-2(1H)-carboxylate (500 mg, 1.16 mmol, 1.00 equiv), 4,4,4',4',5,5,5',5'-octamethyl-2,2'-bi(1,3,2-dioxaborolane) (444 mg, 1.75 mmol, 1.50 equiv), bis (triphenylphosphine) palladium dichloride (246 mg, 0.35 mmol, 0.30 equiv), potassium acetate (341 mg, 3.48 mmol, 3.00 equiv), 1,4-dioxane (10 mL) and nitrogen. The resulting solution was stirred overnight at 80° C. and quenched with water (20 mL). The resulting solution was extracted with EtOAc (3×30 mL) and the organic layers were combined, washed with brine (1×20 mL), dried over anhydrous sodium sulfate, filtered and concentrated under reduced pressure. The residue was chromatographed on a silica gel column to provide 480 mg (86% yield) of t-butyl (3aR,5s,6aS)-5-((2-chloro-3-(4,4,5,5-tetramethyl-1,3,2-dioxaborolan-2-yl)benzyl)oxy)hexahydrocyclopenta[c]pyrrole-2(1H)-carboxylate as a white solid. LCMS (ESI, m/z): 478 [M+H]$^+$.

Step 7: Preparation of t-butyl (3aR,5s,6aS)-5-((2-chloro-3-hydroxybenzyl)oxy)hexahydrocyclopenta[c]pyrrole-2(1H)-carboxylate

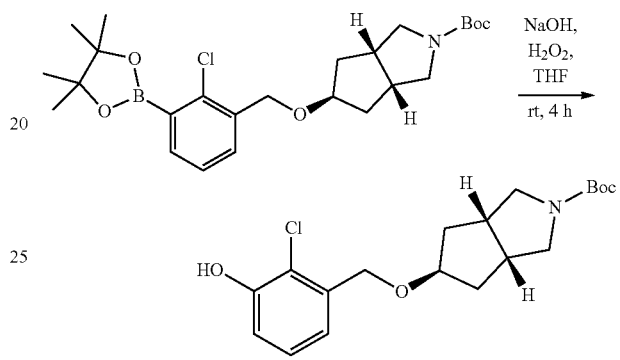

A flask was charged with t-butyl (3aR,5s,6aS)-5-((2-chloro-3-(4,4,5,5-tetramethyl-1,3,2-dioxaborolan-2-yl)benzyl)oxy)hexahydrocyclopenta[c]pyrrole-2(1H)-carboxylate (430 mg, 0.90 mmol, 1.00 equiv), sodium hydroxide (72 mg, 1.80 mmol, 2.00 equiv), hydrogen peroxide (1.80 ml, 1.80 mmol, 2.00 equiv), and THF (10 mL). The resulting solution was stirred for 4 h at room temperature and quenched with water (5 mL). The mixture was extracted with EtOAc (3×40 mL) and the organic layers were combined, washed with water (1×50 mL), dried over anhydrous sodium sulfate, filtered and concentrated under reduced pressure. The residue was chromatographed on a silica gel column to provide 260 mg (quantitative) of t-butyl (3aR,5s,6aS)-5-((2-chloro-3-hydroxybenzyl)oxy)hexahydrocyclopenta[c]pyrrole-2(1H)-carboxylate as a white solid. LCMS (ESI, m/z): 368 [M+H]$^+$.

Step 8: Preparation of t-butyl (3aR,5s,6aS)-5-((2-chloro-3-(2-hydroxy-2-methylpropoxy)benzyl)oxy)hexahydrocyclopenta[c]pyrrole-2(1H)-carboxylate

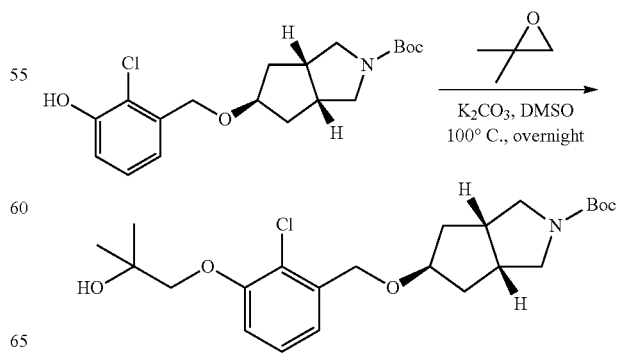

275

A flask was charged with t-butyl (3aR,5s,6aS)-5-(2-chloro-3-hydroxybenzyl)oxy)hexahydrocyclopenta[c]pyrrole-2(1H)-carboxylate (260 mg, 0.708 mmol, 1.00 equiv), 2,2-dimethyloxirane (61 mg, 0.850 mmol, 1.20 equiv), potassium carbonate (294 mg, 2.12 mmol, 3.00 equiv), and DMSO (5 mL). The resulting solution was stirred overnight at 100° C. and quenched with water (5 mL), as described in Example 41, Step 1. The residue was chromatographed on a silica gel column to provide 200 mg (64% yield) of t-butyl (3aR,5s,6aS)-5-((2-chloro-3-(2-hydroxy-2-methylpropoxy)benzyl)oxy)hexahydrocyclopenta[c]pyrrole-2(1H)-carboxylate as a white solid. LCMS (ESI, m/z): 440 [M+H]+.

Step 9: Preparation of 1-(2-chloro-34(03aR,5s,6aS)-octahydrocyclopenta[c]pyrrol-5-yl)oxy)methyl)phenoxy)-2-methylpropan-2-ol

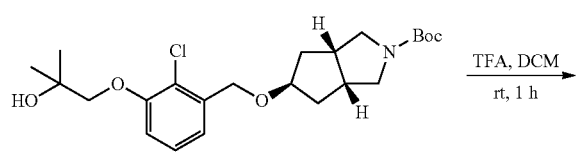

276

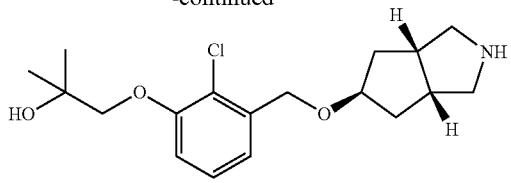

A flask was charged with t-butyl (3aR,5s,6aS)-5-((2-chloro-3-(2-hydroxy-2-methylpropoxy)benzyl)oxy)hexahydrocyclopenta[c]pyrrole-2(1H)-carboxylate (200 mg, 0.456 mmol, 1.00 equiv), DCM (8 mL), and TFA (2 mL). The resulting solution was stirred for 1 h at room temperature and concentrated under reduced pressure. The crude product was worked up as described in Example 1, Step 5 to provide 136 mg (quantitative) of 1-(2-chloro-3-((((3aR,5s,6aS)-octahydrocyclopenta[c]pyrrol-5-yl)oxy)methyl)phenoxy)-2-methylpropan-2-ol as a white solid. LCMS (ESI, m/z): 340 [M+H]+.

Step 10: Preparation of t-butyl 1-(trans-5-((2-chloro-3-(2-hydroxy-2-methylpropoxy)benzyl)oxy) octahydrocyclopenta[c]pyrrole-2-carbonyl)-1H-pyrazole-3-carboxylate

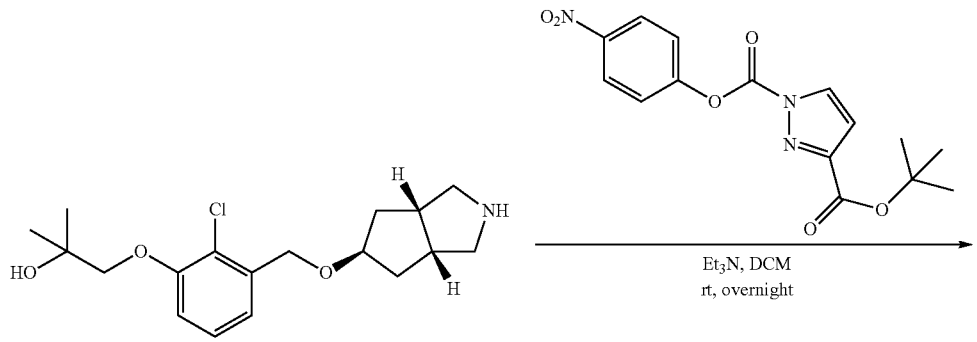

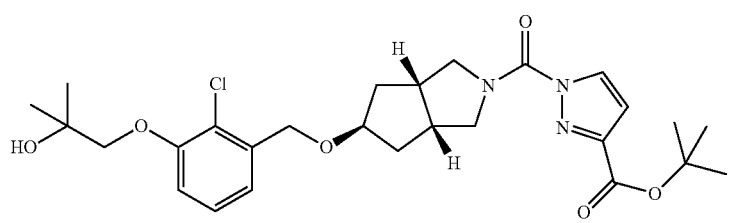

A flask was charged with 1-(2-chloro-3-((((3aR,5s, 6aS)-octahydrocyclopenta[c]pyrrol-5-yl)oxy)methyl)phenoxy)-2-methylpropan-2-ol (136 mg, 0.401 mmol, 1.00 equiv), 3-t-butyl 1-(4-nitrophenyl) 1H-pyrazole-1,3-dicarboxylate (160 mg, 0.481 mmol, 1.20 equiv), triethylamine (121 mg, 1.20 mmol, 3.00 equiv), and DCM (5 mL). The resulting solution was stirred overnight at room temperature and quenched with water (20 mL), as described in Example 4, Step 3. The residue was chromatographed on a silica gel column to provide 180 mg (82% yield) of t-butyl 1-((3aR, 5s,6aS)-5-((2-chloro-3-(2-hydroxy-2-methylpropoxy)benzyl)oxy)octahydrocyclopenta[c]pyrrole-2-carbonyl)-1H-pyrazole-3-carboxylate as a white solid. LCMS (ESI, m/z): 534 [M+H]$^+$.

Step 11: Preparation of 1-(trans-5-((2-chloro-3-(2-hydroxy-2-methylpropoxy)benzyl)oxy)octahydrocyclopenta[c]pyrrole-2-carbonyl)-1H-pyrazole-3-carboxylic Acid

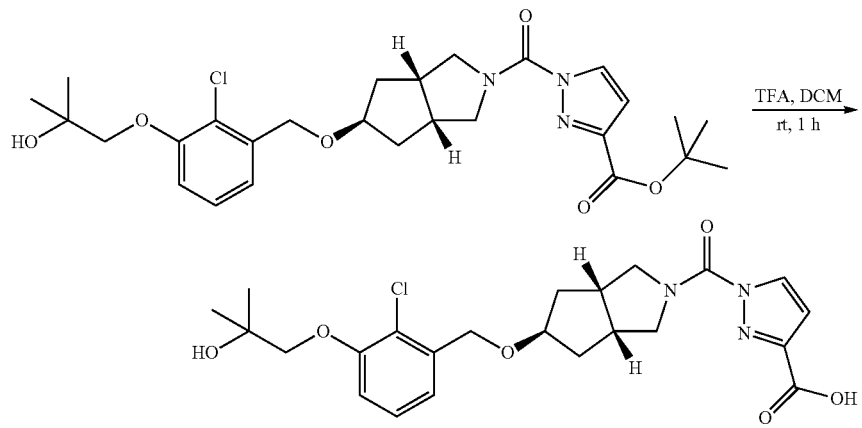

A flask was charged with t-butyl 1-((3aR,5s,6aS)-5-((2-chloro-3-(2-hydroxy-2-methylpropoxy)benzyl)oxy)octahydrocyclopenta[c]pyrrole-2-carbonyl)-1H-pyrazole-3-carboxylate (180 mg, 0.338 mmol, 1.00 equiv), DCM (8 mL), and TFA (1 mL). The resulting solution was stirred for 1 h at room temperature and concentrated under reduced pressure, as described in Example 1, Step 5. The crude product (200 mg) was purified by preparative HPLC to provide 32.8 mg (21% yield) of 1-(trans-5-((2-chloro-3-(2-hydroxy-2-methylpropoxy)benzyl)oxy)octahydrocyclopenta[c]pyrrole-2-carbonyl)-1H-pyrazole-3-carboxylic acid as a white solid. $^1$H NMR (400 MHz, Methanol-$d_4$) δ 8.16 (d, J=2.6 Hz, 1H), 7.26 (t, J=7.9 Hz, 1H), 7.12 (d, J=7.7 Hz, 1H), 7.01 (d, J=8.2 Hz, 1H), 6.76 (d, J=2.6 Hz, 1H), 4.59 (s, 2H), 4.28 (t, J=4.1 Hz, 1H), 3.85 (s, 6H), 2.94 (s, 2H), 2.14 (s, 2H), 1.84 (dd, J=13.1, 6.4 Hz, 2H), 1.38 (s, 6H). LCMS (ESI, m/z): 495 [M+NH$_4$]$^+$.

Examples 39-456: Examples 39-456 were Prepared by Similar Procedures as Described in Examples 1-38

| Ex | Name | Structure | NMR (¹H NMR, 300 MHz or 400 MHz, Methanol-d) | MS [M + H]⁺ |
|---|---|---|---|---|
| 39 | 1-(4-((4-chloro-3-(pyrrolidin-1-yl)benzyl)(methyl)amino)-4-methylpiperidine-1-carbonyl)-1H-pyrazole-3-carboxylic acid | 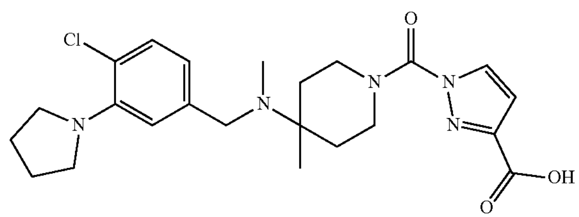 [SMILES: CN(Cc1ccc(Cl)c(N2CCCC2)c1)C1(C)CCN(C(=O)n2ccc(C(=O)O)n2)CC1] | δ 8.05-8.08 (m, 1H), 7.20-7.32 (m, 1H), 6.95-7.09 (m, 1H), 6.83-6.87 (m, 1H), 6.71-6.79 (m, 1H), 3.51-4.25 (m, 6H), 3.30-3.41 (m, 4H), 2.26 (s, 3H), 2.02-2.15 (m, 2H), 1.90-1.99 (m, 4H), 1.71-1.85 (m, 2H), 1.20 (s, 3H) | 460.1 |
| 40 | 1-(4-(3-oxa-8-azabicyclo[3.2.1]octan-8-yl)-4-(trifluoromethyl)benzyl)piperazine-1-carbonyl)-1H-pyrazole-3-carboxylic acid | 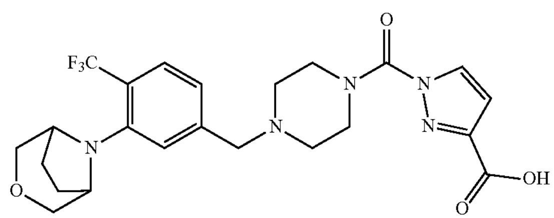 [SMILES: O=C(O)c1ccn(C(=O)N2CCN(Cc3ccc(C(F)(F)F)c(N4C5CCC4COC5)c3)CC2)n1] | δ 8.05-8.17 (m, 1H), 7.52-7.64 (m, 1H), 7.05-7.21 (m, 2H), 6.74-6.87 (m, 1H), 3.54-4.01 (m, 12H), 2.63-2.71 (m, 4H), 1.91-2.04 (m, 4H) | 494.5 |
| 41 | 1-(cis-5-((2-chlorobenzyl)oxy)octahydrocyclopenta[c]pyrrole-2-carbonyl)-1H-pyrazole-3-carboxylic acid | 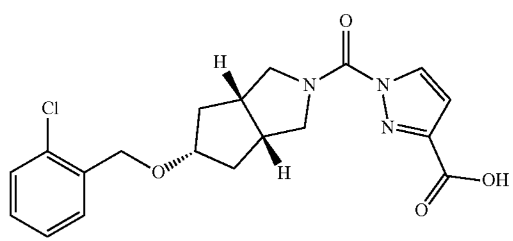 [SMILES: O=C(O)c1ccn(C(=O)N2C[C@H]3C[C@@H](OCc4ccccc4Cl)C[C@H]3C2)n1] | δ 8.05 (d, J = 2.4 Hz, 1H), 7.41-7.44 (m, 1H), 7.30-7.37 (m, 1H), 7.22-7.26 (m, 2H), 6.72 (d, J = 2.4 Hz, 1H), 4.56 (s, 2H), 4.24-4.45 (m, 1H), 4.15-4.20 (m, 1H), 3.88-4.06 (m, 3H), 2.83 (br, 2H), 2.18-2.23 (m, 2H), 1.82-1.85 (m, 2H) | 412.4 [M + Na]⁺ |
| 42 | 1-(4-((3-chloro-5-fluorobenzyl)oxy)piperidine-1-carbonyl)-1H-pyrazole-3-carboxylic acid | 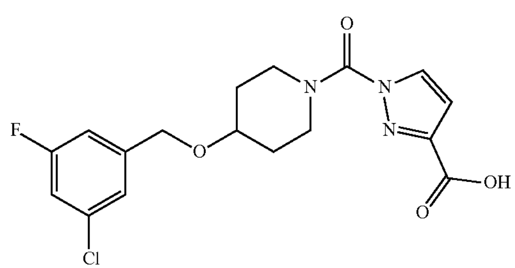 [SMILES: O=C(O)c1ccn(C(=O)N2CCC(OCc3cc(F)cc(Cl)c3)CC2)n1] | δ 8.05 (d, J = 2.6 Hz, 1H), 7.22 (s, 1H), 7.07-7.10 (m, 2H), 6.75 (d, J = 2.6 Hz, 1H), 4.59 (s, 2H), 4.04 (br, 2H), 3.72-3.80 (m, 1H), 3.60-3.66 (m, 2H), 1.99-2.07 (m, 2H), 1.73-1.83 (m, 2H) | 399.1 [M + NH₄]⁺ |

| Ex | Name | Structure | NMR (¹H NMR, 300 MHz or 400 MHz, Methanol-d) | MS [M + H]⁺ |
|---|---|---|---|---|
| 43 | 1-(2-(5-chloro-2-(trifluoromethyl)-benzyl)-2,8-diazaspiro[4.5]-decane-8-carbonyl)-1H-pyrazole-3-carboxylic acid | 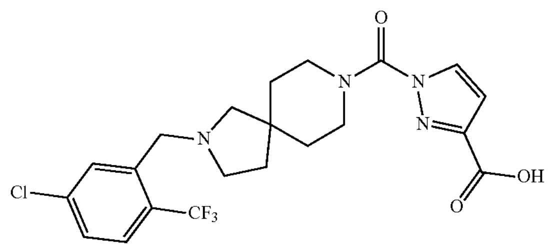 [SMILES: O=C(O)c1ccn(C(=O)N2CCC3(CCN(Cc4cc(Cl)ccc4C(F)(F)F)C3)CC2)n1] | δ 8.05 (s, 1H), 7.86 (s, 1H), 7.67 (d, J = 8.4 Hz, 1H), 7.45 (d, J = 8.4 Hz, 1H), 6.76 (s, 1H), 3.76-3.80 (m, 6H), 2.71 (t, J = 6.9 Hz, 2H), 2.56 (s, 2H), 1.72-1.84 (m, 6H) | 471.4 |
| 44 | 1-(2-(3-chloro-5-(pyrrolidin-1-yl)benzyl)-2,8-diazaspiro[4.5]-decane-8-carbonyl)-1H-pyrazole-3-carboxylic acid | 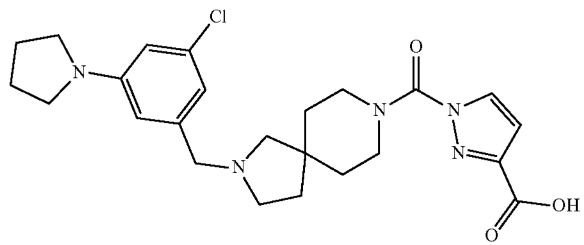 [SMILES: O=C(O)c1ccn(C(=O)N2CCC3(CCN(Cc4cc(Cl)cc(N5CCCC5)c4)C3)CC2)n1] | δ 8.06 (d, J = 2.7 Hz, 1H), 6.74-6.82 (m, 2H), 6.64 (s, 1H), 6.60 (s, 1H), 4.22 (s, 2H), 3.85 (br, 2H), 3.69-3.71 (m, 2H), 3.48-3.52 (m, 2H), 3.23-3.32 (m, 6H), 1.91-2.08 (m, 6H), 1.76-1.88 (m, 4H) | 472.2 |
| 45 | 1-(4-(4-chlorophenoxy)-benzyl)piperazine-1-carbonyl)-1H-pyrazole-3-carboxylic acid | 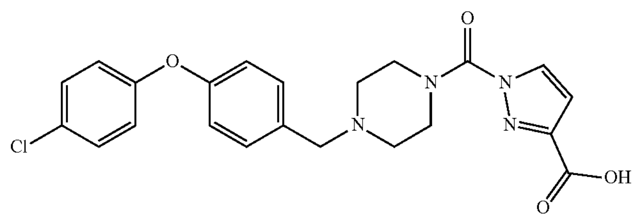 [SMILES: O=C(O)c1ccn(C(=O)N2CCN(Cc3ccc(Oc4ccc(Cl)cc4)cc3)CC2)n1] | δ 8.06 (d, J = 2.7 Hz, 1H), 7.31-7.38 (m, 4H), 6.94-6.99 (m, 4H), 6.74 (d, J = 2.7 Hz, 1H), 3.87 (br, 4H), 3.58 (s, 2H), 2.59 (t, J = 4.8 Hz, 4H) | 441.2 |
| 46 | 1-(4-((4-chloro-2-(pyrrolidin-1-yl)benzyl)(methyl)-amino)-4-methylpiperidine-1-carbonyl)-1H-pyrazole-3-carboxylic acid | 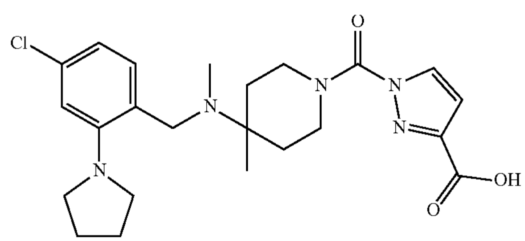 [SMILES: CN(Cc1ccc(Cl)cc1N1CCCC1)C1(C)CCN(C(=O)n2ccc(C(=O)O)n2)CC1] | δ 8.07-8.11 (m, 1H), 7.45-7.56 (m, 1H), 7.19-7.25 (m, 1H), 7.07-7.17 (m, 1H), 6.75 (s, 1H), 3.76-4.75 (m, 4H), 3.37-3.64 (m, 2H), 3.14 (s, 4H), 2.52 (s, 3H), 1.90-2.17 (m, 8H), 2.48 (s, 3H) | 460.1 |

| Ex | Name | Structure | NMR (¹H NMR, 300 MHz or 400 MHz, Methanol-d) | MS [M + H]⁺ |
|---|---|---|---|---|
| 47 | 1-(4-((3-chloro-2-(pyrrolidin-1-yl)benzyl)(methyl)-amino)-4-methylpiperidine-1-carbonyl)-1H-pyrazole-3-carboxylic acid | 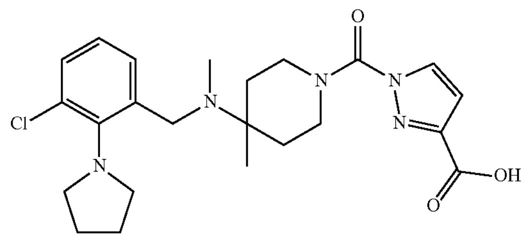 [SMILES: CN(Cc1cccc(Cl)c1N1CCCC1)C1(C)CCN(C(=O)n2ccc(C(=O)O)n2)CC1] | δ 8.07-8.15 (m, 1H), 7.47-7.55 (m, 2H), 7.25-7.31 (m, 1H), 6.75 (s, 1H), 3.90-4.78 (m, 4H), 3.32-3.83 (m, 6H), 2.60 (s, 3H), 1.85-2.27 (m, 8H), 1.49 (s, 3H) | 460.3 |
| 48 | (R)-1-(4-(2-(hexahydropyrrolo[1,2-a]pyrazin-2(1H)-yl)-4-(trifluoromethyl)-benzyl)piperazine-1-carbonyl)-1H-pyrazole-3-carboxylic acid | 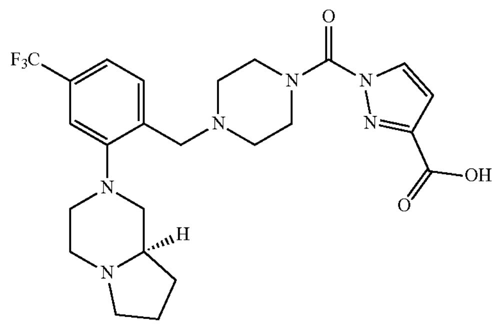 [SMILES: O=C(O)c1ccn(C(=O)N2CCN(Cc3ccc(C(F)(F)F)cc3N3CCN4CCC[C@@H]4C3)CC2)n1] | δ 8.07 (d, J = 2.7 Hz, 1H), 7.66 (d, J = 7.8 Hz, 1H), 7.43-7.47 (m, 2H), 6.76 (d, J = 2.7 Hz, 1H), 3.83 (br, 4H), 3.70 (s, 2H), 3.50-3.57 (m, 5H), 3.01-3.26 (m, 4H), 2.62 (t, J = 4.8 Hz, 4H), 2.09-2.23 (m, 3H), 1.91 (br, 1H) | 507.5 |
| 49 | (S)-1-(4-(2-(hexahydropyrrolo[1,2-a]pyrazin-2(1H)-yl)-4-(trifluoromethyl)-benzyl)piperazine-1-carbonyl)-1H-pyrazole-3-carboxylic acid | 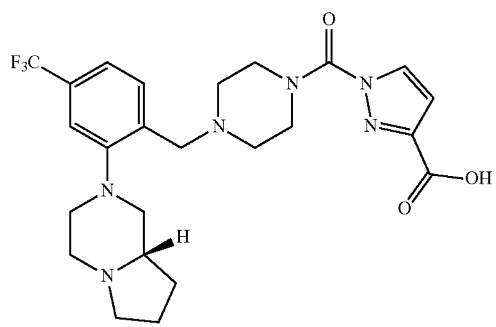 [SMILES: O=C(O)c1ccn(C(=O)N2CCN(Cc3ccc(C(F)(F)F)cc3N3CCN4CCC[C@H]4C3)CC2)n1] | δ 8.07 (d, J = 2.7 Hz, 1H), 7.66 (d, J = 8.1 Hz, 1H), 7.42-7.46 (m, 2H), 6.75 (d, J = 2.7 Hz, 1H), 3.83 (br, 4H), 3.69 (s, 2H), 3.43-3.50 (m, 5H), 3.12-3.15 (m, 2H), 2.93-3.00 (m, 2H), 2.61 (t, J = 4.8 Hz, 4H), 2.06-2.13 (m, 3H), 1.82 (br, 1H) | 507.5 |

-continued

| Ex | Name | Structure | NMR (¹H NMR, 300 MHz or 400 MHz, Methanol-d) | MS [M + H]⁺ |
|---|---|---|---|---|
| 50 | 1-(4-(4-ethynylbenzyl)piperazine-1-carbonyl)-1H-pyrazole-3-carboxylic acid | 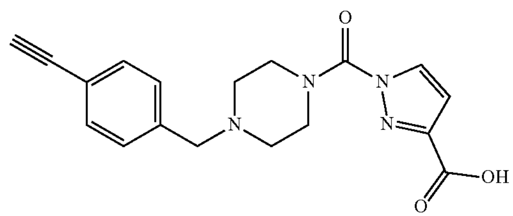 [SMILES: C#Cc1ccc(CN2CCN(C(=O)n3ccc(C(=O)O)n3)CC2)cc1] | δ 8.08 (d, J = 2.7 Hz, 1H), 7.44 (d, J = 8.3 Hz, 2H), 7.36 (d, J = 8.3 Hz, 2H), 6.76 (d, J = 2.7 Hz, 1H), 3.87 (br, 4H), 3.65 (s, 2H), 3.47 (s, 1H), 2.63 (t, J = 5.0 Hz, 4H) | 339.0 |
| 51 | 1-(4-(3-(4-fluorophenoxy)benzyl)piperazine-1-carbonyl)-1H-pyrazole-3-carboxylic acid | 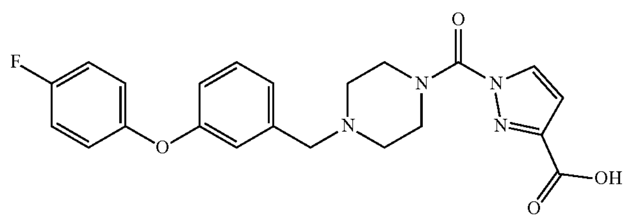 | δ 8.11 (d, J = 2.7 Hz, 1H), 7.33 (t, J = 7.8 Hz, 1H), 6.98-7.13 (m, 6H), 6.88-6.92 (m, 1H), 6.79 (d, J = 2.7 Hz, 1H), 3.88 (br, 4H), 3.68 (br, 2H), 2.70 (br, 4H) | 425.0 |
| 52 | 1-(4-(3-(pyridin-2-yloxy)benzyl)piperazine-1-carbonyl)-1H-pyrazole-3-carboxylic acid | 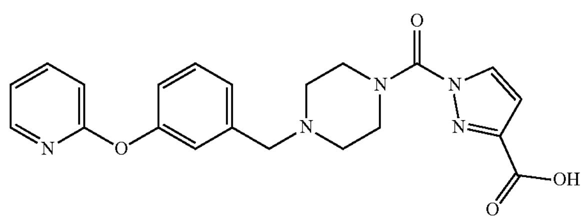 [SMILES: O=C(O)c1ccn(C(=O)N2CCN(Cc3cccc(Oc4ccccn4)c3)CC2)n1] | δ 8.12-8.14 (m, 2H), 7.80-7.86 (m, 1H), 7.41 (t, J = 7.8 Hz, 1H), 7.25 (d, J = 7.5 Hz, 1H), 7.18 (br, 1H), 7.04-7.14 (m, 2H), 6.95 (d, J = 8.7 Hz, 1H), 6.80 (d, J = 2.7 Hz, 1H), 3.89 (br, 4H), 3.76 (br, 2H), 2.77 (br, 4H) | 408.0 |
| 53 | 1-(trans-5-((3-chloro-5-fluorobenzyl)oxy)octahydrocyclopenta[c]pyrrole-2-carbonyl)-1H-pyrazole-3-carboxylic acid | 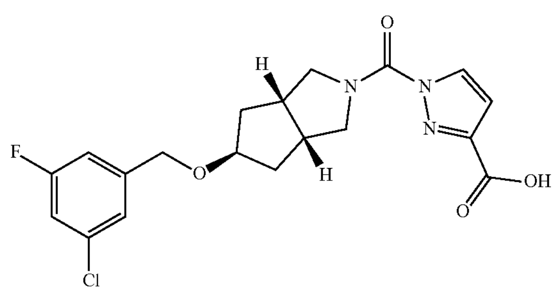 [SMILES: O=C(O)c1ccn(C(=O)N2C[C@H]3C[C@H](OCc4cc(F)cc(Cl)c4)C[C@H]3C2)n1] | δ 8.13 (d, J = 2.8 Hz, 1H), 7.19 (s, 1H), 7.03-7.09 (m, 2H), 6.73 (d, J = 2.8 Hz, 1H), 4.47 (s, 2H), 4.20-4.24 (m, 1H), 3.87-4.10 (m, 3H), 3.68-3.75 (m, 1H), 2.91 (br, 2H), 2.03-2.11 (m, 2H), 1.77-1.83 (m, 2H) | 425.2 [M + NH₄]⁺ |

| Ex | Name | Structure | NMR (1H NMR, 300 MHz or 400 MHz, Methanol-d) | MS [M + H]+ |
|---|---|---|---|---|
| 54 | 4-chloro-1-(4-(((5-chloro-2-(trifluoromethyl)-benzyl)(methyl)-amino)-methyl)piperidine-1-carbonyl)-1H-pyrazole-3-carboxylic acid | 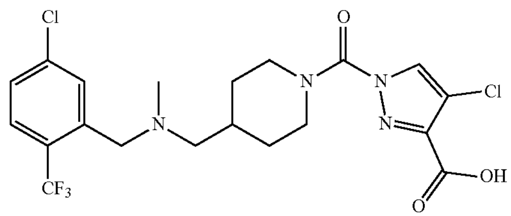 [SMILES: CN(Cc1cc(Cl)ccc1C(F)(F)F)CC1CCN(C(=O)n2cc(Cl)c(C(=O)O)n2)CC1] | δ 8.13 (s, 1H), 7.88 (s, 1H), 7.64 (d, J = 8.4 Hz, 1H), 7.41-7.43 (m, 1H), 4.37-4.40 (m, 2H), 3.67 (s, 2H), 3.08-3.14 (m, 2H), 2.33 (d, J = 6.8 Hz, 2H), 2.24 (s, 3H), 1.86-1.93 (m, 3H), 1.22-1.32 (m, 2H) | 493.0 |
| 55 | 1-(trans-5-((4-(4-chlorophenoxy)-benzyl)oxy)octahydrocyclopenta[c]pyrrole-2-carbonyl)-1H-pyrazole-3-carboxylic acid | 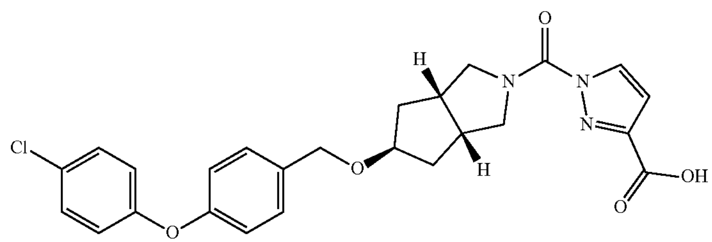 [SMILES: O=C(O)c1ccn(C(=O)N2C[C@H]3C[C@H](OCc4ccc(Oc5ccc(Cl)cc5)cc4)C[C@H]3C2)n1] | δ 8.16 (d, J = 2.7 Hz, 1H), 7.32-7.38 (m, 4H), 6.95-7.00 (m, 4H), 6.77 (d, J = 2.7 Hz, 1H), 4.48 (s, 2H), 3.60-4.27 (m, 5H), 2.92 (br, 2H), 2.09-2.12 (m, 2H), 1.77-1.86 (m, 2H) | 499.2 [M + NH4]+ |
| 56 | 1-(1-(6-(trifluoromethyl)-benzo[b]thiophene-2-carbonyl)-1,8-diazaspiro[4.5]-decane-8-carbonyl)-1H-pyrazole-3-carboxylic acid | 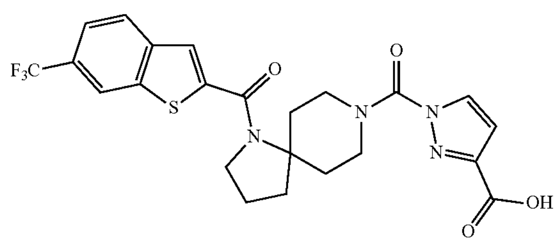 [SMILES: O=C(O)c1ccn(C(=O)N2CCC3(CCCN3C(=O)c3cc4ccc(C(F)(F)F)cc4s3)CC2)n1] | δ 8.29 (s, 1H), 8.12 (d, J = 2.7 Hz, 1H), 8.06 (d, J = 8.4 Hz, 1H), 7.84 (s, 1H), 7.63-7.67 (m, 1H), 6.78 (d, J = 2.7 Hz, 1H), 4.61 (br, 2H), 3.92 (t, J = 6.6 Hz, 2H), 3.12-3.32 (m, 4H), 2.25 (t, J = 6.6 Hz, 2H), 1.98-2.00 (m, 2H), 1.60-1.64 (m, 2H) | 507.0 |
| 57 | 1-(4-(3-((4-(trifluoromethyl)-pyridin-2-yl)oxy)benzyl)-piperazine-1-carbonyl)-1H-pyrazole-3-carboxylic acid | 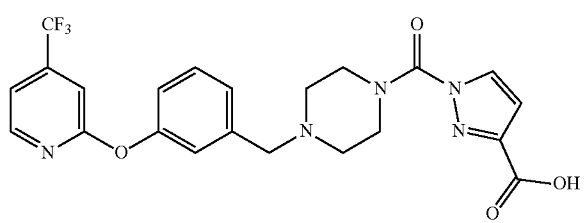 [SMILES: O=C(O)c1ccn(C(=O)N2CCN(Cc3cccc(Oc4cc(C(F)(F)F)ccn4)c3)CC2)n1] | δ 8.32 (d, J = 5.2 Hz, 1H), 8.10 (d, J = 2.7 Hz, 1H), 7.35-7.45 (m, 2H), 7.23-7.30 (m, 3H), 7.09-7.12 (m, 1H), 6.78 (d, J = 2.7 Hz, 1H), 3.89 (br, 4H), 3.75 (s, 2H), 2.74 (br, 4H) | 476.4 |

| Ex | Name | Structure | NMR (¹H NMR, 300 MHz or 400 MHz, Methanol-d) | MS [M + H]⁺ |
|---|---|---|---|---|
| 58 | 1-(2-(6-(trifluoromethyl)-benzo[b]-thiophene-2-carbonyl)-2,8-diazaspiro[4.5]-decane-8-carbonyl)-1H-pyrazole-3-carboxylic acid | 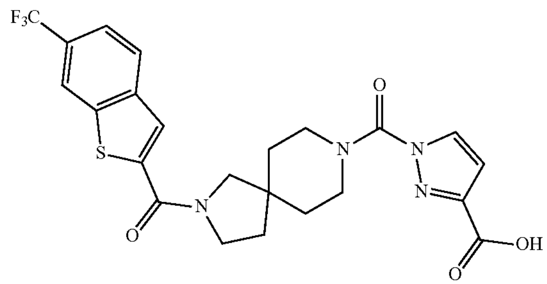 [SMILES: O=C(O)c1ccn(C(=O)N2CCC3(CCN(C(=O)c4cc5ccc(C(F)(F)F)cc5s4)C3)CC2)n1] | δ 8.32 (s, 1H), 8.04-8.12 (m, 2H), 8.00 (s, 1H), 7.67 (d, J = 8.4 Hz, 1H), 6.75-6.79 (m, 1H), 4.02-4.06 (m, 1H), 3.76-3.84 (m, 6H), 3.63 (br, 1H), 2.02-2.07 (m, 2H), 1.78-1.83 (m, 4H) | 507.2 |
| 59 | 1-(4-(3-(pyridin-4-yloxy)benzyl)-piperazine-1-carbonyl)-1H-pyrazole-3-carboxylic acid | 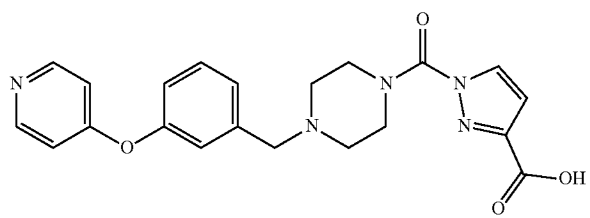 [SMILES: O=C(O)c1ccn(C(=O)N2CCN(Cc3cccc(Oc4ccncc4)c3)CC2)n1] | δ 8.40-8.42 (m, 2H), 8.13 (d, J = 2.7 Hz, 1H), 7.48 (t, J = 7.8 Hz, 1H), 7.34 (d, J = 7.8 Hz, 1H), 7.22 (br, 1H), 7.08-7.12 (m, 1H), 6.97-6.99 (m, 2H), 6.82 (d, J = 2.7 Hz, 1H), 3.87 (br, 4H), 3.73 (br, 2H), 2.72 (br, 4H) | 408.2 |
| 60 | 1-(4-(3-(pyrazin-2-yloxy)benzyl)-piperazine-1-carbonyl)-1H-pyrazole-3-carboxylic acid | 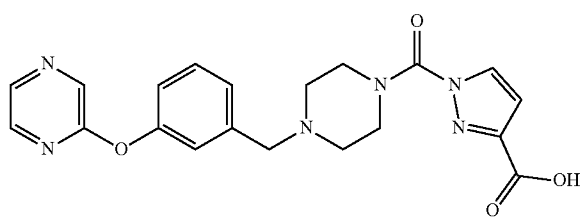 [SMILES: O=C(O)c1ccn(C(=O)N2CCN(Cc3cccc(Oc4cnccn4)c3)CC2)n1] | δ 8.41 (s, 1H), 8.28 (s, 1H), 8.13-8.14 (m, 1H), 8.05 (d, J = 2.7 Hz, 1H), 7.38-7.42 (m, 1H), 7.21-7.27 (m, 2H), 7.07-7.10 (m, 1H), 6.72 (d, J = 2.7 Hz, 1H), 3.87 (br, 4H), 3.61 (s, 2H), 2.57-2.60 (t, J = 2.7 Hz, 4H) | 409.4 |
| 61 | 1-(4-(3-((5-(trifluoromethyl)-pyridin-2-yl)oxy)benzyl)-piperazine-1-carbonyl)-1H-pyrazole-3-carboxylic acid | 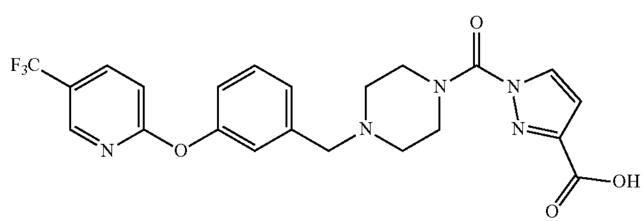 [SMILES: O=C(O)c1ccn(C(=O)N2CCN(Cc3cccc(Oc4ccc(C(F)(F)F)cn4)c3)CC2)n1] | δ 8.42 (br, 1H), 8.08-8.12 (m, 2H), 7.44 (t, J = 8.0 Hz, 1H), 7.24-7.32 (m, 2H), 7.11-7.18 (m, 2H), 6.79 (d, J = 2.4 Hz, 1H), 3.79-3.90 (m, 6H), 2.78 (br, 4H) | 476.4 |

-continued

| Ex | Name | Structure | NMR (¹H NMR, 300 MHz or 400 MHz, Methanol-d) | MS [M + H]⁺ |
|---|---|---|---|---|
| 62 | 1-(4-(3-(pyrimidin-2-yloxy)benzyl)-piperazine-1-carbonyl)-1H-pyrazole-3-carboxylic acid | 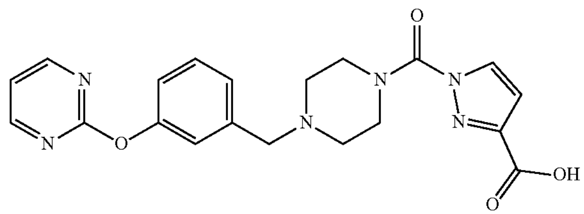 | δ 8.59 (d, J = 4.8 Hz, 2H), 8.12 (d, J = 2.8 Hz, 1H), 7.44 (t, J = 8.0 Hz, 1H), 7.30 (d, J = 8.0 Hz, 1H), 7.20-7.25 (m, 2H), 7.12-7.15 (m, 1H), 6.880 (d, J = 2.8 Hz, 1H), 3.89 (br, 4H), 3.77 (s, 2H), 2.76 (t, J = 4.8 Hz, 4H) | 409.4 |
| 63 | 1-(4-(3-(pyrimidin-4-yloxy)benzyl)-piperazine-1-carbonyl)-1H-pyrazole-3-carboxylic acid | 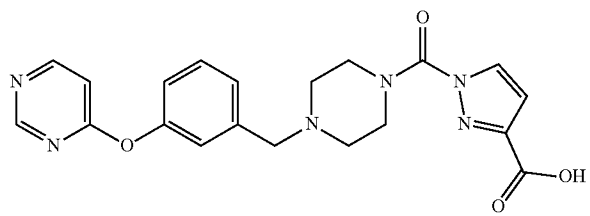 [SMILES: O=C(O)c1ccn(C(=O)N2CCN(Cc3cccc(Oc4ccncn4)c3)CC2)n1] | δ 8.70 (s, 1H), 8.60 (d, J = 6.0 Hz, 1H), 8.05 (d, J = 2.7 Hz, 1H), 7.43 (t, J = 7.8 Hz, 1H), 7.31 (d, J = 7.8 Hz, 1H), 7.22 (s, 1H), 7.03-7.11 (m, 2H), 6.73 (d, J = 2.7 Hz, 1H), 3.87 (br, 4H), 3.62 (s, 2H), 2.59 (t, J = 4.8 Hz, 4H) | 409.0 |
| 64 | 1-(4-(3-(pyrimidin-2-yl)benzyl)-piperazine-1-carbonyl)-1H-pyrazole-3-carboxylic acid | 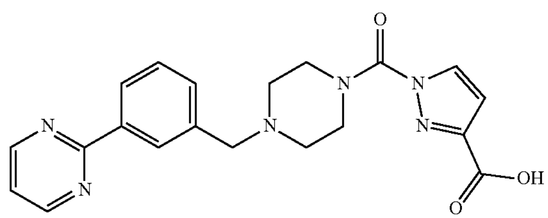 [SMILES: O=C(O)c1ccn(C(=O)N2CCN(Cc3cccc(-c4ncccn4)c3)CC2)n1] | δ 8.85 (d, J = 5.2 Hz, 2H), 8.47 (s, 1H), 8.37 (d, J = 7.6 Hz, 1H), 8.12 (d, J = 2.4 Hz, 1H), 7.50-7.57 (m, 2H), 7.37 (t, J = 4.8 Hz, 1H), 6.79 (d, J = 2.4 Hz, 1H), 3.88-4.04 (m, 6H), 2.83 (t, J = 4.8 Hz, 4H) | 393.4 |
| 65 | 1-(4-(3-(pyrimidin-5-yloxy)benzyl)-piperazine-1-carbonyl)-1H-pyrazole-3-carboxylic acid | 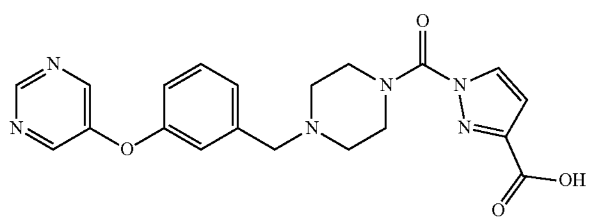 [SMILES: O=C(O)c1ccn(C(=O)N2CCN(Cc3cccc(Oc4cncnc4)c3)CC2)n1] | δ 8.90 (s, 1H), 8.53 (s, 2H), 8.08 (d, J = 2.4 Hz, 1H), 7.43 (t, J = 7.8 Hz, 1H), 7.27 (d, J = 7.8 Hz, 1H), 7.19 (s, 1H), 7.04-7.07 (m, 1H), 6.76 (d, J = 2.4 Hz, 1H), 3.86 (br, 4H), 3.62 (s, 2H), 2.60 (t, J = 4.8 Hz, 4H) | 409.1 |

| Ex | Name | Structure | NMR (¹H NMR, 300 MHz or 400 MHz, Methanol-d) | MS [M + H]⁺ |
|---|---|---|---|---|
| 66 | 1-(4-(4-methyl-2-(1,3,4-oxadiazol-2-yl)benzyl)-piperazine-1-carbonyl)-1H-pyrazole-3-carboxylic acid | 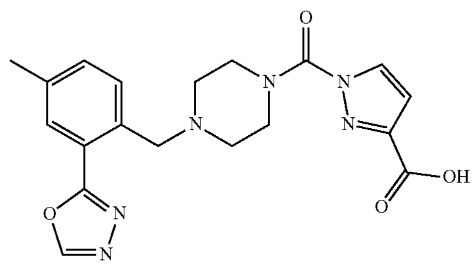 [SMILES: Cc1ccc(CN2CCN(C(=O)n3ccc(C(=O)O)n3)CC2)c(-c2nnco2)c1] | δ 9.07 (s, 1H), 8.09 (d, J = 2.8 Hz, 1H), 7.76 (s, 1H), 7.49-7.51 (m, 1H), 7.42-7.44 (m, 1H), 6.77 (d, J = 2.8 Hz, 1H), 4.13 (s, 2H), 3.78 (br, 4H), 2.80 (br, 4H), 2.43 (s, 3H) | 397.5 |
| 67 | 1-(4-(4-chloro-2-(1,3,4-oxadiazol-2-yl)benzyl)-piperazine-1-carbonyl)-1H-pyrazole-3-carboxylic acid | 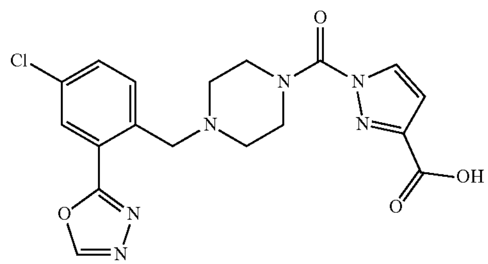 [SMILES: O=C(O)c1ccn(C(=O)N2CCN(Cc3ccc(Cl)cc3-c3nnco3)CC2)n1] | δ 9.09 (s, 1H), 8.12 (d, J = 2.4 Hz, 1H), 7.92 (s, 1H), 7.60-7.64 (m, 2H), 6.82 (d, J = 2.4 Hz, 1H), 4.01 (s, 2H), 3.69 (br, 4H), 2.62-2.64 (m, 4H) | 417.4 |
| 68 | 1-(4-(2-(1,3,4-oxadiazol-2-yl)-4-(trifluoromethoxy)-benzyl)-piperazine-1-carbonyl)-1H-pyrazole-3-carboxylic acid | 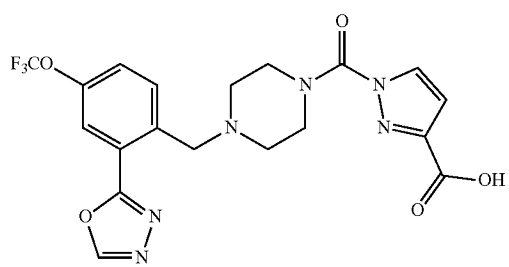 [SMILES: O=C(O)c1ccn(C(=O)N2CCN(Cc3ccc(OC(F)(F)F)cc3-c3nnco3)CC2)n1] | δ 9.10 (s, 1H), 8.09 (d, J = 2.4 Hz, 1H), 7.80 (s, 1H), 7.74 (d, J = 8.5 Hz, 1H), 7.51-7.54 (m, 1H), 6.79 (d, J = 2.4 Hz, 1H), 4.01 (s, 2H), 3.68 (br, 4H), 2.57-2.59 (m, 4H) | 467.4 |

| Ex | Name | Structure | NMR (¹H NMR, 300 MHz or 400 MHz, Methanol-d) | MS [M + H]⁺ |
|---|---|---|---|---|
| 69 | 1-(4-(2-(1,3,4-oxadiazol-2-yl)-4-(trifluoromethyl)-benzyl)-piperazine-1-carbonyl)-1H-pyrazole-3-carboxylic acid | 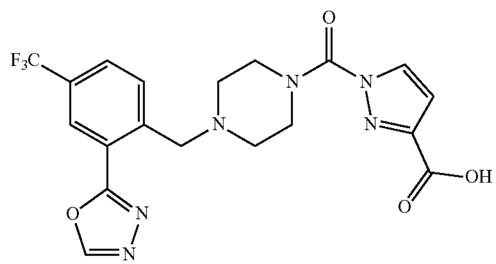 [SMILES: O=C(O)c1ccn(C(=O)N2CCN(Cc3ccc(C(F)(F)F)cc3-c3nnco3)CC2)n1] | δ 9.12 (s, 1H), 8.09 (s, 1H), 8.09 (d, J = 2.8 Hz, 1H), 7.85-7.91 (m, 2H), 6.80 (d, J = 2.8 Hz, 1H), 4.04 (s, 2H), 3.67 (br, 4H), 2.54-2.56 (m, 4H) | 451.5 |
| 70 | 1-(2-(3-chloro-5-fluorobenzyl)-2,8-diazaspiro[4.5]-decane-8-carbonyl)-1H-pyrazole-3-carboxylic acid | 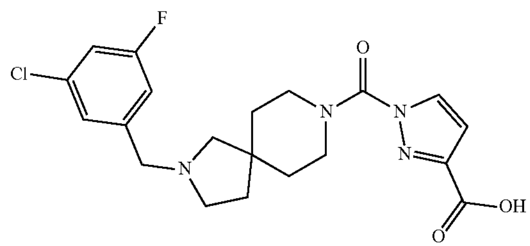 [SMILES: O=C(O)c1ccn(C(=O)N2CCC3(CCN(Cc4cc(F)cc(Cl)c4)C3)CC2)n1] | δ 8.04 (d, J = 2.7 Hz, 1H), 7.40 (s, 1H), 7.22-7.28 (m, 2H), 6.76 (d, J = 2.7 Hz, 1H), 4.13-4.19 (m, 2H), 3.77 (br, 2H), 3.63-3.68 (m, 2H), 3.22-3.32 (m, 2H), 3.10 (br, 2H), 1.96-2.01 (m, 2H), 1.68-1.83 (m, 4H) | 421.1 |
| 71 | 1-(2-(2-methyl-3-(trifluoromethyl)-benzyl)-2,8-diazaspiro[4.5]-decane-8-carbonyl)-1H-pyrazole-3-carboxylic acid | 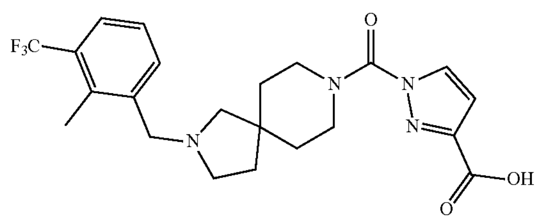 [SMILES: Cc1c(CN2CCC3(CCN(C(=O)n4ccc(C(=O)O)n4)CC3)C2)cccc1C(F)(F)F] | δ 8.05 (d, J = 2.4 Hz, 1H), 7.61-7.65 (m, 2H), 7.31-7.39 (m, 1H), 6.76 (d, J = 2.4 Hz, 1H), 3.99 (s, 2H), 3.83 (br, 2H), 3.72 (br, 2H), 2.90 (t, J = 6.6 Hz, 2H), 2.78 (s, 2H), 2.53 (s, 3H), 1.86 (t, J = 7.2 Hz, 2H), 1.75-1.82 (m, 4H) | 451.2 |
| 72 | 1-(2-(3-chloro-5-(trifluoromethyl)-benzyl)-2,8-diazaspiro[4.5]-decane-8-carbonyl)-1H-pyrazole-3-carboxylic acid | 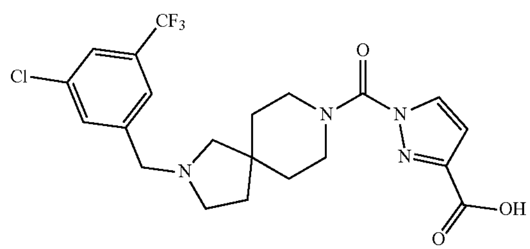 | δ 8.05 (d, J = 2.7 Hz, 1H), 7.73 (s, 1H), 7.68 (s, 1H), 7.65 (s, 1H), 6.76 (d, J = 2.7 Hz, 1H), 3.81-3.86 (m, 4H), 3.68-3.71 (m, 2H), 2.83 (t, J = 6.9 Hz, 2H), 2.68 (s, 2H), 1.85 (t, J = 6.9 Hz, 2H), 1.81-1.70 (m, 4H) | 471.2 |

-continued

| Ex | Name | Structure | NMR (1H NMR, 300 MHz or 400 MHz, Methanol-d) | MS [M + H]+ |
|---|---|---|---|---|
| 73 | 1-(2-([1,1'-biphenyl]-3-ylmethyl)-2,8-diazaspiro[4.5]decane-8-carbonyl)-1H-pyrazole-3-carboxylic acid | 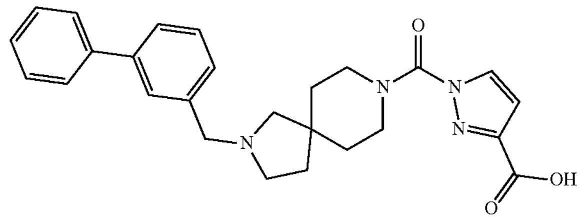 [SMILES: O=C(O)c1ccn(C(=O)N2CCC3(CCN(Cc4cccc(-c5ccccc5)c4)C3)CC2)n1] | δ 8.05 (d, J = 2.7 Hz, 1H), 7.83 (s, 1H), 7.74-7.66 (m, 3H), 7.66-7.49 (m, 2H), 7.36-7.49 (m, 3H), 6.75 (s, 1H), 4.40 (s, 2H), 3.86 (br, 2H), 3.68 (br, 2H), 3.42 (t, J = 6.9 Hz, 2H), 3.26 (s, 2H), 2.06 (t, J = 6.9 Hz, 2H), 1.84-1.76 (m, 4H) | 445.3 |
| 74 | 1-(2-(2-chloro-6-(trifluoromethyl)-benzyl)-2,8-diazaspiro[4.5]decane-8-carbonyl)-1H-pyrazole-3-carboxylic acid | 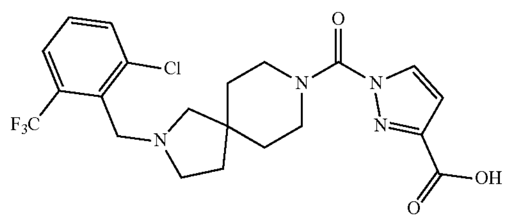 [SMILES: O=C(O)c1ccn(C(=O)N2CCC3(CCN(Cc4c(Cl)cccc4C(F)(F)F)C3)CC2)n1] | δ 8.06 (br, 1H), 7.68-7.73 (m, 2H), 7.46 (d, J = 7.8 Hz, 1H), 6.78 (br, 1H), 3.98 (s, 2H), 3.70-3.77 (m, 4H), 2.76 (t, J = 6.9 Hz, 2H), 2.63 (s, 2H), 1.64-1.74 (m, 6H) | 471.2 |
| 75 | 1-(2-(4-(4-chlorophenoxy)-benzyl)-2,8-diazaspiro[4.5]decane-8-carbonyl)-1H-pyrazole-3-carboxylic acid | 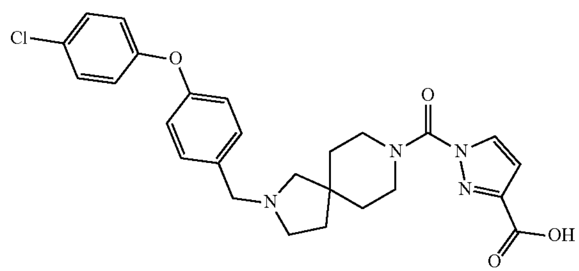 [SMILES: O=C(O)c1ccn(C(=O)N2CCC3(CCN(Cc4ccc(Oc5ccc(Cl)cc5)cc4)C3)CC2)n1] | δ 8.06 (d, J = 2.7 Hz, 1H), 7.53 (d, J = 8.7 Hz, 2H), 7.49-7.37 (m, 2H), 7.00-7.08 (m, 4H), 6.76 (d, J = 2.7 Hz, 1H) 4.31 s, 2H), 3.82-3.88 (m, 2H), 3.65-3.78 (m, 2H), 3.40 (t, J = 7.2 Hz, 2H), 3.23 (s, 2H), 2.06 (t, J = 7.2 Hz, 2H), 1.86-1.76 (m, 4H) | 495.2 |
| 76 | 1-(1-(2-chloro-4-(trifluoromethyl)-benzyl)-1,8-diazaspiro[4.5]decane-8-carbonyl)-1H-pyrazole-3-carboxylic acid | 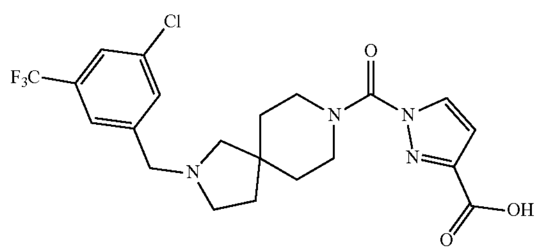 [SMILES: O=C(O)c1ccn(C(=O)N2CCC3(CCN(Cc4cc(Cl)cc(C(F)(F)F)c4)C3)CC2)n1] | δ 8.07 (d, J = 2.7 Hz, 1H), 7.72-7.77 (m, 1H), 7.67 (s, 1H), 7.58-7.61 (m, 1H), 6.77 (d, J = 2.7 Hz, 1H), 4.54-4.58 (m, 2H), 3.89 (s, 2H), 3.09-3.19 (m, 2H), 2.75-2.80 (m, 2H), 2.00-2.04 (m, 4H),1.91-1.98 (m, 2H), 1.82-1.89 (m, 2H) | 471.3 |

-continued

| Ex | Name | Structure | NMR (¹H NMR, 300 MHz or 400 MHz, Methanol-d) | MS [M + H]⁺ |
|---|---|---|---|---|
| 77 | 1-(2-(2-chloro-4-(trifluoromethyl)-benzyl)-2,8-diazaspiro[4.5]-decane-8-carbonyl)-1H-pyrazole-3-carboxylic acid | 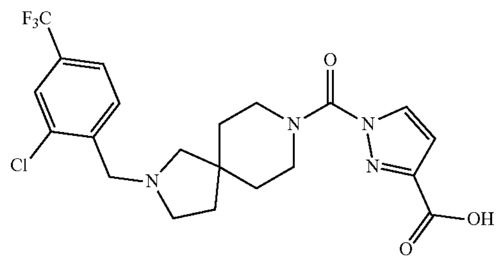 [SMILES: O=C(O)c1ccn(C(=O)N2CCC3(CCN(Cc4ccc(C(F)(F)F)cc4Cl)C3)CC2)n1] | δ 8.07 (d, J = 2.7 Hz, 1H), 7.75-7.81 (m, 2H), 7.66 (d, J = 8.1 Hz, 1H), 6.78 (d, J = 2.7 Hz, 1H), 4.00 (s, 2H), 3.72-3.86 (m, 4H), 2.91 (t, J = 6.9 Hz, 2H), 2.76 (s, 2H), 1.86 (t, J = 6.9 Hz, 2H), 1.80-1.72 (m, 4H) | 471.2 |
| 78 | 1-(2-(3-chloro-4-(trifluoromethyl)-benzyl)-2,8-diazaspiro[4.5]-decane-8-carbonyl)-1H-pyrazole-3-carboxylic acid | 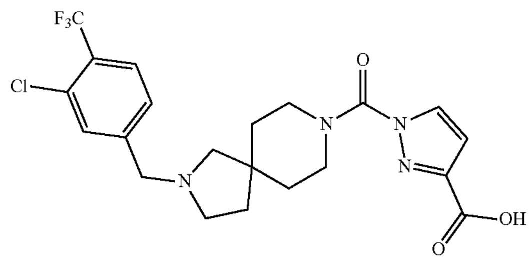 [SMILES: O=C(O)c1ccn(C(=O)N2CCC3(CCN(Cc4ccc(C(F)(F)F)c(Cl)c4)C3)CC2)n1] | δ 8.07 (d, J = 2.7 Hz, 1H), 7.83-7.81 (m, 2H), 7.62 (d, J = 7.8 Hz, 1H), 6.79 (d, J = 2.7 Hz, 1H), 4.22-4.16 (m, 2H), 3.71-3.80 (m, 4H), 2.94-3.22 (m, 4H), 1.99 (t, J = 6.9 Hz, 2H), 1.85-1.73 (m, 4H) | 471.2 |
| 79 | 1-(2-(3,5-difluorobenzyl)-2,8-diazaspiro[4.5]-decane-8-carbonyl)-1H-pyrazole-3-carboxylic acid | 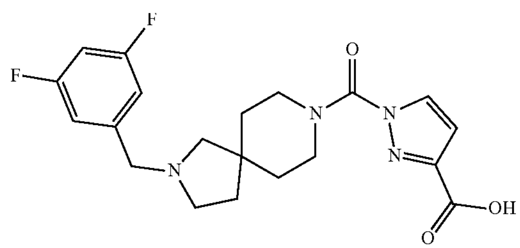 [SMILES: O=C(O)c1ccn(C(=O)N2CCC3(CCN(Cc4cc(F)cc(F)c4)C3)CC2)n1] | δ 8.08 (d, J = 2.7 Hz, 1H), 7.16-7.20 (m, 2H), 7.06-6.99 (m, 1H), 6.79 (d, J = 2.7 Hz, 1H), 4.19 (s, 2H), 3.82-3.87 (m, 2H), 3.67-3.72 (m, 2H), 3.25 (t, J = 6.9 Hz, 2H), 3.09 (s, 2H), 2.01 (t, J = 6.9 Hz, 2H), 1.75-1.87 (m, 4H) | 405.2 |

-continued

| Ex | Name | Structure | NMR (¹H NMR, 300 MHz or 400 MHz, Methanol-d) | MS [M + H]⁺ |
|---|---|---|---|---|
| 80 | 1-(1-(2-((2R,5S)-2,5-dimethylpyrrolidin-1-yl)-4-(trifluoromethyl)benzyl)-1,8-diazaspiro[4.5]decane-8-carbonyl)-1H-pyrazole-3-carboxylic acid | 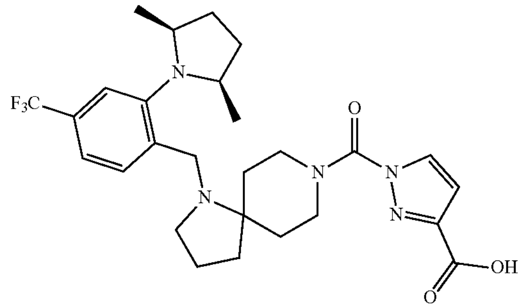 [SMILES: C[C@@H]1CC[C@H](C)N1c1cc(C(F)(F)F)ccc1CN1CCCC12CCN(C(=O)n1ccc(C(=O)O)n1)CC2] | δ 8.08 (d, J = 2.7 Hz, 1H), 7.81 (d, J = 7.8 Hz, 1H), 7.66 (s, 1H), 7.50 (d, J = 7.8 Hz, 1H), 6.76 (d, J = 2.7 Hz, 1H), 4.62 (br, 2H), 4.16 (s, 2H), 3.10-3.32 (m, 4H), 2.89 (t, J = 6.9 Hz, 2H), 2.01-2.13 (m, 6H), 1.86-1.96 (m, 2H), 1.61-1.88 (m, 2H), 1.57-1.60 (m, 2H), 0.90 (d, J = 6.0 Hz, 6H) | 534.3 |
| 81 | 1-(4-(5-chloro-2-(trifluoromethyl)benzyl)(methyl)amino)piperidine-1-carbonyl)-1H-pyrazole-3-carboxylic acid | 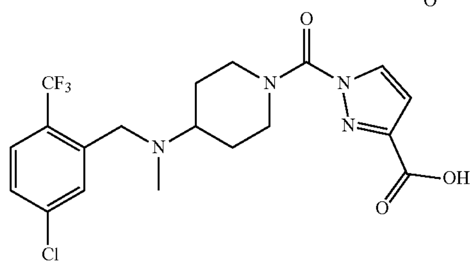 | δ 8.08 (d, J = 2.7 Hz, 1H), 7.90 (s, 1H), 7.64 (d, J = 8.4 Hz, 1H), 7.40-7.44 (m, 1H), 6.80 (d, J = 2.7 Hz, 1H), 4.47-4.52 (m, 2H), 3.83 (s, 2H), 3.06-3.14 (m, 2H), 2.81-2.89 (m, 1H), 2.26 (s, 3H), 1.93-1.96 (m, 2H), 1.69-1.82 (m, 2H) | 445.1 |
| 82 | 1-(1-(2-(3-oxa-8-azabicyclo[3.2.1]octan-8-yl)-4-(trifluoromethyl)benzyl)-1,8-diazaspiro[4.5]decane-8-carbonyl)-1H-pyrazole-3-carboxylic acid | 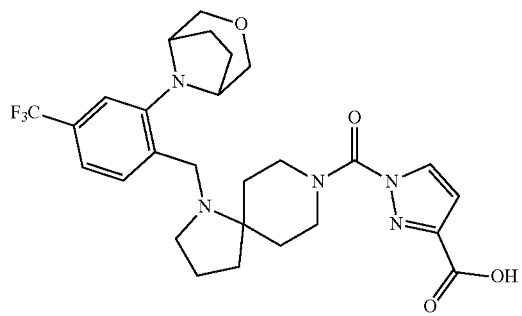 [SMILES: O=C(O)c1ccn(C(=O)N2CCC3(CCCN3Cc3ccc(C(F)(F)F)cc3N3C4CCC3COC4)CC2)n1] | δ 8.09 (d, J = 2.7 Hz, 1H), 7.75 (d, J = 8.1 Hz, 1H), 7.34 (d, J = 8.1 Hz, 1H), 7.23 (s, 1H), 6.78 (d, J = 2.7 Hz, 1H), 4.63 (br, 2H), 4.26 (s, 2H), 3.92 (d, J = 9.3 Hz, 2H), 3.60-3.75 (m, 4H), 3.07-3.29 (m, 4H), 2.14-2.26 (m, 4H), 1.88-2.06 (m, 6H), 1.66-1.85 (m, 2H) | 548.3 |

| Ex | Name | Structure | NMR (¹H NMR, 300 MHz or 400 MHz, Methanol-d) | MS [M + H]⁺ |
|---|---|---|---|---|
| 83 | 1-(4-(2-(pyrrolidin-1-yl)-4-(trifluoromethyl)-benzyl)-piperazine-1-carbonyl)-1H-pyrazole-3-carboxylic acid | 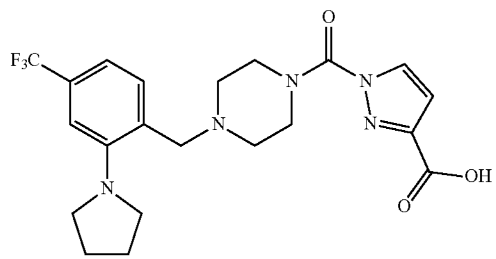 [SMILES: O=C(O)c1ccn(C(=O)N2CCN(Cc3ccc(C(F)(F)F)cc3N3CCCC3)CC2)n1] | δ 8.10 (d, J = 2.6 Hz, 1H), 7.61 (d, J = 7.8 Hz, 1H), 7.12-7.15 (m, 2H), 6.79 (d, J = 2.6 Hz, 1H), 3.88 (br, 4H), 3.71 (s, 2H), 3.24-3.28 (m, 4H), 2.61 (t, J = 4.9 Hz, 4H), 1.96-2.03 (m, 4H) | 452.0 |
| 84 | 1-(4-(3-chlorophenoxy)-benzyl)-piperazine-1-carbonyl)-1H-pyrazole-3-carboxylic acid | 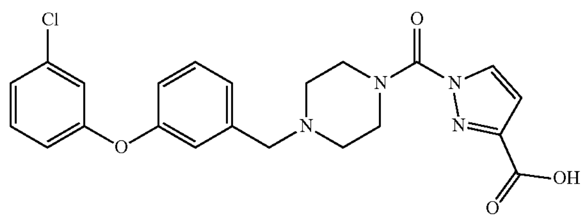 [SMILES: O=C(O)c1ccn(C(=O)N2CCN(Cc3cccc(Oc4cccc(Cl)c4)c3)CC2)n1] | δ 8.10 (d, J = 2.7 Hz, 1H), 7.35-7.47 (m, 1H), 7.28-7.34 (m, 1H), 7.21-7.27 (m, 1H), 7.08-7.18 (m, 2H), 6.92-6.99 (m, 2H), 6.89-6.92 (m, 1H), 6.80 (d, J = 2.7 Hz, 1H), 3.89 (br, 4H), 3.73 (s, 2H), 2.72-2.76 (m, 4H) | 441.2 |
| 85 | 1-(4-(3-(2-chlorophenoxy)benzyl)piperazine-1-carbonyl)-1H-pyrazole-3-carboxylic acid | 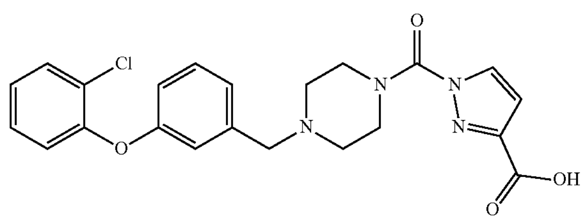 [SMILES: O=C(O)c1ccn(C(=O)N2CCN(Cc3cccc(Oc4ccccc4Cl)c3)CC2)n1] | δ 8.10 (d, J = 2.7 Hz, 1H), 7.47-7.50 (m, 1H), 7.26-7.36 (m, 2H), 7.12-7.18 (m, 2H), 7.01-7.08 (m, 2H), 6.85-6.88 (m, 1H), 6.78 (d, J = 2.7 Hz, 1H), 3.89 (br, 4H), 3.76 (s, 2H), 2.76-2.88 (m, 4H) | 441.2 |
| 86 | 1-(1-(3-chloro-5-(trifluoromethyl)-benzyl)-1,8-diazaspiro[4.5]-decane-8-carbonyl)-1H-pyrazole-3-carboxylic acid | 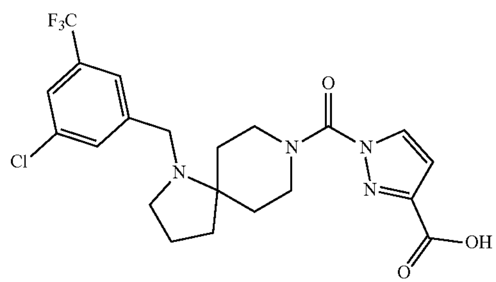 [SMILES: O=C(O)c1ccn(C(=O)N2CCC3(CCCN3Cc3cc(Cl)cc(C(F)(F)F)c3)CC2)n1] | δ 8.10 (d, J = 2.7 Hz, 1H), 7.62-7.75 (m, 3H), 6.81 (d, J = 2.7 Hz, 1H), 4.55-4.59 (m, 2H), 3.99 (s, 2H), 3.09-3.32 (m, 2H), 2.89-2.94 (m, 2H), 2.05-2.15 (m, 4H), 1.91-1.99 (m, 2H), 1.71-1.89 (m, 2H) | 471.0 |

| Ex | Name | Structure | NMR (¹H NMR, 300 MHz or 400 MHz, Methanol-d) | MS [M + H]⁺ |
|---|---|---|---|---|
| 87 | 1-(4-(3-(pyrrolidin-1-yl)-5-(trifluoromethyl)-benzyl)-piperazine-1-carbonyl)-1H-pyrazole-3-carboxylic acid | 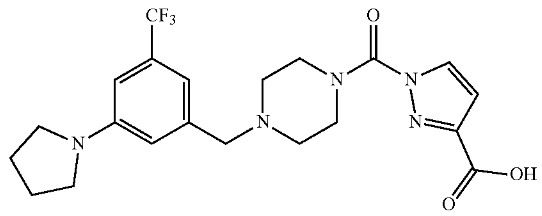 [SMILES: O=C(O)c1ccn(C(=O)N2CCN(Cc3cc(N4CCCC4)cc(C(F)(F)F)c3)CC2)n1] | δ 8.11 (d, J = 2.7 Hz, 1H), 6.91 (s, 1H), 6.83 (s, 1H), 6.80 (d, J = 2.7 Hz, 1H), 6.70 (s, 1H), 3.93 (br, 4H), 3.73 (s, 2H), 3.34-3.35 (m, 2H), 3.31-3.32 (m, 2H), 2.74-2.78 (m, 4H), 2.04-2.10 (m, 4H) | 452.0 |
| 88 | 1-(1-(3-(pyrrolidin-1-yl)-5-(trifluoromethyl)-benzyl)-1,8-diazaspiro[4.5]-decane-8-carbonyl)-1H-pyrazole-3-carboxylic acid | 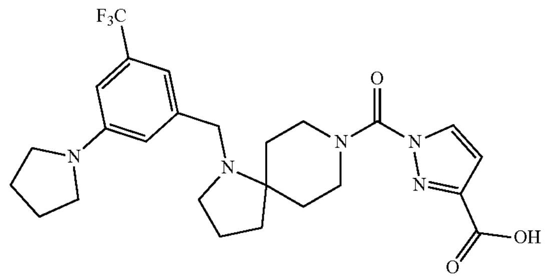 [SMILES: O=C(O)c1ccn(C(=O)N2CCC3(CCCN3Cc3cc(N4CCCC4)cc(C(F)(F)F)c3)CC2)n1] | δ 8.11 (d, J = 2.7 Hz, 1H), 7.01 (s, 1H), 6.90 (s, 1H), 6.79-6.80 (m, 2H), 4.76 (br, 2H), 4.32 (s, 2H), 3.34-3.56 (m, 4H), 3.09-3.32 (m, 4H), 2.26-2.46 (m, 4H), 1.96-2.12 (m, 6H), 1.81-1.85 (m, 2H) | 506.1 |
| 89 | 1-(2-methyl-4-((3-methyl-[1,1'-biphenyl]-4-yl)methyl)-piperazine-1-carbonyl)-1H-pyrazole-3-carboxylic acid | 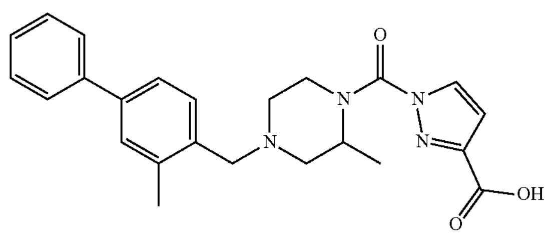 | δ 8.11 (d, J = 2.7 Hz, 1H), 7.59 (d, J = 7.2 Hz, 2H), 7.28-7.43 (m, 6H), 6.82 (d, J = 2.7 Hz, 1H), 4.63 (br, 1H), 4.20-4.25 (m, 1H), 3.56 (s, 2H), 3.40-3.48 (m, 1H), 2.87-2.91 (m, 1H), 2.77-2.81 (m, 1H), 2.48 (s, 3H), 2.38-2.43 (m, 1H), 2.22-2.31 (m, 1H), 1.41 (d, J = 6.6 Hz, 3H) | 419.2 |
| 90 | 1-(4-(2-(pyrrolidin-1-yl)-3-(trifluoromethyl)-benzyl)-piperazine-1-carbonyl)-1H-pyrazole-3-carboxylic acid | 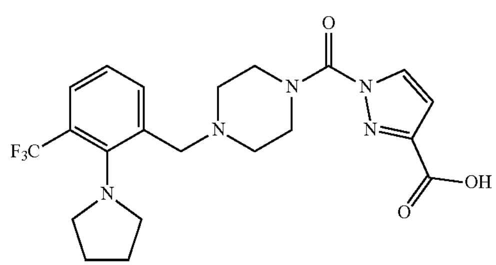 [SMILES: O=C(O)c1ccn(C(=O)N2CCN(Cc3cccc(C(F)(F)F)c3N3CCCC3)CC2)n1] | δ 8.11 (d, J = 2.7 Hz, 1H), 7.92-7.94 (m, 1H), 7.56-7.60 (m, 1H), 7.33-7.38 (m, 1H), 6.79 (s, J = 2.7 Hz, 1H), 3.89 (br, 4H), 3.67 (s, 2H), 3.21-3.32 (m, 4H), 2.60-2.63 (m, 4H), 1.99-2.05 (m, 4H) | 452.0 |

| Ex | Name | Structure | NMR (¹H NMR, 300 MHz or 400 MHz, Methanol-d) | MS [M + H]⁺ |
|---|---|---|---|---|
| 91 | 1-(4-(2-chloro-4-(trifluoromethyl)-benzyl)-piperazine-1-carbonyl)-1H-pyrazole-3-carboxylic acid | 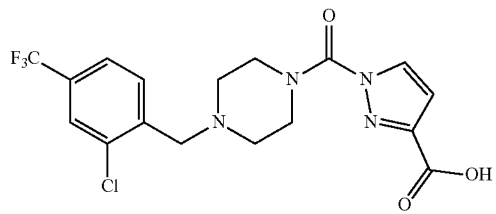 [SMILES: O=C(O)c1ccn(C(=O)N2CCN(Cc3ccc(C(F)(F)F)cc3Cl)CC2)n1] | δ 8.12 (d, J = 2.7 Hz, 1H), 7.72-7.81 (m, 1H), 7.65 (s, 1H), 7.60-7.65 (m, 1H), 6.80 (d, J = 2.7 Hz, 1H), 3.89 (br, 4H), 3.78 (s, 2H), 2.67 (t, J = 5.0 Hz, 4H) | 416.9 |
| 92 | (S)-1-(4-(2-(3-fluoropyrrolidin-1-yl)-4-(trifluoromethyl)-benzyl)-piperazine-1-carbonyl)-1H-pyrazole-3-carboxylic acid | 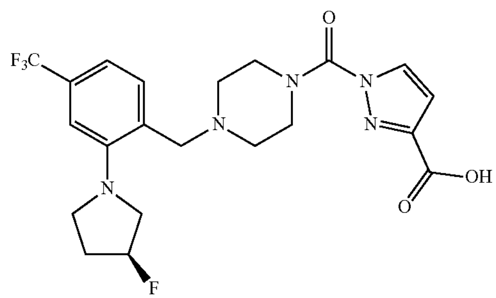 | δ 8.13 (d, J = 2.6 Hz, 1H), 7.62 (d, J = 8.0 Hz, 1H), 7.19-7.21 (m, 2H), 6.82 (d, J = 2.6 Hz, 1H), 5.27-5.41 (m, 1H), 3.87 (br, 4H), 3.76 (br, 2H), 3.46-3.69 (m, 3H), 3.21-3.26 (m, 1H), 2.65-2.67 (m, 4H), 2.22-2.34 (m, 2H) | 470.5 |
| 93 | 1-(1-(2-(pyrrolidin-1-yl)-4-(trifluoromethyl)-benzyl)-1,8-diazaspiro[4.5]-decane-8-carbonyl)-1H-pyrazole-3-carboxylic acid | 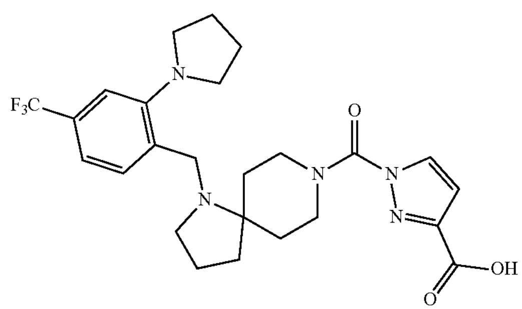 [SMILES: O=C(O)c1ccn(C(=O)N2CCC3(CCCN3Cc3ccc(C(F)(F)F)cc3N3CCCC3)CC2)n1] | δ 8.13 (d, J = 2.6 Hz, 1H), 7.67 (d, J = 7.8 Hz, 1H), 7.49 (s, 1H), 7.39 (d, J = 7.8 Hz, 1H), 6.80 (d, J = 2.6 Hz, 1H), 4.70 (br, 2H), 4.39 (br, 2H), 3.19-3.24 (m, 8H), 2.56 (br, 4H), 2.02-2.08 (m, 6H), 1.80-1.84 (m, 2H) | 506.1 |

| Ex | Name | Structure | NMR (¹H NMR, 300 MHz or 400 MHz, Methanol-d) | MS [M + H]⁺ |
|---|---|---|---|---|
| 94 | 1-(4-(2-((2R,5S)-2,5-dimethylpyrrolidin-1-yl)-4-(trifluoromethyl)-benzyl)-piperazine-1-carbonyl)-1H-pyrazole-3-carboxylic acid | 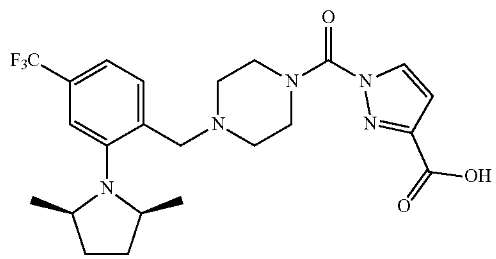 [SMILES: C[C@@H]1CC[C@H](C)N1c1cc(C(F)(F)F)ccc1CN1CCN(C(=O)n2ccc(C(=O)O)n2)CC1] | δ 8.13 (d, J = 2.7 Hz, 1H), 7.86 (d, J = 8.1 Hz, 1H), 7.64 (s, 1H), 7.49 (d, J = 8.1 Hz, 1H), 6.81 (d, J = 2.7 Hz, 1H), 3.89-4.02 (m, 6H), 3.06-3.20 (m, 2H), 2.55-2.67 (m, 4H), 2.05-2.12 (m, 2H), 1.53-1.58 (m, 2H), 0.90 (d, J = 6.0 Hz, 6H) | 480.3 |
| 95 | (R)-1-(4-(2-(2-methylpyrrolidin-1-yl)-4-(trifluoromethyl)benzyl)piperazine-1-carbonyl)-1H-pyrazole-3-carboxylic acid | 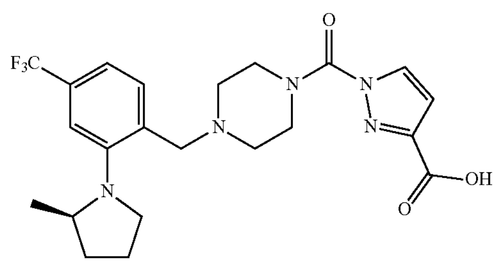 [SMILES: C[C@@H]1CCCN1c1cc(C(F)(F)F)ccc1CN1CCN(C(=O)n2ccc(C(=O)O)n2)CC1] | δ 8.13 (d, J = 2.8 Hz, 1H), 7.72 (d, J = 8.0 Hz, 1H), 7.32 (s, 1H), 7.27 (d, J = 8.0 Hz, 1H), 6.81 (d, J = 2.8 Hz, 1H), 3.60-3.90 (m, 7H), 3.56-3.58 (m, 1H), 2.81-2.87 (m, 1H), 2.70 (br, 4H), 2.21-2.23 (m, 1H), 1.90-2.00 (m, 1H), 1.82-1.88 (m, 1H), 1.52-1.70 (m, 1H), 0.98-1.02 (m, 3H) | 466.5 |
| 96 | 1-(5-(4-(trifluoromethyl)-benzyl)-octahydropyrrolo-[3,4-c]pyrrole-2-carbonyl)-1H-pyrazole-3-carboxylic acid | 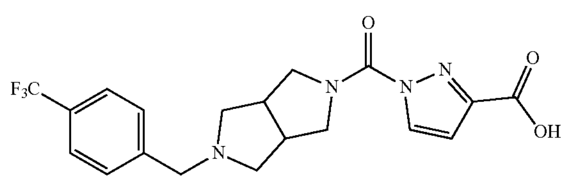 [SMILES: O=C(O)c1ccn(C(=O)N2CC3CN(Cc4ccc(C(F)(F)F)cc4)CC3C2)n1] | δ 8.14-8.30 (d, J = 2.7 Hz, 1H), 7.66-7.73 (d, J = 0.8 Hz, 2H), 7.59-7.66 (d, J = 0.8 Hz, 2H), 6.78 (d, J = 2.7 Hz, 1H), 3.80-4.27 (m, 6H), 2.97-3.14 (m, 4H), 2.63-2.92 (d, J = 6.4 Hz, 2H) | 409.1 |

| Ex | Name | Structure | NMR (¹H NMR, 300 MHz or 400 MHz, Methanol-d) | MS [M + H]⁺ |
|---|---|---|---|---|
| 97 | 1-(4-(4-chloro-2-(4-cyclopropyl-piperazin-1-yl)benzyl)-piperazine-1-carbonyl)-1H-pyrazole-3-carboxylic acid | 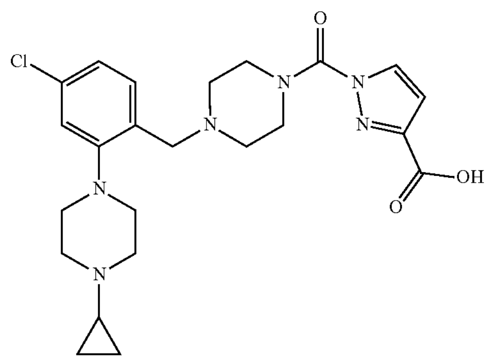 [SMILES: O=C(O)c1ccn(C(=O)N2CCN(Cc3ccc(Cl)cc3N3CCN(C4CC4)CC3)CC2)n1] | δ 8.14 (d, J = 2.5 Hz, 1H), 7.45 (d, J = 8.0 Hz, 1H), 7.14-7.16 (m, 2H), 6.82 (d, J = 2.5 Hz, 1H), 3.87 (br, 4H), 3.74 (s, 2H), 3.12-3.17 (m, 8H), 2.72-2.74 (m, 4H), 2.29 (br, 1H), 0.74 (br, 4H) | 473.0 |
| 98 | 1-(4-(3-(4-chlorophenoxy)-benzyl)-piperazine-1-carbonyl)-1H-pyrazole-3-carboxylic acid | 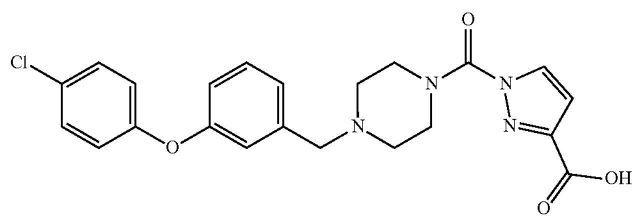 [SMILES: O=C(O)c1ccn(C(=O)N2CCN(Cc3cccc(Oc4ccc(Cl)cc4)c3)CC2)n1] | δ 8.14 (d, J = 2.6 Hz, 1H), 7.35-7.40 (m, 3H), 7.19 (s, 1H), 7.6 Hz, 1H), 7.09 (s, 1H), 6.92-7.01 (m, 3H), 6.82 (d, J = 2.6 Hz, 1H), 3.92 (br, 4H), 3.76 (br, 2H), 2.79 (br, 4H) | 441.4 |
| 99 | 1-(2-(5-chloro-2-(trifluoromethyl)-benzyl)-2,8-diazaspiro[4.5]-decane-8-carbonyl)-1H-pyrazole-3-carboxamide | 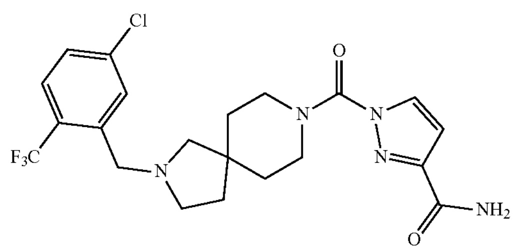 [SMILES: NC(=O)c1ccn(C(=O)N2CCC3(CCN(Cc4cc(Cl)ccc4C(F)(F)F)C3)CC2)n1] | (Chloroform-d) δ 8.08 (d, J = 2.7 Hz, 1H), 7.78 (s, 1H), 7.57 (d, J = 8.4 Hz, 1H), 7.32 (d, J = 8.4 Hz, 1H), 6.91 (d, J = 2.7 Hz, 1H), 6.68 (br, 1H), 5.49 (br, 1H), 3.54-3.90 (m, 6H), 2.60-2.76 (m, 2H), 2.52 (s, 2H), 1.75-1.77 (m, 6H) | 470.2 |

| Ex | Name | Structure | NMR (¹H NMR, 300 MHz or 400 MHz, Methanol-d) | MS [M + H]⁺ |
|---|---|---|---|---|
| 100 | 1-(4-(2-(piperidin-1-yl)-4-(trifluoromethyl)-benzyl)-piperazine-1-carbonyl)-1H-pyrazole-3-carboxylic acid | 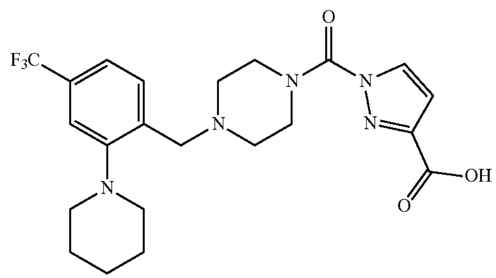 [SMILES: O=C(O)c1ccn(C(=O)N2CCN(Cc3ccc(C(F)(F)F)cc3N3CCCCC3)CC2)n1] | δ 8.14 (d, J = 2.6 Hz, 1H), 7.72 (d, J = 7.8 Hz, 1H), 7.36-7.39 (m, 2H), 6.82 (d, J = 2.6 Hz, 1H), 3.88-3.90 (m, 6H), 2.92 (br, 4H), 2.77 (br, 4H), 1.76-1.77 (m, 4H), 1.63 (br, 2H) | 466.5 |
| 101 | (R)-1-(4-(2-(3-fluoropyrrolidin-1-yl)-4-(trifluoromethyl)-benzyl)-piperazine-1-carbonyl)-1H-pyrazole-3-carboxylic acid | 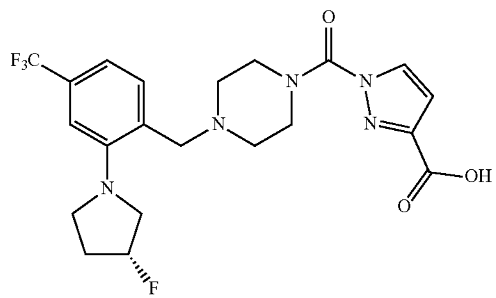 [SMILES: O=C(O)c1ccn(C(=O)N2CCN(Cc3ccc(C(F)(F)F)cc3N3CC[C@@H](F)C3)CC2)n1] | δ 8.14 (d, J = 2.7 Hz, 1H), 7.62 (d, J = 7.8 Hz, 1H), 7.20-7.23 (m, 2H), 6.83 (d, J = 2.7 Hz, 1H), 5.27-5.41 (m, 1H), 3.71-4.04 (m, 6H), 3.45-3.71 (m, 3H), 3.21-3.26 (m, 1H), 2.55-2.89 (m, 4H), 2.24-2.36 (m, 2H) | 470.5 |
| 102 | 1-(4-(2-(4-fluoropiperidin-1-yl)-4-(trifluoromethyl)-benzyl)-piperazine-1-carbonyl)-1H-pyrazole-3-carboxylic acid | 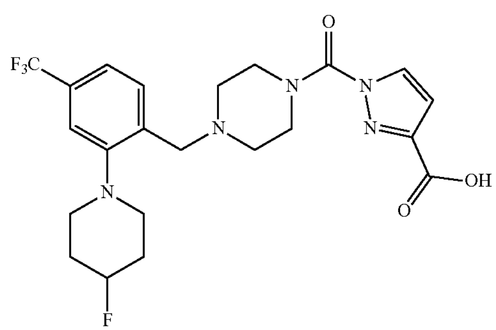 [SMILES: O=C(O)c1ccn(C(=O)N2CCN(Cc3ccc(C(F)(F)F)cc3N3CCC(F)CC3)CC2)n1] | δ 8.14 (d, J = 2.7 Hz, 1H), 7.71 (d, J = 7.7 Hz, 1H), 7.41 (s, 1H), 7.39 (d, J = 7.7 Hz, 1H), 6.82 (d, J = 2.7 Hz, 1H), 4.69-4.88 (m, 1H), 3.87 (br, 4H), 3.79 (br, 2H), 3.11-3.17 (m, 2H), 2.88-2.95 (m, 2H), 2.70 (br, 4H), 2.08-2.18 (m, 1H), 1.89-2.05 (m, 3H) | 484.5 |

| Ex | Name | Structure | NMR (¹H NMR, 300 MHz or 400 MHz, Methanol-d) | MS [M + H]⁺ |
|---|---|---|---|---|
| 103 | (R)-1-(4-(2-(2-methylpiperidin-1-yl)-4-(trifluoromethyl)-benzyl)-piperazine-1-carbonyl)-1H-pyrazole-3-carboxylic acid | 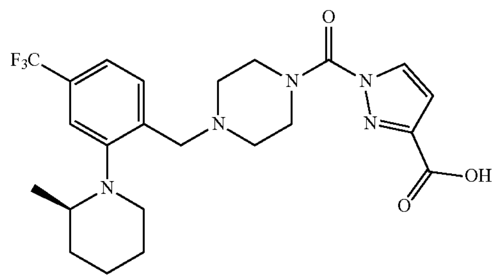 [SMILES: C[C@@H]1CCCCN1c1cc(C(F)(F)F)ccc1CN1CCN(C(=O)n2ccc(C(=O)O)n2)CC1] | δ 8.14 (d, J = 2.7 Hz, 1H), 7.74 (d, J = 8.0 Hz, 1H), 7.51 (s, 1H), 7.44 (d, J = 8.0 Hz, 1H), 6.82 (d, J = 2.7 Hz, 1H), 3.80-3.89 (m, 6H), 3.02-3.11 (m, 2H), 2.69 (br, 4H), 2.57-2.64 (m, 1H), 1.83-1.88 (m, 2H), 1.70-1.75 (m, 2H), 1.44-1.56 (m, 2H), 0.83 (d, J = 6.4 Hz, 3H) | 480.5 |
| 104 | (S)-1-(4-(2-(2-methylpyrrolidin-1-yl)-4-(trifluoromethyl)-benzyl)-piperazine-1-carbonyl)-1H-pyrazole-3-carboxylic acid | 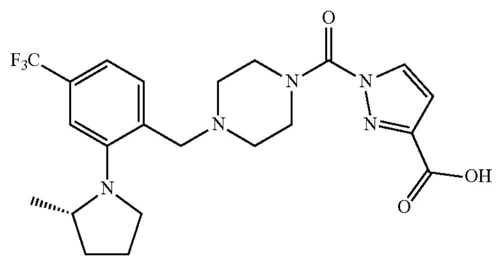 [SMILES: C[C@H]1CCCN1c1cc(C(F)(F)F)ccc1CN1CCN(C(=O)n2ccc(C(=O)O)n2)CC1] | δ 8.14 (d, J = 2.8 Hz, 1H), 7.72 (d, J = 8.0 Hz, 1H), 7.32 (s, 1H), 7.28 (d, J = 8.0 Hz, 1H), 6.82 (d, J = 2.8 Hz, 1H), 3.63-3.90 (m, 7H), 3.57-3.61 (m, 1H), 2.82-2.87 (m, 1H), 2.70 (br, 4H), 2.12-2.26 (m, 1H), 1.98-1.99 (m, 1H), 1.84-1.91 (m, 1H), 1.61-1.68 (m, 1H), 1.02 (d, J = 6.0 Hz, 3H) | 466.5 |
| 105 | 1-(4-(2-(3-oxa-8-azabicyclo[3.2.1]-octan-8-yl)-4-chlorobenzyl)-piperazine-1-carbonyl)-1H-pyrazole-3-carboxylic acid | 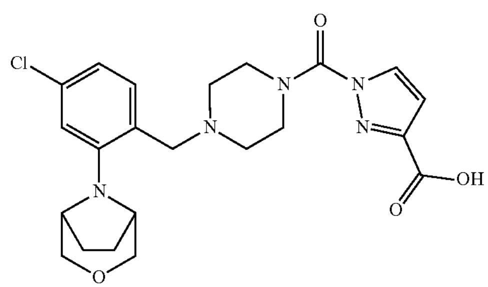 [SMILES: O=C(O)c1ccn(C(=O)N2CCN(Cc3ccc(Cl)cc3N3C4CCC3COC4)CC2)n1] | δ 8.15 (d, J = 2.5 Hz, 1H), 7.45 (d, J = 8.0 Hz, 1H), 6.99-7.01 (m, 1H), 6.95 (s, 1H), 6.84 (d, J = 2.5 Hz, 1H), 3.80-3.95 (m, 10H), 3.66-3.68 (m, 2H), 2.77 (br, 4H), 1.96-2.05 (m, 4H) | 460.4 |

| Ex | Name | Structure | NMR (¹H NMR, 300 MHz or 400 MHz, Methanol-d) | MS [M + H]⁺ |
|---|---|---|---|---|
| 106 | 1-(4-(2-(tetrahydro-1H-furo[3,4-c]pyrrol-5(3H)-yl)-4-(trifluoromethyl)-benzyl)-piperazine-1-carbonyl)-1H-pyrazole-3-carboxylic acid | 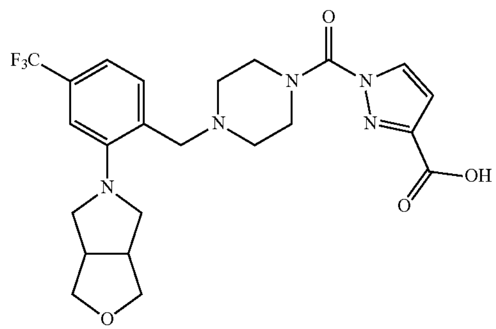 [SMILES: O=C(O)c1ccn(C(=O)N2CCN(Cc3ccc(C(F)(F)F)cc3N3CC4COCC4C3)CC2)n1] | δ 8.15 (d, J = 2.6 Hz, 1H), 7.68 (d, J = 7.8 Hz, 1H), 7.39-7.41 (m, 2H), 6.82 (d, J = 2.6 Hz, 1H), 3.96 (br, 8H), 3.74-3.79 (m, 2H), 3.02-3.20 (m, 4H), 3.02 (br, 2H), 2.82 (br, 4H) | 494.5 |
| 107 | 1-(4-(4-chloro-2-(pyrrolidin-1-yl)benzyl)-piperazine-1-carbonyl)-1H-pyrazole-3-carboxylic acid | 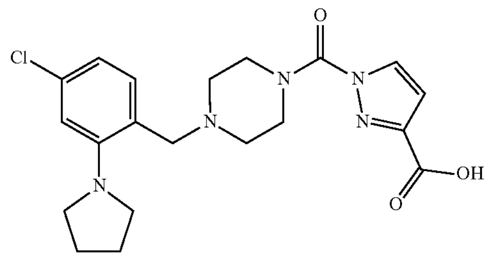 [SMILES: O=C(O)c1ccn(C(=O)N2CCN(Cc3ccc(Cl)cc3N3CCCC3)CC2)n1] | δ 8.15 (d, J = 2.7 Hz, 1H), 7.37 (d, J = 8.2 Hz, 1H), 7.00 (s, 1H), 6.89-6.92 (m, 1H), 6.83 (d, J = 2.7 Hz, 1H), 3.86-3.91 (m, 6H), 3.30-3.19 (m, 4H), 2.80 (br, 4H), 2.06-1.92 (m, 4H) | 418.5 |
| 108 | 1-(4-(2-(4,4-difluoropiperidin-1-yl)-4-(trifluoromethyl)-benzyl)-piperazine-1-carbonyl)-1H-pyrazole-3-carboxylic acid | 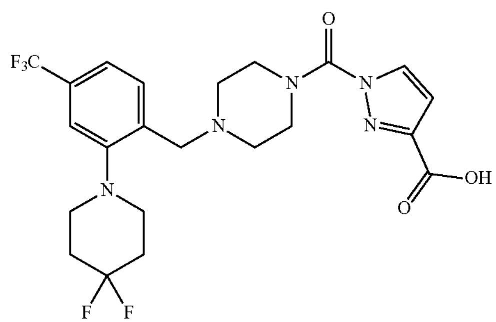 [SMILES: O=C(O)c1ccn(C(=O)N2CCN(Cc3ccc(C(F)(F)F)cc3N3CCC(F)(F)CC3)CC2)n1] | δ 8.15 (d, J = 2.7 Hz, 1H), 7.72 (d, J = 7.8 Hz, 1H), 7.40-7.43 (m, 2H), 6.85 (d, J = 2.7 Hz, 1H), 3.87 (br, 4H), 3.80 (s, 2H), 3.10-3.13 (m, 4H), 2.69-2.72 (m, 4H), 2.12-2.24 (m, 4H) | 502.5 |

| Ex | Name | Structure | NMR (¹H NMR, 300 MHz or 400 MHz, Methanol-d) | MS [M + H]⁺ |
|---|---|---|---|---|
| 109 | 1-(4-(2-(4-(2-hydroxypropan-2-yl)piperidin-1-yl)-4-(trifluoromethyl)benzyl)piperazine-1-carbonyl)-1H-pyrazole-3-carboxylic acid | 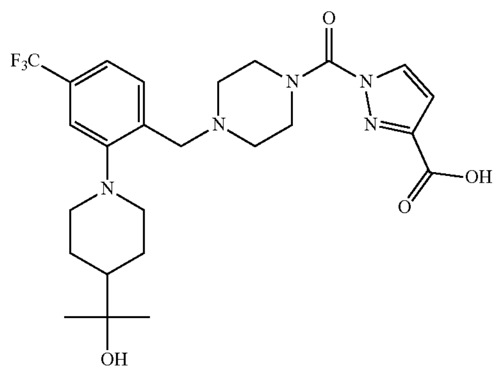 [SMILES: CC(C)(O)C1CCN(c2cc(C(F)(F)F)ccc2CN2CCN(C(=O)n3ccc(C(=O)O)n3)CC2)CC1] | δ 8.15 (d, J = 2.7 Hz, 1H), 7.72 (d, J = 8.0 Hz, 1H), 7.38-7.42 (m, 2H), 6.85 (d, J = 2.7 Hz, 1H), 3.89 (br, 6H), 3.24-3.27 (m, 2H), 2.70-2.77 (m, 6H), 1.89-1.92 (m, 2H), 1.55-1.65 (m, 2H), 1.44-1.50 (m, 1H), 1.25 (s, 6H) | 524.5 |
| 110 | (S)-1-(4-(2-(2-methylpiperidin-1-yl)-4-(trifluoromethyl)benzyl)piperazine-1-carbonyl)-1H-pyrazole-3-carboxylic acid | 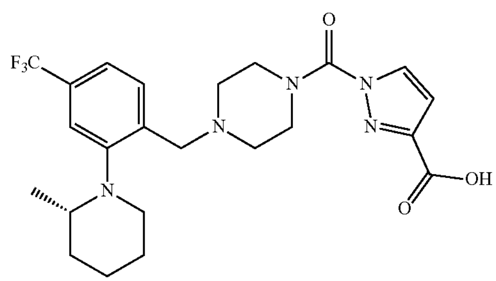 [SMILES: C[C@H]1CCCCN1c1cc(C(F)(F)F)ccc1CN1CCN(C(=O)n2ccc(C(=O)O)n2)CC1] | δ 8.15 (d, J = 2.7 Hz, 1H), 7.72 (d, J = 8.0 Hz, 1H), 7.51 (s, 1H), 7.74 (d, J = 8.0 Hz, 1H), 6.83 (d, J = 2.7 Hz, 1H), 3.84-3.90 (m, 6H), 3.02-3.04 (m, 2H), 2.71 (br, 4H), 2.57-2.62 (m, 1H), 1.84-1.85 (m, 2H), 1.69-1.72 (m, 2H), 1.41-1.58 (m, 2H), 0.82 (d, J = 6.0 Hz, 3H) | 480.2 |
| 111 | 1-(4-(4-chloro-2-(tetrahydro-1H-furo[3,4-c]pyrrol-5(3H)-yl)benzyl)piperazine-1-carbonyl)-1H-pyrazole-3-carboxylic acid | 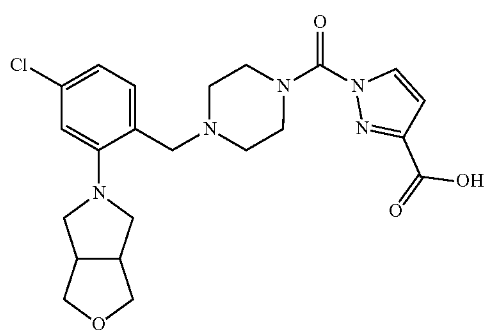 [SMILES: O=C(O)c1ccn(C(=O)N2CCN(Cc3ccc(Cl)cc3N3CC4COCC4C3)CC2)n1] | δ 8.15 (s, 1H), 7.42 (d, J = 8.0 Hz, 1H), 7.22 (s, 1H), 7.16-7.21 (m, 1H), 7.15 (s, 1H), 3.93-4.91 (m, 10H), 3.11-3.16 (m, 4H), 2.96-3.01 (m, 6H) | 460.4 |

| Ex | Name | Structure | NMR (¹H NMR, 300 MHz or 400 MHz, Methanol-d) | MS [M + H]⁺ |
|---|---|---|---|---|
| 112 | 4-chloro-1-(4-((5-chloro-2-(trifluoromethyl)-benzyl)-(methyl)amino)-piperidine-1-carbonyl)-1H-pyrazole-3-carboxylic acid | 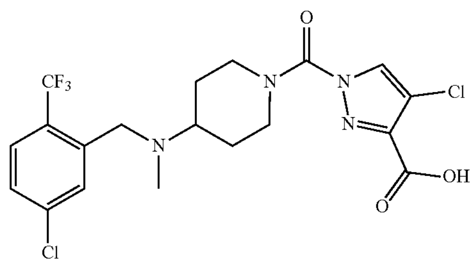 [SMILES: CN(Cc1cc(Cl)ccc1C(F)(F)F)C1CCN(C(=O)n2cc(Cl)c(C(=O)O)n2)CC1] | δ 8.15 (s, 1H), 7.90 (s, 1H), 7.65 (d, J = 8.7 Hz, 1H), 7.41-7.47 (m, 1H), 4.49-4.53 (m, 2H), 3.84 (s, 2H), 3.05-3.16 (m, 2H), 2.84-2.89 (m, 1H), 2.27 (s, 3H), 1.93-2.03 (m, 2H), 1.71-1.81 (m, 2H) | 479.1 |
| 113 | 1-(4-(2-(4-carbamoylpiperidin-1-yl)-4-(trifluoromethyl)-benzyl)piperazine-1-carbonyl)-1H-pyrazole-3-carboxylic acid | 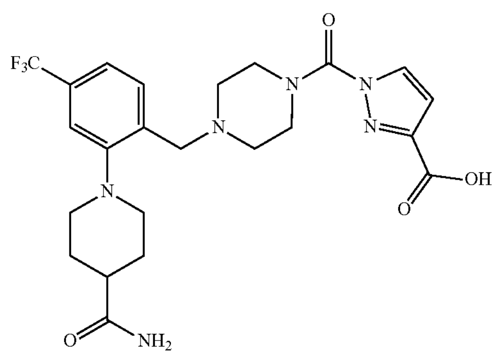 [SMILES: NC(=O)C1CCN(c2cc(C(F)(F)F)ccc2CN2CCN(C(=O)n3ccc(C(=O)O)n3)CC2)CC1] | δ 8.16 (d, J = 2.7 Hz, 1H), 7.70-7.73 (m, 1H), 7.39-7.41 (m, 2H), 6.84 (d, J = 2.7 Hz, 1H), 3.83-3.89 (m, 6H), 3.24-3.30 (m, 2H), 2.66-2.85 (m, 6H), 2.36-2.46 (m, 1H), 1.95-1.98 (m, 4H) | 509.2 |
| 114 | 1-(4-(2-(2,5-dimethyl)pyrrolidin-1-yl)-4-(trifluoromethyl)piperazine-1-carbonyl)-1H-pyrazole-3-carboxylic acid | 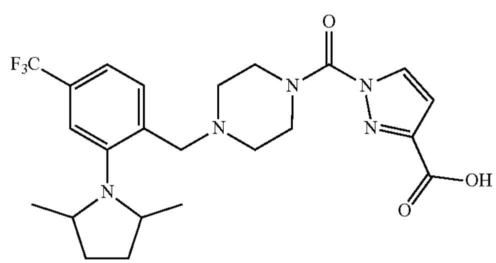 [SMILES: CC1CCC(C)N1c1cc(C(F)(F)F)ccc1CN1CCN(C(=O)n2ccc(C(=O)O)n2)CC1] | δ 8.17 (d, J = 2.3 Hz, 1H), 7.86 (d, J = 8.1 Hz, 1H), 7.66 (s, 1H), 7.51 (d, J = 8.1 Hz, 1H), 6.86 (d, J = 2.3 Hz, 1H), 3.96 (br, 2H), 3.87 (br, 4H), 3.16-3.20 (m, 2H), 2.68 (br, 4H), 2.06-2.12 (m, 2H), 1.54-1.58 (m, 2H), 0.91 (d, J = 6.0 Hz, 6H) | 480.3 |

| Ex | Name | Structure | NMR (¹H NMR, 300 MHz or 400 MHz, Methanol-d) | MS [M + H]⁺ |
|---|---|---|---|---|
| 115 | 1-(5-(3-chloro-5-fluorobenzyl)-octahydropyrrolo[3,4-c]pyrrole-2-carbonyl)-1H-pyrazole-3-carboxylic acid | 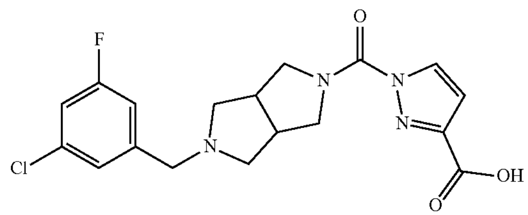 [SMILES: O=C(O)c1ccn(C(=O)N2CC3CN(Cc4cc(F)cc(Cl)c4)CC3C2)n1] | δ 8.17 (d, J = 2.4 Hz, 1H), 7.30 (s, 1H), 7.15-7.18 (m, 2H), 6.77 (d, J = 2.4 Hz, 1H), 3.98 (br, 6H), 3.08 (br, 4H), 2.91-2.93 (m, 2H) | 393.1 |
| 116 | 1-(5-(3-(4-chlorophenoxy)-benzyl)-octahydropyrrolo[3,4-c]pyrrole-2-carbonyl)-1H-pyrazole-3-carboxylic acid | 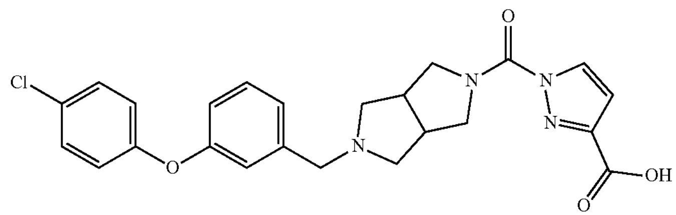 [SMILES: O=C(O)c1ccn(C(=O)N2CC3CN(Cc4cccc(Oc5ccc(Cl)cc5)c4)CC3C2)n1] | δ 8.17 (d, J = 2.4 Hz, 1H), 7.42 (t, J = 8.0 Hz, 1H), 7.32-7.36 (m, 2H), 7.24 (d, J = 7.6 Hz, 1H), 7.14 (s, 1H), 7.01-7.05 (m, 1H), 6.97-7.00 (m, 2H), 6.75 (d, J = 2.4 Hz, 1H), 3.96-4.30 (m, 6H), 3.35 (br, 1H), 3.33-3.34 (m, 1H), 3.13 (br, 2H), 3.03-3.06 (m, 2H) | 467.4 |
| 117 | 1-(5-(3-(trifluoromethoxy)-benzyl)-octahydropyrrolo[3,4-c]pyrrole-2-carbonyl)-1H-pyrazole-3-carboxylic acid | 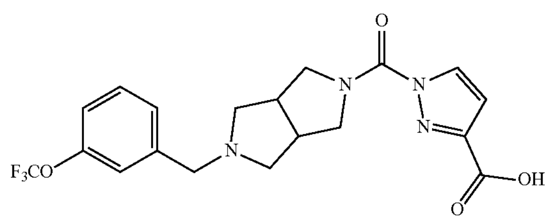 [SMILES: O=C(O)c1ccn(C(=O)N2CC3CN(Cc4cccc(OC(F)(F)F)c4)CC3C2)n1] | δ 8.17 (d, J = 2.5 Hz, 1H), 7.41-7.52 (m, 3H), 7.24-7.30 (m, 1H), 6.76 (d, J = 2.5 Hz, 1H), 3.96-4.12 (m, 6H), 3.27-3.32 (m, 2H), 3.00-3.11 (m, 4H) | 425.2 |
| 118 | 1-(4-(2-(3-oxa-8-azabicyclo[3.2.1]-octan-8-yl)-4-(trifluoromethyl)benzyl)piperazine-1-carbonyl)-1H-pyrazole-3-carboxylic acid | 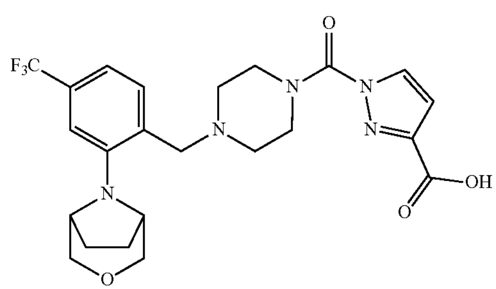 [SMILES: O=C(O)c1ccn(C(=O)N2CCN(Cc3ccc(C(F)(F)F)cc3N3C4CCC3COC4)CC2)n1] | δ 8.17 (d, J = 2.7 Hz, 1H), 7.70 (d, J = 7.9 Hz, 1H), 7.28 (d, J = 7.9 Hz, 1H), 7.17 (s, 1H), 6.85 (d, J = 2.7 Hz, 1H), 3.96 (d, J = 9.6 Hz, 2H), 3.81-3.85 (m, 8H), 3.68-3.70 (m, 2H), 2.70 (br, 4H), 2.03-2.08 (m, 2H), 1.95-1.99 (m, 2H) | 494.5 |

-continued

| Ex | Name | Structure | NMR (¹H NMR, 300 MHz or 400 MHz, Methanol-d) | MS [M + H]⁺ |
|---|---|---|---|---|
| 119 | 1-(4-(2-(4-acetamidopiperidin-1-yl)-4-(trifluoromethyl)-benzyl)piperazine-1-carbonyl)-1H-pyrazole-3-carboxylic acid | 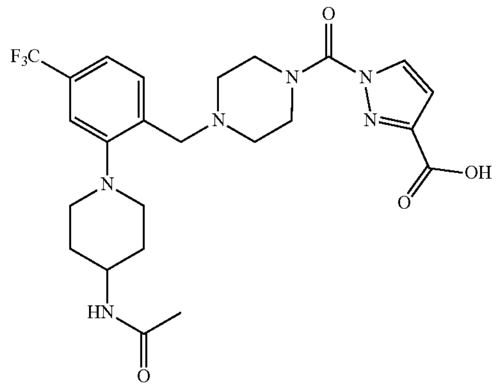 [SMILES: CC(=O)NC1CCN(c2cc(C(F)(F)F)ccc2CN2CCN(C(=O)n3ccc(C(=O)O)n3)CC2)CC1] | δ 8.17 (d, J = 2.7 Hz, 1H), 7.71 (d, J = 8.0 Hz, 1H), 7.44 (s, 1H), 7.40 (d, J = 8.0 Hz, 1H), 6.86 (d, J = 2.7 Hz, 1H), 3.82-3.88 (m, 7H), 3.18-3.21 (m, 2H), 2.83-2.88 (m, 2H), 2.74 (br, 4H), 1.97-201 (m, 5H), 1.67-1.76 (m, 2H) | 523.3 |
| 120 | 1-(4-(4-hydroxypiperidin-1-yl)-4-(trifluoromethyl)-benzyl)piperazine-1-carbonyl)-1H-pyrazole-3-carboxylic acid | 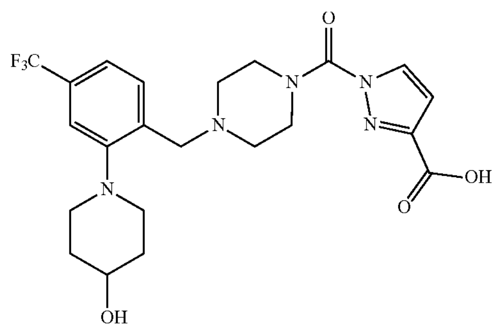 [SMILES: O=C(O)c1ccn(C(=O)N2CCN(Cc3ccc(C(F)(F)F)cc3N3CCC(O)CC3)CC2)n1] | δ 8.18 (d, J = 2.6 Hz, 1H), 7.71 (d, J = 7.6 Hz, 1H), 7.38-7.42 (m, 2H), 6.86 (d, J = 2.6 Hz, 1H), 3.77-3.89 (m, 7H), 3.16-3.32 (m, 2H), 2.76-2.85 (m, 6H), 1.92-2.05 (m, 2H), 1.71-1.79 (m, 2H) | 482.5 |
| 121 | 1-(4-(4-chloro-3-(pyrrolidin-1-yl)phenoxy)-piperidine-1-carbonyl)-1H-pyrazole-3-carboxylic acid | 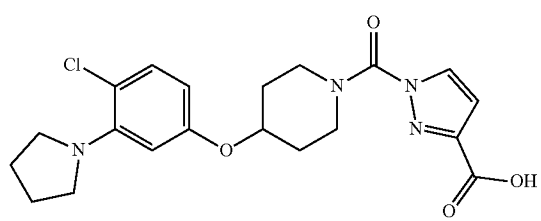 [SMILES: O=C(O)c1ccn(C(=O)N2CCC(Oc3ccc(Cl)c(N4CCCC4)c3)CC2)n1] | δ 8.19 (d, J = 2.7 Hz, 1H), 7.21 (d, J = 8.7 Hz, 1H), 6.90 (m, 1H), 6.66 (m, 1H), 6.58 (m, 1H), 4.68 (m, 1H), 3.87-4.05 (m, 2H), 3.69-3.85 (m, 2H), 3.36-3.47 (m, 4H), 1.77-2.20 (m, 8H) | 419.3 |

| Ex | Name | Structure | NMR (¹H NMR, 300 MHz or 400 MHz, Methanol-d) | MS [M + H]⁺ |
|---|---|---|---|---|
| 122 | 1-(5-(3-(trifluoromethyl)-benzyl)-octahydropyrrolo[3,4-c]pyrrole-2-carbonyl)-1H-pyrazole-3-carboxylic acid | 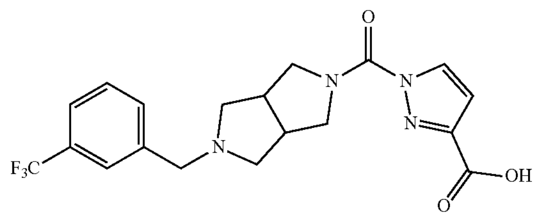 [SMILES: O=C(O)c1ccn(C(=O)N2CC3CN(Cc4cccc(C(F)(F)F)c4)CC3C2)n1] | δ 8.19 (d, J = 2.7 Hz, 1H), 7.58-7.78 (m, 4H), 6.78 (d, J = 2.7 Hz, 1H), 4.16 (s, 2H), 3.96 (br, 4H), 3.23-3.32 (m, 2H), 2.99-3.11 (m, 4H) | 409.4 |
| 123 | 1-(5-(4-(pyrrolidin-1-yl)-2-(trifluoromethyl)-benzyl)-octahydropyrrolo[3,4-c]pyrrole-2-carbonyl)-1H-pyrazole-3-carboxylic acid | 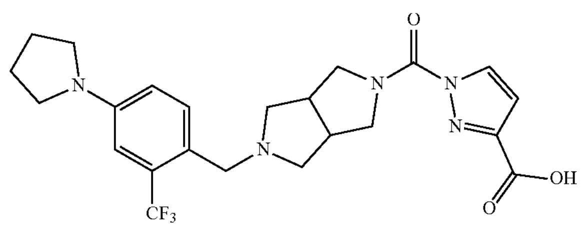 [SMILES: O=C(O)c1ccn(C(=O)N2CC3CN(Cc4ccc(N5CCCC5)cc4C(F)(F)F)CC3C2)n1] | δ 8.19 (s, 1H), 7.53 (d, J = 8.5 Hz, 1H), 6.74-6.82 (m, 3H), 3.51-4.61 (m, 6H), 3.28-3.37 (m, 6H), 2.92-3.18 (m, 4H), 2.05 (br, 4H) | 478.5 |
| 124 | 1-(5-(3-chloro-5-(trifluoromethyl)-benzyl)-octahydropyrrolo[3,4-c]pyrrole-2-carbonyl)-1H-pyrazole-3-carboxylic acid | 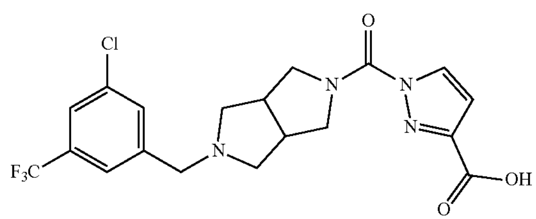 [SMILES: O=C(O)c1ccn(C(=O)N2CC3CN(Cc4cc(Cl)cc(C(F)(F)F)c4)CC3C2)n1] | δ 8.22 (d, J = 2.7 Hz, 1H), 7.66-7.79 (m, 3H), 6.82 (d, J = 2.7 Hz, 1H), 3.69-4.16 (m, 6H), 3.04 (br, 4H), 2.84 (br, 2H) | 443.1 |
| 125 | 1-(trans-5-([1,1'-biphenyl]-3-yloxy)-octahydrocyclopenta[c]pyrrole-1H-pyrazole-3-carbonyl)-1H-pyrazole-3-carboxylic acid | 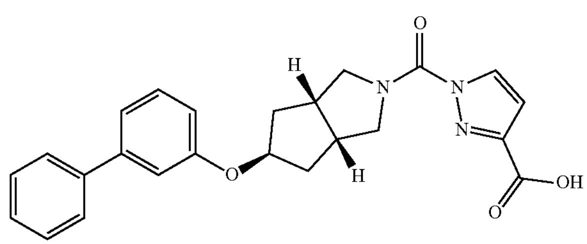 [SMILES: O=C(O)c1ccn(C(=O)N2C[C@H]3C[C@H](Oc4cccc(-c5ccccc5)c4)C[C@H]3C2)n1] | δ 8.23 (m, 1H), 7.54-7.69 (m, 2H), 7.24-7.51 (m, 4H), 7.08-7.23 (m, 2H), 6.87-6.98 (m, 1H), 6.83 (m, 1H), 5.03-5.16 (m, 1H), 3.50-4.41 (m, 4H), 2.88-3.13 (m, 2H), 2.10-2.40 (m, 2H), 1.87-2.10 (m, 2H) | 435.2 [M + NH₄]⁺ |

| Ex | Name | Structure | NMR (¹H NMR, 300 MHz or 400 MHz, Methanol-d) | MS [M + H]⁺ |
|---|---|---|---|---|
| 126 | 1-(1-(2-(1H-tetrazol-5-yl)-4-(trifluoromethyl)benzyl)-1,8-diazaspiro[4.5]decane-8-carbonyl)-1H-pyrazole-3-carboxylic acid | 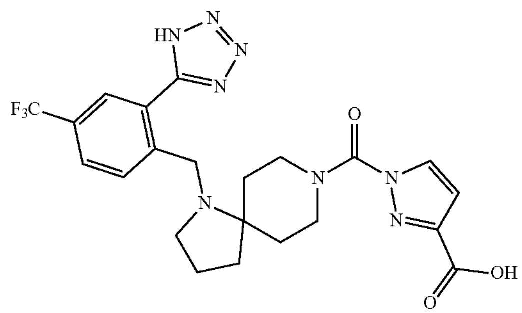 [SMILES: O=C(O)c1ccn(C(=O)N2CCC3(CCCN3Cc3ccc(C(F)(F)F)cc3-c3nnn[nH]3)CC2)n1] | δ 8.45 (s, 1H), 8.14 (d, J = 2.7 Hz, 1H), 7.80-7.88 (m, 2H), 6.82 (d, J = 2.7 Hz, 1H), 4.43-4.68 (m, 2H), 4.40 (s, 2H), 3.36-3.58 (m, 4H), 2.45-2.70 (m, 4H), 2.15-2.22 (m, 4H) | 505.5 |
| 127 | 1-(2-((4-(trifluoromethyl)pyridin-3-yl)methyl)-2,8-diazaspiro[4.5]decane-8-carbonyl)-1H-pyrazole-3-carboxylic acid | 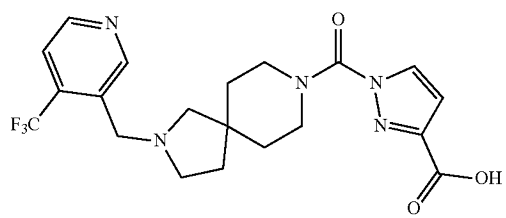 [SMILES: O=C(O)c1ccn(C(=O)N2CCC3(CCN(Cc4cnccc4C(F)(F)F)C3)CC2)n1] | δ 8.97 (s, 1H), 8.70 (d, J = 5.1 Hz, 1H), 8.07 (d, J = 2.7 Hz, 1H), 7.70 (d, J = 5.1 Hz, 1H), 6.78 (d, J = 2.7 Hz, 1H), 3.90 (s, 2H), 3.73-3.90 (m, 4H), 2.74 (t, J = 6.9 Hz, 2H), 2.60 (s, 2H), 1.84-1.68 (m, 6H) | 438.3 |
| 128 | 4-chloro-1-(trans-5-((2-chlorobenzyl)(methyl)amino)octahydrocyclopenta[c]pyrrole-2-carbonyl)-1H-pyrazole-3-carboxamide | 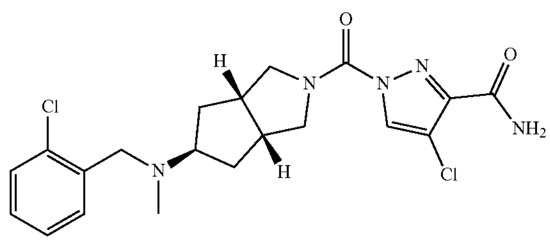 [SMILES: CN(Cc1ccccc1Cl)[C@H]1C[C@@H]2CN(C(=O)n3cc(Cl)c(C(N)=O)n3)C[C@@H]2C1] | (Chloroform-d) δ 8.25 (s, 1H), 7.44-7.46 (m, 1H), 7.33-7.35 (m, 1H), 7.16-7.22 (m, 2H), 6.62 (s, 1H), 5.75 (s, 1H), 3.96-4.15 (m, 2H), 3.60-3.77 (m, 4H), 3.13-3.21 (m, 1H), 2.90 (s, 2H), 2.17 (s, 3H), 1.94-2.02 (m, 2H), 1.61 (s, 2H) | 436.0 |
| 129 | 1-(4-(3-(4-chlorophenoxy)benzyl)piperazine-1-carbonyl)-4-methyl-1H-pyrazole-3-carboxylic acid | 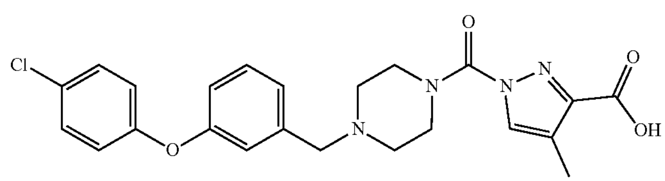 [SMILES: Cc1cn(C(=O)N2CCN(Cc3cccc(Oc4ccc(Cl)cc4)c3)CC2)nc1C(=O)O] | δ 7.87 (s, 1H), 7.32-7.37 (m, 3H), 7.13-7.16 (m, 1H), 7.05 (s, 1H), 6.91-6.99 (m, 3H), 3.85 (s, 4H), 3.62 (s, 2H), 2.60-2.63 (m, 4H), 2.26 (s, 3H) | 455.2 |

-continued

| Ex | Name | Structure | NMR (¹H NMR, 300 MHz or 400 MHz, Methanol-d) | MS [M + H]⁺ |
|---|---|---|---|---|
| 130 | 1-(2-(5-chloro-2-(trifluoromethyl)-benzyl)-2,8-diazaspiro[4.5]-decane-8-carbonyl)-4-methyl-1H-pyrazole-3-carboxylic acid | 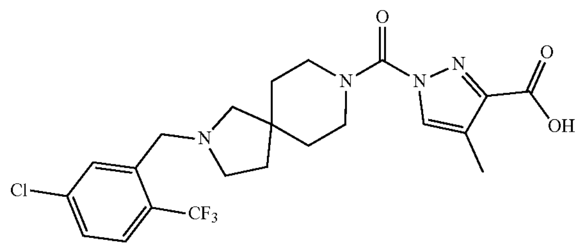 [SMILES: Cc1cn(C(=O)N2CCC3(CCN(Cc4cc(Cl)ccc4C(F)(F)F)C3)CC2)nc1C(=O)O] | δ 8.33 (s, 1H), 7.62-7.67 (m, 2H), 7.40-7.43 (m, 1H), 3.66-3.86 (m, 6H), 2.75-2.79 (m, 2H), 2.62 (s, 2H), 2.27-2.29 (m, 3H), 1.70-1.85 (m, 6H) | 485.2 |
| 131 | 1-(2-(5-chloro-2-(trifluoromethyl)-benzyl)-2,7-diazaspiro[3.5]-nonane-7-carbonyl)-4-methyl-1H-pyrazole-3-carboxylic acid | 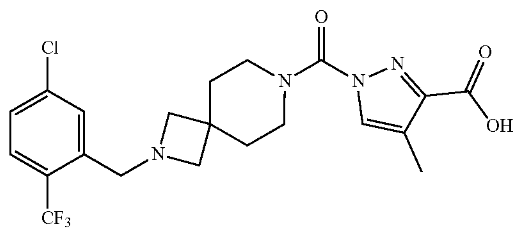 | δ 7.89 (br, 1H), 7.71-7.76 (m, 2H), 7.50-7.53 (m, 1H), 4.09 (s, 2H), 3.73 (s, 4H), 3.47 (m, 4H), 2.29 (s, 3H), 1.96 (m, 4H) | 471.2 |
| 132 | 4-chloro-1-(4-(3-(4-chlorophenoxy)-benzyl)-piperazine-1-carbonyl)-1H-pyrazole-3-carboxylic acid | 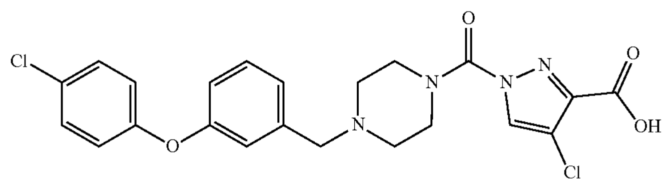 [SMILES: O=C(O)c1nn(C(=O)N2CCN(Cc3cccc(Oc4ccc(Cl)cc4)c3)CC2)cc1Cl] | δ 8.20 (s, 1H), 7.35-7.38 (m, 3H), 7.18 (d, J = 7.5 Hz, 1H), 7.09 (s, 1H), 6.99-7.02 (m, 3H), 3.89 (br, 4H), 3.70-3.74 (m, 2H), 2.72 (br, 4H) | 475.1 |
| 133 | 4-chloro-1-(2-(5-chloro-2-(trifluoromethyl)-benzyl)-2,8-diazaspiro[4.5]-decane-8-carbonyl)-1H-pyrazole-3-carboxylic acid | 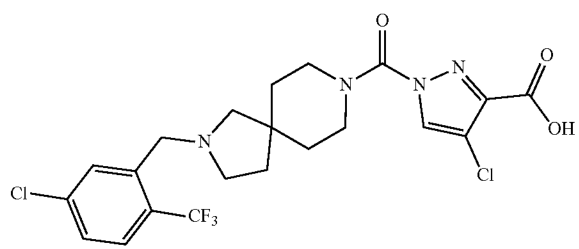 [SMILES: O=C(O)c1nn(C(=O)N2CCC3(CCN(Cc4cc(Cl)ccc4C(F)(F)F)C3)CC2)cc1Cl] | δ 8.17 (s, 1H), 7.94 (s, 1H), 7.71-7.74 (m, 1H), 7.51-7.54 (m, 1H), 4.09 (s, 2H), 3.67-3.84 (m, 4H), 2.97-3.02 (m, 2H), 2.86 (s, 2H), 1.89-1.94 (m, 2H), 1.74-1.86 (m, 4H) | 505.0 |

| Ex | Name | Structure | NMR (¹H NMR, 300 MHz or 400 MHz, Methanol-d) | MS [M + H]⁺ |
|---|---|---|---|---|
| 134 | 4-chloro-1-(2-(5-chloro-2-(trifluoromethyl)benzyl)-2,7-diazaspiro[3.5]nonane-7-carbonyl)-1H-pyrazole-3-carboxylic acid | 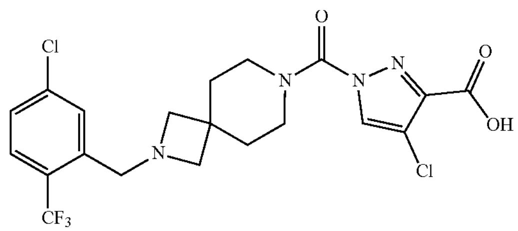 | δ 8.12 (s, 1H), 7.71-7.76 (m, 2H), 7.51-7.54 (m, 1H), 4.23-4.27 (m, 2H), 3.65-3.82 (m, 8H), 1.93-1.97 (m, 4H) | 491.0 |
| 135 | 4-methyl-1-(2-(2-(pyrrolidin-1-yl)-4-(trifluoromethyl)benzyl)-2,7-diazaspiro[3.5]nonane-7-carbonyl)-1H-pyrazole-3-carboxylic acid | 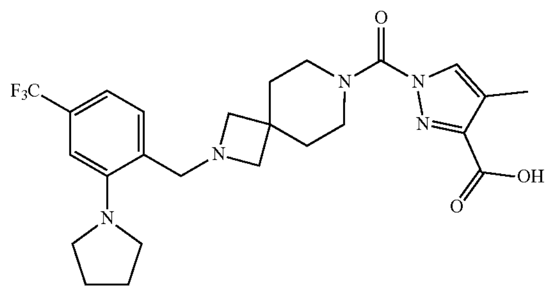 [SMILES: Cc1cn(C(=O)N2CCC3(CC2)CN(Cc2ccc(C(F)(F)F)cc2N2CCCC2)C3)nc1C(=O)O] | δ 7.83 (s, 1H), 7.53-7.55 (m, 1H), 7.31 (s, 1H), 7.24-7.26 (m, 1H), 4.40 (s, 2H), 3.74-3.75 (m, 8H), 3.24-3.32 (m, 4H), 2.27 (s, 3H), 1.91-2.06 (m, 8H) | 506.1 |
| 136 | 4-chloro-1-(5-(2,5-dichlorobenzyl)octahydropyrrolo[3,4-c]pyrrole-2-carbonyl)-1H-pyrazole-3-carboxylic acid | 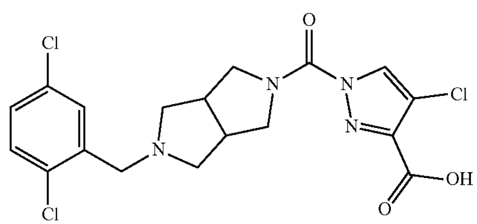 [SMILES: O=C(O)c1nn(C(=O)N2CC3CN(Cc4cc(Cl)ccc4Cl)CC3C2)cc1Cl] | δ 8.24 (s, 1H), 7.53 (d, J = 2.7 Hz,1H), 7.38 (d, J = 8.4 Hz, 1H), 7.25-7.29 (m, 1H), 3.79-4.01 (m, 6H), 2.98 (br, 2H), 2.70-2.82 (m, 4H) | 443.0 |
| 137 | 4-chloro-1-(5-(3-(4-chlorophenoxy)benzyl)octahydropyrrolo[3,4-c]pyrrole-2-carbonyl)-1H-pyrazole-3-carboxylic acid | 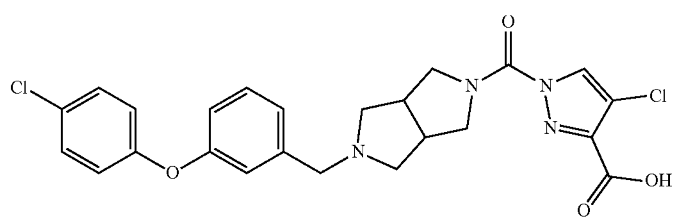 [SMILES: O=C(O)c1nn(C(=O)N2CC3CN(Cc4cccc(Oc5ccc(Cl)cc5)c4)CC3C2)cc1Cl] | δ 8.21 (s, 1H), 7.33-7.44 (m, 3H), 7.22 (d, J = 7.5 Hz, 1H), 7.13 (s, 1H), 6.98-7.03 (m, 3H), 3.98-4.04 (m, 6H), 3.19-3.22 (m, 2H), 3.10 (br, 2H), 2.97-3.00 (m, 2H) | 501.1 |

| Ex | Name | Structure | NMR (¹H NMR, 300 MHz or 400 MHz, Methanol-d) | MS [M + H]⁺ |
|---|---|---|---|---|
| 138 | 4-chloro-1-(2-(4-(pyrrolidin-1-yl)-2-(trifluoromethyl)-benzyl)-2,8-diazaspiro[4.5]-decane-8-carbonyl)-1H-pyrazole-3-carboxylic acid | 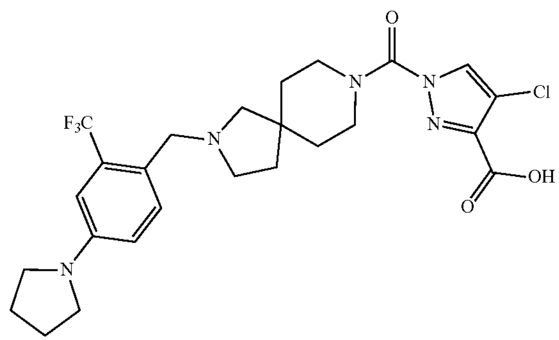 [SMILES: O=C(O)c1nn(C(=O)N2CCC3(CCN(Cc4ccc(N5CCCC5)cc4C(F)(F)F)C3)CC2)cc1Cl] | δ 8.11 (s, 1H), 7.56 (d, J = 8.4 Hz, 1H), 6.79-6.86 (m, 2H), 4.22 (br, 2H), 3.82 (br, 2H), 3.71 (br, 2H), 3.52-3.61 (m, 4H), 3.26 (br, 2H), 3.11 (br, 2H), 2.04-2.08 (m, 4H), 1.99-2.01 (m, 2H), 1.73-1.84 (m, 4H) | 540.2 |
| 139 | 4-chloro-1-(1-((6-(trifluoromethyl)-benzo[b]thiophen-2-yl)methyl)-1,8-diazaspiro[4.5]-decane-8-carbonyl)-1H-pyrazole-3-carboxylic acid | 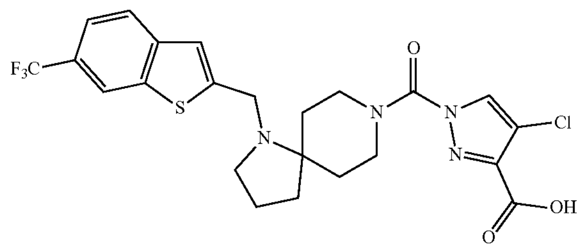 [SMILES: O=C(O)c1nn(C(=O)N2CCC3(CCCN3Cc3cc4ccc(C(F)(F)F)cc4s3)CC2)cc1Cl] | δ 8.15 (s, 2H), 7.86 (d, J = 8.1 Hz, 1H), 7.55-7.58 (m, 1H), 7.38 (s, 1H), 4.49-4.53 (m, 2H), 4.11 (br, 2H), 3.13-3.22 (m, 2H), 2.93-2.98 (m, 2H), 1.84-2.03 (m, 6H), 1.59-1.64 (m, 2H) | 527.0 |
| 140 | 4-chloro-1-(5-(4-(pyrrolidin-1-yl)-2-(trifluoromethyl)-benzyl)-octahydropyrrolo-[3,4-c]pyrrole-2-carbonyl)-1H-pyrazole-3-carboxylic acid | 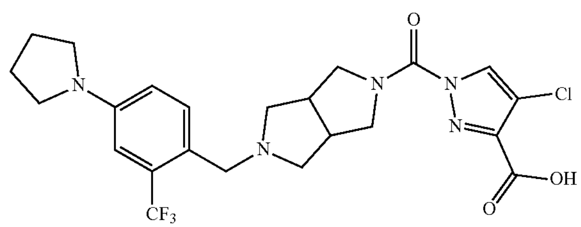 | δ 8.24 (d, J = 2.4 Hz, 1H), 7.51-7.57 (m, 1H), 6.77-6.82 (m, 2H), 3.79-4.22 (m, 6H), 3.42 (br, 2H), 3.33-3.35 (m, 3H), 3.24-3.28 (m, 1H), 3.01-3.13 (m, 4H), 1.99-2.08 (m, 4H) | 512.3 |
| 141 | 1-(5-(4-(1H-tetrazol-5-yl)-2-(trifluoromethyl)-benzyl)-octahydropyrrolo-[3,4-c]pyrrole-2-carbonyl)-4-chloro-1H-pyrazole-3-carboxylic acid | 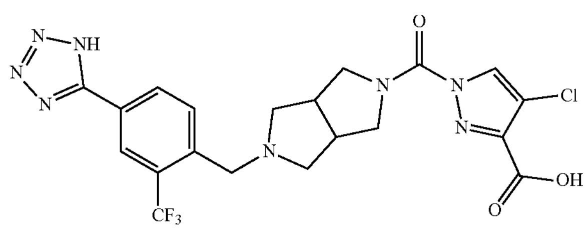 [SMILES: O=C(O)c1nn(C(=O)N2CC3CN(Cc4ccc(-c5nnn[nH]5)cc4C(F)(F)F)CC3C2)cc1Cl] | (DMSO-d₆) δ 8.61 (s, 1H), 8.23-8.28 (m, 2H), 7.83-7.86 (m, 1H), 4.24 (br, 6H), 2.89 (br, 2H), 2.57-2.73 (m, 4H) | 511.4 |

| Ex | Name | Structure | NMR (¹H NMR, 300 MHz or 400 MHz, Methanol-d) | MS [M + H]⁺ |
|---|---|---|---|---|
| 142 | 1-(4-(4-(1H-tetrazol-5-yl)-2-(trifluoromethyl)benzyl)piperazine-1-carbonyl)-4-chloro-1H-pyrazole-3-carboxylic acid | 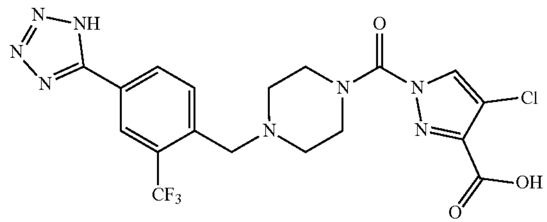 [SMILES: O=C(O)c1nn(C(=O)N2CCN(Cc3ccc(-c4nnn[nH]4)cc3C(F)(F)F)CC2)cc1Cl] | δ 8.38 (s, 1H), 8.25-8.28 (m, 2H), 8.00-8.03 (m, 1H), 3.81-3.84 (m, 6H), 2.65 (t, J = 4.6 Hz, 4H) | 484.9 |
| 143 | 1-(5-((2-chlorobenzyl)oxy)octahydrocyclopenta[c]pyrrole-2-carbonyl)-4-(trifluoromethyl)-1H-pyrazole-3-carboxylic acid | 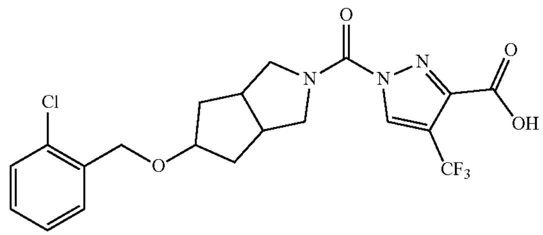 [SMILES: O=C(O)c1nn(C(=O)N2CC3CC(OCc4ccccc4Cl)CC3C2)cc1C(F)(F)F] | δ 8.46 (s, 1H), 7.36-7.40 (m, 1H), 7.30-7.34 (m, 1H), 7.17-7.24 (m, 2H), 4.53 (s, 2H), 3.82-4.19 (m, 5H), 2.83 (br, 2H), 2.16 (br, 2H), 1.82-1.87 (m, 2H) | 480.0 [M + Na]⁺ |
| 144 | 1-(4-(4-ethynylbenzyl)piperazine-1-carbonyl)-1H-pyrazole-3-carboxamide | 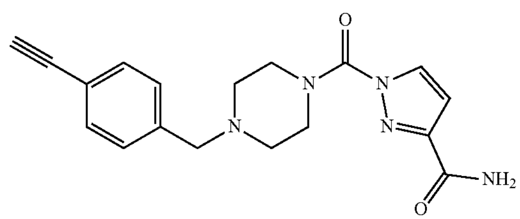 [SMILES: C#Cc1ccc(CN2CCN(C(=O)n3ccc(C(N)=O)n3)CC2)cc1] | (Chloroform-d) δ 8.09 (d, J = 2.7 Hz, 1H), 7.46 (d, J = 8.1 Hz, 2H), 7.29 (d, J = 8.1 Hz, 2H), 6.89 (d, J = 2.7 Hz, 1H), 6.66 (br, 1H), 5.63 (br, 1H), 3.84 (br, 4H), 3.56 (s, 2H), 3.08 (s, 1H), 2.54 (t, J = 4.7 Hz, 4H) | 338.0 |
| 145 | 4-chloro-1-(4-(4-(imidazo[1,2-a]pyridin-3-yl)-2-(trifluoromethyl)benzyl)piperazine-1-carbonyl)-1H-pyrazole-3-carboxylic acid | 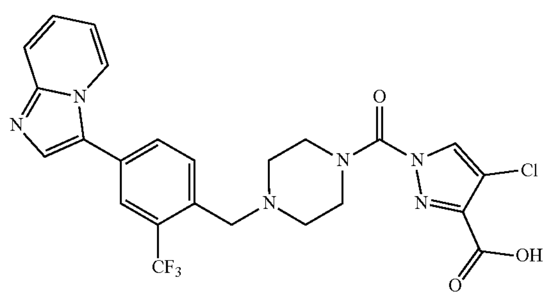 [SMILES: O=C(O)c1nn(C(=O)N2CCN(Cc3ccc(-c4cnc5ccccn45)cc3C(F)(F)F)CC2)cc1Cl] | (Chloroform-d) δ 8.28-8.30 (m, 1H), 8.07-8.11 (m, 2H), 7.95-7.98 (m, 1H), 7.80-7.82 (m, 2H), 7.68-7.70 (m, 1H), 7.35-7.39 (m, 1HG153G162), 6.95-6.99 (m, 1H), 3.77-4.15 (m, 6H), 2.61 (br, 4H) | 533.0 |

| Ex | Name | Structure | NMR (¹H NMR, 300 MHz or 400 MHz, Methanol-d) | MS [M + H]⁺ |
|---|---|---|---|---|
| 146 | 1-(5-(2,5-dichlorobenzyl)-octahydropyrrolo[3,4-c]pyrrole-2-carbonyl)-4-(trifluoromethyl)-1H-pyrazole-3-carboxylic acid | 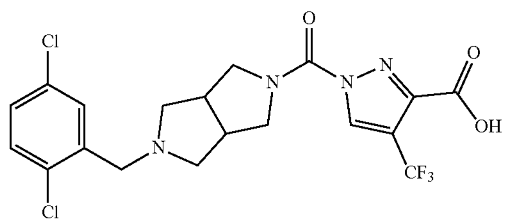 [SMILES: O=C(O)c1nn(C(=O)N2CC3CN(Cc4cc(Cl)ccc4Cl)CC3C2)cc1C(F)(F)F] | (DMSO-d₆) δ 8.62 (s, 1H), 7.46-7.49 (m, 1H), 7.43 (s, 1H), 7.20-7.36 (m, 1H), 3.65 (s, 7H), 2.87 (br, 2H), 2.50-2.58 (m, 4H) | 476.9 |
| 147 | 1-(5-(3-(4-chlorophenoxy)benzyl)-octahydropyrrolo[3,4-c]pyrrole-2-carbonyl)-4-(trifluoromethyl)-1H-pyrazole-3-carboxylic acid | 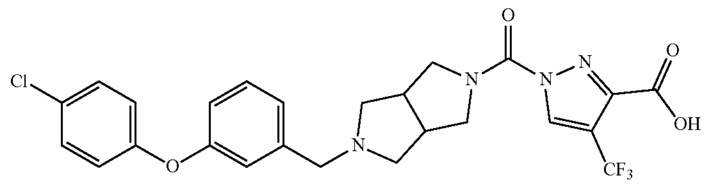 [SMILES: O=C(O)c1nn(C(=O)N2CC3CN(Cc4cccc(Oc5ccc(Cl)cc5)c4)CC3C2)cc1C(F)(F)F] | δ 8.45 (s, 1H), 7.37-7.43 (m, 1H), 7.29-7.34 (m, 2H), 7.19-7.27 (m, 1H), 6.90-7.10 (m, 4H), 4.00 (br, 6H), 3.10 (br, 6H) | 535.0 |
| 148 | 1-(2-(5-chloro-2-(trifluoromethyl)benzyl)-2,8-diazaspiro[4.5]decane-8-carbonyl)-4-(trifluoromethyl)-1H-pyrazole-3-carboxylic acid | 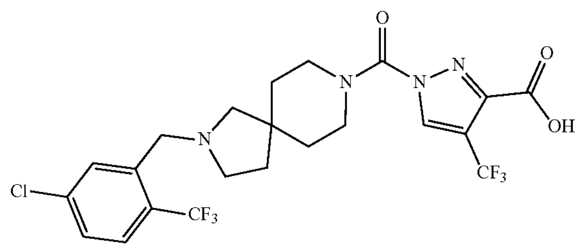 | δ 8.61 (s, 1H), 7.90 (s, 1H), 7.64-7.72 (m, 1H), 7.43-7.46 (m, 1H), 3.88 (s, 2H), 3.54-3.80 (m, 4H), 2.72-2.77 (m, 2H), 2.61 (s, 2H), 1.74-1.95 (m, 6H) | 539.5 |
| 149 | 4-(trifluoromethyl)-1-(1-((6-(trifluoromethyl)benzo[b]thiophen-2-yl)methyl)-1,8-diazaspiro[4.5]decane-8-carbonyl)-1H-pyrazole-3-carboxylic acid | 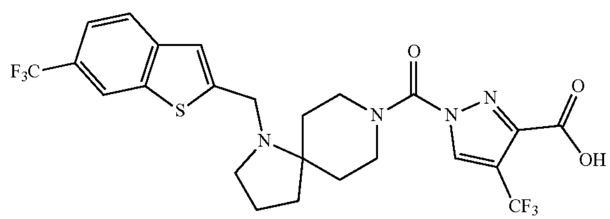 [SMILES: O=C(O)c1nn(C(=O)N2CCC3(CCCN3Cc3cc4ccc(C(F)(F)F)cc4s3)CC2)cc1C(F)(F)F] | δ 8.63 (s, 1H), 8.17 (s, 1H), 7.87 (d, J = 8.4 Hz, 1H), 7.56-7.59 (m, 1H), 7.39 (s, 1H), 4.41-4.45 (m, 2H), 4.13 (s, 2H), 3.20-3.28 (m, 2H), 2.97 (t, J = 7.2 Hz, 2H), 1.86-2.05 (m, 6H), 1.64-1.68 (m, 2H) | 561.2 |

| Ex | Name | Structure | NMR (¹H NMR, 300 MHz or 400 MHz, Methanol-d) | MS [M + H]⁺ |
|---|---|---|---|---|
| 150 | 1-(2-(4-(pyrrolidin-1-yl)-2-(trifluoromethyl)benzyl)-2,8-diazaspiro[4.5]decane-8-carbonyl)-4-(trifluoromethyl)-1H-pyrazole-3-carboxylic acid | 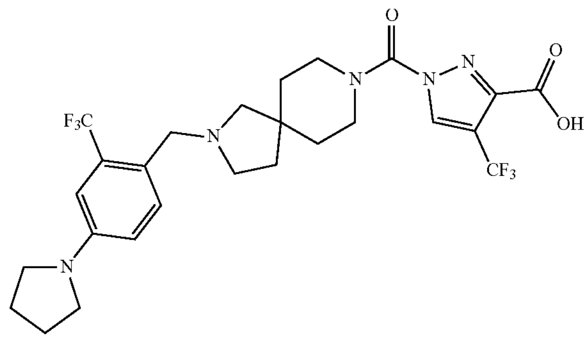 [SMILES: O=C(O)c1nn(C(=O)N2CCC3(CCN(Cc4ccc(N5CCCC5)cc4C(F)(F)F)C3)CC2)cc1C(F)(F)F] | δ 8.41 (s, 1H), 7.55-7.58 (m, 1H), 6.77-6.82 (m, 2H), 4.20 (s, 2H), 3.63-3.80 (m, 4H), 3.30-3.32 (m, 4H), 3.23 (t, J = 6.9 Hz, 2H), 3.09 (s, 2H), 1.96-2.04 (m, 6H), 1.67-1.86 (m, 4H) | 574.3 |
| 151 | 4-chloro-1-(5-(3-(pyrrolidin-1-yl)-5-(trifluoromethyl)benzyl)octahydropyrrolo[3,4-c]pyrrole-2-carbonyl)-1H-pyrazole-3-carboxylic acid | 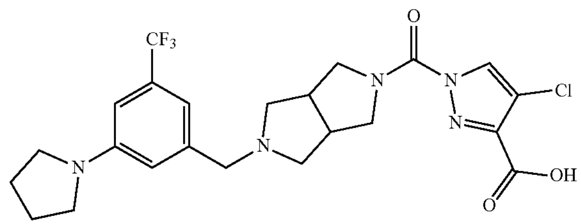 [SMILES: O=C(O)c1nn(C(=O)N2CC3CN(Cc4cc(N5CCCC5)cc(C(F)(F)F)c4)CC3C2)cc1Cl] | δ 8.19 (s, 1H), 6.87-6.92 (m, 2H), 6.71 (s, 1H), 3.70-4.28 (m, 6H), 3.27-3.32 (m, 6H), 3.05-3.11 (m, 4H), 2.00-2.03 (m, 4H) | 512.5 |
| 152 | 1-(2-(3-fluoro-5-(trifluoromethyl)benzyl)-2,8-diazaspiro[4.5]decane-8-carbonyl)-1H-pyrazole-3-carboxylic acid | 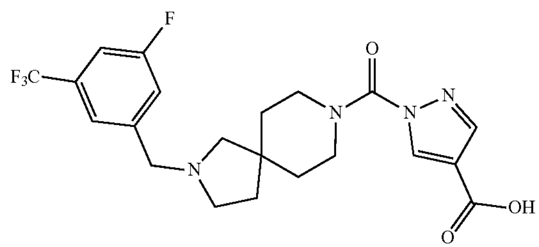 [SMILES: O=C(O)c1cnn(C(=O)N2CCC3(CCN(Cc4cc(F)cc(C(F)(F)F)c4)C3)CC2)c1] | δ 8.07 (d, J = 2.7 Hz, 1H), 7.65 (s, 1H), 7.45-7.56 (m, 2H), 6.78 (d, J = 2.7 Hz, 1H), 4.08 (s, 2H), 3.83-3.87 (m, 2H), 3.68-3.73 (m, 2H), 3.09 (t, J = 1.8 Hz, 2H), 2.90 (s, 2H), 1.96 (t, J = 6.9 Hz, 2H), 1.73-1.85 (m, 4H) | 455.2 |
| 153 | 1-(2-(3-(trifluoromethoxy)benzyl)-2,8-diazaspiro[4.5]decane-8-carbonyl)-1H-pyrazole-3-carboxylic acid | 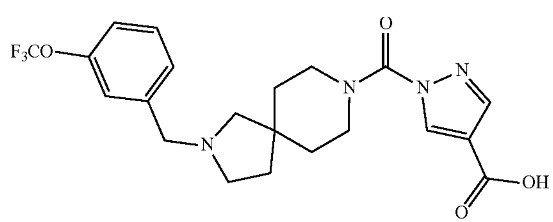 [SMILES: O=C(O)c1cnn(C(=O)N2CCC3(CCN(Cc4cccc(OC(F)(F)F)c4)C3)CC2)c1] | δ 8.07 (d, J = 2.7 Hz, 1H), 7.53-7.58 (m, 3H), 7.34-7.36 (m, 1H), 6.77 (d, J = 2.7 Hz, 1H), 4.23 (s, 2H), 3.84-3.87 (m, 2H), 3.60-3.71 (m, 2H), 3.28-3.20 (m, 2H), 3.09 (s, 2H), 2.00 (t, J = 6.9 Hz, 2H), 1.86-1.75 (m, 4H) | 453.2 |

| Ex | Name | Structure | NMR (¹H NMR, 300 MHz or 400 MHz, Methanol-d) | MS [M + H]⁺ |
|---|---|---|---|---|
| 154 | 1-(2-(3-chloro-4-methylbenzyl)-2,8-diazaspiro[4.5]-decane-8-carbonyl)-1H-pyrazole-3-carboxylic acid | 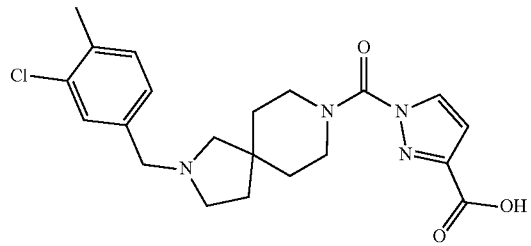 [SMILES: Cc1ccc(CN2CCC3(CCN(C(=O)n4ccc(C(=O)O)n4)CC3)C2)cc1Cl] | δ 8.06 (d, J = 2.7 Hz, 1H), 7.58 (s, 1H), 7.35-3.38 (m, 2H), 6.77 (d, J = 2.7 Hz, 1H), 4.29 (s, 2H), 3.84-3.89 (m, 2H), 3.66-3.71 (m, 2H), 3.32-3.40 (m, 2H), 3.22 (s, 2H), 2.40 (s, 3H), 2.05 (t, J = 6.9 Hz, 2H), 1.88-1.75 (m, 4H) | 417.2 |
| 155 | 1-(2-(3-methyl-4-(trifluoromethyl)-benzyl)-2,8-diazaspiro[4.5]-decane-8-carbonyl)-1H-pyrazole-3-carboxylic acid | 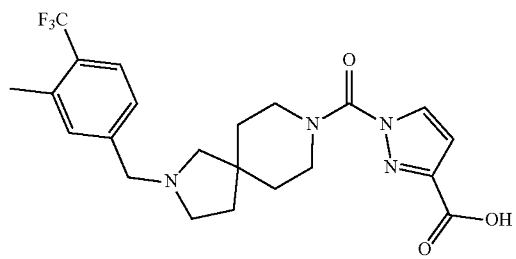 [SMILES: Cc1cc(CN2CCC3(CCN(C(=O)n4ccc(C(=O)O)n4)CC3)C2)ccc1C(F)(F)F] | δ 8.06 (d, J = 2.7 Hz, 1H), 7.71 (d, J = 7.8 Hz, 1H), 7.49-7.54 (m, 2H), 6.77 (d, J = 2.7 Hz, 1H), 4.29 (s, 2H), 3.83-3.88 (m, 2H), 3.67-3.72 (m, 2H), 3.30-3.32 (m, 2H), 3.17 (s, 2H), 2.51 (s, 3H), 2.03 (t, J = 6.9 Hz, 2H), 1.88-1.74 (m, 4H) | 451.3 |
| 156 | 1-(5-(([1,1'-biphenyl]-3-ylmethyl)-octahydropyrrolo[3,4-c]pyrrole-2-carbonyl)-1H-pyrazole-3-carboxylic acid | 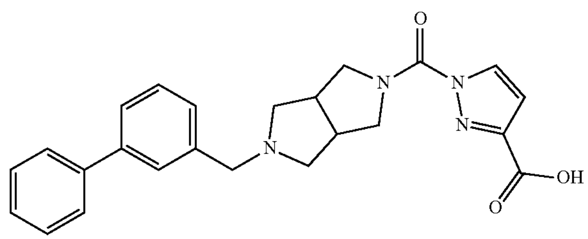 [SMILES: O=C(O)c1ccn(C(=O)N2CC3CN(Cc4cccc(-c5ccccc5)c4)CC3C2)n1] | δ 8.12 (m, 1H), 7.72 (m, 1H), 7.50-7.64 (m, 3H), 7.33-7.49 (m, 4H), 7.11-7.33 (m, 1H), 6.72 (s, 1H), 3.63-4.37 (m, 6H), 3.33-3.42 (m, 2H), 2.97-3.18 (m, 4H) | 417.2 |
| 157 | 1-(trans-5-((3-(trifluoromethyl)-benzyl)oxy)-octahydrocyclopenta[c]pyrrole-2-carbonyl)-1H-pyrazole-3-carboxylic acid | 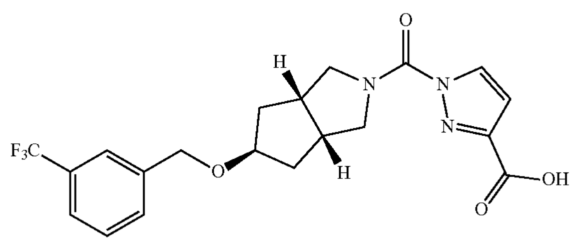 [SMILES: O=C(O)c1ccn(C(=O)N2C[C@H]3C[C@H](OCc4cccc(C(F)(F)F)c4)C[C@H]3C2)n1] | δ 8.17 (m, 1H), 7.61-7.72 (m, 1H), 7.40-7.61 (m, 3H), 6.77 (m, 1H), 4.55 (s, 2H), 4.20-4.30 (m, 1H), 3.50-4.20 (m, 4H), 2.92 (s, 2H), 2.00-2.23 (m, 2H), 1.68-1.94 (m, 2H) | 441.2 [M + NH₄]⁺ |

| Ex | Name | Structure | NMR (¹H NMR, 300 MHz or 400 MHz, Methanol-d) | MS [M + H]⁺ |
|---|---|---|---|---|
| 158 | 1-(trans-5-((3-(4-chlorophenoxy)benzyl)oxy)octahydrocyclopenta[c]pyrrole-2-carbonyl)-1H-pyrazole-3-carboxylic acid | 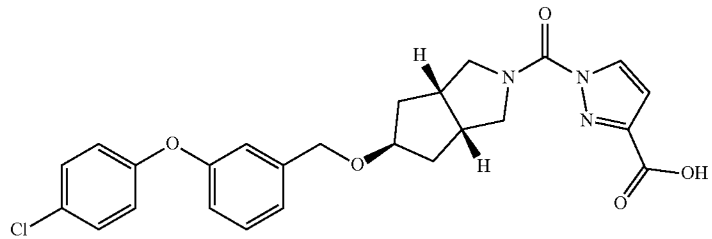 [SMILES: O=C(O)c1ccn(C(=O)N2C[C@H]3C[C@H](OCc4cccc(Oc5ccc(Cl)cc5)c4)C[C@H]3C2)n1] | δ 8.16 (m, 1H), 7.28-7.43 (m, 3H), 7.06-7.19 (m, 1H), 6.87-7.03 (m, 4H), 6.75 (m, 1H), 4.49 (s, 2H), 3.43-4.32 (m, 5H), 2.90 (s, 2H), 1.99-2.18 (m, 2H), 1.70-1.91 (m, 2H) | 504.2 [M + Na]⁺ |
| 159 | 1-(trans-5-((2-methyl-3-(trifluoromethyl)benzyl)oxy)octahydrocyclopenta-nl [c]pyrrole-2-carbonyl)-1H-pyrazole-3-carboxylic acid | 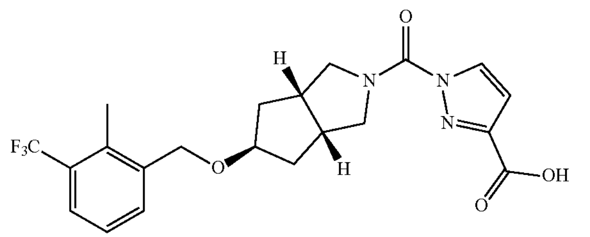 [SMILES: Cc1c(CO[C@H]2C[C@@H]3CN(C(=O)n4ccc(C(=O)O)n4)C[C@@H]3C2)cccc1C(F)(F)F] | δ 8.17 (m, 1H), 7.60 (m, 2H), 7.27-7.41 (m, 1H), 6.77 (m, 1H), 4.57 (s, 2H), 4.22-4.37 (m, 1H), 3.47-4.19 (m, 4H), 2.94 (s, 2H), 2.45 (d, J = 1.2 Hz, 3H), 1.99-2.23 (m, 2H), 1.77-1.91 (m, 2H) | 460.2 [M + Na]⁺ |
| 160 | 1-(4-((2-((2R,5S)-2,5-dimethylpyrrolidin-1-yl)-4-(trifluoromethyl)benzyl)(methyl)amino)-4-methylpiperidine-1-carbonyl)-1H-pyrazole-3-carboxylic acid | 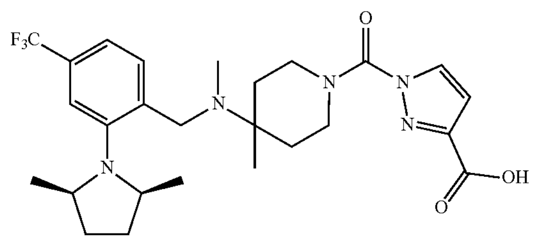 [SMILES: C[C@@H]1CC[C@H](C)N1c1cc(C(F)(F)F)ccc1CN(C)C1(C)CCN(C(=O)n2ccc(C(=O)O)n2)CC1] | δ 8.11 (d, J = 2.7 Hz, 1H), 7.88 (d, J = 8.0 Hz, 1H), 7.70 (s, 1H), 7.57 (d, J = 8.0 Hz, 1H), 6.81 (d, J = 2.7 Hz, 1H), 4.17 (br, 4H), 3.70 (br, 2H), 3.11-3.28 (m, 2H), 2.33 (s, 3H), 2.01-2.21 (m, 4H), 1.87 (br, 2H), 1.50-1.66 (m, 2H), 1.32 (s, 3H), 0.93 (d, J = 6.1 Hz, 6H) | 522.3 |
| 161 | 1-(4-(3-(4-chlorophenoxy)-5-fluorobenzyl)piperazine-1-carbonyl)-1H-pyrazole-3-carboxylic acid | 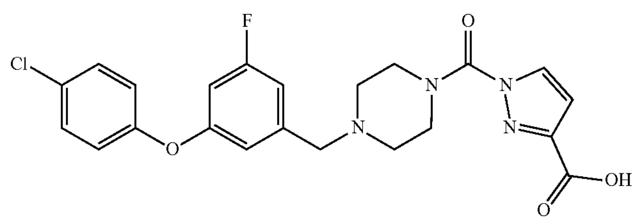 [SMILES: O=C(O)c1ccn(C(=O)N2CCN(Cc3cc(F)cc(Oc4ccc(Cl)cc4)c3)CC2)n1] | δ 8.14 (d, J = 2.7 Hz, 1H),7.37-7.42 (m, 2H), 6.99-7.07 (m, 2H), 6.92-6.95 (m, 1H), 6.86 (s, 1H), 6.84 (d, J = 2.7 Hz, 1H), 6.67 (d, J = 6.0 Hz, 1H), 3.86 (br, 4H), 3.62 (s, 2H), 2.62-2.67 (m, 4H) | 459.2 |

| Ex | Name | Structure | NMR (¹H NMR, 300 MHz or 400 MHz, Methanol-d) | MS [M + H]⁺ |
|---|---|---|---|---|
| 162 | 1-(2-(3,5-dichlorobenzyl)-2,8-diazaspiro[4.5]-decane-8-carbonyl)-1H-pyrazole-3-carboxylic acid | 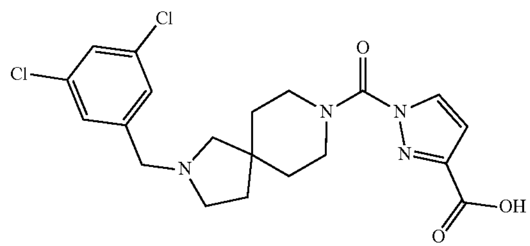 | δ 8.07 (d, J = 2.7 Hz, 1H), 7.48-7.51 (m, 3H), 6.79 (d, J = 2.7 Hz, 1H), 4.14 (s, 2H), 3.82-3.88 (m, 2H), 3.70-3.78 (m, 2H), 3.20 (t, J = 7.2 Hz, 2H), 3.05 (s, 2H), 1.99 (t, J = 7.2 Hz, 2H), 1.86-1.74 (m, 4H) | 437.1 |
| 163 | 1-(cis-5-([[1,1'-biphenyl]-3-ylmethyl)(methyl)-amino)-octahydrocyclopenta-[c]pyrrole-2-carbonyl)-1H-pyrazole-3-carboxylic acid | 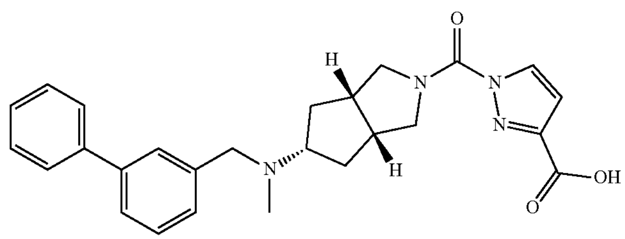 [SMILES: CN(Cc1cccc(-c2ccccc2)c1)[C@@H]1C[C@@H]2CN(C(=O)n3ccc(C(=O)O)n3)C[C@@H]2C1] | δ 8.13 (s, 1H), 8.12 (s, 1H), 7.69-7.82 (m, 1H), 7.60-7.63 (m, 2H), 7.46-7.60 (m, 2H), 7.30-7.42 (m, 3H), 6.69 (d, J = 2.7 Hz, 1H), 4.34 (s, 2H), 4.00 (br, 4H), 3.62-3.74 (m, 1H), 2.82 (br, 2H), 2.67 (s, 3H), 2.46-2.55 (m, 2H), 1.89-2.04 (m, 2H) | 445.2 |
| 164 | 1-(cis-5-([1,1'-biphenyl]-3-yloxy)-octahydrocyclopenta-[c]pyrrole-2-carbonyl)-1H-pyrazole-3-carboxylic acid | 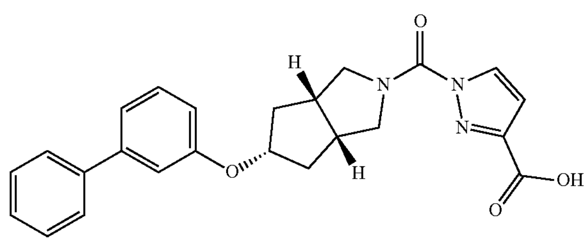 [SMILES: O=C(O)c1ccn(C(=O)N2C[C@H]3C[C@@H](Oc4cccc(-c5ccccc5)c4)C[C@H]3C2)n1] | δ 8.04-8.14 (m, 1H), 7.47-7.60 (m, 2H), 7.37-7.47 (m, 2H), 7.24-7.37 (m, 2H), 7.09-7.17 (d, J = 8.2 Hz, 1H), 6.97-7.07 (t, J = 4.0 Hz, 1H), 6.77-6.87 (m, 1H), 6.64-6.74 (d, J = 2.7 Hz, 1H), 4.92-5.02 (m, 1H), 3.70-4.44 (m, 4H), 2.90 (s, 2H), 2.23-2.40 (m, 2H), 1.81-2.00 (m, 2H) | 435.3 [M + NH₄]⁺ |
| 165 | 1-(4-(2-chloro-4-morpholinobenzyl)-piperazine-1-carbonyl)-1H-pyrazole-3-carboxamide | 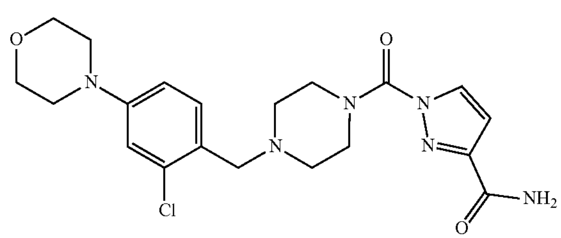 [SMILES: NC(=O)c1ccn(C(=O)N2CCN(Cc3ccc(N4CCOCC4)cc3Cl)CC2)n1] | δ 8.10 (d, J = 2.7 Hz, 1H), 7.27-7.33 (m, 1H), 6.89-6.96 (m, 2H), 6.78-6.82 (m, 1H), 6.67 (br, 1H), 5.56 (br, 1H), 3.84-3.88 (m, 8H), 3.63 (br, 2H), 3.15-3.18 (m, 4H), 2.63 (br, 4H) | 433.2 |

| Ex | Name | Structure | NMR (¹H NMR, 300 MHz or 400 MHz, Methanol-d) | MS [M + H]⁺ |
|---|---|---|---|---|
| 166 | 1-(5-(4-chloro-3-(tetrahydro-1H-furo[3,4-c]pyrrol-5(3H)-yl)benzyl)-octahydropyrrolo[3,4-c]pyrrol-2-carbonyl)-1H-pyrazole-3-carboxylic acid | 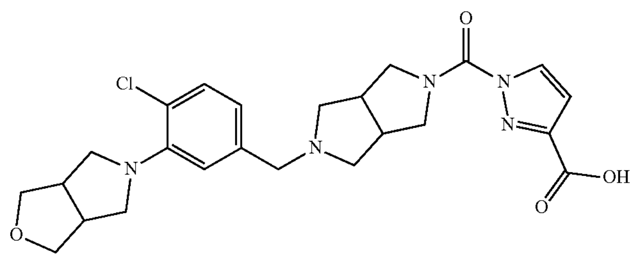 [SMILES: O=C(O)c1ccn(C(=O)N2CC3CN(Cc4ccc(Cl)c(N5CC6COCC6C5)c4)CC3C2)n1] | δ 8.17 (d, J = 2.7 Hz, 1H), 7.39 (d, J = 8.1 Hz, 1H), 7.17 (s, 1H), 7.02 (d, J = 8.1 Hz, 1H), 6.75 (d, J = 2.7 Hz, 1H), 3.94-4.40 (m, 8H), 3.94-3.64 (m, 2H), 3.31-3.36 (m, 2H), 3.08-3.30 (m, 8H), 2.92-2.99 (m, 2H) | 486.2 |
| 167 | 1-(4-(4-(pyrrolidin-1-yl)-2-(trifluoromethyl)benzyl)piperazine-1-carbonyl)-1H-pyrazole-3-carboxylic acid | 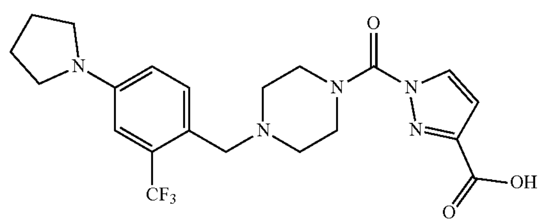 [SMILES: O=C(O)c1ccn(C(=O)N2CCN(Cc3ccc(N4CCCC4)cc3C(F)(F)F)CC2)n1] | δ 8.11 (d, J = 2.7 Hz, 1H),7.51 (d, J = 8.1 Hz, 1H), 6.75-6.79 (m, 3H), 3.86 (br, 4H), 3.68 (s, 2H), 3.28-3.32 (m, 4H), 2.65 (t, J = 4.8 Hz, 4H), 2.02-2.06 (m, 4H) | 452.2 |
| 168 | 1-(2-(3-chloro-4-(pyrrolidin-1-yl)benzyl)-2,8-diazaspiro[4.5]decane-8-carbonyl)-1H-pyrazole-3-carboxylic acid | 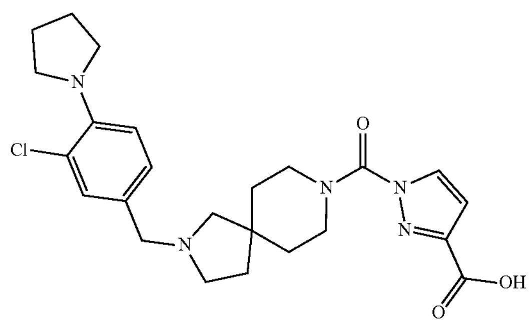 [SMILES: O=C(O)c1ccn(C(=O)N2CCC3(CCN(Cc4ccc(N5CCCC5)c(Cl)c4)C3)CC2)n1] | δ 8.07 (d, J = 2.7 Hz, 1H), 7.46 (d, J = 2.7 Hz, 1H), 7.28-7.31 (m, 1H), 6.95 (d, J = 8.7 Hz, 1H), 6.77 (d, J = 2.7 Hz, 1H), 4.23 (s, 2H), 3.84-3.89 (m, 2H), 3.72-3.68 (m, 2H), 3.37-3.45 (m, 6H), 3.22 (s, 2H), 2.05 (t, J = 7.2 Hz, 2H), 2.01-1.95 (m, 4H), 1.83-1.75 (m, 4H) | 472.2 |

| Ex | Name | Structure | NMR (¹H NMR, 300 MHz or 400 MHz, Methanol-d) | MS [M + H]⁺ |
|---|---|---|---|---|
| 169 | 1-(2-(2-chloro-4-morpholinobenzyl)-2,8-diazaspiro[4.5]-decane-8-carbonyl)-1H-pyrazole-3-carboxylic acid | 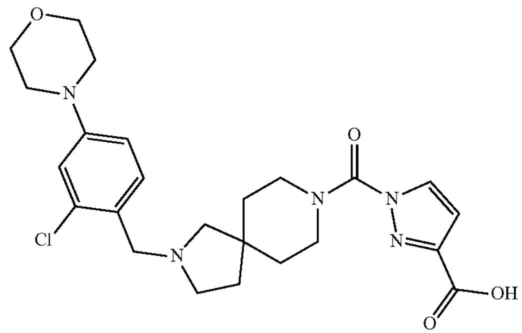 [SMILES: O=C(O)c1ccn(C(=O)N2CCC3(CCN(Cc4ccc(N5CCOCC5)cc4Cl)C3)CC2)n1] | δ 8.06 (d, J = 2.7 Hz, 1H), 7.49 (d, J = 8.7 Hz, 1H), 7.07 (d, J = 2.7 Hz, 1H), 6.95-6.99 (m, 1H), 6.76 (d, J = 2.7 Hz, 1H), 4.42 (s, 2H), 3.81-3.88 (m, 6H), 3.72-3.62 (m, 2H), 3.45 (t, J = 7.2 Hz, 2H), 3.32-3.33 (m, 2H), 3.21-3.24 (m, 4H), 2.06 (t, J = 7.2 Hz, 2H), 1.89-1.78 (m, 4H) | 488.2 |
| 170 | 1-(2-((3-(trifluoromethyl)-[1,1'-biphenyl]-4-yl)methyl)-2,8-diazaspiro[4.5]-decane-8-carbonyl)-1H-pyrazole-3-carboxylic acid | 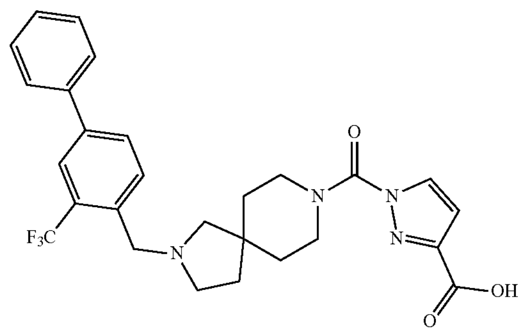 [SMILES: O=C(O)c1ccn(C(=O)N2CCC3(CCN(Cc4ccc(-c5ccccc5)cc4C(F)(F)F)C3)CC2)n1] | δ 8.06 (d, J = 2.8 Hz, 1H), 7.93-7.88 (m, 3H), 7.68-7.66 (m, 2H), 7.51-7.48 (m, 2H), 7.39-7.43 (m, 1H), 6.77 (d, J = 2.8 Hz, 1H), 3.97 (s, 2H), 3.81 (br, 2H), 3.74 (br, 2H), 2.86 (t, J = 7.2 Hz, 2H), 2.70 (s, 2H), 1.85 (t, J = 7.2 Hz, 2H), 1.82-1.73 (m, 4H) | 513.3 |
| 171 | 1-(2-(4-chloro-2-(pyrrolidin-1-yl)benzyl)-2,8-diazaspiro[4.5]-decane-8-carbonyl)-1H-pyrazole-3-carboxylic acid | 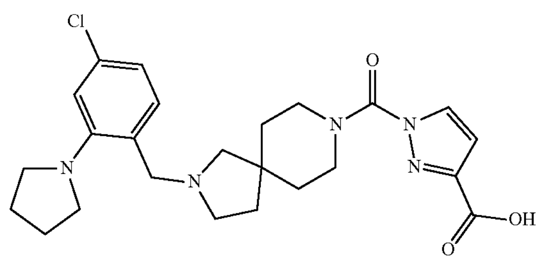 [SMILES: O=C(O)c1ccn(C(=O)N2CCC3(CCN(Cc4ccc(Cl)cc4N4CCCC4)C3)CC2)n1] | δ 8.06 (d, J = 2.7 Hz, 1H), 7.42 (d, J = 8.4 Hz, 1H), 7.15 (s, 1H), 7.02 (d, J = 8.4 Hz, 1H), 6.76 (d, J = 2.7 Hz, 1H), 4.38 (s, 2H), 3.83 (br, 2H), 3.72 (br, 2H), 3.34-3.40 (m, 1H), 3.27-3.30 (m, 1H), 3.10-3.25 (m, 6H), 2.05-2.00 (m, 6H), 1.86-1.74 (m, 4H) | 472.3 |

| Ex | Name | Structure | NMR (¹H NMR, 300 MHz or 400 MHz, Methanol-d) | MS [M + H]⁺ |
|---|---|---|---|---|
| 172 | 1-(trans-5-((3-methyl-4-(trifluoromethyl)benzyl)oxy)octahydrocyclopenta[c]pyrrole-2-carbonyl)-1H-pyrazole-3-carboxylic acid | 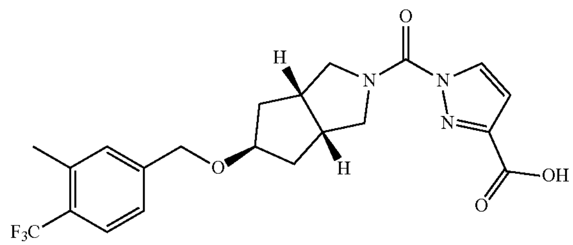 [SMILES: Cc1cc(CO[C@H]2C[C@@H]3CN(C(=O)n4ccc(C(=O)O)n4)C[C@@H]3C2)ccc1C(F)(F)F] | δ 8.10-8.23 (d, J = 2.8 Hz, 1H), 7.53-65 (d, J = 8.0 Hz, 1H), 7.25-7.40 (m, 2H), 6.70-6.84 (d, J = 2.8 Hz, 1H), 4.53 (s, 2H), 4.22-4.30 (m, 1H), 3.38-4.21 (m, 4H), 2.82-3.03 (s, 2H), 2.43-2.56 (d, J = 1.2 Hz, 3H), 2.02-2.22 (m, 2H), 1.73-1.91 (m, 2H) | 438.2 |
| 173 | 1-(4-(2-(pyrrolidin-1-yl)-4-(trifluoromethyl)benzyl)piperazine-1-carbonyl)-1H-pyrazole-3-carboxamide | 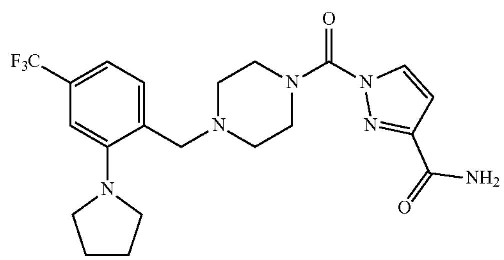 [SMILES: NC(=O)c1ccn(C(=O)N2CCN(Cc3ccc(C(F)(F)F)cc3N3CCCC3)CC2)n1] | δ 8.09 (d, J = 2.7 Hz, 1H), 7.54 (d, J = 8.1 Hz, 1H), 7.10-7.12 (m, 2H), 6.90 (d, J = 2.7 Hz, 1H), 6.65 (br, 1H), 5.57 (br, 1H), 3.84 (br, 4H), 3.61 (s, 2H), 3.22-3.26 (m, 4H), 2.56 (br, 4H), 1.93-2.00 (m, 4H) | 451.2 |
| 174 | 1-(1-(2-(pyrrolidin-1-yl)-4-(trifluoromethyl)benzyl)-1,8-diazaspiro[4.5]decane-8-carbonyl)-1H-pyrazole-3-carboxamide | 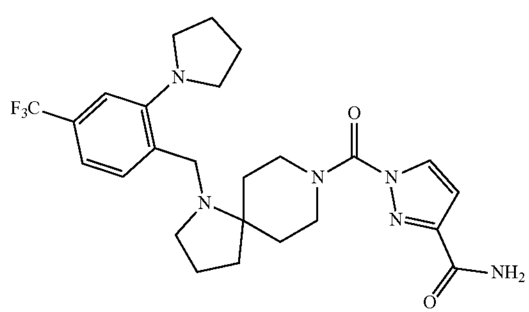 [SMILES: NC(=O)c1ccn(C(=O)N2CCC3(CCCN3Cc3ccc(C(F)(F)F)cc3N3CCCC3)CC2)n1] | δ 8.09 (d, J = 2.8 Hz, 1H), 7.69 (d, J = 8.0 Hz, 1H), 7.12-7.16 (m, 2H), 6.91 (d, J = 2.8 Hz, 1H), 6.66 (br, 1H), 5.53 (br, 1H), 4.53-4.56 (m, 2H), 3.67 (s, 2H), 3.13-3.17 (m, 6H), 2.64-2.67 (m, 2H), 1.81-1.95 (m, 10H), 1.58 (br, 2H) | 505.3 |
| 175 | 1-(4-((4-(trifluoromethyl)pyridin-3-yl)methyl)piperazine-1-carbonyl)-1H-pyrazole-3-carboxamide | 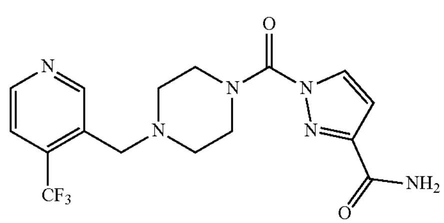 [SMILES: NC(=O)c1ccn(C(=O)N2CCN(Cc3cnccc3C(F)(F)F)CC2)n1] | δ 9.00 (s, 1H), 8.71 (d, J = 5.1 Hz, 1H), 8.10 (d, J = 2.7 Hz, 1H), 7.53 (d, J = 5.4 Hz, 1H), 6.91 (d, J = 2.7 Hz, 1H), 6.65 (br, 1H), 5.50 (br, 1H), 3.86 (br, 4H), 3.76 (s, 2H), 2.60-2.63 (m, 4H) | 383.2 |

| Ex | Name | Structure | NMR (¹H NMR, 300 MHz or 400 MHz, Methanol-d) | MS [M + H]⁺ |
|---|---|---|---|---|
| 176 | 1-(4-(methyl(3-(trifluoromethyl)-benzyl)amino)-piperidine-1-carbonyl)-1H-pyrazole-3-carboxamide | 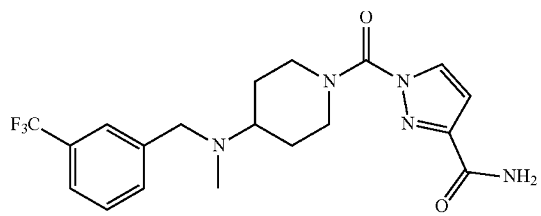 [SMILES: CN(Cc1cccc(C(F)(F)F)c1)C1CCN(C(=O)n2ccc(C(N)=O)n2)CC1] | δ 8.08 (d, J = 2.8 Hz, 1H), 7.60 (s, 1H), 7.51-7.53 (m, 2H), 7.42-7.46 (m, 1H), 6.91 (d, J = 2.8 Hz, 1H), 6.68 (br, 1H), 5.56 (br, 1H), 4.52-4.56 (m, 2H), 3.67 (s, 2H), 3.04-3.10 (m, 2H), 2.74-2.79 (m, 1H), 2.24 (s, 3H), 1.95-1.98 (m, 2H), 1.69-1.79 (m, 2H) | 410.2 |
| 177 | 1-(4-(3-(pyridazin-4-yloxy)benzyl)-piperazine-1-carbonyl)-1H-pyrazole-3-carboxylic acid | 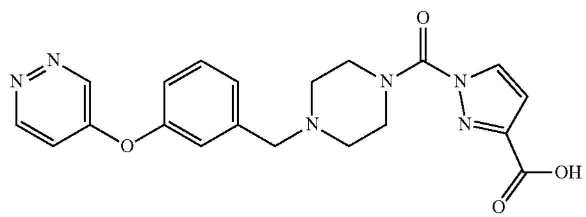 [SMILES: O=C(O)c1ccn(C(=O)N2CCN(Cc3cccc(Oc4ccnnc4)c3)CC2)n1] | δ 8.80 (d, J = 7.5 Hz, 1H), 8.09-8.10 (m, 2H), 7.75 (s, 1H), 7.62-7.67 (m, 1H), 7.50-7.54 (m, 2H), 6.78 (d, J = 2.7 Hz, 1H), 6.69-6.73 (m, 1H), 3.86 (br, 4H), 3.70 (s, 2H), 2.63 (t, J = 4.8 Hz, 4H) | 409.2 |
| 178 | 1-(2-(3-chloro-5-fluorobenzyl)-2,8-diazaspiro[4.5]-decane-8-carbonyl)-1H-pyrazole-3-carboxamide | 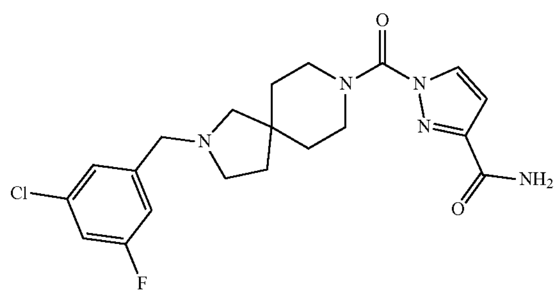 [SMILES: NC(=O)c1ccn(C(=O)N2CCC3(CCN(Cc4cc(F)cc(Cl)c4)C3)CC2)n1] | δ 8.06 (d, J = 2.4 Hz, 1H), 7.11 (s, 1H), 6.98 (s, 1H), 6.95 (s, 1H), 6.90 (d, J = 2.7 Hz, 1H), 6.66 (br, 1H), 5.46 (br, 1H), 3.62-3.81 (m, 4H), 3.56 (s, 2H), 2.63 (t, J = 6.9 Hz, 2H), 2.44 (s, 2H), 1.68-1.79 (m, 6H) | 420.2 |
| 179 | 1-(4-(3-(pyrimidin-5-yl)benzyl)-piperazine-1-carbonyl)-1H-pyrazole-3-carboxamide | 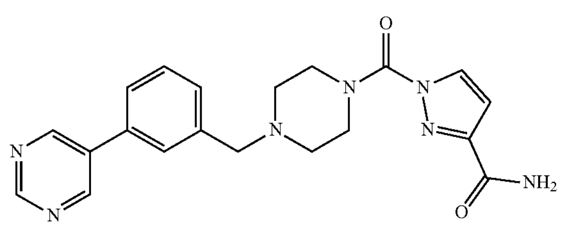 [SMILES: NC(=O)c1ccn(C(=O)N2CCN(Cc3cccc(-c4cncnc4)c3)CC2)n1] | δ 9.22 (s, 1H), 8.97 (s, 2H), 8.10 (d, J = 2.7 Hz, 1H), 7.60 (s, 1H), 7.51 (d, J = 5.1 Hz, 2H), 7.46 (t, J = 5.1 Hz, 1H), 6.90 (d, J = 2.7 Hz, 1H), 6.64 (br, 1H), 5.44 (br, 1H), 4.00 (br, 4H), 3.67 (br, 2H), 2.62 (br, 4H) | 392.2 |

| Ex | Name | Structure | NMR (¹H NMR, 300 MHz or 400 MHz, Methanol-d) | MS [M + H]⁺ |
|---|---|---|---|---|
| 180 | 1-(1-(4-chloro-2-(pyrrolidin-1-yl)benzyl)-1,8-diazaspiro[4.5]decane-8-carbonyl)-1H-pyrazole-3-carboxylic acid | 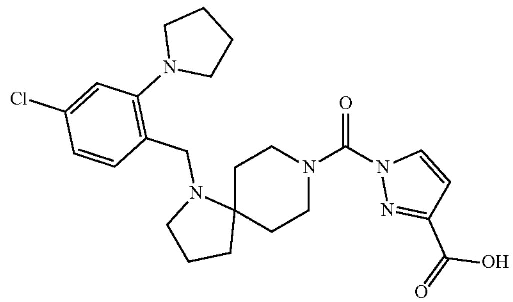 [SMILES: O=C(O)c1ccn(C(=O)N2CCC3(CCCN3Cc3ccc(Cl)cc3N3CCCC3)CC2)n1] | δ 8.09 (d, J = 2.7 Hz, 1H), 7.42 (d, J = 8.1 Hz, 1H), 7.25 (s, 1H), 7.10 (d, J = 8.1 Hz, 1H), 6.77 (d, J = 2.7 Hz, 1H), 4.70 (br, 2H), 4.31 (br, 2H), 3.05-3.24 (m, 8H), 2.15-2.41 (m, 4H), 1.90-2.10 (m, 6H), 1.77-1.82 (m, 2H) | 472.3 |
| 181 | 1-(4-(4-chlorobenzyl)-piperazine-1 carbonyl)-1H-pyrazole-3-carboxamide | 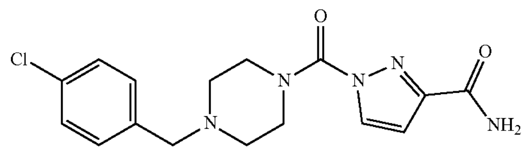 [SMILES: NC(=O)c1ccn(C(=O)N2CCN(Cc3ccc(Cl)cc3)CC2)n1] | (Chloroform-d) d 8.10 (d, J = 2.7 Hz, 1H), 7.25-7.33 (m, 4H), 6.90 (d, J = 2.7 Hz, 1H), 6.66 (br, 1H), 5.70 (br, 1H), 3.74-3.84 (m, 4H), 3.53 (s, 2H), 2.53-2.56 (m, 4H) | 348.0 |
| 182 | 1-(5-(4-(trifluoromethyl)-benzyl) octahydropyrrolo-[3,4-c]pyrrole-2-carbonyl)-1H-pyrazole-3-carboxamide | 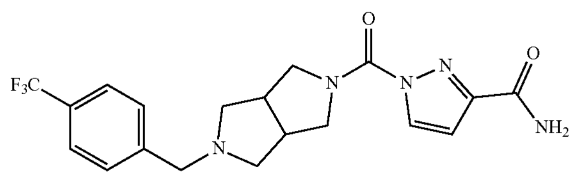 [SMILES: NC(=O)c1ccn(C(=O)N2CC3CN(Cc4ccc(C(F)(F)F)cc4)CC3C2)n1] | (DMSO-d₆) δ 8.78 (s, 1H), 8.07 (s, 1H), 7.80 (s, 1H), 7.61-7.73 (m, 2H), 7.42-7.60 (m, 2H), 7.28 (s, 1H), 3.43-4.16 (m, 6H), 2.85 (s, 2H), 2.53-2.60 (m, 2H), 2.41-2.51 (m, 2H) | 408.2 |
| 183 | 1-(5-(4-chlorobenzyl)-octahydropyrrolo-[3,4-c]pyrrole-2-carbonyl)-1H-pyrazole-3-carboxylic acid | 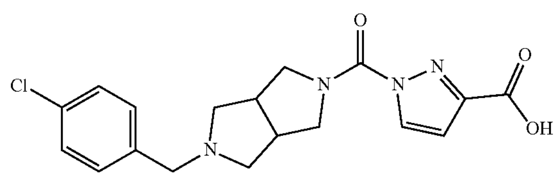 [SMILES: O=C(O)c1ccn(C(=O)N2CC3CN(Cc4ccc(Cl)cc4)CC3C2)n1] | δ 8.19 (s, 1H), 7.41-7.50 (m, 4H), 6.78 (s, 1H), 3.70-4.50 (m, 6H), 3.37 (s, 1H), 3.31 (s, 1H), 3.16 (s, 2H), 2.96-3.10 (m, 2H) | 375.1 |

| Ex | Name | Structure | NMR (¹H NMR, 300 MHz or 400 MHz, Methanol-d) | MS [M + H]⁺ |
|---|---|---|---|---|
| 184 | 1-(trans-5-((2-chlorobenzyl)(methyl)amino)-octahydrocyclopenta-[c]pyrrole-2-carbonyl)-1H-pyrazole-3-carboxylic | 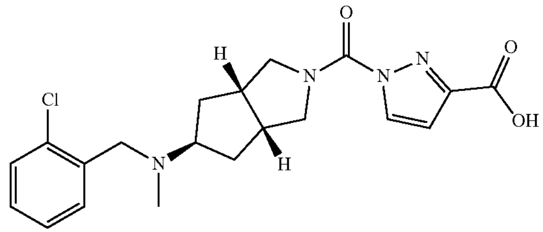 [SMILES: CN(Cc1ccccc1Cl)[C@H]1C[C@@H]2CN(C(=O)n3ccc(C(=O)O)n3)C[C@@H]2C1] | δ 8.10 (d, J = 2.7 Hz, 1H), 7.52-7.65 (m, 1H), 7.43-7.52 (m, 1H), 7.28-7.43 (m, 2H), 6.78 (d, J = 2.7 Hz, 1H), 3.76-4.30 (m, 5H), 3.42-3.75 (m, 2H), 2.75-3.08 (m, 2H), 2.42 (s, 3H), 2.00-2.25 (m, 4H) | 403.2 |
| 185 | 1-(1-((6-(trifluoromethyl)-benzo[b]-thiophen-2-yl)methyl)-1,8-diazaspiro[4.5]-decane-8-carbonyl)-1H-pyrazole-3-carboxylic acid | 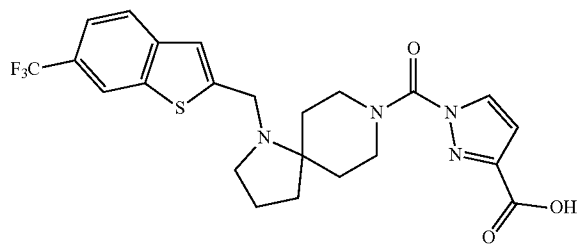 [SMILES: O=C(O)c1ccn(C(=O)N2CCC3(CCCN3Cc3cc4ccc(C(F)(F)F)cc4s3)CC2)n1] | δ 8.15 (s, 1H), 8.07 (d, J = 2.7 Hz, 1H), 7.84-7.87 (m, 1H), 7.54-7.61 (m, 1H), 7.35 (s, 1H), 6.78 (d, J = 2.7 Hz, 1H), 4.53-4.57 (m, 2H), 4.08 (s, 2H), 3.09-3.32 (m, 2H), 2.88-2.92 (m, 2H), 1.92-2.03 (m,4H), 1.83-1.90 (m, 2H), 1.57-1.62 (m, 2H) | 493.0 |
| 186 | 1-(8-(2-(4-fluoropiperidin-1-yl)-4-(trifluoromethyl)-benzyl)-2,8-diazaspiro[4.5]-decane-2-carbonyl)-1H-pyrazole-3-carboxylic acid | 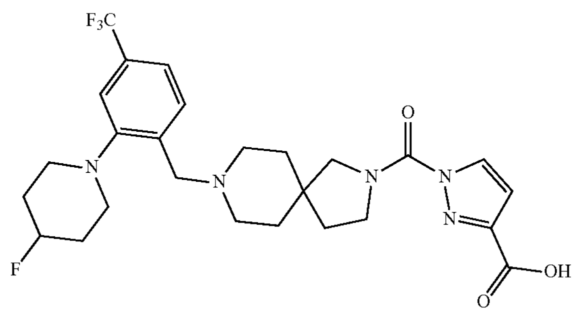 [SMILES: O=C(O)c1ccn(C(=O)N2CCC3(CCN(Cc4ccc(C(F)(F)F)cc4N4CCC(F)CC4)CC3)C2)n1] | (Chloroform-d) δ 8.20 (s, 1H), 7.79-7.82 (m, 1H), 7.40-7.43 (m, 2H), 6.83 (s, 1H), 4.78-4.94 (m, 1H), 4.36 (br, 1H), 3.77-4.22 (m, 4H), 3.39-3.53 (m, 2H), 3.08-3.57 (m, 3H), 2.67-2.81 (m, 4H), 1.67-2.08 (m, 10H) | 538.1 |
| 187 | 1-(4-((5-chlorobenzo[b]-thiophen-2-yl)methyl)-piperazine-1-carbonyl)-1H-pyrazole-3-carboxylic acid | 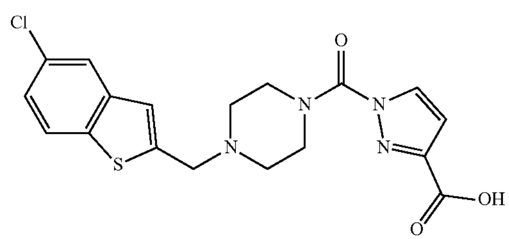 [SMILES: O=C(O)c1ccn(C(=O)N2CCN(Cc3cc4cc(Cl)ccc4s3)CC2)n1] | δ 8.09-8.15 (m, 1H), 7.64-7.85 (m, 2H), 7.18-7.33 (m, 2H), 6.80-6.89 (m, 1H), 3.78-4.02 (m, 6H), 2.61-2.78 (m, 4H) | 405.4 |

| Ex | Name | Structure | NMR (¹H NMR, 300 MHz or 400 MHz, Methanol-d) | MS [M + H]⁺ |
|---|---|---|---|---|
| 188 | 1-(4-((5-chloro-3-methyl-1H-indol-2-yl)methyl)-piperazine-1-carbonyl)-1H-pyrazole-3-carboxylic acid | 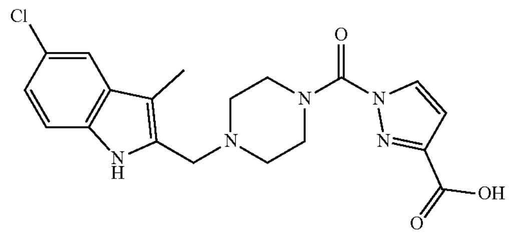 [SMILES: Cc1c(CN2CCN(C(=O)n3ccc(C(=O)O)n3)CC2)[nH]c2ccc(Cl)cc12] | (DMSO-d₆) δ 11.02 (s, 1H), 7.46-7.51 (m, 1H), 7.23-7.32 (m, 1H), 6.98-7.06 (m, 1H), 6.72 (s, 1H), 3.60-3.83 (m, 6H), 2.37-2.62 (m, 4H), 2.20 (s, 3H) | 424.0 [M + Na]⁺ |
| 189 | 1-(4-(benzo[d]thiazol-2-ylmethyl)-piperazine-1-carbonyl)-1H-pyrazole-3-carboxylic acid | 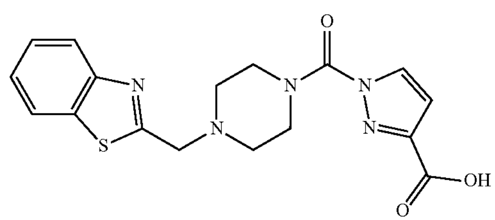 [SMILES: O=C(O)c1ccn(C(=O)N2CCN(Cc3nc4ccccc4s3)CC2)n1] | δ 7.90-8.10 (m, 2H), 7.40-7.55 (m, 2H), 6.70-6.79 (m, 1H), 4.05 (s, 2H), 3.80-3.90 (m, 4H), 2.70-2.85 (m, 4H) | 372.2 |
| 190 | 1-(4-((3-(4-chlorophenoxy)-benzyl)-aminopiperidine-1-carbonyl)-1H-pyrazole-3-carboxylic acid | 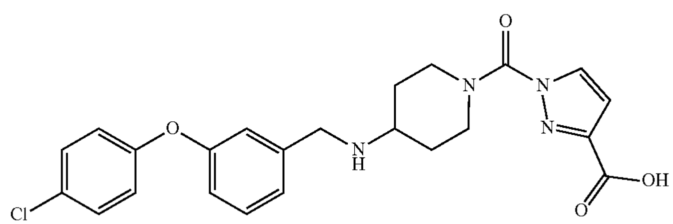 [SMILES: O=C(O)c1ccn(C(=O)N2CCC(NCc3cccc(Oc4ccc(Cl)cc4)c3)CC2)n1] | δ 8.08 (d, J = 2.7 Hz, 1H), 7.37-7.63 (m, 3H), 7.24-7.26 (m, 1H), 7.16 (s, 1H), 6.93-7.06 (m, 3H), 6.77 (d, J = 2.7 Hz, 1H), 4.51-4.70 (m, 2H), 4.11 (s, 2H), 3.01-3.32 (m, 4H), 2.14-2.24 (m, 2H), 1.60-1.91 (m, 2H) | 455.1 |
| 191 | 1-(2-(4-(pyrrolidin-1-yl)-2-(trifluoromethyl)-benzyl)-2,8-diazaspiro[4.5]-decane-8-carbonyl)-1H-pyrazole-3-carboxylic acid | 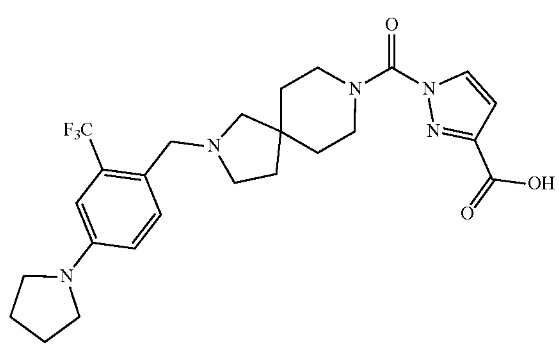 [SMILES: O=C(O)c1ccn(C(=O)N2CCC3(CCN(Cc4ccc(N5CCCC5)cc4C(F)(F)F)C3)CC2)n1] | δ 8.06 (d, J = 2.7 Hz, 1H), 7.58-7.60 (m, 1H), 6.76-6.85 (m, 3H), 4.33 (s, 2H), 3.73-3.84 (m, 2H), 3.57-3.71 (m, 2H), 3.328-3.46 (m, 6H), 3.14-3.22 (m, 2H), 2.01-2.10 (m, 6H), 1.81-1.87 (m, 4H) | 506.3 |

-continued

| Ex | Name | Structure | NMR (¹H NMR, 300 MHz or 400 MHz, Methanol-d) | MS [M + H]⁺ |
|---|---|---|---|---|
| 192 | 1-(2-(3-(trifluoromethyl)-benzyl)-2,8-diazaspiro[4.5]-decane-8-carbonyl)-1H-pyrazole-3-carboxylic acid | 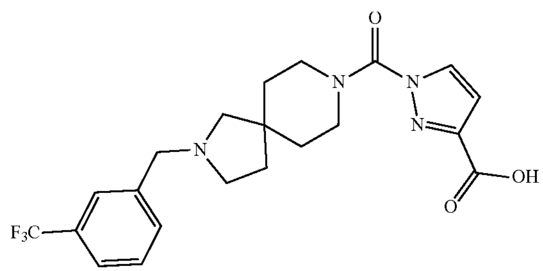 [SMILES: O=C(O)c1ccn(C(=O)N2CCC3(CCN(Cc4cccc(C(F)(F)F)c4)C3)CC2)n1] | δ 8.06 (d, J = 2.7 Hz, 1H), 7.88 (s, 1H), 7.73-7.82 (m, 2H), 7.62-7.67 (m, 1H), 6.77 (d, J = 2.7 Hz, 1H), 4.42 (s, 2H), 3.82 (br, 2H), 3.56-3.70 (m, 2H), 3.17-3.32 (m, 2H), 3.06-3.17 (m, 2H), 2.02-2.05 (m, 2H), 1.80-1.96 (m, 4H) | 437.2 |
| 193 | 1-(cis-5-((3-chloro-5-fluorobenzyl)oxy)-octahydrocyclopenta-[c]pyrrole-2-carbonyl)-1H-pyrazole-3-carboxylic acid | 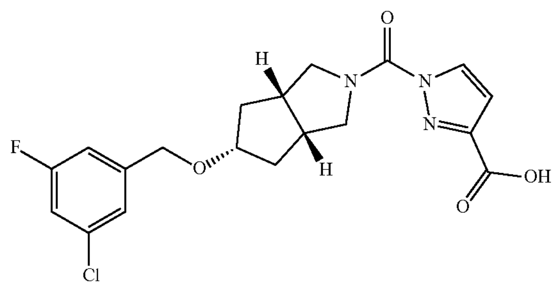 [SMILES: O=C(O)c1ccn(C(=O)N2C[C@H]3C[C@@H](OCc4cc(F)cc(Cl)c4)C[C@H]3C2)n1] | δ 8.03 (d, J = 2.8 Hz, 1H), 7.13 (s, 1H), 7.03-7.06 (m, 1H), 6.97-6.99 (m, 1H), 6.69 (d, J = 2.8 Hz, 1H), 4.45 (s, 2H), 4.15-4.35 (m, 1H), 4.07-4.12 (m, 2H), 3.07-3.96 (m, 2H), 2.80 (br, 2H), 2.12-2.19 (m, 2H), 1.78-1.82 (m, 2H) | 430.1 [M + Na]⁺ |
| 194 | 1-(trans-5-((4-(4-chlorophenoxy)-benzyl)amino)-octahydrocyclopenta-[c]pyrrole-2-carbonyl)-1H-pyrazole-3-carboxylic acid | 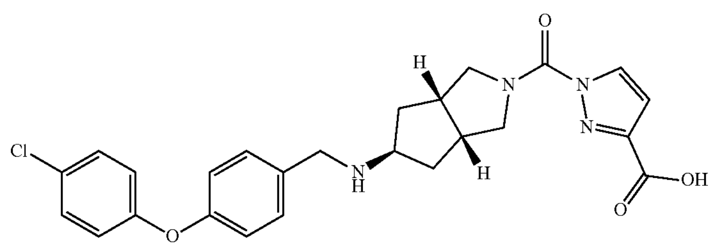 [SMILES: O=C(O)c1ccn(C(=O)N2C[C@H]3C[C@H](NCc4ccc(Oc5ccc(Cl)cc5)cc4)C[C@H]3C2)n1] | δ 8.14 (d, J = 2.7 Hz, 1H), 7.48 (d, J = 8.7 Hz, 2H), 7.35-7.38 (m, 2H), 6.97-7.06 (m, 4H), 6.74 (d, J = 2.7 Hz, 1H), 4.16 (s, 2H), 3.82-3.87 (m, 5H), 2.98 (br, 2H), 2.17-2.20 (m, 2H), 2.01-2.03 (m, 2H) | 481.2 |

| Ex | Name | Structure | NMR (¹H NMR, 300 MHz or 400 MHz, Methanol-d) | MS [M + H]⁺ |
|---|---|---|---|---|
| 195 | 1-(2-(4-(pyrrolidin-1-yl)-2-(trifluoromethyl)benzyl)-2,8-diazaspiro[4.5]decane-8-carbonyl)-1H-pyrazole-3-carboxamide | 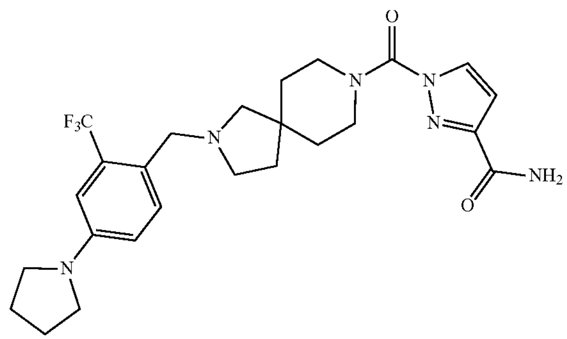 [SMILES: NC(=O)c1ccn(C(=O)N2CCC3(CCN(Cc4ccc(N5CCCC5)cc4C(F)(F)F)C3)CC2)n1] | (Chloroform-d) δ 8.05 (d, J = 2.7 Hz, 1H), 7.48 (br, 1H), 6.89 (d, J = 2.7 Hz, 1H), 6.76 (d, J = 2.4 Hz, 1H), 6.66 (br, 2H), 5.43 (br, 1H), 3.65-3.71 (m, 6H), 3.30 (t, J = 6.6 Hz, 4H), 2.64 (br, 2H), 2.44 (br, 2H), 2.03 (t, J = 6.6 Hz, 4H), 1.72 (br, 6H) | 505.3 |
| 196 | 1-(2-(3-chloro-5-(trifluoromethyl)benzyl)-2,8-diazaspiro[4.5]decane-8-carbonyl)-1H-pyrazole-3-carboxamide | 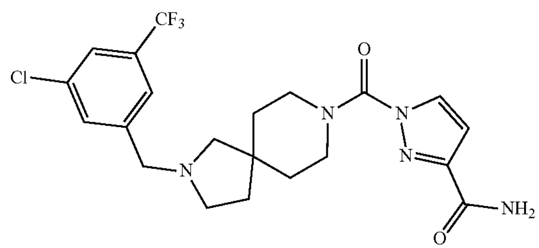 [SMILES: NC(=O)c1ccn(C(=O)N2CCC3(CCN(Cc4cc(Cl)cc(C(F)(F)F)c4)C3)CC2)n1] | (Chloroform-d) δ 8.07 (d, J = 2.7 Hz, 1H), 7.62-7.65 (m, 3H), 6.91 (d, J = 2.7 Hz, 1H), 6.68 (br, 1H), 5.55 (br, 1H), 3.51-3.91 (m, 6H), 2.65-2.77 (m, 2H), 2.47 (s, 2H), 1.75-1.76 (m, 6H) | 470.2 |
| 197 | 1-(2-(2-chloro-4-morpholinobenzyl)-2,8-diazaspiro[4.5]decane-8-carbonyl)-1H-pyrazole-3-carboxamide | 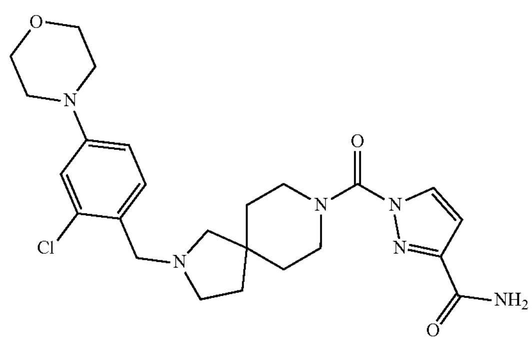 [SMILES: NC(=O)c1ccn(C(=O)N2CCC3(CCN(Cc4ccc(N5CCOCC5)cc4Cl)C3)CC2)n1] | (Chloroform-d) δ 8.05 (d, J = 2.7 Hz, 1H), 7.27 (br, 1H), 6.87-6.91 (m, 2H), 6.79 (d, J = 8.7 Hz, 1H), 6.66 (br, 1H), 5.46 (br, 1H), 3.83-3.86 (m, 4H), 3.64-3.77 (m, 6H), 3.13-3.17 (m, 4H), 2.69 (br, 2H), 2.51 (br, 2H), 1.73 (br, 6H) | 487.3 |

| Ex | Name | Structure | NMR (¹H NMR, 300 MHz or 400 MHz, Methanol-d) | MS [M + H]⁺ |
|---|---|---|---|---|
| 198 | 1-(4-(3-phenoxybenzyl)-piperazine-1-carbonyl)-1H-pyrazole-3-carboxamide | 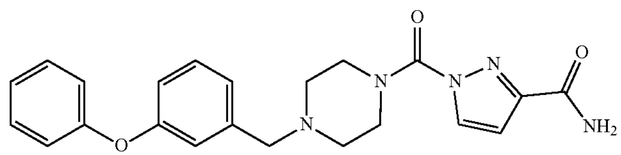 [SMILES: NC(=O)c1ccn(C(=O)N2CCN(Cc3cccc(Oc4ccccc4)c3)CC2)n1] | (Chloroform-d) δ 8.09 (s, 1H), 7.26-7.37 (m, 3H), 6.69-7.13 (m, 7H), 6.66 (s, 1H), 5.61 (s, 1H), 3.82 (m, 4H), 3.54 (m, 2H), 2.54-2.57 (m, 4H) | 406.2 |
| 199 | 1-(4-(2-morpholino-3-(trifluoromethyl)-benzyl)piperazine-1-carbonyl)-1H-pyrazole-3-carboxamide | 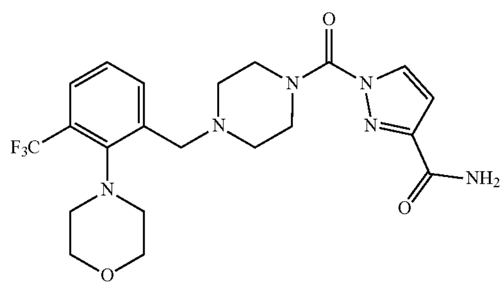 [SMILES: NC(=O)c1ccn(C(=O)N2CCN(Cc3cccc(C(F)(F)F)c3N3CCOCC3)CC2)n1] | (Chloroform-d) d 8.10-8.12 (m, 1H), 7.79 (d, J = 7.7 Hz, 1H), 7.59 (d, J = 7.7 Hz, 1H), 7.28-7.32 (m, 1H), 6.88-6.91 (m, 1H), 6.75 (br, 1H), 6.23-6.41 (m, 1H), 3.76-3.86 (m, 8H), 3.68 (s, 2H), 3.36-3.42 (m, 2H), 2.78-2.86 (m, 2H), 2.60-2.61 (m, 4H) | 467.0 |
| 200 | 1-(trans-5-((2-chlorobenzyl)-(methyl)amino)-octahydrocyclopenta-[c]pyrrole-2-carbonyl)-1H-pyrazole-3-carboxamide | 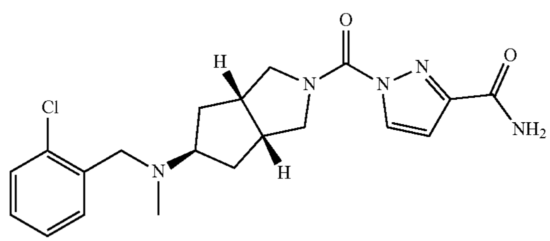 [SMILES: CN(Cc1ccccc1Cl)[C@H]1C[C@@H]2CN(C(=O)n3ccc(C(N)=O)n3)C[C@@H]2C1] | (Chloroform-d) δ 8.25 (d, J = 2.7 Hz, 1H), 740-760 (m, 1H), 7.36-7.40 (m, 1H), 7.17-7.22 (m, 2H), 6.92 (d, J = 2.7 Hz, 1H), 6.58-6.80 (m, 1H), 5.45-5.80 (m, 1H), 3.40-4.32 (m, 6H), 2.72-3.36 (m, 3H), 1.82-2.39 (m, 7H) | 402.2 |
| 201 | 1-(5-(3-chloro-5-(trifluoromethyl)-benzyl)-octahydropyrrolo-[3,4-c]pyrrole-2-carbonyl)-1H-pyrazole-3-carboxamide | 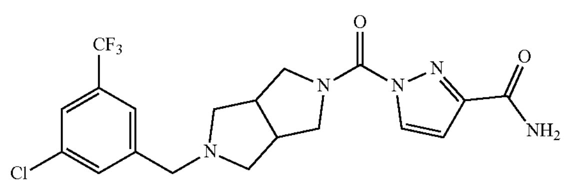 [SMILES: NC(=O)c1ccn(C(=O)N2CC3CN(Cc4cc(Cl)cc(C(F)(F)F)c4)CC3C2)n1] | (Chloroform-d) δ 8.26 (d, J = 2.6 Hz, 1H), 7.36-7.56 (m, 3H), 7.90 (d, J = 2.6 Hz, 1H), 6.70 (s, 1H), 5.80 (s, 1H), 4.00-4.30 (br, 2H), 3.70-4.00 (br, 2H), 3.60 (s, 2H), 2.90 (s, 2H), 2.60 (s, 4H) | 442.2 |

| Ex | Name | Structure | NMR (¹H NMR, 300 MHz or 400 MHz, Methanol-d) | MS [M + H]⁺ |
|---|---|---|---|---|
| 202 | 1-(5-(2,5-dichlorobenzyl)-octahydropyrrolo[3,4-c]pyrrole-2-carbonyl)-1H-pyrazole-3-carboxamide | 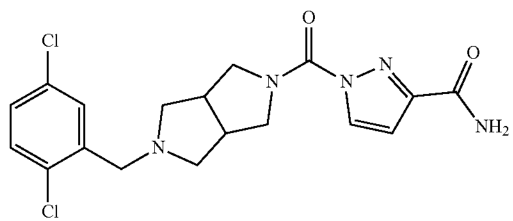 [SMILES: NC(=O)c1ccn(C(=O)N2CC3CN(Cc4cc(Cl)ccc4Cl)CC3C2)n1] | (Chloroform-d) δ 8.26 (s, 1H), 7.50-7.56 (m, 1H), 7.28-7.30 (m, 1H), 7.10-7.20 (m, 1H), 6.90 (s, 1H), 6.60-6.80 (m, 1H), 5.60 (s, 1H), 4.00-4.20 (br, 2H), 3.70-4.00 (m, 4H), 2.90-3.10 (br, 2H), 2.70 (s, 4H) | 407.9 |
| 203 | 1-(5-(4-chlorobenzyl)-octahydropyrrolo[3,4-c]pyrrole-2-carbonyl)-1H-pyrazole-3-carboxamide | 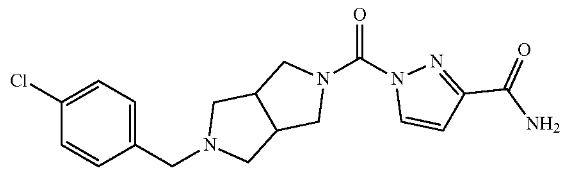 [SMILES: NC(=O)c1ccn(C(=O)N2CC3CN(Cc4ccc(Cl)cc4)CC3C2)n1] | (Chloroform-d) δ 8.25 (d, J = 2.7 Hz, 1H), 7.20-7.30 (m, 4H), 6.90 (d, J = 2.7 Hz, 1H), 6.71 (s, 1H), 6.10 (s, 1H), 3.63-4.40 (m, 4H), 3.56 (s, 2H), 2.90 (s, 2H), 2.58 (s, 4H) | 374.0 |
| 204 | 1-(cis-5-(methyl(2-(trifluoromethyl)benzyl)amino)octahydrocyclopenta[c]pyrrole-2-carbonyl)-1H-pyrazole-3-carboxamide | 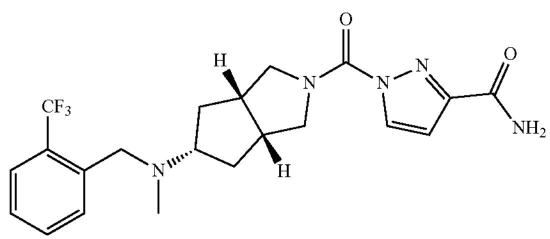 [SMILES: CN(Cc1ccccc1C(F)(F)F)[C@@H]1C[C@@H]2CN(C(=O)n3ccc(C(N)=O)n3)C[C@@H]2C1] | (Chloroform-d) δ 8.25 (d, J = 2.7 Hz, 1H), 7.55 (m, 2H), 7.42 (m, 2H), 6.90 (d, J = 2.7 Hz, 1H), 6.73 (br, 1H), 5.88 (br, 1H), 3.91 (br, 4H), 3.57 (s, 2H), 2.87-2.98 (m, 1H), 2.73 (br, 2H), 2.17-2.26 (m, 2H), 2.13 (s, 3H), 1.49-1.59 (m, 2H) | 436.0 |
| 205 | 1-(cis-5-(methyl(4-(trifluoromethyl)benzyl)amino)octahydrocyclopenta[c]pyrrole-2-carbonyl)-1H-pyrazole-3-carboxamide | 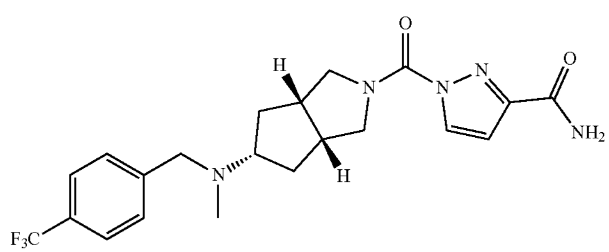 [SMILES: CN(Cc1ccc(C(F)(F)F)cc1)[C@@H]1C[C@@H]2CN(C(=O)n3ccc(C(N)=O)n3)C[C@@H]2C1] | (Chloroform-d) δ 8.25 (d, J = 2.7 Hz, 1H), 7.82 (d, J = 7.8 Hz, 1H), 7.60 (d, J = 7.8 Hz, 1H), 7.52 (t, J = 7.6 Hz, 1H), 7.32 (t, J = 7.6 Hz, 1H), 6.90 (d, J = 2.7 Hz, 1H), 6.75 (br, 1H), 6.18 (br, 1H), 3.68-4.11 (m, 6H), 2.94-3.02 (m, 1H), 2.73 (br, 2H), 2.14-2.22 (m, 5H), 1.52 (br, 2H) | 436.2 |

| Ex | Name | Structure | NMR (¹H NMR, 300 MHz or 400 MHz, Methanol-d) | MS [M + H]⁺ |
|---|---|---|---|---|
| 206 | 1-(cis-5-((2-chlorobenzyl)(methyl)amino)-octahydrocyclopenta[c]pyrrole-2-carbonyl)-1H-pyrazole-3-carboxamide | 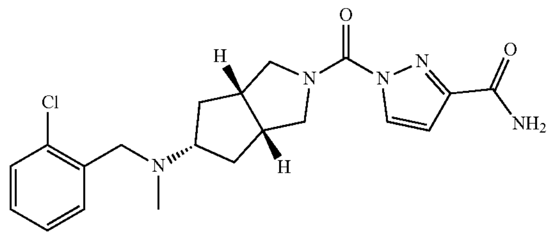 [SMILES: CN(Cc1ccccc1Cl)[C@@H]1C[C@@H]2CN(C(=O)n3ccc(C(N)=O)n3)C[C@@H]2C1] | (Chloroform-d) δ 8.25 (s, 1H), 7.47 (d, J = 6.4 Hz, 1H), 7.33-7.36 (m, 1H), 7.15-7.26 (m, 2H), 6.89-6.90 (m, 1H), 6.71 (br, 1H), 5.70 (br, 1H), 3.95 (br, 4H), 3.63 (s, 2H), 2.97-3.02 (m, 1H), 2.73 (br, 2H), 2.18-2.27 (m, 5H), 1.60 (br, 2H) | 402.1 |
| 207 | 1-(4-((2-(3-oxa-8-azabicyclo[3.2.1]-octan-8-yl)-4-(trifluoromethyl)-benzyl)(methyl)amino)-4-methylpiperidine-1-carbonyl)-1H-pyrazole-3-carboxylic acid | 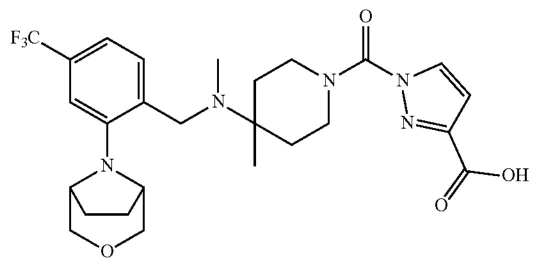 [SMILES: CN(Cc1ccc(C(F)(F)F)cc1N1C2CCC1COC2)C1(C)CCN(C(=O)n2ccc(C(=O)O)n2)CC1] | (DMSO-d₆) δ 8.22 (d, J = 2.7 Hz, 1H), 7.86-7.89 (m, 1H), 7.32-7.35 (m, 1H), 7.05 (s, 1H), 6.80 (d, J = 2.7 Hz, 1H), 3.58-3.81 (m, 12H), 1.80-2.09 (m, 9H), 1.52-1.59 (m, 2H), 1.06 (s, 3H) | 536.5 |
| 208 | 1-(5-(3-(trifluoromethyl)-benzyl)octahydropyrrolo[3,4-c]pyrrole-2-carbonyl)-1H-pyrazole-3-carboxamide | 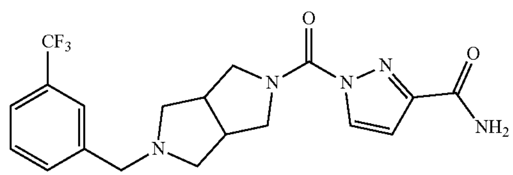 [SMILES: NC(=O)c1ccn(C(=O)N2CC3CN(Cc4cccc(C(F)(F)F)c4)CC3C2)n1] | (Chloroform-d) δ 8.24 (d, J = 2.7 Hz, 1H), 7.40-7.70 (m, 4H), 8.90 (d, J = 2.7 Hz, 1H), 6.60-6.80 (m, 1H), 5.46-5.60 (m, 1H), 4.00-4.20 (br, 2H), 3.60-4.00 (m, 4H), 3.00 (s, 2H), 2.60 (s, 4H) | 408.0 |
| 209 | 1-(4-(((5-chloro-2-(trifluoromethyl)-benzyl)(methyl)amino)methyl)piperidine-1-carbonyl)-1H-pyrazole-3-carboxylic acid | 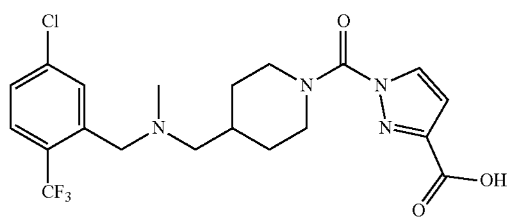 [SMILES: CN(Cc1cc(Cl)ccc1C(F)(F)F)CC1CCN(C(=O)n2ccc(C(=O)O)n2)CC1] | δ 8.06 (d, J = 2.7 Hz, 1H), 7.88 (s, 1H), 7.63 (d, J = 8.4 Hz, 1H), 7.40-7.43 (m, 1H), 6.79 (d, J = 2.7 Hz, 1H), 4.39-4.42 (m, 2H), 3.66 (s, 2H), 3.09-3.15 (m, 2H), 2.33 (d, J = 6.8 Hz, 2H), 2.23 (s, 3H), 1.90-1.93 (m, 3H), 1.22-1.32 (m, 2H) | 459.1 |

| Ex | Name | Structure | NMR (¹H NMR, 300 MHz or 400 MHz, Methanol-d) | MS [M + H]⁺ |
|---|---|---|---|---|
| 210 | 1-(2-(3-(4-chlorophenoxy)benzyl)-2,8-diazaspiro[4.5]decane-8-carbonyl)-1H-pyrazole-3-carboxylic acid | 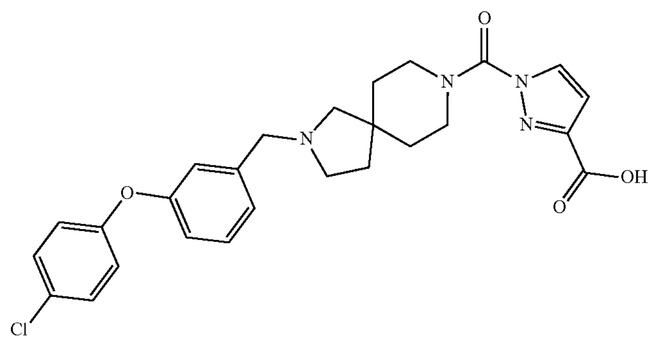 [SMILES: O=C(O)c1ccn(C(=O)N2CCC3(CCN(Cc4cccc(Oc5ccc(Cl)cc5)c4)C3)CC2)n1] | δ 8.02 (d, J = 2.7 Hz, 1H), 7.40-7.45 (m, 1H), 7.24-7.33 (m, 3H), 7.16-7.18 (m, 1H), 7.04-7.11 (m, 1H), 6.96-7.01 (m, 2H), 6.72 (d, J = 2.7 Hz, 1H), 4.22 (s, 2H), 3.74-3.83 (m, 2H), 3.64-3.68 (m, 2H), 3.27-3.34 (m, 2H), 3.07-3.13 (m, 2H), 1.97-2.02 (m, 2H), 1.71-1.82 (m, 4H) | 495.2 |
| 211 | 1-(4-(3-chloro-2-(tetrahydro-1H-furo[3,4-c]pyrrol-5(3H)-yl)benzyl)piperazine-1-carbonyl)-1H-pyrazole-3-carboxylic acid | 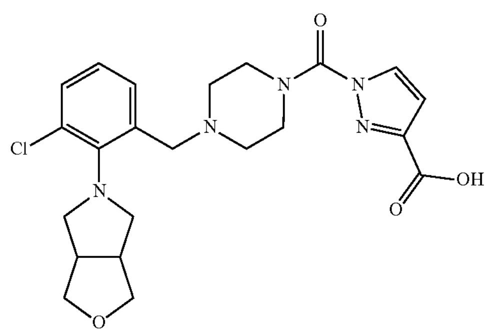 [SMILES: O=C(O)c1ccn(C(=O)N2CCN(Cc3cccc(Cl)c3N3CC4COCC4C3)CC2)n1] | δ 8.03-8.14 (m, 1H), 7.26-7.43 (m, 2H), 7.13-7.24 (m, 1H), 6.68-6.82 (m, 1H), 3.62-4.05 (m, 12H), 2.90-3.09 (m, 4H), 2.74-2.90 (m, 4H) | 460.1 |
| 212 | 1-(4-(2-(3-oxa-8-azabicyclo[3.2.1]octan-8-yl)-3-chlorobenzyl)piperazine-1-carbonyl)-1H-pyrazole-3-carboxylic acid | 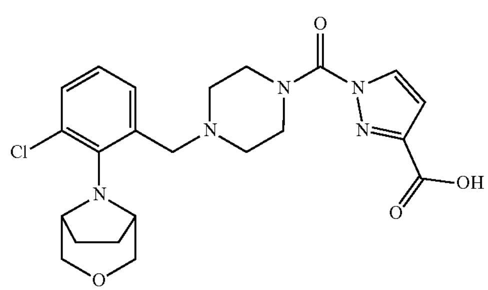 [SMILES: O=C(O)c1ccn(C(=O)N2CCN(Cc3cccc(Cl)c3N3C4CCC3COC4)CC2)n1] | δ 8.03-8.14 (m, 1H), 7.34-7.42 (m, 1H), 7.15-7.24 (m, 1H), 6.83-6.94 (m, 1H), 6.77-6.83 (m, 1H), 3.98-4.12 (m, 2H), 3.95 (s, 2H), 3.75-3.88(m, 6H), 3.54-3.67 (m, 2H), 2.54-3.73 (m, 4H), 2.01-2.24 (m, 4H) | 460.3 |

-continued

| Ex | Name | Structure | NMR (¹H NMR, 300 MHz or 400 MHz, Methanol-d) | MS [M + H]⁺ |
|---|---|---|---|---|
| 213 | 1-(4-(2-chloro-3-(2-hydroxy-2-methyl)propoxy)-benzyl)piperazine-1-carbonyl)-1H-pyrazole-3-carboxylic acid | 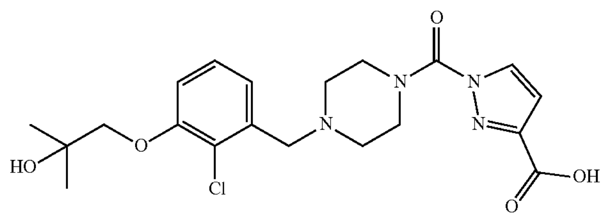 [SMILES: CC(C)(O)COc1cccc(CN2CCN(C(=O)n3ccc(C(=O)O)n3)CC2)c1Cl] | δ 8.09 (d, J = 2.7 Hz, 1H), 7.24 (t, J = 7.8 Hz, 1H), 7.13 (d, J = 7.8 Hz, 1H), 6.98 (d, J = 7.8 Hz, 1H), 6.77 (d, J = 2.7 Hz, 1H), 3.85-3.82 (m, 6H), 3.73 (s, 2H), 2.68-2.64 (m, 4H), 1.36 (s, 6H) | 437.1 |
| 214 | (R)-1-(4-(2-chloro-3-(2-hydroxy-2-methyl)propoxy)-benzyl)-2-methylpiperazine-1-carbonyl)-1H-pyrazole-3-carboxylic acid | 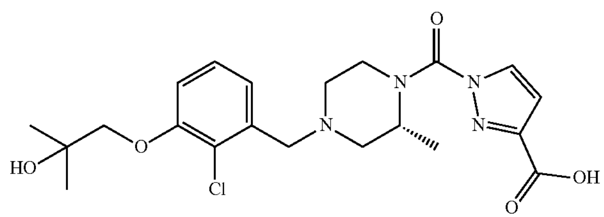 [SMILES: C[C@@H]1CN(Cc2cccc(OCC(C)(C)O)c2Cl)CCN1C(=O)n1ccc(C(=O)O)n1] | δ 8.07 (d, J = 2.7 Hz, 1H), 7.23 (t, J = 7.8 Hz, 1H), 7.14 (d, J = 7.8 Hz, 1H), 6.97 (d, J = 7.8 Hz, 1H), 6.77 (d, J = 2.7 Hz, 1H), 4.84 (br, 1H), 4.30-4.26 (m, 1H), 3.82 (s, 2H), 3.64 (s, 2H), 3.51-3.42 (m, 1H), 2.91-2.86 (m, 1H), 2.80-2.76 (m, 1H), 2.46-2.41 (m, 1H), 2.34-2.25 (m, 1H), 1.44 (d, J = 6.4 Hz, 3H), 1.36 s, 6H) | 451.1 |
| 215 | (S)-1-(4-(2-chloro-3-(2-hydroxy-2-methyl)propoxy)-benzyl)-2-methylpiperazine-1-carbonyl)-1H-pyrazole-3-carboxylic acid | 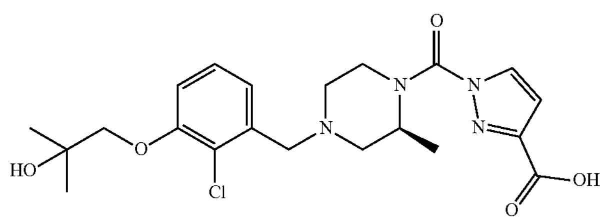 [SMILES: C[C@H]1CN(Cc2cccc(OCC(C)(C)O)c2Cl)CCN1C(=O)n1ccc(C(=O)O)n1] | δ 8.04 (d, J = 2.7 Hz, 1H), 7.23 (t, J = 7.8 Hz, 1H), 7.14 (d, J = 7.8 Hz, 1H), 6.96 (d, J = 7.8 Hz, 1H), 6.74 (d, J = 2.7 Hz, 1H), 4.70 (br, 1H), 4.34-4.29 (m, 1H), 3.82 (s, 2H), 3.63 (s, 2H), 3.46-3.41 (m, 1H), 2.89-2.86 (m, 1H), 2.79-2.75 (m, 1H), 2.45-2.40 (m, 1H), 2.33-2.24 (m, 1H), 1.44 (d, J = 6.4 Hz, 3H), 1.36 (s, 6H) | 451.1 |
| 216 | (R)-1-(4-(2-chloro-3-(2-hydroxy-2-methyl)propoxy)-benzyl)-2-methylpiperazine-1-carbonyl)-1H-pyrazole-3-carboxamide | 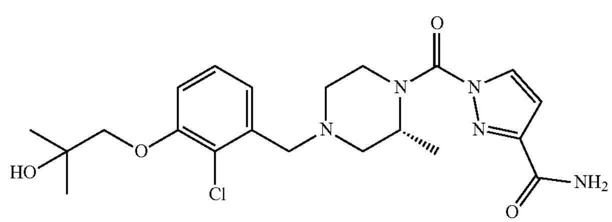 [SMILES: C[C@@H]1CN(Cc2cccc(OCC(C)(C)O)c2Cl)CCN1C(=O)n1ccc(C(N)=O)n1] | (Chloroform-d) δ 8.10 (d, J = 2.7 Hz, 1H), 7.24-7.20 (m, 1H), 7.15-7.13 (m, 1H), 6.92 (d, J = 2.7 Hz, 1H), 6.89-6.86 (m, 1H), 6.69 (br, 1H), 5.63 (br, 1H), 4.65 (br, 1H), 4.28-4.23 (m, 1H), 3.87 (s, 2H), 3.71-3.60 (m, 2H), 3.54-3.44 (m, 1H), 2.93-2.89 (m, 1H), 2.80-2.76 (m, 1H), 2.48-2.43 (m, 2H), 2.37-2.28 (m, 1H), 1.52 (d, J = 6.6 Hz, 3H), 1.41 (s, 6H) | 450.2 |

| Ex | Name | Structure | NMR (¹H NMR, 300 MHz or 400 MHz, Methanol-d) | MS [M + H]⁺ |
|---|---|---|---|---|
| 217 | 1-(9-(5-chloro-2-(trifluoromethyl)-benzyl)-3,9-diazaspiro[5.5]-undecane-3-carbonyl)-1H-pyrazole-3-carboxylic acid | 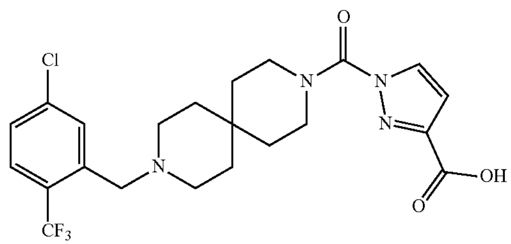 [SMILES: O=C(O)c1ccn(C(=O)N2CCC3(CCN(Cc4cc(Cl)ccc4C(F)(F)F)CC3)CC2)n1] | δ 8.06 (d, J = 2.7 Hz, 1H), 7.91 (s, 1H), 7.67 (d, J = 8.7 Hz, 1H), 7.46 (d, J = 8.7 Hz, 1H), 6.78 (d, J = 2.7 Hz, 1H), 3.87-3.74 (m, 6H), 2.61-2.56 (m, 4H), 1.70-1.64 (m, 8H) | 485.5 |
| 218 | 1-(trans-5-(m-tolyloxy)-octahydrocyclopenta-[c]pyrrole-2-carbonyl)-1H-pyrazole-3-carboxylic acid | 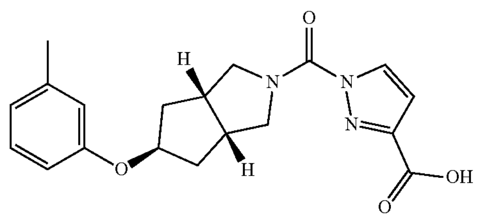 [SMILES: Cc1cccc(O[C@H]2C[C@@H]3CN(C(=O)n4ccc(C(=O)O)n4)C[C@@H]3C2)c1] | δ 8.16 (d, J = 2.7 Hz, 1H), 7.12 (t, J = 7.8 Hz, 1H), 6.79-6.65 (m, 4H), 5.02-4.98 (m, 1H), 4.35-3.51 (m, 4H), 2.98 (br, 2H), 2.28 (s, 3H), 2.21-2.11 (m, 2H), 2.01-1.91 (m, 2H) | 356.1 |
| 219 | 1-(trans-5-(3-cyclopropyl-phenoxy)-octahydrocyclopenta-[c]pyrrole-2-carbonyl)-1H-pyrazole-3-carboxylic acid | 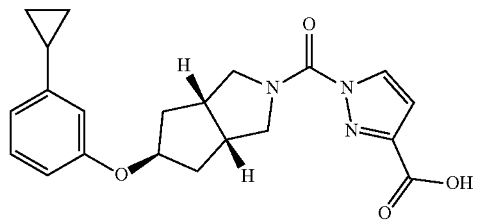 [SMILES: O=C(O)c1ccn(C(=O)N2C[C@H]3C[C@H](Oc4cccc(C5CC5)c4)C[C@H]3C2)n1] | δ 8.14 (br, 1H), 7.09 (t, J = 8.0 Hz, 1H), 6.74 (d, J = 2.8 Hz, 1H), 6.64-6.55 (m, 3H), 4.98-4.92 (m, 1H), 4.28-3.51 (m, 4H), 2.96 (br, 2H), 2.18-2.08 (m, 2H), 2.01-1.89 (m, 2H), 1.88-1.79 (m, 1H), 0.95-0.88 (m, 2H), 0.68-0.61 (m, 2H) | 404.1 [M + Na]⁺ |
| 220 | 1-(trans-5-(3-isopropylphenoxy)-octahydrocyclopenta-[c]pyrrole-2-carbonyl)-1H-pyrazole-3-carboxylic acid | 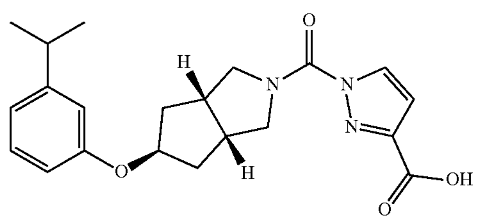 [SMILES: CC(C)c1cccc(O[C@H]2C[C@@H]3CN(C(=O)n4ccc(C(=O)O)n4)C[C@@H]3C2)c1] | δ 8.16 (d, J = 2.7 Hz, 1H), 7.15 (t, J = 7.9 Hz, 1H), 6.81-6.65 (m, 4H), 5.02-4.98 (m, 1H), 4.43-3.48 (m, 4H), 2.98 (br, 2H), 2.88-2.81 (m, 1H), 2.21-2.11 (m, 2H), 2.01-1.91 (m, 2H), 1.23 (d, J = 6.9 Hz, 6H) | 384.2 |

| Ex | Name | Structure | NMR (¹H NMR, 300 MHz or 400 MHz, Methanol-d) | MS [M + H]⁺ |
|---|---|---|---|---|
| 221 | 1-(trans-5-(2-isopropylphenoxy)-octahydrocyclopenta[c]pyrrole-2-carbonyl)-1H-pyrazole-3-carboxylic acid | 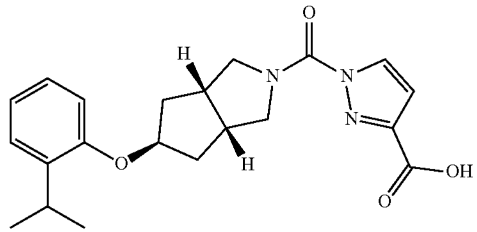 [SMILES: CC(C)c1ccccc1O[C@H]1C[C@@H]2CN(C(=O)n3ccc(C(=O)O)n3)C[C@@H]2C1] | δ 8.14 (d, J = 2.8 Hz, 1H), 7.14 (d, J = 8.0 Hz, 1H), 7.08-7.01 (m, 1H), 6.85 (t, J = 7.6 Hz, 2H), 6.75 (d, J = 2.4 Hz, 1H), 5.05-4.97 (m, 1H), 4.29-3.52 (m, 4H), 3.28-3.22 (m, 1H), 2.97 (br, 2H), 2.24-2.15 (m, 2H), 2.01-1.91 (m, 2H), 1.18 (d, J = 7.2 Hz, 6H) | 406.2 [M + Na]⁺ |
| 222 | 1-(trans-5-(3-chloro-5-fluorophenoxy)-octahydrocyclopenta[c]pyrrole-2-carbonyl)-1H-pyrazole-3-carboxylic acid | 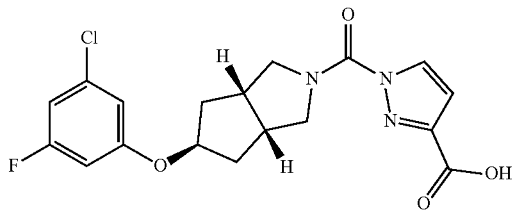 [SMILES: O=C(O)c1ccn(C(=O)N2C[C@H]3C[C@H](Oc4cc(F)cc(Cl)c4)C[C@H]3C2)n1] | δ 8.18 (d, J = 2.7 Hz, 1H), 6.82-6.58 (m, 4H), 5.08-4.98 (m, 1H), 4.51-3.38 (m, 4H), 3.11-2.88 (m, 2H), 2.24-2.09 (m, 2H), 2.07-1.91 (m, 2H) | 416.0 [M + Na]⁺ |
| 223 | 1-(2-(2,5-dimethylbenzyl)-2,8-diazaspiro[4.5]-decane-8-carbonyl)-1H-pyrazole-2-carboxylic acid | 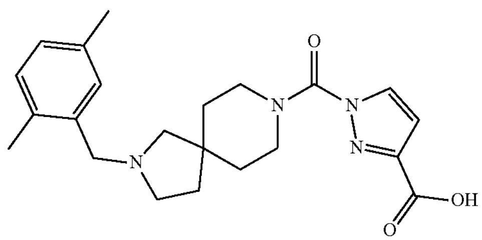 [SMILES: Cc1ccc(C)c(CN2CCC3(CCN(C(=O)n4ccc(C(=O)O)n4)CC3)C2)c1] | δ 8.04 (d, J = 2.7 Hz, 1H), 7.20 (s, 1H), 7.13-7.05 (m, 2H), 6.75 (d, J = 2.7 Hz, 1H), 3.97 (s, 2H), 3.90-3.84 (m, 2H), 3.71-3.68 (m, 2H), 3.07-3.02 (m, 2H), 2.90 (s, 2H), 2.38-2.32 (m, 6H), 1.93-1.88 (m, 2H), 1.84-1.71 (m, 4H) | 397.2 |
| 224 | 1-(4-(3,5-dichlorobenzyl)-oxy)piperidine-1-carbonyl)-1H-pyrazole-3-carboxylic acid | 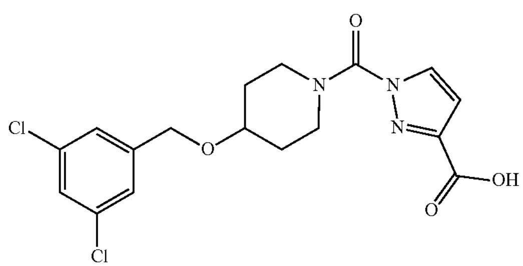 [SMILES: O=C(O)c1ccn(C(=O)N2CCC(OCc3cc(Cl)cc(Cl)c3)CC2)n1] | δ 8.04 (d, J = 2.7 Hz, 1H), 7.33 (s, 3H), 6.75 (d, J = 2.7 Hz, 1H), 4.57 (s, 2H), 4.07-4.01 (m, 2H), 3.79-3.72 (m, 1H), 3.66-3.58 (m, 2H), 2.07-1.98 (m, 2H), 1.82-1.81 (m, 2H) | 396.1 [M − H]⁻ |

| Ex | Name | Structure | NMR (¹H NMR, 300 MHz or 400 MHz, Methanol-d) | MS [M + H]⁺ |
|---|---|---|---|---|
| 225 | 1-(4-((3-(trifluoromethyl)-benzyl)oxy)piperidine-1-carbonyl)-1H-pyrazole-3-carboxylic acid | 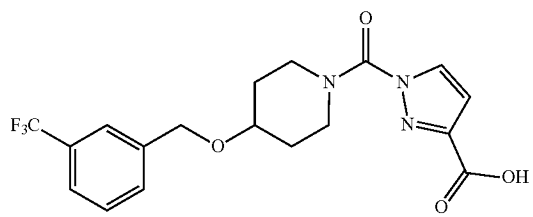 [SMILES: O=C(O)c1ccn(C(=O)N2CCC(OCc3cccc(C(F)(F)F)c3)CC2)n1] | δ 8.05 (d, J = 2.7 Hz, 1H), 7.67-7.63 (m, 2H), 7.56-7.50 (m, 2H), 6.75 (d, J = 2.7 Hz, 1H), 4.67 (s, 2H), 4.06-4.04 (m, 2H), 3.82-3.73 (m, 1H), 3.64-3.56 (m, 2H), 2.09-2.01 (m, 2H), 1.84-1.73 (m, 2H) | 396.1 [M − H]⁻ |
| 226 | 1-(4-(3-(pyrrolidin-1-yl)benzyl)oxy)-piperidine-1-carbonyl)-1H-pyrazole-3-carboxylic acid | 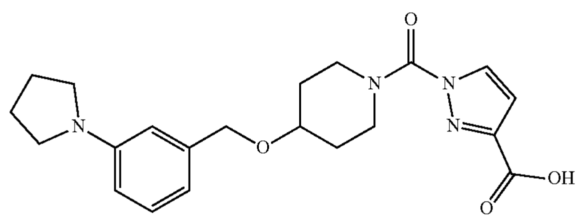 [SMILES: O=C(O)c1ccn(C(=O)N2CCC(OCc3cccc(N4CCCC4)c3)CC2)n1] | δ 8.03 (d, J = 2.8 Hz, 1H), 7.13 (t, J = 7.8 Hz, 1H), 6.73 (d, J = 2.8 Hz, 1H), 6.62-6.58 (m, 2H), 6.50-6.48 (m, 1H), 4.53 (s, 2H), 4.05 (br, 2H), 3.76-3.71 (m, 1H), 3.59 (br, 2H), 3.31-3.23 (m, 4H), 2.04-1.96 (m, 6H), 1.80-1.70 (m, 2H) | 399.2 |
| 227 | 1-(2-(3-chlorobenzyl)-2,8-diazaspiro[4.5]-decane-8-carbonyl)-1H-pyrazole-3-carboxylic acid | 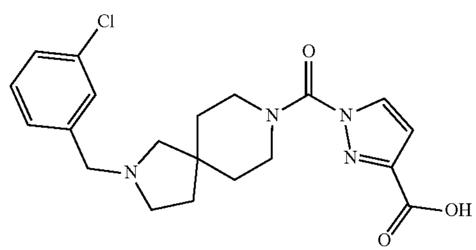 [SMILES: O=C(O)c1ccn(C(=O)N2CCC3(CCN(Cc4cccc(Cl)c4)C3)CC2)n1] | δ 8.04 (d, J = 2.4 Hz, 1H), 7.58 (s, 1H), 7.47-7.39 (m, 3H), 6.74 (d, J = 2.4 Hz, 1H), 4.27 (s, 2H), 3.80 (br, 2H), 3.66 (br, 2H), 3.34-3.30 (m, 2H), 3.12 (br, 2H), 2.01 (t, J = 6.8 Hz, 2H), 1.84-1.73 (m, 4H) | 403.2 |
| 228 | (R)-1-(4-(([1,1'-biphenyl]-4-ylmethyl)-2-methyl)piperazine-1-carbonyl)-1H-pyrazole-3-carboxylic acid | 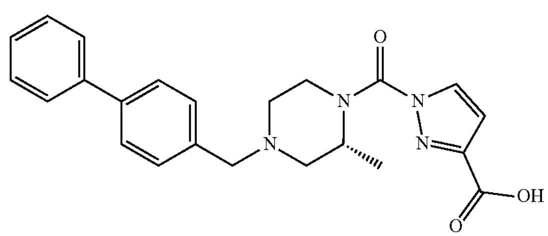 | δ 8.11 (d, J = 2.7 Hz, 1H), 7.62-4H), 7.47-7.40 (m, 4H), 7.35-7.29 (m, 1H), 6.82 (d, J = 2.7 Hz, 1H), 4.67-4.63 (m, 1H), 4.32-4.28 (m, 1H), 3.74-3.70 (m, 1H), 3.64-3.55 (m, 1H), 3.54-3.46 (m, 1H), 3.07-2.96 (m, 1H), 2.88-2.84 (m, 1H), 2.48-2.33 (m, 2H), 1.46 (d, J = 6.9 Hz, 3H) | 405.2 |

| Ex | Name | Structure | NMR (¹H NMR, 300 MHz or 400 MHz, Methanol-d) | MS [M + H]⁺ |
|---|---|---|---|---|
| 229 | 1-(4-(3-(pyridazin-3-yloxy)benzyl)piperazine-1-carbonyl)-1H-pyrazole-3-carboxylic acid | 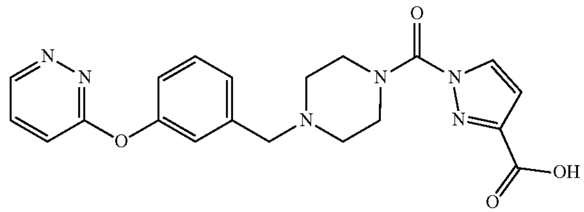 | δ 8.93-8.91 (m, 1H), 8.10 (d, J = 2.7 Hz, 1H), 7.76-7.72 (m, 1H), 7.47-7.39 (m, 2H), 7.31-7.26 (m, 2H), 7.16-7.12 (m, 1H), 6.78 (d, J = 2.7 Hz, 1H), 3.88 (br, 4H), 3.72 (s, 2H), 2.70 (t, J = 4.5 Hz, 4H) | 409.2 |
| 230 | 1-(trans-5-(3,5-dichlorophenoxy)-octahydrocyclopenta[c]pyrrole-2-carbonyl)-1H-pyrazole-3-carboxylic acid | 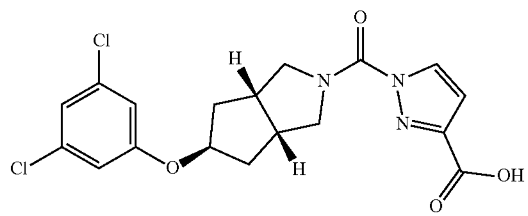 [SMILES: O=C(O)c1ccn(C(=O)N2C[C@H]3C[C@H](Oc4cc(Cl)cc(Cl)c4)C[C@H]3C2)n1] | δ 8.16 (d, J = 2.7 Hz, 1H), 6.97 (t, J = 1.8 Hz, 1H), 6.91 (d, J = 1.8 Hz, 2H), 6.76 (d, J = 2.7 Hz, 1H), 5.08-5.01 (m, 1H), 4.62-3.42 (m, 4H), 3.18-2.88 (m, 2H), 2.24-2.11 (m, 2H), 2.10-1.89 (m, 2H) | 432.0 [M + Na]⁺ |
| 231 | 1-(trans-5-(3-(trifluoromethyl)phenoxy)-octahydrocyclopenta[c]pyrrole-2-carbonyl)-1H-pyrazole-3-carboxylic acid | 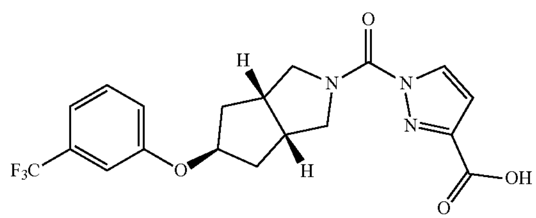 [SMILES: O=C(O)c1ccn(C(=O)N2C[C@H]3C[C@H](Oc4cccc(C(F)(F)F)c4)C[C@H]3C2)n1] | δ 8.19 (d, J = 2.7 Hz, 1H), 7.53-7.42 (m, 1H), 7.28-7.11 (m, 3H), 6.77 (d, J = 2.7 Hz, 1H), 5.13-5.04 (m, 1H), 4.38-3.51 (m, 4H), 3.08-2.96 (m, 2H), 2.29-2.11 (m, 2H), 2.11-1.94 (m, 2H) | 431.8 [M + Na]⁺ |
| 232 | 1-(trans-5-(3-cyclopentylphenoxy)-octahydrocyclopenta[c]pyrrole-2-carbonyl)-1H-pyrazole-3-carboxylic acid | 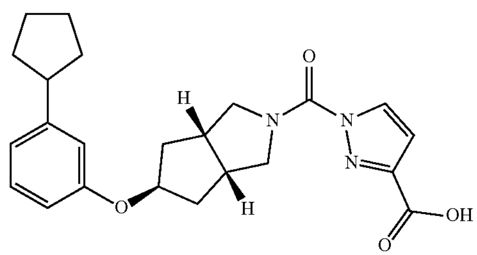 [SMILES: O=C(O)c1ccn(C(=O)N2C[C@H]3C[C@H](Oc4cccc(C5CCCC5)c4)C[C@H]3C2)n1] | δ 8.17 (d, J = 2.7 Hz, 1H), 7.21-7.03 (m, 1H), 6.87-6.63 (m, 4H), 5.10-4.91 (m, 1H), 4.43-3.40 (m, 4H), 3.06-2.83 (m, 3H), 2.24-1.38 (m, 12H) | 432.1 [M + Na]⁺ |

| Ex | Name | Structure | NMR (¹H NMR, 300 MHz or 400 MHz, Methanol-d) | MS [M + H]⁺ |
|---|---|---|---|---|
| 233 | 1-(trans-5-((4-(trifluoromethyl)-pyridin-3-yl)oxy)-octahydrocyclopenta[c]pyrrole-2-carbonyl)-1H-pyrazole-3-carboxylic acid | 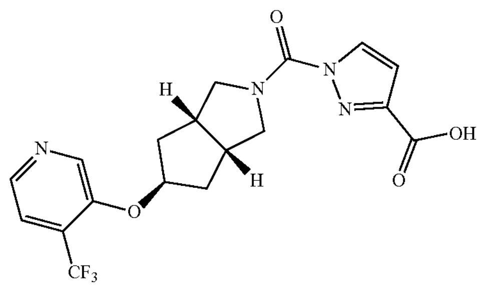 [SMILES: O=C(O)c1ccn(C(=O)N2C[C@H]3C[C@H](Oc4cnccc4C(F)(F)F)C[C@H]3C2)n1] | δ 8.57 (s, 1H), 8.33 (d, J = 4.9 Hz, 1H), 8.17 (d, J = 2.7 Hz, 1H), 7.60 (d, J = 4.9 Hz, 1H), 6.76 (d, J = 2.7 Hz, 1H), 5.38-5.31 (m, 1H), 4.35-3.48 (m, 4H), 3.01 (br, 2H), 2.28-2.18 (m, 2H), 2.11-2.01 (m, 2H) | 411.1 |
| 234 | 1-(trans-5-(3-(pyrrolidin-1-yl)phenoxy)-octahydrocyclopenta[c]pyrrole-2-carbonyl)-1H-pyrazole-3-carboxylic acid | 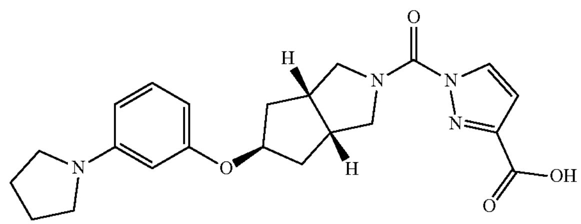 [SMILES: O=C(O)c1ccn(C(=O)N2C[C@H]3C[C@H](Oc4cccc(N5CCCC5)c4)C[C@H]3C2)n1] | δ 8.17 (d, J = 2.7 Hz, 1H), 7.11-6.95 (m, 1H), 6.78 (d, J = 2.7 Hz, 1H), 6.23-6.10 (m, 2H), 6.06 (t, J = 4.4 Hz, 1H), 5.00-4.95 (m, 1H), 4.30-3.47 (m, 4H), 3.28-3.16 (m, 4H), 3.03-2.82 (m, 2H), 2.27-2.08 (m, 2H), 2.07-1.87 (m, 6H) | 411.1 |
| 235 | 1-(4-((2-methyl-3-(trifluoromethyl)-benzyl)oxy)-piperidine-1-carbonyl)-1H-pyrazole-3-carboxylic acid | 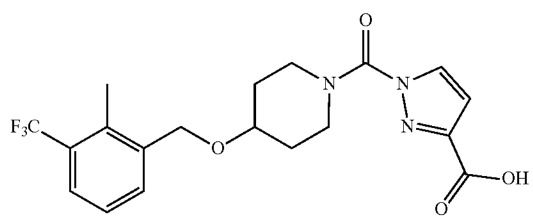 [SMILES: Cc1c(COC2CCN(C(=O)n3ccc(C(=O)O)n3)CC2)cccc1C(F)(F)F] | δ 8.06 (d, J = 2.7 Hz, 1H), 7.64-7.58 (m, 2H), 7.32 (t, J = 7.5 Hz, 1H), 6.77 (d, J = 2.7 Hz, 1H), 4.67 (s, 2H), 4.03 (br, 2H), 3.84-3.77 (m, 1H), 3.67-3.54 (m, 2H), 2.45 (s, 3H), 2.09-2.01 (m, 2H), 1.84-1.73 (m, 2H) | 410.1 [M − H]⁻ |
| 236 | 1-(4-((4-methyl-3-(trifluoromethyl)-benzyl)oxy)-piperidine-1-carbonyl)-1H-pyrazole-3-carboxylic acid | 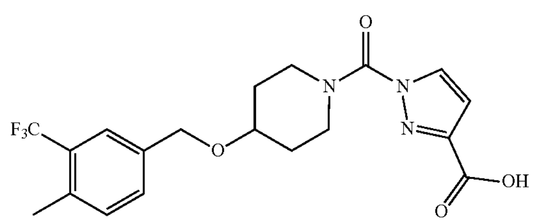 [SMILES: Cc1ccc(COC2CCN(C(=O)n3ccc(C(=O)O)n3)CC2)cc1C(F)(F)F] | δ 8.05 (d, J = 2.7 Hz, 1H), 7.62 (s, 1H), 7.50 (d, J = 7.8 Hz, 1H), 6.50 (d, J = 7.8 Hz, 1H), 6.75 (d, J = 2.7 Hz, 1H), 4.61 (s, 2H), 4.04 (br, 2H), 3.79-3.72 (m, 1H), 3.62 (br, 2H), 2.46 (s, 3H), 2.07-1.99 (m, 2H), 1.82-1.71 (m, 2H) | 412.1 |

| Ex | Name | Structure | NMR (¹H NMR, 300 MHz or 400 MHz, Methanol-d) | MS [M + H]⁺ |
|---|---|---|---|---|
| 237 | 1-(4-(3-(4-hydroxytetrahydro-2H-pyran-4-yl)benzyl)-piperazine-1-carbonyl)-1H-pyrazole-3-carboxamide | 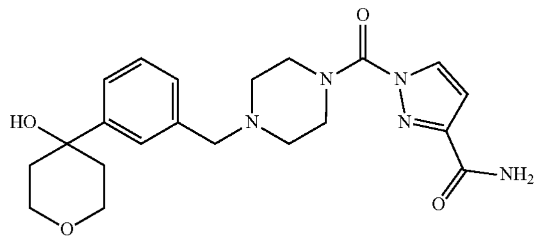 [SMILES: NC(=O)c1ccn(C(=O)N2CCN(Cc3cccc(C4(O)CCOCC4)c3)CC2)n1] | (Chloroform-d) δ 8.10 (d, J = 2.4 Hz, 1H), 7.53-7.50 (m, 1H), 7.44-7.39 (m, 1H), 7.37-7.32 (m, 1H), 7.28-7.27 (m, 1H), 6.91 (d, J = 2.4 Hz, 1H), 6.69 (br, 1H), 5.60 (br, 1H), 4.03-3.85 (m, 8H), 3.60 (s, 2H), 2.58 (br, 4H), 2.25-2.18 (m, 2H), 1.73-1.70 (m, 3H) | 414.2 |
| 238 | 1-(2-(5-chloro-2-methylbenzyl)-2,8-diazaspiro[4.5]-decane-8-carbonyl)-1H-pyrazole-3-carboxylic acid | 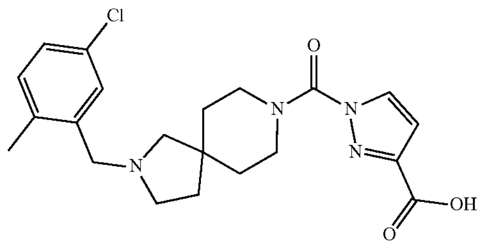 [SMILES: Cc1ccc(Cl)cc1CN1CCC2(CCN(C(=O)n3ccc(C(=O)O)n3)CC2)C1] | δ 8.03 (d, J = 2.7 Hz, 1H), 7.39 (s, 1H), 7.22-7.16 (m, 2H), 6.75 (d, J = 2.4 Hz, 1H), 3.82 (s, 4H), 3.71-3.69 (m, 2H), 2.87 (t, J = 6.6 Hz, 2H), 2.75 (s 2H), 2.37 (s, 3H), 1.85 (t, J = 6.6 Hz, 2H), 1.77-1.70 (m, 4H) | 417.2 |
| 239 | 1-(trans-5-([1,1'-biphenyl]-2-yloxy)-octahydrocyclopenta[c]pyrrole-2-carbonyl)-1H-pyrazole-3-carboxylic acid | 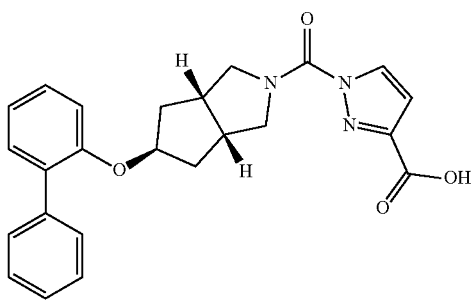 [SMILES: O=C(O)c1ccn(C(=O)N2C[C@H]3C[C@H](Oc4ccccc4-c4ccccc4)C[C@H]3C2)n1] | δ 8.18 (s, 1H), 7.55-7.45 (m, 2H), 7.45-7.33 (m, 2H), 7.33-7.21 (m, 3H), 7.11-6.97 (m, 2H), 6.79 (d, J = 2.7 Hz, 1H), 5.04-4.93 (m, 1H), 4.23-3.50 (m, 4H), 2.77 (br, 2H), 2.24-2.03 (m, 2H), 1.95-1.73 (m, 2H) | 439.8 [M + Na]⁺ |
| 240 | 1-(trans-5-([1,1'-biphenyl]-4-yloxy)-octahydrocyclopenta[c]pyrrole-2-carbonyl)-1H-pyrazole-3-carboxylic acid | 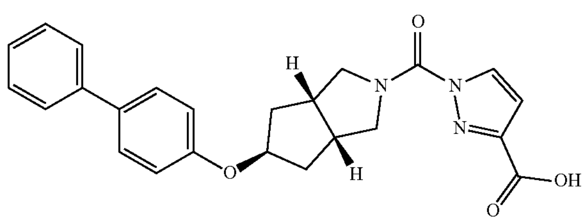 [SMILES: O=C(O)c1ccn(C(=O)N2C[C@H]3C[C@H](Oc4ccc(-c5ccccc5)cc4)C[C@H]3C2)n1] | δ 8.18 (s, 1H), 7.64-7.47 (m, 4H), 7.47-7.35 (m, 2H), 7.35-7.20 (m, 1H), 7.03-6.91 (m, 2H), 6.78 (d, J = 2.7 Hz, 1H), 5.13-5.01 (m, 1H), 4.39-3.46 (m, 4H), 3.00 (br, 2H), 2.34-2.11 (m, 2H), 2.11-1.89 (m, 2H) | 439.8 [M + Na]⁺ |

-continued

| Ex | Name | Structure | NMR (¹H NMR, 300 MHz or 400 MHz, Methanol-d) | MS [M + H]⁺ |
|---|---|---|---|---|
| 241 | 1-(trans-5-(3-(pyridin-3-yl)phenoxy)-octahydrocyclopenta-[c]pyrrole-2-carbonyl)-1H-pyrazole-3-carboxylic acid | 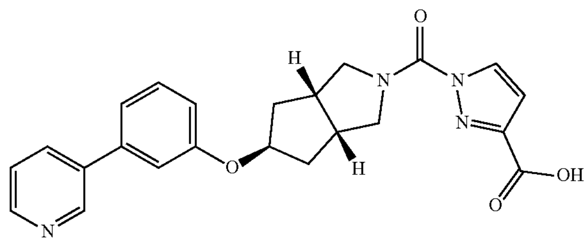 [SMILES: O=C(O)c1ccn(C(=O)N2C[C@H]3C[C@H](Oc4cccc(-c5cccnc5)c4)C[C@H]3C2)n1] | (DMSO-d₆) δ 8.89 (d, J = 2.7 Hz, 1H), 8.62-8.50 (m, 1H), 8.25 (d, J = 2.7 Hz, 1H), 8.15-8.01 (m, 1H), 7.57-7.35 (m, 2H), 7.32-7.26 (m, 2H), 7.06-6.90 (m, 1H), 6.74 (d, J = 2.6 Hz, 1H), 5.20-5.03 (m, 1H), 4.29-3.29 (m, 4H), 3.00-2.80 (m, 2H), 2.14-1.90 (m, 4H) | 419.2 |
| 242 | 1-(trans-5-(3-(pyridin-2-yl)phenoxy)-octahydrocyclopenta-[c]pyrrole-2-carbonyl)-1H-pyrazole-3-carboxylic acid | 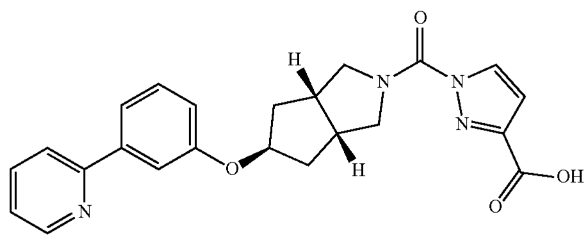 | δ 8.61-8.55 (m, 1H), 8.15 (d, J = 2.7 Hz, 1H), 7.91-7.78 (m, 2H), 7.47-7.42 (m, 2H), 7.38-7.31 (m, 2H), 6.99-6.95 (m, 1H), 6.73 (d, J = 2.7 Hz, 1H), 5.13-5.08 (m, 1H), 4.38-3.51 (m, 4H), 2.98 (br, 2H), 2.25-2.15 (m, 2H), 2.05-1.95 (m, 2H) | 418.8 |
| 243 | 1-(trans-5-(3-(pyridin-4-yl)phenoxy)-octahydrocyclopenta-[c]pyrrole-2-carbonyl)-1H-pyrazole-3-carboxylic acid | 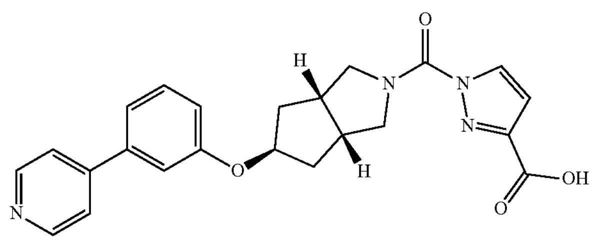 | δ 8.52 (d, J = 4.0 Hz, 2H), 8.16 (d, J = 2.4 Hz, 1H), 7.64 (d, J = 6.2 Hz, 2H), 7.35 (t, J = 7.9 Hz, 1H), 7.24 (d, J = 8.0 Hz, 1H), 7.13 (t, J = 2.0 Hz, 1H), 6.97-6.93 (m, 1H), 6.75 (d, J = 2.6 Hz, 1H), 5.05-4.98 (m, 1H), 4.31-3.79 (m, 4H), 2.92 (br, 2H), 2.41-2.28 (m, 2H), 1.92 (d, J = 13.6 Hz, 2H) | 419.1 |
| 244 | 1-(trans-5-(2-(pyridin-3-yl)phenoxy)-octahydrocyclopenta-[c]pyrrole-2-carbonyl)-1H-pyrazole-3-carboxylic acid | 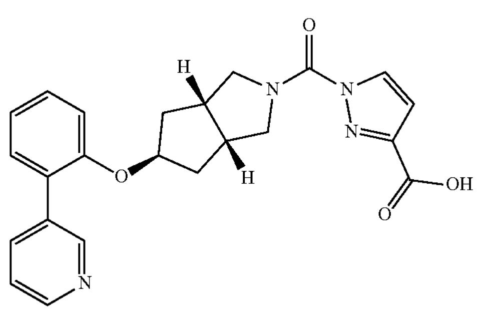 [SMILES: O=C(O)c1ccn(C(=O)N2C[C@H]3C[C@H](Oc4ccccc4-c4cccnc4)C[C@H]3C2)n1] | δ 8.64 (d, J = 4.0 Hz, 1H), 8.47-8.41 (m, 1H), 8.16 (d, J = 2.8 Hz, 1H), 8.00-7.93 (m, 1H), 7.49-7.42 (m, 1H), 7.38-7.31 (m, 2H), 7.11-7.01 (m, 2H), 6.76 (d, J = 2.8 Hz, 1H), 5.07-5.01 (m, 1H), 4.19-3.52 (m, 4H), 2.78 (br, 2H), 2.17-2.02 (m, 2H), 1.96-1.82 (m, 2H) | 419.0 |

| Ex | Name | Structure | NMR (¹H NMR, 300 MHz or 400 MHz, Methanol-d) | MS [M + H]⁺ |
|---|---|---|---|---|
| 245 | (R)-1-(2-methyl-4-((3-methyl-[1,1'-biphenyl]-4-yl)methyl)piperazine-1-carbonyl)-1H-pyrazole-3-carboxylic acid | 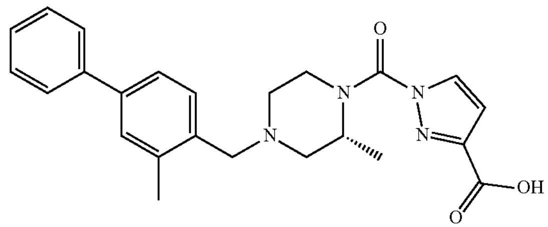 | δ 8.13 (d, J = 2.7 Hz, 1H), 7.62-7.59 (m, 2H), 7.45-7.38 (m, 4H), 7.34-7.29 (m, 2H), 6.83 (d, J = 2.7 Hz, 1H), 4.66 (br, 1H), 4.27-4.23 (m, 1H), 3.57 (s, 2H), 3.51-3.41 (m, 1H), 2.93-2.89 (m, 1H), 2.83-2.79 (m, 1H), 2.50 (s, 3H), 2.45-2.40 (m, 1H), 2.31-2.23 (m, 1H), 1.43 (d, J = 6.9 Hz, 3H) | 419.3 |
| 246 | (S)-1-(2-methyl-4-((3-methyl-[1,1'-biphenyl]-4-yl)methyl)piperazine-1-carbonyl)-1H-pyrazole-3-carboxylic acid | 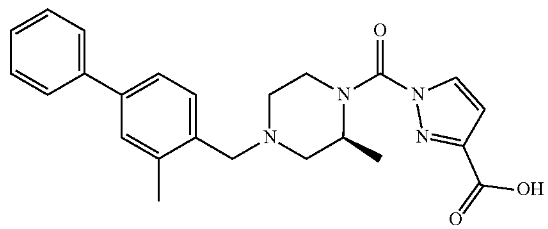 [SMILES: Cc1cc(-c2ccccc2)ccc1CN1CCN(C(=O)n2ccc(C(=O)O)n2)[C@@H](C)C1] | δ 8.11 (d, J = 2.7 Hz, 1H), 7.61-7.58 (m, 2H), 7.43-7.37 (m, 4H), 7.33-7.28 (m, 2H), 6.81 (d, J = 2.7 Hz, 1H), 4.64 (br, 1H), 4.26-4.21 (m, 1H), 3.56 (s, 2H), 3.50-3.40 (m, 1H), 2.91-2.87 (m, 1H), 2.81-2.77 (m, 1H), 2.48 (s, 3H), 2.43-2.31 (m, 1H), 2.30-2.22 (m, 1H), 1.43 (d, J = 6.9 Hz, 3H) | 419.3 |
| 247 | (R)-1-(2-methyl-4-((2-methyl-[1,1'-biphenyl]-4-yl)methyl)piperazine-1-carbonyl)-1H-pyrazole-3-carboxylic acid | 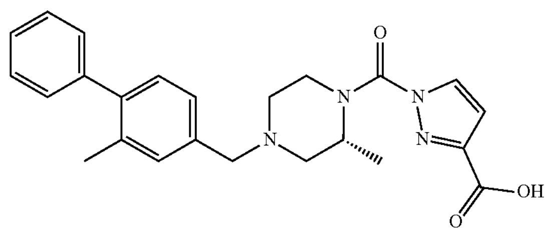 [SMILES: Cc1cc(CN2CCN(C(=O)n3ccc(C(=O)O)n3)[C@H](C)C2)ccc1-c1ccccc1] | δ 8.10 (d, J = 2.7 Hz, 1H), 7.45-7.42 (m, 2H), 7.40-7.25 (m, 5H), 7.18-7.16 (m, 1H), 6.80 (d, J = 2.7 Hz, 1H), 4.72 (br, 1H), 4.36-4.32 (m, 1H), 3.68-3.47 (m, 3H), 2.99-2.95 (m, 1H), 2.88-2.84 (m, 1H), 2.45-2.40 (m, 1H), 2.37-2.33 (m, 1H), 2.30-2.26 (m, 3H), 1.43 (d, J = 6.8 Hz, 3H) | 419.5 |
| 248 | 1-(trans-5-(3-(pyridazin-4-yl)phenoxy)-octahydrocyclopenta[c]pyrrole-2-carbonyl)-1H-pyrazole-3-carboxylic acid | 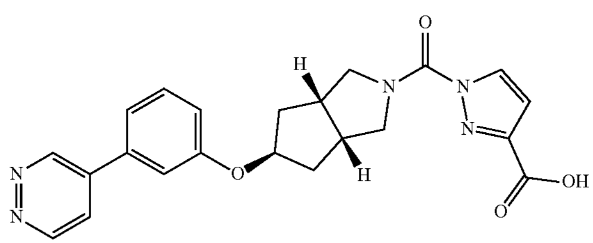 | δ 9.55-9.48 (m, 1H), 9.24-9.17 (m, 1H), 8.14 (d, J = 2.7 Hz, 1H), 8.01-7.96 (m, 1H), 7.52-7.43 (m, 1H), 7.41-7.31 (m, 2H), 7.11-7.05 (m, 1H), 6.74 (d, J = 2.7 Hz, 1H), 5.17-5.08 (m, 1H), 4.41-3.53 (m, 4H), 3.01 (br, 2H), 2.28-2.12 (m, 2H), 2.09-1.96 (m, 2H) | 419.9 |

| Ex | Name | Structure | NMR (¹H NMR, 300 MHz or 400 MHz, Methanol-d) | MS [M + H]⁺ |
|---|---|---|---|---|
| 249 | 1-(trans-5-(3-(pyrimidin-2-yl)phenoxy)octahydrocyclopenta[c]pyrrole-2-carbonyl)-1H-pyrazole-3-carboxylic acid | 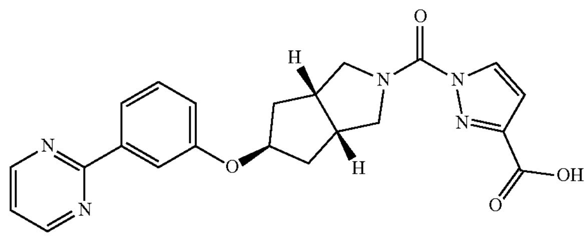 [SMILES: O=C(O)c1ccn(C(=O)N2C[C@H]3C[C@H](Oc4cccc(-c5ncccn5)c4)C[C@H]3C2)n1] | δ 8.80 (d, J = 4.0 Hz, 2H), 8.16 (d, J = 2.8 Hz, 1H), 7.96-7.91 (m, 2H), 7.41-7.31 (m, 2H), 7.07-7.01 (m, 1H), 6.74 (d, J = 2.8 Hz, 1H), 5.15-5.08 (m, 1H), 4.35-3.53 (m, 4H), 3.01 (br, 2H), 2.25-2.15 (m, 2H), 2.06-1.97 (m, 2H) | 419.8 |
| 250 | (R)-1-(2-methyl-4-(2-methyl-4-(pyridin-2-yl)benzyl)-piperazine-1-carbonyl)-1H-pyrazole-3-carboxylic acid | 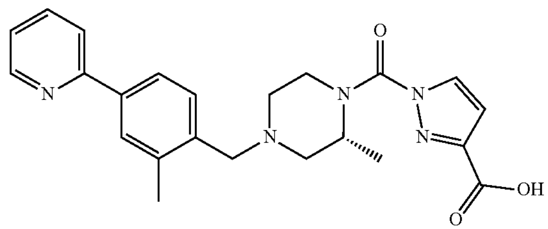 [SMILES: Cc1cc(-c2ccccn2)ccc1CN1CCN(C(=O)n2ccc(C(=O)O)n2)[C@H](C)C1] | δ 8.59-8.57 (m, 1H), 8.07 (d, J = 2.7 Hz, 1H), 7.88-7.82 (m, 2H), 7.76 (s, 1H), 7.71-7.68 (m, 1H), 7.40-7.32 (m, 2H), 6.76 (d, J = 2.7 Hz, 1H), 4.68 (br, 1H), 4.30-4.25 (m, 1H), 3.55 (s, 2H), 3.45-3.44 (m, 1H), 2.89-2.85 (m, 1H), 2.78-2.74 (m, 1H), 2.51 (s, 3H), 2.41-2.36 (m, 1H), 2.28-2.24 (m, 1H), 1.40 (d, J = 6.6 Hz, 3H) | 420.5 |
| 251 | 1-(4-(3-(p-tolyloxy)benzyl)-piperazine-1-carbonyl)-1H-pyrazole-3-carboxylic acid | 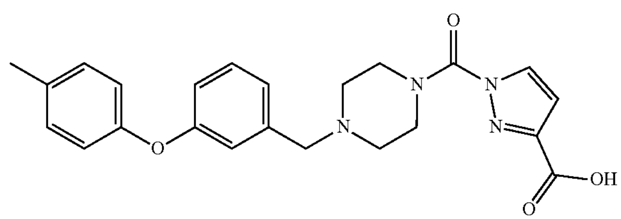 [SMILES: Cc1ccc(Oc2cccc(CN3CCN(C(=O)n4ccc(C(=O)O)n4)CC3)c2)cc1] | δ 8.12 (d, J = 2.7 Hz, 1H), 7.31 (t, J = 7.8 Hz, 1H), 7.17-7.02 (m, 3H), 7.02-7.01 (m, 1H), 6.91-6.86 (m, 3H), 6.80 (d, J = 2.7 Hz, 1H), 3.88 (br, 4H), 3.72 (s, 2H), 2.75 (t, J = 5.1 Hz, 4H), 2.31 (s, 3H) | 421.2 |
| 252 | 1-(trans-5-((3-chloro-5-fluorobenzyl)oxy)-octahydrocyclopenta[c]pyrrole-2-carbonyl)-4-methyl-1H-pyrazole-3-carboxylic acid | 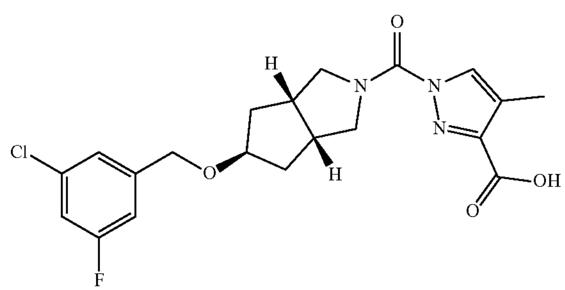 [SMILES: Cc1cn(C(=O)N2C[C@H]3C[C@H](OCc4cc(F)cc(Cl)c4)C[C@H]3C2)nc1C(=O)O] | δ 7.95-7.86 (m, 1H), 7.23-7.17 (br, 1H), 7.13-6.98 (m, 2H), 4.48 (s, 2H), 4.27-4.16 (m, 1H), 4.16-3.41 (m, 4H), 2.99-2.80 (br, 2H), 2.26 (d, J = 0.9 Hz, 3H), 2.19-2.01 (m, 2H), 1.87-1.71 (m, 2H) | 443.8 [M + Na]⁺ |

| Ex | Name | Structure | NMR (¹H NMR, 300 MHz or 400 MHz, Methanol-d) | MS [M + H]⁺ |
|---|---|---|---|---|
| 253 | (R)-1-(4-((3-fluoro-[1,1'-biphenyl]-4-yl)methyl)-2-methylpiperazine-1-carbonyl)-1H-pyrazole-3-carboxylic acid | 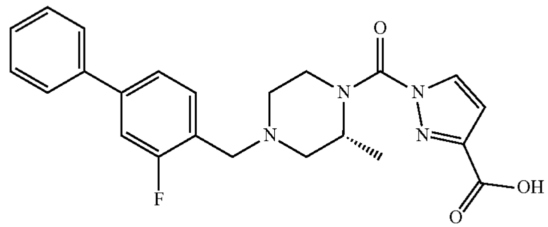 | δ 8.11 (d, J = 2.7 Hz, 1H), 7.64-7.61 (m, 2H), 7.56-7.51 (m, 1H), 7.47-7.42 (m, 3H), 7.38-7.33 (m, 2H), 6.82 (d, J = 2.4 Hz, 1H), 4.65 (br, 1H), 4.28-4.23 (m, 1H), 3.67 (s, 2H), 3.54-3.45 (m, 1H), 2.96-2.81 (m, 2H), 2.46-2.27 (m, 2H), 1.45 (d, J = 6.9 HZ, 3H) | 423.2 |
| 254 | 1-(trans-5-(3-methyl-4-(trifluoromethyl)phenoxy)octahydrocyclopenta[c]pyrrole-2-carbonyl)-1H-pyrazole-3-carboxylic acid | 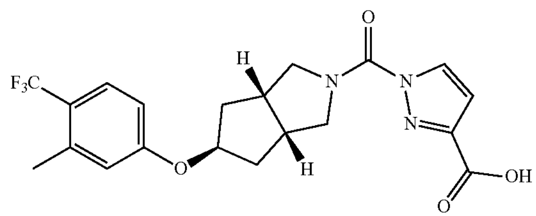 [SMILES: Cc1cc(O[C@H]2C[C@@H]3CN(C(=O)n4ccc(C(=O)O)n4)C[C@@H]3C2)ccc1C(F)(F)F] | δ 8.16 (d, J = 2.7 Hz, 1H), 7.51 (d, J = 8.7 Hz, 1H), 6.92-6.84 (m, 1H), 6.84-6.78 (m, 1H), 6.74 (d, J = 2.7 Hz, 1H), 5.11-5.01 (m, 1H), 4.39-3.50 (m, 4H), 3.06-2.85 (m, 2H), 2.48-2.33 (m, 3H), 2.27-2.09 (m, 2H), 2.09-1.92 (m, 2H) | 445.8 [M + Na]⁺ |
| 255 | 1-(trans-5-((3-(trifluoromethyl)benzyl)oxy)octahydrocyclopenta[c]pyrrole-2-carbonyl)-1H-pyrazole-3-carboxylic acid | 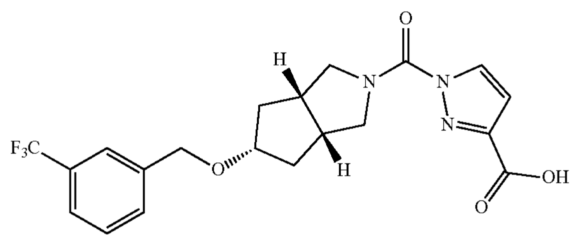 [SMILES: O=C(O)c1ccn(C(=O)N2C[C@H]3C[C@@H](OCc4cccc(C(F)(F)F)c4)C[C@H]3C2)n1] | δ 8.18-7.96 (m, 1H),7.68-7.41 (m, 4H), 6.78-6.62 (m, 1H), 4.60-4.48 (m, 2H), 4.40-3.66 (m, 5H), 2.98-2.67 (m, 2H), 2.29-2.05 (m, 2H), 1.91-1.68 (m, 2H) | 423.8 |
| 256 | 1-(trans-5-(2-methyl-3-(trifluoromethyl)phenoxy)octahydrocyclopenta[c]pyrrole-2-carbonyl)-1H-pyrazole-3-carboxylic acid | 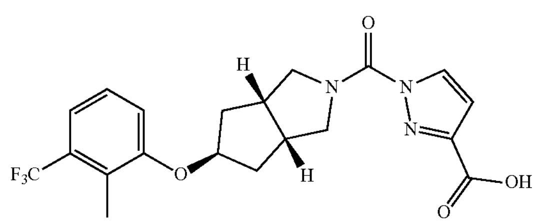 [SMILES: Cc1c(O[C@H]2C[C@@H]3CN(C(=O)n4ccc(C(=O)O)n4)C[C@@H]3C2)cccc1C(F)(F)F] | δ 8.18 (d, J = 2.7 Hz, 1H), 7.27 (t, J = 8.0 Hz, 1H), 7.21-7.14 (m, 2H), 6.76 (d, J = 2.7 Hz, 1H), 5.13-5.08 (m, 1H), 4.38-3.56 (m, 4H), 3.02 (br, 2H), 2.96 (d, J = 1.4 Hz, 3H), 2.28-2.15 (m, 2H), 2.08-1.96 (m, 2H) | 441.2 [M + NH₄]⁺ |

| Ex | Name | Structure | NMR (¹H NMR, 300 MHz or 400 MHz, Methanol-d) | MS [M + H]⁺ |
|---|---|---|---|---|
| 257 | 1-((2R,4R)-2-methyl-4-(methyl(3-(trifluoromethyl)-benzyl)amino)-piperidine-1-carbonyl)-1H-pyrazole-3-carboxamide | 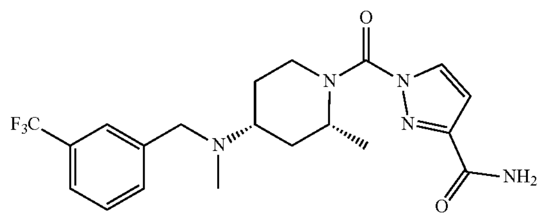 [SMILES: C[C@@H]1C[C@H](N(C)Cc2cccc(C(F)(F)F)c2)CCN1C(=O)n1ccc(C(N)=O)n1] | (Chloroform-d) δ 8.09 (d, J = 2.7 Hz, 1H), 7.60 (s, 1H), 7.53-7.51 (m, 2H), 7.46-7.41 (m, 1H), 6.90 (d, J = 2.7 Hz, 1H), 6.68 (br, 1H), 5.67 (br, 1H), 4.30-4.21 (m, 1H), 4.14-4.07 (m, 1H), 3.64 (br, 2H), 3.52-3.42 (m, 1H), 2.81 (br, 1H), 2.20 (s, 3H), 2.07-2.03 (m, 2H), 1.81-1.67 (m, 2H), 1.49 (d, J = 6.3 Hz, 3H) | 424.2 |
| 258 | 1-(4-methyl-4-methyl(3-(trifluoromethyl)-benzyl)amino)-piperidine-1-carbonyl)-1H-pyrazole-3-carboxamide | 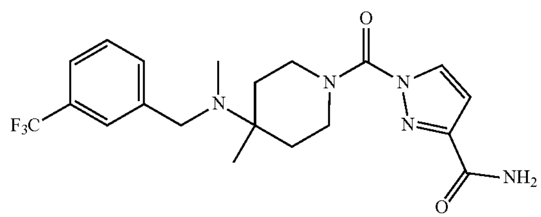 [SMILES: CN(Cc1cccc(C(F)(F)F)c1)C1(C)CCN(C(=O)n2ccc(C(N)=O)n2)CC1] | δ 8.18 (d, J = 2.4 Hz, 1H), 7.69-7.67 (m, 2H), 7.56-7.51 (m, 2H), 6.88 (d, J = 2.4 Hz, 1H), 3.94-3.82 (m, 4H), 3.72 (s, 2H), 2.15-2.08 (m, 5H), 1.75-1.68 (m, 2H), 1.15 (s, 3H) | 446.1 [M + Na]⁺ |
| 259 | 1-((2S,4R)-2-methyl-4-(methyl(3-(trifluoromethyl)-benzyl)amino)-piperidine-1-carbonyl)-1H-pyrazole-3-carboxamide | 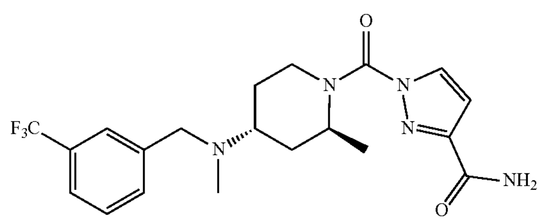 [SMILES: C[C@H]1C[C@H](N(C)Cc2cccc(C(F)(F)F)c2)CCN1C(=O)n1ccc(C(N)=O)n1] | (Chloroform-d) δ 8.07 (d, J = 2.7 Hz, 1H), 7.60-7.42 (m, 4H), 6.90 (d, J = 2.7 Hz, 1H), 6.70 (br, 1H), 5.94 (br, 1H), 4.88-4.86 (m, 1H), 4.43-4.39 (m, 1H), 3.68 (br, 2H), 3.23-3.15 (m, 1H), 3.02 (br, 1H), 2.24 (s, 3H), 2.24-1.63 (m, 4H), 1.37 (d, J = 6.9 Hz, 3H) | 424.2 |
| 260 | 1-((2R,4S)-2-methyl-4-(methyl(3-(trifluoromethyl)-benzyl)amino)-piperidine-1-carbonyl)-1H-pyrazole-3-carboxamide | 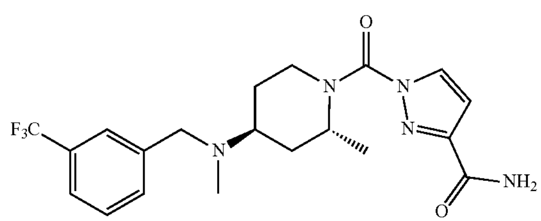 [SMILES: C[C@@H]1C[C@@H](N(C)Cc2cccc(C(F)(F)F)c2)CCN1C(=O)n1ccc(C(N)=O)n1] | (Chloroform-d) δ 8.07 (d, J = 2.7 Hz, 1H), 7.60-7.41 (m, 4H), 6.90 (d, J = 2.7 Hz, 1H), 5.91 (br, 1H), 4.88-4.84 (m, 1H), 4.43-4.38 (m, 1H), 3.66 (br, 2H), 3.23-3.15 (m, 1H), 3.03-3.00 (m, 1H), 2.23 (s, 3H), 1.98-1.83 (m, 3H), 1.76-1.62 (m, 1H), 1.65 (d, J = 5.4 Hz, 3H) | 424.2 |

| Ex | Name | Structure | NMR (¹H NMR, 300 MHz or 400 MHz, Methanol-d) | MS [M + H]⁺ |
|---|---|---|---|---|
| 261 | 1-(trans-5-(3-(thiazol-2-yl)phenoxy)-octahydrocyclopenta[c]pyrrole-2-carbonyl)-1H-pyrazole-3-carboxylic acid | 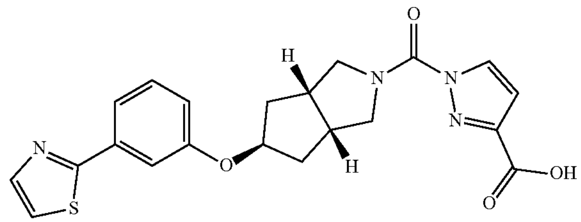 [SMILES: O=C(O)c1ccn(C(=O)N2C[C@H]3C[C@H](Oc4cccc(-c5nccs5)c4)C[C@H]3C2)n1] | δ 8.24 (d, J = 3.0 Hz, 1H), 7.85 (d, J = 3.3 Hz, 1H), 7.56 (d, J = 3.3 Hz, 1H), 7.48-7.41 (m, 2H), 7.37-7.31 (m, 1H), 7.04-6.98 (m, 1H), 6.82 (d, J = 2.7 Hz, 1H), 5.17-5.06 (m, 1H), 4.31-3.58 (m, 4H), 3.11-2.88 (m, 2H), 2.28-2.12 (m, 2H), 2.10-1.97 (m, 2H) | 425.1 |
| 262 | 1-(trans-5-(3-(thiazol-5-yl)phenoxy)-octahydrocyclopenta[c]pyrrole-2-carbonyl)-1H-pyrazole-3-carboxylic acid | 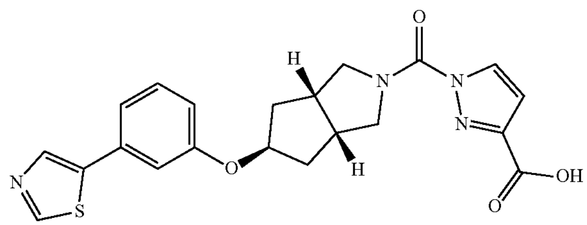 [SMILES: O=C(O)c1ccn(C(=O)N2C[C@H]3C[C@H](Oc4cccc(-c5cncs5)c4)C[C@H]3C2)n1] | δ 8.95 (s, 1H), 8.16 (d, J = 2.7 Hz, 1H), 8.13 (s, 1H), 7.33-7.25 (m, 1H), 7.18-7.12 (m, 1H), 7.11-7.08 (m, 1H), 6.87-6.83 (m, 1H), 6.75 (d, J = 2.7 Hz, 1H), 5.01-4.96 (m, 1H), 4.41-3.65 (m, 4H), 2.91 (br, 2H), 2.42-2.28 (m, 2H), 1.90 (d, J = 13.6 Hz, 2H) | 425.1 |
| 263 | 1-(4-(4-fluoro-3-phenoxybenzyl)-piperazine-1-carbonyl)-1H-pyrazole-3-carboxylic acid | 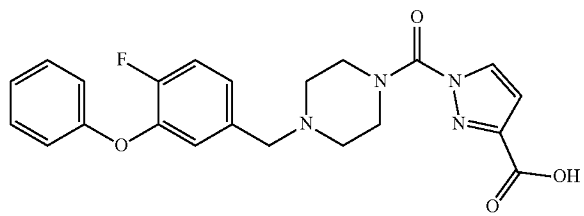 [SMILES: O=C(O)c1ccn(C(=O)N2CCN(Cc3ccc(F)c(Oc4ccccc4)c3)CC2)n1] | δ 8.13 (d, J = 2.5 Hz, 1H), 7.35-7.26 (m, 2H), 7.23-7.15 (m, 3H), 7.11-7.06 (m, 1H), 7.96-7.94 (m, 2H), 6.82 (d, J = 2.5 Hz, 1H), 3.87 (br, 4H), 3.73-3.62 (m, 2H), 2.88-2.61 (m, 4H) | 425.5 |
| 264 | 1-(4-(3-((3-fluoropyridin-2-yl)oxy)benzyl)-piperazine-1-carbonyl)-1H-pyrazole-3-carboxylic acid | 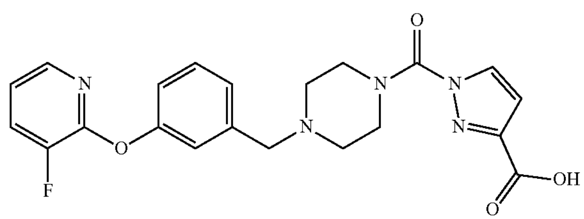 [SMILES: O=C(O)c1ccn(C(=O)N2CCN(Cc3cccc(Oc4ncccc4F)c3)CC2)n1] | δ 8.11 (d, J = 2.7 Hz, 1H), 7.90-7.87 (m, 1H), 7.70-7.64 (m, 1H), 7.40 (t, J = 7.8 Hz, 1H), 7.25 (d, J = 7.8 Hz, 1H), 7.20 (s, 1H), 7.17-7.12 (m, 1H), 7.11-7.06 (m, 1H), 6.79 (d, J = 2.7 Hz, 1H), 3.89 (br, 4H), 3.76 (s, 2H), 2.77-2.74 (m, 4H) | 426.3 |

| Ex | Name | Structure | NMR (¹H NMR, 300 MHz or 400 MHz, Methanol-d) | MS [M + H]⁺ |
|---|---|---|---|---|
| 265 | 1-(4-(3-((5-fluoropyridin-3-yl)oxy)benzyl)piperazine-1-carbonyl)-1H-pyrazole-3-carboxylic acid | 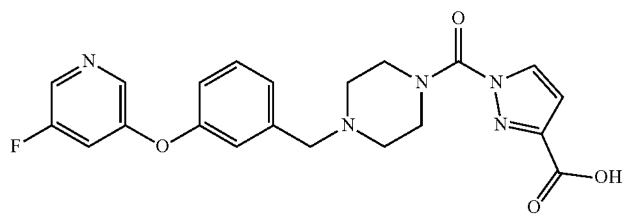 [SMILES: O=C(O)c1ccn(C(=O)N2CCN(Cc3cccc(Oc4cncc(F)c4)c3)CC2)n1] | δ 8.22 (d, J = 2.4 Hz, 1H), 8.17 (d, J = 2.1 Hz, 1H), 8.06 (d, J = 2.7 Hz, 1H), 7.42 (t, J = 7.8 Hz, 1H), 7.28-7.23 (m, 2H), 7.16 (s, 1H), 7.05-7.01 (m, 1H), 6.73 (d, J = 2.7 Hz, 1H), 3.86 (br, 4H), 3.60 (s, 2H), 2.65-2.51 (m, 4H) | 426.3 |
| 266 | 1-(4-(3-((5-fluoropyridin-2-yl)oxy)benzyl)piperazine-1-carbonyl)-1H-pyrazole-3-carboxylic acid | 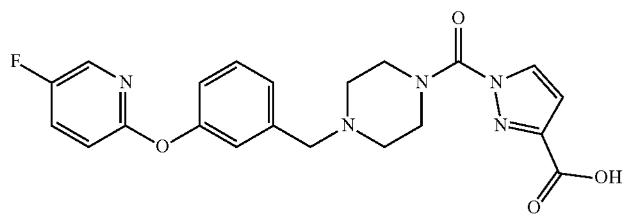 [SMILES: O=C(O)c1ccn(C(=O)N2CCN(Cc3cccc(Oc4ccc(F)cn4)c3)CC2)n1] | δ 8.12 (d, J = 2.4 Hz, 1H), 8.05-8.00 (m, 1H), 7.72-7.62 (m, 1H), 7.43-7.32 (m, 1H), 7.26-7.18 (m, 1H), 7.15-7.14 (m, 1H), 7.07-6.98 (m, 2H), 6.88-6.79 (m, 2H), 3.91 (br, 4H), 3.83-3.79 (m, 2H), 2.81 (br, 4H) | 426.3 |
| 267 | 1-(trans-5-(3-(tetrahydro-2H-pyran-4-yl)phenoxy)octahydrocyclopenta[c]pyrrole-2-carbonyl)-1H-pyrazole-3-carboxylic acid | 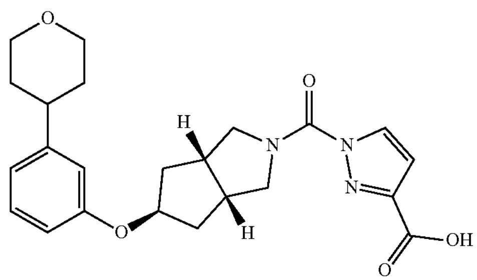 [SMILES: O=C(O)c1ccn(C(=O)N2C[C@H]3C[C@H](Oc4cccc(C5CCOCC5)c4)C[C@H]3C2)n1] | δ 8.14 (d, J = 2.7 Hz, 1H), 7.31-7.10 (m, 1H), 6.85-6.67 (m, 4H), 5.12-4.95 (m, 1H), 4.46-3.42 (m, 8H), 3.03-2.87 (br, 2H), 2.84-2.68 (m, 1H), 2.30-2.08 (m, 2H), 2.07-1.90 (m, 2H), 1.90-1.71 (m, 4H) | 448.1 [M + Na]⁺ |
| 268 | 1-(trans-5-(2-(tetrahydro-2H-pyran-4-yl)phenoxy)octahydrocyclopenta[c]pyrrole-2-carbonyl)-1H-pyrazole-3-carboxylic acid | 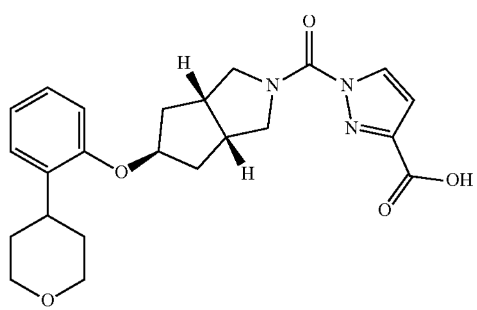 [SMILES: O=C(O)c1ccn(C(=O)N2C[C@H]3C[C@H](Oc4ccccc4C4CCOCC4)C[C@H]3C2)n1] | δ 8.21 (d, J = 2.7 Hz, 1H), 7.21-7.11 (m, 2H), 6.93 (d, J = 7.5 Hz, 2H), 6.81 (d, J = 2.7 Hz, 1H), 5.08-5.01 (m, 1H), 4.29-3.52 (m, 8H), 3.28-3.11 (m, 1H), 3.01 (br, 2H), 2.28-2.12 (m, 2H), 2.07-1.93 (m, 2H), 1.88-1.66 (m, 4H) | 448.2 [M + Na]⁺ |

| Ex | Name | Structure | NMR (¹H NMR, 300 MHz or 400 MHz, Methanol-d) | MS [M + H]⁺ |
|---|---|---|---|---|
| 269 | 1-(4-(3-chloro-5-(pyrimidin-5-yl)benzyl)-piperazine-1-carbonyl)-1H-pyrazole-3-carboxylic acid | 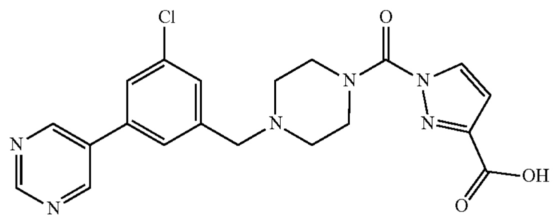 [SMILES: O=C(O)c1ccn(C(=O)N2CCN(Cc3cc(Cl)cc(-c4cncnc4)c3)CC2)n1] | δ 9.16 (s, 1H), 9.08 (s, 2H), 8.12 (d, J = 2.7 Hz, 1H), 7.70 (s, 1H), 7.68 (s, 1H), 7.56 (s, 1H), 6.80 (d, J = 2.7 Hz, 1H), 3.88 (br, 4H), 3.72 (s, 2H), 2.67 (t, J = 4.8 Hz, 4H) | 427.1 |
| 270 | 4-chloro-1-(4-(3-(pyrimidin-5-yl)benzyl)-piperazine-1-carbonyl)-1H-pyrazole-3-carboxylic acid | 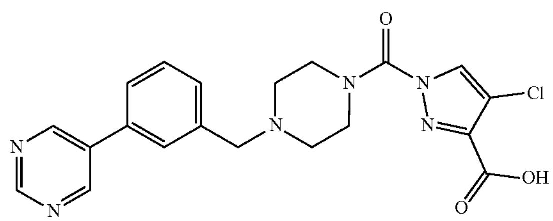 | δ 8.84 (d, J = 4.8 Hz, 2H), 8.41 (s, 1H), 8.33-8.29 (m, 1H), 8.12 (s, 1H), 7.54-7.45 (m, 2H), 7.38-7.34 (m, 1H), 3.86 (br, 4H), 3.67 (s, 2H), 2.63-2.59 (m, 4H) | 427.3 |
| 271 | (S)-1-(4-(3-chloro-5-(trifluoromethyl)-benzyl)-2-methylpiperazine-1-carbonyl)-1H-pyrazole-3-carboxamide | 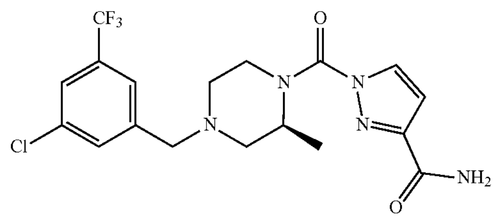 [SMILES: C[C@H]1CN(Cc2cc(Cl)cc(C(F)(F)F)c2)CCN1C(=O)n1ccc(C(N)=O)n1] | (Chloroform-d) δ 8.09 (d, J = 2.7 Hz, 1H), 7.61-7.53 (m, 3H), 6.90 (d, J = 2.7 Hz, 1H), 6.64 (br, 1H), 5.52 (br, 1H), 4.65 (br, 1H), 4.31-4.27 (m, 1H), 3.63-3.47 (m, 3H), 2.88-2.84 (m, 1H), 2.69-2.65 (m, 1H), 2.38-2.24 (m, 2H), 1.51 (d, J = 6.9 Hz, 3H) | 430.1 |
| 272 | (R)-1-(4-(3-chloro-5-(trifluoromethyl)benzyl)-2-methylpiperazine-1-carbonyl)-1H-pyrazole-3-carboxamide | 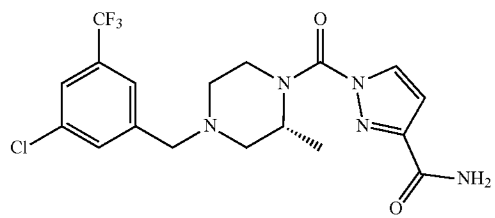 [SMILES: C[C@@H]1CN(Cc2cc(Cl)cc(C(F)(F)F)c2)CCN1C(=O)n1ccc(C(N)=O)n1] | (Chloroform-d) δ 8.09 (d, J = 2.7 Hz, 1H), 7.61-7.53 (m, 3H), 6.90 (d, J = 2.7 Hz, 1H), 6.65 (br, 1H), 5.61 (br, 1H), 4.66-4.64 (m, 1H), 4.31-4.27 (m, 1H), 3.63-3.55 (m, 1H), 3.54-3.46 (m, 2H), 2.88-2.84 (m, 1H), 2.69-2.65 (m, 1H), 2.38-2.24 (m, 2H), 1.51 (d, J = 6.9 Hz, 3H) | 430.1 |

| Ex | Name | Structure | NMR (¹H NMR, 300 MHz or 400 MHz, Methanol-d) | MS [M + H]⁺ |
|---|---|---|---|---|
| 273 | 1-(trans-5-(([1,1'-biphenyl]-3-ylmethyl)amino)-octahydrocyclopenta-[c]pyrrole-2-carbonyl)-1H-pyrazole-3-carboxylic acid | 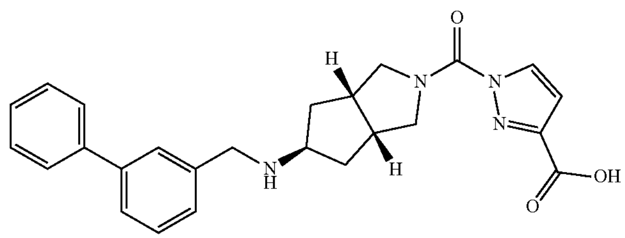 [SMILES: O=C(O)c1ccn(C(=O)N2C[C@H]3C[C@H](NCc4cccc(-c5ccccc5)c4)C[C@H]3C2)n1] | (DMSO-d₆) δ 8.25 (d, J = 2.4 Hz, 1H), 7.76 (s, 1H), 7.76-7.66 (m, 2H), 7.62-7.59 (m, 1H), 7.49-7.40 (m, 5H), 6.75 (d, J = 2.2 Hz, 1H), 3.97 (s, 4H), 3.56 (br, 3H), 2.87 (br, 2H), 1.89 (d, J = 5.1 Hz, 4H) | 431.2 |
| 274 | 1-(4-(4-chloro-3-(thiazol-2-yl)benzyl)piperazine-1-carbonyl)-1H-pyrazole-3-carboxylic acid | 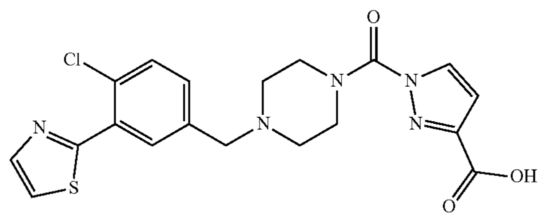 [SMILES: O=C(O)c1ccn(C(=O)N2CCN(Cc3ccc(Cl)c(-c4nccs4)c3)CC2)n1] | δ 8.11-8.09 (m, 2H), 7.95 (d, J =3.3 Hz, 1H), 7.76 (d, J = 3.3 Hz, 1H), 7.56-7.53 (m, 1H), 7.49-7.45 (m, 1H), 6.78 (d, J = 2.7 Hz, 1H), 3.87 (br, 4H), 3.71 (s, 2H), 2.68 (br, 4H) | 432.4 |
| 275 | 1-(4-(3-chloro-5-(trifluoromethyl)-benzyl)oxy)-piperidine-1-carbonyl)-1H-pyrazole-3-carboxylic acid | 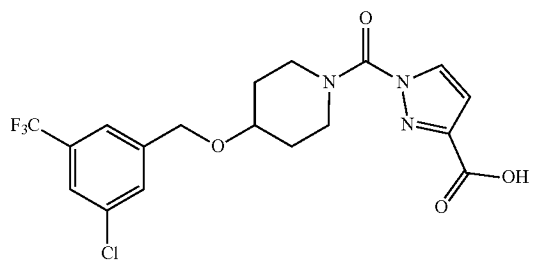 [SMILES: O=C(O)c1ccn(C(=O)N2CCC(OCc3cc(Cl)cc(C(F)(F)F)c3)CC2)n1] | δ 8.06 (d, J = 2.8 Hz, 1H), 7.69 (s, 1H), 7.63-7.61 (m, 2H), 6.76 (d, J = 2.8 Hz, 1H), 4.69 (s, 2H), 4.08 (br, 2H), 3.84-3.78 (m, 1H), 3.68-3.65 (m, 2H), 2.10-2.03 (m, 2H), 1.85-1.83 (m, 2H) | 449.1 [M + NH₄]⁺ |
| 276 | 1-(4-((4-chloro-3-(trifluoromethyl)-benzyl)oxy)-piperidine-1-carbonyl)-1H-pyrazole-3-carboxylic acid | 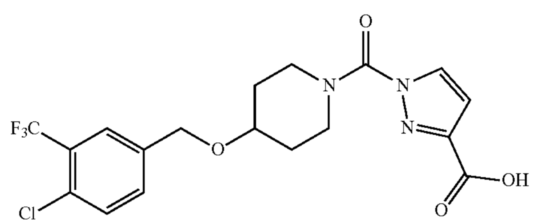 [SMILES: O=C(O)c1ccn(C(=O)N2CCC(OCc3ccc(Cl)c(C(F)(F)F)c3)CC2)n1] | δ 8.24 (d, J = 2.7 Hz, 1H), 7.76 (s, 1H), 7.63-7.56 (m, 2H), 6.75 (d, J = 2.7 Hz, 1H), 4.64 (s, 2H), 4.05 (br, 2H), 3.82-3.75 (m, 1H), 3.66-3.60 (m, 2H), 2.08-2.00 (m, 2H), 1.84-1.81 (m, 2H) | 454.1 [M + Na]⁺ |

| Ex | Name | Structure | NMR (¹H NMR, 300 MHz or 400 MHz, Methanol-d) | MS [M + H]⁺ |
|---|---|---|---|---|
| 277 | 1-(4-((5-chloro-2-(trifluoromethyl)-benzyl)oxy)-piperidine-1-carbonyl)-1H-pyrazole-3-carboxylic acid | 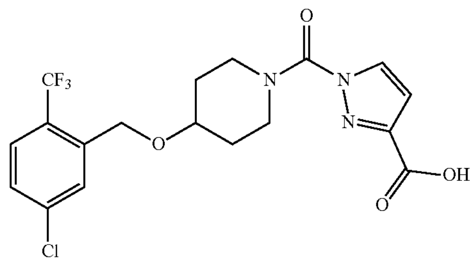 [SMILES: O=C(O)c1ccn(C(=O)N2CCC(OCc3cc(Cl)ccc3C(F)(F)F)CC2)n1] | δ 8.04 (d, J = 2.1 Hz, 1H), 7.78 (s, 1H), 7.68-7.63 (m, 1H), 7.60-7.46 (m, 1H), 6.75 (d, J = 2.1 Hz, 1H), 4.75-4.64 (m, 2H), 4.05 (br, 2H), 3.85-3.75 (m, 1H), 3.66-3.62 (m, 2H), 2.10-1.96 (m, 2H), 1.86-1.73 (m, 2H) | 430.0 [M − H] |
| 278 | 1-(trans-5-([1,1'-biphenyl]-3-ylmethoxy)-octahydrocyclopenta[c]pyrrole-2-carbonyl)-1H-pyrazole-3-carboxylic acid | 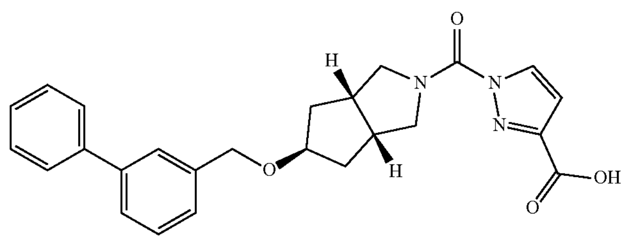 [SMILES: O=C(O)c1ccn(C(=O)N2C[C@H]3C[C@H](OCc4cccc(-c5ccccc5)c4)C[C@H]3C2)n1] | δ 8.00 (d, J = 2.7 Hz, 1H), 7.64-7.55 (m, 2H), 7.53-7.45 (m, 2H), 7.45-7.19 (m, 5H), 6.70 (d, J = 2.7 Hz, 1H), 4.50 (s, 2H), 4.30-4.04 (m, 2H), 4.04-3.72 (m, 3H), 2.88-2.64 (m, 2H), 2.22-2.01 (m, 2H), 1.90-1.67 (m, 2H) | 432.2 |
| 279 | 1-(cis-5-([1,1'-biphenyl]-3-ylmethoxy)-octahydrocyclopenta[c]pyrrole-2-carbonyl)-1H-pyrazole-3-carboxylic acid | 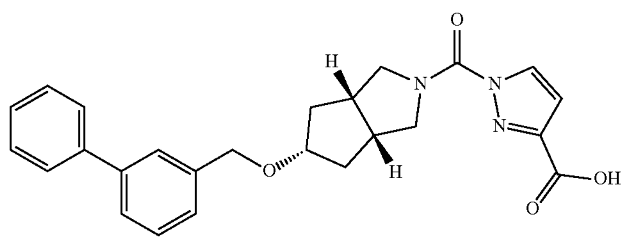 [SMILES: O=C(O)c1ccn(C(=O)N2C[C@H]3C[C@@H](OCc4cccc(-c5ccccc5)c4)C[C@H]3C2)n1] | δ 8.23 (d, J = 2.7 Hz, 1H), 7.70-7.58 (m, 3H), 7.58-7.50 (m, 1H), 7.50-7.39 (m, 3H), 7.39-7.28 (m, 2H), 6.85 (d, J = 2.7 Hz 1H) 4.56 (s, 2H), 4.32-4.21 (m, 1H), 4.20-3.51 (br, 4H), 3.03-2.87 (m, 2H), 2.23-2.08 (m, 2H), 1.90-1.71 (m, 2H) | 432.2 |
| 280 | 1-(trans-5-([1,1'-biphenyl]-3-yloxy)-octahydrocyclopenta[c]pyrrole-2-carbonyl)-4-methyl-1H-pyrazole-3-carboxylic acid | 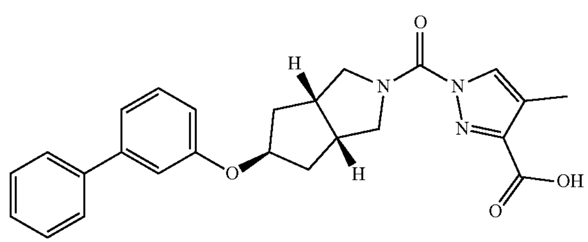 [SMILES: Cc1cn(C(=O)N2C[C@H]3C[C@H](Oc4cccc(-c5ccccc5)c4)C[C@H]3C2)nc1C(=O)O] | δ 8.06-7.98 (m, 1H), 7.61-7.53 (m, 2H), 7.47-7.36 (m, 2H), 7.36-7.25 (m, 2H), 7.19-7.11 (m, 1H), 7.11-7.02 (m, 1H), 6.90-6.81 (m, 1H), 5.13-5.00 (m, 1H), 4.29-3.48 (m, 4H), 3.07-2.84 (m, 2H), 2.32 (d, J = 0.9 Hz, 3H), 2.25-2.09 (m, 2H), 2.08-1.88 (m, 2H) | 431.9 |

| Ex | Name | Structure | NMR (¹H NMR, 300 MHz or 400 MHz, Methanol-d) | MS [M + H]⁺ |
|---|---|---|---|---|
| 281 | 1-(trans-5-([1,1'-biphenyl]-2-yloxy)-octahydrocyclopenta-[c]pyrrole-2-carbonyl)-4-methyl-1H-pyrazole-3-carboxylic acid | 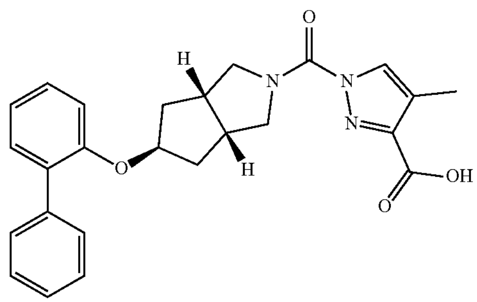 [SMILES: Cc1cn(C(=O)N2C[C@H]3C[C@H](Oc4ccccc4-c4ccccc4)C[C@H]3C2)nc1C(=O)O] | δ 7.96 (s, 1H), 7.48-7.42 (m, 2H), 7.37-7.31 (m, 2H), 7.29-7.22 (m, 3H), 7.05-6.95 (m, 2H), 4.97-4.91 (m, 1H), 4.17-3.48 (m, 4H), 2.73 (br, 2H), 2.25 (s, 3H), 2.15-2.05 (m, 2H), 1.85-1.75 (m, 2H) | 454.2 [M + Na]⁺ |
| 282 | 1-(2-(5-chloro-2-methoxybenzyl)-2,8-diazaspiro[4.5]-decane-8-carbonyl)-1H-pyrazole-3-carboxylic acid | 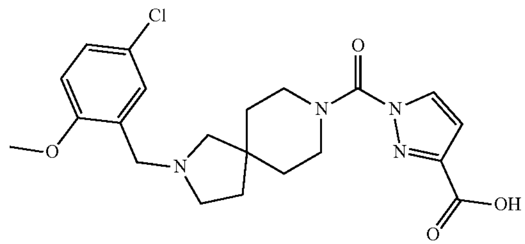 [SMILES: COc1ccc(Cl)cc1CN1CCC2(CCN(C(=O)n3ccc(C(=O)O)n3)CC2)C1] | δ 8.02 (d, J = 2.4 Hz, 1H), 7.46 (d, J = 2.4 Hz, 1H), 7.40-7.37 (m, 1H), 7.07-7.05 (m, 1H), 6.74 (d, J = 2.4 Hz, 1H), 4.21 (s, 2H), 3.88-3.82 (m, 5H), 3.68 (br, 2H), 3.31-3.28 (m, 2H), 3.15 (s, 2H), 2.00 (t, J = 6.8 Hz, 2H), 1.84-1.72 (m, 4H) | 433.2 |
| 283 | (R)-1-(4-((3-methoxy-[1,1'-biphenyl]-4-yl)methyl)-2-methylpiperazine-1-carbonyl)-1H-pyrazole-3-carboxylic acid | 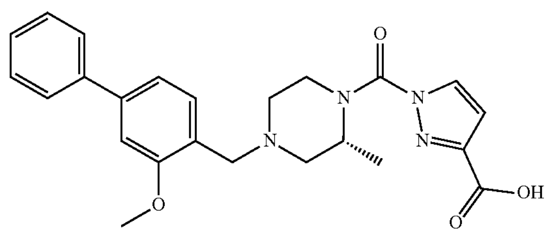 [SMILES: COc1cc(-c2ccccc2)ccc1CN1CCN(C(=O)n2ccc(C(=O)O)n2)[C@H](C)C1] | δ 8.10 (d, J = 2.7 Hz, 1H), 7.65-7.62 (m, 2H), 7.48-7.41 (m, 3H), 7.36-7.31 (m, 1H), 7.24-7.22 (m, 2H), 6.79 (d, J = 2.7 Hz, 1H), 4.77-4.76 (m, 1H), 4.45-4.41 (m, 1H), 3.94 (s, 3H), 3.87 (m, 2H), 3.57-3.47 (m, 1H), 3.14-3.09 (m, 1H), 3.02-2.98 (m, 1H), 2.72-2.59 (m, 2H), 1.46 (d, J = 6.9 Hz, 3H) | 435.2 |
| 284 | 1-(2-(3-(trifluoromethyl)-benzyl)-2,8-diazaspiro[4.5]-decane-8-carbonyl)-1H-pyrazole-3-carboxamide | 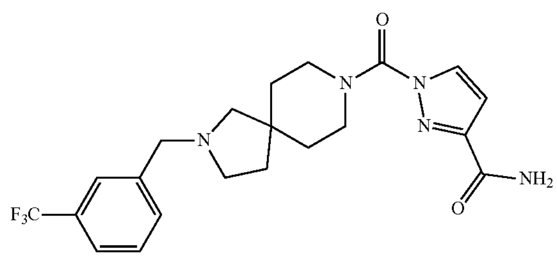 [SMILES: NC(=O)c1ccn(C(=O)N2CCC3(CCN(Cc4cccc(C(F)(F)F)c4)C3)CC2)n1] | (Chloroform-d) δ 8.05 (d, J = 2.7 Hz, 1H), 7.59 (s, 1H), 7.52-7.50 (m, 2H), 7.45-7.40 (m, 1H), 6.90 (d, J = 2.7 Hz, 1H), 6.66 (br, 1H), 5.56 (br, 1H), 3.80-3.62 (m, 6H), 2.64 (t, J = 6.9 Hz, 2H), 2.44 (s, 2H), 1.76-1.68 (m, 6H) | 436.2 |

| Ex | Name | Structure | NMR (¹H NMR, 300 MHz or 400 MHz, Methanol-d) | MS [M + H]⁺ |
|---|---|---|---|---|
| 285 | 1-(2-(2,5-dichlorobenzyl)-2,8-diazaspiro[4.5]decane-8-carbonyl)-1H-pyrazole-3-carboxylic acid | 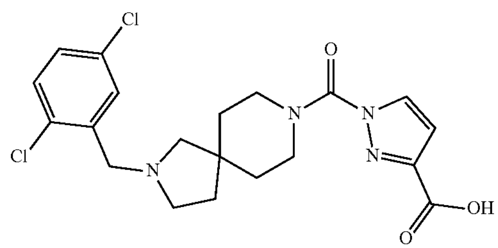 [SMILES: O=C(O)c1ccn(C(=O)N2CCC3(CCN(Cc4cc(Cl)ccc4Cl)C3)CC2)n1] | δ 8.02 (d, J = 2.4 Hz, 1H), 7.54 (d, J = 2.4 Hz, 1H), 7.38-7.36 (m, 1H), 7.28-7.25 (m, 1H), 6.74 (d, J = 2.4 Hz, 1H), 3.95-3.72 (m, 6H), 2.77-2.74 (m, 2H), 2.62 (s, 2H), 1.81-1.68 (m, 6H) | 437.2 |
| 286 | 1-(2-(2,3-dichlorobenzyl)-2,8-diazaspiro[4.5]decane-8-carbonyl)-1H-pyrazole-3-carboxylic acid | 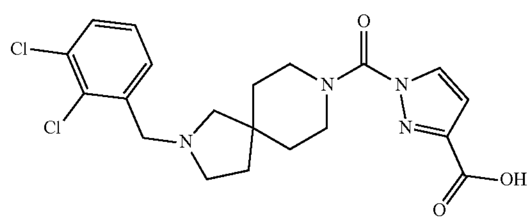 [SMILES: O=C(O)c1ccn(C(=O)N2CCC3(CCN(Cc4cccc(Cl)c4Cl)C3)CC2)n1] | δ 8.02 (d, J = 2.7 Hz, 1H), 7.50-7.44 (m, 2H), 7.31-7.26 (m, 1H), 6.73 (d, J = 2.7 Hz, 1H), 3.94-3.53 (m, 6H), 2.83-2.78 (m, 2H), 2.66 (s, 2H), 1.82-1.70 (m, 6H) | 437.2 |
| 287 | 1-(8-(3-(trifluoromethyl)benzyl)-2,8-diazaspiro[4.5]decane-2-carbonyl)-1H-pyrazole-3-carboxylic acid | 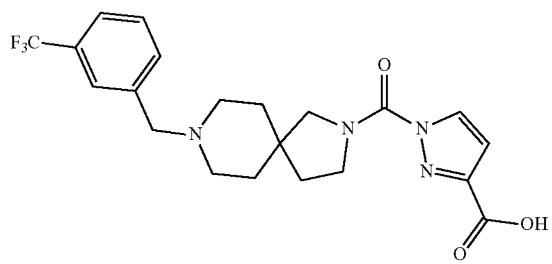 [SMILES: O=C(O)c1ccn(C(=O)N2CCC3(CCN(Cc4cccc(C(F)(F)F)c4)CC3)C2)n1] | δ 8.22 (d, J = 2.4 Hz, 1H), 7.88 (s, 1H), 7.80-7.76 (m, 2H), 7.73-7.65 (m, 1H), 6.80 (d, J = 2.4 Hz, 1H), 4.32-4.15 (m, 2H), 4.07-4.02 (m, 2H), 3.86-3.58 (m, 2H), 3.32-3.09 (m, 4H), 2.17-1.88 (m, 6H) | 437.2 |
| 288 | 1-(4-(3-(2-methoxyphenoxy)-benzyl)-piperazine-1-carbonyl)-1H-pyrazole-3-carboxylic acid | 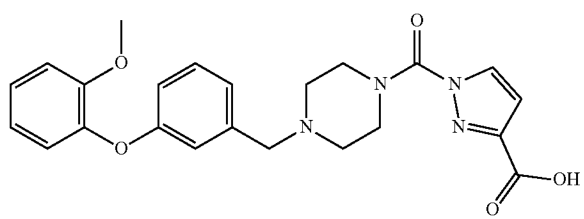 [SMILES: COc1ccccc1Oc1cccc(CN2CCN(C(=O)n3ccc(C(=O)O)n3)CC2)c1] | δ 8.16 (d, J = 2.7 Hz, 1H),7.33-7.21 (m, 1H), 7.20-7.19 (m, 1H), 7.18-7.13 (m, 1H), 7.08-6.95 (m, 4H), 6.85-6.81 (m, 2H), 3.93 (br, 4H), 3.82-3.78 (m, 5H), 2.85 (br, 4H) | 437.2 |

| Ex | Name | Structure | NMR (¹H NMR, 300 MHz or 400 MHz, Methanol-d) | MS [M + H]⁺ |
|---|---|---|---|---|
| 289 | 1-(cis-5-((2-methyl-3-(trifluoromethyl)-benzyl)oxy)-octahydrocyclopenta-[c]pyrrole-2-carbonyl)-1H-pyrazole-3-carboxylic acid | 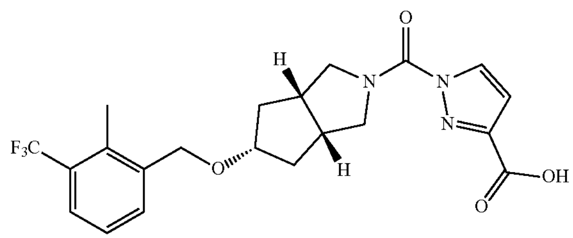 [SMILES: Cc1c(CO[C@@H]2C[C@@H]3CN(C(=O)n4ccc(C(=O)O)n4)C[C@@H]3C2)cccc1C(F)(F)F] | δ 8.18-7.90 (m, 1H), 7.63-7.48 (m, 2H), 7.35-7.15 (m, 1H), 6.77-6.62 (m, 1H), 4.62-4.47 (m, 2H), 4.40-3.52 (m, 5H), 2.98-2.69 (br, 2H), 2.48-2.30 (m, 3H), 2.28-2.07 (m, 2H), 1.91-1.72 (m, 2H) | 459.8 [M + Na]⁺ |
| 290 | 4-methyl-1-(trans-5-((3-(trifluoromethyl)-benzyl)oxy)-octahydrocyclopenta-[c]pyrrole-2-carbonyl)-1H-pyrazole-3-carboxylic acid | 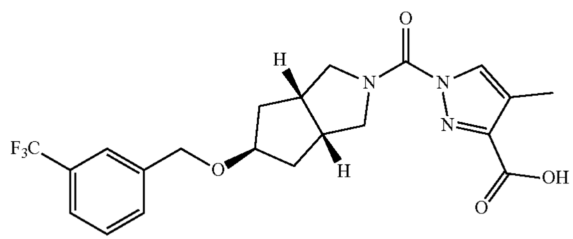 [SMILES: Cc1cn(C(=O)N2C[C@H]3C[C@H](OCc4cccc(C(F)(F)F)c4)C[C@H]3C2)nc1C(=O)O] | δ 7.95 (d, J = 0.8 Hz, 1H), 7.77-7.44 (m, 4H), 4.56 (s, 2H), 4.38-4.20 (m, 1H), 4.20-3.42 (m, 4H), 3.03-2.75 (br, 2H), 2.30 (d, J = 0.8 Hz, 3H), 2.21-2.00 (m, 2H), 1.90-1.68 (m, 2H) | 437.8 |
| 291 | (R)-1-(4-((3-chloro-[1,1'-biphenyl]-4-yl)methyl)-2-methylpiperazine-1-carbonyl)-1H-pyrazole-3-carboxylic acid | 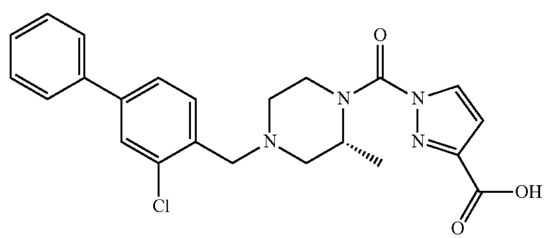 [SMILES: C[C@@H]1CN(Cc2ccc(-c3ccccc3)cc2Cl)CCN1C(=O)n1ccc(C(=O)O)n1] | δ 8.11 (d, J = 2.7 Hz, 1H), 7.54-7.64 (m, 5H), 7.42-7.47 (m, 2H), 7.33-7.38 (m, 1H), 6.82 (d, J = 2.7 Hz, 1H), 4.66 (br, 1H), 4.24-4.28 (m, 1H), 3.68 (s, 2H), 3.45-3.54 (m, 1H), 2.90-2.95 (m, 1H), 2.80-2.84 (m, 1H), 2.44-2.49 (m, 1H), 2.30-2.38 (m, 1H), 1.47 (d, J = 6.9 Hz, 3H) | 439.2 |
| 292 | (R)-1-(4-(3-(4-fluorophenoxy)-benzyl)-2-methylpiperazine-1-carbonyl)-1H-pyrazole-3-carboxylic acid | 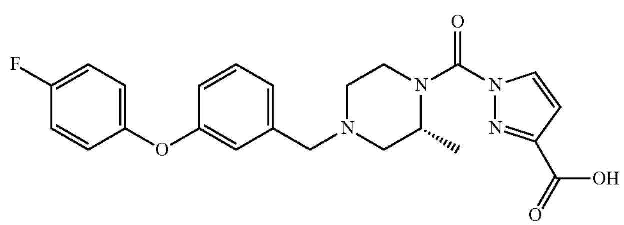 [SMILES: C[C@@H]1CN(Cc2cccc(Oc3ccc(F)cc3)c2)CCN1C(=O)n1ccc(C(=O)O)n1] | δ 8.11 (d, J = 2.7 Hz, 1H),7.33-7.28 (m, 1H), 7.12-7.06 (m, 3H), 7.05-6.97 (m, 3H), 6.89-6.86 (m, 1H), 6.82 (d, J = 2.7 Hz, 1H), 4.62 (br, 1H), 4.27-4.23 (m, 1H), 3.65-3.61 (m, 1H), 3.54-3.41 (m, 2H), 2.92-2.88 (m, 1H), 2.78-2.74 (m, 1H), 2.38-2.27 (m, 2H), 1.38 (d, J = 6.6 Hz, 3H) | 439.1 |

| Ex | Name | Structure | NMR (1H NMR, 300 MHz or 400 MHz, Methanol-d) | MS [M + H]+ |
|---|---|---|---|---|
| 293 | (S)-1-(4-(3-(4-fluorophenoxy)-benzyl)-2-methylpiperazine-1-carbonyl)-1H-pyrazole-3-carboxylic acid | 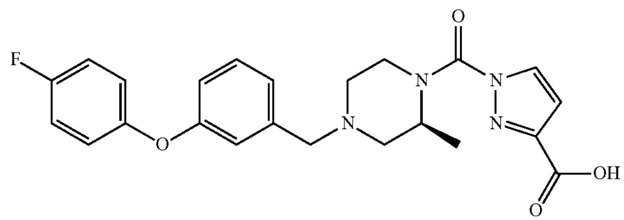 [SMILES: C[C@H]1CN(Cc2cccc(Oc3ccc(F)cc3)c2)CCN1C(=O)n1ccc(C(=O)O)n1] | δ 8.12 (d, J = 2.7 Hz, 1H), 7.33-7.28 (m, 1H), 7.12-7.03 (m, 3H), 7.01-6.98 (m, 3H), 6.90-6.87 (m, 1H), 6.83 (d, J = 2.7 Hz, 1H), 4.61 (br, 1H), 4.26-4.21 (m, 1H), 3.67-3.62 (m, 1H), 3.52-3.41 (m, 2H), 2.93-2.89 (m, 1H), 2.79-2.75 (m, 1H), 2.39-2.28 (m, 2H), 1.38 (d, J = 6.6 Hz, 3H) | 439.2 |
| 294 | (R)-1-(4-(4-fluoro-3-phenoxybenzyl)-2-methylpiperazine-1-carbonyl)-1H-pyrazole-3-carboxylic acid | 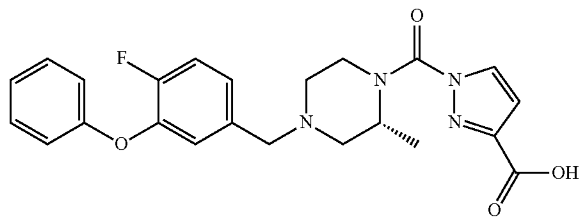 [SMILES: C[C@@H]1CN(Cc2ccc(F)c(Oc3ccccc3)c2)CCN1C(=O)n1ccc(C(=O)O)n1] | δ 8.12 (s, 1H), 7.36-7.22 (m, 2H), 7.22-7.07 (m, 4H), 7.10-6.94 (m, 2H), 6.84 (d, J = 3.0 Hz, 1H), 4.59 (br, 1H), 4.23-4.19 (m, 1H), 3.63-3.54 (m, 1H), 3.49-3.32 (m, 2H), 2.91-2.87 (m, 1H), 2.75-2.72 (m, 1H), 2.37-2.27 (m, 2H), 1.40-1.35 (m, 3H) | 439.2 |
| 295 | (R)-1-(4-(3-((5-fluoropyridin-2-yl)oxy)benzyl)-2-methylpiperazine-1-carbonyl)-1H-pyrazole-3-carboxylic acid | 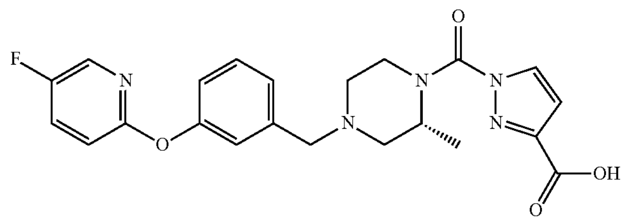 | δ 8.10 (d, J = 2.4 Hz, 1H), 8.02 (d, J = 3.0 Hz, 1H), 7.68-7.62 (m, 1H), 7.39-7.34 (m, 1H), 7.22-7.20 (m, 1H), 7.14 (s, 1H), 7.02-6.97 (m, 2H), 6.81-6.80 (m, 1H), 4.64 (br, 1H), 4.29-4.24 (m, 1H), 3.69-3.65 (m, 1H), 3.56-3.43 (m, 2H), 2.96-2.92 (m, 1H), 2.82-2.78 (m, 1H), 2.41-2.29 (m, 2H), 1.40 (d, J = 6.9 Hz, 3H) | 440.3 |
| 296 | 4-chloro-1-(trans-5-((3-chloro-5-fluorobenzyl)oxy)-octahydrocyclopenta[c]pyrrole-2-carbonyl)-1H-pyrazole-3-carboxylic acid | 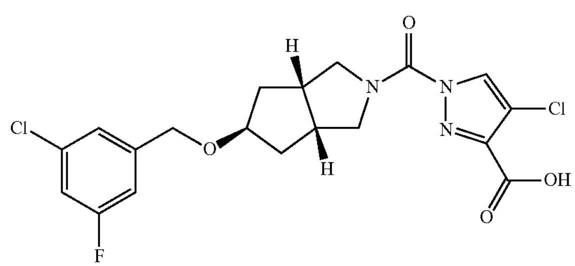 [SMILES: O=C(O)c1nn(C(=O)N2C[C@H]3C[C@H](OCc4cc(F)cc(Cl)c4)C[C@H]3C2)cc1Cl] | δ 8.22 (s, 1H), 7.21 (s, 1H), 7.12-7.01 (m, 2H), 4.48 (s, 2H), 4.26-4.18 (m, 1H), 4.15-3.47 (m, 4H), 2.92 (br, 2H), 2.18-2.05 (m, 2H), 1.87-1.73 (m, 2H) | 459.1 [M + NH4]+ |

| Ex | Name | Structure | NMR (¹H NMR, 300 MHz or 400 MHz, Methanol-d) | MS [M + H]⁺ |
|---|---|---|---|---|
| 297 | 1-(trans-5-(5-chloro-2-(trifluoromethyl)-phenoxy)-octahydrocyclopenta[c]pyrrole-2-carbonyl)-1H-pyrazole-3-carboxylic acid | 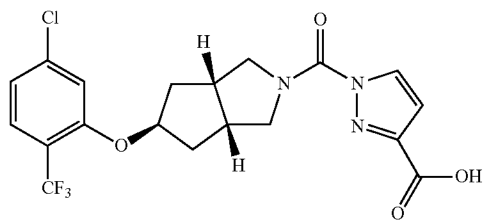 [SMILES: O=C(O)c1ccn(C(=O)N2C[C@H]3C[C@H](Oc4cc(Cl)ccc4C(F)(F)F)C[C@H]3C2)n1] | δ 8.16 (d, J = 2.7 Hz, 1H), 7.58 (d, J = 8.4 Hz, 1H), 7.28-7.17 (m, 1H), 7.11-6.99 (m, 1H), 6.78 (d, J = 2.7 Hz, 1H), 5.25-5.11 (m, 1H), 4.38-3.50 (m, 4H), 3.09-2.84 (m, 2H), 2.30-2.10 (m, 2H), 2.10-1.88 (m, 2H) | 466.8 [M + Na]⁺ |
| 298 | 1-(trans-5-(([1,1'-biphenyl]-3-ylmethyl)(methyl)-amino)-octahydrocyclopenta[c]pyrrole-2-carbonyl)-1H-pyrazole-3-carboxylic acid | 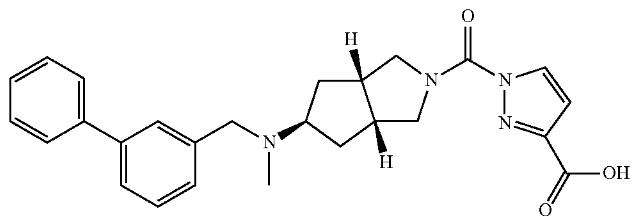 [SMILES: CN(Cc1cccc(-c2ccccc2)c1)[C@H]1C[C@@H]2CN(C(=O)n3ccc(C(=O)O)n3)C[C@@H]2C1] | δ 8.18 (s, 1H), 7.70 (s, 1H), 7.62-7.53 (m, 3H), 7.44-7.30 (m, 5H), 6.80 (s, 1H), 4.35-3.80 (m, 5H), 3.65-3.56 (m, 2H), 2.91 (s, 2H), 2.50 (s, 3H), 2.44-2.34 (m, 2H), 2.07-2.00 (m, 2H) | 445.2 |
| 299 | (R)-1-(4-(4-chloro-3-(thiazol-2-yl)benzyl)-2-methylpiperazine-1-carbonyl)-1H-pyrazole-3-carboxylic acid | 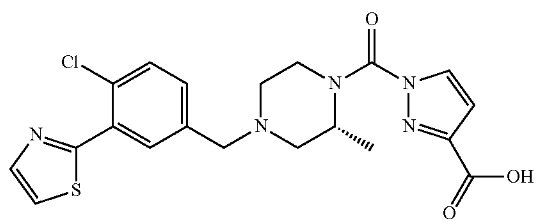 [SMILES: C[C@@H]1CN(Cc2ccc(Cl)c(-c3nccs3)c2)CCN1C(=O)n1ccc(C(=O)O)n1] | δ 8.12-8.10 (m, 2H), 7.97 (d, J = 3.3 Hz, 1H), 7.79-7.76 (m, 1H), 7.57-7.55 (m, 1H), 7.51-7.48 (m, 1H), 6.82 (d, J = 2.7 Hz, 1H), 4.66 (br, 1H), 4.30-4.27 (m, 1H), 3.70-3.65 (m, 1H), 3.59-3.48 (m, 2H), 2.95-2.91 (m, 1H), 2.82-2.78 (m, 1H), 2.43-2.35 (m, 1H), 2.32-2.27 (m, 1H), 1.43 (d, J = 6.0 Hz, 3H) | 446.4 |
| 300 | 1-(2-(2-carbamoyl-5-chlorobenzyl)-2,8-diazaspiro[4.5]-decane-8-carbonyl)-1H-pyrazole-3-carboxylic acid | 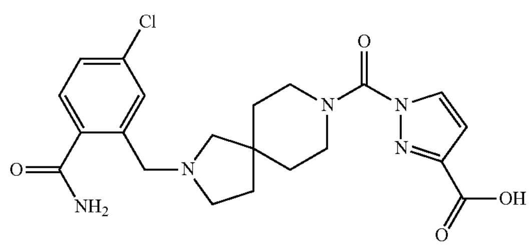 [SMILES: NC(=O)c1ccc(Cl)cc1CN1CCC2(CCN(C(=O)n3ccc(C(=O)O)n3)CC2)C1] | δ 8.06 (d, J = 2.7 Hz, 1H), 7.81-7.78 (m, 1H), 7.66 (s, 1H), 7.59-7.57 (m, 1H), 6.67 (d, J = 2.7 Hz, 1H), 4.29 (s, 2H), 3.89 (br, 2H), 3.70 (br, 2H), 3.31-3.27 (m, 2H), 3.14 (s, 2H), 2.06-2.01 (m, 2H), 1.87-1.70 (m, 4H) | 446.2 |

| Ex | Name | Structure | NMR (¹H NMR, 300 MHz or 400 MHz, Methanol-d) | MS [M + H]⁺ |
|---|---|---|---|---|
| 301 | 1-(2-(3-(pyridin-2-yl)benzyl)-2,8-diazaspiro[4.5]decane-8-carbonyl)-1H-pyrazole-3-carboxylic acid | 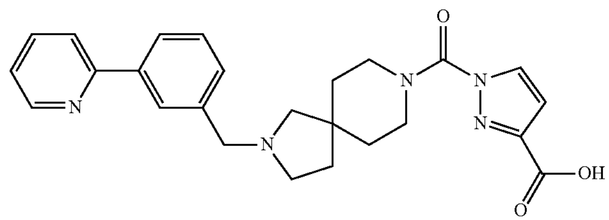 | δ 8.62-8.60 (m, 1H), 8.13 (s, 1H), 8.03-8.00 (m, 2H), 7.88-7.86 (m, 2H), 7.62-7.53 (m, 2H), 7.39-7.35 (m, 1H), 6.73 (d, J = 2.7 Hz, 1H), 4.41 (s, 2H), 3.84-3.79 (m, 2H), 3.68-3.63 (m, 2H), 3.40-3.30 (m, 2H), 3.32-3.27 (m, 2H), 2.06-1.97 (m, 2H), 1.84-1.73 (m, 4H) | 446.2 |
| 302 | 1-(2-(3-(pyrimidin-5-yl)benzyl)-2,8-diazaspiro[4.5]decane-8-carbonyl)-1H-pyrazole-3-carboxylic acid | 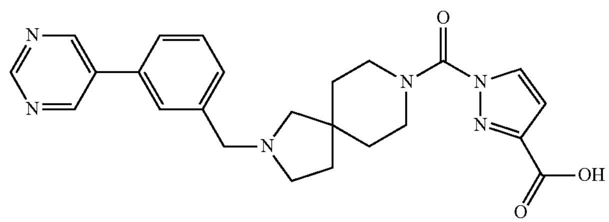 | δ 9.13 (s, 1H), 9.08-9.06 (m, 2H), 8.10 (d, J = 2.7 Hz, 1H), 7.90 (s, 1H), 7.78 (d, J = 6.3 Hz, 1H), 7.62 (t, J = 6.3 Hz, 2H), 6.72 (d, J = 2.7 Hz, 1H), 4.37 (s, 2H), 3.84-3.79 (m, 2H), 3.67-3.65 (m, 2H), 3.38-3.36 (m, 2H), 3.24 (br, 2H), 2.03 (t, J = 7.2 Hz, 2H), 1.85-1.75 (m, 4H) | 447.2 |
| 303 | 1-(1-(3-methyl-5-(trifluoromethyl)benzyl)-1,8-diazaspiro[4.5]decane-8-carbonyl)-1H-pyrazole-3-carboxylic acid | 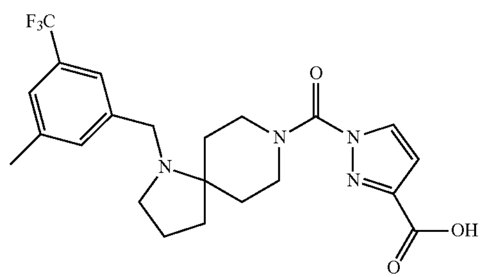 [SMILES: Cc1cc(CN2CCCC23CCN(C(=O)n2ccc(C(=O)O)n2)CC3)cc(C(F)(F)F)c1] | δ 8.09 (d, J = 2.4 Hz, 1H), 7.55-7.52 (m, 2H), 7.46 (s, 1H), 6.79 (d, J = 2.4 Hz, 1H), 4.63 (br, 2H), 3.99 (br, 2H), 3.24-3.15 (m, 2H), 2.99-2.93 (m, 2H), 2.45 (s, 3H), 2.29-2.06 (m, 4H), 1.98-1.93 (m, 2H), 1.71-1.68 (m, 2H) | 451.2 |
| 304 | 1-(trans-5-([1,1'-biphenyl]-3-yloxy)-octahydrocyclopenta[c]pyrrole-2-carbonyl)-4-chloro-1H-pyrazole-3-carboxylic acid | 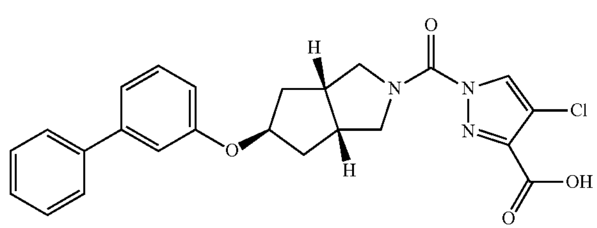 [SMILES: O=C(O)c1nn(C(=O)N2C[C@H]3C[C@H](Oc4cccc(-c5ccccc5)c4)C[C@H]3C2)cc1Cl] | δ 8.26 (s, 1H), 7.63-7.52 (m, 2H), 7.47-7.36 (m, 2H), 7.35-7.23 (m, 2H), 7.18-7.12 (m, 1H), 7.11-7.08 (m, 1H), 6.91-6.85 (m, 1H), 5.15-5.06 (m, 1H), 4.33-3.53 (m, 4H), 2.88 (br, 2H), 2.28-2.12 (m, 2H), 2.09-1.91 (m, 2H) | 450.1 [M − H]⁻ |

| Ex | Name | Structure | NMR (1H NMR, 300 MHz or 400 MHz, Methanol-d) | MS [M + H]+ |
|---|---|---|---|---|
| 305 | 1-(2-(3-(thiazol-2-yl)benzyl)-2,8-diazaspiro[4.5]-decane-8-carbonyl)-1H-pyrazole-3-carboxylic acid | 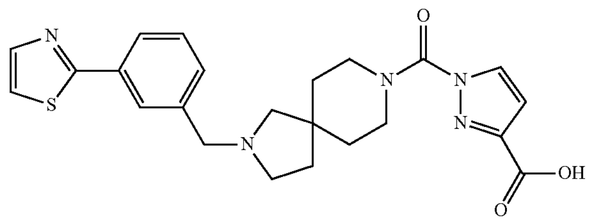 [SMILES: O=C(O)c1ccn(C(=O)N2CCC3(CCN(Cc4cccc(-c5nccs5)c4)C3)CC2)n1] | δ 8.18 (s, 1H), 8.01-8.00 (m, 2H), 7.88 (s, 1H), 7.64-7.62 (m, 2H), 7.61-7.53 (m, 1H), 6.73 (d, J = 2.7Hz, 1H), 4.38 (s, 2H), 3.85-3.81 (m, 2H), 3.69-3.64 (m, 2H), 3.39-3.31 (m, 2H), 3.29-3.23 (m, 2H), 2.06-1.98 (m, 2H), 1.86-1.70 (m, 4H) | 452.2 |
| 306 | 4-methyl-1-(trans-5-((2-methyl-3-(trifluoromethyl)-benzyl)oxy)-octahydrocyclopenta[c]pyrrole-2-carbonyl)-1H-pyrazole-3-carboxylic acid | 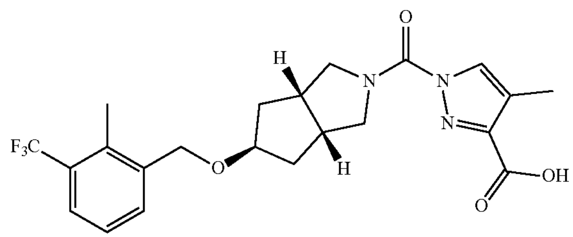 [SMILES: Cc1cn(C(=O)N2C[C@H]3C[C@H](OCc4cccc(C(F)(F)F)c4C)C[C@H]3C2)nc1C(=O)O] | δ 7.95 (s, 1H), 7.55 (d, J = 7.8 Hz, 2H), 7.28 (t, J = 7.7 Hz, 1H), 4.52 (s, 2H), 4.27-4.18 (m, 1H), 4.15-3.47 (m, 4H), 2.87 (br, 2H), 2.40 (d, J = 1.3 Hz, 3H), 2.24 (d, J = 0.84 Hz, 3H), 2.19-2.02 (m, 2H), 1.85-1.17 (m, 2H) | 452.2 |
| 307 | 1-(4-(2-(pyrrolidin-1-yl)-4-(trifluoromethyl)-phenoxy)-piperidine-1-carbonyl)-1H-pyrazole-3-carboxylic acid | 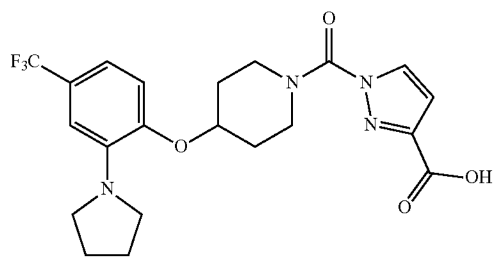 [SMILES: O=C(O)c1ccn(C(=O)N2CCC(Oc3ccc(C(F)(F)F)cc3N3CCCC3)CC2)n1] | δ 8.10 (d, J = 2.7 Hz, 1H), 7.09-7.01 (m, 2H), 6.93 (s, 1H), 6.79 (d, J = 2.7 Hz, 1H), 4.81-4.72 (m, 1H), 4.04 (br, 2H), 3.77 (br, 2H), 3.38-3.31 (m, 4H), 2.18-2.11 (m, 2H), 2.03-1.91 (m, 6H) | 453.2 |
| 308 | 1-(4-(3-(pyrrolidin-1-yl)-5-(trifluoromethyl)-phenoxy)-piperidine-1-carbonyl)-1H-pyrazole-3-carboxylic acid | 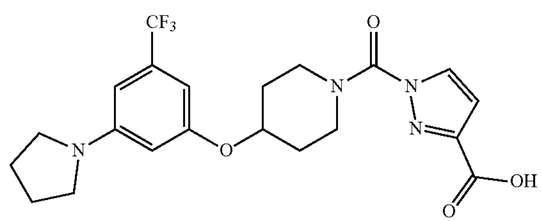 [SMILES: O=C(O)c1ccn(C(=O)N2CCC(Oc3cc(N4CCCC4)cc(C(F)(F)F)c3)CC2)n1] | δ 8.12 (d, J = 2.7 Hz, 1H), 6.82 (d, J = 2.7 Hz, 1H), 6.48 (s, 1H), 6.39 (s, 1H), 6.34 (s, 1H), 4.76-4.70 (m, 1H), 3.98 (br, 2H), 3.85 (br, 2H), 3.30-3.28 (m, 4H), 2.16-2.00 (m, 6H), 1.96-1.92 (m, 2H) | 453.2 |

| Ex | Name | Structure | NMR (¹H NMR, 300 MHz or 400 MHz, Methanol-d) | MS [M + H]⁺ |
|---|---|---|---|---|
| 309 | N-(1-(3-carbamoyl-1H-pyrazole-1-carbonyl)piperidin-4-yl)-N-(3-(trifluoromethyl)benzyl)glycine | 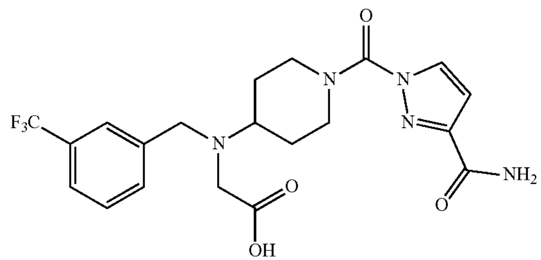 [SMILES: NC(=O)c1ccn(C(=O)N2CCC(N(CC(=O)O)Cc3cccc(C(F)(F)F)c3)CC2)n1] | δ 8.16 (d, J = 2.7 Hz, 1H), 7.84 (s, 1H), 7.75 (d, J = 7.5 Hz, 1H), 7.62-7.52 (m, 2H), 6.85 (d, J = 2.7 Hz, 1H), 4.52-4.48 (m, 2H), 4.13 (s, 2H), 3.40 (s, 2H), 3.26-3.22 (m, 1H), 3.14-3.05 (m, 2H), 2.18-2.08 (m, 2H), 1.84-1.74 (m, 2H) | 454.1 |
| 310 | (R)-1-(4-(3-(4-chlorophenoxy)benzyl)-2-methylpiperazine-1-carbonyl)-1H-pyrazole-3-carboxamide | 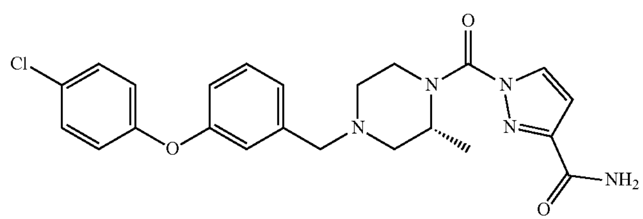 [SMILES: C[C@@H]1CN(Cc2cccc(Oc3ccc(Cl)cc3)c2)CCN1C(=O)n1ccc(C(N)=O)n1] | δ 8.10 (d, J = 2.7 Hz, 1H), 8.09-7.28 (m, 3H), 7.12 (d, J = 8.1 Hz, 1H), 7.07 (s, 1H), 6.99-6.91 (m, 4H), 6.66 (br, 1H), 5.53 (br, 1H), 4.65-4.63 (m, 1H), 4.31-4.26 (m, 1H), 3.65-3.42 (m, 3H), 2.92-2.96 (m, 1H), 2.72-2.76 (m, 1H), 2.36-2.24 (m, 2H), 1.48 (d, J = 6.6 Hz, 3H) | 454.2 |
| 311 | (S)-1-(4-(3-(4-chlorophenoxy)benzyl)-2-methylpiperazine-1-carbonyl)-1H-pyrazole-3-carboxylic acid | 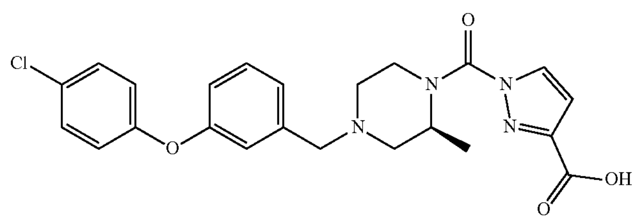 [SMILES: C[C@H]1CN(Cc2cccc(Oc3ccc(Cl)cc3)c2)CCN1C(=O)n1ccc(C(=O)O)n1] | δ 8.12 (d, J = 2.7 Hz, 1H),7.36-7.31 (m, 3H), 7.00 (s, 1H), 6.98-6.90 (m, 3H), 6.83 (d, J = 2.7 Hz, 1H), 4.61 (br, 1H), 4.26-4.22 (m, 1H), 3.66-3.62 (m, 1H), 3.54-3.42 (m, 2H), 2.92-2.89 (m, 1H), 2.78-2.74 (m, 1H), 2.39-2.26 (m, 2H), 1.39 (d, J = 6.8 Hz, 3H) | 455.2 |
| 312 | 2-methyl-2-(piperazin-1-ylmethyl)-5-(trifluoromethyl)phenoxy)propanoic acid | 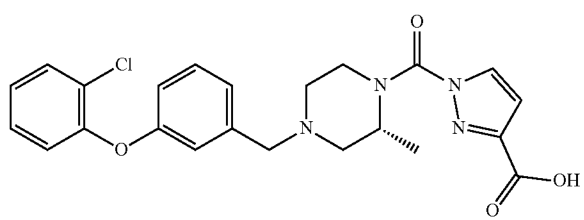 [SMILES: C[C@@H]1CN(Cc2cccc(Oc3ccccc3Cl)c2)CCN1C(=O)n1ccc(C(=O)O)n1] | δ 8.14 (d, J = 2.8 Hz, 1H), 7.52 (d, J = 8.0 Hz, 1H), 7.35-7.31 (m, 2H), 7.21-7.11 (m, 1H), 7.10-7.06 (m, 2H), 6.97 (s, 1H), 6.90-6.85 (m, 2H), 4.63 (br, 1H), 4.28-4.24 (m, 1H), 3.68-3.65 (m, 1H), 3.52-3.43 (m, 2H), 2.94-2.91 (m, 1H), 2.78-2.76 (m, 1H), 2.39-2.30 (m, 2H), 1.39-1.33 (m, 3H) | 455.2 |

| Ex | Name | Structure | NMR (¹H NMR, 300 MHz or 400 MHz, Methanol-d) | MS [M + H]⁺ |
|---|---|---|---|---|
| 313 | 1-(2-(5-chloro-2-(trifluoromethyl)-benzyl)-2,7-diazaspiro[3.5]-nonane-7-carbonyl)-1H-pyrazole-3-carboxylic acid | 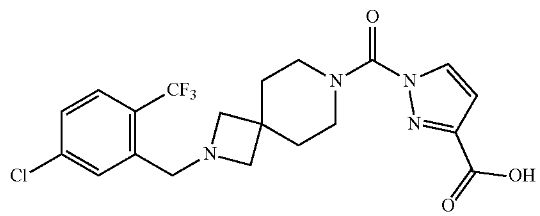 [SMILES: O=C(O)c1ccn(C(=O)N2CCC3(CC2)CN(Cc2cc(Cl)ccc2C(F)(F)F)C3)n1] | δ 8.03 (d, J = 2.7 Hz, 1H), 7.70-7.67 (m, 1H), 7.64 (s, 1H), 7.49-7.43 (m, 1H), 6.74 (d, J = 2.7 Hz, 1H), 3.89 (s, 2H), 3.75 (br, 4H), 3.31 (s, 4H), 1.94-1.86 (m, 4H) | 457.2 |
| 314 | 4-chloro-1-(trans-5-(((3-(trifluoromethyl)-benzyl)oxy)-octahydrocyclopenta[c]pyrrole-2-carbonyl)-1H-pyrazole-3-carboxylic acid | 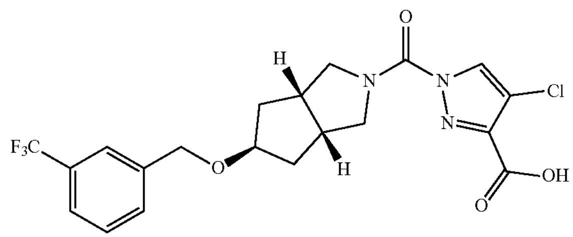 | δ 8.19 (s, 1H), 7.69-7.49 (m, 4H), 4.5 (s, 2H), 4.26-4.21 (m, 1H), 4.19-3.37 (m, 4H), 2.93 (br, 2H), 2.18-2.05 (m, 2H), 1.86-1.75 (m, 2H) | 475.1 [M + NH₄]⁺ |
| 315 | 1-((3aR,6aS)-5-(4-chloro-3-(thiazol-2-yl)benzyl)-octahydropyrrolo[3,4-c]pyrrole-2-carbonyl)-1H-pyrazole-3-carboxylic acid | 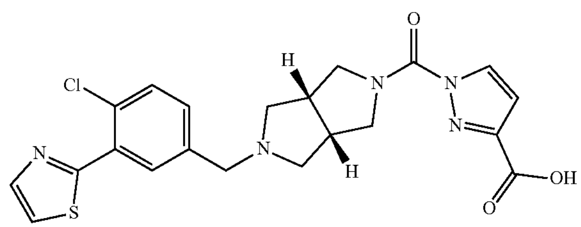 [SMILES: O=C(O)c1ccn(C(=O)N2C[C@H]3CN(Cc4ccc(Cl)c(-c5nccs5)c4)C[C@H]3C2)n1] | δ 8.20 (d, J = 2.4 Hz, 1H), 8.16 (d, J = 2.8 Hz, 1H), 7.94 (d, J = 3.6 Hz, 1H), 7.76 (d, J = 3.2 Hz, 1H), 7.60 (d, J = 8.4 Hz, 1H), 7.53-7.48 (m, 1H), 6.76 (d, J = 2.8 Hz, 1H), 4.13 (s, 3H), 3.95 (br, 3H), 3.31-3.21 (m, 2H), 3.13-3.01 (m, 4H) | 458.1 |
| 316 | 1-(2-(3,5-dichlorobenzyl)-2,8-diazaspiro[4.5]-decane-8-carbonyl)-4-methyl-1H-pyrazole-3-carboxylic acid | 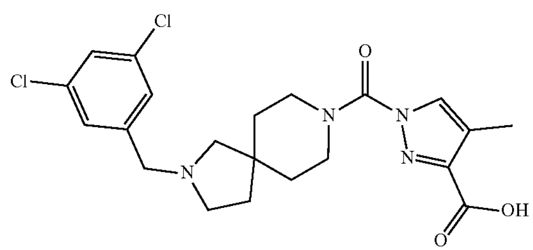 [SMILES: Cc1cn(C(=O)N2CCC3(CCN(Cc4cc(Cl)cc(Cl)c4)C3)CC2)nc1C(=O)O] | δ 7.84 (s, 1H), 7.50-7.48 (m, 3H), 4.17 (s, 2H), 3.81-3.77 (m, 2H), 3.67-3.60 (m, 2H), 3.24 (br, 2H), 3.10 (br, 2H), 2.27 (s, 3H), 1.99 (t, J = 9.0 Hz, 2H), 1.83-1.71 (m, 4H) | 451.1 |

| Ex | Name | Structure | NMR (¹H NMR, 300 MHz or 400 MHz, Methanol-d) | MS [M + H]⁺ |
|---|---|---|---|---|
| 317 | 1-(2-(2-(azetidin-1-yl)-5-chlorobenzyl)-2,8-diazaspiro[4.5]decane-8-carbonyl)-1H-pyrazole-3-carboxylic acid | 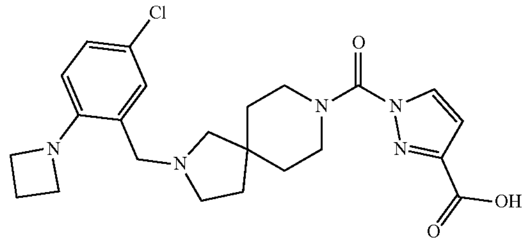 [SMILES: O=C(O)c1ccn(C(=O)N2CCC3(CCN(Cc4cc(Cl)ccc4N4CCC4)C3)CC2)n1] | δ 8.07 (d, J = 2.4 Hz, 1H), 7.38 (s, 1H), 7.32-7.29 (m, 1H), 6.75 (d, J = 2.4 Hz, 1H), 6.73-6.70 (m, 1H), 4.27 (s, 2H), 4.03-3.98 (m, 4H), 3.93-3.86 (m, 2H), 3.73-3.71 (m, 2H), 3.42-3.32 (m, 2H), 3.25-3.21 (m, 2H), 2.43-2.33 (m, 2H), 2.05 (t, J = 6.9 Hz, 2H), 1.90-1.77 (m, 4H) | 458.2 |
| 318 | 1-(trans-5-(4-chloro-3-(thiazol-2-yl)phenoxy)-octahydrocyclopenta[c]pyrrole-2-carbonyl)-1H-pyrazole-3-carboxylic acid | 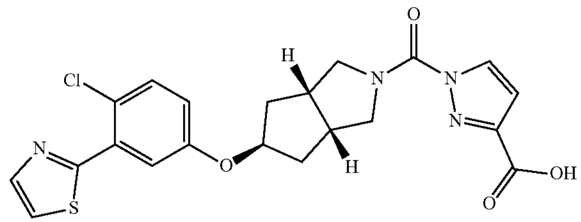 [SMILES: O=C(O)c1ccn(C(=O)N2C[C@H]3C[C@H](Oc4ccc(Cl)c(-c5nccs5)c4)C[C@H]3C2)n1] | δ 8.16 (d, J = 4.0 Hz, 1H), 7.94 (d, J = 3.3 Hz, 1H), 7.74 (d, J = 3.3 Hz, 1H), 7.60 (d, J = 3.0 Hz, 1H), 7.42 (d, J = 8.9 Hz, 1H), 7.03-6.97 (m, 1H), 6.77 (d, J = 2.7 Hz, 1H), 5.07-5.01 (m, 1H), 4.48-3.51 (m, 4H), 2.98 (br, 2H), 2.21-2.11 (m, 2H), 2.05-1.91 (m, 2H) | 459.1 |
| 319 | 1-(4-(3-(2-chlorophenoxy)-5-fluorobenzyl)-piperazine-1-carbonyl)-1H-pyrazole-3-carboxylic acid | 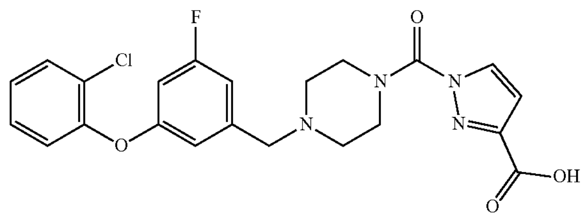 [SMILES: O=C(O)c1ccn(C(=O)N2CCN(Cc3cc(F)cc(Oc4ccccc4Cl)c3)CC2)n1] | δ 8.05 (d, J = 2.7 Hz, 1H), 7.54-7.51 (m, 1H), 7.39-7.33 (m, 1H), 7.25-7.20 (m, 1H), 7.15-7.12 (m, 1H), 6.89-6.86 (m, 1H), 6.73 (d, J = 2.7 Hz, 2H), 6.56-6.51 (m, 1H), 3.84 (br, 4H), 3.53 (s, 2H), 2.56-2.53 (m, 4H) | 459.2 |
| 320 | 4-chloro-1-(4-(3-(4-fluorophenoxy)-benzyl)-piperazine-1-carbonyl)-1H-pyrazole-3-carboxylic acid | 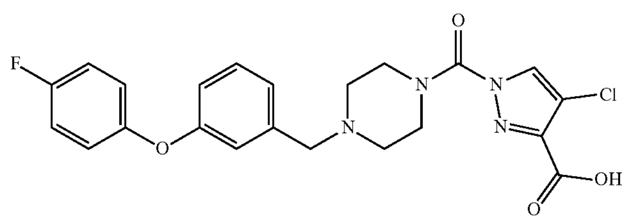 [SMILES: O=C(O)c1nn(C(=O)N2CCN(Cc3cccc(Oc4ccc(F)cc4)c3)CC2)cc1Cl] | δ 8.15 (s, 1H), 7.38-7.29 (m, 1H), 7.12-7.03 (m, 3H), 7.01-6.98 (m, 3H), 6.90-6.88 (m, 1H), 3.85 (br, 4H), 3.65 (s, 2H), 2.68-2.64 (m, 4H) | 459.2 |

| Ex | Name | Structure | NMR (1H NMR, 300 MHz or 400 MHz, Methanol-d) | MS [M + H]+ |
|---|---|---|---|---|
| 321 | 1-(4-(3-chlorophenoxy)-5-fluorobenzyl)-piperazine-1-carbonyl)-1H-pyrazole-3-carboxylic acid | 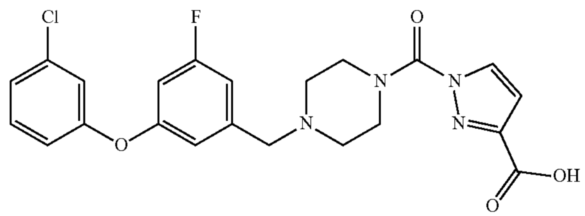 [SMILES: O=C(O)c1ccn(C(=O)N2CCN(Cc3cc(F)cc(Oc4cccc(Cl)c4)c3)CC2)n1] | δ 8.16 (d, J = 2.8 Hz, 1H), 7.41-7.37 (m, 1H), 7.21-7.19 (m, 1H), 7.08 (s, 1H), 7.00-6.97 (m, 2H), 6.90 (s, 1H), 6.86 (d, J = 2.8 Hz, 1H), 6.74-6.71 (m, 1H), 3.87 (br, 4H), 3.65 (s, 2H), 2.66 (br, 4H) | 459.2 |
| 322 | 1-(2-((2-methyl-[1,1'-biphenyl]-3-yl)methyl)-2,8-diazaspiro[4.5]decane-8-carbonyl)-1H-pyrazole-3-carboxylic acid | 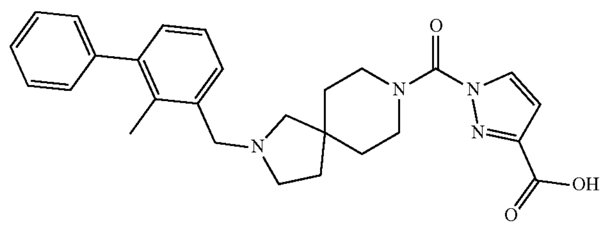 [SMILES: Cc1c(CN2CCC3(CCN(C(=O)n4ccc(C(=O)O)n4)CC3)C2)cccc1-c1ccccc1] | δ 8.05 (d, J = 2.7 Hz, 1H),7.53-7.33 (m, 5H), 7.30-7.25 (m, 3H), 6.76 (d, J = 2.7 Hz, 1H), 4.42 (s, 2H), 3.90-3.85 (m, 2H), 3.72-3.68 (m, 2H), 3.46-3.42 (m, 2H), 3.34-3.30 (m, 2H), 2.32 (s, 3H), 2.06 (t, J = 7.2 Hz, 2H), 1.87-1.78 (m, 4H) | 459.3 |
| 323 | 4-chloro-1-(4-(3-chloro-5-(pyrimidin-5-yl)benzyl)-piperazine-1-carbonyl)-1H-pyrazole-3-carboxylic acid | 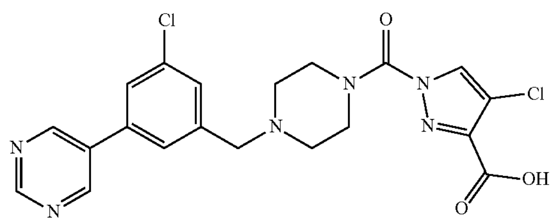 [SMILES: O=C(O)c1nn(C(=O)N2CCN(Cc3cc(Cl)cc(-c4cncnc4)c3)CC2)cc1Cl] | δ 9.15 (d, J = 4.8 Hz, 1H), 9.09 (s, 2H), 9.18 (s, 1H), 7.71 (t, J = 1.8 Hz, 1H), 7.67 (s, 1H), 7.55 (s, 1H), 3.86 (br, 4H), 3.71 (s, 2H), 2.66 (br, 4H) | 461.4 |
| 324 | 1-(2-(3-(pyridin-2-yloxy)benzyl)-2,8-diazaspiro[4.5]decane-8-carbonyl)-1H-pyrazole-3-carboxylic acid | 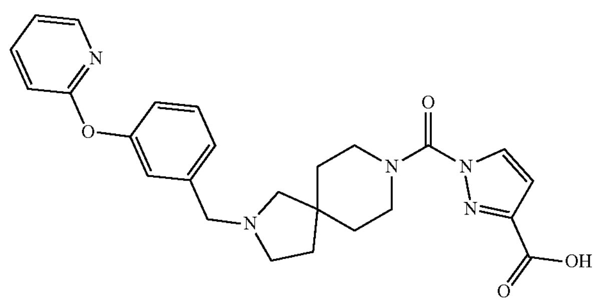 [SMILES: O=C(O)c1ccn(C(=O)N2CCC3(CCN(Cc4cccc(Oc5ccccn5)c4)C3)CC2)n1] | δ 8.12-8.10 (m, 1H), 8.03 (d, J = 2.7 Hz, 1H), 7.82-7.80 (m, 1H), 7.50-7.45 (m, 1H), 7.36-7.30 (m, 1H), 7.28 (s, 1H), 7.20-7.10 (m, 2H), 6.99 (d, J = 8.1 Hz, 1H), 6.72 (d, J = 2.7 Hz, 1H), 4.25 (s, 2H), 3.82-3.79 (m, 2H), 3.70-3.63 (m, 2H), 3.42-3.31 (m, 2H), 3.15 (br, 2H), 2.00 (t, J = 7.2 Hz, 2H), 1.82-1.71 (m, 4H) | 462.3 |

| Ex | Name | Structure | NMR (¹H NMR, 300 MHz or 400 MHz, Methanol-d) | MS [M + H]⁺ |
|---|---|---|---|---|
| 325 | (R)-1-(2-methyl-4-(2-(pyrrolidin-1-yl)-4-(trifluoromethyl)-benzyl)piperazine-1-carbonyl)-1H-pyrazole-3-carboxamide | 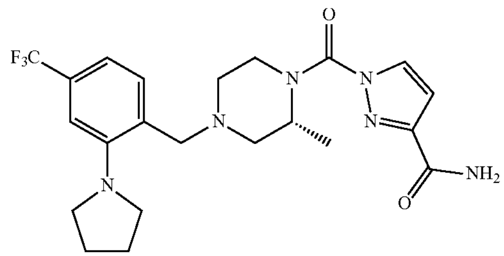 [SMILES: C[C@@H]1CN(Cc2ccc(C(F)(F)F)cc2N2CCCC2)CCN1C(=O)n1ccc(C(N)=O)n1] | δ 8.10 (d, J = 2.7 Hz, 1H), 7.54 (d, J = 7.8 Hz, 1H), 7.12-7.10 (m, 2H), 6.92 (d, J = 2.7 Hz, 1H), 6.66 (br, 1H), 5.52 (br, 1H), 4.65 (br, 1H), 4.29-4.25 (m, 1H), 3.56-3.45 (m, 3H), 3.34-3.23 (m, 4H), 2.90-2.87 (m, 1H), 2.72-2.68 (m, 1H), 2.38-2.20 (m, 2H), 2.03-1.92 (m, 4H), 1.51 (d, J = 6.6 Hz, 3H) | 465.3 |
| 326 | (S)-1-(2-methyl-4-(2-(pyrrolidin-1-yl)-4-(trifluoromethyl)-benzyl)-piperazine-1-carbonyl)-1H-pyrazole-3-carboxamide | 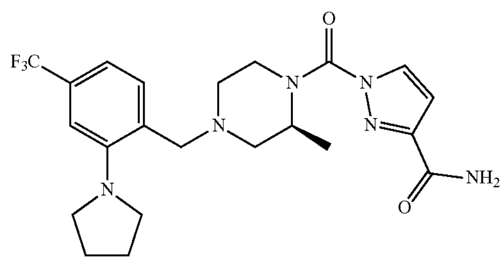 [SMILES: C[C@H]1CN(Cc2ccc(C(F)(F)F)cc2N2CCCC2)CCN1C(=O)n1ccc(C(N)=O)n1] | (Chloroform-d) δ 8.08 (d, J = 2.7 Hz, 1H), 9.53 (d, J = 6.9 Hz, 1H), 7.26-7.10 (m, 2H), 6.70 (d, J = 2.7 Hz, 1H), 6.64 (br, 1H), 5.48 (br, 1H), 4.63 (br, 1H), 4.27-4.23 (m, 1H), 3.55-3.32 (m, 3H), 3.38-3.18 (m, 4H), 2.88-2.81 (m, 1H), 2.70-2.61 (m, 1H), 2.35-2.32 (m, 1H), 2.32-2.19 (m, 1H), 2.01-1.92 (m, 4H), 1.26 (d, J = 5.4 Hz, 3H) | 465.2 |
| 327 | (R)-1-(2-methyl-4-(2-(pyrrolidin-1-yl)-4-(trifluoromethyl)-benzyl)-piperazine-1-carbonyl)-1H-pyrazole-3-carboxylic acid | 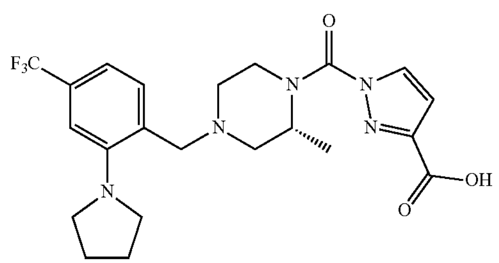 [SMILES: C[C@@H]1CN(Cc2ccc(C(F)(F)F)cc2N2CCCC2)CCN1C(=O)n1ccc(C(=O)O)n1] | δ 8.11 (d, J = 2.7 Hz, 1H), 7.58 (d, J = 7.5 Hz, 1H), 7.16-7.09 (m, 2H), 6.82 (d, J = 2.7 Hz, 1H), 4.66-4.61 (m, 1H), 4.28-4.23 (m, 1H), 3.63 (s, 2H), 3.56-3.45 (m, 1H), 3.32-3.22 (m, 4H), 2.92-2.82 (m, 1H), 2.74-2.67 (m, 1H), 2.42-2.30 (m, 1H), 2.30-2.22 (m, 1H), 2.09-1.97 (m, 4H), 1.46 (d, J = 6.6 Hz, 3H) | 466.3 |
| 328 | (S)-1-(2-methyl-4-(2-(pyrrolidin-1-yl)-4-(trifluoromethyl)-benzyl)-piperazine-1-carbonyl)-1H-pyrazole-3-carboxylic acid | 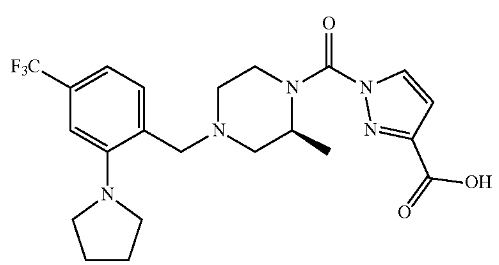 [SMILES: C[C@H]1CN(Cc2ccc(C(F)(F)F)cc2N2CCCC2)CCN1C(=O)n1ccc(C(=O)O)n1] | δ 8.11 (d, J = 2.7 Hz, 1H), 7.59 (d, J = 7.8 Hz, 1H), 7.12-7.09 (m, 2H), 6.83 (d, J = 2.7 Hz, 1H), 4.63 (br, 1H), 4.28-4.24 (m, 1H), 3.63 (s, 2H), 3.56-3.41 (m, 1H), 3.34-3.26 (m, 4H), 2.91-2.86 (m, 1H), 2.75-2.68 (m, 1H), 2.39-2.30 (m, 1H), 2.29-2.21 (m, 1H), 2.04-1.98 (m, 4H), 1.46 (d, J = 6.6 Hz, 3H) | 466.2 |

| Ex | Name | Structure | NMR (¹H NMR, 300 MHz or 400 MHz, Methanol-d) | MS [M + H]⁺ |
|---|---|---|---|---|
| 329 | (S)-1-(2-methyl-4-(4-(pyrrolidin-1-yl)-2-(trifluoromethyl)-benzyl)-piperazine-1-carbonyl)-1H-pyrazole-3-carboxylic acid | 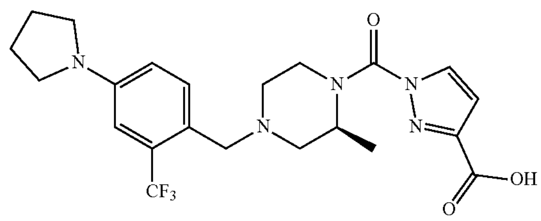 [SMILES: C[C@H]1CN(Cc2ccc(N3CCCC3)cc2C(F)(F)F)CCN1C(=O)n1ccc(C(=O)O)n1] | δ 8.12 (d, J = 2.7 Hz, 1H), 7.50 (d, J = 8.1 Hz, 1H), 6.83 (d, J = 2.7 Hz, 1H), 6.76-6.74 (m, 2H), 4.60 (br, 1H), 4.23-4.18 (m, 1H), 3.56-3.51 (m, 2H), 3.51-3.31 (m, 1H), 3.30-3.28 (m, 4H), 2.89-2.80 (m, 1H), 2.76-2.72 (m, 1H), 2.39-2.29 (m, 1H), 2.34-2.12 (m, 1H), 2.12-2.02 (m, 4H), 1.43 (d, J = 6.6 Hz, 3H) | 466.2 |
| 330 | (R)-1-(2-methyl-4-(4-(pyrrolidin-1-yl)-2-(trifluoromethyl)-benzyl)-piperazine-1-carbonyl)-1H-pyrazole-3-carboxylic acid | 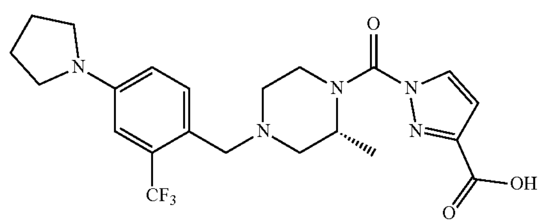 | δ 8.11 (d, J = 2.7 Hz, 1H), 7.51 (d, J = 8.1 Hz, 1H), 6.81 (d, J = 2.7 Hz, 1H), 6.76-6.74 (m, 2H), 4.62 (br, 1H), 4.24-4.17 (m, 1H), 2.55-2.50 (m, 2H), 3.49-3.32 (m, 1H), 3.30-3.28 (m, 4H), 2.88-2.84 (m, 1H), 2.75-2.71 (m, 1H), 2.37-2.32 (m, 1H), 2.32-2.14 (m, 1H), 2.06-2.02 (m, 4H), 1.42 (d, J = 6.9 Hz, 3H) | 466.2 |
| 331 | 1-(4-((3-(pyrrolidin-1-yl)-5-(trifluoromethyl)-benzyl)oxy)piperidine-1-carbonyl)-1H-pyrazole-3-carboxylic acid | 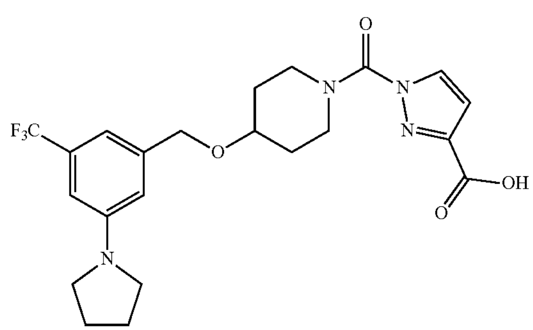 [SMILES: O=C(O)c1ccn(C(=O)N2CCC(OCc3cc(N4CCCC4)cc(C(F)(F)F)c3)CC2)n1] | δ 8.05 (d, J = 2.8 Hz, 1H), 6.85 (s, 1H), 6.77-6.76 (m, 2H), 6.65 (s, 1H), 4.58 (s, 2H), 4.03 (br, 2H), 3.78-3.72 (m, 1H), 3.62-3.58 (m, 2H), 3.32-3.28 (m, 4H), 2.07-1.99 (m, 6H), 1.85-1.75 (m, 2H) | 467.1 |

| Ex | Name | Structure | NMR (¹H NMR, 300 MHz or 400 MHz, Methanol-d) | MS [M + H]⁺ |
|---|---|---|---|---|
| 332 | (S)-1-(4-(2-(3-hydroxypyrrolidin-1-yl)-4-(trifluoromethyl)-benzyl)-piperazine-1-carbonyl)-1H-pyrazole-3-carboxylic acid | 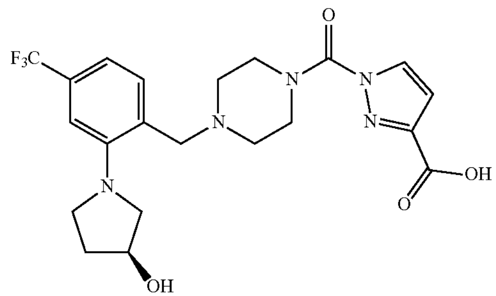 [SMILES: O=C(O)c1ccn(C(=O)N2CCN(Cc3ccc(C(F)(F)F)cc3N3CC[C@H](O)C3)CC2)n1] | δ 8.12 (d, J = 2.7 Hz, 1H), 7.60-7.57 (m, 1H), 7.30-7.25 (m, 1H), 7.25-7.23 (m, 1H), 6.83 (d, J = 2.7 Hz, 1H), 4.53-4.49 (m, 1H), 4.09-3.94 (m, 6H), 3.57-3.49 (m, 1H), 3.46-3.41 (m, 1H), 3.28-3.12 (m, 2H), 2.88 (br, 4H), 2.30-2.18 (m, 1H), 1.99-1.95 (m, 1H) | 468.2 |
| 333 | (R)-1-(4-(2-(3-hydroxypyrrolidin-1-yl)-4-(trifluoromethyl)-benzyl)-piperazine-1-carbonyl)-1H-pyrazole-3-carboxylic acid | 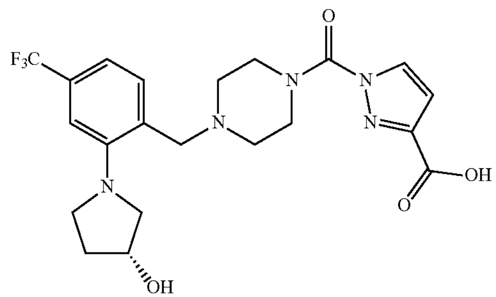 | δ 8.13 (d, J = 2.4 Hz, 1H), 7.60-7.57 (m, 1H), 7.28 (s, 1H), 7.24-7.21 (m, 1H), 6.81 (d, J = 2.4 Hz, 1H), 4.52-4.49 (m, 1H), 4.18-3.71 (m, 6H), 3.67-3.31 (m, 2H), 3.30-3.17 (m, 2H), 2.85 (br, 4H), 2.29-2.18 (m, 1H), 1.99-1.94 (m, 1H) | 468.2 |
| 334 | 1-((2R,4S)-4-((3-(4-chlorophenoxy)-benzyl)oxy)-2-methylpiperidine-1-carbonyl)-1H-pyrazole-3-carboxylic acid | 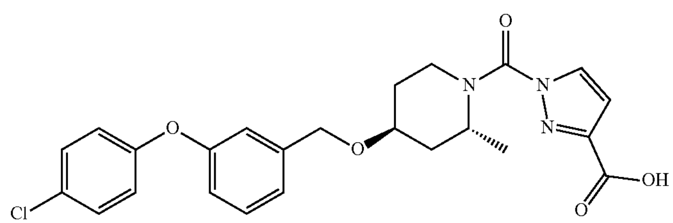 [SMILES: C[C@@H]1C[C@@H](OCc2cccc(Oc3ccc(Cl)cc3)c2)CCN1C(=O)n1ccc(C(=O)O)n1] | δ 8.24-8.00 (br, 1H), 7.43-7.26 (m, 3H), 7.16 (d, J = 7.7 Hz, 1H), 7.05-6.90 (m, 4H), 6.90-6.78 (br, 1H), 4.87-4.72 (m, 1H), 4.60 (s, 2H), 4.42-4.26 (m, 1H), 4.00-3.80 (m, 1H), 3.31-3.19 (m, 1H), 2.23-1.97 (m, 2H), 1.80-1.50 (m, 2H), 1.38 (d, J = 7.0 Hz, 3H) | 487.2 [M + NH₄]⁺ |

-continued

| Ex | Name | Structure | NMR (¹H NMR, 300 MHz or 400 MHz, Methanol-d) | MS [M + H]⁺ |
|---|---|---|---|---|
| 335 | 1-((2S,4R)-4-((3-(4-chlorophenoxy)benzyl)oxy)-2-methylpiperidine-1-carbonyl)-1H-pyrazole-3-carboxylic acid | 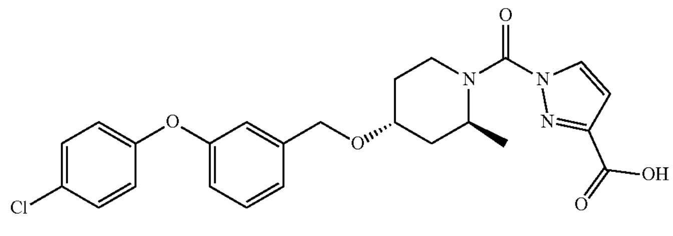 [SMILES: C[C@H]1C[C@H](OCc2cccc(Oc3ccc(Cl)cc3)c2)CCN1C(=O)n1ccc(C(=O)O)n1] | δ 8.02 (d, J = 2.7 Hz, 1H), 7.36-7.30 (m, 3H), 7.14-7.11 (m, 1H), 6.98 (s, 1H), 6.97-6.93 (m, 2H), 6.91-6.88 (m, 1H), 6.73 (d, J = 2.7 Hz, 1H), 4.91 (br, 1H), 4.57 (br, 2H), 4.44-4.38 (m, 1H), 3.88-3.82 (m, 1H), 3.25-3.21 (m, 1H), 2.14-2.09 (m, 1H), 2.04-1.98 (m, 1H), 1.74-1.68 (m, 1H), 1.59-1.54 (m, 1H), 1.33 (d, J = 7.2 Hz, 3H) | 492.0 [M + Na]⁺ |
| 336 | 1-((2S,4S)-4-((3-(4-chlorophenoxy)benzyl)oxy)-2-methylpiperidine-1-carbonyl)-1H-pyrazole-3-carboxylic acid | 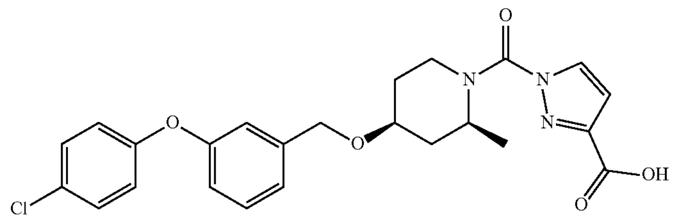 [SMILES: C[C@H]1C[C@@H](OCc2cccc(Oc3ccc(Cl)cc3)c2)CCN1C(=O)n1ccc(C(=O)O)n1] | δ 8.02 (d, J = 2.4 Hz, 1H), 7.36-7.30 (m, 3H), 7.14-7.12 (m, 1H), 7.01 (s, 1H), 6.98-6.94 (m, 2H), 6.92-6.89 (m, 1H), 6.75 (d, J = 2.4 Hz, 1H), 4.62-4.59 (m, 1H), 4.55 (s, 2H), 4.14-4.10 (m, 1H), 3.86-3.84 (m, 1H), 3.56-3.46 (m, 1H), 1.95-1.86 (m, 4H), 1.46 (d, J = 6.6 Hz, 3H) | 492.2 [M + Na]⁺ |
| 337 | 1-(2-(2,3,5-trichlorobenzyl)-2,8-diazaspiro[4.5]decane-8-carbonyl)-1H-pyrazole-3-carboxylic acid | 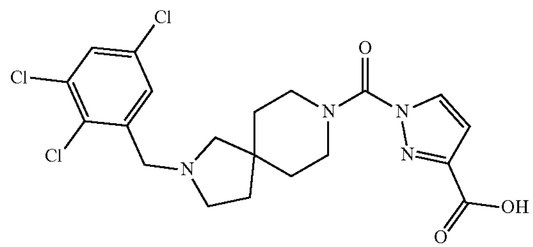 [SMILES: O=C(O)c1ccn(C(=O)N2CCC3(CCN(Cc4cc(Cl)cc(Cl)c4Cl)C3)CC2)n1] | δ 8.02 (d, J = 2.7 Hz, 1H), 7.52 (s, 2H), 6.74 (d, J = 2.7 Hz, 1H), 3.79-3.54 (m, 6H), 2.77-2.72 (m, 2H), 2.61 (s, 2H), 1.82-1.71 (m, 6H) | 471.2 |
| 338 | 4-chloro-1-(2-(3,5-dichlorobenzyl)-2,8-diazaspiro[4.5]decane-8-carbonyl)-1H-pyrazole-3-carboxylic acid | 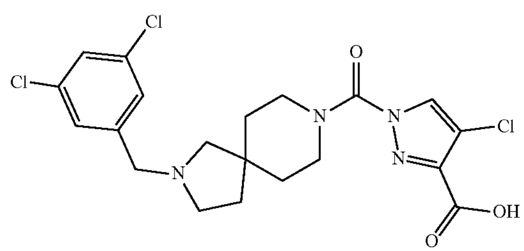 [SMILES: O=C(O)c1nn(C(=O)N2CCC3(CCN(Cc4cc(Cl)cc(Cl)c4)C3)CC2)cc1Cl] | δ 8.12 (s, 1H), 7.61-7.51 (m, 3H), 4.21 (s, 2H), 3.80 (br, 2H), 3.68 (br, 2H), 3.32-3.25 (m, 2H), 3.13 (s, 2H), 2.00 (t, J = 7.2 Hz, 2H), 1.85-1.73 (m, 4H) | 471.0 |

| Ex | Name | Structure | NMR (¹H NMR, 300 MHz or 400 MHz, Methanol-d) | MS [M + H]⁺ |
|---|---|---|---|---|
| 339 | 1-(2-(2-chloro-3-(trifluoromethyl)-benzyl)-2,8-diazaspiro[4.5]-decane-8-carbonyl)-1H-pyrazole-3-carboxylic acid | 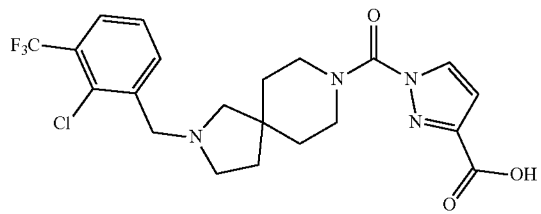 [SMILES: O=C(O)c1ccn(C(=O)N2CCC3(CCN(Cc4cccc(C(F)(F)F)c4Cl)C3)CC2)n1] | δ 8.07 (d, J = 2.7 Hz, 1H), 7.97-7.87 (m, 1H), 7.82-7.79 (m, 1H), 7.57-7.52 (m, 1H), 6.78 (d, J = 2.7 Hz, 1H), 4.25-4.23 (m, 2H), 3.81-3.70 (m, 2H), 3.70-3.54 (m, 2H), 3.14-3.12 (m, 2H), 3.07-2.97 (m, 2H), 1.96-1.91 (m, 2H), 1.84-1.73 (m, 4H) | 471.2 |
| 340 | 1-(2-(3-chloro-2-(trifluoromethyl)-benzyl)-2,8-diazaspiro[4.5]-decane-8-carbonyl)-1H-pyrazole-3-carboxylic acid | 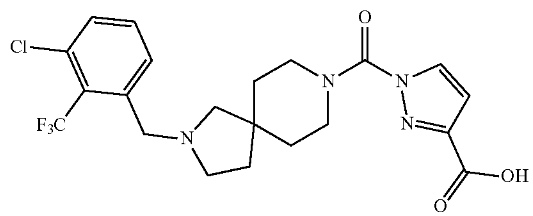 [SMILES: O=C(O)c1ccn(C(=O)N2CCC3(CCN(Cc4cccc(Cl)c4C(F)(F)F)C3)CC2)n1] | δ 8.01 (d, J = 3.0 Hz, 1H), 7.65-7.59 (m, 1H), 7.53-7.48 (m, 2H), 6.73 (d, J = 3.0 Hz, 1H), 3.81-3.57 (m, 6H), 2.65-2.61 (m, 2H), 2.47 (s, 2H), 1.80-1.64 (m, 6H) | 471.5 |
| 341 | 4-chloro-1-(trans-5-((2-methyl-3-(trifluoromethyl)-benzyl)oxy)-octahydrocyclopenta-[c]pyrrole-2-carbonyl)-1H-pyrazole-3-carboxylic acid | 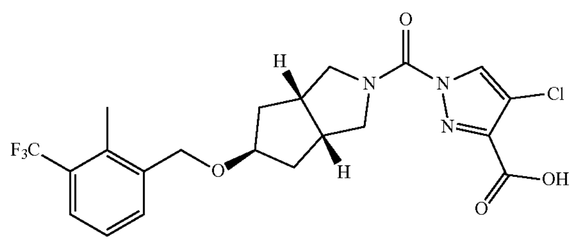 | δ 8.21 (s, 1H), 7.60 (d, J = 7.8 Hz, 2H), 7.31 (t, J = 7.8 Hz, 1H), 4.55 (s, 2H), 4.28-4.21 (m, 1H), 4.23-3.43 (m, 4H), 2.88 (br, 2H), 2.40 (d, J = 1.2 Hz, 3H), 2.21-2.08 (m, 2H), 1.85-1.71 (m, 2H) | 472.2 |
| 342 | 1-(2-(5-chloro-2-(pyrrolidin-1-yl)benzyl)-2,8-diazaspiro[4.5]-decane-8-carbonyl)-1H-pyrazole-3-carboxylic acid | 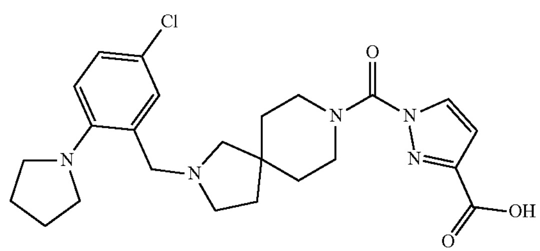 [SMILES: O=C(O)c1ccn(C(=O)N2CCC3(CCN(Cc4cc(Cl)ccc4N4CCCC4)C3)CC2)n1] | δ 8.06 (d, J = 2.7 Hz, 1H), 7.49-7.48 (m, 1H), 7.38-7.34 (m, 1H), 7.24-7.21 (m, 1H), 6.76 (d, J = 2.7 Hz, 1H), 4.40 (s, 2H), 3.87 (br, 2H), 3.61 (br, 2H), 3.38-3.32 (m, 2H), 3.19-3.10 (m, 6H), 2.07-1.99 (m, 6H), 1.86-1.74 (m, 4H) | 472.2 |

| Ex | Name | Structure | NMR (¹H NMR, 300 MHz or 400 MHz, Methanol-d) | MS [M + H]⁺ |
|---|---|---|---|---|
| 343 | 1-(2-(4-chloro-3-(pyrrolidin-1-yl)benzyl)-2,8-diazaspiro[4.5]decane-8-carbonyl)-1H-pyrazole-3-carboxylic acid | 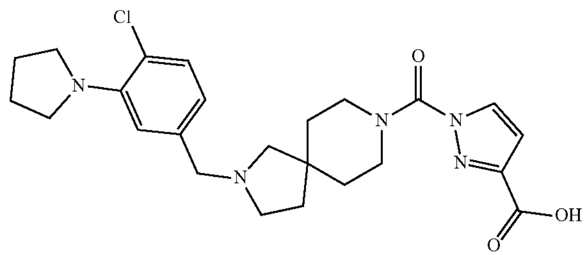 [SMILES: O=C(O)c1ccn(C(=O)N2CCC3(CCN(Cc4ccc(Cl)c(N5CCCC5)c4)C3)CC2)n1] | δ 8.05 (d, J = 2.7 Hz, 1H), 7.32 (d, J = 8.1 Hz, 1H), 7.14 (d, J = 2.7 Hz, 1H), 6.93-6.89 (m, 1H), 6.76 (d, J = 2.7 Hz, 1H), 4.31 (s, 2H), 3.84-3.80 (m, 2H), 3.72-3.66 (m, 2H), 3.43-3.32 (m, 6H), 3.32-3.30 (m, 2H), 2.06 (t, J = 7.2 Hz, 2H), 1.96-1.90 (m, 4H), 1.83-1.76 (m, 4H) | 472.3 |
| 344 | 1-(1-(3-chloro-5-(pyrrolidin-1-yl)benzyl)-1,8-diazaspiro[4.5]-decane-8-carbonyl)-1H-pyrazole-3-carboxylic acid | 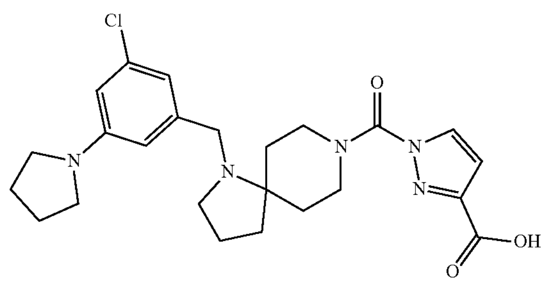 [SMILES: O=C(O)c1ccn(C(=O)N2CCC3(CCCN3Cc3cc(Cl)cc(N4CCCC4)c3)CC2)n1] | (DMSO-d₆) δ 8.27 (d, J = 2.4 Hz, 1H), 6.86 (d, J = 2.4 Hz, 1H), 6.56 (s, 1H), 6.43-6.37 (m, 2H), 4.28-4.25 (m, 2H), 3.57 (br, 2H), 3.22-3.16 (m, 6H), 2.68 (br, 2H), 1.95-1.92 (m, 4H), 1.86-1.74 (m, 6H), 1.48 (br, 2H) | 472.2 |
| 345 | 1-(trans-5-(4-chloro-3-(thiazol-2-yl)benzyl)oxy)octahydrocyclopenta-[c]pyrrole-2-carbonyl)-1H-pyrazole-3-carboxylic acid | 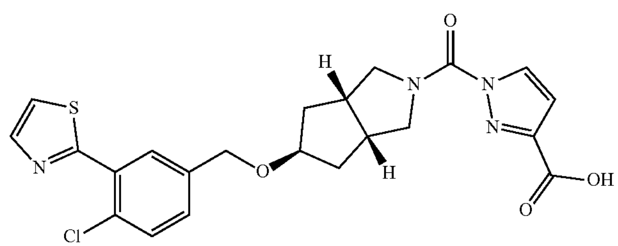 [SMILES: O=C(O)c1ccn(C(=O)N2C[C@H]3C[C@H](OCc4ccc(Cl)c(-c5nccs5)c4)C[C@H]3C2)n1] | δ 8.21 (d, J = 2.4 Hz, 1H), 8.06 (d, J = 2.0 Hz, 1H), 7.94 (d, J = 3.2 Hz, 1H), 7.78 (d, J = 3.2 Hz, 1H), 7.55 (d, J = 8.4 Hz, 1H), 7.49-7.39 (m, 1H), 6.78 (d, J = 2.8 Hz 1H), 4.52 (s 2H) 4.38-4.21 (m, 1H), 4.20-3.50 (m, 4H), 3.02-2.80 (m, 2H), 2.26-2.02 (m, 2H), 1.86-1.65 (m, 2H) | 473.0 |
| 346 | 1-(4-(3-(4-chlorophenoxy)-5-fluorobenzyl)-piperazine-1-carbonyl)-4-methyl-1H-pyrazole-3-carboxylic acid | 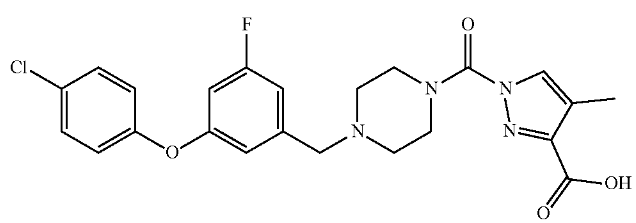 [SMILES: Cc1cn(C(=O)N2CCN(Cc3cc(F)cc(Oc4ccc(Cl)cc4)c3)CC2)nc1C(=O)O] | δ 7.93 (s, 1H), 7.42-7.39 (m, 2H), 7.07-7.03 (m, 2H), 6.95-6.92 (m, 1H), 6.86 (s, 1H), 6.69-6.65 (m, 1H), 3.84 (br, 4H), 3.60 (s, 2H), 2.60 (br, 4H), 2.28 (s, 3H) | 473.1 |

| Ex | Name | Structure | NMR (¹H NMR, 300 MHz or 400 MHz, Methanol-d) | MS [M + H]⁺ |
|---|---|---|---|---|
| 347 | (S)-1-(4-(3-(4-chlorophenoxy)-5-fluorobenzyl)-2-methylpiperazine-1-carbonyl)-1H-pyrazole-3-carboxylic acid | 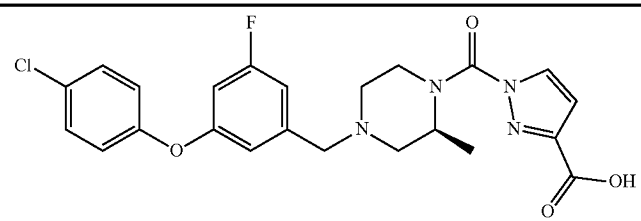 | δ 8.09 (d, J = 2.4 Hz, 1H), 7.39 (d, J = 2.4 Hz, 2H), 7.03 (d, J = 2.0 Hz, 2H), 6.89 (d, J = 8.8 Hz, 1H), 6.83-6.79 (m, 2H), 6.66 (d, J = 2.4 Hz, 1H), 4.64 (s, 1H), 4.27 (d, J = 12.4 Hz, 1H), 3.57 (d, J = 16.0 Hz, 1H), 3.49-3.40 (m, 2H), 2.85 (d, J = 10.8 Hz, 1H), 2.70 (d, J = 11.2 Hz, 1H), 2.34-2.22 (m, 2H), 1.38 (d, J = 6.8 Hz, 3H) | 473.2 |
| 348 | (R)-1-(4-(3-(4-chlorophenoxy)-5-fluorobenzyl)-2-methylpiperazine-1-carbonyl)-1H-pyrazole-3-carboxylic acid | 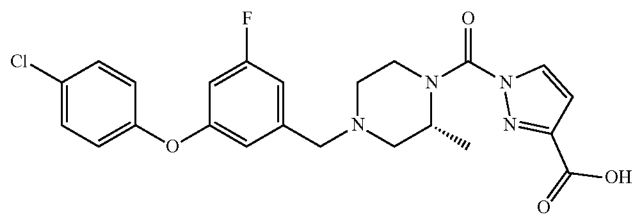 [SMILES: C[C@@H]1CN(Cc2cc(F)cc(Oc3ccc(Cl)cc3)c2)CCN1C(=O)n1ccc(C(=O)O)n1] | δ 8.11 (d, J = 2.4 Hz, 1H), 7.40-7.36 (m, 2H), 7.05-7.01 (m, 2H), 6.89 (d, J = 8.8 Hz, 1H), 6.83-6.79 (m, 2H), 6.67-6.63 (m, 1H), 4.60 (s, 1H), 4.23 (d, J = 13.2 Hz, 1H), 3.56 (d, J = 13.6 Hz, 1H), 3.49-3.41 (m, 2H), 2.86 (d, J = 11.6 Hz, 1H), 2.71 (d, J = 11.6 Hz, 1H), 2.34-2.23 (m, 2H), 1.38 (d, J = 6.8 Hz, 3H) | 473.2 |
| 349 | (S)-1-(4-(3-(2-chlorophenoxy)-5-fluorobenzyl)-2-methylpiperazine-1-carbonyl)-1H-pyrazole-3-carboxylic acid | 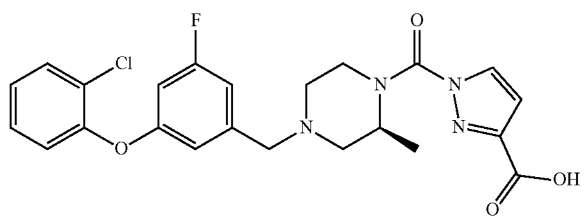 [SMILES: C[C@H]1CN(Cc2cc(F)cc(Oc3ccccc3Cl)c2)CCN1C(=O)n1ccc(C(=O)O)n1] | δ 8.10 (d, J = 2.4 Hz, 1H), 7.53-7.51 (m, 1H), 7.38-7.33 (m, 1H), 7.25-7.21 (m, 1H), 7.16-7.13 (m, 1H), 6.85-6.81 (m, 2H), 6.72 (s, 1H), 6.58-6.55 (m, 1H), 4.60 (br, 1H), 4.22 (d, J = 13.6 Hz, 1H), 3.57 (d, J = 13.6 Hz, 1H), 3.47-3.39 (m, 2H), 2.86-2.83 (m, 1H), 2.70-2.67 (m, 1H), 2.32-2.24 (m, 2H), 1.35 (d, J = 6.8 Hz, 3H) | 473.2 |
| 350 | (R)-1-(4-(3-(2-chlorophenoxy)-5-fluorobenzyl)-2-methylpiperazine-1-carbonyl)-1H-pyrazole-3-carboxylic acid | 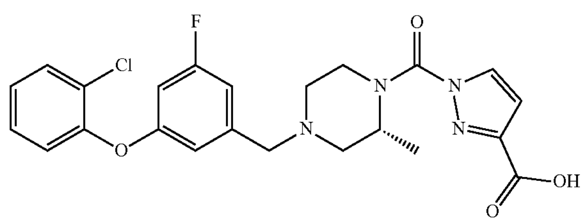 [SMILES: C[C@@H]1CN(Cc2cc(F)cc(Oc3ccccc3Cl)c2)CCN1C(=O)n1ccc(C(=O)O)n1] | δ 8.12 (d, J = 2.8 Hz, 1H), 7.54-7.51 (m, 1H), 7.38-7.34 (m, 1H), 7.25-7.21 (m, 1H), 7.16-7.14 (m, 1H), 6.85-6.83 (m, 2H), 6.72 (s, 1H), 6.59-6.56 (m, 1H), 4.58 (br, 1H), 4.20 (d, J = 13.6 Hz, 1H), 3.57 (d, J = 13.6 Hz, 1H), 3.47-3.39 (m, 2H), 2.86-2.83 (m, 1H), 2.70-2.67 (m, 1H), 2.33-2.22 (m, 2H), 1.35 (d, J = 6.8 Hz, 3H) | 473.1 |

| Ex | Name | Structure | NMR (¹H NMR, 300 MHz or 400 MHz, Methanol-d) | MS [M + H]⁺ |
|---|---|---|---|---|
| 351 | (R)-1-(2-methyl-4-((3-(trifluoromethyl)-[1,1'-biphenyl]-4-yl)methyl)-piperazine-1-carbonyl)-1H-pyrazole-3-carboxylic acid | 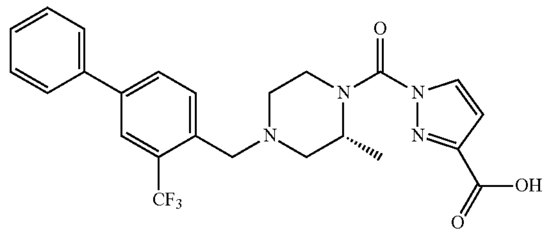 [SMILES: C[C@@H]1CN(Cc2ccc(-c3ccccc3)cc2C(F)(F)F)CCN1C(=O)n1ccc(C(=O)O)n1] | δ 8.08 (d, J = 2.7 Hz, 1H), 7.95-7.85 (m, 3H), 7.67-7.64 (m, 2H), 7.50-7.36 (m, 3H), 6.78 (d, J = 2.7 Hz, 1H), 4.70 (br, 1H), 4.33-4.29 (m, 1H), 3.72 (s, 2H), 3.56-3.47 (m, 1H), 2.91-2.75 (m, 2H), 2.46-2.26 (m, 2H), 1.48 (d, J = 6.9 Hz, 3H) | 473.2 |
| 352 | 1-(4-(3-((4-(trifluoromethyl)-pyridin-3-yl)oxy)-benzyl)-piperazine-1-carbonyl)-1H-pyrazole-3-carboxylic acid | 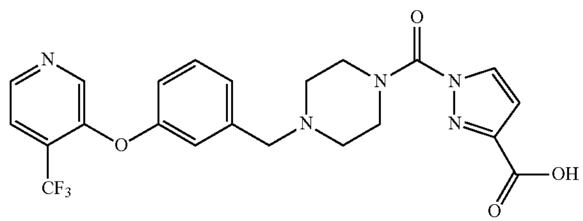 [SMILES: O=C(O)c1ccn(C(=O)N2CCN(Cc3cccc(Oc4cnccc4C(F)(F)F)c3)CC2)n1] | δ 8.53 (d, J = 4.8 Hz, 1H), 8.32 (s, 1H), 8.12 (d, J = 2.7 Hz, 1H), 7.77 (d, J = 4.8 Hz, 1H), 7.48-7.43 (m, 1H), 7.30 (d, J = 7.5 Hz, 1H), 7.20 (br, 1H), 7.05 (d, J = 8.1 Hz, 1H), 6.80 (d, J = 2.7 Hz, 1H), 3.89 (br, 4H), 3.72 (br, 2H), 2.70 (br, 4H) | 476.5 |
| 353 | 1-(4-(3-((6-(trifluoromethyl)-pyridin-2-yl)oxy)-benzyl)-piperazine-1-carbonyl)-1H-pyrazole-3-carboxylic acid | 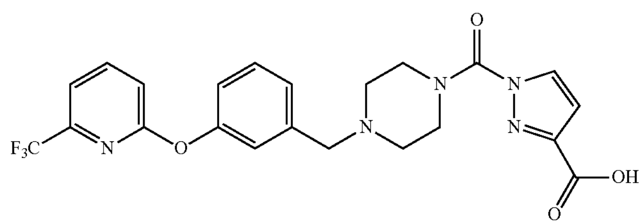 [SMILES: O=C(O)c1ccn(C(=O)N2CCN(Cc3cccc(Oc4cccc(C(F)(F)F)n4)c3)CC2)n1] | δ 8.14 (d, J = 2.7 Hz, 1H), 8.04-7.98 (m, 1H), 7.50-7.42 (m, 2H), 7.31-7.28 (m, 1H), 7.25-7.23 (m, 1H), 7.23-7.20 (m, 1H), 7.16-7.13 (m, 1H), 6.82 (d, J = 2.7 Hz, 1H), 4.02-3.84 (m, 6H), 2.83 (br, 4H) | 476.2 |
| 354 | 1-(4-(3-((6-(trifluoromethyl)-pyridin-3-yl)oxy)benzyl)-piperazine-1-carbonyl)-1H-pyrazole-3-carboxylic acid | 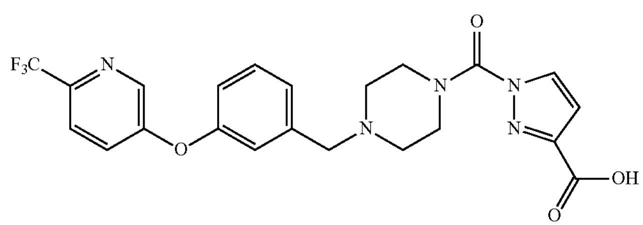 [SMILES: O=C(O)c1ccn(C(=O)N2CCN(Cc3cccc(Oc4ccc(C(F)(F)F)nc4)c3)CC2)n1] | δ 8.43 (d, J = 3.3 Hz, 1H), 8.09 (d, J = 2.7 Hz, 1H), 7.80-7.77 (m, 1H), 7.52-7.47 (m, 1H), 7.45-7.42 (m, 1H), 7.30-7.28 (m, 1H), 7.20 (s, 1H), 7.09-7.07 (m, 1H), 6.78 (d, J = 2.7 Hz, 1H), 3.85 (br, 4H), 3.64 (s, 2H), 2.62 (t, J = 4.8 Hz, 4H) | 476.3 |

| Ex | Name | Structure | NMR (¹H NMR, 300 MHz or 400 MHz, Methanol-d) | MS [M + H]⁺ |
|---|---|---|---|---|
| 355 | 1-(4-(3-((2-(trifluoromethyl)-pyridin-4-yl)oxy)benzyl)piperazine-1-carbonyl)-1H-pyrazole-3-carboxylic acid | 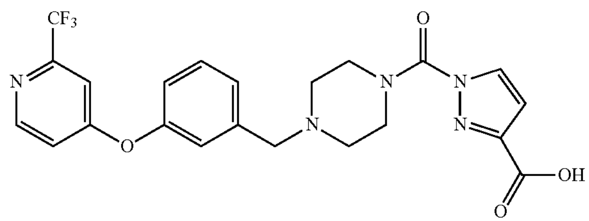 [SMILES: O=C(O)c1ccn(C(=O)N2CCN(Cc3cccc(Oc4ccnc(C(F)(F)F)c4)c3)CC2)n1] | δ 8.69 (d, J = 5.7 Hz, 1H), 8.11 (d, J = 2.7 Hz, 1H), 7.50 (t, J = 7.8 Hz, 1H), 7.38-7.35 (m, 1H), 7.33-7.32 (m, 1H), 7.25 (s, 1H), 7.14-7.09 (m, 2H), 6.79 (d, J = 2.7 Hz, 1H), 3.86 (br, 4H), 3.69 (s, 2H), 2.65 (br, 4H) | 476.3 |
| 356 | 1-(4-(3-((3-(trifluoromethyl)-pyridin-4-yl)oxy)benzyl)piperazine-1-carbonyl)-1H-pyrazole-3-carboxylic acid | 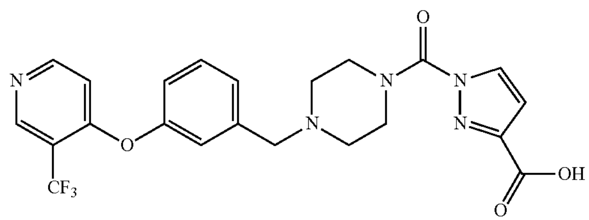 [SMILES: O=C(O)c1ccn(C(=O)N2CCN(Cc3cccc(Oc4ccncc4C(F)(F)F)c3)CC2)n1] | δ 8.77 (s, 1H), 8.58-8.56 (m, 1H), 8.12 (d, J = 2.7 Hz, 1H), 7.54-7.40 (m, 1H), 7.40-7.38 (m, 1H), 7.25 (s, 1H), 7.18-7.11 (m, 1H), 6.93-6.86 (m, 1H), 6.81 (d, J = 2.7 Hz, 1H), 3.86 (br, 4H), 3.72 (s, 2H), 2.68 (br, 4H) | 476.3 |
| 357 | 4-chloro-1-(5-(3-chloro-5-(trifluoromethyl)-benzyl)octahydropyrrolo[3,4-c]pyrrole-2-carbonyl)-1H-pyrazole-3-carboxylic acid | 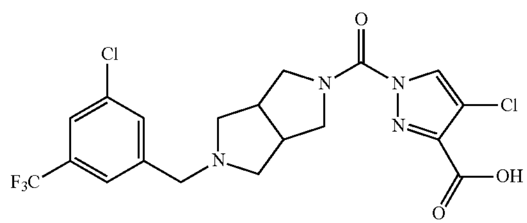 [SMILES: O=C(O)c1nn(C(=O)N2CC3CN(Cc4cc(Cl)cc(C(F)(F)F)c4)CC3C2)cc1Cl] | δ 8.28 (s, 1H), 7.78 (s, 1H), 7.72 (s, 2H), 4.08-3.82 (m, 6H), 3.14 (br, 4H), 3.00 (br, 2H) | 477.1 |
| 358 | 1-(2-((2-chloro-[1,1'-biphenyl]-3-yl)methyl)-2,8-diazaspiro[4.5]decane-8-carbonyl)-1H-pyrazole-3-carboxylic acid | 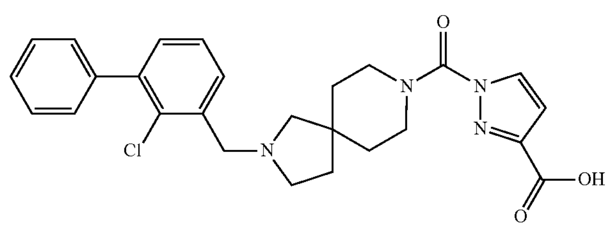 [SMILES: O=C(O)c1ccn(C(=O)N2CCC3(CCN(Cc4cccc(-c5ccccc5)c4Cl)C3)CC2)n1] | δ 8.06 (d, J = 2.7 Hz, 1H), 7.65-7.62 (d, J = 8.1 Hz, 1H), 7.48-7.35 (m, 7H), 6.77 (d, J = 2.7 Hz, 1H), 4.28 (s, 2H), 3.88-3.83 (m, 2H), 3.74-3.72 (m, 2H), 3.20 (t, J = 7.2 Hz, 2H), 3.09 (s, 2H), 1.97 (t, J = 7.2 Hz, 2H), 1.88-1.80 (m, 4H) | 479.3 |

| Ex | Name | Structure | NMR (¹H NMR, 300 MHz or 400 MHz, Methanol-d) | MS [M + H]⁺ |
|---|---|---|---|---|
| 359 | 1-(4-(2-((2R,5R)-2,5-dimethylpyrrolidin-1-yl)-4-(trifluoromethyl)benzyl)piperazine-1-carbonyl)-1H-pyrazole-3-carboxylic acid | 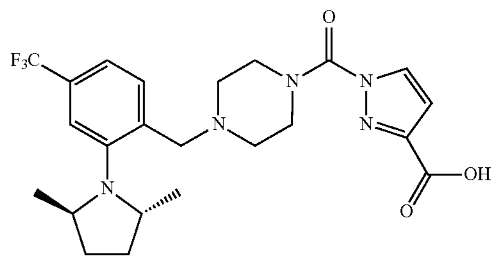 [SMILES: C[C@@H]1CC[C@@H](C)N1c1cc(C(F)(F)F)ccc1CN1CCN(C(=O)n2ccc(C(=O)O)n2)CC1] | δ 8.14 (d, J = 2.7 Hz, 1H), 7.72 (d, J = 8.7 Hz, 1H), 7.32-7.25 (m, 2H), 6.83 (d, J = 2.7 Hz, 1H), 3.87 (br, 6H), 3.72-3.54 (m, 2H), 2.71-2.59 (m, 4H), 2.38-2.08 (m, 2H), 1.63-1.57 (m, 2H), 0.91 (d, J = 6.3 Hz, 3H), 0.71 (d, J = 5.7 Hz, 3H) | 480.3 |
| 360 | 1-(4-(2-((2S,5S)-2,5-dimethylpyrrolidin-1-yl)-4-(trifluoromethyl)benzyl)piperazine-1-carbonyl)-1H-pyrazole-3-carboxylic acid | 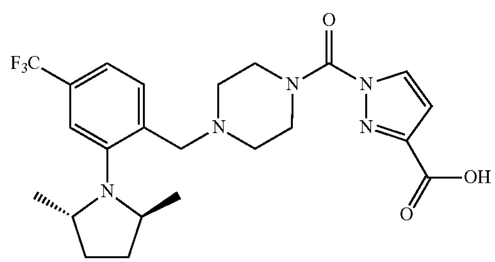 [SMILES: C[C@H]1CC[C@H](C)N1c1cc(C(F)(F)F)ccc1CN1CCN(C(=O)n2ccc(C(=O)O)n2)CC1] | δ 8.14 (d, J = 2.7 Hz, 1H), 7.72 (d, J = 8.1 Hz, 1H), 7.29-7.27 (m, 2H), 6.83 (d, J = 2.7 Hz, 1H), 3.87 (br, 6H), 3.71-3.60 (m, 2H), 2.74-2.65 (br, 4H), 2.29-2.16 (m, 2H), 1.03 (d, J = 6.0 Hz, 3H), 0.70 (d, J = 6.0 Hz, 3H) | 480.3 |
| 361 | 1-(4-methyl-4-((2-(pyrrolidin-1-yl)-4-(trifluoromethyl)benzyl)amino)piperidine-1-carbonyl)-1H-pyrazole-3-carboxylic acid | 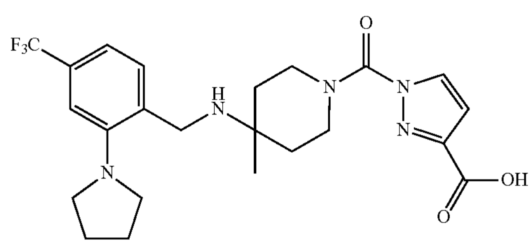 [SMILES: CC1(NCc2ccc(C(F)(F)F)cc2N2CCCC2)CCN(C(=O)n2ccc(C(=O)O)n2)CC1] | δ 8.07 (d, J = 2.7 Hz, 1H), 7.61 (d, J = 8.1 Hz, 1H), 7.44 (s, 1H), 7.35 (d, J = 8.1 Hz, 1H), 6.75 (d, J = 2.7 Hz, 1H), 4.57-4.46 (m, 2H), 4.33 (s, 2H), 3.50-3.38 (m, 2H), 3.25-3.21 (m, 4H), 2.11-1.84 (m, 8H), 1.59 (s, 3H) | 480.3 |
| 362 | 1-(4-((2-(azetidin-1-yl)-4-(trifluoromethyl)benzyl)(methyl)amino)-4-methylpiperidine-1-carbonyl)-1H-pyrazole-3-carboxylic acid | 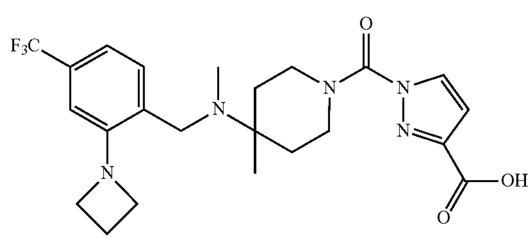 [SMILES: CN(Cc1ccc(C(F)(F)F)cc1N1CCC1)C1(C)CCN(C(=O)n2ccc(C(=O)O)n2)CC1] | δ 8.11 (d, J = 2.7 Hz, 1H), 7.64 (d, J = 7.8 Hz, 1H), 7.18 (d, J = 7.5 Hz, 1H), 6.87 (s, 1H), 6.80 (d, J = 2.7 Hz, 1H), 4.24 (br, 2H), 4.03-3.98 (m, 6H), 3.58-3.53 (m, 2H), 2.47 (s, 3H), 2.42-2.32 (m, 2H), 2.14-2.09 (m, 2H), 1.98 (br, 2H), 1.42 (s, 3H) | 480.3 |

| Ex | Name | Structure | NMR (¹H NMR, 300 MHz or 400 MHz, Methanol-d) | MS [M + H]⁺ |
|---|---|---|---|---|
| 363 | 1-(cis-5-((4-(4-chlorophenoxy)benzyl)amino)octahydrocyclopenta[c]pyrrole-2-carbonyl)-1H-pyrazole-3-carboxylic acid | 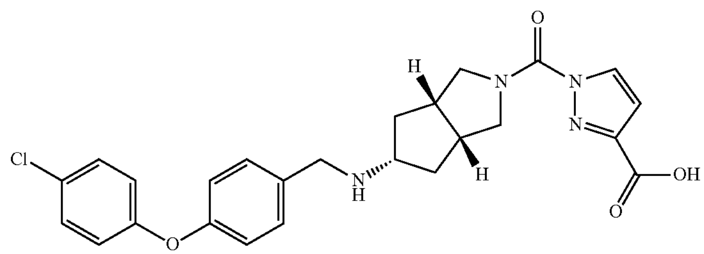 [SMILES: O=C(O)c1ccn(C(=O)N2C[C@H]3C[C@@H](NCc4ccc(Oc5ccc(Cl)cc5)cc4)C[C@H]3C2)n1] | δ 8.14 (d, J = 2.7 Hz, 1H), 7.47-7.44 (m, 2H), 7.37-7.34 (m, 2H), 7.04-6.97 (m, 4H), 6.74 (d, J = 2.7 Hz, 1H), 4.07-3.93 (m, 6H), 3.60-3.45 (m, 1H), 2.85-2.72 (m, 2H), 2.48-2.35 (m, 2H), 1.69-1.53 (m, 2H) | 481.3 |
| 364 | 1-((R)-4-(2-((S)-3-fluoropyrrolidin-1-yl)-4-(trifluoromethyl)-benzyl)-2-methylpiperazine-1-carbonyl)-1H-pyrazole-3-carboxylic acid | 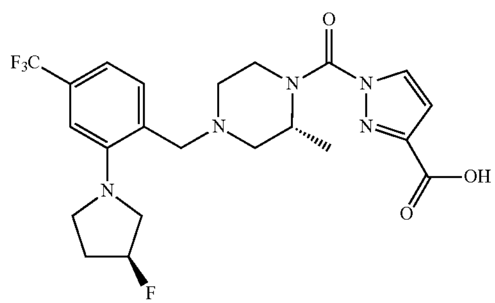 [SMILES: C[C@@H]1CN(Cc2ccc(C(F)(F)F)cc2N2CC[C@H](F)C2)CCN1C(=O)n1ccc(C(=O)O)n1] | δ 8.11 (d, J = 2.7 Hz, 1H), 7.59 (d, J = 8.1 Hz, 1H), 7.17-7.16 (m, 2H), 6.82 (d, J = 2.7 Hz, 1H), 5.44-5.26 (m, 1H), 4.67 (br, 1H), 4.30-4.25 (m, 1H), 3.74-3.44 (m, 6H), 3.31-3.22 (m, 1H), 2.89-2.85 (m, 1H), 2.77-2.74 (m, 1H), 2.37-2.29 (m, 3H), 2.28-2.17 (m, 1H), 1.45 (d, J = 6.9 Hz, 3H) | 484.2 |
| 365 | 1-((S)-4-(2-((S)-3-fluoropyrrolidin-1-yl)-4-(trifluoromethyl)-benzyl)-2-methylpiperazine-1-carbonyl)-1H-pyrazole-3-carboxylic acid | 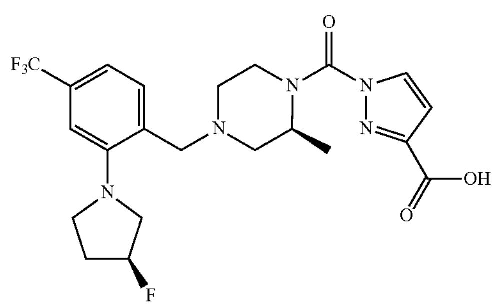 [SMILES: C[C@H]1CN(Cc2ccc(C(F)(F)F)cc2N2CC[C@H](F)C2)CCN1C(=O)n1ccc(C(=O)O)n1] | δ 8.13 (d, J = 2.7 Hz, 1H),7.58-7.55 (m, 1H), 7.15-7.14 (m, 2H), 6.85 (d, J = 2.7 Hz, 1H), 5.45-5.27 (m, 1H), 4.64 (br, 1H), 4.26-4.22 (m, 1H), 3.74-3.46 (m, 6H), 3.30-3.22 (m, 1H), 2.93-2.89 (m, 1H), 2.74-2.70 (m, 1H), 2.43-2.20 (m, 4H), 1.45 (d, J = 6.9 Hz, 3H) | 484.2 |

| Ex | Name | Structure | NMR (¹H NMR, 300 MHz or 400 MHz, Methanol-d) | MS [M + H]⁺ |
|---|---|---|---|---|
| 366 | 1-(2-(5-chloro-2-(trifluoromethyl)benzoyl)-2,8-diazaspiro[4.5]decane-8-carbonyl)-1H-pyrazole-3-carboxylic acid | 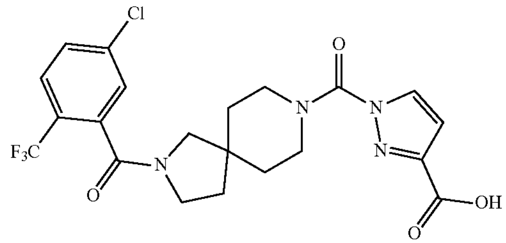 [SMILES: O=C(O)c1ccn(C(=O)N2CCC3(CCN(C(=O)c4cc(Cl)ccc4C(F)(F)F)C3)CC2)n1] | δ 8.14-8.11 (m, 1H), 7.84-7.80 (m, 1H), 7.71-7.68 (m, 1H), 7.65-7.61 (m, 1H), 6.86-6.83 (m, 1H), 3.88-3.68 (m, 5H), 3.58 (s, 1H), 3.28 (s, 1H), 3.18 (s, 1H), 2.05-1.93 (m, 2H), 1.80-1.70 (m, 4H) | 485.2 |
| 367 | 1-(2-(4-chloro-3-(thiazol-2-yl)benzyl)-2,8-diazaspiro[4.5]decane-8-carbonyl)-1H-pyrazole-3-carboxylic acid | 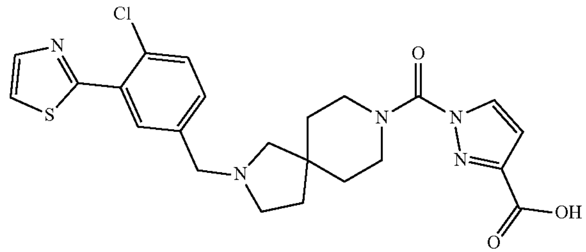 [SMILES: O=C(O)c1ccn(C(=O)N2CCC3(CCN(Cc4ccc(Cl)c(-c5nccs5)c4)C3)CC2)n1] | δ 8.26 (s, 1H), 8.02 (d, J = 2.7 Hz, 1H), 7.96-7.94 (m, 1H), 7.78-7.76 (m, 1H), 7.61-7.55 (m, 2H), 6.74 (d, J = 2.7 Hz, 1H), 4.27 (s, 2H), 3.80-3.76 (m, 2H), 3.67-3.57(m 2H), 3.32-3.27 (m, 2H), 3.13 (s, 2H), 2.00 (t, J = 7.2 Hz, 2H), 1.82-1.69 (m, 4H) | 486.2 |
| 368 | 4-chloro-1-(4-(4-(pyrrolidin-1-yl)-2-(trifluoromethyl)benzyl)piperazine-1-carbonyl)-1H-pyrazole-3-carboxylic acid | 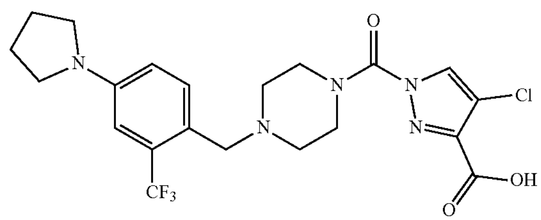 [SMILES: O=C(O)c1nn(C(=O)N2CCN(Cc3ccc(N4CCCC4)cc3C(F)(F)F)CC2)cc1Cl] | δ 8.19 (s, 1H), 7.53-7.50 (m, 1H), 6.78-6.75 (m, 2H), 3.88 (br, 4H), 3.77 (s, 2H), 3.41-3.32 (m, 3H), 3.29-3.24 (m, 1H), 2.77-2.73 (m, 4H), 2.14-2.02 (m, 4H) | 486.0 |
| 369 | 1-(trans-5-([1,1'-biphenyl]-3-yloxy)-octahydrocyclopenta[c]pyrrole-2-carbonyl)-4-(trifluoromethyl)-1H-pyrazole-3-carboxylic acid | 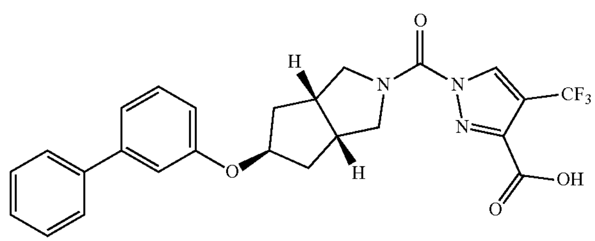 [SMILES: O=C(O)c1nn(C(=O)N2C[C@H]3C[C@H](Oc4cccc(-c5ccccc5)c4)C[C@H]3C2)cc1C(F)(F)F] | δ 8.72-8.60 (m, 1H), 7.64-7.53 (m, 2H), 7.49-7.37 (m, 2H), 7.37-7.27 (m, 2H), 7.21-7.12 (m, 1H), 7.12-7.02 (m, 1H), 6.93-6.78 (m, 1H), 5.14-4.98 (m, 1H), 4.27-4.01 (br, 1H), 4.01-3.74 (br, 2H), 3.74-3.56 (br, 1H), 3.08-2.91 (br, 2H), 2.33-2.12 (m, 2H), 2.08-1.87 (m, 2H) | 484.1 [M − H]⁻ |

| Ex | Name | Structure | NMR (¹H NMR, 300 MHz or 400 MHz, Methanol-d) | MS [M + H]⁺ |
|---|---|---|---|---|
| 370 | 1-(1-(4-chloro-2-(piperidin-1-yl)benzyl)-1,8-diazaspiro[4.5]-decane-8-carbonyl)-1H-pyrazole-3-carboxylic acid | 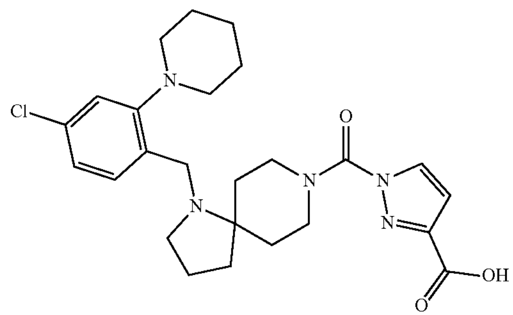 [SMILES: O=C(O)c1ccn(C(=O)N2CCC3(CCCN3Cc3ccc(Cl)cc3N3CCCCC3)CC2)n1] | δ 8.13 (d, J = 2.8 Hz, 1H), 7.49 (d, J = 8.0 Hz, 1H), 7.34 (s, 1H), 7.25-7.23 (m, 1H), 6.79 (d, J = 2.8 Hz, 1H), 4.76 (br, 2H), 4.28 (br, 2H), 3.32 (s, 2H), 3.27-3.21 (m, 2H), 2.90 (br, 4H), 2.36-2.20 (m, 4H), 2.09 (br, 2H), 1.87-1.84 (m, 2H), 1.78-1.75 (m, 4H), 1.63 (br, 2H) | 486.2 |
| 371 | 1-(2-(5-chloro-2-(trifluoromethoxy)-benzyl)-2,8-diazaspiro[4.5]-decane-8-carbonyl)-1H-pyrazole-3-carboxylic acid | 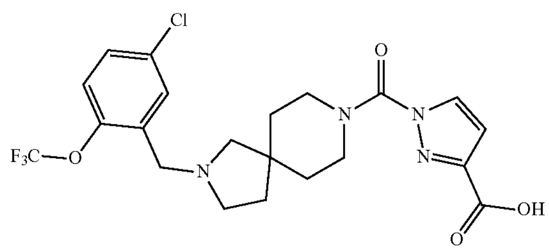 [SMILES: O=C(O)c1ccn(C(=O)N2CCC3(CCN(Cc4cc(Cl)ccc4OC(F)(F)F)C3)CC2)n1] | δ 8.05 (d, J = 2.7 Hz, 1H), 7.64 (d, J = 2.7 Hz, 1H), 7.43-7.42 (m, 1H), 7.40-7.39 (m, 1H), 6.76 (d, J = 2.7 Hz, 1H), 3.88-3.59 (m, 6H), 2.78 (d, J = 6.6 Hz, 2H), 2.63 (s, 2H), 1.84-1.76 (m, 2H), 1.75-1.69 (m, 4H) | 487.2 |
| 372 | 1-(2-(4-chloro-3-morpholinobenzyl)-2,8-diazaspiro[4.5]-decane-8-carbonyl)-1H-pyrazole-3-carboxylic acid | 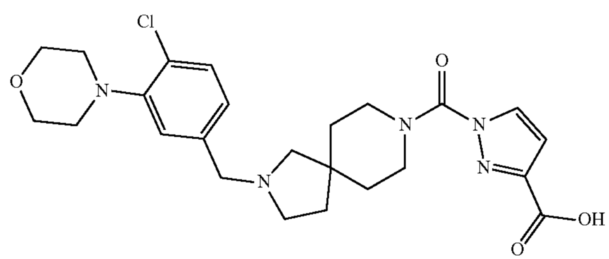 [SMILES: O=C(O)c1ccn(C(=O)N2CCC3(CCN(Cc4ccc(Cl)c(N5CCOCC5)c4)C3)CC2)n1] | δ 8.06 (d, J = 2.7 Hz, 1H), 7.46-7.43 (m, 1H), 7.35 (s, 1H), 7.19-7.16 (m, 1H), 6.77 (d, J = 2.7 Hz, 1H), 4.30 (s, 2H), 3.82-3.79 (m, 6H), 3.70-3.68 (m, 2H), 3.40-3.36 (m, 2H), 3.24 (br, 2H), 3.05-3.02 (m, 4H), 2.06 (t, J = 7.2 Hz, 2H), 1.87-1.78 (m, 4H) | 488.2 |
| 373 | (S)-1-(2-methyl-4-((3-((4-(trifluoromethyl)-pyridin-2-yl)oxy)benzyl)piperazine-1-carbonyl)-1H-pyrazole-3-carboxylic acid | 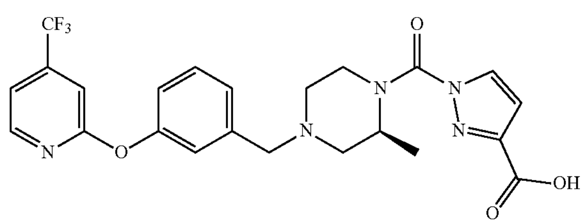 [SMILES: C[C@H]1CN(Cc2cccc(Oc3cc(C(F)(F)F)ccn3)c2)CCN1C(=O)n1ccc(C(=O)O)n1] | δ 8.35 (d, J = 5.4 Hz, 1H), 8.12 (d, J = 2.7 Hz, 1H), 7.45-7.37 (m, 2H), 7.30-7.23 (m, 3H), 7.10-7.07 (m, 1H), 6.83 (d, J = 2.7 Hz, 1H), 4.67 (br, 1H), 4.32-4.27 (m, 1H), 3.72-3.68 (m, 1H), 3.59-3.46 (m, 2H), 2.98-2.94 (m, 1H), 2.84-2.81 (m, 1H), 2.43-2.30 (m, 2H), 1.43 (d, J = 6.9 Hz, 3H) | 490.1 |

| Ex | Name | Structure | NMR (¹H NMR, 300 MHz or 400 MHz, Methanol-d) | MS [M + H]⁺ |
|---|---|---|---|---|
| 374 | (R)-1-(2-methyl-4-(3-((4-(trifluoromethyl)-pyridin-2-yl)oxy)benzyl)piperazine-1-carbonyl)-1H-pyrazole-3-carboxylic acid | 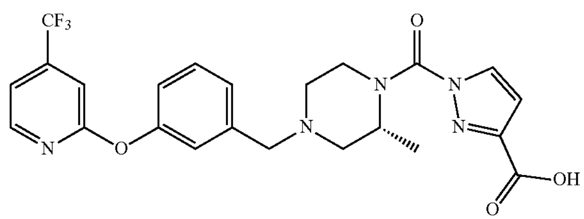 [SMILES: C[C@@H]1CN(Cc2cccc(Oc3cc(C(F)(F)F)ccn3)c2)CCN1C(=O)n1ccc(C(=O)O)n1] | δ 8.35 (d, J = 5.4 Hz, 1H), 8.14 (d, J = 2.7 Hz, 1H), 7.46-7.43 (m, 1H), 7.41-7.37 (m, 1H), 7.30-7.23 (m, 3H), 7.14-7.08 (m, 1H), 6.84 (d, J = 2.7 Hz, 1H), 4.65 (br, 1H), 4.30-4.26 (m, 1H), 3.73-3.68 (m, 1H), 3.59-3.46 (m, 2H), 2.98-2.95 (m, 1H), 2.85-2.81 (m, 1H), 2.44-2.30 (m, 2H), 1.43 (d, J = 6.9 Hz, H) | 490.1 |
| 375 | (S)-1-(2-methyl-4-(3-((5-(trifluoromethyl)-pyridin-2-yl)oxy)benzyl)piperazine-1-carbonyl)-1H-pyrazole-3-carboxylic acid | 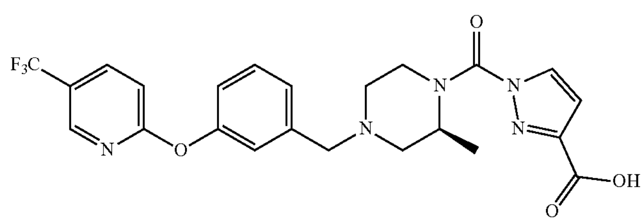 [SMILES: C[C@H]1CN(Cc2cccc(Oc3ccc(C(F)(F)F)cn3)c2)CCN1C(=O)n1ccc(C(=O)O)n1] | δ 8.42 (s, 1H), 8.12-8.08 (m, 2H), 7.43-7.39 (m, 1H), 7.28-7.26 (m, 1H), 7.21 (s, 1H), 7.13-7.11 (m, 1H), 7.08-7.06 (m, 1H), 6.82 (d, J = 2.8 Hz, 1H), 4.62-4.58 (m, 1H), 4.26-4.23 (m, 1H), 3.68-3.67 (m, 1H), 3.55-3.45 (m, 2H), 2.95-2.91 (m, 1H), 2.81-2.78 (m, 1H), 2.39-2.28 (m, 2H), 1.41 (d, J = 7.8 Hz, 3H) | 490.1 |
| 376 | (R)-1-(2-methyl-4-(3-((5-(trifluoromethyl)-pyridin-2-yl)oxy)benzyl)piperazine-1-carbonyl)-1H-pyrazole-3-carboxylic acid | 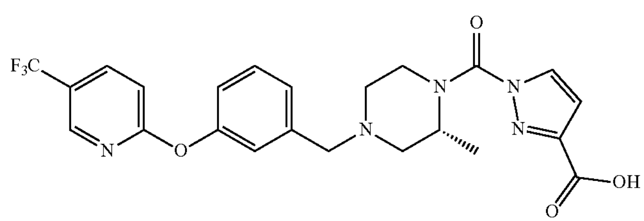 [SMILES: C[C@@H]1CN(Cc2cccc(Oc3ccc(C(F)(F)F)cn3)c2)CCN1C(=O)n1ccc(C(=O)O)n1] | δ 8.42 (s, 1H), 8.13 (d, J = 2.4 Hz, 1H), 8.13-8.10 (m, 1H), 7.44-7.40 (m, 1H), 7.29-7.27 (m, 1H), 7.21 (s, 1H), 7.14-7.09 (m, 1H), 7.07-7.06 (m, 1H), 6.84 (d, J = 2.4 Hz, 1H), 4.62 (br, 1H), 4.26-4.23 (m, 1H), 3.71-3.67 (m, 1H), 3.57-3.46 (m, 2H), 2.96-2.94 (m, 1H), 2.83-2.80 (m, 1H), 2.41-2.31 (m, 2H), 1.42 (d, J = 7.8 Hz, 3H) | 490.2 |
| 377 | 1-(2-((6-(trifluoromethyl)-benzo[b]thiophen-2-yl)methyl)-2,8-diazaspiro[4.5]-decane-8-carbonyl)-1H-pyrazole-3-carboxamide | 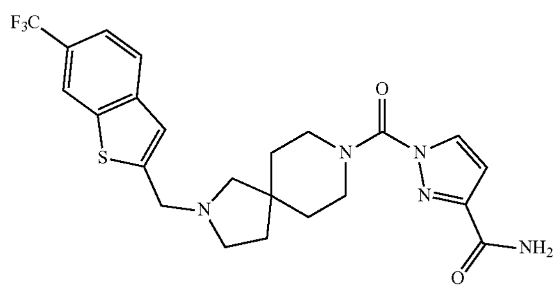 [SMILES: NC(=O)c1ccn(C(=O)N2CCC3(CCN(Cc4cc5ccc(C(F)(F)F)cc5s4)C3)CC2)n1] | δ 8.19 (d, J = 2.4 Hz, 1H), 7.90 (d, J = 8.0 Hz, 1H), 7.75 (s, 1H), 7.60-7.58 (m, 1H), 7.36 (s, 1H), 6.86 (d, J = 2.4 Hz, 1H), 3.98 (s, 2H), 3.58-3.50 (m, 4H), 2.79 (t, J = 7.0 Hz, 2H), 2.61 (s, 2H), 1.79 (t, J = 7.0 Hz, 2H), 1.74-1.66 (m, 4H) | 492.2 |

| Ex | Name | Structure | NMR (¹H NMR, 300 MHz or 400 MHz, Methanol-d) | MS [M + H]⁺ |
|---|---|---|---|---|
| 378 | 4-chloro-1-(4-(3-(4-chlorophenoxy)-5-fluorobenzyl)-piperazine-1-carbonyl)-1H-pyrazole-3-carboxylic acid | 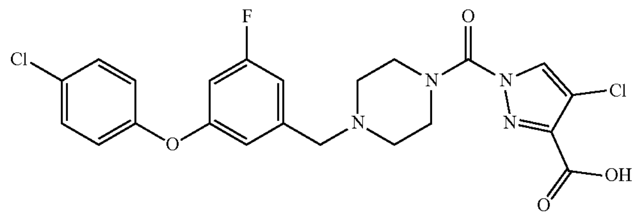 | δ 8.20 (s, 1H), 7.42-7.39 (m, 2H), 7.08-7.04 (m, 2H), 6.92 (d, J = 9.0 Hz, 1H), 6.87 (s, 1H), 6.70-6.67 (m, 1H), 3.86 (br, 4H), 3.70 (s, 2H), 2.66 (br, 4H) | 493.1 |
| 379 | 1-(4-(4-(tetrahydro-1H-furo[3,4-c]pyrrol-5(3H)-yl)-2-(trifluoromethyl)-benzyl)-piperazine-1-carbonyl)-1H-pyrazole-3-carboxylic acid | 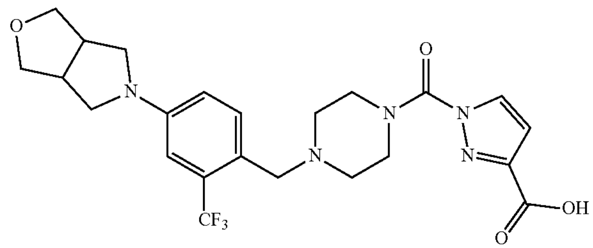 [SMILES: O=C(O)c1ccn(C(=O)N2CCN(Cc3ccc(N4CC5COCC5C4)cc3C(F)(F)F)CC2)n1] | δ 8.13 (br, 1H), 7.56 (d, J = 8.1 Hz, 1H), 6.87-6.81 (m, 3H), 3.99-3.94 (m, 2H), 3.85 (br, 4H), 3.69-3.65 (m, 4H), 3.48-3.43 (m, 2H), 3.32-3.24 (m, 2H), 3.11-3.08 (m, 2H), 2.65 (br, 4H) | 494.3 |
| 380 | 1-(4-(2-(8-oxa-3-azabicyclo[3.2.1]-octan-3-yl)-4-(trifluoromethyl)-benzyl)piperazine-1-carbonyl)-1H-pyrazole-3-carboxylic acid | 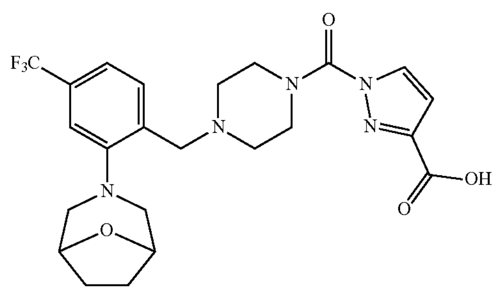 [SMILES: O=C(O)c1ccn(C(=O)N2CCN(Cc3ccc(C(F)(F)F)cc3N3CC4CCC(C3)O4)CC2)n1] | δ 8.20 (d, J = 2.0 Hz, 1H), 7.79-7.77 (m, 1H), 7.51 (s, 1H), 7.48-7.45 (m, 1H), 6.88 (d, J = 2.0 Hz, 1H), 4.41 (br, 2H), 4.05 (br, 2H), 3.93 (br, 4H), 3.09-3.05 (m, 2H), 2.91-2.84 (m, 6H), 2.23-2.09 (m, 2H), 2.09-1.94 (m, 2H) | 494.3 |
| 381 | 1-(4-methyl-4-(methyl(3-(pyrrolidin-1-yl)-5-(trifluoromethyl)-benzyl)amino)-piperidine-1-carbonyl)-1H-pyrazole-3-carboxylic acid | 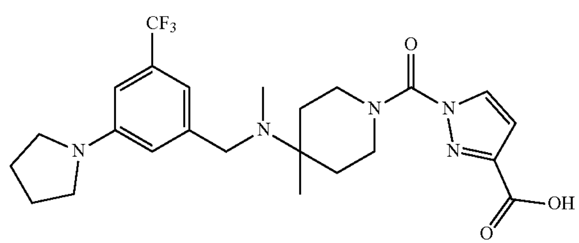 [SMILES: CN(Cc1cc(N2CCCC2)cc(C(F)(F)F)c1)C1(C)CCN(C(=O)n2ccc(C(=O)O)n2)CC1] | δ 8.09 (d, J = 2.7 Hz, 1H), 7.96 (s, 1H), 7.87 (s, 1H), 7.78 (s, 1H), 6.77 (d, J = 2.7 Hz, 1H), 4.58-4.39 (m, 2H), 4.10-3.98 (m, 2H), 3.58-3.36 (m, 2H), 3.34-3.31 (m, 4H), 2.52 (s, 3H), 2.14-1.84 (m, 8H), 1.46 (s, 3H) | 494.3 |

| Ex | Name | Structure | NMR (¹H NMR, 300 MHz or 400 MHz, Methanol-d) | MS [M + H]⁺ |
|---|---|---|---|---|
| 382 | 1-(4-methyl-4-(methyl(2-(pyrrolidin-1-yl)-3-(trifluoromethyl)benzyl)amino)-piperidine-1-carbonyl)-1H-pyrazole-3-carboxylic acid | 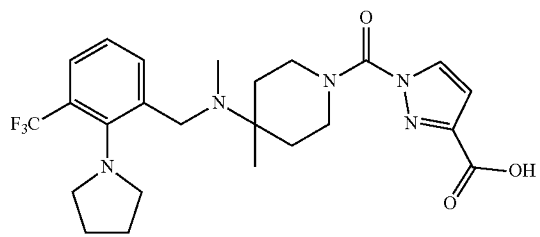 [SMILES: CN(Cc1cccc(C(F)(F)F)c1N1CCCC1)C1(C)CCN(C(=O)n2ccc(C(=O)O)n2)CC1] | δ 8.07 (d, J = 2.7 Hz, 1H), 8.04 (d, J = 7.5 Hz, 1H), 7.54 (d, J = 7.5 Hz, 1H), 7.37 (t, J = 7.8 Hz, 1H), 6.77 (d, J = 2.7 Hz, 1H), 3.91 (br, 4H), 3.69 (br, 2H), 3.21-3.17 (m, 4H), 2.17 (s, 3H), 2.09-1.99 (m, 6H), 1.82-1.63 (m, 2H), 1.17 (s, 3H) | 494.3 |
| 383 | 1-(4-methyl-4-(methyl(4-(pyrrolidin-1-yl)-3-(trifluoromethyl)benzyl)amino)-piperidine-1-carbonyl)-1H-pyrazole-3-carboxylic acid | 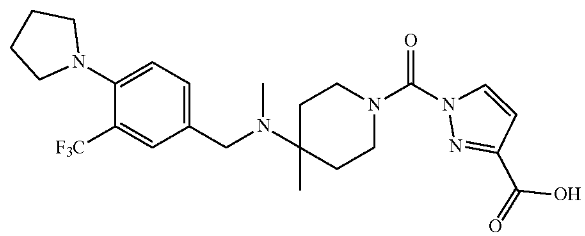 [SMILES: CN(Cc1ccc(N2CCCC2)c(C(F)(F)F)c1)C1(C)CCN(C(=O)n2ccc(C(=O)O)n2)CC1] | δ 8.09 (d, J = 2.7 Hz, 1H), 7.69 (s, 1H), 7.51 (d, J = 5.7 Hz, 1H), 7.10 (d, J = 5.7 Hz, 1H), 6.77 (d, J = 2.7 Hz, 1H), 4.53 (br, 2H), 4.18 (br, 2H), 3.38-3.34 (m, 6H), 2.58 (s, 3H), 2.10 (br, 4H), 2.00-1.96 (m, 4H), 1.52 (s, 3H) | 494.3 |
| 384 | 1-(4-methyl-4-(methyl(2-(pyrrolidin-1-yl)-5-(trifluoromethyl)benzyl)amino)-piperidine-1-carbonyl)-1H-pyrazole-3-carboxylic acid | 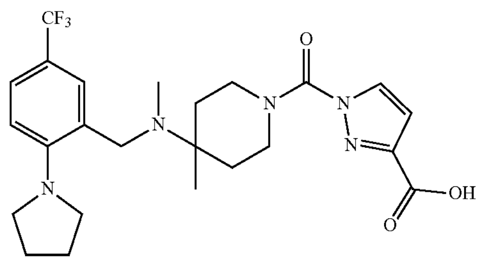 [SMILES: CN(Cc1cc(C(F)(F)F)ccc1N1CCCC1)C1(C)CCN(C(=O)n2ccc(C(=O)O)n2)CC1] | δ 8.07 (d, J = 2.7 Hz, 1H), 7.90 (s, 1H), 7.44 (d, J = 4.2 Hz, 1H), 7.11 (d, J = 6.3 Hz, 1H), 6.77 (d, J = 2.4 Hz, 1H), 4.02-3.78 (m, 6H), 3.32-3.22 (m, 4H), 2.23 (s, 3H), 2.06-1.98 (m, 6H), 1.96-1.81 (m, 2H), 1.27 (s, 3H) | 494.3 |
| 385 | 1-(4-methyl-4-(methyl(3-(pyrrolidin-1-yl)-4-(trifluoromethyl)benzyl)amino)-piperidine-1-carbonyl)-1H-pyrazole-3-carboxylic acid | 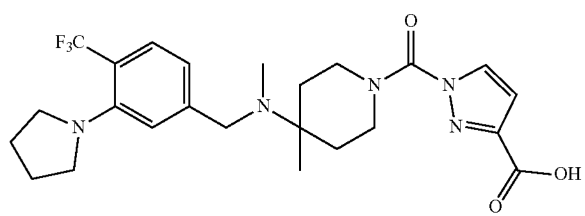 [SMILES: CN(Cc1ccc(C(F)(F)F)c(N2CCCC2)c1)C1(C)CCN(C(=O)n2ccc(C(=O)O)n2)CC1] | δ 8.08 (d, J = 2.7 Hz, 1H), 7.58 (d, J = 8.1 Hz, 1H), 7.16 (s, 1H), 6.96 (d, J = 7.8 Hz, 1H), 6.77 (d, J = 2.7 Hz, 1H), 4.41-4.09 (m, 2H), 3.97 (br, 2H), 3.60-3.54 (m, 2H), 3.48-3.31 (m, 4H), 2.44 (s, 3H), 2.14-2.11 (m, 2H), 2.03-1.91 (m, 6H), 1.27 (s, 3H) | 494.3 |

| Ex | Name | Structure | NMR (¹H NMR, 300 MHz or 400 MHz, Methanol-d) | MS [M + H]⁺ |
|---|---|---|---|---|
| 386 | (R)-1-(2-methyl-4-((3-methyl-3'-(methylsulfonyl)-[1,1'-biphenyl]-4-yl)methyl)piperazine-1-carbonyl)-1H-pyrazole-3-carboxylic acid | 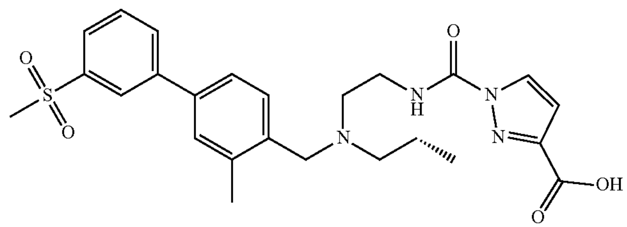 | δ 8.17 (t, J = 1.5 Hz, 1H), 8.10 (d, J = 2.4 Hz, 1H), 7.99-7.93 (m, 1H), 7.93-7.90 (m, 1H), 7.73-7.68 (m, 1H), 7.52 (s, 1H), 7.49-41 (m, 1H), 7.41-7.38 (m, 1H), 6.81 (d, J = 2.4 Hz, 1H), 4.65 (br, 1H), 4.27-4.23 (m, 1H), 3.56-3.53 (m, 2H), 3.50-3.40 (m, 1H), 3.18 (s, 3H), 2.91-2.87 (m, 1H), 2.80-2.76 (m, 1H), 2.51 (s, 3H), 2.43-2.38 (m, 1H), 2.31-2.22 (m, 1H), 1.42 (d, J = 6.6 Hz, 3H) | 497.5 |
| 387 | 1-(1-(4-chloro-2-(4-fluoropiperidin-1-yl)benzyl)-1,8-diazaspiro[4.5]decane-8-carbonyl)-1H-pyrazole-3-carboxylic acid | 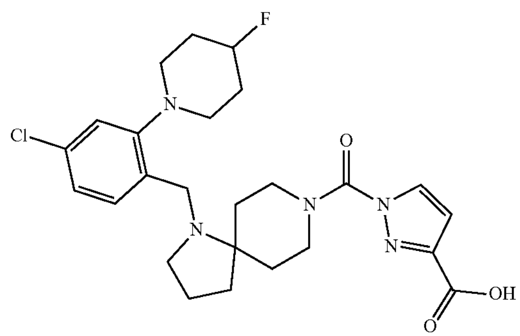 [SMILES: O=C(O)c1ccn(C(=O)N2CCC3(CCCN3Cc3ccc(Cl)cc3N3CCC(F)CC3)CC2)n1] | δ 8.13 (d, J = 2.4 Hz, 1H), 7.53 (d, J = 8.0 Hz, 1H), 7.36 (s, 1H), 7.26-7.24 (m, 1H), 6.79 (d, J = 2.4 Hz, 1H), 4.92-4.42 (m, 3H), 4.27 (br, 2H), 3.30-3.20 (m, 4H), 3.11-3.06 (m, 2H), 2.89-2.86 (m, 2H), 2.35-2.26 (m, 4H), 2.15-1.99 (m, 6H), 1.85-1.83 (m, 2H) | 504.2 |
| 388 | 4-chloro-1-(2-(3-chloro-5-(trifluoromethyl)benzyl)-2,8-diazaspiro[4.5]decane-8-carbonyl)-1H-pyrazole-3-carboxylic acid | 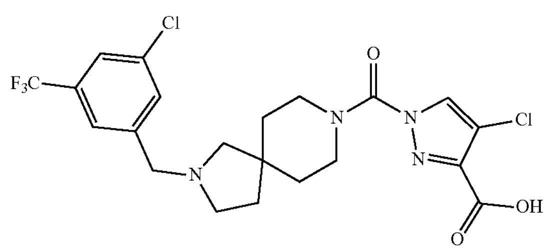 [SMILES: O=C(O)c1nn(C(=O)N2CCC3(CCN(Cc4cc(Cl)cc(C(F)(F)F)c4)C3)CC2)cc1Cl] | δ 8.19 (s, 1H), 7.87 (s, 1H), 7.84 (s, 1H), 7.78 (s, 1H), 4.36 (s, 2H), 3.82-3.77 (m, 2H) 3.69-3.64 (m, 2H), 3.42-3.37 (m, 2H), 3.22 (br, 2H), 2.03 (t, J = 7.2 Hz, 2H), 1.75-1.70 (m, 4H) | 505.1 |

| Ex | Name | Structure | NMR (1H NMR, 300 MHz or 400 MHz, Methanol-d) | MS [M + H]+ |
|---|---|---|---|---|
| 389 | 1-(1-(6-(trifluoromethyl)-benzo[b]thiophene-2-carbonyl)-1,8-diazaspiro[4.5]decane-8-carbonyl)-1H-pyrazole-3-carboxamide | 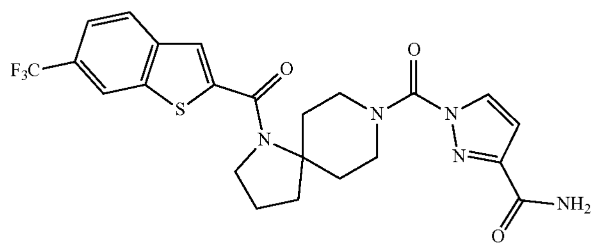 [SMILES: NC(=O)c1ccn(C(=O)N2CCC3(CCCN3C(=O)c3cc4ccc(C(F)(F)F)cc4s3)CC2)n1] | (Chloroform-d) δ 8.15 (s, 1H), 8.10 (d, J = 2.7 Hz, 1H), 7.91 (d, J = 8.4 Hz, 1H), 7.71 (s, 1H), 7.61 (d, J = 8.4 Hz, 1H), 6.90 (d, J = 2.7 Hz, 1H), 6.75 (br, 1H), 5.52 (br, 1H), 4.55-4.51 (m, 2H), 3.92 (t, J = 6.6 Hz, 2H), 3.35-3.14 (m, 4H), 2.19-2.14 (m, 2H), 2.05-1.96 (m, 2H), 1.64-1.47 (m, 2H) | 523.2 [M + NH4]+ |
| 390 | 1-(2-(6-(trifluoromethyl)-benzo[b]thiophene-2-carbonyl)-2,8-diazaspiro[4.5]-decane-8-carbonyl)-1H-pyrazole-3-carboxamide | 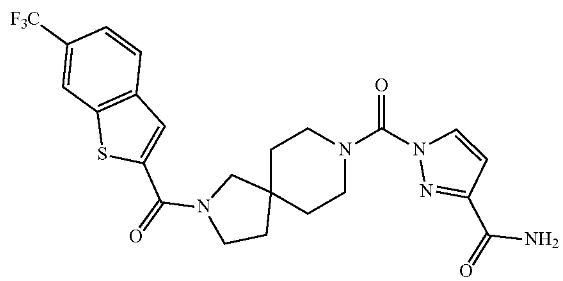 [SMILES: NC(=O)c1ccn(C(=O)N2CCC3(CCN(C(=O)c4cc5ccc(C(F)(F)F)cc5s4)C3)CC2)n1] | δ 8.34 (s, 1H), 8.14-8.10 (m, 1H), 8.01 (s, 1H), 7.75-7.69 (m, 2H), 6.91-6.86 (m, 1H), 4.06 (t, J = 7.0 Hz, 1H), 3.85-3.80 (m, 2H), 3.78-3.58 (m, 5H), 2.09-2.01 (m, 2H), 1.82-1.68 (m, 4H) | 506.1 |
| 391 | 1-(2-(5-(pyrrolidin-1-yl)-2-(trifluoromethyl)-benzyl)-2,8-diazaspiro[4.5]-decane-8-carbonyl)-1H-pyrazole-3-carboxylic acid | 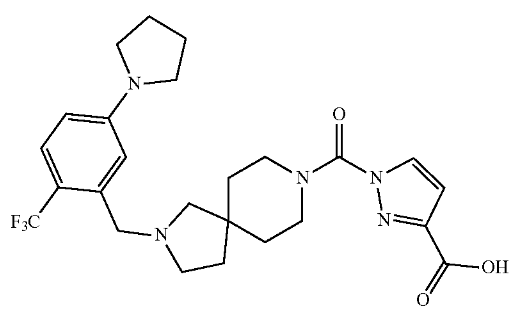 [SMILES: O=C(O)c1ccn(C(=O)N2CCC3(CCN(Cc4cc(N5CCCC5)ccc4C(F)(F)F)C3)CC2)n1] | δ 8.06 (d, J = 2.7 Hz, 1H), 7.53-7.50 (m, 1H), 7.04 (s, 1H), 6.78 (d, J = 2.7 Hz, 1H), 6.61 (d, J = 7.8 Hz, 1H), 4.35 (s, 2H), 3.83-3.79 (m, 2H), 3.72-3.67 (m, 2H), 3.32 (br, 4H), 3.21-3.14 (m, 4H), 2.06-1.99 (m, 6H), 1.82-1.69 (m, 4H) | 506.3 |

| Ex | Name | Structure | NMR (¹H NMR, 300 MHz or 400 MHz, Methanol-d) | MS [M + H]⁺ |
|---|---|---|---|---|
| 392 | 1-((2R)-2-methyl-4-(2-(tetrahydro-1H-furo[3,4-c]pyrrol-5(3H)-yl)-4-(trifluoromethyl)-benzyl)-piperazine-1-carbonyl)-1H-pyrazole-3-carboxylic acid | 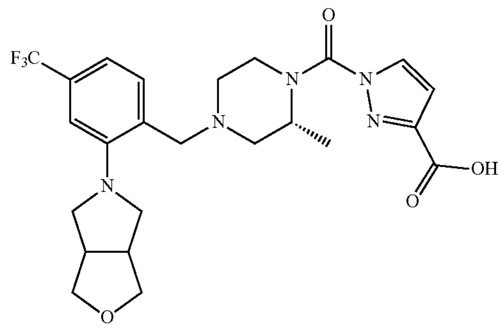 [SMILES: C[C@@H]1CN(Cc2ccc(C(F)(F)F)cc2N2CC3COCC3C2)CCN1C(=O)n1ccc(C(=O)O)n1] | δ 8.14 (d, J = 2.7 Hz, 1H), 7.70 (d, J = 8.1 Hz, 1H), 7.33-7.30 (m, 2H), 6.84 (d, J = 2.7 Hz, 1H), 4.65 (br, 1H), 4.30-4.25 (m, 1H), 4.02-3.97 (m, 2H), 3.71-3.67 (m, 4H), 3.67-3.47 (m, 1H), 3.24-3.12 (m, 2H), 3.12-3.06 (m, 2H), 3.06-2.91 (m, 3H), 2.79-2.75 (m, 1H), 2.44-2.36 (m, 1H), 2.36-2.28 (m, 1H), 1.47 (d, J = 6.9 Hz, 3H) | 508.2 |
| 393 | 1-((2R)-4-(2-(3-oxa-8-azabicyclo[3.2.1]-octan-8-yl)-4-(trifluoromethyl)-benzyl)-2-methylpiperazine-1-carbonyl)-1H-pyrazole-3-carboxylic acid | 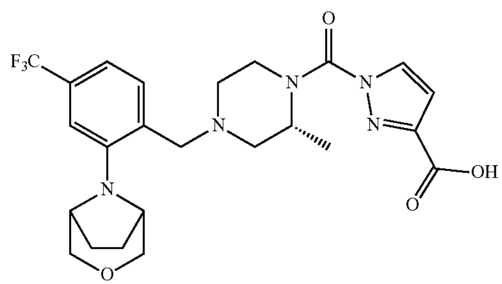 [SMILES: C[C@@H]1CN(Cc2ccc(C(F)(F)F)cc2N2C3CCC2COC3)CCN1C(=O)n1ccc(C(=O)O)n1] | δ 8.13 (d, J = 2.7 Hz, 1H), 7.67 (d, J = 7.8 Hz, 1H), 7.30-7.25 (m, 1H), 7.15 (s, 1H), 6.84 (d, J = 2.7 Hz, 1H), 4.67 (br, 1H), 4.33-4.25 (m, 1H), 4.03-3.89 (m, 4H), 3.74-3.63 (m, 4H), 3.56-3.42 (m, 1H), 2.96-2.81 (m, 1H), 2.81-2.78 (m, 1H), 2.47-2.42 (m, 1H), 2.37-2.28 (m, 1H), 2.06-1.94 (m, 4H), 1.43 (d, J = 6.6 Hz, 3H) | 508.3 |
| 394 | 1-((2S)-2-methyl-4-(2-(tetrahydro-1H-furo[3,4-c]pyrrol-5(3H)-yl)-4-(trifluoromethyl)-benzyl)-piperazine-1-carbonyl)-1H-pyrazole-3-carboxylic acid | 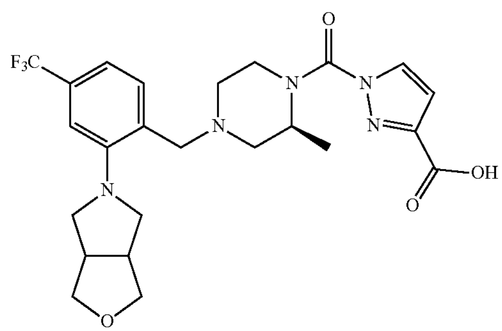 [SMILES: C[C@H]1CN(Cc2ccc(C(F)(F)F)cc2N2CC3COCC3C2)CCN1C(=O)n1ccc(C(=O)O)n1] | δ 8.13 (d, J = 2.7 Hz, 1H), 7.72-7.69 (m, 1H), 7.33-7.30 (m, 2H), 6.84 (d, J = 2.7 Hz, 1H), 4.67 (br, 1H), 4.31-4.26 (m, 1H), 4.01-3.96 (m, 2H), 3.71-3.62 (m, 4H), 3.57-3.48 (m, 1H), 3.23-3.19 (m, 2H), 3.13-3.07 (m, 2H), 3.10-2.92 (m, 3H), 2.79-2.75 (m, 1H), 2.44-2.29 (m, 2H), 1.47 (d, J = 6.9 Hz, 3H) | 508.2 |

| Ex | Name | Structure | NMR (¹H NMR, 300 MHz or 400 MHz, Methanol-d) | MS [M + H]⁺ |
|---|---|---|---|---|
| 395 | 1-((2S)-4-(2-(3-oxa-8-azabicyclo[3.2.1]-octan-8-yl)-4-(trifluoromethyl)-benzyl)-2-methylpiperazine-1-carbonyl)-1H-pyrazole-3-carboxylic acid | 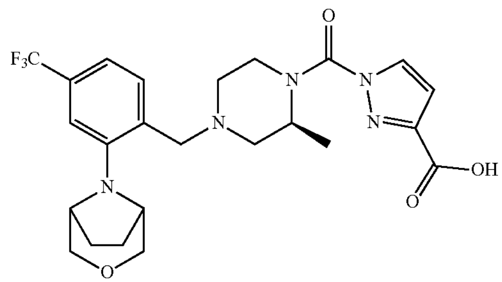 [SMILES: C[C@H]1CN(Cc2ccc(C(F)(F)F)cc2N2C3CCC2COC3)CCN1C(=O)n1ccc(C(=O)O)n1] | δ 8.14 (d, J = 2.7 Hz, 1H), 7.69-7.66 (m, 1H), 7.27-7.25 (m, 1H), 7.16 (s, 1H), 6.84 (d, J = 2.7 Hz, 1H), 4.67 (br, 1H), 4.30-4.25 (m, 1H), 4.00-3.89 (m, 4H), 3.75-3.63 (m, 4H), 3.56-3.43 (m, 1H), 3.00-2.92 (m, 1H), 2.82-2.78 (m, 1H), 2.47-2.42 (m, 1H), 2.37-2.28 (m, 1H), 2.09-1.92 (m, 4H), 1.44 (d, J = 6.6 Hz, 3H) | 508.2 |
| 396 | 1-(5-(4-(4-hydroxytetrahydro-2H-pyrm-4-yl)-2-(trifluoromethyl)-benzyl)-octahydropyrrolo[3,4-c]pyrrole-2-carbonyl)-1H-pyrazole-3-carboxamide | 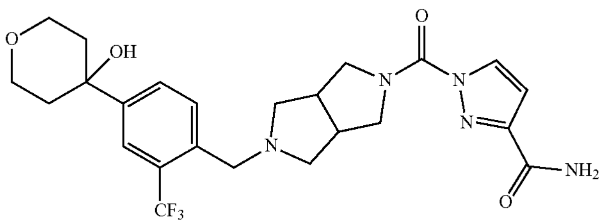 [SMILES: NC(=O)c1ccn(C(=O)N2CC3CN(Cc4ccc(C5(O)CCOCC5)cc4C(F)(F)F)CC3C2)n1] | δ 8.31 (d, J = 2.7 Hz, 1H), 7.84 (s, 1H), 7.76 (d, J = 8.1 Hz, 1H), 7.68 (d, J = 8.1 Hz, 1H), 6.89 (d, J = 2.7 Hz, 1H), 4.35-3.78 (m, 10H), 2.97 (br, 2H), 2.78-2.70 (m, 2H), 2.62-2.57 (m, 2H), 2.20-2.10 (m, 2H), 1.67-1.63 (m, 2H) | 508.3 |
| 397 | 1-(4-methyl-4-(methyl(2-(piperidin-1-yl)-4-(trifluoromethyl)-benzyl)amino)-piperidine-1-carbonyl)-1H-pyrazole-3-carboxylic acid | 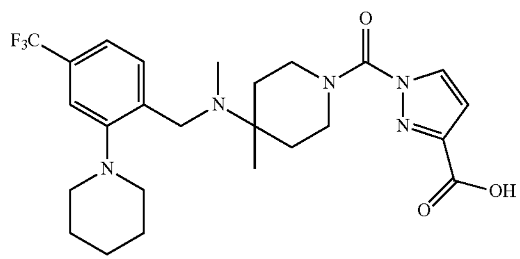 [SMILES: CN(Cc1ccc(C(F)(F)F)cc1N1CCCCC1)C1(C)CCN(C(=O)n2ccc(C(=O)O)n2)CC1] | δ 8.08 (d, J = 2.7 Hz, 1H), 7.77 (d, J = 8.1 Hz, 1H), 7.51 (s, 1H), 7.48 (d, J = 8.4 Hz, 1H), 6.77 (d, J = 2.7 Hz, 1H), 4.58-4.34 (m, 2H), 4.19-4.09 (m, 2H), 3.61-3.54 (m, 2H), 2.90 (t, J = 5.1 Hz, 4H), 2.48 (s, 3H), 2.24-2.10 (m, 2H), 2.03-1.89 (m, 2H), 1.80-1.75 (m, 4H), 1.64-1.62 (m, 2H), 1.46 (s, 3H) | 508.3 |
| 398 | 1,1,1,3,3,3-hexafluoropropan-2-yl 4-(7-cyclobutyl-N-methyl-5,6,7,8-tetrahydroimidazo[1,2-a]pyrazine-2-carboxamido)-4-methylpiperidine-1-carboxylate | 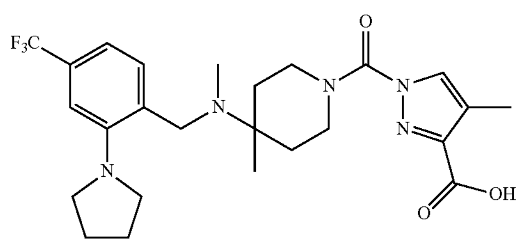 [SMILES: Cc1cn(C(=O)N2CCC(C)(N(C)Cc3ccc(C(F)(F)F)cc3N3CCCC3)CC2)nc1C(=O)O] | δ 7.86 (s, 1H), 7.78 (d, J = 8.0 Hz, 1H), 7.36-7.31 (m, 2H), 4.16-4.02 (m, 4H), 3.63 (br, 2H), 3.19-3.13 (m, 4H), 2.35 (br, 3H), 2.26 (s, 3H), 2.10-2.04 (m, 2H), 2.02-1.96 (m, 4H), 1.89 (br, 2H), 1.34 (s, 3H) | 508.3 |

| Ex | Name | Structure | NMR (¹H NMR, 300 MHz or 400 MHz, Methanol-d) | MS [M + H]⁺ |
|---|---|---|---|---|
| 399 | 4-chloro-1-(4-(3-((4-(trifluoromethyl)-pyridin-2-yl)oxy)benzyl)piperazine-1-carbonyl)-1H-pyrazole-3-carboxylic acid | 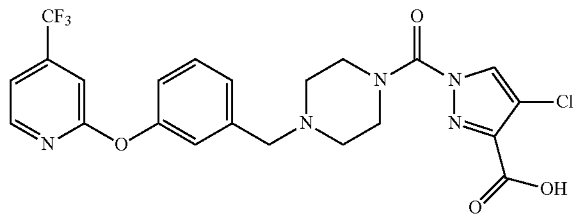 [SMILES: O=C(O)c1nn(C(=O)N2CCN(Cc3cccc(Oc4cc(C(F)(F)F)ccn4)c3)CC2)cc1Cl] | δ 8.32 (d, J = 5.4 Hz, 1H), 8.19 (s, 1H), 7.47-7.42 (m, 1H), 7.37-7.29 (m, 2H), 7.26 (s, 2H), 7.15-7.12 (m, 1H), 3.91 (br, 4H), 3.85 (s, 2H), 2.91-2.82 (m, 4H) | 510.2 |
| 400 | 1-(2-(2-chloro-4-(tetrahydro-1H-furo[3,4-c]pyrrol-5(3H)-yl)benzyl)-2,8-diazaspiro[4.5]-decane-8-carbonyl)-1H-pyrazole-3-carboxylic acid | 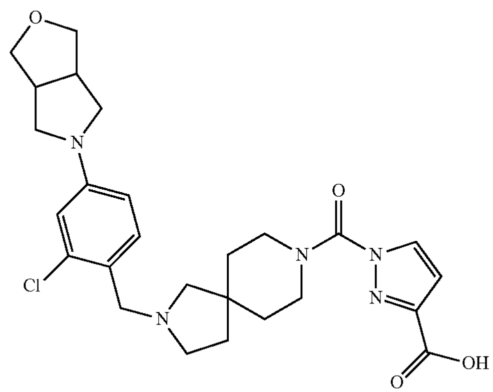 [SMILES: O=C(O)c1ccn(C(=O)N2CCC3(CCN(Cc4ccc(N5CC6COCC6C5)cc4Cl)C3)CC2)n1] | δ 8.06 (d, J = 2.8 Hz, 1H), 7.42 (d, J = 8.8 Hz, 1H), 6.76-6.74 (m, 2H), 6.67-6.65 (m, 1H), 4.39 (s, 2H), 3.99-3.95 (m, 2H), 3.88 (br, 2H), 3.71-3.68 (m, 4H), 3.50-3.48 (m, 2H), 3.43 (br, 2H), 3.34-3.28 (m, 4H), 3.12 (t, J = 3.2 Hz, 2H), 2.06 (t, J = 7.2 Hz, 2H), 1.88-1.80 (m, 4H) | 514.3 |
| 401 | 1-(2-(4-chloro-3-(tetrahydro-1H-furo[3,4-c]pyrrol-5(3H)-yl)benzyl)-2,8-diazaspiro[4.5]-decane-8-carbonyl)-1H-pyrazole-3-carboxylic acid | 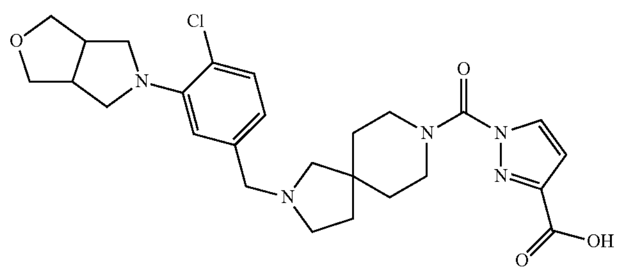 [SMILES: O=C(O)c1ccn(C(=O)N2CCC3(CCN(Cc4ccc(Cl)c(N5CC6COCC6C5)c4)C3)CC2)n1] | δ 8.06 (d, J = 2.7 Hz, 1H), 7.49 (d, J = 8.1 Hz, 1H), 7.26 (s, 1H), 7.09 (d, J = 8.1 Hz, 1H), 6.76 (d, J = 2.7 Hz, 1H), 4.27 (s, 2H), 3.99-3.94 (m, 2H), 3.82 (br, 2H), 3.70 (br, 2H), 3.61-3.56 (m, 2H), 3.39-3.34 (m, 2H), 3.22 (s, 6H), 2.92 (br, 2H), 2.05 (t, J = 7.2 Hz, 2H), 1.84-1.76 (m, 4H) | 514.3 |

-continued

| Ex | Name | Structure | NMR (¹H NMR, 300 MHz or 400 MHz, Methanol-d) | MS [M + H]⁺ |
|---|---|---|---|---|
| 402 | 1-(1-(3-(pyrimidin-5-yl)-5-(trifluoromethyl)benzyl)-1,8-diazaspiro[4.5]decane-8-carbonyl)-1H-pyrazole-3-carboxylic acid | 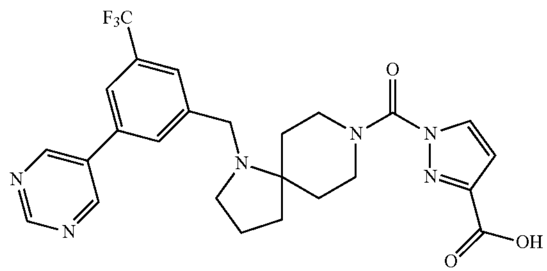 [SMILES: O=C(O)c1ccn(C(=O)N2CCC3(CCCN3Cc3cc(-c4cncnc4)cc(C(F)(F)F)c3)CC2)n1] | δ 9.23-9.17 (m, 3H), 8.13-8.08 (m, 3H), 7.95 (s, 1H), 6.82 (s, 1H), 4.64 (br, 2H), 4.26 (br, 2H), 3.27-3.20 (m, 2H), 3.15 (br, 2H), 2.27-2.20 (m, 4H), 2.05-2.01 (m, 2H), 1.82-1.70 (m, 2H) | 515.2 |
| 403 | 1-(1-(2-(pyrrolidin-1-yl)-4-(trifluoromethyl)benzoyl)-1,8-diazaspiro[4.5]decane-8-carbonyl)-1H-pyrazole-3-carboxylic acid | 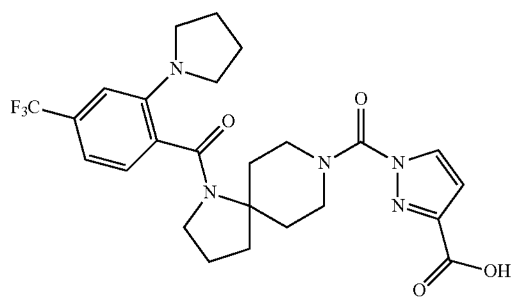 [SMILES: O=C(O)c1ccn(C(=O)N2CCC3(CCCN3C(=O)c3ccc(C(F)(F)F)cc3N3CCCC3)CC2)n1] | δ 8.17 (d, J = 2.7 Hz, 1H), 7.24 (d, J = 7.8 Hz, 1H), 6.96-6.93 (m, 2H), 6.84 (d, J = 2.7 Hz, 1H), 4.57 (br, 2H), 3.50-3.38 (m, 4H), 3.32-3.09 (m, 6H), 2.31-2.13 (m, 2H), 2.03-1.97 (m, 4H), 1.93-1.84 (m, 2H), 1.64 (br, 2H) | 520.3 |
| 404 | 1-(1-(2-(piperidin-1-yl)-4-(trifluoromethyl)benzoyl)-1,8-diazaspiro[4.5]decane-8-carbonyl)-1H-pyrazole-3-carboxylic acid | 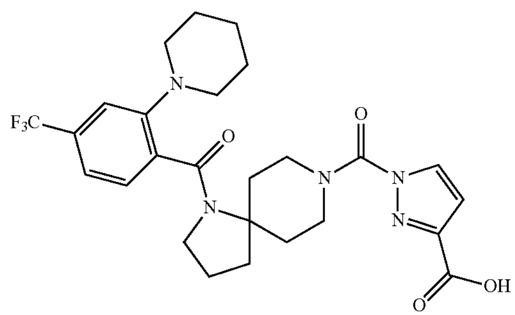 [SMILES: O=C(O)c1ccn(C(=O)N2CCC3(CCCN3C(=O)c3ccc(C(F)(F)F)cc3N3CCCCC3)CC2)n1] | δ 8.08 (d, J = 2.7 Hz, 1H), 7.69 (d, J = 7.8 Hz, 1H), 7.47 (s, 1H), 7.43-7.41 (m, 1H), 6.76 (d, J = 2.7 Hz, 1H), 4.83-4.60 (m, 2H), 4.25-4.06 (m, 2H), 3.30-3.21 (m, 2H), 3.17-3.01 (m, 2H), 2.99-2.88 (m, 4H), 2.30-2.14 (m, 4H), 2.03-1.95 (m, 2H), 1.75 (br, 6H), 1.63 (br, 2H) | 520.3 |

| Ex | Name | Structure | NMR (¹H NMR, 300 MHz or 400 MHz, Methanol-d) | MS [M + H]⁺ |
|---|---|---|---|---|
| 405 | 1-(1-(2-morpholino-4-(trifluoromethyl)benzyl)-1,8-diazaspiro[4.5]decane-8-carbonyl)-1H-pyrazole-3-carboxylic acid | 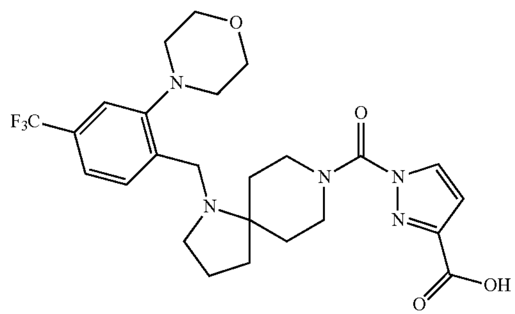 [SMILES: O=C(O)c1ccn(C(=O)N2CCC3(CCCN3Cc3ccc(C(F)(F)F)cc3N3CCOCC3)CC2)n1] | δ 8.11 (d, J = 2.7 Hz, 1H), 7.74 (d, J = 8.1 Hz, 1H), 7.60 (s, 1H), 7.56-7.50 (m, 1H), 6.79 (d, J = 2.7 Hz, 1H), 4.80-4.67 (m, 2H), 4.27-4.19 (m, 2H), 3.87-3.84 (m, 4H), 3.32-3.18 (m, 4H), 3.07-2.89 (m, 4H), 2.40-2.21 (m, 4H), 2.11-2.00 (m, 2H), 1.82-1.78 (m, 2H) | 522.3 |
| 406 | 1-(4-(((2R,5R)-2,5-dimethylpyrrolidin-1-yl)-4-(trifluoromethyl)benzyl)(methyl)amino)-4-methylpiperidine-1-carbonyl)-1H-pyrazole-3-carboxylic acid | 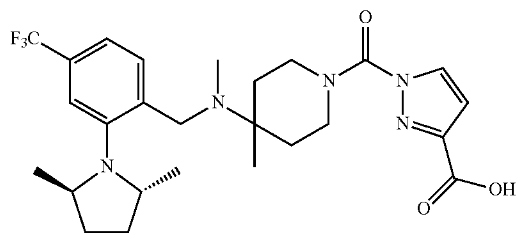 [SMILES: C[C@@H]1CC[C@@H](C)N1c1cc(C(F)(F)F)ccc1CN(C)C1(C)CCN(C(=O)n2ccc(C(=O)O)n2)CC1] | δ 8.07 (d, J = 2.7 Hz, 1H), 7.88 (d, J = 8.4 Hz, 1H), 7.33 (d, J = 8.0 Hz, 1H), 7.28 (s, 1H), 6.77 (d, J = 2.7 Hz, 1H), 4.17-3.83 (m, 6H), 3.77-3.50 (m, 2H), 2.35-2.26 (m, 1H), 2.19-2.11 (m, 4H), 2.08-2.00 (m, 2H), 1.85-1.62 (m, 2H), 1.60-1.58 (m, 2H), 1.19 (s, 3H), 1.04 (d, J = 5.6 Hz, 3H), 0.70 (d, J = 6.4 Hz, 3H) | 522.3 |
| 407 | 1-(4-(((2S,5S)-2,5-dimethylpyrrolidin-1-yl)-4-(trifluoromethyl)benzyl)(methyl)amino)-4-methylpiperidine-1-carbonyl)-1H-pyrazole-3-carboxylic acid | 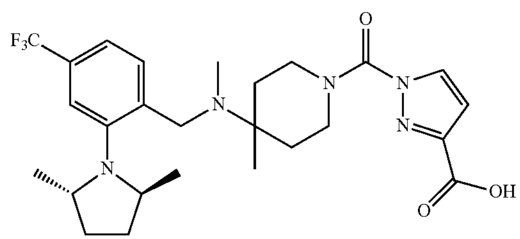 [SMILES: C[C@H]1CC[C@H](C)N1c1cc(C(F)(F)F)ccc1CN(C)C1(C)CCN(C(=O)n2ccc(C(=O)O)n2)CC1] | δ 8.11 (d, J = 2.4 Hz, 1H), 7.81 (d, J = 8.0 Hz, 1H), 7.42-7.37 (m, 2H), 6.80 (d, J = 2.4 Hz, 1H), 4.65-3.80 (m, 6H), 3.86-3.50 (m, 2H), 2.63-2.12 (m, 5H), 2.14-1.80 (m, 4H), 1.66-1.54 (m, 2H), 1.37-1.20 (m, 3H), 1.08 (d, J = 6.0 Hz, 3H), 0.73 (d, J = 6.0 Hz, 3H) | 522.3 |
| 408 | 1-(3-(4-chlorophenoxy)-5-fluorobenzyl)-piperazine-1-carbonyl)-4-(trifluoromethyl)-1H-pyrazole-3-carboxylic acid | 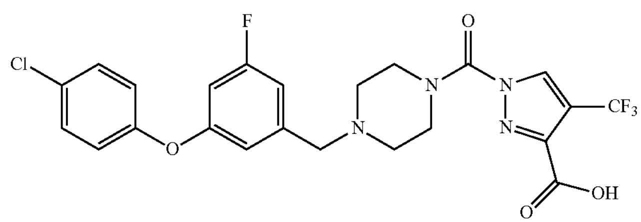 [SMILES: O=C(O)c1nn(C(=O)N2CCN(Cc3cc(F)cc(Oc4ccc(Cl)cc4)c3)CC2)cc1C(F)(F)F] | δ 8.54 (s, 1H), 7.42-7.39 (m, 2H), 7.08-7.04 (m, 2H), 6.92 (d, J = 9.0 Hz, 1H), 6.87 (s, 1H), 6.70-6.67 (m, 1H), 3.86 (s, 2H), 3.70 (s, 2H), 2.66 (br, 4H) | 527.1 |

| Ex | Name | Structure | NMR (¹H NMR, 300 MHz or 400 MHz, Methanol-d) | MS [M + H]⁺ |
|---|---|---|---|---|
| 409 | 4-chloro-1-(4-methyl-4-(methyl(2-(pyrrolidin-1-yl)-4-(trifluoromethyl)benzyl)amino)piperidine-1-carbonyl)-1H-pyrazole-3-carboxylic acid | 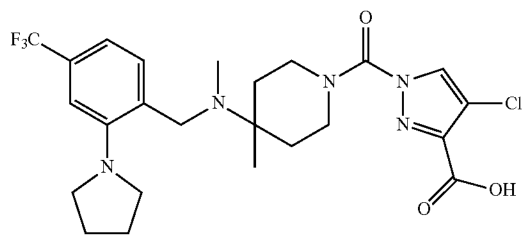 [SMILES: CN(Cc1ccc(C(F)(F)F)cc1N1CCCC1)C1(C)CCN(C(=O)n2cc(Cl)c(C(=O)O)n2)CC1] | δ 8.12 (s, 1H), 7.91 (d, J = 8.1 Hz, 1H), 7.25-7.20 (m, 2H), 3.96 (br, 2H), 3.81 (br, 2H), 3.68 (s, 2H), 3.20-3.09 (m, 4H), 2.11-1.90 (m, 9H), 1.72-1.65 (m, 2H), 1.15 (s, 3H) | 528.2 |
| 410 | 1-(1-(2-((2S,5S)-2,5-dimethylpyrrolidin-1-yl)-4-(trifluoromethyl)benzyl)-1,8-diazaspiro[4.5]decane-8-carbonyl)-1H-pyrazole-3-carboxylic acid | 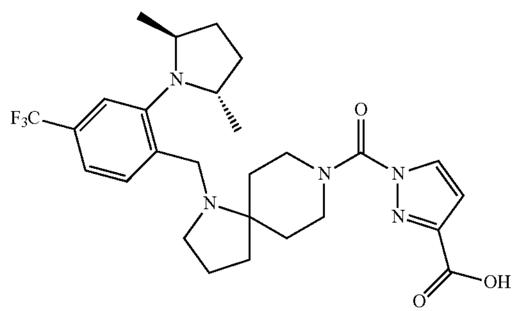 [SMILES: C[C@H]1CC[C@H](C)N1c1cc(C(F)(F)F)ccc1CN1CCCC12CCN(C(=O)n1ccc(C(=O)O)n1)CC2] | δ 8.13 (d, J = 2.8 Hz, 1H), 7.71-7.70 (m, 1H), 7.49-7.47 (m, 2H), 6.81 (d, J = 2.8 Hz, 1H), 4.89-4.32 (m, 3H), 4.24-4.21 (m, 1H), 4.01-3.94 (m, 2H), 3.33-3.06 (m, 4H), 2.36-2.25 (m, 6H), 2.09-2.05 (m, 2H), 1.95-1.86 (m, 2H), 1.67-1.57 (m, 2H), 1.11 (d, J = 6.0 Hz, 3H), 0.75 (d, J = 6.4 Hz, 3H) | 534.3 |
| 411 | 1-(1-(2-((2R,5R)-2,5-dimethylpyrrolidin-1-yl)-4-(trifluoromethyl)benzyl)-1,8-diazaspiro[4.5]decane-8-carbonyl)-1H-pyrazole-3-carboxylic acid | 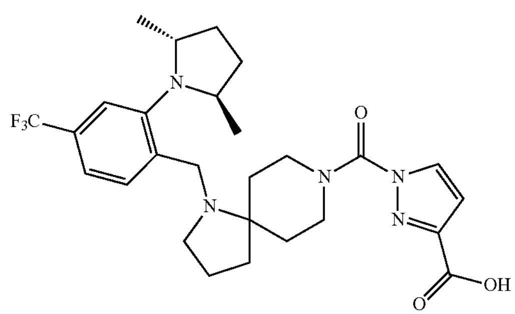 [SMILES: C[C@@H]1CC[C@@H](C)N1c1cc(C(F)(F)F)ccc1CN1CCCC12CCN(C(=O)n1ccc(C(=O)O)n1)CC2] | δ 8.13 (d, J = 2.8 Hz, 1H), 7.71-7.69 (m, 1H), 7.49-7.42 (m, 2H), 6.81 (d, J = 2.8 Hz, 1H), 4.89-4.41 (m, 3H), 4.30-4.20 (m, 1H), 4.01-3.94 (m, 2H), 3.33-3.10 (m, 4H), 2.49-2.25 (m, 6H), 2.08-2.00 (m, 2H), 2.00-1.77 (m, 2H), 1.67-1.57 (m, 2H), 1.11 (d, J = 6.0 Hz, 3H), 0.75 (d, J = 6.4 Hz, 3H) | 534.3 |

| Ex | Name | Structure | NMR (¹H NMR, 300 MHz or 400 MHz, Methanol-d) | MS [M + H]⁺ |
|---|---|---|---|---|
| 412 | 1-(1-(3-(4-methylpiperazin-1-yl)-5-(trifluoromethyl)benzyl)-1,8-diazaspiro[4.5]decane-8-carbonyl)-1H-pyrazole-3-carboxylic acid | 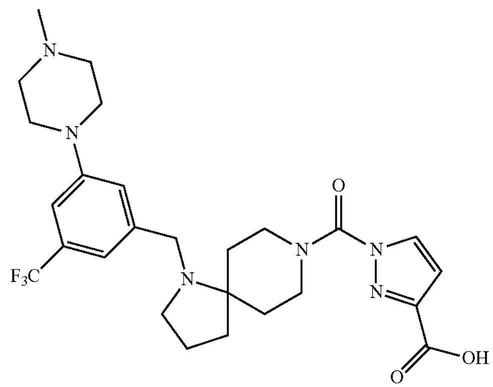 [SMILES: CN1CCN(c2cc(CN3CCCC34CCN(C(=O)n3ccc(C(=O)O)n3)CC4)cc(C(F)(F)F)c2)CC1] | δ 8.09 (d, J = 2.8 Hz, 1H), 7.33 (s, 1H), 7.24 (s, 1H), 7.21 (s, 1H), 6.79 (d, J = 2.8 Hz, 1H), 4.60 (br, 2H), 4.04 (br, 2H), 3.42 (br, 4H), 3.22-3.15 (m, 2H), 3.06 (br, 2H), 2.98 (br, 4H), 2.64 (s, 3H), 2.32-2.13 (m, 4H), 1.98-1.95 (m, 2H), 1.78-1.69 (m, 2H) | 535.3 |
| 413 | 1-(1-(2-(4-fluoropiperidin-1-yl)-4-(trifluoromethyl)benzyl)-1,8-diazaspiro[4.5]decane-8-carbonyl)-1H-pyrazole-3-carboxylic acid | 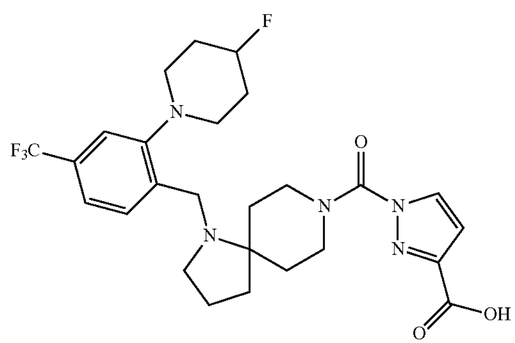 [SMILES: O=C(O)c1ccn(C(=O)N2CCC3(CCCN3Cc3ccc(C(F)(F)F)cc3N3CCC(F)CC3)CC2)n1] | δ 8.11 (d, J = 2.7 Hz, 1H), 7.73 (d, J = 8.0 Hz, 1H), 7.55-7.48 (m, 2H), 6.78 (d, J = 2.7 Hz, 1H), 4.87 (s, 1H), 4.77-4.46 (m, 2H), 4.27 (br, 2H), 3.31-3.08 (m, 6H), 2.91-2.88 (m, 2H), 2.31-2.15 (m, 4H), 2.13-1.90 (m, 6H), 1.89-1.68 (m, 2H) | 538.3 |
| 414 | 4-(trifluoromethyl)-1-(4-(3-((4-(trifluoromethyl)pyridin-2-yl)oxy)benzyl)piperazine-1-carbonyl)-1H-pyrazole-3-carboxylic acid | 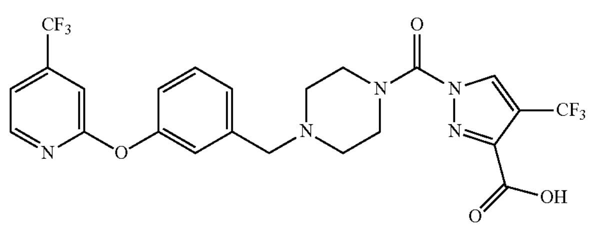 [SMILES: O=C(O)c1nn(C(=O)N2CCN(Cc3cccc(Oc4cc(C(F)(F)F)ccn4)c3)CC2)cc1C(F)(F)F] | δ 8.65 (s, 1H), 8.37 (d, J = 5.1 Hz, 1H), 7.47-7.37 (m, 2H), 7.30-7.23 (m, 3H), 7.13-7.10 (m, 1H), 3.83 (br, 4H), 3.70 (s, 2H), 2.69 (br, 4H) | 544.2 |

-continued

| Ex | Name | Structure | NMR (¹H NMR, 300 MHz or 400 MHz, Methanol-d) | MS [M + H]⁺ |
|---|---|---|---|---|
| 415 | 1-(1-(2-(tetrahydro-1H-furo[3,4-c]pyrrol-5(3H)-yl)-4-(trifluoromethly)-benzyl)-1,8-diazaspiro[4.5]-decane-8-carbonyl)-1H-pyrazole-3-carboxylic acid | 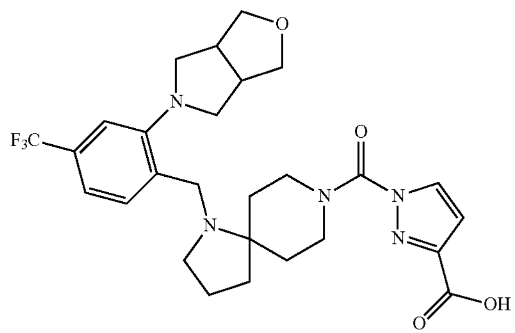 [SMILES: O=C(O)c1ccn(C(=O)N2CCC3(CCCN3Cc3ccc(C(F)(F)F)cc3N3CC4COCC4C3)CC2)n1] | δ 8.07 (d, J = 2.7 Hz, 1H), 7.71 (d, J = 8.1 Hz, 1H), 7.51-7.47 (m, 1H), 7.44-7.41 (m, 1H), 6.76 (d, J = 2.7 Hz, 1H), 4.86-4.41 (m, 2H), 4.41-4.24 (m, 2H), 3.94-3.79 (m, 4H), 3.29-3.01 (m, 6H), 3.07-2.96 (m, 4H), 2.33-2.19 (m, 4H), 2.09-1.92 (m, 2H), 1.87-1.69 (m, 2H) | 548.2 |
| 416 | 1-(1-(2-(8-oxa-3-azabicyclo[3.2.1]-octan-3-yl)-4-(trifluoromethyl)-benzyl)-1,8-diazaspiro[4.5]-decane-8-carbonyl)-1H-pyrazole-3-carboxylic acid | 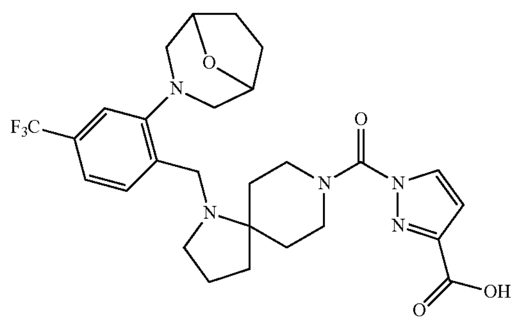 [SMILES: O=C(O)c1ccn(C(=O)N2CCC3(CCCN3Cc3ccc(C(F)(F)F)cc3N3CC4CCC(C3)O4)CC2)n1] | δ 8.11 (d, J = 2.7 Hz, 1H), 7.79 (d, J = 7.8 Hz, 1H), 7.46-7.42 (m, 2H), 6.81 (d, J = 2.7 Hz, 1H), 4.73-4.52 (m, 2H), 4.43 (br, 2H), 4.10 (s, 2H), 3.34-3.10 (m, 2H), 3.09-3.05 (m, 2H), 2.94-2.89 (m, 2H), 2.83-2.78 (m, 2H), 2.18-2.01 (m, 6H), 2.00-1.92 (m, 4H), 1.73-1.65 (m, 2H) | 548.2 |
| 417 | (R)-1-(1-(2-(hexahydropyrrolo-[1,2-a]pyrazin-2(1H)-yl)-4-(trifluoromethyl)-benzyl)-1,8-diazaspiro[4.5]-decane-8-carbonyl)-1H-pyrazole-3-carboxylic acid | 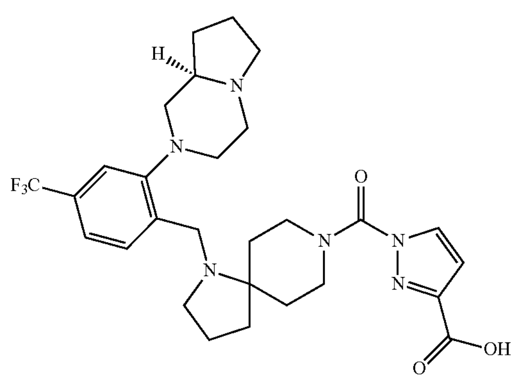 [SMILES: O=C(O)c1ccn(C(=O)N2CCC3(CCCN3Cc3ccc(C(F)(F)F)cc3N3CCN4CCC[C@@H]4C3)CC2)n1] | δ 8.07 (d, J = 2.7 Hz, 1H), 7.63 (d, J = 8.1 Hz, 1H), 7.56 (s, 1H), 7.46 (d, J = 8.1 Hz, 1H), 6.78 (d, J = 2.7 Hz, 1H), 4.58 (br, 2H), 4.35-3.70 (m, 3H), 3.55-3.31 (m, 5H), 3.20-2.85 (m, 8H), 2.14 (br, 3H), 2.10-1.70 (m, 6H), 1.59-1.54 (m, 2H) | 561.3 |

| Ex | Name | Structure | NMR (¹H NMR, 300 MHz or 400 MHz, Methanol-d) | MS [M + H]⁺ |
|---|---|---|---|---|
| 418 | (S)-1-(1-(2-(hexahydropyrrolo[1,2-a]pyrazin-2(1H)-yl)-4-(trifluoromethyl)-benzyl)-1,8-diazaspiro[4.5]-decane-8-carbonyl)-1H-pyrazole-3-carboxylic acid | 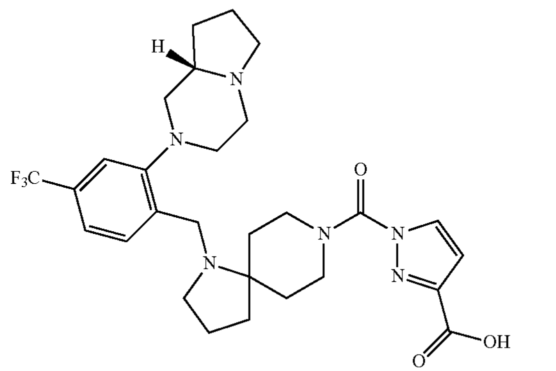 [SMILES: O=C(O)c1ccn(C(=O)N2CCC3(CCCN3Cc3ccc(C(F)(F)F)cc3N3CCN4CCC[C@H]4C3)CC2)n1] | δ 8.07 (d, J = 2.7 Hz, 1H), 7.63 (d, J = 8.1 Hz, 1H), 7.56 (s, 1H), 7.46 (d, J = 8.4 Hz, 1H), 6.78 (d, J = 2.7 Hz, 1H), 4.58 (br, 2H), 4.35-3.70 (m, 3H), 3.55-3.46 (m, 4H), 3.30-3.07 (m, 6H), 2.97 (br, 3H), 2.13 (br, 4H), 2.03-1.78 (m, 5H), 1.58-1.54 (m, 2H) | 561.3 |
| 419 | 1-(1-(3-(8-oxa-2-azaspiro[4.5]decan-2-yl)-5-(trifluoromethyl)-benzyl)-1,8-diazaspiro[4.5]-decane-8-carbonyl)-1H-pyrazole-3-carboxylic acid | 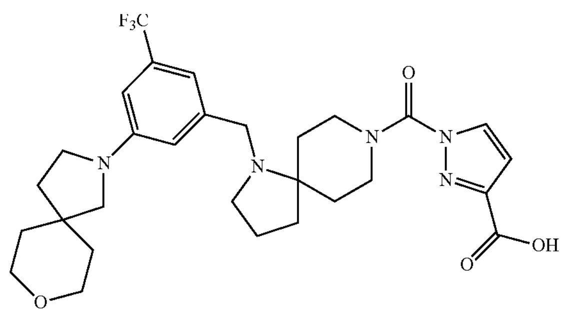 [SMILES: O=C(O)c1ccn(C(=O)N2CCC3(CCCN3Cc3cc(N4CCC5(CCOCC5)C4)cc(C(F)(F)F)c3)CC2)n1] | δ 8.12 (d, J = 2.4 Hz, 1H), 7.04 (s, 1H), 6.94 (s, 1H), 6.82-6.80 (m, 2H), 4.69 (br, 2H), 4.26 (br, 2H), 3.80-3.70 (m, 4H), 3.51-3.43 (m, 2H), 3.32-3.15 (m, 6H), 2.37-2.17 (m, 4H), 2.11-2.07 (m, 2H), 2.03-2.00 (m, 2H), 1.93-1.84 (m, 2H), 1.66 (br, 4H) | 576.3 |
| 420 | 1-(4-(4-chlorobenzyl)-piperazine-1-carbonyl)-N-methyl-1H-pyrazole-3-carboxamide | 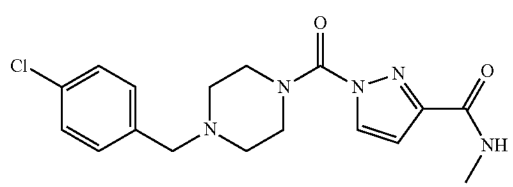 [SMILES: CNC(=O)c1ccn(C(=O)N2CCN(Cc3ccc(Cl)cc3)CC2)n1] | (Chloroform-d) δ 8.07 (s, 1H), 7.32-7.25 (m, 4H), 6.88 (s, 1H), 6.73 (s, 1H), 3.82-3.74 (m, 4H), 3.52 (m, 2H), 3.00-2.98 (m, 3H), 2.55-2.52 (m, 4H) | 362.2 |
| 421 | 1-(7-(4-chlorobenzyl)-2,7-diazaspiro[4.4]-nonane-2-carbonyl)-1H-pyrazole-3-carboxamide | 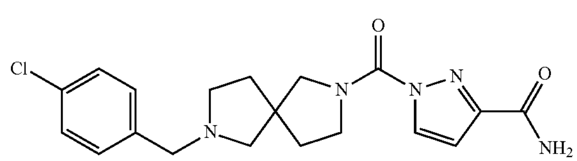 | (Chloroform-d) δ 8.26 (m, 1H), 7.32-7.27 (m, 3H), 7.26-7.20 (m, 1H), 6.90 (s, 1H), 6.65 (s, 1H), 5.66-5.41 (m, 1H), 5.11-4.82 (m, 2H), 3.80-3.49 (m, 4H), 2.79-2.28 (m, 4H), 2.07-1.80 (m, 4H) | 388.2 |

-continued

| Ex | Name | Structure | NMR (¹H NMR, 300 MHz or 400 MHz, Methanol-d) | MS [M + H]⁺ |
|---|---|---|---|---|
| 422 | 1-(7-(4-chlorobenzyl)-2,7-diazaspiro[4.4]-nonane-2-carbonyl)-N-methyl-1H-pyrazole-3-carboxamide | 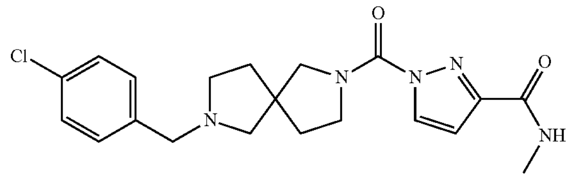 [SMILES: CNC(=O)c1ccn(C(=O)N2CCC3(CCN(Cc4ccc(Cl)cc4)C3)C2)n1] | (Chloroform-d) δ 8.22 (s, 1H), 7.33-7.27 (m, 3H), 7.26-7.20 (m, 1H), 6.88 (s, 1H), 6.73 (s, 1H), 4.11-3.80 (m, 2H), 3.78-3.50 (m, 4H), 3.09-2.93 (m, 3H), 2.84-2.31 (m, 4H), 2.07-1.80 (m, 4H) | 402.2 |
| 423 | N-methyl-1-(4-(3-phenoxybenzyl)-piperazine-1-carbonyl)-1H-pyrazole-3-carboxamide | 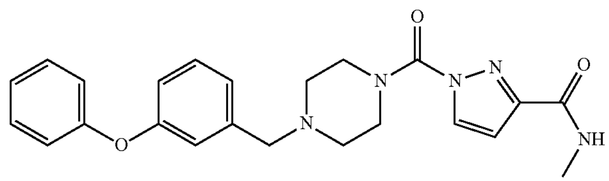 [SMILES: CNC(=O)c1ccn(C(=O)N2CCN(Cc3cccc(Oc4ccccc4)c3)CC2)n1] | (Chloroform-d) δ 8.07 (s, 1H), 7.38-7.30 (m, 2H), 7.28 (s, 1H), 7.13-7.05 (m, 2H), 7.05-6.98 (m, 3H), 6.96-6.89 (m, 1H), 6.89-6.87 (m, 1H), 6.72 (br, 1H), 3.84 (m, 4H), 3.67 (m, 2H), 2.99 (m, 3H), 2.57 (m, 4H) | 420.3 |
| 424 | 1-(5-(4-chlorobenzyl)-octahydropyrrolo[3,4-c]pyrrol-2-carbonyl)-N-methyl-1H-pyrazole-3-carboxamide | 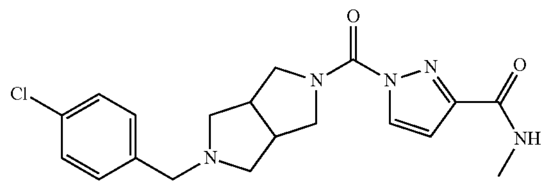 [SMILES: CNC(=O)c1ccn(C(=O)N2CC3CN(Cc4ccc(Cl)cc4)CC3C2)n1] | (Chloroform-d) δ 8.21 (s, 1H), 7.30-7.26 (m, 4H), 6.89 (s, 1H), 6.76 (s, 1H), 4.10 (m, 2H), 3.77 (m, 2H), 3.60 (m, 2H), 3.02 (s, 3H), 2.95 (m, 2H), 2.62 (m, 4H) | 388.1 |
| 425 | N-methyl-1-(5-(4-(trifluoromethyl)-benzyl)-octahydropyrrol o-[3,4-c]pyrrole-2-carbonyl)-1H-pyrazole-3-carboxamide | 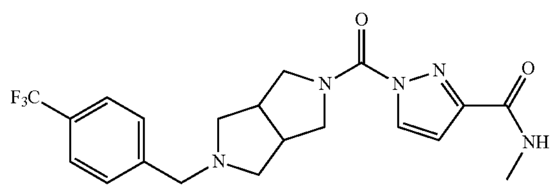 [SMILES: CNC(=O)c1ccn(C(=O)N2CC3CN(Cc4ccc(C(F)(F)F)cc4)CC3C2)n1] | (Chloroform-d) δ 8.22 (s, 1H), 7.58-7.56 (m, 2H), 7.45-7.43 (m, 2H), 6.89-6.74 (s, 2H), 4.11 (m, 2H), 3.78 (m, 2H), 3.68 (m, 2H), 3.05 (s, 3H), 2.95 (m, 2H), 2.63 (m, 4H) | 422.2 |
| 426 | 1-(7-(2,5-dichlorobenzyl)-2,7-diazaspiro[4.4]-nonane-2-carbonyl)-1H-pyrazole-3-carboxamide | 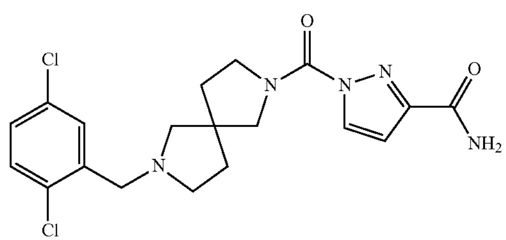 [SMILES: NC(=O)c1ccn(C(=O)N2CCC3(CCN(Cc4cc(Cl)ccc4Cl)C3)C2)n1] | (Chloroform-d) δ 8.26 (s, 1H), 7.52-7.48 (m, 1H), 7.28-7.26 (m, 1H), 7.17-7.15 (m, 1H), 6.90 (s, 1H), 6.69 (br, 1H), 5.61 (br, 1H), 4.10-3.85 (m, 2H), 3.81-3.61 (m, 4H), 2.83-2.45 (m, 4H), 2.08-1.93 (m, 4H) | 422.1 |

| Ex | Name | Structure | NMR (¹H NMR, 300 MHz or 400 MHz, Methanol-d) | MS [M + H]⁺ |
|---|---|---|---|---|
| 427 | 1-(cis-5-((2-chlorobenzyl)(methyl)amino)-octahydrocyclopenta[c]pyrrole-2-carbonyl)-N-methyl-1H-pyrazole-3-carboxamide | 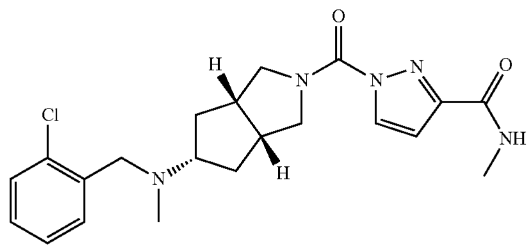 [SMILES: CNC(=O)c1ccn(C(=O)N2C[C@H]3C[C@@H](N(C)Cc4ccccc4Cl)C[C@H]3C2)n1] | (Chloroform-d) δ 8.22 (d, J = 2.7 Hz, 1H), 7.46 (d, J = 7.3 Hz, 1H), 7.37-7.34 (m, 1H), 7.26-7.17 (m, 2H), 6.88 (d, J = 2.7 Hz, 1H), 6.77 (br, 1H), 4.01-3.80 (m, 4H), 3.62 (s, 2H), 3.02-2.96 (m, 4H), 2.74 (br, 2H), 2.28-2.18 (m, 5H), 1.59 (br, 2H) | 416.1 |
| 428 | 1-(7-(2,5-dichlorobenzyl)-2,7-diazaspiro[4.4]nonane-2-carbonyl)-N-methyl-1H-pyrazole-3-carboxamide | 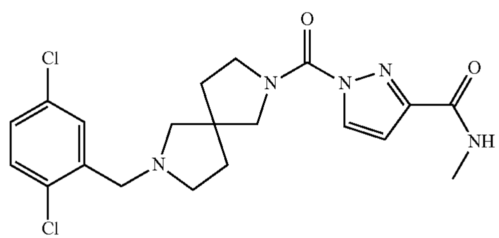 [SMILES: CNC(=O)c1ccn(C(=O)N2CCC3(CCN(Cc4cc(Cl)ccc4Cl)C3)C2)n1] | (Chloroform-d) δ 8.23 (s, 1H), 7.52-7.43 (m, 1H), 7.28-7.26 (m, 1H), 7.18-7.15 (m, 1H), 6.88 (s, 1H), 6.75 (br, 1H), 4.05-3.87 (m, 2H), 3.75-3.60 (m, 4H), 3.01 (br, 3H), 2.75-2.51 (m, 4H), 2.07-1.87 (m, 4H) | 436.1 |
| 429 | 1-(7-(3-(trifluoromethyl)benzyl)-2,7-diazaspiro[4.4]nonane-2-carbonyl)-1H-pyrazole-3-carboxamide | 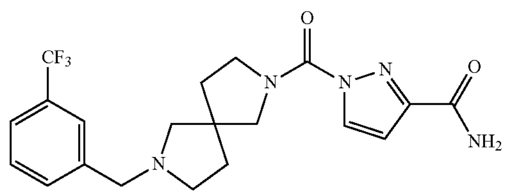 [SMILES: NC(=O)c1ccn(C(=O)N2CCC3(CCN(Cc4cccc(C(F)(F)F)c4)C3)C2)n1] | (Chloroform-d) δ 8.25 (s, 1H), 7.60-7.41 (m, 4H), 6.90 (s, 1H), 6.70-6.65 (m, 1H), 5.58 (br, 1H), 4.06-3.85 (m, 2H), 3.80-3.46 (m, 4H), 2.72-2.42 (m, 4H), 2.02-1.76 (m, 4H) | 422.2 |
| 430 | 1-(5-(2,5-dichlorobenzyl)octahydropyrrolo[3,4-c]pyrrole-2-carbonyl)-N-methyl-1H-pyrazole-3-carboxamide | 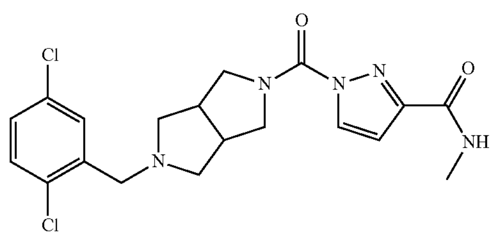 [SMILES: CNC(=O)c1ccn(C(=O)N2CC3CN(Cc4cc(Cl)ccc4Cl)CC3C2)n1] | (Chloroform-d) δ 8.26 (d, J = 2.6 Hz, 1H), 7.48 (s, 1H), 7.25 (m, 1H), 7.16 (m, 1H), 6.90 (s, 1H), 6.86-6.70 (br, 1H) 4.26-4.00 (br, 2H), 3.90-3.76 (br, 2H), 3.70 (s, 2H), 3.05 (d, J = 5.0 Hz, 3H), 2.95 (m, 2H), 2.66 (s, 4H) | 422 |

| Ex | Name | Structure | NMR (¹H NMR, 300 MHz or 400 MHz, Methanol-d) | MS [M + H]⁺ |
|---|---|---|---|---|
| 431 | 1-(trans-5-((2-chlorobenzyl)-(methyl)amino)-octahydrocyclopenta-[c]pyrrole-2-carbonyl)-N-methyl-1H-pyrazole-3-carboxamide | 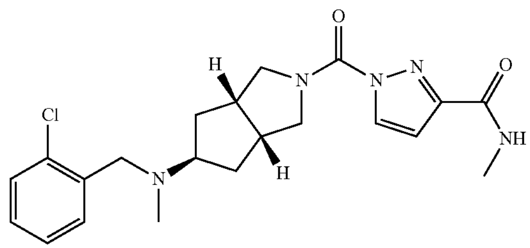 [SMILES: CNC(=O)c1ccn(C(=O)N2C[C@H]3C[C@H](N(C)Cc4ccccc4Cl)C[C@H]3C2)n1] | (Chloroform-d) δ 8.24 (d, J = 2.7 Hz, 1H), 7.60-7.42 (m, 1H), 7.42-7.30 (m, 1H), 7.24-7.15 (m, 2H), 7.90 (d, J = 2.7Hz, 1H), 6.80-6.62 (m, 1H), 4.30-3.90 (m, 2H), 3.85-3.32 (m, 4H), 3.32-3.12 (m, 1H), 3.12-2.98 (m, 3H), 2.98-2.70 (m, 2H), 2.18 (s, 3H), 2.12-1.82 (m, 4H) | 416.2 |
| 432 | N-methyl-1-(5-(3-(trifluoromethyl)-benzyl)-octahydropyrrolo-[3,4-c]pyrrole-2-carbonyl)-1H-pyrazole-3-carboxamide | 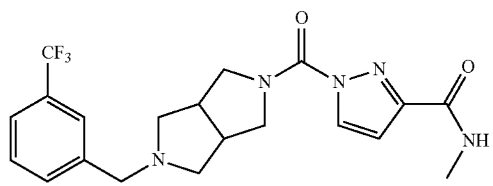 [SMILES: CNC(=O)c1ccn(C(=O)N2CC3CN(Cc4cccc(C(F)(F)F)c4)CC3C2)n1] | (Chloroform-d) δ 8.26 (d, J = 2.8 Hz, 1H), 7.68-7.55 (m, 3H), 7.52-7.40 (m, 1H), 6.90 (d, J = 2.8 Hz, 1H), 6.75 (br, 1H), 4.20-4.00 (br, 2H), 4.00-3.54 (br, 2H), 3.70 (s, 2H), 3.10-2.90 (m, 5H), 2.70 (s, 4H) | 422 |
| 433 | 1-(7-(3-chloro-5-(trifluoromethyl)-benzyl)-2,7-diazaspiro[4.4]-nonane-2-carbonyl)-1H-pyrazole-3-carboxamide | 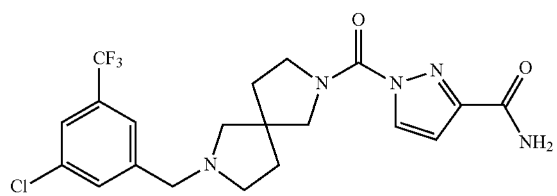 [SMILES: NC(=O)c1ccn(C(=O)N2CCC3(CCN(Cc4cc(Cl)cc(C(F)(F)F)c4)C3)C2)n1] | (Chloroform-d) δ 8.26 (s, 1H), 7.67-7.48 (m, 3H), 6.90 (s, 1H), 6.87-6.66 (m, 1H), 5.59 (br, 1H), 4.05-3.89 (m, 2H), 3.75-3.53 (m, 4H), 2.87-2.34 (m, 4H), 2.01-1.77 (m, 4H) | 456.2 |
| 434 | N-methyl-1-(cis-5-((2-(trifluoromethyl)-benzyl)amino)-octahydrocyclopenta-[c]pyrrole-2-carbonyl)-1H-pyrazole-3-carboxamide | 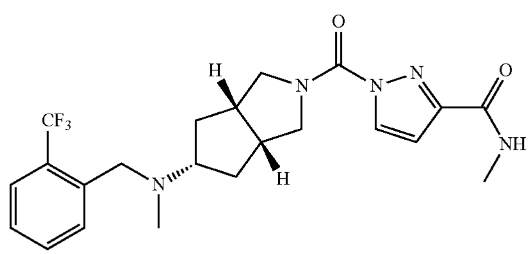 [SMILES: CNC(=O)c1ccn(C(=O)N2C[C@H]3C[C@@H](N(C)Cc4ccccc4C(F)(F)F)C[C@H]3C2)n1] | (Chloroform-d) δ 8.22 (d, J = 2.7 Hz, 1H), 7.55 (d, J = 8.1 Hz, 2H), 7.42 (d, J = 2 Hz, 2H), 6.88-6.82 (m, 2H), 4.01-3.96 (m, 4H), 3.56 (s, 2H), 3.01 (d, J = 5.0 Hz, 3H), 2.97-2.86 (m, 1H), 2.73 (br, 2H), 2.26-2.12 (m, 2H), 2.09 (s, 3H), 1.58-1.48 (m, 2H) | 450.1 |

| Ex | Name | Structure | NMR (¹H NMR, 300 MHz or 400 MHz, Methanol-d) | MS [M + H]⁺ |
|---|---|---|---|---|
| 435 | 1-(7-(3-chloro-5-(trifluoromethyl)-benzyl)-2,7-diazaspiro[4.4]-nonane-2-carbonyl)-N-methyl-1H-pyrazole-3-carboxamide | 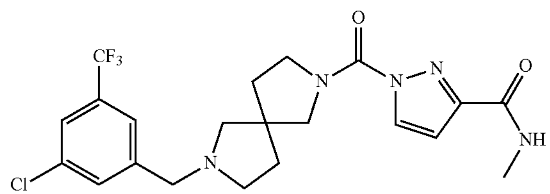 [SMILES: CNC(=O)c1ccn(C(=O)N2CCC3(CCN(Cc4cc(Cl)cc(C(F)(F)F)c4)C3)C2)n1] | (Chloroform-d) δ 8.23 (s, 1H), 7.61-7.48 (m, 3H), 6.89 (s, 1H), 6.88-6.76 (m, 1H), 4.04-3.85 (m, 2H), 3.71-3.43 (m, 4H), 3.03-3.00 (m, 3H), 3.00-2.43 (m, 4H), 2.00-1.75 (m, 4H) | 470.2 |
| 436 | 1-(7-(4-morpholino-2-(trifluoromethyl)-benzyl)-2,7-diazaspiro[4.4]nonane-2-carbonyl)-1H-pyrazole-3-carboxamide | 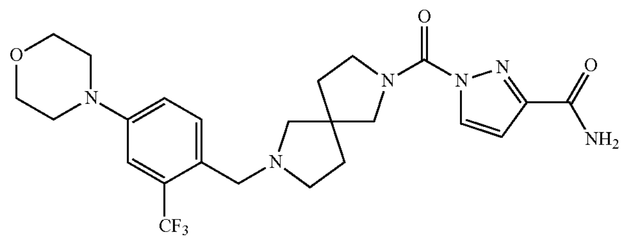 | (Chloroform-d) δ 8.25 (s, 1H), 7.63-7.43 (m, 1H), 7.13-7.11 (m, 1H), 7.04-7.01 (m, 1H), 6.97 (s, 1H), 6.89-6.65 (m, 1H), 5.55 (br, 1H), 4.01-3.96 (m, 2H), 3.88-3.85 (m, 4H), 3.72-3.57 (m, 4H), 3.20-3.17 (t, J = 4.6 Hz, 4H), 2.86-2.77 (m, 1H), 2.66-2.47 (m, 2H), 2.47-2.44 (m, 1H), 1.97-1.73 (m, 4H) | 507.1 |
| 437 | 1-(5-(3-chloro-5-(trifluoromethyl)-benzyl)-octahydropyrrolo[3,4-c]pyrrole-2-carbonyl)-N-methyl-1H-pyrazole-3-carboxamide | 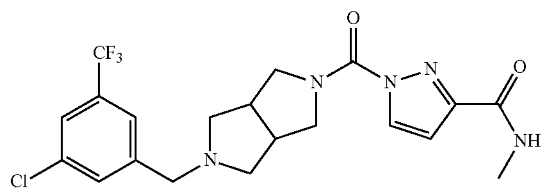 [SMILES: CNC(=O)c1ccn(C(=O)N2CC3CN(Cc4cc(Cl)cc(C(F)(F)F)c4)CC3C2)n1] | (Chloroform-d) δ 8.26 (d, J = 2.6 Hz, 1H), 7.70-7.40 (m, 3H), 6.90 (d, J = 2.6 Hz, 1H), 6.80-6.60 (br, 1H), 4.30-4.00 (m, 2H), 3.98-3.70 (br, 2H), 3.60 (s, 2H), 3.10-2.90 (m, 5H), 2.80-2.50 (m, 4H) | 456.2 |
| 438 | N-methyl-1-(7-(4-morpholino-2-(trifluoromethyl)-benzyl)-2,7-diazaspiro[4.4]nonane-2-carbonyl)-1H-pyrazole-3-carboxamide | 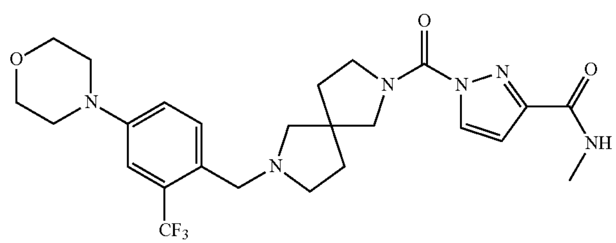 [SMILES: CNC(=O)c1ccn(C(=O)N2CCC3(CCN(Cc4ccc(N5CCOCC5)cc4C(F)(F)F)C3)C2)n1] | (Chloroform-d) δ 8.20 (s, 1H), 7.60-7.54 (m, 1H), 7.10 (s, 1H), 7.09-6.92 (m, 1H), 6.88-6.85 (m, 1H), 6.71 (br, 1H), 4.06-3.71 (m, 6H), 3.82-3.54 (m, 4H), 3.17-3.14 (t, J = 4.8 Hz, 4H), 2.99-2.85 (m, 3H), 2.75-2.61 (m, 1H), 2.61-2.41 (m, 2H), 2.41-2.30 (m, 1H), 1.91-1.69 (m, 4H) | 521.3 |

| Ex | Name | Structure | NMR (1H NMR, 300 MHz or 400 MHz, Methanol-d) | MS [M + H]+ |
|---|---|---|---|---|
| 439 | N-methyl-1-(cis-5-(methyl(4-(trifluoromethyl)-benzyl)amino)-octahydrocyclopenta-[c]pyrrole-2-carbonyl)-1H-pyrazole-3-carboxamide | 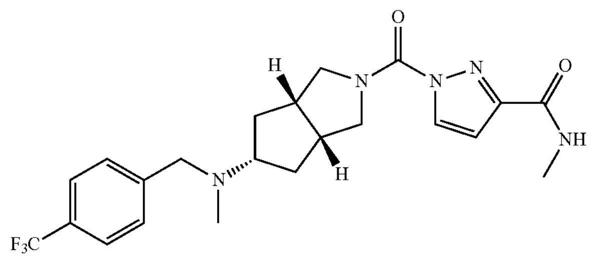 [SMILES: CNC(=O)c1ccn(C(=O)N2C[C@H]3C[C@@H](N(C)Cc4ccc(C(F)(F)F)cc4)C[C@H]3C2)n1] | (Chloroform-d) δ 8.23 (d, J = 2.7 Hz, 1H), 7.82 (d, J = 7.8 Hz, 1H), 7.61-7.52 (m, 2H), 7.32 (t, J = 7.5 Hz, 1H), 6.88-6.84 (m, 2H), 3.93-3.68 (m, 6H), 3.03-2.94 (m, 4H), 2.73 (br, 2H), 2.22-2.15 (m, 5H), 1.57-1.52 (m, 2H) | 450.2 |
| 440 | N-methyl-1-(5-(4-morpholino-2-(trifluoromethyl)-benzyl)octahydropyrrolo-[3,4-c]pyrrole-2-carbonyl)-1H-pyrazole-3-carboxamide | 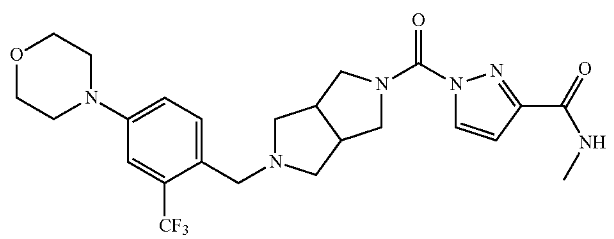 [SMILES: CNC(=O)c1ccn(C(=O)N2CC3CN(Cc4ccc(N5CCOCC5)cc4C(F)(F)F)CC3C2)n1] | (Chloroform-d) δ 8.30 (d, J = 2.6 Hz, 1H), 7.60-7.50 (m, 1H),7.13 (d, J = 2.3 Hz, 1H), 7.05-6.92 (m, 1H), 6.85 (d, J = 2.7 Hz, 1H), 6.80-6.68 (br, 1H), 4.30-4.00 (m, 2H), 3.98-3.85 (m, 4H), 3.82-3.60 (m, 4H), 3.10-3.22 (m, 4H), 3.05 (d, J = 5.0 Hz, 3H), 2.95 (m, 2H), 2.70-2.50 (m, 4H) | 507.1 |
| 441 | N,N-dimethyl-1-(4-(2-morpholino-4-(trifluoromethyl)-benzyl)-piperazine-1-carbonyl)-1H-pyrazole-3-carboxamide | 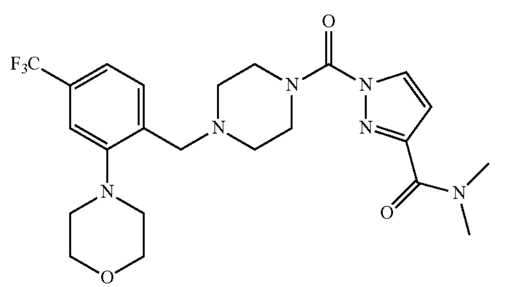 [SMILES: CN(C)C(=O)c1ccn(C(=O)N2CCN(Cc3ccc(C(F)(F)F)cc3N3CCOCC3)CC2)n1] | (Chloroform-d) δ 8.10-8.09 (m, 1H), 7.63-7.62 (m, 1H), 7.36-7.27 (m, 2H), 6.74-6.73 (m, 1H), 4.02 (br, 8H), 3.65 (br, 2H), 3.28-3.27 (m, 3H), 3.13-3.12 (br, 3H), 2.97 (br, 4H), 2.59 (br, 4H) | 495.1 |
| 442 | (S)-1-(4-(3-(4-chlorophenoxy)-benzyl)-2-methylpiperazine-1-carbonyl)-4-methyl-1H-pyrazole-3-carboxylic acid | 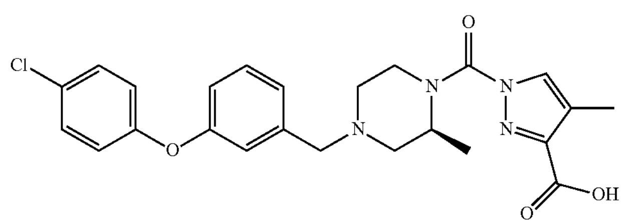 [SMILES: Cc1cn(C(=O)N2CCN(Cc3cccc(Oc4ccc(Cl)cc4)c3)C[C@@H]2C)nc1C(=O)O] | (Chloroform-d) δ 7.77 (br, 1H), 7.30-7.26 (m, 3H), 7.08-7.06 (m, 1H), 7.01 (s, 1H), 6.95-6.92 (m, 2H), 6.90-6.88 (m, 1H), 6.76 (br, 1H), 4.59 (br, 1H), 4.23-4.20 (m, 1H), 3.58-3.54 (m, 1H), 3.49-3.39 (m, 2H), 2.86-2.83 (m, 1H), 2.69-2.66 (m, 1H), 2.32-2.09 (m, 5H), 1.39 (d, J = 6.4 Hz, 3H) | 469.2 |

| Ex | Name | Structure | NMR (¹H NMR, 300 MHz or 400 MHz, Methanol-d) | MS [M + H]⁺ |
|---|---|---|---|---|
| 443 | 4-chloro-1-(4-(2-(pyrrolidin-1-yl)-4-(trifluoromethyl)-benzyl)-piperazine-1-carbonyl)-1H-pyrazole-3-carboxylic acid | 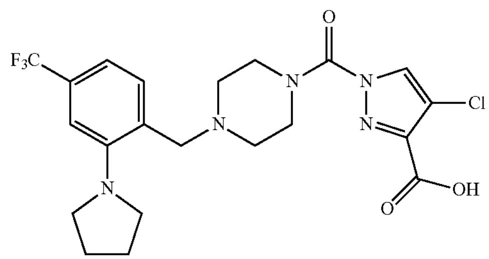 [SMILES: O=C(O)c1nn(C(=O)N2CCN(Cc3ccc(C(F)(F)F)cc3N3CCCC3)CC2)cc1Cl] | (Chloroform-d) δ 8.20 (br, 1H), 8.03 (s, 1H), 7.59 (d, J = 8.0 Hz, 1H), 7.18 (s, 1H), 7.15-7.13 (m, 1H), 4.20-3.80 (m, 6H), 3.20 (br, 4H), 2.82 (br, 4H), 1.96 (br, 4H) | 486.2 |
| 444 | (S)-1-(4-(3-(4-chlorophenoxy)-benzyl)-2-methylpiperazine-1-carbonyl)-4-(trifluoromethyl)-1H-pyrazole-3-carboxylic acid | 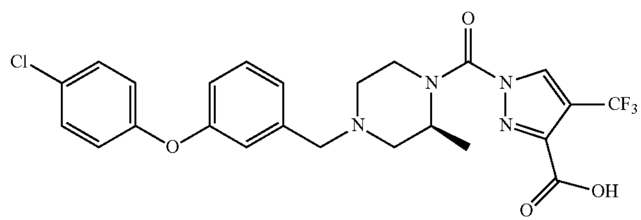 [SMILES: C[C@H]1CN(Cc2cccc(Oc3ccc(Cl)cc3)c2)CCN1C(=O)n1cc(C(F)(F)F)c(C(=O)O)n1] | (Chloroform-d) δ 8.65 (br, 1H), 7.70 (br, 1H), 7.32-7.30 (m, 3H), 7.17-7.08 (m, 1H), 7.03 (s, 1H), 6.96-6.91 (m, 3H), 4.59 (br, 1H), 4.26-4.24 (m, 1H), 3.63-3.60 (m, 1H), 3.48-3.45 (m, 2H), 2.94-2.91 (m, 1H), 2.74-2.71 (m, 1H), 2.34-2.20 (m, 2H), 1.50-1.43 (m, 3H) | 523.1 |
| 445 | 1-(trans-5-(2-chloro-3-methoxyphenoxy)-octahydrocyclopenta[c]pyrrole-2-carbonyl)-1H-pyrazole-3-carboxylic acid | 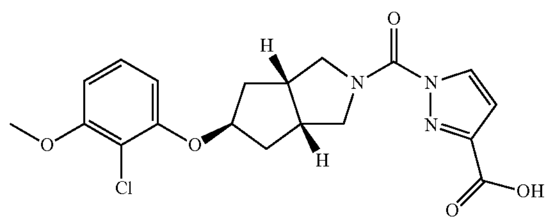 [SMILES: COc1cccc(O[C@H]2C[C@@H]3CN(C(=O)n4ccc(C(=O)O)n4)C[C@@H]3C2)c1Cl] | δ 8.18 (d, J = 2.8 Hz, 1H), 7.22-7.17 (m, 1H), 6.77 (d, J = 2.8 Hz, 1H), 6.71-6.69 (m, 2H), 5.08-5.05 (m, 1H), 4.19-3.69 (m, 7H), 3.04 (br, 2H), 2.22-2.20 (m, 2H), 2.05-1.95 (m, 2H) | 423.2 [M + NH₄]⁺ |
| 446 | 1-(trans-5-(2-chloro-3-(thiazol-4-yl)phenoxy)-octahydrocyclopenta[c]pyrrole-2-carbonyl)-1H-pyrazole-3-carboxylic acid | 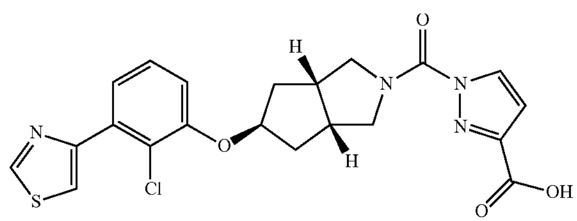 [SMILES: O=C(O)c1ccn(C(=O)N2C[C@H]3C[C@H](Oc4cccc(-c5cscn5)c4Cl)C[C@H]3C2)n1] | δ 9.08 (d, J = 1.6 Hz, 1H), 8.23 (d, J = 2.4 Hz, 1H), 7.93 (d, J = 1.6 Hz, 1H), 7.37-7.34 (m, 2H), 7.17-7.13 (m, 1H), 6.83 (d, J = 2.4 Hz, 1H), 5.15 (br, 1H), 4.35-3.57 (m, 4H), 3.15-3.07 (m, 2H), 2.35-2.17 (m, 2H), 2.04-2.00 (m, 2H) | 459.1 |

| Ex | Name | Structure | NMR (¹H NMR, 300 MHz or 400 MHz, Methanol-d) | MS [M + H]⁺ |
|---|---|---|---|---|
| 447 | 1-(trans-5-((2-chloro-3-(thiazol-4-yl)benzyl)oxy)-octahydrocyclopenta[c]pyrrole-2-carbonyl)-1H-pyrazole-3-carboxylic acid | 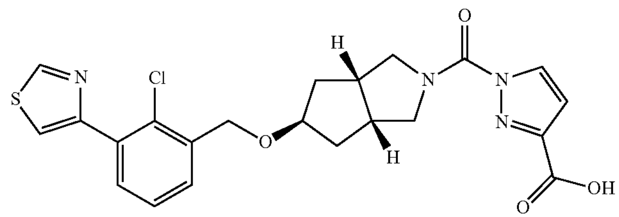 [SMILES: O=C(O)c1ccn(C(=O)N2C[C@H]3C[C@H](OCc4cccc(-c5cscn5)c4Cl)C[C@H]3C2)n1] | δ 9.10(s, 1H), 8.17 (d, J = 2.4 Hz, 1H), 7.91 (s, 1H), 7.67 (d, J = 7.6 Hz, 1H), 7.59 (d, J = 7.6 Hz, 1H), 7.42 (t, J = 7.6 Hz, 1H), 6.76 (d, J = 2.4 Hz, 1H), 4.74 (s, 2H), 4.33 (br, 1H), 4.27-3.50 (m, 4H), 2.96 (br, 2H), 2.20-2.17 (m, 2H), 1.87-1.84 (m, 2H) | 473.2 |
| 448 | 1-(trans-5-(2-chloro-3-isobutoxyphenoxy)-octahydrocyclopenta[c]pyrrole-2-carbonyl)-1H-pyrazole-3-carboxylic acid | 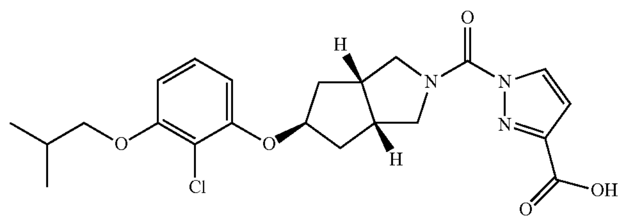 [SMILES: CC(C)COc1cccc(O[C@H]2C[C@@H]3CN(C(=O)n4ccc(C(=O)O)n4)C[C@@H]3C2)c1Cl] | δ 8.18 (s, 1H), 7.18-7.14 (m, 1H), 6.77 (s, 1H), 6.70-6.65 (m, 2H), 5.06 (br, 1H), 4.17-3.87 (m, 3H), 3.81-3.80 (m, 2H), 3.73-3.50 (m, 1H), 3.16-3.04 (m, 2H), 2.20-2.13 (m, 2H), 2.12-2.04 (m, 1H), 1.99-1.96 (m, 2H), 1.11-1.01 (m, 6H) | 465.1 [M + NH₄]⁺ |
| 449 | 4-chloro-1-(4-(2-morpholino-3-(trifluoromethyl)benzyl)piperazine-1-carbonyl)-1H-pyrazole-3-carboxylic acid | 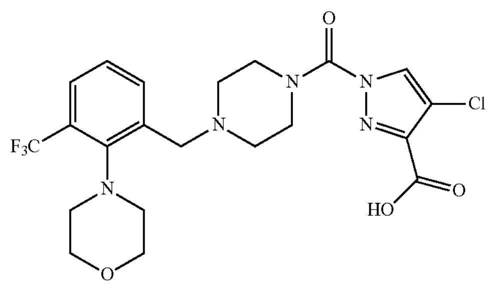 [SMILES: O=C(O)c1nn(C(=O)N2CCN(Cc3cccc(C(F)(F)F)c3N3CCOCC3)CC2)cc1Cl] | δ 8.15 (s, 1H), 7.81 (d, J = 7.8 Hz, 1H), 7.62 (d, J = 8.1 Hz, 1H), 7.34-7.29 (m, 1H), 4.10-3.70 (m, 10H), 3.48-3.25 (m, 2H), 2.90-2.82 (m, 2H), 2.69 (br, 4H) | 502.1 |
| 450 | (S)-1-(4-(2-chloro-3-(2-hydroxy-2-methylpropoxy)-benzyl)-2-methylpiperazine-1-carbonyl)-1H-pyrazole-3-carboxamide | 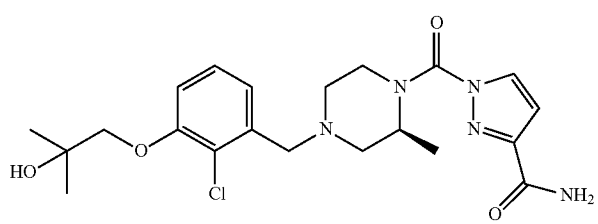 [SMILES: C[C@H]1CN(Cc2cccc(OCC(C)(C)O)c2Cl)CCN1C(=O)n1ccc(C(N)=O)n1] | (Chloroform-d) δ 8.10 (d, J = 2.7 Hz, 1H), 7.25-7.20 (m, 1H), 7.15-7.13 (m, 1H), 6.92 (d, J = 2.7 Hz, 1H), 6.89-6.86 (m, 1H), 6.68 (br, 1H), 5.61 (br, 1H), 4.65 (br, 1H), 4.28-4.24 (m, 1H), 3.87 (s, 2H), 3.67-3.65 (m, 2H), 3.53-3.49 (m, 1H), 2.93-2.89 (m, 1H), 2.80-2.76 (m, 1H), 2.48-2.45 (m, 2H), 2.36-2.29 (m, 1H), 1.52 (d, J = 6.6 Hz, 3H), 1.40 (s, 6H) | 450.2 |

| Ex | Name | Structure | NMR (¹H NMR, 300 MHz or 400 MHz, Methanol-d) | MS [M + H]⁺ |
|---|---|---|---|---|
| 451 | 1-(trans-5-(2-chloro-3-(2-hydroxy-2-methylpropoxy)-phenoxy)-octahydrocyclopenta[c]pyrrole-2-carbonyl)-1H-pyrazole-3-carboxylic acid | 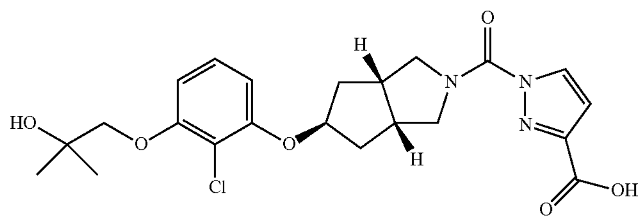 [SMILES: CC(C)(O)COc1cccc(O[C@H]2C[C@@H]3CN(C(=O)n4ccc(C(=O)O)n4)C[C@@H]3C2)c1Cl] | δ 8.25 (d, J = 2.7 Hz, 1H), 7.20 (t, J = 8.4 Hz, 1H), 6.85 (d, J = 2.7 Hz, 1H), 6.79-6.68 (m, 2H), 5.11-5.05 (m, 1H), 4.29-3.89 (m, 3H), 3.89-3.80 (s, 2H), 3.75-3.55 (m, 1H), 3.12-2.99 (m, 2H), 2.30-2.18 (m, 2H), 2.05-1.90 (m, 2H), 1.41-1.31 (s, 6H) | 486.2 [M + Na]⁺ |
| 452 | 1-(trans-5-(2-chloro-3-(2-hydroxy-2-methylpropoxy)-phenoxy)-octahydrocyclopenta[c]pyrrole-2-carbonyl)-1H-pyrazole-3-carboxamide | 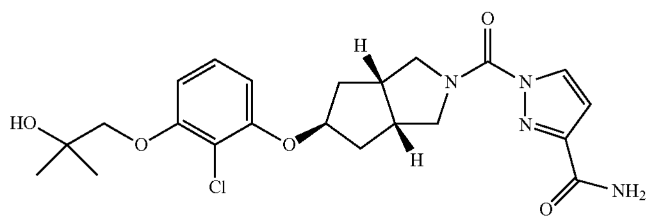 [SMILES: CC(C)(O)COc1cccc(O[C@H]2C[C@@H]3CN(C(=O)n4ccc(C(N)=O)n4)C[C@@H]3C2)c1Cl] | δ 8.34 (d, J = 2.7 Hz, 1H), 7.19 (t, J = 8.4 Hz, 1H), 6.89 (d, J = 2.7 Hz, 1H), 6.77-6.65 (m, 2H), 5.12-5.05 (m, 1H), 4.40-3.89 (m, 3H), 3.89-3.80 (s, 2H), 3.80-3.50 (m, 1H), 3.19-2.99 (m, 2H), 2.32-2.18 (m, 2H), 2.06-1.91 (m, 2H), 1.45-1.34 (s, 6H) | 485.2 [M + Na]⁺ |
| 453 | 1-(4-(2-morpholino-3-(trifluoromethyl)-benzyl)-piperazine-1-carbonyl)-1H-pyrazole-3-carboxylic acid | 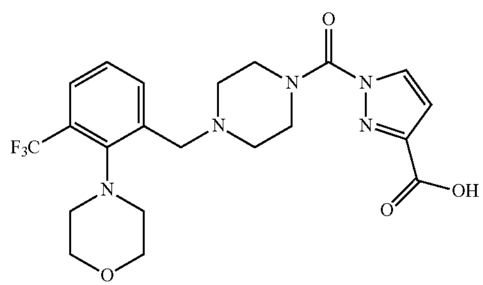 [SMILES: O=C(O)c1ccn(C(=O)N2CCN(Cc3cccc(C(F)(F)F)c3N3CCOCC3)CC2)n1] | δ 8.04 (d, J = 2.7 Hz, 1H), 7.75-7.77 (m, 1H), 7.49-7.51 (m, 1H), 7.23-7.27 (m, 1H), 6.73 (d, J = 2.7 Hz, 1H), 3.61-3.75 (m, 10H), 3.31-3.35 (m, 2H), 2.73-2.76 (m, 2H), 2.52-2.54 (m, 4H) | 468.0 |

| Ex | Name | Structure | NMR (¹H NMR, 300 MHz or 400 MHz, Methanol-d) | MS [M + H]⁺ |
|---|---|---|---|---|
| 454 | 1-(4-(3-(tetrahydro-1H-furo[3,4-c]pyrrol-5(3H)-yl)-4-(trifluoromethyl)-benzyl)piperazine-1-carbonyl)-1H-pyrazole-3-carboxylic acid | 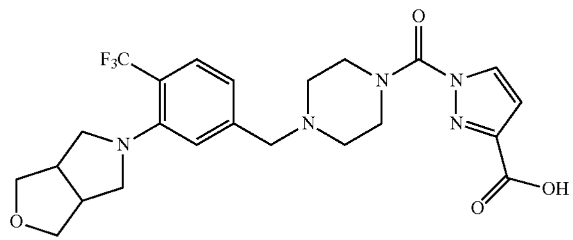 [SMILES: O=C(O)c1ccn(C(=O)N2CCN(Cc3ccc(C(F)(F)F)c(N4CC5COCC5C4)c3)CC2)n1] | δ 8.04-8.16 (m, 1H), 7.57-7.64 (m, 1H), 7.40 (s, 1H), 7.15-7.27 (m, 1H), 6.78-6.88 (m, 1H), 3.94-4.07 (m,2H), 3.89 (s, 4H), 3.74 (s, 2H), 3.44-3.59 (m, 2H), 3.08-3.21 (m, 2H), 2.83-3.02 (m, 4H), 2.71 (s, 4H) | 494.1 |
| 455 | 4-(3-((4-(3-carbamoyl-1H-pyrazole-1-carbonyl)piperazin-1-yl)methyl)phenyl)-tetrahydro-2H-pyran-4-carboxylic acid | 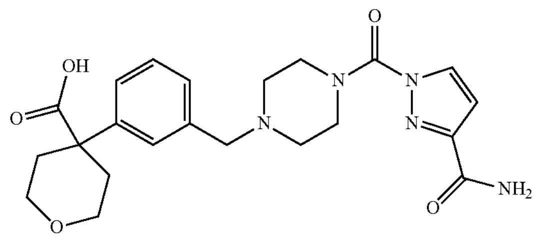 [SMILES: NC(=O)c1ccn(C(=O)N2CCN(Cc3cccc(C4(C(=O)O)CCOCC4)c3)CC2)n1] | δ 8.17 (d, J = 2.4 Hz, 1H), 7.50 (s, 1H), 7.46-7.40 (m, 1H), 7.37-7.28(m, 1H), 7.25-7.20 (m, 1H), 6.84 (d, J = 2.4 Hz, 1H), 3.91-3.83 (m, 6H), 3.68-3.53 (m, 4H), 2.62-2.59 (m, 4H), 2.53-2.48 (m, 2H), 1.95-1.87 (m, 2H) | 442.2 |
| 456 | 1-(4-methyl-4-(methyl(2-(pyrrolidin-1-yl)-4-(trifluoromethyl)-benzyl)amino)-piperidine-1-carbonyl)-1H-pyrazole-3-carboxylic acid | 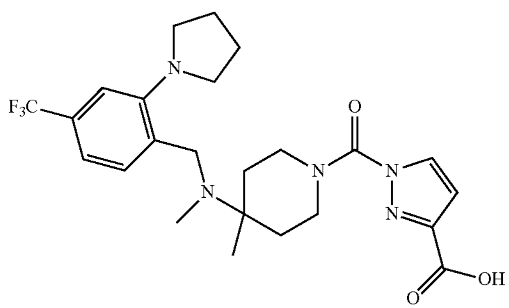 [SMILES: CN(Cc1ccc(C(F)(F)F)cc1N1CCCC1)C1(C)CCN(C(=O)n2ccc(C(=O)O)n2)CC1] | δ 8.04-8.17 (m, 1H), 7.68-7.81 (m, 1H), 7.40-7.50 (m, 1H), 7.29-7.40 (m, 1H), 6.72-6.85 (m, 1H), 4.25-4.51 (m, 2H), 4.00-4.25 (m, 2H), 3.42-3.67 (m, 2H), 3.10-3.26 (m, 4H), 2.37-2.58 (m, 3H), 1.88-2.21 (m, 8H), 1.31-1.56 (m, 3H) | 494.3 |

II. Biological Evaluation
In Vitro Competitive Activity-Based Protein Profiling.

Proteomes (mouse brain membrane fraction for mouse assays; human prefrontal cortex membrane fractions for human assays) (50 mL, 1.0 mg/mL total protein concentration) were preincubated with varying concentrations of inhibitors at 37° C. After 30 min, FP-Rh (1.0 mL, 50 mM in DMSO) was added and the mixture was incubated for another 30 min at 37° C. Reactions were quenched with SDS loading buffer (15 μL-4×) and run on SDS-PAGE. Following gel imaging, serine hydrolase activity was determined by measuring fluorescent intensity of gel bands corresponding to MAGL and FAAH using ImageJ 1.43u software. $IC_{50}$ data from this assay is shown in Table 1. All compounds in Table 1 were more potent inhibitors of MAGL than FAAH.

Preparation of Mouse Brain Proteomes from Inhibitor Treated Mice.

Inhibitors were administered to wild-type $C_{57}B1/6J$ by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 1 | C | A (10 uM) | B | D | | | | |
| 2 | | | A | C | | | | |
| 3 | | | A | D | *** | * | D | D |
| 4 | A | D | A | D | | | D | D |
| 5 | A | D | B | D | | | | |
| 6 | A | D | A | D | | | D | D |
| 7 | A | D | A | D | | | D | D |
| 8 | A | D | A | D | | | D | D |
| 9 | A | D | A | D | | | | |
| 10 | A | D | A | D | | | D | D |
| 11 | A | D | A | D | | | D | D |
| 12 | A | D | A | D | | | D | D |
| 13 | | | A | D | | | | |
| 14 | C | D | C | D | | | | |
| 15 | A | A | A | C | ** | ** | | |
| 16 | A | D | A | B | *** | * | | |
| 17 | | | A | A | *** | *** | | |
| 18 | B | D | C | D | | | | |
| 19 | A | A | A | A | *** | ** | | |
| 20 | A | A | A | A | ** | * | | |
| 21 | C | | C | | | | | |
| 22 | A | | A | | *** | | | |
| 23 | A | | A | | | | | |
| 24 | A | | A | | | | | |
| 25 | A | | A | | ** | | | |
| 26 | A | | A | | *** | | D | |
| 27 | A | | A | | *** | | | |
| 28 | A | | A | | | | | |
| 29 | A | | A | | ** | | | |
| 30 | A | | A | | | | | |
| 31 | D | | B | | | | | |
| 32 | | | | | *** | | | |
| 33 | | | B | | | | | |
| 34 | A | | A | | *** | | | |
| 35 | A | | A | | *** | | D | |
| 36 | | | | | *** | | | |
| 37 | A | | A | | *** | | | |
| 38 | | | | | *** | | | |
| 39 | A | D | A | D | | | | |
| 40 | A | D | A | D | | | D | D |
| 41 | A | A | D | D | | | | |
| 42 | A | A | A | D | ** | ** | | |
| 43 | A | B | A | A | *** | * | D | D |
| 44 | A | D | A | D | | | | |
| 45 | A | A | A | A | *** | ** | | |
| 46 | A | D | A | D | | | | |
| 47 | A | D | A | D | | | | |
| 48 | A | D | A | D | | | D | D |
| 49 | A | D | A | D | | | | |
| 50 | A (10 uM) | A (10 uM) | D | D | | | | |
| 51 | A | B | A | D | *** | ** | D | D |
| 52 | A | D | A | D | | | | |
| 53 | A | A | A | A | *** | ** | | |
| 54 | A | A | A | A | *** | ** | | |
| 55 | A | A | A | A | *** | *** | D | D |
| 56 | A | D | A | B | | | | |
| 57 | A | B | A | B | *** | ** | D | D |
| 58 | A | D | A | B | | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 59 | A | D | A | D | | | | |
| 60 | C | D | D | D | | | | |
| 61 | A | A | A | A | *** | ** | | |
| 62 | B | D | D | D | | | | |
| 63 | C | B | D | D | | | | |
| 64 | A | D | A | D | | | | |
| 65 | B | D | C | D | | | | |
| 66 | A | D | A | D | | | | |
| 67 | A | D | A | D | | | | |
| 68 | A | D | A | D | | | | |
| 69 | A | D | A | D | | | | |
| 70 | C | B | D | D | | | | |
| 71 | A | D | A | D | | | | |
| 72 | A | D | A | D | *** | * | | |
| 73 | A | D | A | B | | | | |
| 74 | A | D | A | D | | | | |
| 75 | A | D | B | B | | | | |
| 76 | A | D | A | D | | | D | D |
| 77 | A | D | A | D | *** | * | | |
| 78 | A | D | A | D | | | | |
| 79 | A (10 uM) | B (10 uM) | D | D | | | | |
| 80 | A | D | A | D | | | | |
| 81 | A | B | A | D | *** | ** | | |
| 82 | A | D | A | D | | | | |
| 83 | A | D | A | D | *** | * | D | D |
| 84 | A | D | A | B | *** | ** | | |
| 85 | A | D | A | B | *** | * | | |
| 86 | A | D | A | D | | | D | D |
| 87 | A | D | A | D | | | | |
| 88 | A | D | A | D | | | D | D |
| 89 | A | A | A | A | *** | ** | | |
| 90 | A | D | A | D | | | D | D |
| 91 | A | D | A | D | | | D | D |
| 92 | A | D | A | D | *** | * | D | D |
| 93 | A | D | A | D | *** | * | D | D |
| 94 | A | D | A | D | | | | |
| 95 | A | D | A | D | | | D | D |
| 96 | | | A | C | | | | |
| 97 | A | D | A | D | | | | |
| 98 | A | A | A | A | *** | ** | D | D |
| 99 | A | A | A | A | *** | *** | | |
| 100 | A | D | A | D | *** | * | D | D |
| 101 | A | D | A | D | | | D | D |
| 102 | A | C | A | D | | | | |
| 103 | A | D | A | D | | | | |
| 104 | A | D | A | D | | | D | D |
| 105 | A | D | A | D | | | D | D |
| 106 | A | D | A | D | | | D | D |
| 107 | A | D | A | D | | | D | D |
| 108 | A | D | A | D | | | | |
| 109 | A | D | A | D | | | D | D |
| 110 | A | D | A | D | | | | |
| 111 | A | D | A | D | | | D | D |
| 112 | A | A | A | A | *** | ** | | |
| 113 | A | D | A | D | | | D | D |
| 114 | A | D | A | D | | | D | D |
| 115 | C | B | D | A | | | | |
| 116 | A | A | A | D | ** | ** | D | D |
| 117 | B | D | B | B | | | | |
| 118 | A | D | A | D | | | D | D |
| 119 | A | D | A | D | | | D | D |
| 120 | A | D | A | D | | | D | D |
| 121 | A | D | A | D | | | D | D |
| 122 | B | D | C | B | | | | |
| 123 | A | B | A | A | | | D | D |
| 124 | A | B | A | A | *** | ** | D | C |
| 125 | A | A | A | A | *** | *** | | |
| 126 | C | D | D | D | | | | |
| 127 | A | D | A | D | | | | |
| 128 | A | A | A | A | *** | *** | | |
| 129 | A | A | A | A | *** | ** | | |
| 130 | A | B | A | B | *** | ** | D | D |
| 131 | A | D | A | D | ** | * | | |
| 132 | A | A | A | A | *** | *** | D | D |
| 133 | A | A | A | A | *** | ** | D | D |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 134 | A | A | A | B | *** | ** | | |
| 135 | A | D | A | D | | | D | D |
| 136 | A | A | A | A | *** | ** | | |
| 137 | A | A | A | A | ** | ** | | |
| 138 | A | D | A | B | *** | ** | | |
| 139 | A | A | A | A | *** | *** | D | D |
| 140 | A | B | A | B | *** | ** | D | D |
| 141 | A (10 uM) | A (50 uM) | D | D | | | | |
| 142 | A (10 uM) | D | D | D | | | | |
| 143 | D | A | D | A | * | ** | | |
| 144 | A | A | A | A | *** | *** | | |
| 145 | A | B | A | A | | | | |
| 146 | A | A | B | A | | | | |
| 147 | A | A | D | A | | | | |
| 148 | A | A | A | A | *** | ** | D | C |
| 149 | A | C | A | A | ** | * | | |
| 150 | C | B | C | A | | | | |
| 151 | A | C | A | C | | | | |
| 152 | A | D | A | B | | | | |
| 153 | A | D | A | C | | | | |
| 154 | A | D | A | D | | | | |
| 155 | A | D | A | D | ** | * | | |
| 156 | A | D | A | A | | | | |
| 157 | A | A | A | A | *** | ** | D | D |
| 158 | A | A | A | A | *** | *** | D | D |
| 159 | A | A | A | A | *** | ** | D | D |
| 160 | A | D | A | D | | | | |
| 161 | A | A | A | A | *** | *** | | |
| 162 | A | A | A | C | *** | ** | | |
| 163 | D | C | D | D | | | | |
| 164 | A | A | A | C | *** | ** | | |
| 165 | A | A | A | B | | | | |
| 166 | B | D | A | D | | | | |
| 167 | A | C | A | D | *** | * | | |
| 168 | B | D | D | D | | | | |
| 169 | C | D | D | D | | | | |
| 170 | A | A | | | *** | ** | | |
| 171 | A | D | A | D | ** | * | | |
| 172 | A | A | A | B | *** | *** | | |
| 173 | A | A | A | B | *** | *** | | |
| 174 | A | D | A | C | | | | |
| 175 | A | A | A | A | *** | ** | | |
| 176 | A | A | A | A | *** | *** | | |
| 177 | C | D | | | | | | |
| 178 | A | A | | | | | | |
| 179 | A | B | | | | | | |
| 180 | A | D | | | | | | |
| 181 | A | A | A | A | | | | |
| 182 | A | A | A | A | | | | |
| 183 | | | C | C | | | | |
| 184 | | | D | C | | | | |
| 185 | A | D | A | D | | | D | D |
| 186 | B | D | A | D | | | | |
| 187 | A | C | A | D | | | D | D |
| 188 | A | D | A | D | | | D | D |
| 189 | A | D | A | D | | | | |
| 190 | C | C | D | B | | | | |
| 191 | A | D | A | D | | | | |
| 192 | A | D | C | D | | | | |
| 193 | C | A | C | A | | | | |
| 194 | | | | | | | | |
| 195 | A | A | D | A | *** | *** | | |
| 196 | A | A | | | *** | *** | | |
| 197 | A | A | A | A | *** | ** | | |
| 198 | A | A | | | | | | |
| 199 | A | A | A | A | *** | ** | A | D |
| 200 | | | A | A | *** | *** | | |
| 201 | | | A | A | *** | *** | | |
| 202 | | | A | A | *** | *** | | |
| 203 | A | A | A | A | | | | |
| 204 | | | A | A | *** | *** | | |
| 205 | | | A | A | *** | *** | | |
| 206 | | | A | A | *** | *** | | |
| 207 | A | D | A | D | | | D | D |
| 208 | | | A | A | *** | *** | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 209 | A | A | A | A | *** | ** | | |
| 210 | A | A | A | A | ** | * | D | D |
| 211 | A | D | A | D | | | D | D |
| 212 | A | D | A | D | | | D | D |
| 213 | A | | A | | *** | | | |
| 214 | B | | A | | | | | |
| 215 | A | | A | | ** | | | |
| 216 | A | | A | | *** | | | |
| 217 | A | | A | | *** | | | |
| 218 | A | | A | | ** | | | |
| 219 | A | | A | | *** | | | |
| 220 | A | | A | | *** | | C | |
| 221 | A | | A | | *** | | | |
| 222 | A | | A | | *** | | | |
| 223 | A | | D | | | | | |
| 224 | A | | A | | | | | |
| 225 | A | | A | | ** | | | |
| 226 | A | | A | | | | | |
| 227 | A | | C | | | | | |
| 228 | A | | A | | ** | | | |
| 229 | C | | D | | | | | |
| 230 | A | | A | | *** | | D | |
| 231 | A | | A | | *** | | | |
| 232 | A | | A | | *** | | | |
| 233 | A | | A | | ** | | | |
| 234 | A | | A | | *** | | | |
| 235 | A | | A | | *** | | | |
| 236 | A | | A | | *** | | | |
| 237 | | | A | | | | | |
| 238 | A | | A | | ** | | | |
| 239 | A | | A | | *** | | | |
| 240 | A | | A | | *** | | | |
| 241 | A | | A | | *** | | D | |
| 242 | A | | A | | *** | | | |
| 243 | A | | A | | ** | | | |
| 244 | A | | A | | *** | | | |
| 245 | A | | A | | *** | | D | |
| 246 | A | | A | | ** | | | |
| 247 | A | | A | | ** | | | |
| 248 | C | | D | | | | | |
| 249 | A | | A | | ** | | | |
| 250 | A | | A | | ** | | | |
| 251 | A | | A | | *** | | D | |
| 252 | A | | A | | *** | | D | |
| 253 | A | | A | | *** | | | |
| 254 | A | | A | | *** | | | |
| 255 | A | | A | | ** | | | |
| 256 | A | | B | | ** | | | |
| 257 | A | | A | | *** | | A | |
| 258 | A | | A | | *** | | | |
| 259 | A | | A | | *** | | | |
| 260 | A | | A | | *** | | A | |
| 261 | A | | A | | *** | | | |
| 262 | A | | B | | ** | | | |
| 263 | A | | A | | | | | |
| 264 | A | | A | | | | | |
| 265 | A | | A | | ** | | | |
| 266 | A | | A | | *** | | | |
| 267 | A | | A | | ** | | | |
| 268 | A | | A | | *** | | | |
| 269 | A | | A | | *** | | D | |
| 270 | A | | A | | | | | |
| 271 | A | | A | | *** | | | |
| 272 | A | | A | | *** | | | |
| 273 | A (10 uM) | | | | | | | |
| 274 | A | | A | | *** | | | |
| 275 | A | | A | | *** | | | |
| 276 | A | | A | | *** | | | |
| 277 | A | | A | | | | | |
| 278 | A | | A | | *** | | | |
| 279 | A | | A | | | | | |
| 280 | A | | A | | *** | | | |
| 281 | A | | A | | | | | |
| 282 | B | | D | | | | | |
| 283 | A | | A | | *** | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 284 | A | | A | | *** | | | |
| 285 | A | | A | | ** | | | |
| 286 | A | | A | | *** | | | |
| 287 | C | | D | | | | | |
| 288 | A | | A | | ** | | | |
| 289 | A | | A | | *** | | | |
| 290 | A | | A | | *** | | | |
| 291 | A | | A | | *** | | C | |
| 292 | A | | A | | ** | | | |
| 293 | A | | A | | *** | | | |
| 294 | A | | A | | | | | |
| 295 | B | | A | | | | | |
| 296 | A | | A | | *** | | | |
| 297 | A | | A | | *** | | | |
| 298 | A | | A | | | | | |
| 299 | A | | A | | *** | | | |
| 300 | A (10 uM) | | D | | | | | |
| 301 | A (10 uM) | | D | | | | | |
| 302 | A (10 uM) | | D | | | | | |
| 303 | | | A | | *** | | | |
| 304 | A | | A | | *** | | | |
| 305 | B | | D | | | | | |
| 306 | A | | A | | *** | | | |
| 307 | A | | A | | *** | | D | |
| 308 | A | | A | | *** | | D | |
| 309 | A | | A | | ** | | | |
| 310 | A | | A | | | | | |
| 311 | A | | A | | *** | | D | |
| 312 | A | | A | | ** | | | |
| 313 | A | | A | | *** | | | |
| 314 | A | | A | | *** | | | |
| 315 | A | | A | | | | | |
| 316 | A | | A | | | | | |
| 317 | A | | A | | | | | |
| 318 | A | | A | | *** | | | |
| 319 | A | | A | | *** | | | |
| 320 | A | | A | | *** | | | |
| 321 | A | | A | | *** | | | |
| 322 | A | | A | | | | | |
| 323 | A | | A | | *** | | | |
| 324 | C | | D | | | | | |
| 325 | A | | A | | *** | | | |
| 326 | A | | A | | | | | |
| 327 | A | | A | | *** | | D | |
| 328 | A | | A | | | | D | |
| 329 | A | | A | | *** | | | |
| 330 | A | | A | | ** | | | |
| 331 | A | | A | | *** | | | |
| 332 | A | | A | | | | | |
| 333 | A | | A | | *** | | | |
| 334 | B | | D | | | | | |
| 335 | A | | A | | ** | | | |
| 336 | A | | B | | | | | |
| 337 | A | | A | | *** | | D | |
| 338 | A | | A | | ** | | | |
| 339 | A | | A | | *** | | | |
| 340 | A | | A | | | | | |
| 341 | A | | A | | *** | | | |
| 342 | A | | A | | ** | | | |
| 343 | C | | D | | | | | |
| 344 | | | A | | | | | |
| 345 | A | | A | | *** | | | |
| 346 | A | | A | | *** | | | |
| 347 | A | | A | | *** | | D | |
| 348 | A | | A | | *** | | | |
| 349 | A | | A | | *** | | | |
| 350 | A | | A | | | | | |
| 351 | A | | A | | *** | | | |
| 352 | A | | A | | *** | | | |
| 353 | A | | A | | *** | | | |
| 354 | A | | A | | | | | |
| 355 | A | | A | | *** | | | |
| 356 | A | | A | | ** | | | |
| 357 | A | | A | | *** | | | |
| 358 | A | | A | | *** | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 359 | A | | A | | *** | | D | |
| 360 | A | | A | | *** | | D | |
| 361 | A | | A | | | | | |
| 362 | A | | A | | | | | |
| 363 | D | | D | | | | | |
| 364 | A | | A | | ** | | D | |
| 365 | A | | A | | | | D | |
| 366 | A (10 uM) | | D | | | | | |
| 367 | A | | A | | ** | | | |
| 368 | A | | A | | *** | | | |
| 369 | A | | A | | | | | |
| 370 | | | A | | ** | | | |
| 371 | A | | A | | *** | | | |
| 372 | D | | C | | | | | |
| 373 | A | | A | | *** | | | |
| 374 | A | | A | | *** | | | |
| 375 | A | | A | | *** | | | |
| 376 | A | | A | | ** | | | |
| 377 | D | | D | | | | | |
| 378 | A | | A | | *** | | | |
| 379 | A | | A | | | | | |
| 380 | A | | A | | *** | | | |
| 381 | A | | A | | *** | | D | |
| 382 | A | | A | | | | D | |
| 383 | A | | A | | | | | |
| 384 | A | | A | | *** | | D | |
| 385 | A | | A | | *** | | D | |
| 386 | B | | A | | | | | |
| 387 | | | A | | ** | | | |
| 388 | A | | A | | *** | | D | |
| 389 | A | | A | | *** | | | |
| 390 | A | | A | | ** | | | |
| 391 | A | | A | | *** | | | |
| 392 | A | | A | | ** | | D | |
| 393 | A | | A | | | | D | |
| 394 | A | | A | | | | D | |
| 395 | A | | A | | | | D | |
| 396 | A | | A | | *** | | | |
| 397 | A | | A | | *** | | D | |
| 398 | A | | A | | *** | | | |
| 399 | A | | A | | *** | | | |
| 400 | A (10 uM) | | D | | | | | |
| 401 | C | | D | | | | | |
| 402 | | | | | * | | | |
| 403 | A | | A | | | | | D |
| 404 | A | | A | | | | | D |
| 405 | A | | A | | | | | |
| 406 | | | | | ** | | | |
| 407 | | | | | ** | | | |
| 408 | A | | A | | *** | | | |
| 409 | A | | A | | ** | | | |
| 410 | | | A | | ** | | | |
| 411 | | | A | | ** | | | |
| 412 | | | D | | * | | | |
| 413 | A | | A | | | | D | |
| 414 | A | | A | | *** | | | |
| 415 | A | | A | | | | | |
| 416 | A | | A | | *** | | | |
| 417 | C | | D | | | | | |
| 418 | C | | D | | | | | |
| 419 | | | A | | ** | | | |
| 420 | | | A | | | | | |
| 421 | | | A | | | | | |
| 422 | | | A | | ** | | | |
| 423 | | | A | | | | | |
| 424 | | | A | | *** | | A | |
| 425 | | | A | | | | | |
| 426 | | | A | | *** | | A | |
| 427 | | | A | | ** | | | |
| 428 | | | A | | *** | | | |
| 429 | | | A | | *** | | | |
| 430 | | | A | | *** | | | |
| 431 | | | A | | *** | | | |
| 432 | | | A | | *** | | | |
| 433 | | | A | | *** | | A | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC50 (μM) (human) | FAAH IC50 (μM) (human) | MAGL % inh. 5 mg/kg (mouse) | FAAH % inh. 5 mg/kg (mouse) |
|---|---|---|---|---|---|---|---|---|
| 434 | | | A | | *** | | | |
| 435 | | | A | | *** | | | |
| 436 | | | A | | *** | | | |
| 437 | | | A | | *** | | | |
| 438 | | | A | | ** | | | |
| 439 | | | A | | *** | | | |
| 440 | | | A | | *** | | | |
| 441 | | | A | | ** | | | |
| 442 | | | A | | *** | | | |
| 443 | | | A | | *** | | | |
| 444 | | | B | | * | | | |
| 445 | | | A | | | | | |
| 446 | | | A | | | | | |
| 447 | A (10 uM) | | | | | | | |
| 448 | | | A | | *** | | | |
| 449 | | | A | | | | | |
| 450 | A | | A | | *** | | | |
| 451 | A | | A | | *** | | D | |
| 452 | A | | A | | | | | |
| 453 | | | A | D | *** | * | D | D |
| 454 | A | D | A | D | | | D | D |
| 455 | A | | A | | | | | |
| 456 | A | D | A | D | | | D | D |

* IC$_{50}$ is less than or equal to 100 nM;  IC$_{50}$ is greater than 100 nM and less than 1 μM; * IC$_{50}$ is greater than or equal to 1 μM and less or equal to 10 μM.
A = % inhibition is greater than or equal to 75%; B = % inhibition is greater than or equal to 50% and less than 75%; C = % inhibition is greater than or equal to 25% and less than 50%; D = % inhibition is greater than or equal to 0% and less than 25%.

What is claimed is:

1. A compound:

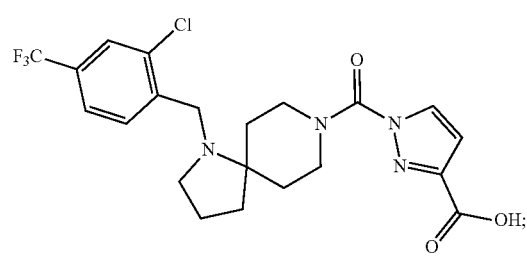 [SMILES: O=C(O)c1ccn(C(=O)N2CCC3(CCCN3Cc3ccc(C(F)(F)F)cc3Cl)CC2)n1]

or a pharmaceutically acceptable salt thereof.

2. The compound of claim 1:

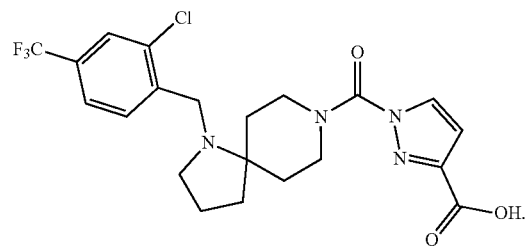 [SMILES: O=C(O)c1ccn(C(=O)N2CCC3(CCCN3Cc3ccc(C(F)(F)F)cc3Cl)CC2)n1]

3. A pharmaceutical composition comprising the compound of claim 1, or a pharmaceutically acceptable salt thereof, and at least one pharmaceutically acceptable excipient.

4. A compound:

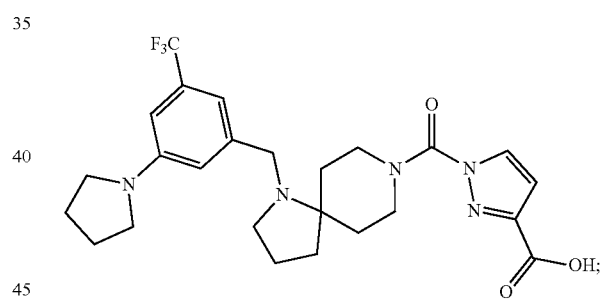

or a pharmaceutically acceptable salt thereof.

5. The compound of claim 4:

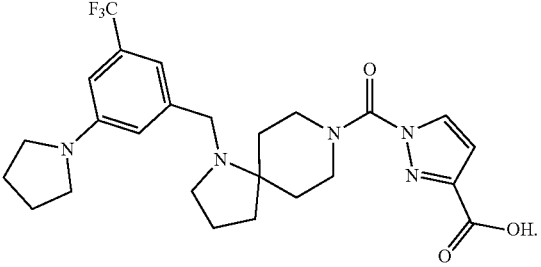 [SMILES: O=C(O)c1ccn(C(=O)N2CCC3(CCCN3Cc3cc(N4CCCC4)cc(C(F)(F)F)c3)CC2)n1]

6. A pharmaceutical composition comprising the compound of claim 4, or a pharmaceutically acceptable salt thereof, and at least one pharmaceutically acceptable excipient.

7. A compound:

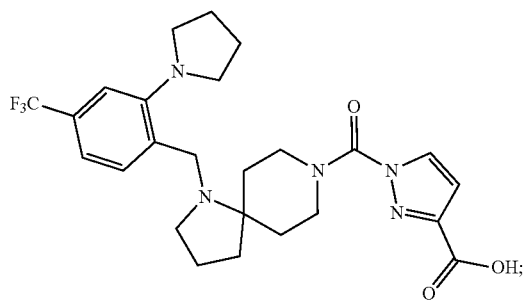 [SMILES: O=C(O)c1ccn(C(=O)N2CCC3(CCCN3Cc3ccc(C(F)(F)F)cc3N3CCCC3)CC2)n1]

or a pharmaceutically acceptable salt thereof.

8. The compound of claim 7:

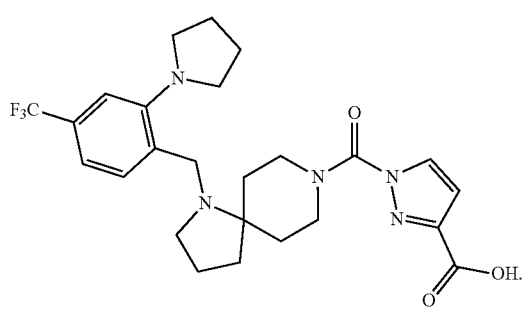 [SMILES: O=C(O)c1ccn(C(=O)N2CCC3(CCCN3Cc3ccc(C(F)(F)F)cc3N3CCCC3)CC2)n1]

9. A pharmaceutical composition comprising the compound of claim 7, or a pharmaceutically acceptable salt thereof, and at least one pharmaceutically acceptable excipient.

10. A compound:

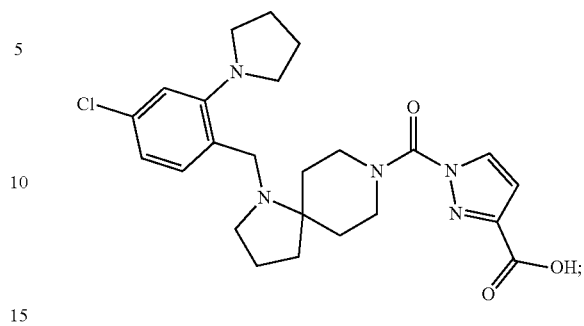

or a pharmaceutically acceptable salt thereof.

11. The compound of claim 10:

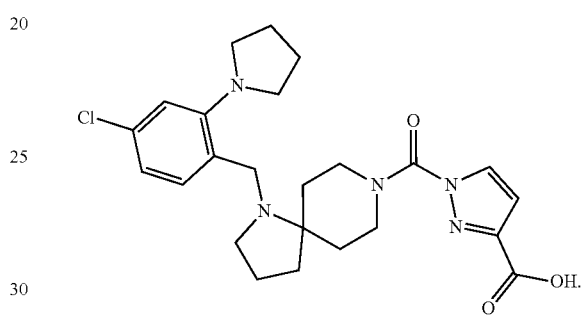

12. A pharmaceutical composition comprising the compound of claim 10, or a pharmaceutically acceptable salt thereof, and at least one pharmaceutically acceptable excipient.

* * * * *